US011597727B2

(12) United States Patent
Sheppard et al.

(10) Patent No.: US 11,597,727 B2
(45) Date of Patent: Mar. 7, 2023

(54) INHIBITORS OF INTEGRIN ALPHA 2 BETA 1 AND METHODS OF USE

(71) Applicant: THE REGENTS OF THE UNIVERSITY OF CALIFORNIA, Oakland, CA (US)

(72) Inventors: Dean Sheppard, Oakland, CA (US); Aparna Sundaram, San Francisco, CA (US); William F. DeGrado, San Francisco, CA (US); Hyunil Jo, Lafayette, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/979,096

(22) PCT Filed: Mar. 13, 2019

(86) PCT No.: PCT/US2019/022078
§ 371 (c)(1),
(2) Date: Sep. 8, 2020

(87) PCT Pub. No.: WO2019/178248
PCT Pub. Date: Sep. 19, 2019

(65) Prior Publication Data
US 2021/0387986 A1  Dec. 16, 2021

Related U.S. Application Data

(60) Provisional application No. 62/642,553, filed on Mar. 13, 2018.

(51) Int. Cl.
| | |
|---|---|
| *C07D 471/08* | (2006.01) |
| *C07C 275/24* | (2006.01) |
| *C07C 275/26* | (2006.01) |
| *C07D 207/48* | (2006.01) |
| *C07D 213/81* | (2006.01) |
| *C07D 277/06* | (2006.01) |

(52) U.S. Cl.
CPC .......... *C07D 471/08* (2013.01); *C07C 275/24* (2013.01); *C07C 275/26* (2013.01); *C07D 207/48* (2013.01); *C07D 213/81* (2013.01); *C07D 277/06* (2013.01); *C07C 2602/08* (2017.05); *C07C 2602/10* (2017.05); *C07C 2602/42* (2017.05); *C07C 2603/74* (2017.05)

(58) Field of Classification Search
CPC ... C07D 471/08; C07D 213/81; C07D 275/24
See application file for complete search history.

(56) References Cited

U.S. PATENT DOCUMENTS

| | | | |
|---|---|---|---|
| 4,676,980 A | 6/1987 | Segal et al. | |
| 4,816,567 A | 3/1989 | Cabilly et al. | |
| 4,946,778 A | 8/1990 | Ladner et al. | |
| 5,034,506 A | 7/1991 | Summerton et al. | |
| 5,235,033 A | 8/1993 | Summerton et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 8,258,159 B2 | 9/2012 | DeGrado et al. | |
| 8,946,159 B2 | 2/2015 | Feng | |
| 2009/0197861 A1 | 8/2009 | DeGrado et al. | |
| 2010/0179119 A1 | 7/2010 | DeGrado et al. | |
| 2016/0376266 A1 | 12/2016 | DeGrado et al. | |

FOREIGN PATENT DOCUMENTS

| | | |
|---|---|---|
| EP | 0 308 936 A2 | 3/1989 |
| EP | 0 308 936 A3 | 3/1989 |
| EP | 0 308 936 B1 | 3/1989 |
| JP | 2003-277340 | 10/2003 |
| JP | 2003277340 * | 10/2003 |
| WO | WO-91/00360 A1 | 1/1991 |
| WO | WO-92/20373 A1 | 11/1992 |
| WO | WO-93/08829 A1 | 5/1993 |
| WO | WO-2006/133338 A1 | 12/2006 |
| WO | WO-2017/173302 A2 | 10/2017 |
| WO | WO-2017/173302 A3 | 10/2017 |
| WO | WO-2021/222789 A1 | 11/2021 |

OTHER PUBLICATIONS

Berger, P. et al. (Nov. 2003). "Tryptase-stimulated human airway smooth muscle cells induce cytokine synthesis and mast cell Chemotaxis," *FASEB J* 17(14):2139-2141.
Holgate, S.T. (Sep. 2011). "Pathophysiology of asthma: what has our current understanding taught us about new therapeutic approaches?" *J Allergy Clin Immunol* 128(3):495-505.
International Search Report dated Oct. 12, 2021 for PCT Application No. PCT/US2021/030233, filed Apr. 30, 2021, 5 pages.
Liu, S. et al. (Jun. 15, 2021). "Integrin α2β1 regulates collagen I tethering to modulate hyperresponsiveness in reactive airway disease models," *J Clin Invest* 131(12):e138140.
Written Opinion dated Oct. 12, 2021 for PCT Application No. PCT/US2021/030233, filed Apr. 30, 2021, 6 pages.
Benayoun, L. et al. (May 15, 2003, e-published Jan. 16, 2003). "Airway structural alterations selectively associated with severe asthma," *Am J Respir Crit Care Med* 167(10):1360-1368.
Borza, C.M. et al. (Jun. 2012, e-published Mar. 22, 2012). "Inhibition of integrin α2β1 ameliorates glomerular injury," *J Am Soc Nephrol* 23(6):1027-1038.
Brightling, C.E. et al. (May 2012, e-published Dec. 22, 2011). "Lung damage and airway remodelling in severe asthma," *Clin Exp Allergy* 42(5):638-649.
Chiba, Y. et al. (Feb. 2009, e-published Aug. 7, 2008). "Interleukin-13 augments bronchial smooth muscle contractility with an upregulation of RhoA protein," *Am J Respir Cell Mol Biol* 40(2):159-167.
Choi, S. et al. (Nov. 1, 2007, e-published Oct. 4, 2007). "Small molecule inhibitors of integrin $\alpha_2\beta_1$," *J Med Chem* 50(22):5457-5462.

(Continued)

*Primary Examiner* — Kamal A Saeed
(74) *Attorney, Agent, or Firm* — Mintz, Levin, Cohn, Ferris, Glovsky and Popeo, P.C.

(57) ABSTRACT

Disclosed herein, inter alia, are inhibitors of integrin alpha 2 beta 1 and methods of using the same.

27 Claims, 6 Drawing Sheets

(56) References Cited

OTHER PUBLICATIONS

Cole, S.P.C. et al. (1985). "The EBV—Hybridoma Technique and Its Application to Human Lung Cancer," *Monoclonal Antibodies and Cancer Therapy* pp. 77-96.

Halland, N. et al. (Jan. 10, 2014, e-published Feb. 13, 2014). "Small Macrocycles As Highly Active Integrin α2β1 Antagonists," *ACS Medicinal Chemistry Letters* 5(2):193-198.

International Search Report dated Jul. 5, 2019, for PCT Application No. PCT/US2019/022078, filed Mar. 13, 2019, 4 pages.

Jones. P.T. et al. (May 29-Jun. 4, 1986). "Replacing the complementarity-determining regions in a human antibody with those from a mouse," *Nature* 321(6069):522-525.

Kudo, M. et al.(Mar. 4, 2012). "IL-17A produced by αβ T cells drives airway hyper-responsiveness in mice and enhances mouse and human airway smooth muscle contraction," *Nat Med* 18(4)547-554.

Marcus-Sakura, C.J. (Aug. 1, 1988). "Techniques for using antisense oligodeoxyribonucleotides to study gene expression," *Anal. Biochem.* 172(2):289-295.

McCafferty, J. et al. (Dec. 6, 1990). "Phage antibodies: filamentous phage displaying antibody variable domains," *Nature* 348(6301):552-554.

Mehta, D. et al. (Sep. 15, 1999). "Actin polymerization stimulated by contractile activation regulates force development in canine tracheal smooth muscle," *J Physiol* 519(Pt 3):829-840.

Miller, M.W. et al. (Jan. 20, 2009, e-published Jan. 13, 2009). "Small-molecule inhibitors of integrin alpha2beta1 that prevent pathological thrombus formation via an allosteric mechanism," *Proc Natl Acad Sci USA* 106(3):719-724.

Presta, L. (1992). "Antibody engineering," *Curr Opin Struc Biol* 2(4):593-596.

Sundaram, A. et al. (Jan. 3, 2017, e-published Dec. 5, 2016). "Targeting integrin α5β1 ameliorates severe airway hyperresponsiveness in experimental asthma," *J Clin Invest* 127(1):365-374.

Suresh. M.R. et al. (1986). "Bispecific monoclonal antibodies from hybrid hybridomas," *Methods Enzymol* 121:210-228.

Tang,D. et al. "Mechanosensitive tyrosine phosphorylation of paxillin and focal adhesion kinase in tracheal smooth muscle," *Am J Physiol* 276(1):C250-C258.

Traunecker, A. et al. (Dec. 1991). "Bispecific single chain molecules (Janusins) target cytotoxic lymphocytes on HIV infected cells," *EMBO J* 10(12):3655-3659.

Verhoeyen, M. et al. (Mar. 25, 1988). "Reshaping human antibodies: grafting an antilysozyme activity," *Science* 239(4847):1534-1536.

Wenzel, S.E. (Aug. 26, 2006). "Asthma: defining of the persistent adult phenotypes," *Lancet* 368(9537):804-813.

World Health Organization. Global surveillance, prevention and control of chronic respiratory diseases: a comprehensive approach. 2007, 155 pages.

Written Opinion dated Jul. 5, 2019, for PCT Application No. PCT/US2019/022078, filed Mar. 13, 2019, 6 pages.

* cited by examiner

Integrin α2β1

Structure of A2-4

INHIBITORS OF INTEGRIN ALPHA 2 BETA 1 AND METHODS OF USE

CROSS-REFERENCES TO RELATED APPLICATIONS

This application is the national stage filing under USC 371 of international application PCT/US2019/022078, filed Mar. 13, 2019, which claims the benefit of U.S. Provisional Application No. 62/642,553, filed on Mar. 13, 2018, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant nos. AI077439, HL119893 and HL124049 awarded by the National Institutes of Health. The government has certain rights in the invention.

BACKGROUND

Severe asthma accounts for approximately 10% of the 300 million people worldwide that carry a diagnosis of asthma. These patients have persistent symptoms of exaggerated airway narrowing despite maximal medical therapy including anti-inflammatories (inhaled and oral corticosteroids, leukotriene inhibitors, and antibodies to IgE), and muscle-targeted therapies (beta-adrenergic agonists). Despite the initial promise of biologic therapies that target specific cytokine mediators of both T2 high and T2 low asthma, early clinical trials have shown inconsistent benefit only in a small subset of severe asthmatics. Meanwhile, there have been no significant advances in therapies that directly target airway smooth muscle in over half a century. It is clear that novel approaches that specifically target smooth muscle are required. Currently available muscle-targeted therapies have focused on the classical actin-myosin machinery contributing to force generation. We recently identified a parallel pathway involved in tension transmission from the cell to the extracellular matrix, and found that disruption of specific integrin interactions with matrix proteins can effectively impair tension transmission in airway smooth muscle, a critical step for airway narrowing in asthma.

Asthma is a life-threatening disease affecting approximately 300 million people worldwide and contributing to 250,000 deaths annually (1). Although the phenotypes of allergic asthma are heterogeneous (2), common characteristics include bronchial inflammation, reversible obstruction, and airway hyperreactivity (3). Current therapies for allergic asthma remain limited (4, 5), despite the increased interest in targeted biologic therapies over the last two decades. Although promising, these biologic therapies have largely been met with limited success in clinical trials. For example, biologics targeting T2 high cytokines such as IL-13 have failed to show statistically significant reductions in asthma exacerbation rates. In T2 low asthma, numerous clinical trials targeting TNF-α, IL-17, GM-CSF, and CXCR2 have failed to show either consistent clinical responses or statistically significant benefits. Due to the fact that biologic therapies offer inhibition of specific cytokine-mediated pathways in asthma, their spectrum of efficacy is much more narrow than standard therapies. In addition, they do not necessarily address all of the clinical objectives of asthma management, necessitating the need for predictive biomarkers for implementation. In this setting, therapeutic advances that directly target the hypercontractile airway smooth muscle that results in bronchoconstriction have been notably lacking. Such muscle-specific therapy would be a particularly attractive therapeutic addition to severe asthmatics with persistent symptoms as well as those with acute exacerbations due to hypercontractile smooth muscle. These target populations number in the millions worldwide, and could be clearly identified by symptoms alone without the need for an accompanying biomarker.

Exaggerated airway narrowing is a central feature of asthma (6), but the mechanisms regulating contraction are incompletely understood. It is known that smooth muscle contraction is driven by calcium-mediated signaling to the actin-myosin contractile apparatus, and that force generation is triggered by stimuli such as methacholine or potassium chloride, enhanced by cytokines such as IL-13 (7) or IL-17A (8, 9), and transmitted via mediators such as myosin light chain kinase and RhoA. Currently available therapies that target smooth muscle contraction work by inhibiting this core pathway, including beta-adrenergic agonists and muscarinic antagonists that inhibit upstream of intracellular calcium release. Other approaches to inhibit this pathway, such as Rho kinase inhibitors, often have unacceptable vascular toxicity. Described herein, inter alia, are solutions to these and other problems in the art.

BRIEF SUMMARY OF THE INVENTION

Herein are provided, inter alia, methods for treating asthma using an α2β1 inhibitor and compositions of α2β1 inhibitors.

In an aspect is provided a compound, or a pharmaceutically acceptable thereof, having the formula:

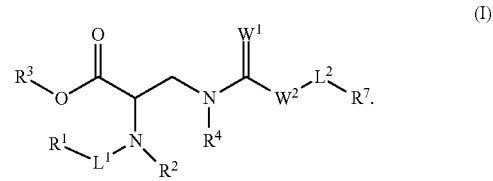

(I)

$R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $L^1$ is a bond or —C(O)—. $R^2$ is hydrogen or substituted or unsubstituted alkyl. $R^3$ is hydrogen, halogen, —CX$^3{}_3$, —CHX$^3{}_2$, —CH$_2$X$^3$, —OCX$^3{}_3$, —OCH$_2$X$^3$, —OCHX$^3{}_2$, —CN, —SO$_{n3}$R$^{3D}$, —SO$_{v3}$NR$^{3A}$R$^{3B}$, —NHC(O)NR$^{3A}$R$^{3B}$, —N(O)$_{m3}$, —NR$^{3A}$R$^{3B}$, —C(O)R$^{3C}$, —C(O)—OR$^{3C}$, —C(O)NR$^{3A}$R$^{3B}$, —OR$^{3D}$, —NR$^{3A}$SO$_2$R$^{3D}$, —NR$^{3A}$C(O)R$^{3C}$, —NR$^{3A}$C(O)O R$^{3C}$, —NR$^{3A}$OR$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^4$ is hydrogen or substituted or unsubstituted alkyl. $W^1$ is O, S, or NR$^8$. $W^2$ is O, S, or NR$^5$. $R^5$ is hydrogen or substituted or unsubstituted alkyl. $L^2$ is a bond or —C(R$^6$)$_2$—. $R^6$ is hydrogen, substituted or unsubstituted alkyl, or substituted or unsubstituted heteroalkyl. $W^1$ and $R^6$ may optionally be joined to form a substituted or unsubstituted 5 to 6 membered heterocycloalkyl, or substituted or unsubstituted 5 to 6 membered heteroaryl. $R^7$ is hydrogen, halogen, $-CX^7_3$, $-CHX^7_2$, $-CH_2X^7$, $-OCX^7_3$, $-OCH_2X^7$, $-OCHX^7_2$, $-CN$, $-SO_{n7}R^{7D}$, $-SO_{v7}NR^{7A}R^{7B}$, $-NHC(O)NR^{7A}R^{7B}$, $-N(O)_{m7}$, $-NR^{7A}R^{7B}$, $-C(O)R^{7C}$, $-C(O)-OR^{7C}$, $-C(O)NR^{7A}R^{7B}$, $-OR^{7D}$, $-NR^{7A}SO_2R^{7D}$, $-NR^{7A}C(O)R^{7C}$, $-NR^{7A}C(O)O\ R^{7C}$, $-NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. $R^8$ is hydrogen or substituted or unsubstituted alkyl. $R^{3A}$, $R^{3B}$, $R^{3C}$, $R^{3D}$, $R^{7A}$, $R^{7B}$, $R^{7C}$, and $R^{7D}$ are independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{3A}$ and $R^{3B}$ substituents bonded to the same nitrogen atom may optionally be joined to form a substituted or unsubstituted heterocycloalkyl or substituted or unsubstituted heteroaryl. $R^{7A}$ and $R^{7B}$ substituents bonded to the same nitrogen atom may optionally be joined to form a substituted or unsubstituted heterocycloalkyl or substituted or unsubstituted heteroaryl. Each $X$, $X^3$, and $X^7$ are independently $-F$, $-Cl$, $-Br$, or $-I$. n3 and n7 are independently an integer from 0 to 4. m3, m7, v3 and v7 are independently 1 or 2.

In an aspect is provided a pharmaceutical composition including a pharmaceutically acceptable excipient and a compound described herein.

In an aspect is provided a method of treating asthma, the method including administering to a subject in need thereof an effective amount of an integrin α2β1 inhibitor.

In an aspect is provided a method of treating asthma, the method including administering to a subject in need thereof an effective amount of a compound, or a pharmaceutically acceptable salt thereof, described herein.

DETAILED DESCRIPTION

Figure 1:
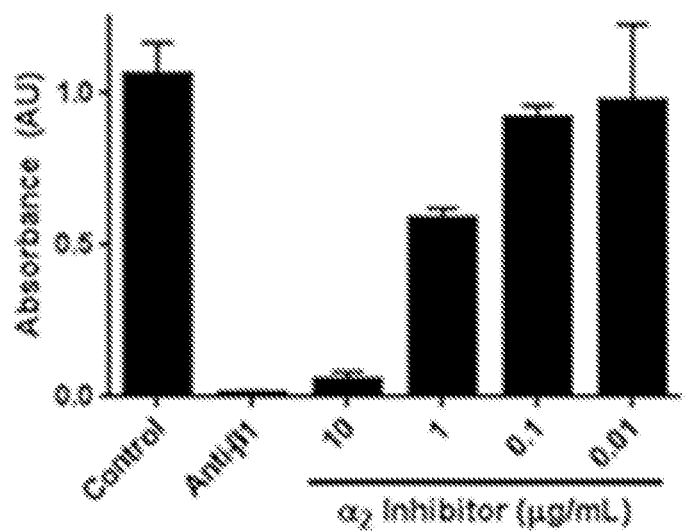
FIG. 1: Blockade of integrin α2β1 with C15 inhibits collagen-mediated adhesion (A, upper) and protects against IL-13 enhanced contraction in mouse tracheal rings (B, lower).
Figure 1:
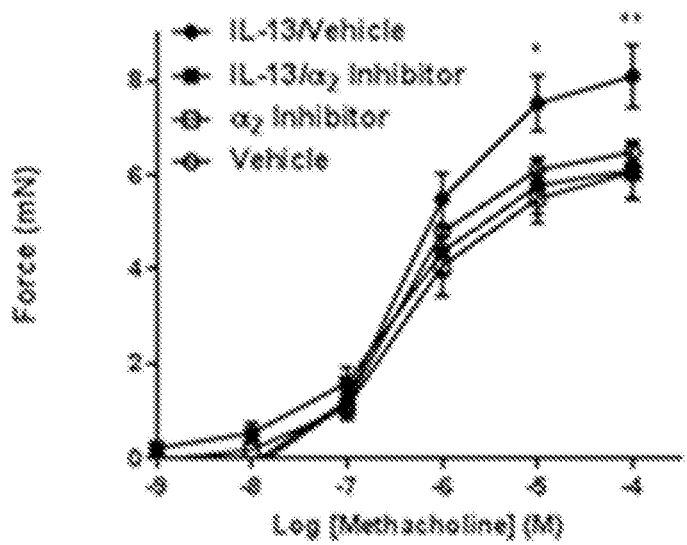

Integrins are present in nearly all multi-cellular organisms and play a conserved role in mediating cell adhesion to fixed extracellular ligands and in the maintenance of tissue integrity. In invertebrates, a surprisingly small number of integrin heterodimers mediate these diverse functions. Much has been learned about the critical in vivo functions of most members of the integrin family through the use of mice with global or conditional inactivating mutations of individual subunits and through the use of heterodimer-specific blocking monoclonal antibodies. Pharmacological modulation of the α2β1 integrin by compounds described herein may be used to treat asthma. Described herein are compounds and methods of use for α2β1 integrin inhibitors.

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $-CH_2O-$ is equivalent to $-OCH_2-$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker ($-O-$). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, $-CH_2CH_2CH_2CH_2-$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'-represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring.

The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

Spirocyclic rings are two or more rings wherein adjacent rings are attached through a single atom. The individual rings within spirocyclic rings may be identical or different.

Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

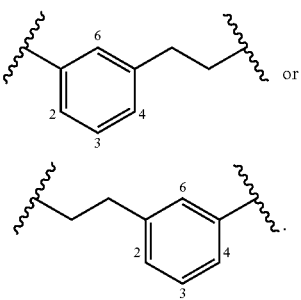

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$—NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O) NR'R", —NR"C(O)R', —NR'—C(O)NR"R'", —NR"C(O)$_2$R', —NR—C(NR'R"R'")=NR"", —NR—C(NR' R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, in a number ranging from zero to (2m'+1), where m' is the total number of carbon atoms in such radical. R, R', R"R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR'NR'"R"", —CN, —NO$_2$, —R', —N3, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R$^{11}$, R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:
(A) oxo, halogen, —CCl$_3$, —CBr$_3$, —CF$_3$, —CI$_{13}$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_{12}$, —OCH Br$_2$, —OCHI$_2$, —OCHF$_2$, —OCH$_2$C$_1$, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
(B) alkyl, heteroalkyl, cycloalkyl, heterocycloalkyl, aryl, heteroaryl, substituted with at least one substituent selected from:
(i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr3, —OCl3, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
(ii) alkyl, heteroalkyl, cycloalkyl, heterocycloalkyl, aryl, heteroaryl, substituted with at least one substituent selected from:
(a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —O CHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and
(b) alkyl, heteroalkyl, cycloalkyl, heterocycloalkyl, aryl, heteroaryl, substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O) H, —NHC(O)OH, —NHOH, —OCCL$_3$, —OCF$_3$, —OC Br$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_5$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group,"

wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_{10}$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkyl ene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted aryl ene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of sub stituent groups, each sub stituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted aryl ene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolysulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present disclosure contain both basic and acidic functionalities that allow the compounds to be converted into either base or acid addition salts. Other pharmaceutically acceptable carriers known to those of skill in the art are suitable for the present disclosure. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present disclosure may exist as salts, such as with pharmaceutically acceptable acids. The present disclosure includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject, in a cancer cell, in the extracellular space near a cancer cell).

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in the art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate reactive moiety" and "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., —NH$_2$, —COOH, —N-hydroxysuccinimide, or maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., sulfoN-hydroxysuccinimide moiety) is covalently attached to the second bioconjugate reactive group (e.g. an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc.;

(j) epoxides, which can react with, for example, amines and hydroxyl compounds;

(k) phosphoramidites and other standard functional groups useful in nucleic acid synthesis;

(l) metal silicon oxide bonding; and (m) metal bonding to reactive phosphorus groups (e.g. phosphines) to form, for example, phosphate diester bonds.

(n) azides coupled to alkynes using copper catalyzed cycloaddition click chemistry.

(o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

The symbol "〜〜" denotes the point of attachment of a chemical moiety to the remainder of a molecule or chemical formula.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

An "α2β1-inhibitor" or "α2β1 inhibitor" as used herein refers to a substance, agent, or composition (e.g. a compound, nucleic acid, polynucleotide, peptide, protein, or antibody) capable of reducing the activity of α2β1 integrin when compared to a control compound (e.g. known to have no reduction in α2β1 integrin activity) or the absence of the α2β1-inhibitor compound. An "α2β1-inhibitor compound" or "α2β1 inhibitor compound" refers to a compound (e.g. compound described herein) that reduce the activity of α2β1 integrin when compared to a control, such as absence of the compound or a compound with known inactivity. An "α2β1-inhibitor-antibody" or "α2β1 inhibitor-antibody" refers to an antibody that reduces the activity of α2β1 integrin when compared to a control (e.g. the absence of the antibody). An "α2β1-inhibitor-RGD peptide" or "α2β1 inhibitor-RGD peptide" refers to a RGD-peptide that reduces the activity of α2β1 integrin when compared to a control (e.g. the absence of the peptide).

"Specific," "specifically", "specificity", or the like of a composition (e.g. a compound, nucleic acid, polynucleotide, peptide, protein, or antibody) refers to the composition's ability to discriminate between particular molecular targets to a significantly greater extent than other proteins in the cell (e.g. a compound having specificity towards α2β1 integrin binds to α2β1 integrin whereas the same compound displays little-to-no binding to other integrins such as αvβ1, α8β1, α5β1, αvβ3, αvβ5, or αvβ6). An "α2β1-specific compound" or "α2β1 specific compound" refers to a compound (e.g. compounds described herein) having specificity towards α2β1 integrin. An "α2β1-specific antibody" or "α2β1 specific antibody" refers to an antibody having specificity towards α2β1 integrin. An "α2β1-specific RGD peptide" or "α2β1 specific RGD peptide" refers to a RGD peptide having specificity towards α2β1 integrin.

The terms "selective," or "selectivity" or the like of a compound refers to the composition's (e.g. a compound, nucleic acid, polynucleotide, peptide, protein, or antibody) ability to cause a particular action in a particular molecular target (e.g. a compound having selectivity toward α2β1 integrin would inhibit only α2β1. An "α2β1-selective compound" or "α2β1 selective compound" refers to a compound (e.g. compounds described herein) having selectivity towards α2β1 integrin. An "α2β1-selective antibody" or "α2β1 selective antibody" refers to an antibody having selectivity towards α2β1 integrin. An "α2β1-selective RGD peptide" or "α2β1 selective RGD peptide" refers to a RGD peptide having selectivity towards α2β1 integrin.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A polypeptide, or a cell is "recombinant" when it is artificial or engineered, or derived from or contains an artificial or engineered protein or nucleic acid (e.g. non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

"RGD peptide" as used herein refers to a tripeptide comprising Arg, Gly, and Asp. RGD peptides typically act as recognition sequences for integrins and in some embodiments, promote cellular adhesion via integrin binding. RGD peptides as used herein refers to naturally occurring RGD sequences, RGD mimetics (e.g. substitutions of R, G, or D with non-proteinogenic amino acids), RGD peptides covalently bound to a targeting-moiety (e.g. a molecule for targeting the peptide to a specific integrin or specific location in a cell or organism), and cyclized RGD peptides of embodiments described herein. Exemplary RGD peptides include Arg-Gly-Asp, Asp-Gly-Arg, cyclo-Gly-Arg-Gly-Asp-Ser-Pro, and KGD peptides include Cys-Asn-Thr-Leu-Lys-Gly-Asp-Cys and Asn-Thr-Leu-Lys-Gly-Asp, and those found in Ann. Rev. Cell & Dev. Biol., 1996, November, Vol. 12: 697-715 and Proteins, 1992 December; 14(4): 509-15.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of suitable antibodies of the invention and for use according to the invention, e.g., recombinant, monoclonal, or polyclonal antibodies, many techniques known in the art can be used (see, e.g., Kohler & Milstein, *Nature* 256:495-497 (1975); Kozbor et al., Immunology Today 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating" and the like in reference to a protein refers to conversion of a protein into a biologically active derivative from an initial inactive or deactivated state. The terms reference activation, or activating, sensitizing, or up-regulating signal transduction or enzymatic activity or the amount of a protein decreased in a disease.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition refers means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease is asthma. The disease may be airway hyperresponsiveness. The disease may be airway hyperresponsiveness in asthma. The disease may be angiogenesis. The disease may be an autoimmune disease (e.g., scleroderma, lupus, diabetes, or rheumatoid arthritis). The disease may be an inflammatory disease (e.g., autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, scleroderma, or atopic dermatitis).

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, scleroderma, and atopic dermatitis.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses.

Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms (e.g. symptoms of asthma). Determination of a therapeutically effective amount of a compound of the invention is well within the capabilities of those skilled in the art, especially in light of the detailed disclosure herein.

As used herein "asthma" refers to any disease or condition characterized by inflammation within the circulatory system, often accompanied with wheezing, airway restriction, shortness of breath, chest tightness, and coughing. In embodiments, asthma is characterized by airway hyperresponsiveness. In embodiments, asthma is airway hyperresponsiveness. Asthma may refer inflammation in the bronchi and bronchioles. Asthma may refer to atopic asthma. Asthma may refer to non-atopic asthma.

The compounds described herein (e.g., compound wherein $R^3$ is not hydrogen) may be prodrugs. The term "prodrug" when referring to a prodrug described herein (e.g. α2β1-inhibitor compound moiety bonded to a prodrug moiety) refers to the compound including the α2β1-inhibitor compound moiety and the prodrug moiety. A "prodrug moiety" is the portion of a prodrug that may be cleaved from the prodrug resulting in an increased activity of the non-prodrug moiety portion of the prodrug, for example an α2β1-inhibitor compound having increased α2β1-inhibitor activity relative to the prodrug of the α2β1-inhibitor compound. In embodiments, the compounds described herein are prodrugs, wherein the prodrug moiety is the component of the compound that is not an α2β1-inhibitor compound moiety and is released from the α2β1-inhibitor compound moiety upon degradation of the prodrug.

In embodiments, degradation of the prodrug includes cleavage of —$OR^3$, wherein $R^3$ is not hydrogen. In embodiments, degradation of the prodrug includes cleavage of $R^3$, wherein $R^3$ is not hydrogen. In embodiments, an α2β1-inhibitor compound is a compound described herein wherein $R^3$ is hydrogen and a prodrug of the α2β1-inhibitor compound is the identical compound except $R^3$ is not a hydrogen. A person having ordinary skill in the art would understand that the α2β1-inhibitor compound moiety includes only those compounds compatible with the chemistry provided herein for connecting the α2β1-inhibitor compound moiety to the prodrug moiety and for release of the α2β1-inhibitor compound from the compound (prodrug) (e.g., in vivo). In embodiments, degradation of the prodrug releases an active agent (e.g., α2β1-inhibitor compound). In such compounds, the resulting active agent includes a higher level of activity compared to the level of activity of the intact prodrug. In embodiments, degradation of the prodrug includes cleavage of —$OR^3$, wherein $R^3$ is not hydrogen, by an esterase or amidase and replacement of —$OR^3$ with —OH or the corresponding anionic moiety.

Integrins are transmembrane proteins that mediate interactions between adhesion molecules on adjacent cells and/or the extracellular matrix (ECM). Integrins have diverse roles in several biological processes including, for example, cell migration during development and wound healing, cell differentiation, and apoptosis. Integrins typically exist as heterodimers consisting of a subunits (about 120-170 kDa in size) and β subunits (about 90-100 kDa in size).

The terms "α2β1" and "α2β1 integrin" refer to an integrin comprised of α2 subunit and a β1 subunit and is used according to its common, ordinary meaning. "α2β1" refers to proteins of the same or similar names, homologs, isoforms, and functional fragments thereof, so long as such fragments retain α2β1 integrin activity. The term includes any recombinant or naturally-occurring form of α2β1, or an α2β1 preprotein, or variants thereof that maintain α2β1 activity (e.g. within at least 30%, 40%, 50%, 60%, 70%, 80%, 90%, 95%, or 100% activity compared to wildtype α2β1). In embodiments, α2 has the protein sequence corresponding to RefSeq NP_002194.2. In embodiments, α2 has the protein sequence corresponding to the proteolytically processed mature version of RefSeq NP_002194.2. In embodiments, α2 has the amino acid sequence corresponding to nucleic acid sequence of the reference number NM_002203.3. In embodiments, β1 has the protein sequence corresponding to RefSeq NP_002202.2 In embodiments, β1 has the amino acid sequence corresponding to the reference number GI: 19743813.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

"Conservatively modified variants" applies to both amino acid and nucleic acid sequences. With respect to particular nucleic acid sequences, "conservatively modified variants" refers to those nucleic acids that encode identical or essentially identical amino acid sequences. Because of the degeneracy of the genetic code, a number of nucleic acid sequences will encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

The term "amino acid side chain" refers to the functional substituent contained on amino acids. For example, an amino acid side chain may be the side chain of a naturally occurring amino acid. Naturally occurring amino acids are those encoded by the genetic code (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, γ-carboxyglutamate, and O-phosphoserine. In embodiments, the amino acid side chain may be a non-natural amino acid side chain. In embodiments, the amino acid side chain is H,

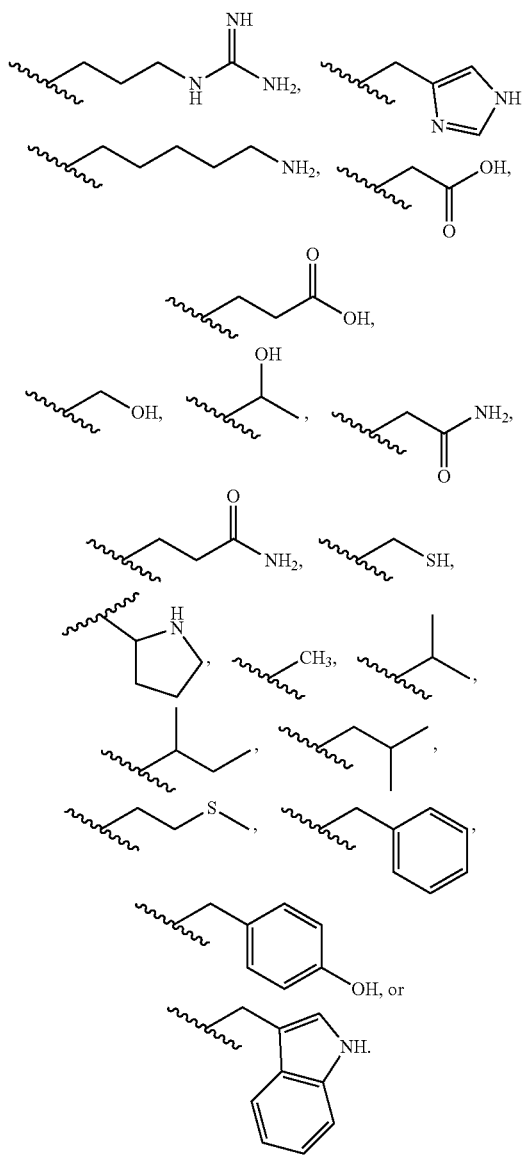

The term "non-natural amino acid side chain" refers to the functional substituent of compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium, allylalanine, 2-aminoisobutryric acid. Non-natural amino acids are non-proteinogenic amino acids that either occur naturally or are chemically synthesized. Such analogs have modified R groups (e.g., norleucine) or modified peptide backbones, but retain the same basic chemical structure as a naturally occurring amino acid. Non-limiting examples include exo-cis-3-Aminobicyclo[2.2.1]hept-5-ene-2-carboxylic acid hydrochloride, cis-2-Aminocycloheptanecarboxylic acid hydrochloride, cis-6-Amino-3-cyclohexene-1-carboxylic acid hydrochloride, cis-2-Amino-2-methylcyclohexanecarboxylic acid hydrochloride, cis-2-Amino-2-methylcyclopentanecarboxylic acid hydrochloride, 2-(Boc-aminomethyl)benzoic acid, 2-(Boc-amino)octanedioic acid, Boc-4,5-dehydro-Leu-OH (dicyclohexylammonium), Boc-4-(Fmoc-amino)-L-phenylalanine, Boc-β-Homopyr-OH, Boc-(2-indanyl)-Gly-OH, 4-Boc-3-morpholineacetic acid, 4-Boc-3-morpholineacetic acid, Boc-pentafluoro-D-phenylalanine, Boc-pentafluoro-L-phenylalanine, Boc-Phe(2-Br)-OH, Boc-Phe(4-Br)—OH, Boc-D-Phe(4-Br)—OH, Boc-D-Phe(3-Cl)—OH, Boc-Phe(4-NH2)-OH, Boc-Phe(3-NO2)-OH, Boc-Phe(3,5-F2)-0H, 2-(4-Boc-piperazino)-2-(3,4-dimethoxyphenyl)acetic acid purum, 2-(4-Boc-piperazino)-2-(2-fluorophenyl)acetic acid purum, 2-(4-Boc-piperazino)-2-(3-fluorophenyl)acetic acid purum, 2-(4-Boc-piperazino)-2-(4-fluorophenyl)acetic acid purum, 2-(4-Boc-piperazino)-2-(4-methoxyphenyl)acetic acid purum, 2-(4-Boc-piperazino)-2-phenylacetic acid purum, 2-(4-Boc-piperazino)-2-(3-pyridyl)acetic acid purum, 2-(4-Boc-piperazino)-2-[4-(trifluoromethyl)phenyl] acetic acid purum, Bocβ-(2-quinolyl)-Ala-OH, N-Boc-1,2,3,6-tetrahydro-2-pyridinecarboxylic acid, Bocβ-(4-thiazolyl)-Ala-OH, Boc-β-(2-thienyl)-D-Ala-OH, Fmoc-N-(4-Boc-aminobutyl)-Gly-OH, Fmoc-N-(2-Boc-aminoethyl)-Gly-OH, Fmoc-N-(2,4-dimethoxybenzyl)-Gly-OH, Fmoc-(2-indanyl)-Gly-OH, Fmoc-pentafluoro-L-phenylalanine, Fmoc-Pen(Trt)-OH, Fmoc-Phe(2-Br)—OH, Fmoc-Phe(4-Br)—OH, Fmoc-Phe(3,5-F2)-OH, Fmoc-β-(4-thiazolyl)-Ala-OH, Fmoc-β-(2-thienyl)-Ala-OH, 4-(Hydroxymethyl)-D-phenylalanine.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine.; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, Asc Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

Nucleic acids can include nonspecific sequences. As used herein, the term "nonspecific sequence" refers to a nucleic acid sequence that contains a series of residues that are not designed to be complementary to or are only partially complementary to any other nucleic acid sequence. By way of example, a nonspecific nucleic acid sequence is a sequence of nucleic acid residues that does not function as an inhibitory nucleic acid when contacted with a cell or organism.

An "antisense nucleic acid" as referred to herein is a nucleic acid (e.g., DNA or RNA molecule) that is complementary to at least a portion of a specific target nucleic acid (e.g., α2 or (β1 or both) and is capable of reducing transcription of the target nucleic acid (e.g. mRNA from DNA), reducing the translation of the target nucleic acid (e.g. mRNA), altering transcript splicing (e.g. single stranded morpholino oligo), or interfering with the endogenous activity of the target nucleic acid. See, e.g., Weintraub, *Scientific American*, 262:40 (1990). Typically, synthetic antisense nucleic acids (e.g. oligonucleotides) are generally between 15 and 25 bases in length. Thus, antisense nucleic acids are capable of hybridizing to (e.g. selectively hybridizing to) a target nucleic acid (e.g., α2 or β31 or both). In embodiments, the antisense nucleic acid hybridizes to the target nucleic acid (e.g. α2 or β1 or both) in vitro. In embodiments, the antisense nucleic acid hybridizes to the target nucleic acid (e.g. α2 or β1 or both) in a cell. In embodiments, the antisense nucleic acid hybridizes to the target nucleic acid (e.g. α2 or β1 or both) in an organism. In embodiments, the antisense nucleic acid hybridizes to the target nucleic acid (e.g. α2 or β1 or both) under physiological conditions. Antisense nucleic acids may comprise naturally occurring nucleotides or modified nucleotides such as, e.g., phosphorothioate, methylphosphonate, and -anomeric sugar-phosphate, backbone modified nucleotides.

In the cell, the antisense nucleic acids hybridize to the corresponding RNA (e.g., α2 RNA or β1 RNA or both) forming a double-stranded molecule. The antisense nucleic acids interfere with the endogenous behavior of the RNA (e.g., α2 RNA or β1 RNA or both) and inhibit its function relative to the absence of the antisense nucleic acid. Furthermore, the double-stranded molecule may be degraded via the RNAi pathway. The use of antisense methods to inhibit the in vitro translation of genes is well known in the art (Marcus-Sakura, *Anal. Biochem.*, 172:289, (1988)). Further, antisense molecules which bind directly to the DNA may be used. Antisense nucleic acids may be single or double stranded nucleic acids. Non-limiting examples of antisense nucleic acids include siRNAs (including their derivatives or pre-cursors, such as nucleotide analogs), short hairpin RNAs (shRNA), micro RNAs (miRNA), saRNAs (small activating RNAs) and small nucleolar RNAs (snoRNA) or certain of their derivatives or pre-cursors.

The term "complement," as used herein, refers to a nucleotide (e.g., RNA or DNA) or a sequence of nucleotides capable of base pairing with a complementary nucleotide or sequence of nucleotides. As described herein and commonly known in the art the complementary (matching) nucleotide of adenosine is thymidine and the complementary (matching) nucleotide of guanidine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and a non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence.

As described herein the complementarity of sequences may be partial, in which only some of the nucleic acids match according to base pairing, or complete, where all the nucleic acids match according to base pairing. Thus, two sequences that are complementary to each other, may have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region).

II. Compounds

In an aspect is provided a compound, or a pharmaceutically acceptable thereof, having the formula:

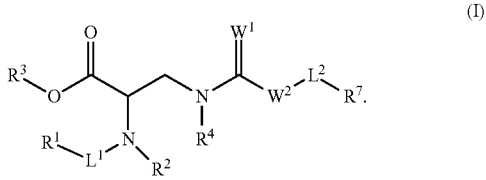

(I)

$R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$L^1$ is a bond or —C(O)—.

$R^2$ is hydrogen or substituted or unsubstituted alkyl.

$R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —NHC(O)$NR^{3A}R^{3B}$, —$N(O)_{m3}$, —$NR^{3A}R^{3B}$, —C(O)$R^{3C}$, —C(O)O$R^{3C}$, —C(O)$NR^{3A}R^{3B}$, —$OR^{3D}$, —$NR^{3A}SO_2R^{3D}$, —$NR^{3A}C(O)R^{3C}$, —$NR^{3A}C(O)O$ $R^{3C}$, —$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

$R^4$ is hydrogen or substituted or unsubstituted alkyl.

$W^1$ is O, S, or $NR^8$.

$W^2$ is O, S, or $NR^5$.

$R^5$ is hydrogen or substituted or unsubstituted alkyl.

$L^2$ is a bond or —C($R^6$)$_2$—.

$R^6$ is hydrogen, =NH, substituted or unsubstituted alkyl, or substituted or unsubstituted heteroalkyl. It will be understood that when $R^6$ is =NH, then $L^2$ is —C(=NH)—, in order to satisfy the proper valency requirements for all atoms and could also be described as two $R^6$ groups combining to form a single =NH. For the purposes of optionally joining $W^1$ and $R^6$, it will be understood that when $R^6$ is =NH, $W^1$ and $R^6$ may be joined to form a 5 to 6 membered heterocycloalkyl, or substituted or unsubstituted 5 to 6 membered heteroaryl, which includes the =N— in place of $R^6$ resulting 5 to 6 membered heterocycloalkyl, or substituted or unsubstituted 5 to 6 membered heteroaryl. In embodiments, $L^2$ is C(=$R^6$)— when $R^6$ is =NH.

$W^1$ and $R^6$ may optionally be joined to form a substituted or unsubstituted 5 to 6 membered heterocycloalkyl, or substituted or unsubstituted 5 to 6 membered heteroaryl.

$R^7$ is hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}NR^{7A}R^{7B}$, —NHC(O)$NR^{7A}R^{7B}$, —$N(O)_{m7}$, —$NR^{7A}R^{7B}$, —C(O)$R^{7C}$, —C(O)—$OR^{7C}$, —C(O)$NR^{7A}R^{7B}$, —$OR^{7D}$, —$NR^{7A}SO_2R^{7D}$, —$NR^{7A}C(O)R^{7C}$, —$NR^{7A}C(O)O$ $R^{7C}$, —$NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

$R^8$ is hydrogen or substituted or unsubstituted alkyl.

$R^{3A}$, $R_{3B}$, $R^{3C}$, $R^{3D}$, $R^{7A}$, $R^{7B}$, $R^{7C}$, and $R^{7D}$ are independently hydrogen, —$CX_3$, —CN, —COOH, —$CONH_2$, —$CHX_2$, —$CH_2X$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl)

$R^{3A}$ and $R^{3B}$ substituents bonded to the same nitrogen atom may optionally be joined to form a substituted or unsubstituted heterocycloalkyl or substituted or unsubstituted heteroaryl.

$R^{7A}$ and $R^{7B}$ substituents bonded to the same nitrogen atom may optionally be joined to form a substituted or unsubstituted heterocycloalkyl or substituted or unsubstituted heteroaryl.

Each X, $X^3$, and $X^7$ are independently —F, —Cl, –Br, or —I.

n3 and n7 are independently an integer from 0 to 4.

m3, m7, v3 and v7 are independently 1 or 2.

In embodiments, the compound has the formula:

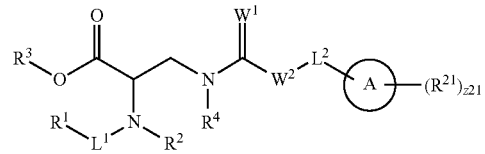

Ring A is cycloalkyl, heterocycloalkyl, aryl, or heteroaryl.

$R^{21}$ is independently halogen, —$CX^{21}_3$, —$CHX^{21}_2$, —$CH_2X^{21}$, —$OCX^{21}_3$, —$OCH_2X^{21}$, —$OCHX^{21}_2$, —CN, —$SO_{v21}R^{21D}$, —$SO_{v21}NR^{21A}R^{21B}$, —NHC(O)$NR^{21A}R^{21B}$, —$N(O)_{m21}$, —$NR^{21A}R^{21B}$, —C(O)$R^{21C}$, —C(O)—$OR^{21C}$, —C(O)$NR^{21A}R^{21B}$, —$OR^{21D}$, —$NR^{21A}SO_2R^{21D}$, —$NR^{21A}C(O)R^{21C}$, —$NR^{21A}C(O)OR^{21C}$, —$NR^{21A}OR^{21C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

Two adjacent $R^{21}$ substituents may optionally be joined to form a substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, two adjacent $R^{21}$ substituents are joined to form an $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22}$-substituted or unsubstituted aryl (e.g., $C_6$-$C_{10}$ aryl, $C_{10}$ aryl, or phenyl), or $R^{22}$-substituted or unsubstituted heteroaryl (e.g., 5 to 10 membered heteroaryl, 5 to 9 membered heteroaryl, or 5 to 6 membered heteroaryl). In embodiments, two adjacent $R^{21}$ substituents are joined to form an $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, two adjacent $R^{21}$ substituents are joined to form an $R^{22}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, two adjacent R$^{22}$ substituents are joined to form an R$^{22}$-substituted or unsubstituted aryl (e.g., C$_6$-C$_{10}$ aryl, C$_{10}$ aryl, or phenyl). In embodiments, two adjacent R$^{21}$ substituents are joined to form an R$^{22}$-substituted or unsubstituted heteroaryl (e.g., 5 to 10 membered heteroaryl, 5 to 9 membered heteroaryl, or 5 to 6 membered heteroaryl).

z21 is an integer from 0 to 5.

R$^{21A}$, R$^{21B}$, R$^{21C}$, and R$^{21D}$ are independently hydrogen, —CX$_3$, —CN, —COOH, —CONH$_2$, —CHX$_2$, —CH$_2$X, substituted or unsubstituted alkyl (e.g., C$_1$-C$_8$ alkyl, C$_1$-C$_6$ alkyl, or C$_1$-C$_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., C$_3$-C$_8$ cycloalkyl, C$_3$-C$_6$ cycloalkyl, or C$_5$-C$_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., C$_6$-C$_{10}$ aryl, C$_{10}$ aryl, or phenyl), or substituted or unsubstituted heteroaryl (e.g., 5 to 10 membered heteroaryl, 5 to 9 membered heteroaryl, or 5 to 6 membered heteroaryl).

R$^{21A}$ and R$^{21B}$ substituents bonded to the same nitrogen atom may optionally be joined to form a substituted or unsubstituted heterocycloalkyl (e.g., 3 to 8 membered heterocycloalkyl, 3 to 6 membered heterocycloalkyl, or 5 to 6 membered heterocycloalkyl) or substituted or unsubstituted heteroaryl (e.g., 5 to 10 membered heteroaryl, 5 to 9 membered heteroaryl, or 5 to 6 membered heteroaryl).

Each X$^{21}$ is independently —F, —Cl, —Br, or —I.

n21 is independently an integer from 0 to 4.

m21 and v21 are independently 1 or 2.

In embodiments, R$^1$ is unsubstituted C$_1$-C$_6$ alkyl.

In embodiments, R$^1$ is

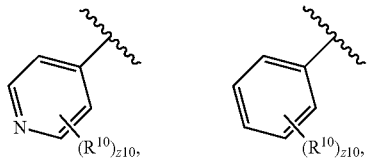

or substituted or unsubstituted C$_4$-C$_8$ alkyl.

R$^{10}$ is independently halogen, —CX$^{10}_3$, —CHX$^{10}_2$, —CH$_2$X$^{10}$, —OCX$^{10}_3$, —OCH$_2$X$^{10}$, —OCHX$^{10}_2$, —CN, —SO$_{n10}$R$^{10D}$, —SO$_{v10}$NR$^{10A}$R$^{10B}$, —NHC(O)NR$^{10A}$R$^{10B}$, —N(O)$_{m10}$, —NR$^{10A}$R$^{10B}$, —C(O)R$^{10C}$, —C(O)—OR$^{10C}$, —C(O)NR$^{10A}$R$_{10B}$, —OR$^{10D}$, —NR$^{10A}$SO$_2$R$_{10D}$, —NR$^{10A}$C(O)R$^{10C}$, —NR$^{10A}$C(O)OR$^{10C}$, —NR$^{10A}$OR$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Two adjacent R$^{10}$ substituents may optionally be joined to form a substituted or unsubstituted cycloalkyl, substituted or unsubstituted heterocycloalkyl, substituted or unsubstituted aryl, or substituted or unsubstituted heteroaryl.

R$^{10A}$, R$^{10B}$, R$^{10C}$, and R$^{10D}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10A}$ and R$^{10B}$ substituents bonded to the same nitrogen atom may optionally be joined to form a substituted or unsubstituted heterocycloalkyl or substituted or unsubstituted heteroaryl;

X$^{10}$ is independently —F, —Cl, —Br, or —I.

n10 is independently an integer from 0 to 4.

m10 and v10 are independently 1 or 2.

z10 is an integer from 0 to 5.

In embodiments, R$^1$ is substituted or unsubstituted alkyl, substituted or unsubstituted heteroalkyl, substituted or unsubstituted aryl, or substituted or unsubstituted heteroaryl.

In embodiments, R$^1$ is

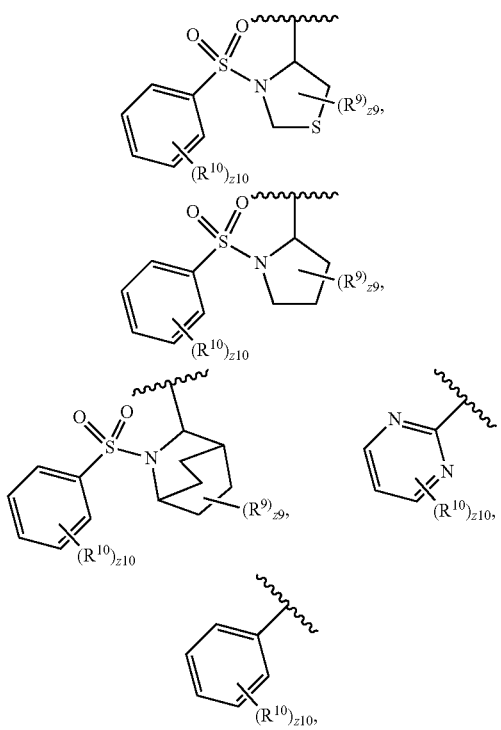

or substituted or unsubstituted C$_4$-C$_8$ alkyl.

R$^9$ is independently halogen, —CX$^9_3$, —CHX$^9_2$, —CH$_2$X$^9$, —OCX$^9_3$, —OCH$_2$X$^9$, —OCHX$^9_2$, —CN, —SO$_{n9}$R$^{9D}$, —SO$_{v9}$NR$^{9A}$R$^{9B}$, —NHC(O)NR$^{9A}$R$^{9B}$, —N(O)$_{m9}$, —NR$^{9A}$R$^{9B}$, —C(O)R$^{9C}$, —C(O)—OR$^{9C}$, —C(O)NR$^{9A}$R$^{9B}$, —OR$^{9D}$, —NR$^{9A}$SO$_2$R$^{9D}$, —NR$^{9A}$C(O) R$^{9C}$, —NR$^{9A}$C(O)O R$^{9C}$, —NR$^{9A}$OR$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, or a detectable moiety; two adjacent R$^9$ substituents may optionally be joined to form a substituted or unsubstituted cycloalkyl, substituted or unsubstituted heterocycloalkyl, substituted or unsubstituted aryl, or substituted or unsubstituted heteroaryl.

Each R$^{9A}$, R$^{9B}$, R$^{9C}$, R$^{9D}$ is independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{9A}$ and R$^{9B}$ substituents bonded to the same nitrogen atom may optionally be joined to form a substituted or unsubstituted heterocycloalkyl or substituted or unsubstituted heteroaryl.

Each X$^9$ is independently —F, —Cl, —Br, or —I.

n9 is independently an integer from 0 to 4.

m9 and v9 are independently 1 or 2.

z9 is an integer from 0 to 5.

In embodiments, R¹ is
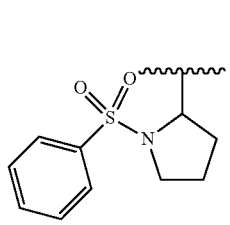 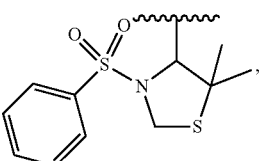
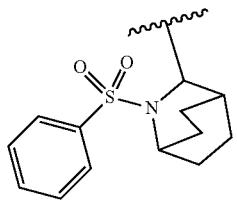 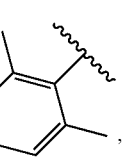 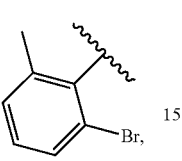
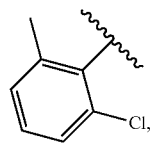 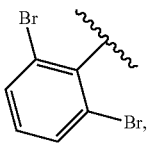 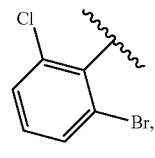 or
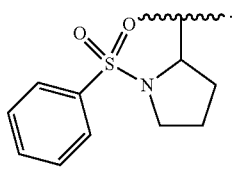 [SMILES: *C1CCCN1S(=O)(=O)c1ccccc1]
In embodiments, R¹ is
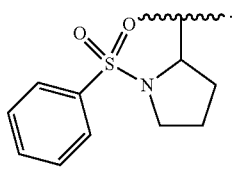 [SMILES: *C1CCCN1S(=O)(=O)c1ccccc1]
In embodiments, R¹ is
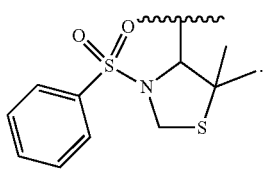 [SMILES: *C1N(S(=O)(=O)c2ccccc2)CSC1(C)C]
In embodiments, R¹ is
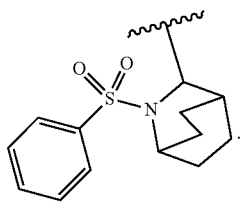 [SMILES: *C1C2CCC(CC2)N1S(=O)(=O)c1ccccc1]
In embodiments, R¹ is
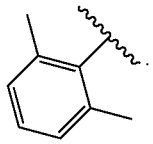 [SMILES: *c1c(C)cccc1C]
In embodiments, R¹ is
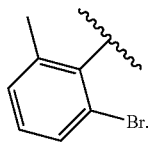 [SMILES: *c1c(C)cccc1Br]
In embodiments, R¹ is
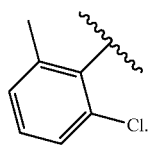 [SMILES: *c1c(C)cccc1Cl]
In embodiments, R¹ is
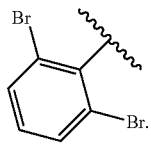
In embodiments, R¹ is
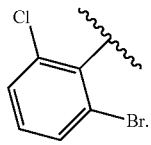 [SMILES: *c1c(Cl)cccc1Br]
In embodiments, R¹ is
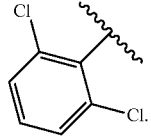 [SMILES: *c1c(Cl)cccc1Cl]
In embodiments, $R^{10}$ is
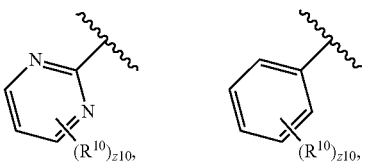
or substituted or unsubstituted $C_4$-$C_8$ alkyl. In embodiments, R¹ is
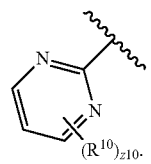

In embodiments, R¹ is

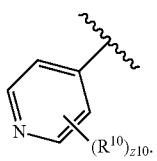

In embodiments, R¹ is

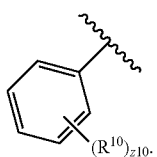

In embodiments, R¹ is substituted or unsubstituted $C_4$-$C_8$ alkyl. In embodiments, R¹ is unsubstituted $C_4$-$C_8$ alkyl. In embodiments, R¹ is unsubstituted $C_5$ alkyl.

In embodiments, R¹ is

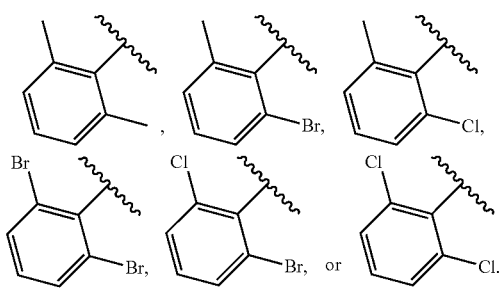

In embodiments, R¹ is

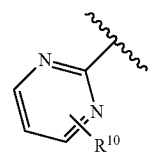

wherein $R^{10}$ is independently substituted or unsubstituted heterocycloalkyl or substituted or unsubstituted heteroaryl,

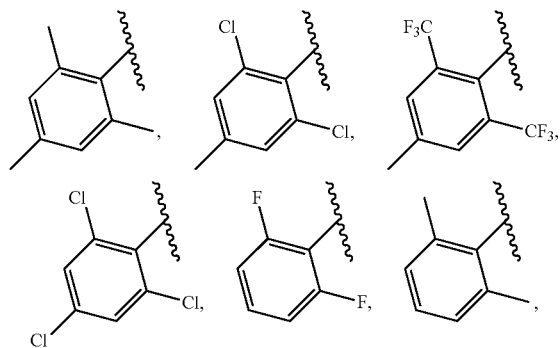

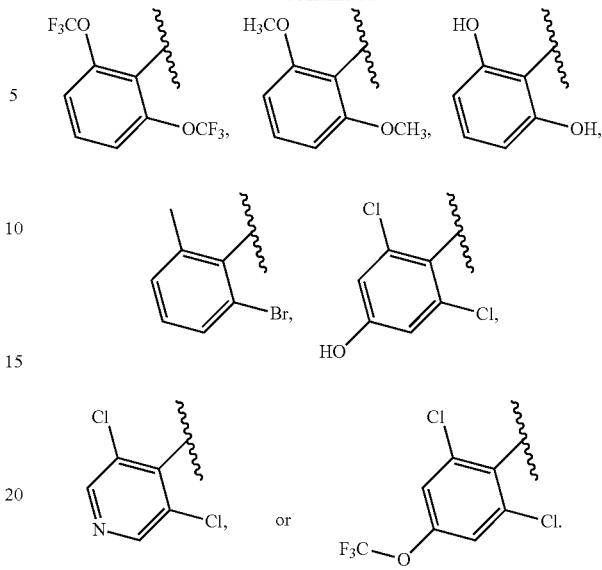

In embodiments, R¹ is

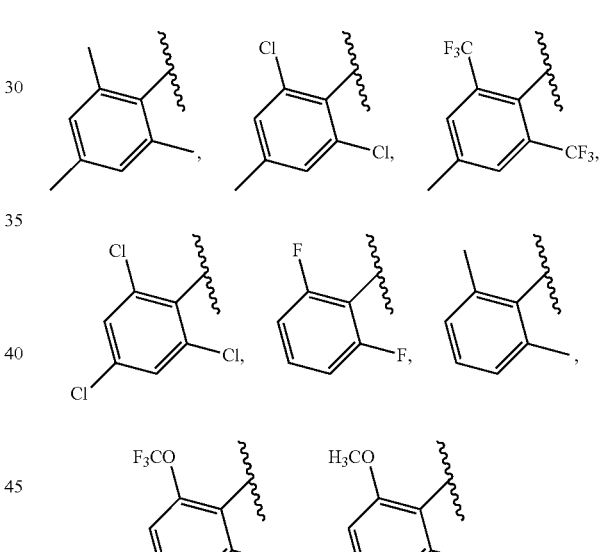

In embodiments, R¹ is

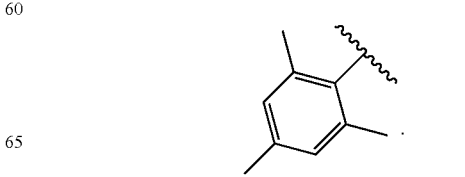

In embodiments, R¹ is
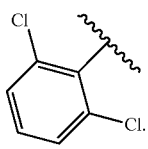 [SMILES: *c1c(Cl)cccc1Cl]
In embodiments, R¹ is
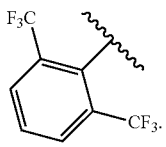
In embodiments, R¹ is
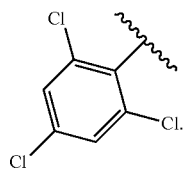 [SMILES: *c1c(Cl)cc(Cl)cc1Cl]
In embodiments, R¹ is
In embodiments, R¹ is
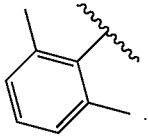 [SMILES: *c1c(C)cccc1C]
In embodiments, R¹ is
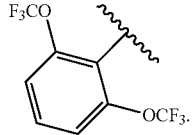
In embodiments, R¹ is
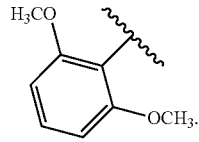
In embodiments, R¹ is
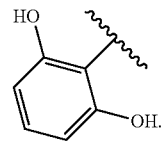
In embodiments, R¹ is
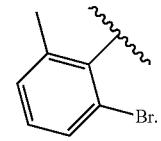 [SMILES: *c1c(C)cccc1Br]
In embodiments, R¹ is
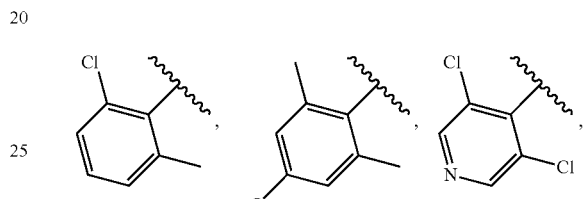
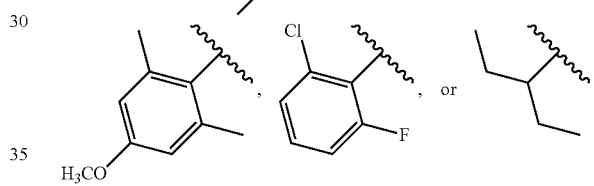
In embodiments, R¹ is
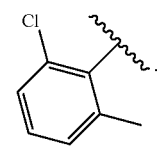 [SMILES: *c1c(C)cccc1Cl]
In embodiments, R¹ is
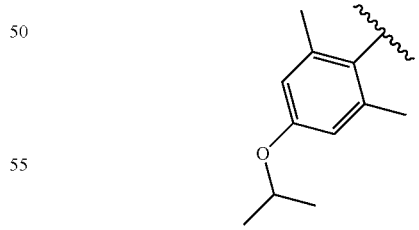
In embodiments, R¹ is
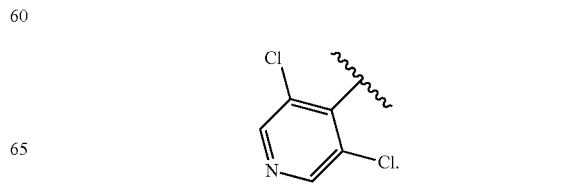

In embodiments, R$^1$ is

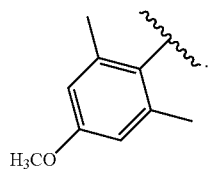

In embodiments, R$^1$ is

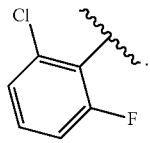

In embodiments, R$^1$ is

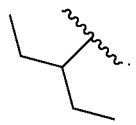

In embodiments, R$^1$ is

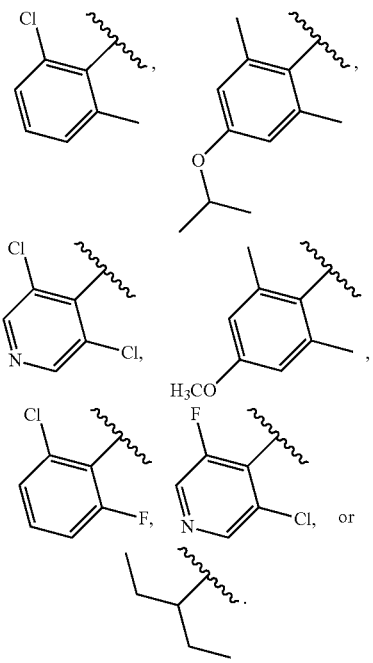

embodiments R$^1$ is

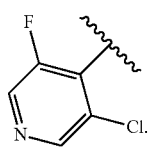 [SMILES: *c1c(F)cccc1Cl]

In embodiments, R$^1$ is substituted or unsubstituted cycloalkyl. In embodiments, R$^1$ is substituted cycloalkyl. In embodiments, R$^1$ is unsubstituted cycloalkyl. In embodiments, R$^1$ is substituted or unsubstituted cyclohexyl. In embodiments, R$^1$ is substituted cyclohexyl. In embodiments, R$^1$ is methyl substituted cyclohexyl. In embodiments, R$^1$ is unsubstituted cyclohexyl. In embodiments, R$^1$ is substituted or unsubstituted adamantyl. In embodiments, R$^1$ is substituted adamantyl. In embodiments, R$^1$ is unsubstituted adamantyl.

In embodiments, R$^1$ is

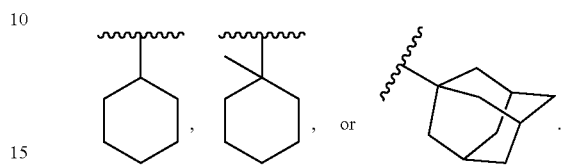

In embodiments, R$^1$ is

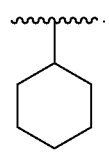

In embodiments, R$^1$ is

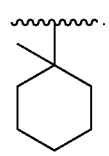

In embodiments, R$^1$ is

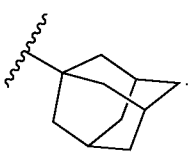 [SMILES: *C12CC3CC(CC(C3)C1)C2]

In embodiments, R$^1$ is

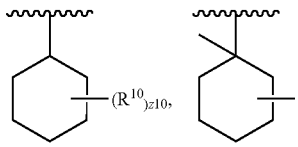

In embodiments, R$^1$ is

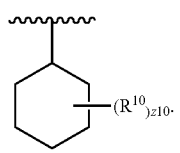

In embodiments, $R^1$ is

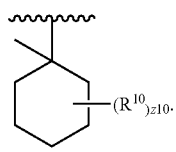

In embodiments, $R^1$ is

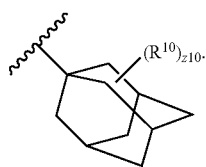

In embodiments, $R^1$ is

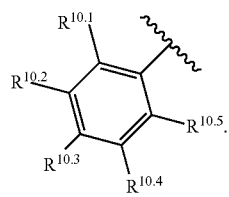

In embodiments, $R^1$ is

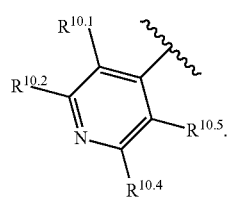

$R^{10.1}$, $R^{10.2}$, $R^{10.3}$, $R^{10.4}$, and $R^{10.5}$ are independently hydrogen or a value of $R^{10}$ as described herein, including in an embodiment.

In embodiments, $R^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl. In embodiments, $R^3$ is substituted or unsubstituted $C_1$-$C_6$ alkyl. In embodiments, $R^3$ is hydrogen. In embodiments, $R^3$ is hydrogen or substituted or unsubstituted alkyl. In embodiments, $R^3$ is a moiety that when combined with the attached —OC(O)— of the compounds described herein forms a prodrug moiety (e.g., moiety —C(O)OR$^3$ is a substrate for an esterase or amidase (e.g., in an organism) that may be catalyzed by the enzyme to form C(O)OH).

In embodiments, $L^2$ is C(R$^6$)$_2$—.

In embodiments, $L^2$ is a bond or —CHR$^6$—. In embodiments, $L^2$ is —CHR$^6$—. In embodiments, $L^2$ is a bond. In embodiments, $L^2$ is —C(CH$_3$)$_2$—. In embodiments, $L^2$ is —C(=NH)—.

In embodiments, $R^6$ is unsubstituted alkyl. In embodiments, $R^6$ is hydrogen. In embodiments, $R^6$ is oxo-substituted alkyl. In embodiments, $R^6$ is =NH.

In embodiments, $R^7$ is unsubstituted $C_1$-$C_6$ alkyl. In embodiments, $R^7$ is unsubstituted alkyl, substituted or unsubstituted cycloalkyl, substituted or unsubstituted heterocycloalkyl, substituted or unsubstituted aryl, or substituted or unsubstituted heteroaryl.

In embodiments, $W^2$ is NH. In embodiments, $W^2$ is S. In embodiments, $W^2$ is O. In embodiments, $W^2$ is NR$^5$. In embodiments, $R^5$ is hydrogen.

In embodiments, $W^1$ is O. In embodiments, $W^1$ is S. In embodiments, $W^1$ is NH. In embodiments, $W^1$ is NR$^8$. In embodiments, $R^8$ is hydrogen.

In embodiments, $W^1$ and $R^6$ are joined to form a substituted or unsubstituted 5 to 6 membered heterocycloalkyl or substituted or unsubstituted 5 to 6 membered heteroaryl.

In embodiments, $W^1$ and $R^6$ are joined to form a substituted or unsubstituted 5 to 6 membered heteroaryl.

In embodiments, $W^1$ and $R^6$ are joined to form

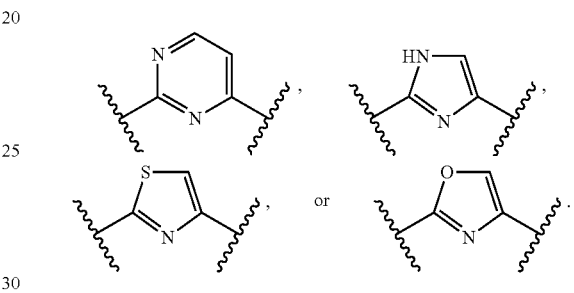

In embodiments, $W^1$ and $R^6$ are joined to form

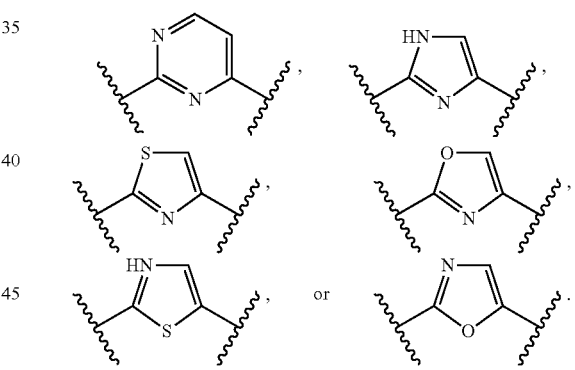

In embodiments, $W^1$ and $R^6$ are joined to form

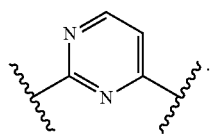 [SMILES: *c1ccnc(*)n1]

In embodiments, $W^1$ and $R^6$ are joined to form

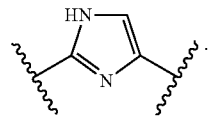 [SMILES: *c1c[nH]c(*)n1]

In embodiments, $W^1$ and $R^6$ are joined to form

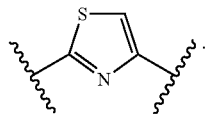 [SMILES: *c1csc(*)n1]

In embodiments, $W^1$ and $R^6$ are joined to form

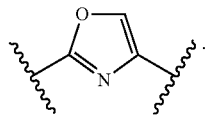 [SMILES: *c1coc(*)n1]

In embodiments, $W^1$ and $R^6$ are joined to form

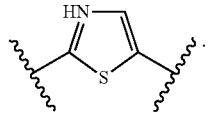 [SMILES: *c1cnc(*)s1]

In embodiments, $W^1$ and $R^6$ are joined to form

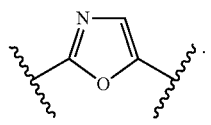 [SMILES: *c1cnc(*)o1]

In embodiments, $W^1$ and $R^6$ are joined to

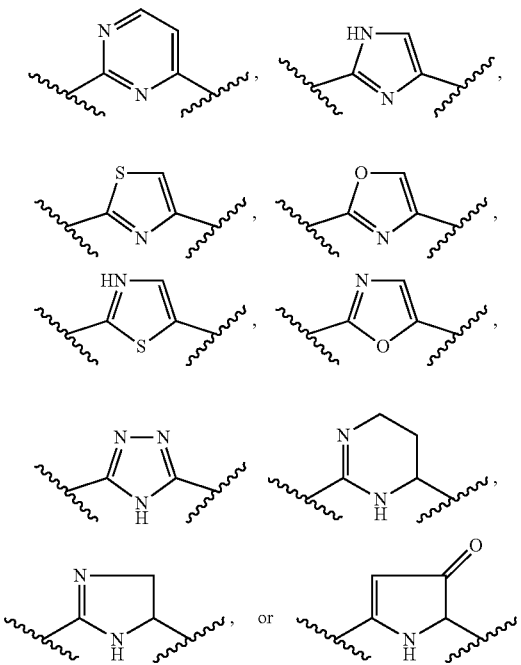

In embodiments, $W^1$ and $R^6$ are joined to form

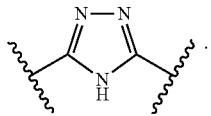 [SMILES: *c1nnc(*)[nH]1]

In embodiments, $W^1$ and $R^6$ are joined to form

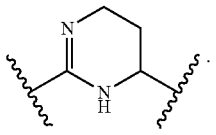 [SMILES: *C1=NCCC(*)N1]

In embodiments, $W^1$ and $R^6$ are joined to form

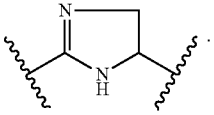 [SMILES: *C1=NCC(*)N1]

In embodiments, $W^1$ and $R^6$ are joined to form

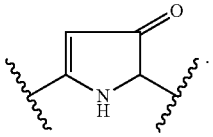 [SMILES: *C1=CC(=O)C(*)N1]

In embodiments,

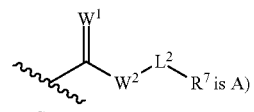

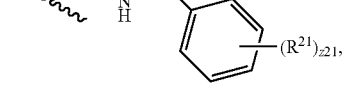

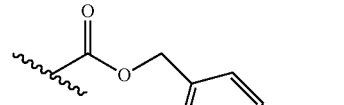

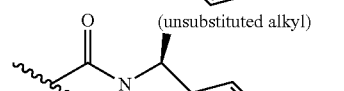

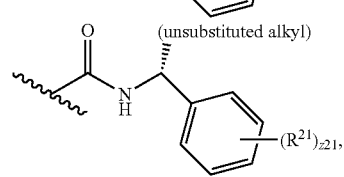

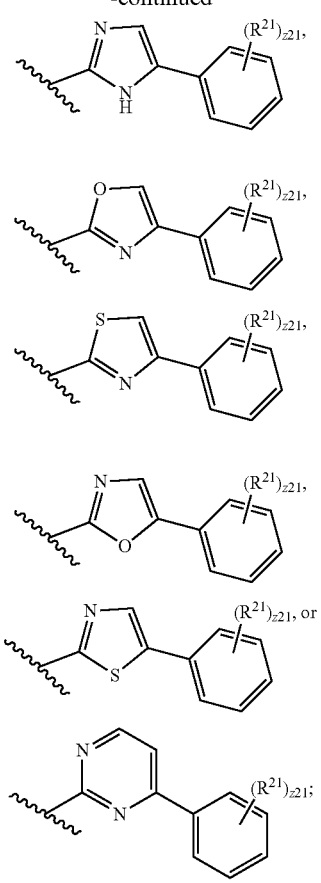
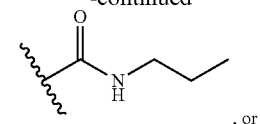
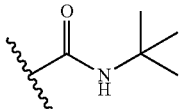
D)
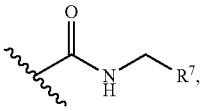
wherein R⁷ is substituted or unsubstituted cycloalkyl; E)
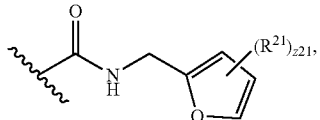
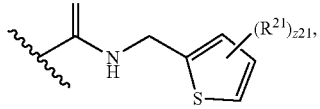
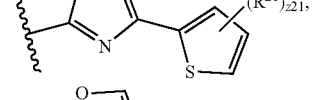
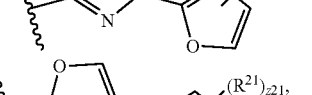
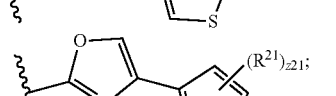
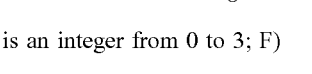
wherein z21 is an integer from 0 to 3; F)
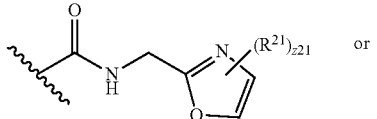
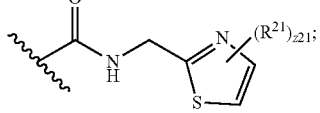
wherein z21 is an integer from 0 to 2; or G)
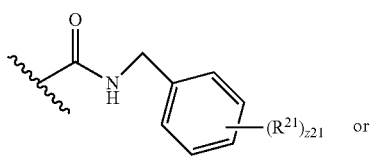
wherein z21 is an integer from 0 to 5; B)
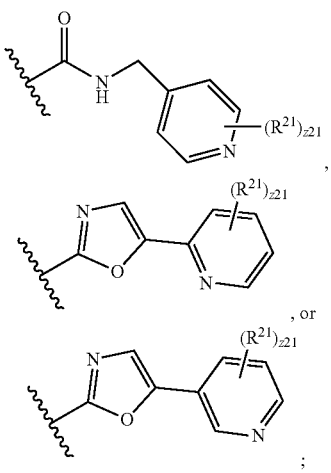
wherein z21 is an integer form 0 to 4; C)
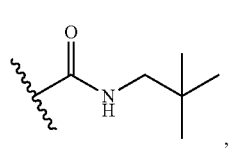

-continued
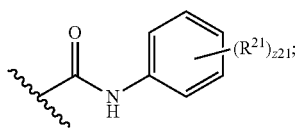
wherein z21 is an integer from 1 to 5.
In embodiments,
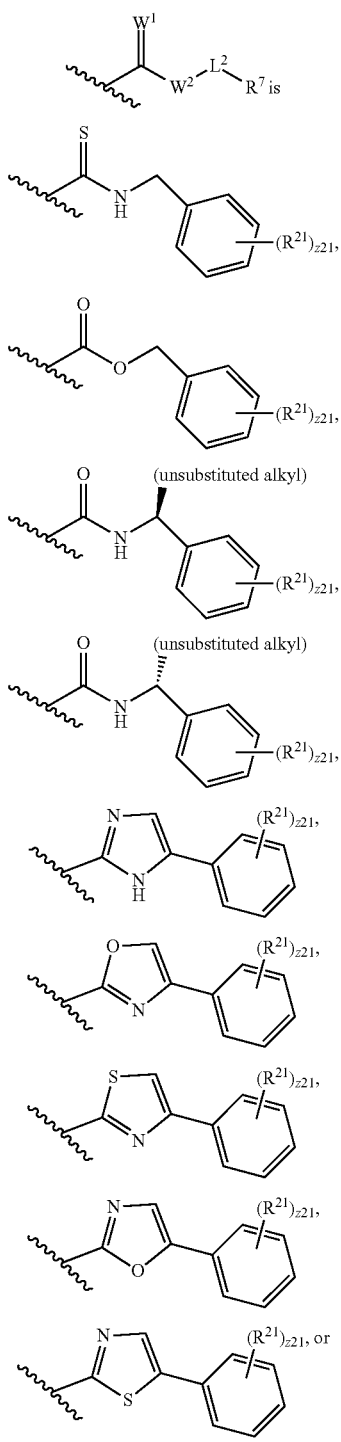
-continued
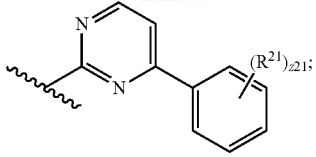
wherein z21 is an integer from 0 to 5.
In embodiments,
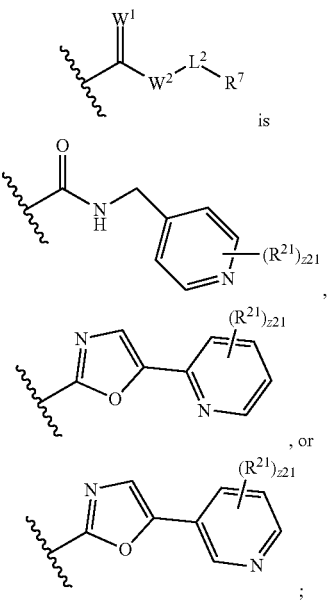
wherein z21 is an integer from 0 to 4. In embodiments,
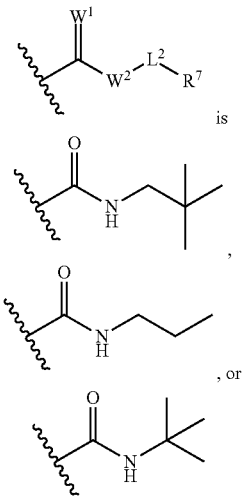
In embodiments,
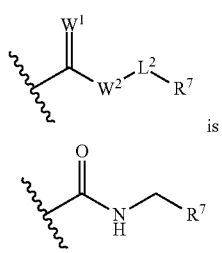

wherein R⁷ is substituted or unsubstituted cycloalkyl. In embodiments,
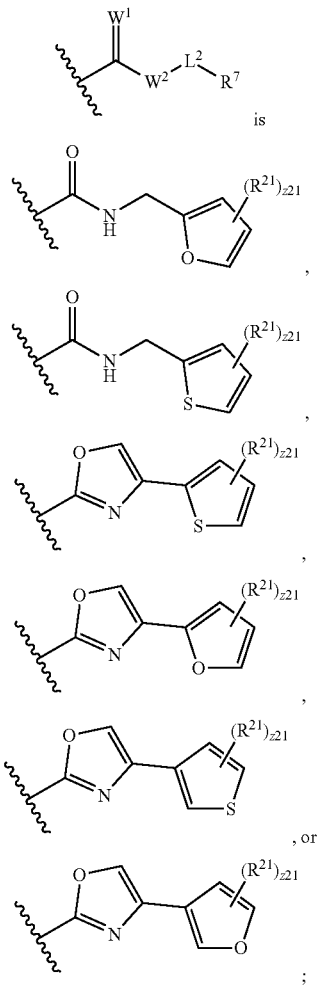
wherein z21 is an integer from 0 to 3. In embodiments,
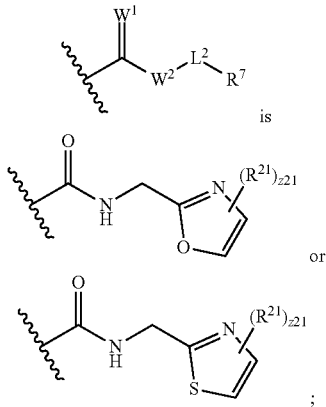
wherein z21 is an integer from 0 to 2. In embodiments,
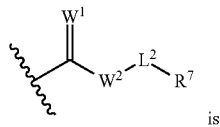
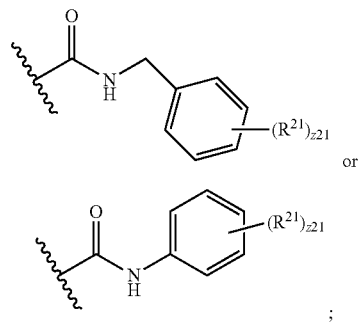
wherein z21 is an integer from 1 to 5.
In embodiments,
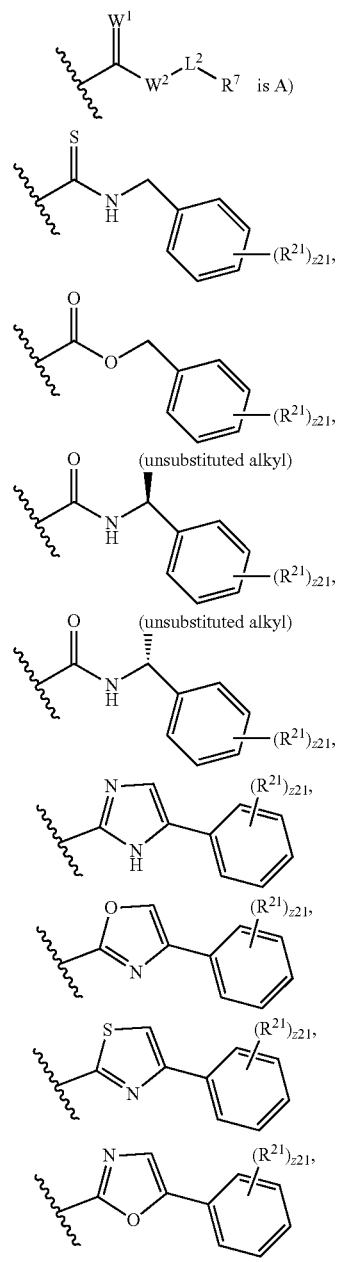

-continued
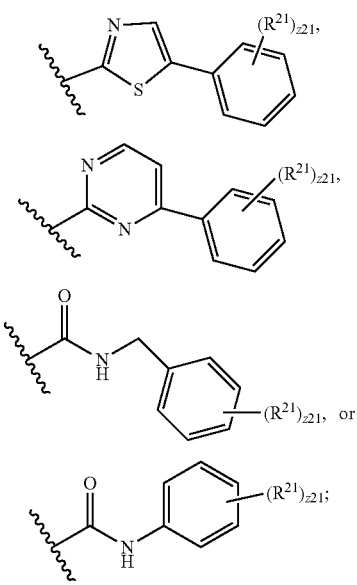
wherein z21 is an integer from 0 to 5; B)
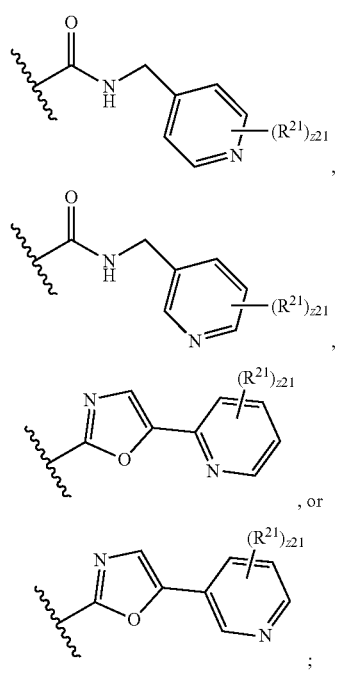
wherein z21 is an integer from 0 to 4; C)
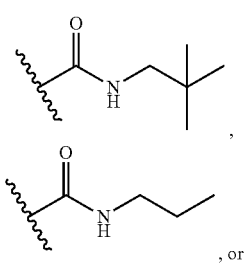
-continued
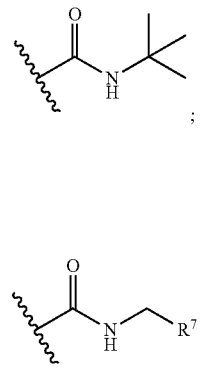
D)
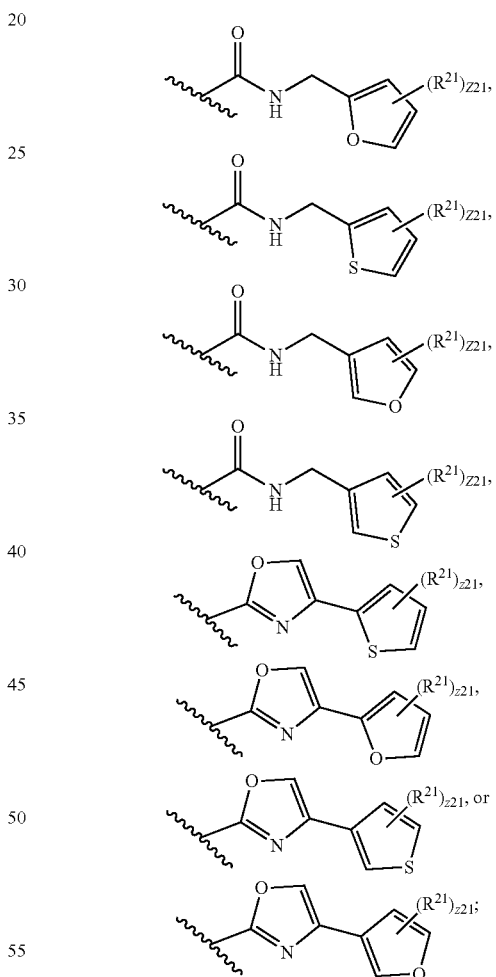
wherein R⁷ is substituted or unsubstituted cycloalkyl; E)
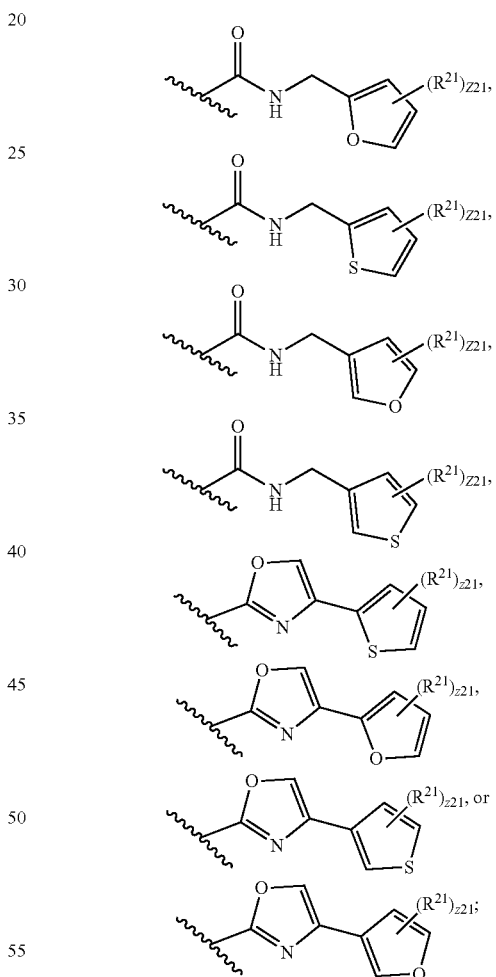
wherein z21 is an integer from 0 to 3; or F)
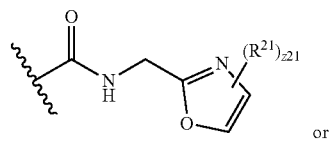
or -continued
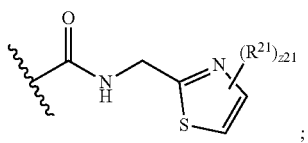
wherein z21 is an integer from 0 to 2.
In embodiments,
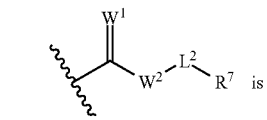 is
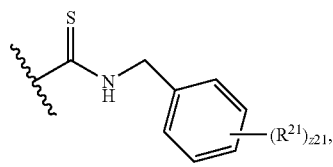
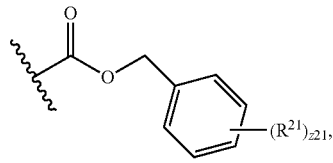
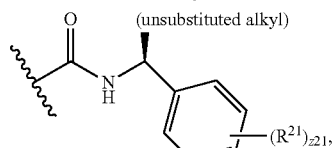
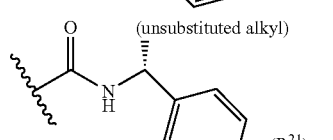
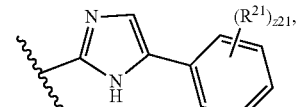
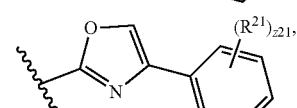
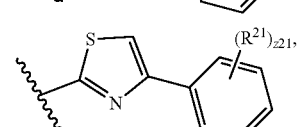
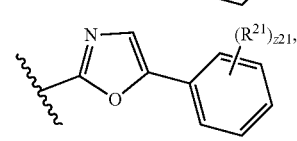
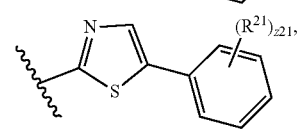
-continued
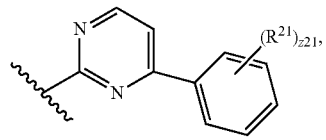
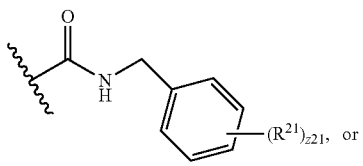
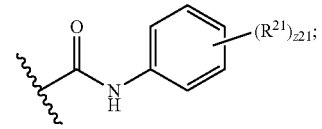
wherein z21 is an integer from 0 to 5. In embodiments,
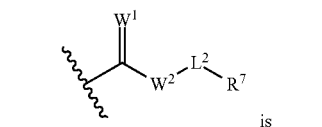 is
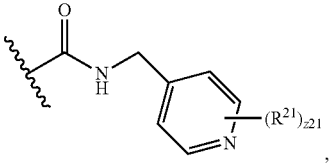
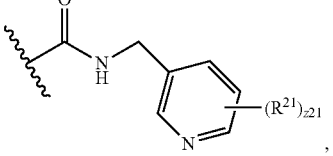
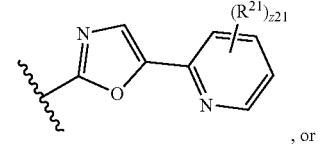
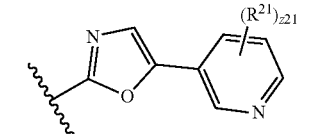
wherein z21 is an integer from 0 to 4. In embodiments,
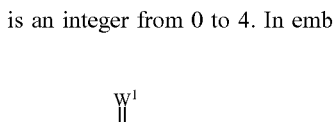 is
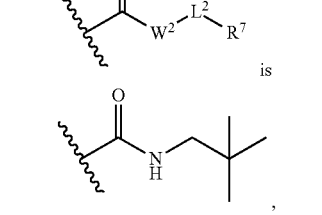

-continued
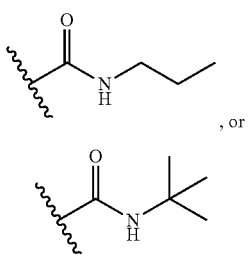
, or
In embodiments,
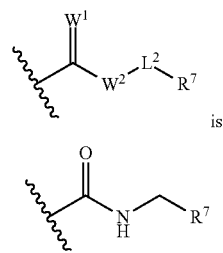
is
wherein R[7] is substituted or unsubstituted cycloalkyl. In embodiments,
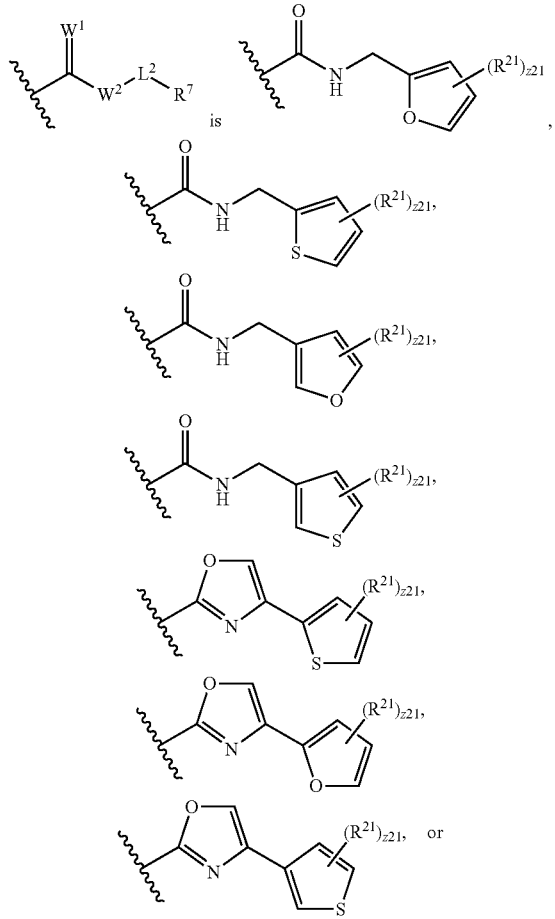
-continued
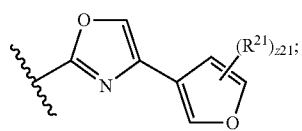
wherein z21 is an integer from 0 to 3. In embodiments,
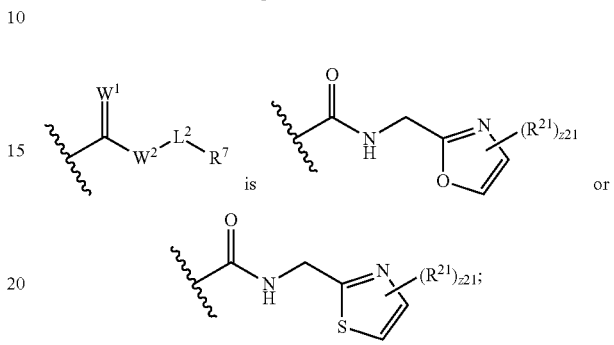
wherein z21 is an integer from 0 to 2.
In embodiments,
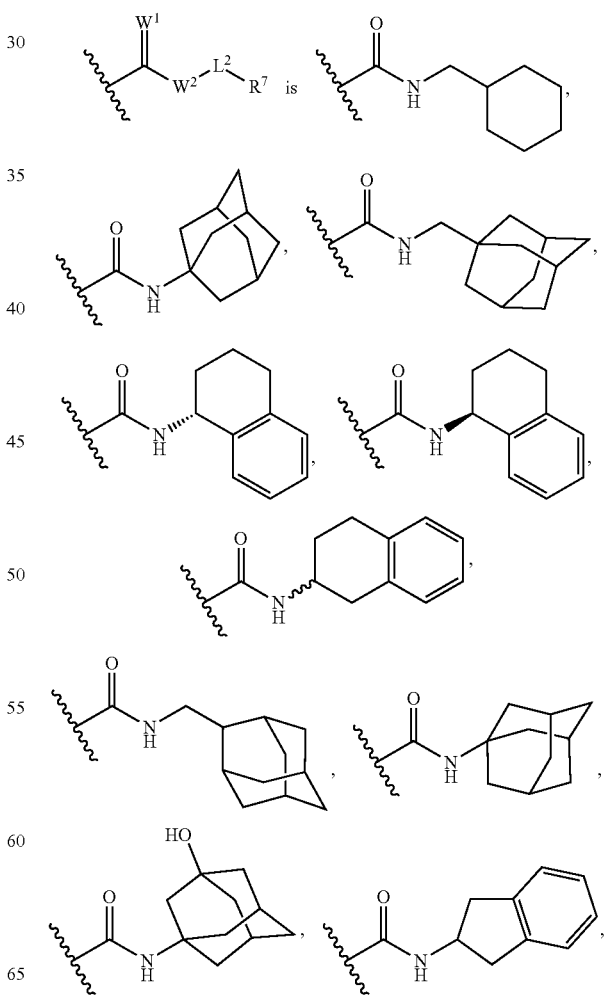

65
-continued
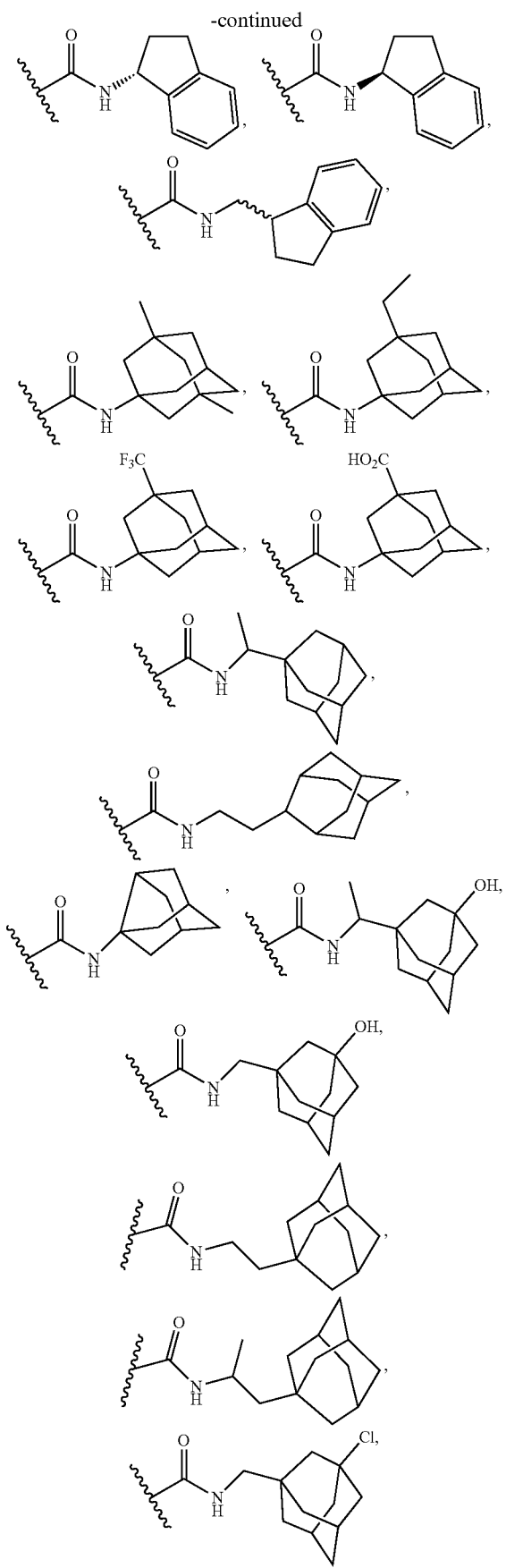
66
-continued
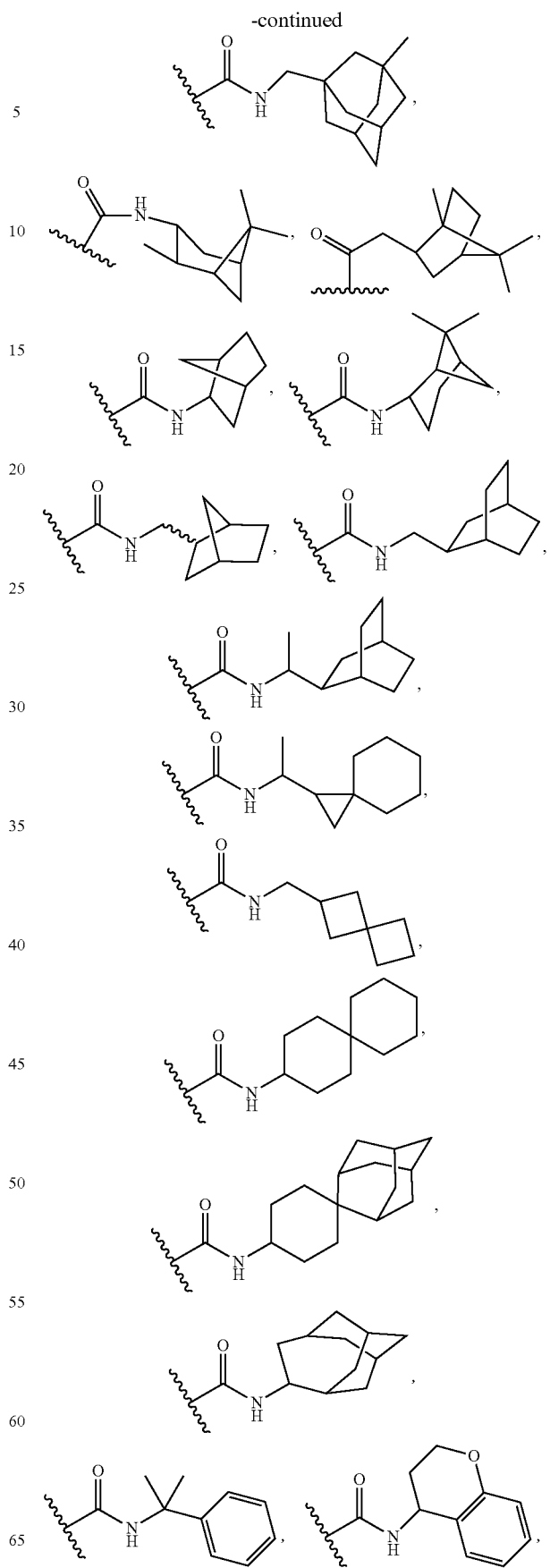

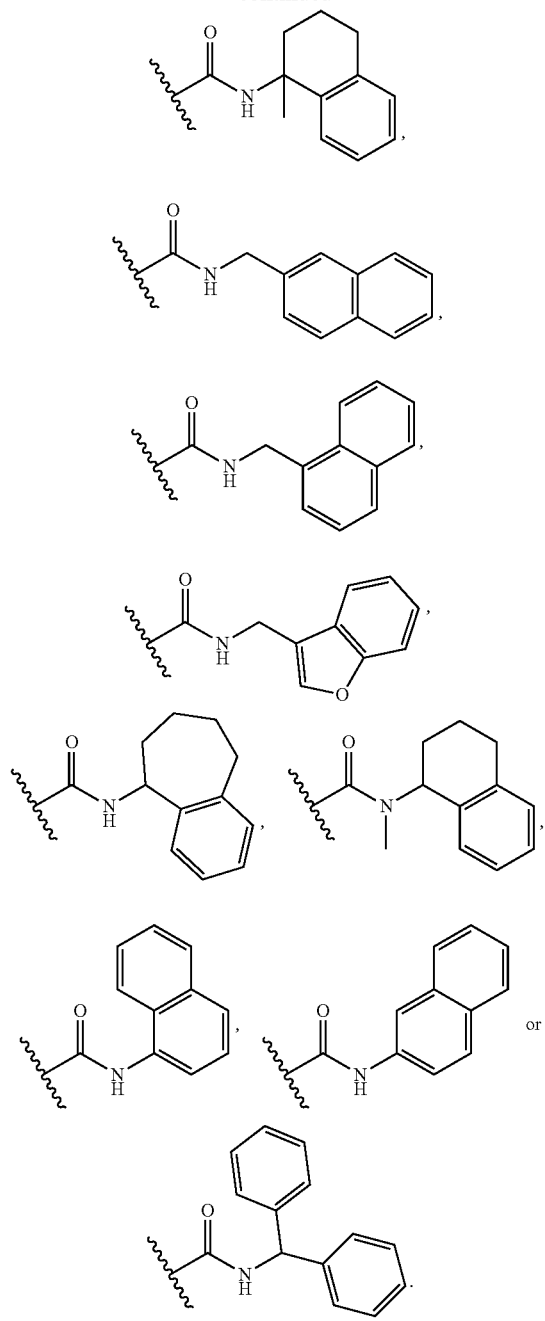
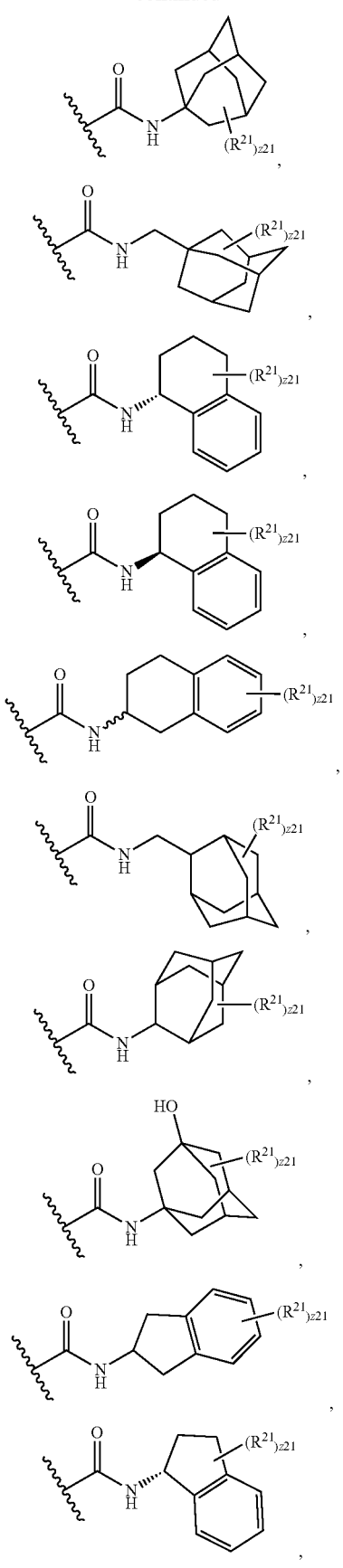
In embodiments,
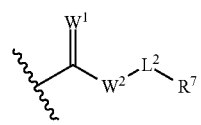
is
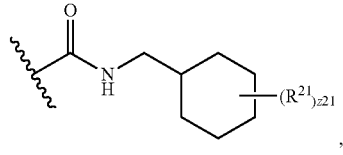

-continued
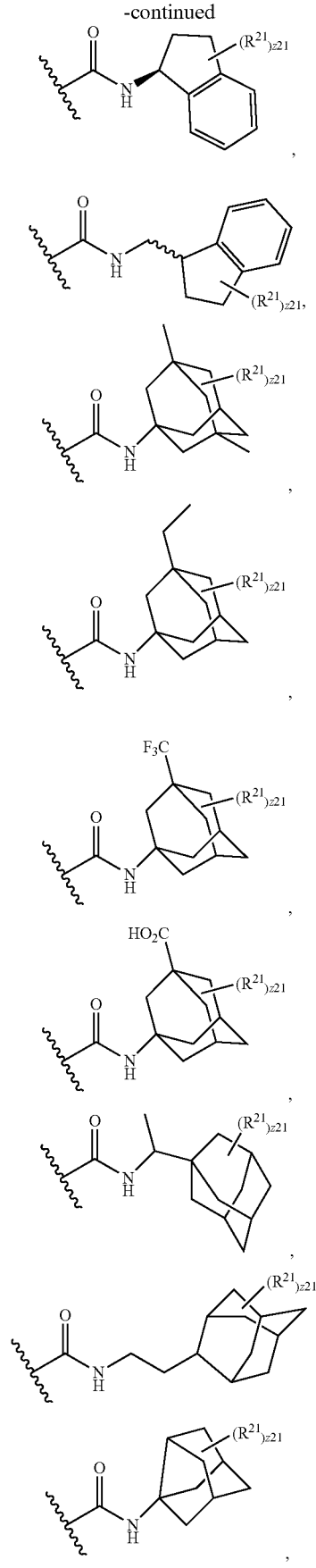
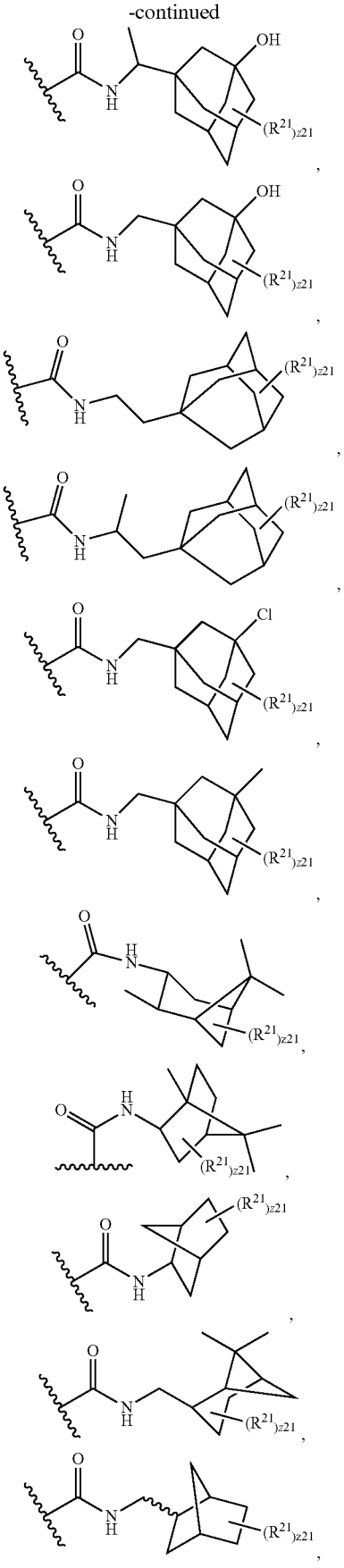

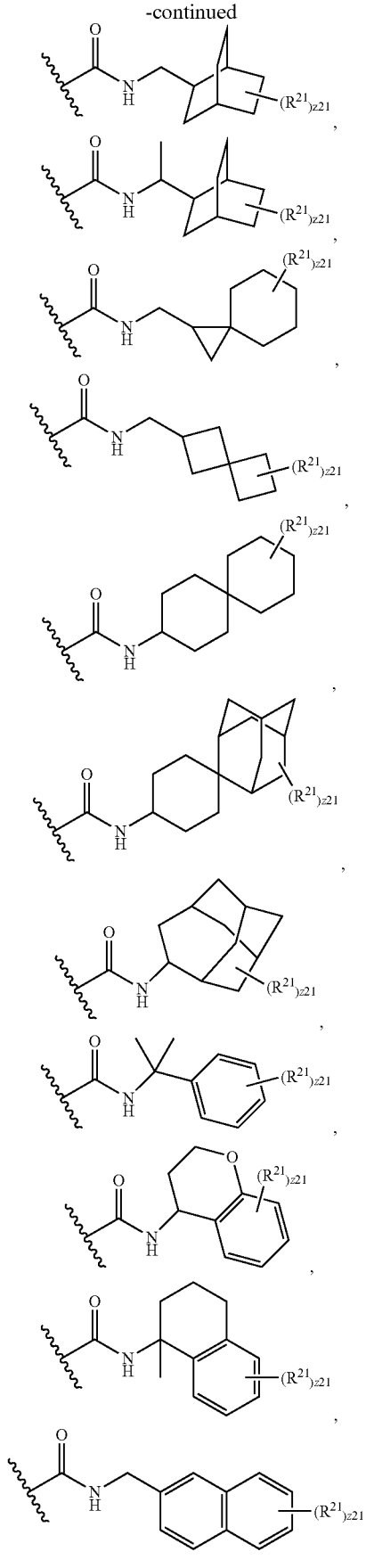
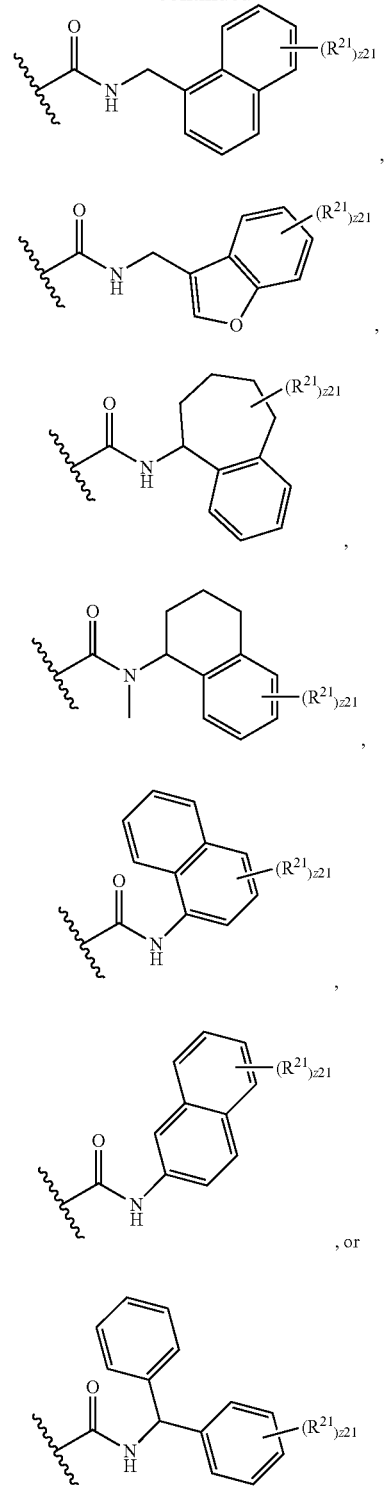
In embodiments, $R^2$, $R^3$, $R^4$, and $R^5$ are hydrogen. In embodiments, $R^2$, $R^4$, $R^5$, and $R^8$ are hydrogen.
In embodiments, $L^1$ is a bond. In embodiments, $L^1$ is —C(O)—.
In embodiments, Ring A is phenyl.
In embodiments, z21 is an integer from 1 to 5. In embodiments, z21 is 0.

In embodiments, the compound has the formula:
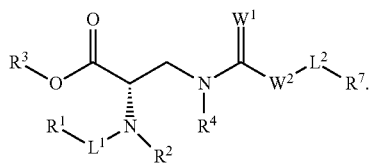
In embodiments, the compound has the formula:
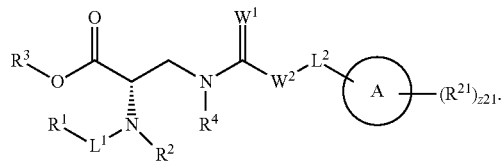
In embodiments, the compound has the formula:
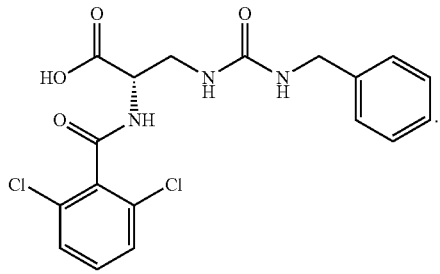 [SMILES: O=C(NCc1ccccc1)NC[C@H](NC(=O)c1c(Cl)cccc1Cl)C(=O)O]
In embodiments, the compound has the formula:
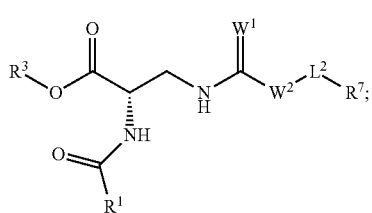
$R^1$ is
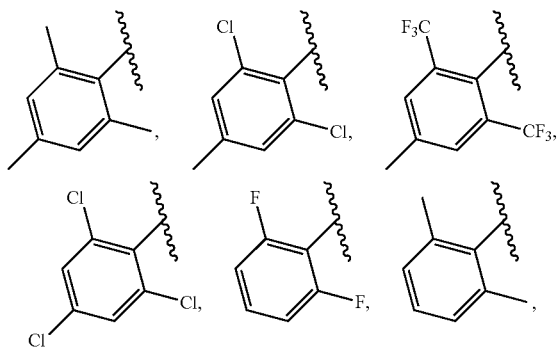
-continued
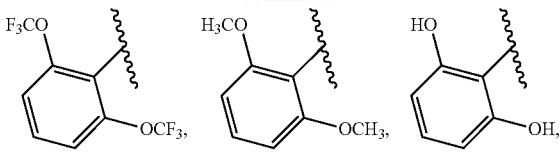
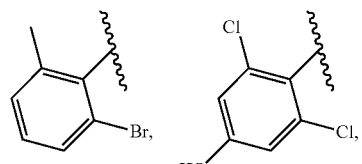
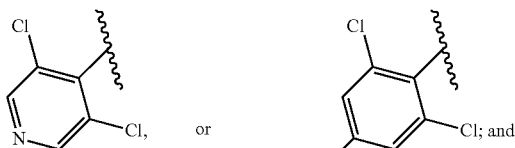
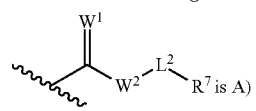 is A)
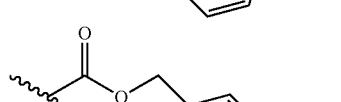
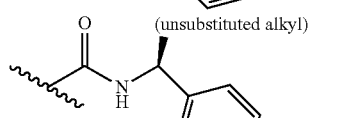
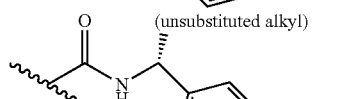
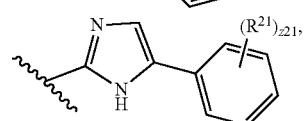
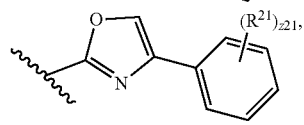
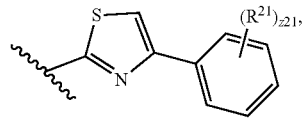
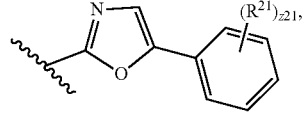

-continued
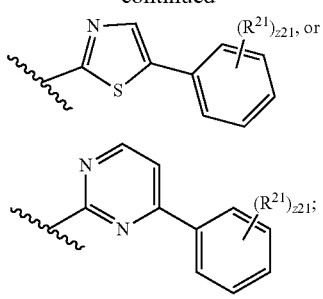
wherein z21 is an integer from 0 to 5; B)
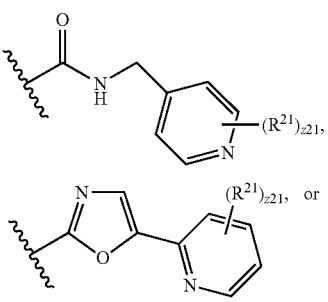
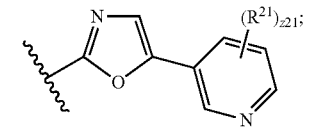
wherein z21 is an integer from 0 to 4; C)
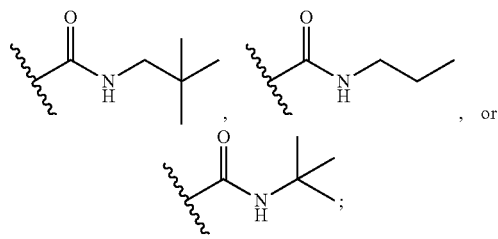
D)
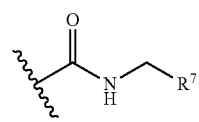
wherein $R^7$ is substituted or unsubstituted cycloalkyl; E)
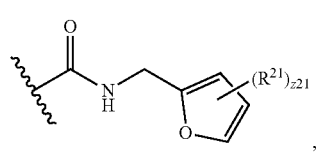
-continued
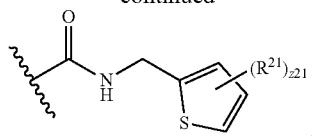
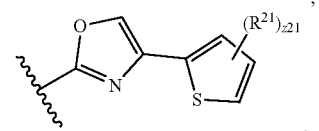

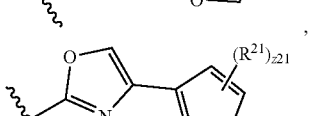
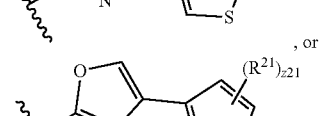
wherein z21 is an integer from 0 to 3; F)
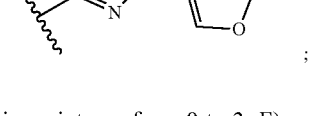
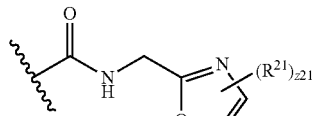
wherein z21 is an integer from 0 to 2; G)
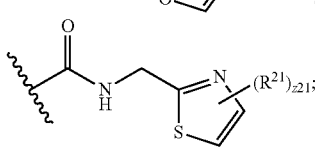
wherein z21 is an integer from 1 to 5; or H)
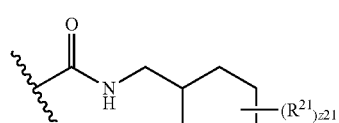

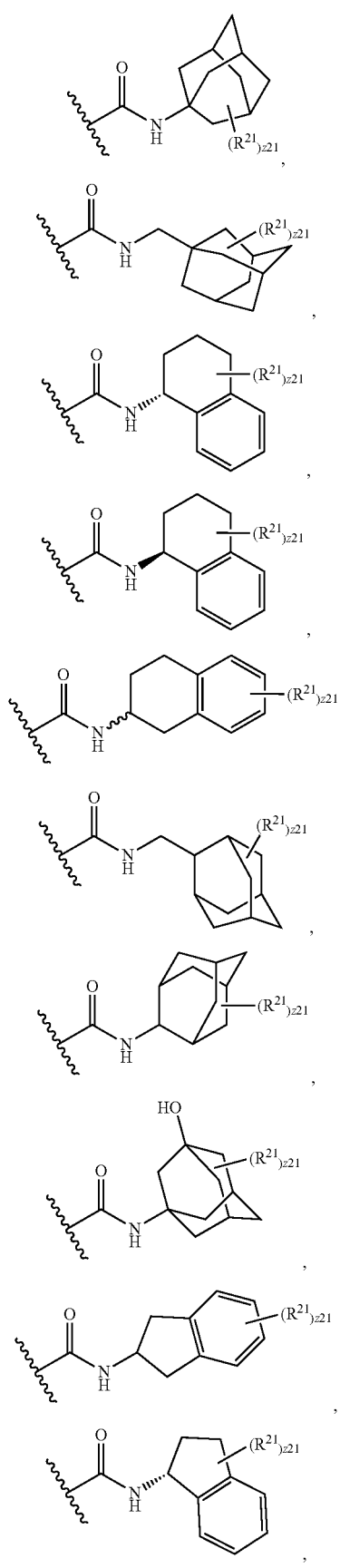
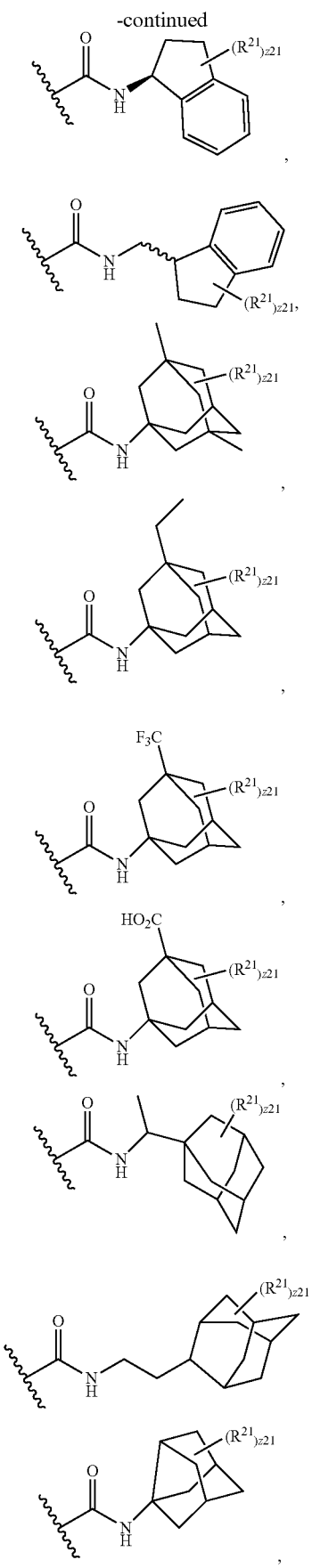

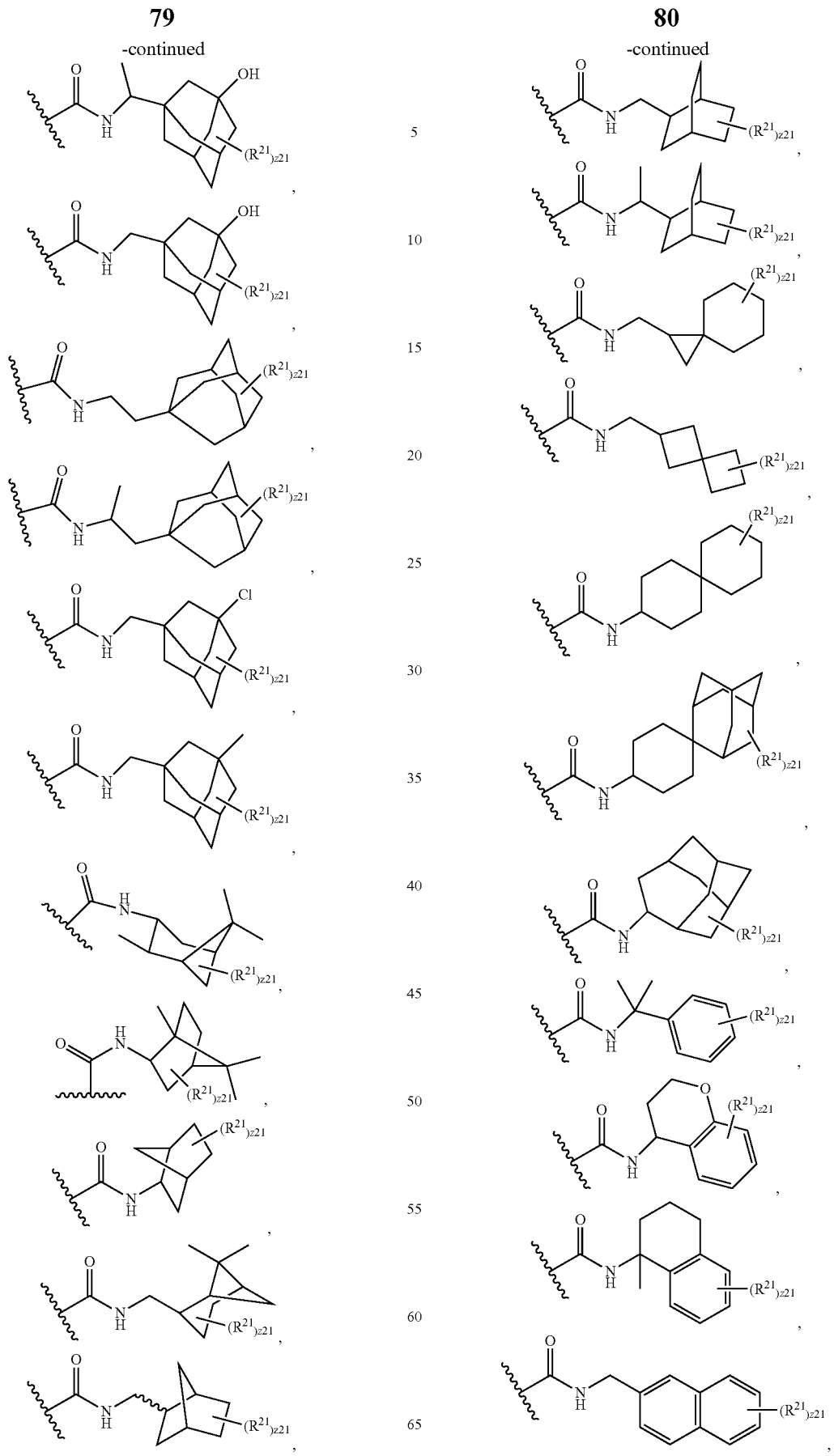

-continued
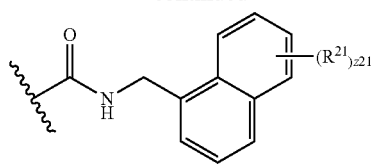
,
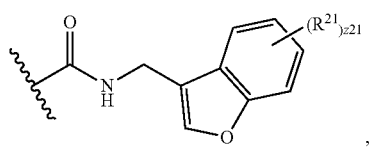
,
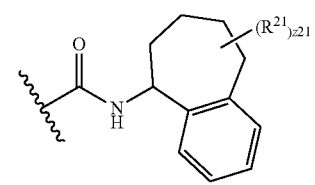
,
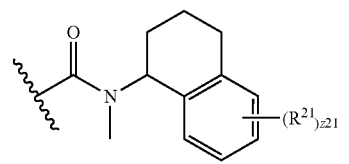
,
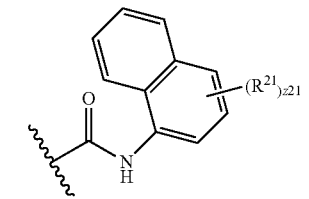
,
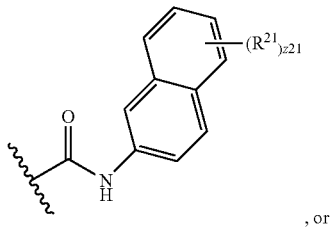
, or
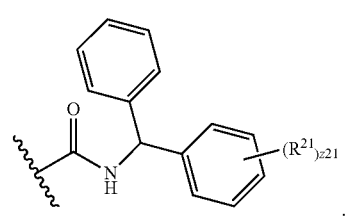
.
wherein z21 is an integer from 1 to 5.
In embodiments, the compound has the formula:
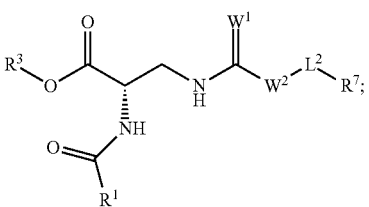
$R^1$ is
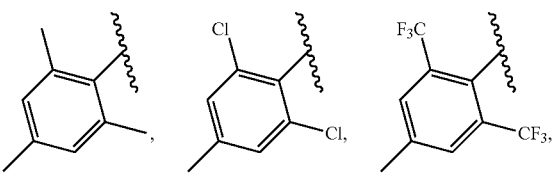
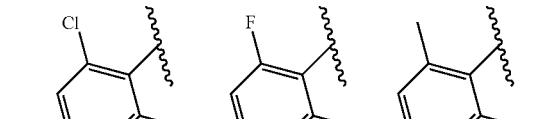
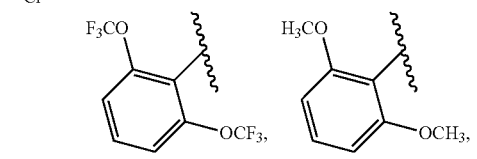
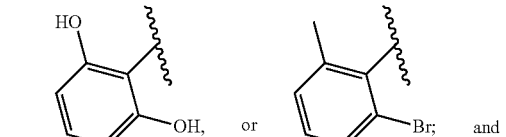
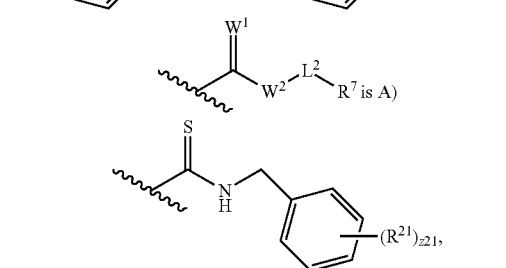
or , and
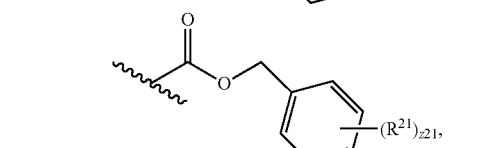
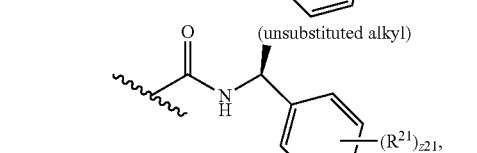
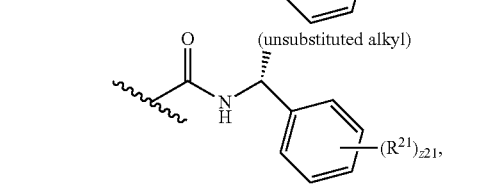

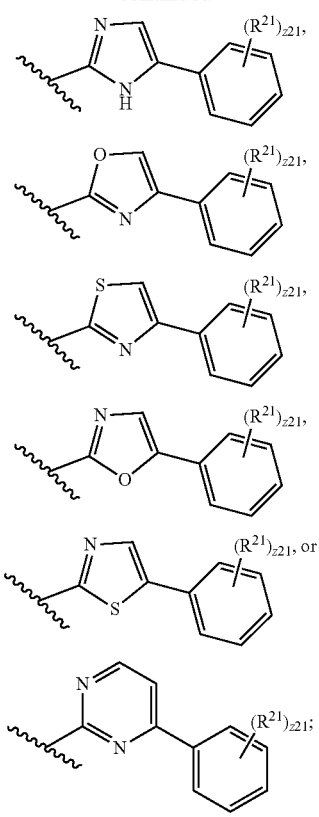
wherein z21 is an integer from 0 to 5; B)
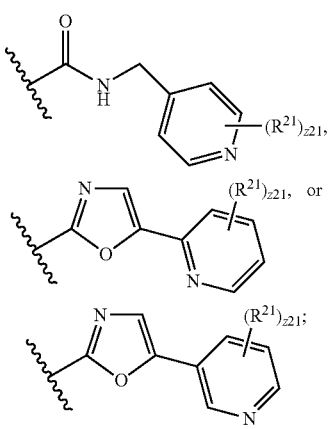
wherein z21 is an integer for 0 to 4; C)
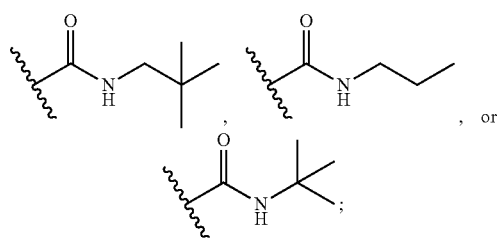
D)
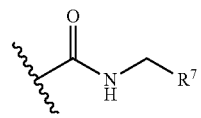
wherein R⁷ is substituted or unsubstituted cycloalkyl; E)
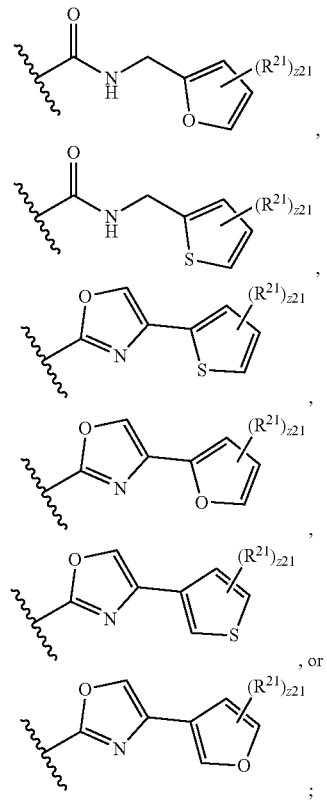
wherein z21 is an integer from 0 to 3; F)
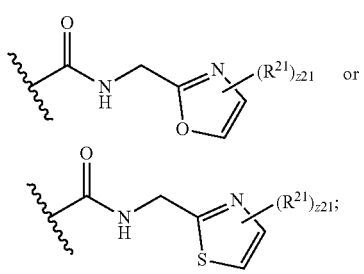
wherein z21 is an integer from 0 to 2; or G)
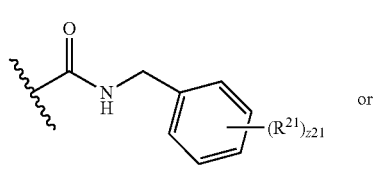

-continued
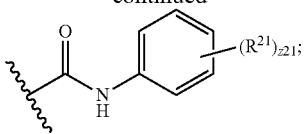
wherein z21 is an integer from 1 to 5.
In embodiments, the compound has the formula:
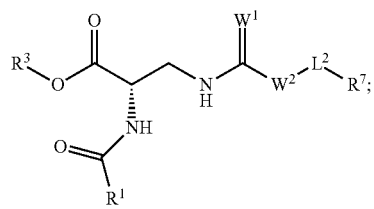
R¹ is
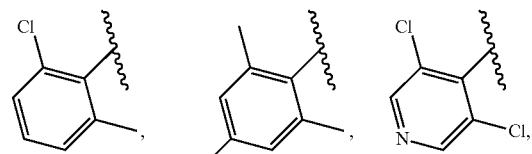
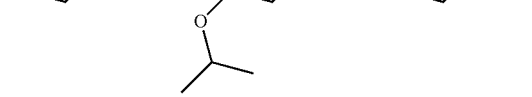
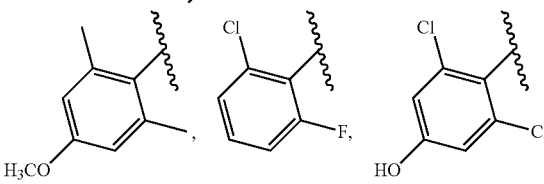
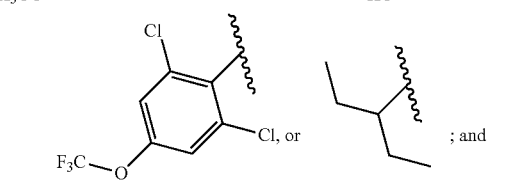
; and
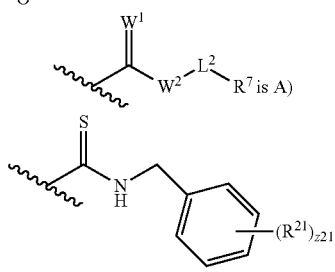
-continued
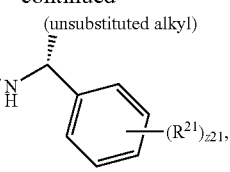
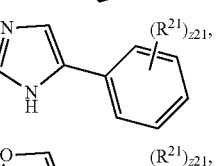
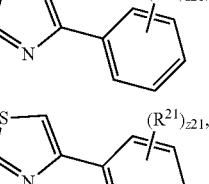
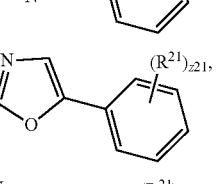
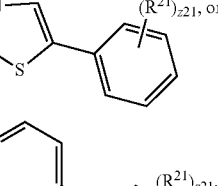
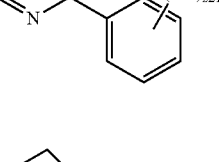
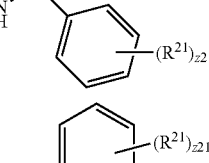
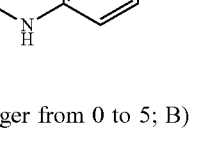
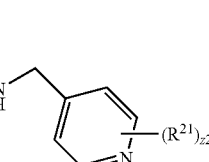
wherein z21 is an integer from 0 to 5; B)
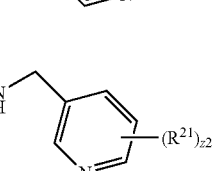

-continued
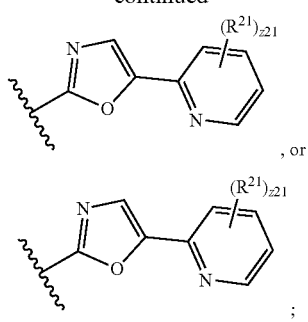, or
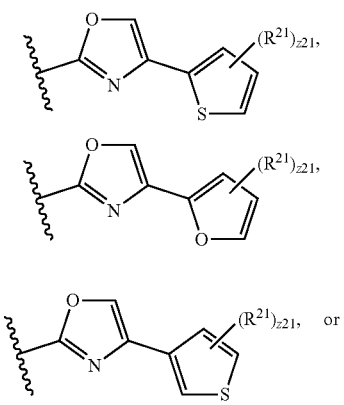
wherein z21 is an integer from 0 to 4; C)
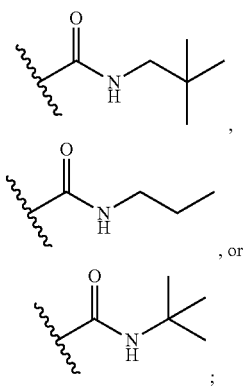
wherein z21 is an integer from 0 to 3; or F)
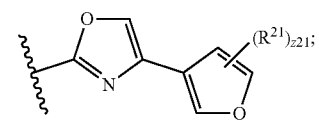
D)
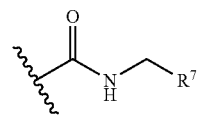
wherein $R^7$ is substituted or unsubstituted cycloalkyl; E)
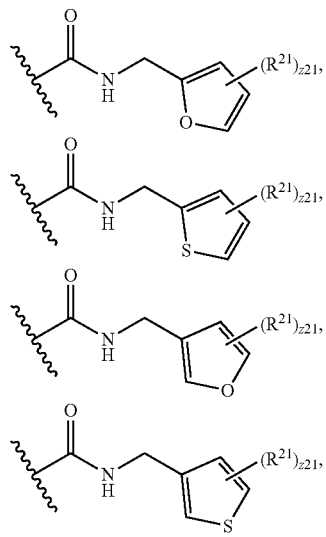
wherein z21 is an integer from 0 to 2; or G)
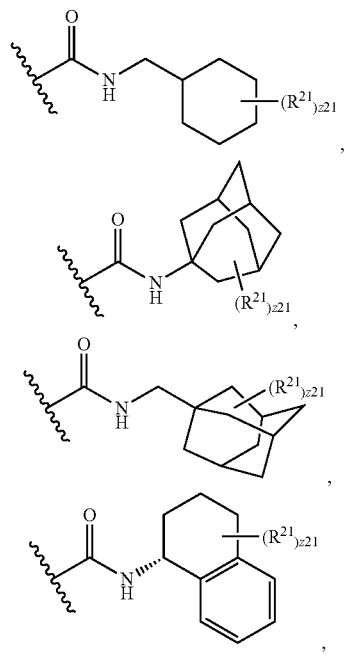

89
-continued
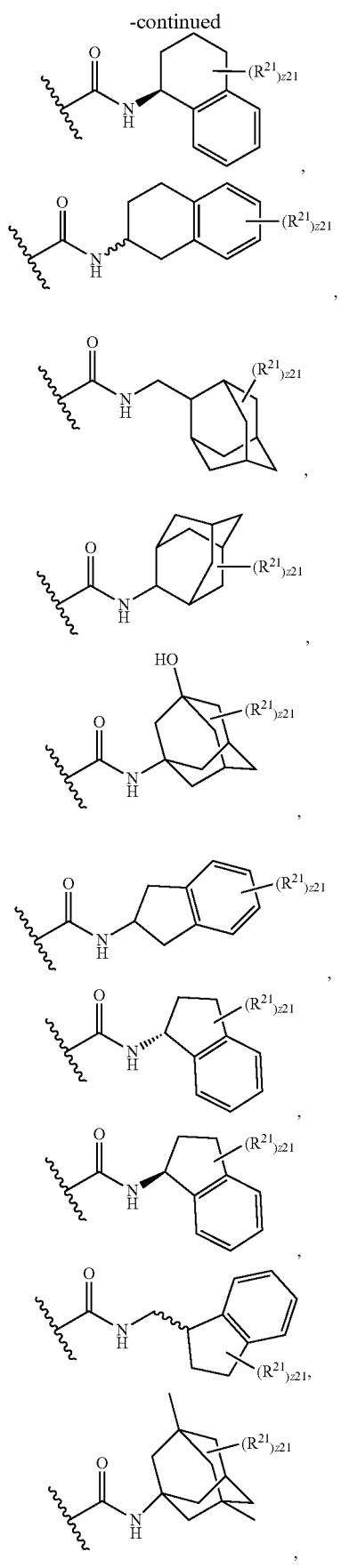
90
-continued
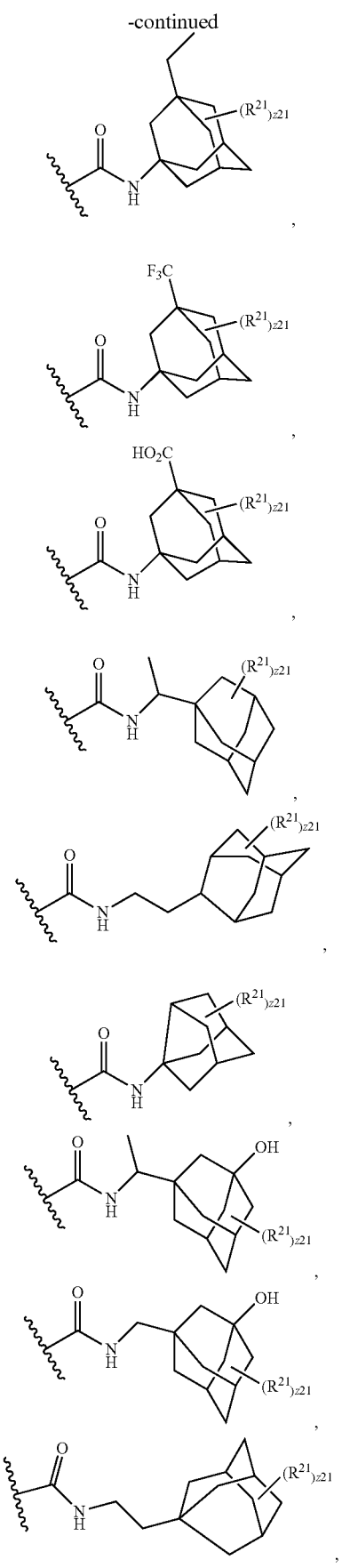

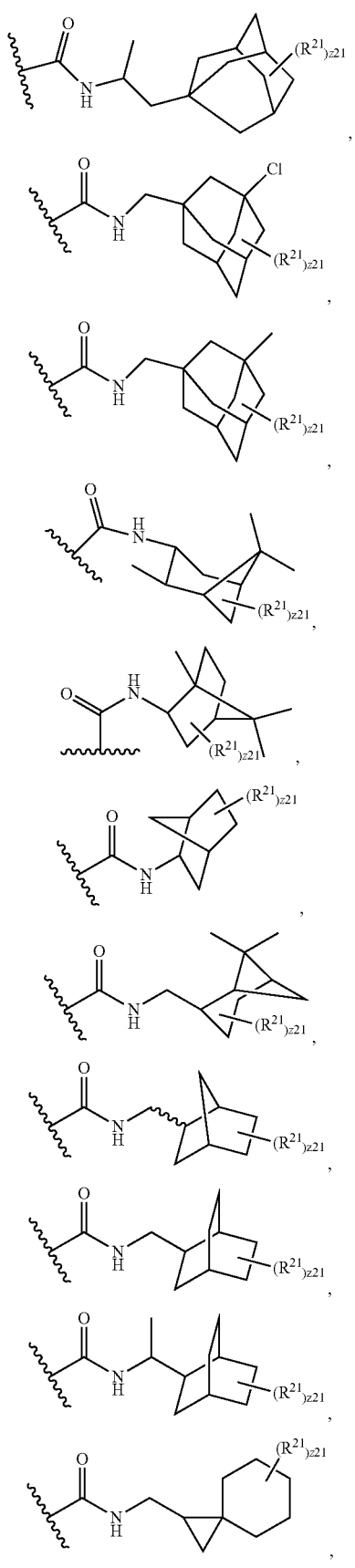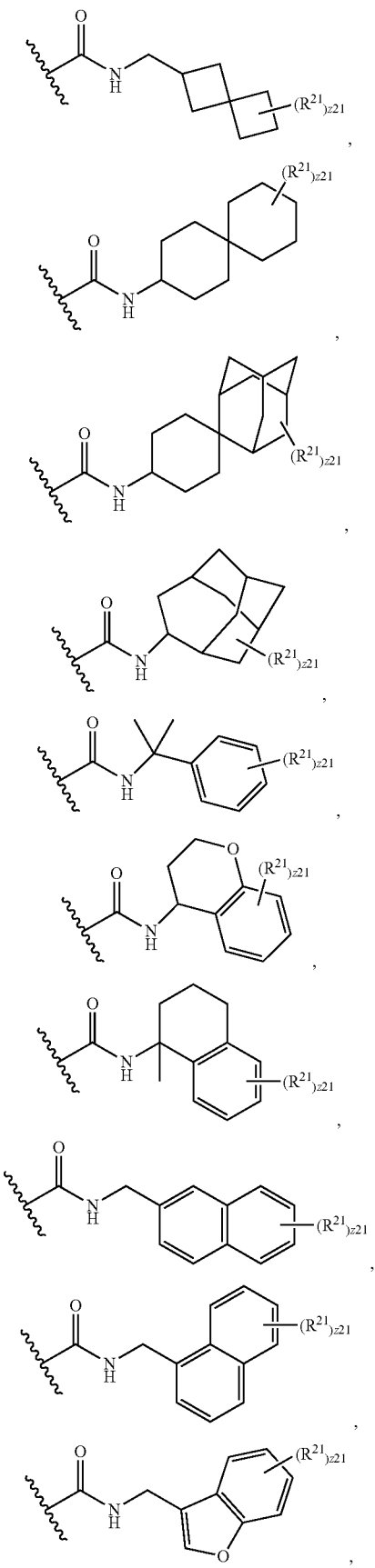

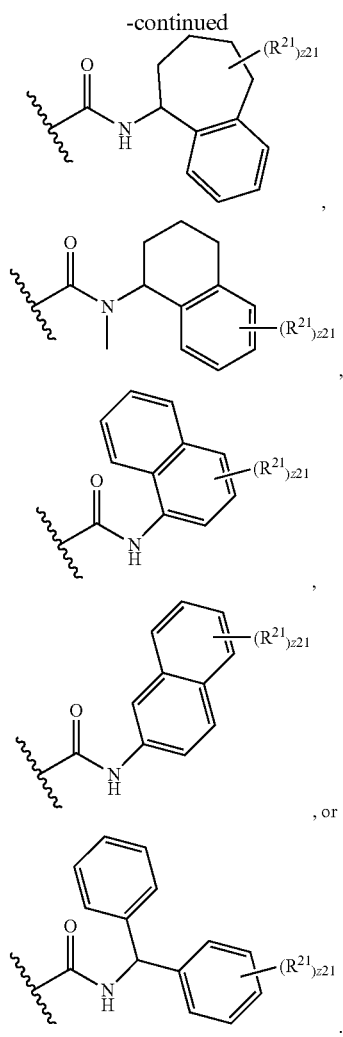
wherein z21 is an integer from 1 to 5.
In embodiments, the compound has the formula: $R^1$ is
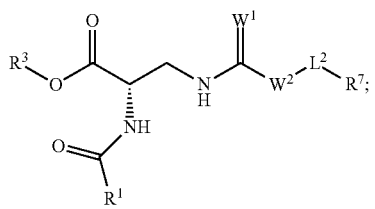
$R^1$ is
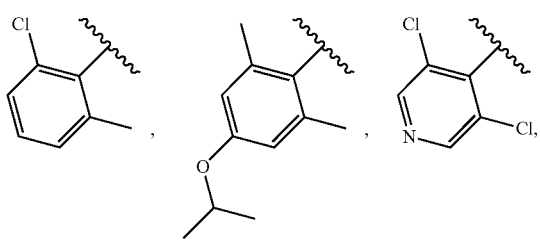
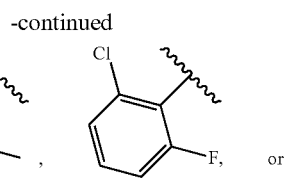
is A)
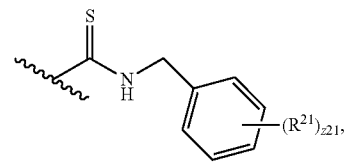
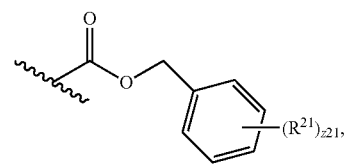
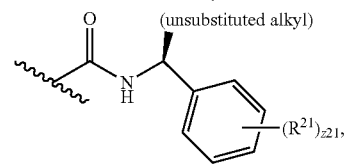
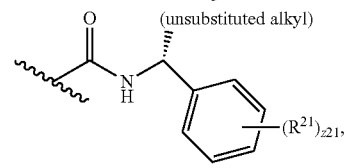
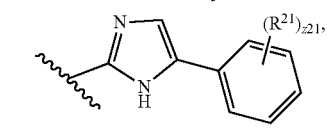
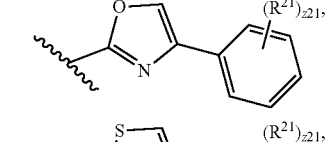
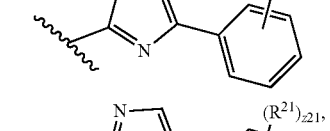
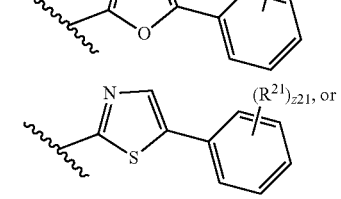

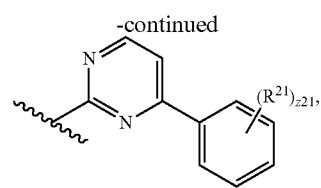
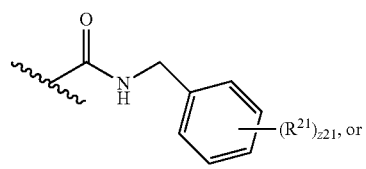
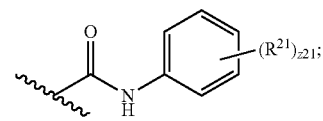
wherein z21 is an integer from 0 to 5; B)
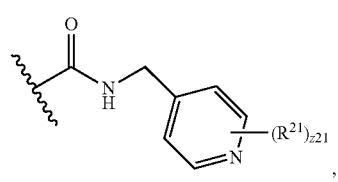
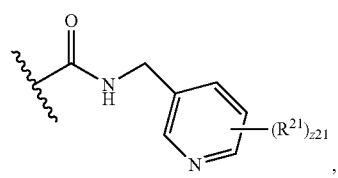
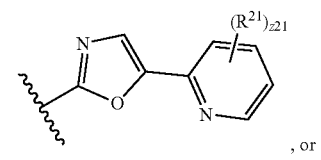
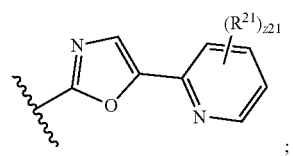
wherein z21 is an integer from 0 to 4; C), D)
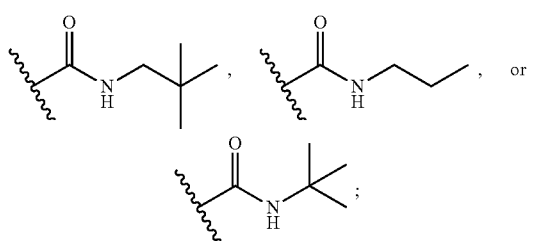
D)
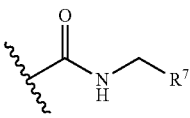
wherein $R^7$ is substituted or unsubstituted cycloalkyl; E)
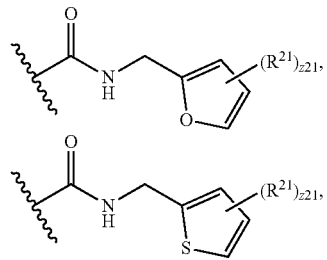
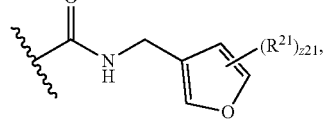
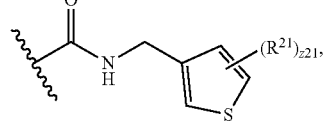
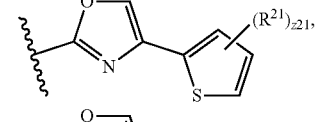
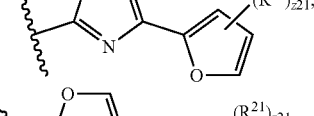

wherein z21 is an integer from 0 to 3; or F)
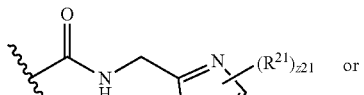
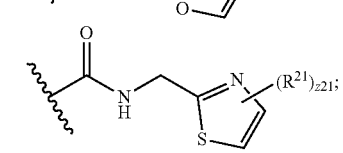
wherein z21 is an integer from 0 to 2.

In embodiments, $R^1$ is independently substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted phenyl, or substituted or unsubstituted 5 to 6 membered heteroaryl. In embodiments, $R^1$ is independently substituted or unsubstituted $C_1$-$C_8$ alkyl, substituted or unsubstituted 2 to 8 membered heteroalkyl, substituted or unsubstituted phenyl, or substituted or unsubstituted 5 to 6 membered heteroaryl. In embodiments, $R^1$ is independently substituted or unsubstituted $C_1$-$C_8$ alkyl, substituted or unsubstituted phenyl, or substituted or unsubstituted 5 to 6 membered heteroaryl.

In embodiments, $R^1$ is $R^{11}$-substituted or unsubstituted alkyl (e.g. $C_1$-$C_8$ alkyl, $C_4$-$C_8$ alkyl, $C_1$-$C_6$ alkyl, or $C_1$-$C_4$ alkyl), $R^{11}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{11}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{11}$-substituted or unsubstituted heterocycloalkyl (e.g. 3 to 8 membered heterocycloalkyl, 4 to 8 membered heterocycloalkyl, or 5 to 6 membered heterocycloalkyl), $R^{11}$-substituted aryl (e.g. $C_6$-$C_{10}$ aryl or $C_6$ aryl), or $R^{11}$-substituted or unsubstituted heteroaryl (e.g. 5 to 10 membered heteroaryl, 5 to 9 membered heteroaryl, or 5 to 6 membered heteroaryl).

In embodiments, $R^1$ is $R^{11}$-substituted alkyl (e.g. $C_1$-$C_8$ alkyl, $C_4$-$C_8$ alkyl, $C_6$-$C_{10}$ alkyl, or $C_1$-$C_4$ alkyl), $R^{11}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{11}$-substituted cycloalkyl (e.g. $C_3$-$C_8$ cycloalkyl, $C_4$-$C_8$ cycloalkyl, or $C_5$-$C_6$ cycloalkyl), $R^{11}$-substituted heterocycloalkyl (e.g. 3 to 8 membered heterocycloalkyl, 4 to 8 membered heterocycloalkyl, or 5 to 6 membered heterocycloalkyl), $R^{11}$-substituted aryl (e.g. $C_6$-$C_{10}$ aryl or $C_6$ aryl), or $R^{11}$-substituted heteroaryl (e.g. 5 to 10 membered heteroaryl, 5 to 9 membered heteroaryl, or 5 to 6 membered heteroaryl). In embodiments, $R_1$ is an unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl).

In embodiments, $R^1$ is $R^{11}$-substituted alkyl (e.g. $C_1$-$C_8$ alkyl, $C_4$-$C_8$ alkyl, $C_1$-$C_6$ alkyl, or $C_1$-$C_4$ alkyl). In embodiments, $R^1$ is $R^{11}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl). In embodiments, $R^1$ is $R^{11}$-substituted cycloalkyl (e.g. $C_3$-$C_8$ cycloalkyl, $C_4$-$C_8$ cycloalkyl, or $C_5$-$C_6$ cycloalkyl). In embodiments, $R^1$ is $R^{11}$-substituted heterocycloalkyl (e.g. 3 to 8 membered heterocycloalkyl, 4 to 8 membered heterocycloalkyl, or 5 to 6 membered heterocycloalkyl). In embodiments, $R^1$ is $R^{11}$-substituted aryl (e.g. $C_6$-$C_{10}$ aryl or $C_6$ aryl). In embodiments, $R^1$ is $R^{11}$-substituted heteroaryl (e.g. 5 to 10 membered heteroaryl, 5 to 9 membered heteroaryl, or 5 to 6 membered heteroaryl). In embodiments, $R^1$ is an unsubstituted alkyl (e.g. $C_1$-$C_8$ alkyl, $C_1$-$C_6$ alkyl, or $C_1$-$C_4$ alkyl). In embodiments, $R^1$ is unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl). In embodiments, $R^1$ is unsubstituted cycloalkyl (e.g. $C_3$-$C_8$ cycloalkyl, $C_4$-$C_8$ cycloalkyl, or $C_5$-$C_6$ cycloalkyl). In embodiments, $R^1$ is unsubstituted heterocycloalkyl (e.g. 3 to 8 membered heterocycloalkyl, 4 to 8 membered heterocycloalkyl, or 5 to 6 membered heterocycloalkyl). In embodiments, $R^1$ is unsubstituted aryl (e.g. $C_6$-$C_{10}$ aryl or $C_6$ aryl). In embodiments, $R^1$ is unsubstituted heteroaryl (e.g. 5 to 10 membered heteroaryl, 5 to 9 membered heteroaryl, or 5 to 6 membered heteroaryl).

In embodiments, $R^1$ is $R^{11}$-substituted or unsubstituted heteroaryl (e.g., 5 to 10 membered heteroaryl, 5 to 9 membered heteroaryl, or 5 to 6 membered heteroaryl). In embodiments, $R^1$ is substituted or unsubstituted pyridyl. In embodiments, $R^1$ is $R^{11}$-substituted pyridyl. In embodiments, $R^1$ is unsubstituted pyridyl. In embodiments, $R^1$ is substituted or unsubstituted pyrimidinyl. In embodiments, $R^1$ is $R^{11}$-substituted pyrimidinyl. In embodiments, $R^1$ is unsubstituted pyrimidinyl. In embodiments, $R^1$ is substituted or unsubstituted phenyl. In embodiments, $R^1$ is $R^{11}$-substituted phenyl. In embodiments, $R^1$ is unsubstituted phenyl.

$R^{11}$ is independently halogen, —$CX^{11}_3$, —$CHX^{11}_2$, —$CH_2X^{11}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, NHC=(O)$NH_2$, —$NHSO_2H$, —NHC=(O)H, —NHC(O)OH, —NHOH, —$OCX^{11}_3$, —$OCHX^{11}_2$, —$OCH_2X^{11}$, $R^{12}$-substituted or unsubstituted alkyl (e.g. $C_1$-$C_8$ alkyl, $C_1$-$C_6$ alkyl, or $C_1$-$C_4$ alkyl), $R^{12}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{12}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{12}$-substituted or unsubstituted heterocycloalkyl (e.g. 3 to 8 membered heterocycloalkyl, 4 to 8 membered heterocycloalkyl, or 5 to 6 membered heterocycloalkyl), $R^{12}$-substituted or unsubstituted aryl (e.g. $C_6$-$C_{10}$ aryl or $C_6$ aryl), or $R^{12}$-substituted or unsubstituted heteroaryl (e.g. 5 to 10 membered heteroaryl, 5 to 9 membered heteroaryl, or 5 to 6 membered heteroaryl). $X^{11}$ is —F, —Cl, —Br, or —I. In embodiments, $R^{11}$ is independently —F. In embodiments, $R^{11}$ is independently —Cl. In embodiments, $R^{11}$ is independently —Br. In embodiments, $R^{11}$ is independently —I.

$R^{12}$ is independently halogen, —$CX^{12}_3$, —$CHX^{12}_2$, —$CH_2X^{12}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, NHC=(O)$NH_2$, —$NHSO_2H$, —HNC=(O)H, —NHC(O)OH, —NHOH, —$OCX^{12}_3$, —$OCHX^{12}_2$, —$OCH_2X^{12}$, $R^{13}$-substituted or unsubstituted alkyl (e.g. $C_1$-$C_8$ alkyl, $C_1$-$C_6$ alkyl, or $C_1$-$C_4$ alkyl), $R^H$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), $R^{13}$-substituted or unsubstituted cycloalkyl (e.g. $C_3$-$C_8$ cycloalkyl, $C_4$-$C_8$ cycloalkyl, or $C_5$-$C_6$ cycloalkyl), $R^{13}$-substituted or unsubstituted heterocycloalkyl (e.g. 3 to 8 membered heterocycloalkyl, 4 to 8 membered heterocycloalkyl, or 5 to 6 membered heterocycloalkyl), $R^{13}$-substituted or unsubstituted aryl (e.g. $C_6$-$C_{10}$ aryl or $C_6$ aryl), or $R^{13}$-substituted or unsubstituted heteroaryl (e.g. 5 to 10 membered heteroaryl, 5 to 9 membered heteroaryl, or 5 to 6 membered heteroaryl). $X^{12}$ is —F, —Cl, —Br, or —I.

$R^{13}$ is independently halogen, $-CX^{13}_3$, $-CHX^{13}_2$, $-CH_2X^{13}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $NHC=(O)NH_2$, $-NHSO_2H$, $-NHC=(O)H$, $-NHC(O)OH$, $-NHOH$, $-OCX^{13}_3$, $-OCHX^{13}_2$, $-OCH_2X^{13}$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^{13}$ is $-F$, $-Cl$, $-Br$, or $-I$.

In embodiments, $R^2$ is substituted or unsubstituted alkyl (e.g. $C_1$-$C_8$ alkyl, $C_1$-$C_6$ alkyl, or $C_1$-$C_4$ alkyl). In embodiments, $R^2$ is substituted alkyl (e.g. $C_1$-$C_8$ alkyl, $C_1$-$C_6$ alkyl, or $C_1$-$C_4$ alkyl). In embodiments, $R^2$ is an unsubstituted alkyl (e.g. $C_1$-$C_8$ alkyl, $C_1$-$C_6$ alkyl, or $C_1$-$C_4$ alkyl).

In embodiments, $R^2$ is $R^{14}$-substituted or unsubstituted alkyl (e.g. $C_1$-$C_8$ alkyl, $C_1$-$C_6$ alkyl, or $C_1$-$C_4$ alkyl). In embodiments, $R^2$ is $R^{14}$-substituted alkyl (e.g. $C_1$-$C_8$ alkyl, $C_1$-$C_6$ alkyl, or $C_1$-$C_4$ alkyl). In embodiments, $R^2$ is an unsubstituted alkyl (e.g. $C_1$-$C_8$ alkyl, $C_1$-$C_6$ alkyl, or $C_1$-$C_4$ alkyl). In embodiments, $R^2$ is hydrogen. In embodiments, $R^2$ is unsubstituted methyl. In embodiments, $R^2$ is unsubstituted ethyl. In embodiments, $R^2$ is unsubstituted propyl.

$R^{14}$ is independently halogen, $-CX^{14}_3$, $-CHX^{14}_2$, $-CH_2X^{14}$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $NHC=(O)NH_2$, $-NHSO_2H$, $-NHC=(O)H$, $-NHC(O)OH$, $-NHOH$, $-OCX^{14}_3$, $-OCHX^{14}_2$, $-OCH_2X^{14}$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^{14}$ is $-F$, $-Cl$, $-Br$, or $-I$.

In embodiments, $R^3$ is independently hydrogen, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2C_1$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2C_1$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^3$ is independently hydrogen, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $R^{15}$-substituted or unsubstituted alkyl (e.g., $C_1$-$C_8$ alkyl, $C_1$-$C_6$ alkyl, or $C_1$-$C_4$ alkyl), $R^{15}$-substituted or unsubstituted heteroalkyl (e.g., 2 to 8 membered heteroalkyl, 2 to 6 membered heteroalkyl, or 2 to 4 membered heteroalkyl), 1V-substituted or unsubstituted cycloalkyl (e.g., $C_3$-$C_8$ cycloalkyl, $C_3$-$C_6$ cycloalkyl, or $C_5$-$C_6$ cycloalkyl), $R^{15}$-substituted or unsubstituted heterocycloalkyl (e.g., 3 to 8 membered heterocycloalkyl, 3 to 6 membered heterocycloalkyl, or 5 to 6 membered heterocycloalkyl), $R^{15}$-substituted or unsubstituted aryl (e.g., $C_6$-$C_{10}$ aryl, $C_{10}$ aryl, or phenyl), or $R^{15}$-substituted or unsubstituted heteroaryl (e.g., 5 to 10 membered heteroaryl, 5 to 9 membered heteroaryl, or 5 to 6 membered heteroaryl).

In embodiments, $R^3$ is independently hydrogen, halogen, $-CF_3$, $-CBr_3$, $-CCl_3$, $-CI_3$, $-CHF_2$, $-CHBr_2$, $-CHCl_2$, $-CHI_2$, $-CH_2F$, $-CH_2Br$, $-CH_2Cl$, $-CH_2I$, $-OCF_3$, $-OCBr_3$, $-OCCl_3$, $-OCI_3$, $-OCHF_2$, $-OCHBr_2$, $-OCHCl_2$, $-OCHI_2$, $-OCH_2F$, $-OCH_2Br$, $-OCH_2Cl$, $-OCH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^3$ is independently hydrogen.

In embodiments, $R^3$ is $R^{15}$-substituted or unsubstituted alkyl (e.g., $C_1$-$C_8$ alkyl, $C_1$-$C_6$ alkyl, or $C_1$-$C_4$ alkyl). In embodiments, $R^3$ is $R^{15}$-substituted alkyl (e.g., $C_1$-$C_8$ alkyl, $C_1$-$C_6$ alkyl, or $C_1$-$C_4$ alkyl). In embodiments, $R^3$ is an unsubstituted alkyl (e.g., $C_1$-$C_8$ alkyl, $C_1$-$C_6$ alkyl, or $C_1$-$C_4$ alkyl). In embodiments, $R^3$ is $R^{15}$-substituted or unsubstituted heteroalkyl (e.g., 2 to 8 membered heteroalkyl, 2 to 6 membered heteroalkyl, or 2 to 4 membered heteroalkyl). In embodiments, $R^3$ is $R^{15}$-substituted heteroalkyl (e.g., 2 to 8 membered heteroalkyl, 2 to 6 membered heteroalkyl, or 2 to 4 membered heteroalkyl). In embodiments, $R^3$ is an unsubstituted heteroalkyl (e.g., 2 to 8 membered heteroalkyl, 2 to 6 membered heteroalkyl, or 2 to 4 membered heteroalkyl). In embodiments, $R^3$ is $R^{15}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is $R^{15}$-substituted cycloalkyl (e.g., $C_3$-$C_8$ cycloalkyl, $C_3$-$C_6$ cycloalkyl, or $C_5$-$C_6$ cycloalkyl). In embodiments, $R^3$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^3$ is $R^{15}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is $R^{15}$-substituted heterocycloalkyl (e.g., 3 to 8 membered heterocycloalkyl, 3 to 6 membered heterocycloalkyl, or 5 to 6 membered heterocycloalkyl). In embodiments, $R^3$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^3$ is $R^{15}$-substituted or unsubstituted aryl (e.g., $C_6$-$C_{10}$ aryl, $C_{10}$ aryl, or phenyl). In embodiments, $R^3$ is $R^{15}$-substituted aryl (e.g., $C_6$-$C_{10}$ aryl, $C_{10}$ aryl, or phenyl). In embodiments, $R^3$ is an unsubstituted aryl (e.g., $C_6$-$C_{10}$ aryl, $C_{10}$ aryl, or phenyl). In embodiments, $R^3$ is $R^{15}$-substituted or unsubstituted heteroaryl (e.g., 5 to 10 membered heteroaryl, 5 to 9 membered heteroaryl, or 5 to 6 membered heteroaryl). In embodiments, $R^3$ is $R^{15}$-substituted heteroaryl (e.g., 5 to 10 membered heteroaryl, 5 to 9 membered heteroaryl, or 5 to 6 membered heteroaryl). In embodiments, $R^3$ is an unsubstituted heteroaryl (e.g., 5 to 10 membered heteroaryl, 5 to 9 membered heteroaryl, or 5 to 6 membered heteroaryl).

In embodiments, $R^3$ is $R^{15}$-substituted or unsubstituted $C_1$-$C_8$ alkyl. In embodiments, $R^3$ is $R^{15}$-substituted or unsubstituted $C_3$-$C_8$ alkyl. In embodiments, $R^3$ is $R^{15}$-substituted or unsubstituted $C_1$-$C_6$ alkyl. In embodiments, $R^3$ is $R^{15}$-substituted $C_1$ alkyl. In embodiments, $R^3$ is $R^{15}$-substituted $C_2$ alkyl. In embodiments, $R^3$ is $R^{15}$-substituted $C_3$ alkyl. In embodiments, $R^3$ is $R^{15}$-substituted $C_4$ alkyl. In embodiments, $R^3$ is $R^{15}$-substituted $C_5$ alkyl. In embodiments, $R^3$ is $R^{15}$-substituted $C_6$ alkyl. In embodiments, $R^3$ is $R^{15}$-substituted $C_7$ alkyl. In embodiments, $R^3$ is $R^{15}$-substituted $C_8$ alkyl. In embodiments, $R^3$ is unsubstituted $C_1$ alkyl. In embodiments, $R^3$ is unsubstituted $C_2$ alkyl. In embodiments, $R^3$ is unsubstituted $C_3$ alkyl. In embodiments, $R^3$ is unsubstituted $C_4$ alkyl. In embodiments, $R^3$ is unsubstituted $C_5$ alkyl. In embodiments, $R^3$ is unsubstituted $C_6$ alkyl. In embodiments, $R^3$ is unsubstituted $C_7$ alkyl. In embodiments, $R^3$ is unsubstituted $C_8$ alkyl. In embodiments, $R^3$ is $R^{15}$-substituted or unsubstituted linear $C_1$-$C_8$ alkyl. In embodiments, $R^3$ is $R^{15}$-substituted or unsubstituted linear $C_3$-$C_8$ alkyl. In embodiments, $R^3$ is $R^{15}$-substituted or unsubstituted linear $C_1$-$C_6$ alkyl. In embodiments, $R^3$ is $R^{15}$-substituted linear $C_1$ alkyl. In embodiments, $R^3$ is $R^{15}$-substituted linear $C_2$ alkyl. In embodiments, $R^3$ is $R^{15}$-substituted linear $C_3$ alkyl. In embodiments, $R^3$ is $R^{15}$-substituted linear $C_4$ alkyl. In embodiments, $R^3$ is $R^{15}$-substituted linear $C_5$ alkyl. In embodiments, $R^3$ is $R^{15}$-substituted linear $C_6$ alkyl. In embodiments, $R^3$ is $R^{15}$-substituted linear $C_7$ alkyl. In embodiments, $R^3$ is $R^{15}$-substituted linear $C_8$ alkyl. In embodiments, $R^3$ is substituted linear $C_1$-$C_8$ alkyl. In embodiments, $R^3$ is substituted linear $C_3$-$C_8$ alkyl. In embodiments, $R^3$ is substituted linear $C_1$-$C_6$ alkyl. In embodiments, $R^3$ is unsubstituted linear $C_1$-$C_8$ alkyl. In embodiments, $R^3$ is unsubstituted linear $C_3$-$C_8$ alkyl. In embodiments, $R^3$ is unsubstituted linear $C_1$-$C_6$ alkyl. In embodiments, $R^3$ is substituted linear $C_1$ alkyl. In embodiments, $R^3$ is substituted linear $C_2$ alkyl. In embodiments, $R^3$ is substituted linear $C_3$ alkyl. In embodiments, $R^3$ is substituted linear $C_4$ alkyl. In embodiments, $R^3$ is substituted linear $C_5$ alkyl. In embodiments, $R^3$ is substituted linear $C_6$ alkyl. In embodiments, $R^3$ is substituted linear $C_7$ alkyl. In embodiments, $R^3$ is substituted linear $C_8$ alkyl. In embodiments, $R^3$ is unsubstituted linear $C_1$ alkyl. In embodiments, $R^3$ is unsubstituted linear $C_2$ alkyl. In embodiments, $R^3$ is unsubstituted linear $C_3$ alkyl. In embodiments, $R^3$ is unsubstituted linear $C_4$ alkyl. In embodiments, $R^3$ is unsubstituted linear $C_5$ alkyl. In embodiments, $R^3$ is unsubstituted linear $C_6$ alkyl. In embodiments, $R^3$ is unsubstituted linear $C_7$ alkyl. In embodiments, $R^3$ is unsubstituted linear $C_8$ alkyl. In embodiments, $R^3$ is $R^{15}$-substituted or unsubstituted branched $C_3$-$C_8$ alkyl. In embodiments, $R^3$ is $R^{15}$-substituted branched $C_3$ alkyl. In embodiments, $R^3$ is $R^{15}$-substituted branched $C_4$ alkyl. In embodiments, $R^3$ is $R^{15}$-substituted branched $C_5$ alkyl. In embodiments, $R^3$ is $R^{15}$-substituted branched $C_6$ alkyl. In embodiments, $R^3$ is $R^{15}$-substituted branched $C_7$ alkyl. In embodiments, $R^3$ is $R^{15}$-substituted branched $C_8$ alkyl. In embodiments, $R^3$ is substituted branched $C_3$-$C_8$ alkyl. In embodiments, $R^3$ is unsubstituted branched $C_3$-$C_8$ alkyl. In embodiments, $R^3$ is substituted branched $C_3$-$C_8$ alkyl. In embodiments, $R^3$ is substituted branched $C_3$ alkyl. In embodiments, $R^3$ is substituted branched $C_4$ alkyl. In embodiments, $R^3$ is substituted branched $C_5$ alkyl. In embodiments, $R^3$ is substituted branched $C_6$ alkyl. In embodiments, $R^3$ is substituted branched $C_7$ alkyl. In embodiments, $R^3$ is substituted branched $C_8$ alkyl. In embodiments, $R^3$ is unsubstituted branched $C_3$ alkyl. In embodiments, $R^3$ is unsubstituted branched $C_4$ alkyl. In embodiments, $R^3$ is unsubstituted branched $C_5$ alkyl. In embodiments, $R^3$ is unsubstituted branched $C_6$ alkyl. In embodiments, $R^3$ is unsubstituted branched $C_7$ alkyl. In embodiments, $R^3$ is unsubstituted branched $C_8$ alkyl.

In embodiments, $R^3$ is $R^{15}$-substituted or unsubstituted $C_4$-$C_7$ cycloalkyl. In embodiments, $R^3$ is $R^{15}$-substituted $C_4$ cycloalkyl. In embodiments, $R^3$ is $R^{15}$-substituted $C_5$ cycloalkyl. In embodiments, $R^3$ is $R^{15}$-substituted $C_6$ cycloalkyl. In embodiments, $R^3$ is $R^{15}$-substituted $C_7$ cycloalkyl. In embodiments, $R^3$ is unsubstituted $C_4$ cycloalkyl. In embodiments, $R^3$ is unsubstituted $C_5$ cycloalkyl. In embodiments, $R^3$ is unsubstituted $C_6$ cycloalkyl. In embodiments, $R^3$ is unsubstituted $C_7$ cycloalkyl.

In embodiments, $R^3$ is unsubstituted methyl. In embodiments, $R^3$ is unsubstituted ethyl. In embodiments, $R^3$ is unsubstituted propyl. In embodiments, $R^3$ is unsubstituted butyl. In embodiments, $R^3$ is unsubstituted tert-butyl. In embodiments, $R^3$ is unsubstituted cyclopropyl. In embodiments, $R^3$ is unsubstituted cyclobutyl. In embodiments, $R^3$ is unsubstituted cyclopentyl. In embodiments, $R^3$ is unsubstituted cyclohexyl.

In embodiments, $R^3$ is (acyloxy)alkyl or [(alkoxycarbonyl)oxy]methyl. In embodiments, $R^3$ is (acyloxy)alkyl. In embodiments, $R^3$ is [(alkoxycarbonyl)oxy]methyl. In embodiments, $R^3$ is [($C_1$-$C_4$ alkoxycarbonyl)oxy]methyl. In embodiments, $R^3$ is $R^{15}$-substituted $C_1$-$C_4$ alkyl and $R^{15}$ is (acyloxy)alkyl. In embodiments, $R^3$ is $R^{15}$-substituted $C_1$-$C_4$ alkyl and $R^{15}$ is [(alkoxycarbonyl)oxy]methyl. In embodiments, $R^3$ is $R^{15}$-substituted $C_1$-$C_4$ alkyl and $R^{15}$ is [($C_1$-$C_4$ alkoxycarbonyl)oxy]methyl.

In embodiments, $R^3$ is (oxodioxolyl)methyl. In embodiments, $R^3$ is

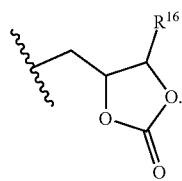

In embodiments, $R^3$ is

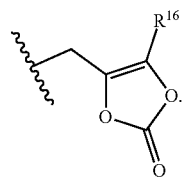

In embodiments, R³ is

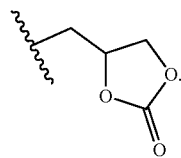 [SMILES: *CC1COC(=O)O1]

In embodiments, R³ is

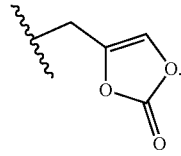 [SMILES: *Cc1coc(=O)o1]

In embodiments, R³ is R¹⁵-substituted C₁-C₄ alkyl and R¹⁵ is oxodioxolyl. In embodiments, R³ is R¹⁵-substituted C₁-C₄ alkyl and R¹⁵ is

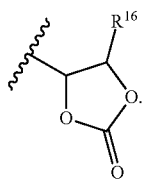

In embodiments, R³ is R¹⁵-substituted C₁-C₄ alkyl and R¹⁵ is

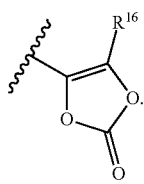

In embodiments, R³ is R¹⁵-substituted C₁-C₄ alkyl and R¹⁵ is

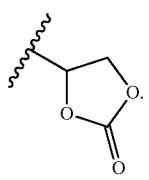

In embodiments, R³ is R¹⁵-substituted C₁-C₄ alkyl and R¹⁵ is

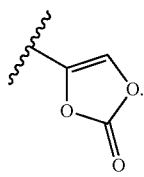 [SMILES: *c1coc(=O)o1]

In embodiments, —R³ is

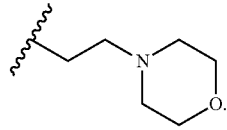 [SMILES: *CCN1CCOCC1]

In embodiments, R³ is R¹⁵-substituted C₁-C₄ alkyl and R¹⁵ is substituted morpholinyl. In embodiments, R³ is R¹⁵-substituted C₁-C₄ alkyl and R¹⁵ is R¹⁶-substituted morpholinyl. In embodiments, R³ is R¹⁵-substituted C₁-C₄ alkyl and R¹⁵ is unsubstituted morpholinyl. In embodiments, R³ is R¹⁵-substituted C₁-C₄ alkyl and R¹⁵ is

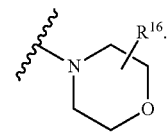

In embodiments, R³ is R¹⁵-substituted C₁-C₄ alkyl and R¹⁵ is

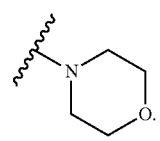

In embodiments, R³ is R¹⁵-substituted C₆-C₁₂ aryl. In embodiments, R³ is R¹⁵-substituted phenyl. In embodiments, R³ is R¹⁵-substituted naphthyl. In embodiments, R³ is substituted C₆-C₁₂ aryl. In embodiments, R³ is substituted phenyl. In embodiments, R³ is substituted naphthyl. In embodiments, R³ is unsubstituted C₆-C₁₂ aryl. In embodiments, R³ is unsubstituted phenyl. In embodiments, R³ is unsubstituted naphthyl.

In embodiments, R³ is R¹⁵-substituted or unsubstituted 4 to 8 membered heterocycloalkyl. In embodiments, R³ is R¹⁵-substituted 4-membered heterocycloalkyl. In embodiments, R³ is R¹⁵-substituted 5-membered heterocycloalkyl. In embodiments, R³ is R¹⁵-substituted 6-membered heterocycloalkyl. In embodiments, R³ is R¹⁵-substituted 7-membered heterocycloalkyl. In embodiments, R³ is R¹⁵-substituted 8-membered heterocycloalkyl. In embodiments, R³ is unsubstituted 4-membered heterocycloalkyl. In embodiments, R³ is unsubstituted 5-membered heterocycloalkyl. In embodiments, R³ is unsubstituted 6-membered heterocycloalkyl. In embodiments, R³ is unsubstituted 7-membered heterocycloalkyl. In embodiments, R³ is unsubstituted 8-membered heterocycloalkyl.

R¹⁵ is independently oxo, halogen, —CCl₃, —CBr₃, —CF₃, —CI₃, CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, NHNH₂, ONH₂, NHC(O)NHNH₂, NHC(O)NH₂, —NHSO₂H, —NHC(O)H, —NHC(O)OH, —NHOH, —OCCl₃, —OCI₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, R¹⁶-substituted or unsubstituted alkyl (e.g., C₁-C₈ alkyl, C₁-C₆ alkyl, or C₁-C₄ alkyl), $R^{16}$-substituted or unsubstituted heteroalkyl (e.g., 2 to 8 membered heteroalkyl, 2 to 6 membered heteroalkyl, or 2 to 4 membered heteroalkyl), $R^{16}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{16}$-substituted or unsubstituted heterocycloalkyl (e.g., 3 to 8 membered heterocycloalkyl, 3 to 6 membered heterocycloalkyl, or 5 to 6 membered heterocycloalkyl), $R^{16}$-substituted or unsubstituted aryl (e.g., $C_6$-$C_{10}$ aryl, $C_{10}$ aryl, or phenyl), or $R^{16}$-substituted or unsubstituted heteroaryl (e.g., 5 to 10 membered heteroaryl, 5 to 9 membered heteroaryl, or 5 to 6 membered heteroaryl). In embodiments, $R^{15}$ is independently oxo, halogen, —$CF_3$, —$CBr_3$, —$CCl_3$, —$CI_3$, —$CHF_2$, —$CHBr_2$, —$CHCl_2$, $CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{15}$ is independently oxo. In embodiments, $R^{15}$ is independently halogen. In embodiments, $R^{15}$ is independently —$CCl_3$. In embodiments, $R^{15}$ is independently —$CBr_3$. In embodiments, $R^{15}$ is independently —$CF_3$. In embodiments, $R^{15}$ is independently —$CI_3$. In embodiments, $R^{15}$ is independently $CHCl_2$. In embodiments, $R^{15}$ is independently —$CHBr_2$. In embodiments, $R^{15}$ is independently —$CHF_2$. In embodiments, $R^{15}$ is independently —$CHI_2$. In embodiments, $R^{15}$ is independently —$CH_2Cl$. In embodiments, $R^{15}$ is independently —$CH_2Br$. In embodiments, $R^{15}$ is independently —$CH_2F$. In embodiments, $R^{15}$ is independently —$CH_2I$. In embodiments, $R^{15}$ is independently —CN. In embodiments, $R^{15}$ is independently —OH. In embodiments, $R^{15}$ is independently —$NH_2$. In embodiments, $R^{15}$ is independently —COOH. In embodiments, $R^{15}$ is independently —$CONH_2$. In embodiments, $R^{15}$ is independently —$NO_2$. In embodiments, $R^{15}$ is independently —SH. In embodiments, $R^{15}$ is independently —$SO_3H$. In embodiments, $R^{15}$ is independently —$SO_4H$. In embodiments, $R^{15}$ is independently —$SO_2NH_2$. In embodiments, $R^{15}$ is independently $NHNH_2$. In embodiments, $R^{15}$ is independently $ONH_2$. In embodiments, $R^{15}$ is independently $NHC(O)NHNH_2$. In embodiments, $R^{15}$ is independently $NHC(O)NH_2$. In embodiments, $R^{15}$ is independently —$NHSO_2H$. In embodiments, $R^{15}$ is independently —NHC(O)H. In embodiments, $R^{15}$ is independently —NHC(O)OH. In embodiments, $R^{15}$ is independently —NHOH. In embodiments, $R^{15}$ is independently —$OCCl_3$. In embodiments, $R^{15}$ is independently —$OCF_3$. In embodiments, $R^{15}$ is independently —$OCBr_3$. In embodiments, $R^{15}$ is independently —$OCI_3$. In embodiments, $R^{15}$ is independently —$OCHCl_2$. In embodiments, $R^{15}$ is independently —$OCHBr_2$. In embodiments, $R^{15}$ is independently —$OCHI_2$. In embodiments, $R^{15}$ is independently —$OCHF_2$. In embodiments, $R^{15}$ is independently —$OCH_2Cl$. In embodiments, $R^{15}$ is independently —$OCH_2Br$. In embodiments, $R^{15}$ is independently —$OCH_2I$. In embodiments, $R^{15}$ is independently —$OCH_2F$. In embodiments, $R^{15}$ is independently —$N_3$.

In embodiments, $R^{15}$ is $R^{16}$-substituted or unsubstituted alkyl (e.g., $C_1$-$C_8$ alkyl, $C_1$-$C_6$ alkyl, or $C_1$-$C_4$ alkyl). In embodiments, $R^{15}$ is $R^{15}$-substituted alkyl (e.g., $C_1$-$C_8$ alkyl, $C_1$-$C_6$ alkyl, or $C_1$-$C_4$ alkyl). In embodiments, $R^{15}$ is an unsubstituted alkyl (e.g., $C_1$-$C_8$ alkyl, $C_1$-$C_6$ alkyl, or $C_1$-$C_4$ alkyl).

In embodiments, $R^{15}$ is $R^{16}$-substituted or unsubstituted heteroalkyl (e.g., 2 to 8 membered heteroalkyl, 2 to 6 membered heteroalkyl, or 2 to 4 membered heteroalkyl). In embodiments, $R^{15}$ is $R^{16}$-substituted heteroalkyl (e.g., 2 to 8 membered heteroalkyl, 2 to 6 membered heteroalkyl, or 2 to 4 membered heteroalkyl). In embodiments, $R^{15}$ is an unsubstituted heteroalkyl (e.g., 2 to 8 membered heteroalkyl, 2 to 6 membered heteroalkyl, or 2 to 4 membered heteroalkyl).

In embodiments, $R^{15}$ is $R^{16}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{15}$ is $R^{16}$-substituted cycloalkyl (e.g., $C_3$-$C_8$ cycloalkyl, $C_3$-$C_6$ cycloalkyl, or $C_5$-$C_6$ cycloalkyl). In embodiments, $R^{15}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{15}$ is $R^{16}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{15}$ is $R^{16}$-substituted heterocycloalkyl (e.g., 3 to 8 membered heterocycloalkyl, 3 to 6 membered heterocycloalkyl, or 5 to 6 membered heterocycloalkyl). In embodiments, $R^{15}$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^{15}$ is morpholinyl.

In embodiments, —$R^3$ is

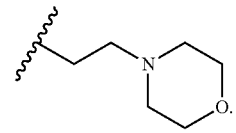

In embodiments, $R^{15}$ is $R^{16}$-substituted or unsubstituted aryl (e.g., $C_6$-$C_{10}$ aryl, $C_{10}$ aryl, or phenyl). In embodiments, $R^{15}$ is $R^{16}$-substituted aryl (e.g., $C_6$-$C_{10}$ aryl, $C_{10}$ aryl, or phenyl). In embodiments, $R^{15}$ is an unsubstituted aryl (e.g., $C_6$-$C_{10}$ aryl, $C_{10}$ aryl, or phenyl).

In embodiments, $R^{15}$ is $R^{16}$-substituted or unsubstituted heteroaryl (e.g., 5 to 10 membered heteroaryl, 5 to 9 membered heteroaryl, or 5 to 6 membered heteroaryl). In embodiments, $R^{15}$ is V-substituted heteroaryl (e.g., 5 to 10 membered heteroaryl, 5 to 9 membered heteroaryl, or 5 to 6 membered heteroaryl). In embodiments, $R^{15}$ is an unsubstituted heteroaryl (e.g., 5 to 10 membered heteroaryl, 5 to 9 membered heteroaryl, or 5 to 6 membered heteroaryl).

$R^{16}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{17}$-substituted or unsubstituted alkyl (e.g., $C_1$-$C_8$ alkyl, $C_1$-$C_6$ alkyl, or $C_1$-$C_4$ alkyl), $R^{17}$-substituted or unsubstituted heteroalkyl (e.g., 2 to 8 membered heteroalkyl, 2 to 6 membered heteroalkyl, or 2 to 4 membered heteroalkyl), $R^{17}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{17}$-substituted or unsubstituted heterocycloalkyl (e.g., 3 to 8 membered heterocycloalkyl, 3 to 6 membered heterocycloalkyl, or 5 to 6 membered heterocycloalkyl), $R^{17}$-substituted or unsubstituted aryl (e.g., $C_6$-$C_{10}$ aryl, $C_{10}$ aryl, or phenyl), or $R^{17}$-substituted or unsubstituted heteroaryl (e.g., 5 to 10 membered heteroaryl, 5 to 9 membered heteroaryl, or 5 to 6 membered heteroaryl). In embodiments, $R^{16}$ is independently oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{16}$ is independently —OH. In embodiments, $R^{16}$ is independently —$OCH_3$. In embodiments, $R^{16}$ is independently —$OCH_2CH_3$. In embodiments, $R^{16}$ is independently —F. In embodiments, $R^{16}$ is independently —$NHC(O)CH_3$. In embodiments, $R^{16}$ is independently —COOH. In embodiments, $R^{16}$ is independently —$SO_2NH_2$.

In embodiments, $R^{17}$ is independently oxo, halogen, —$CF_3$, —$CBr_3$, —$CCl_3$, —$CI_3$, —$CHF_2$, —$CHBr_2$, —$CHC_{l2}$, —$CHI_2$, -$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{3A}$, $R^{3B}$, $R^{3C}$, and $R^{3D}$ are independently hydrogen, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{15}$-substituted or unsubstituted alkyl (e.g., $C_1$-$C_8$ alkyl, $C_1$-$C_6$ alkyl, or $C_1$-$C_4$ alkyl), $R^{15}$-substituted or unsubstituted heteroalkyl (e.g., 2 to 8 membered heteroalkyl, 2 to 6 membered heteroalkyl, or 2 to 4 membered heteroalkyl), $R^{15}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{15}$-substituted or unsubstituted heterocycloalkyl (e.g., 3 to 8 membered heterocycloalkyl, 3 to 6 membered heterocycloalkyl, or 5 to 6 membered heterocycloalkyl), $R^{15}$-substituted or unsubstituted aryl (e.g., $C_6$-$C_{10}$ aryl, $C_{10}$ aryl, or phenyl), or $R^{15}$-substituted or unsubstituted heteroaryl (e.g., 5 to 10 membered heteroaryl, 5 to 9 membered heteroaryl, or 5 to 6 membered heteroaryl). In embodiments, $R^{3A}$ and $R^{3B}$ substituents bonded to the same nitrogen atom are joined to form an $R^{15}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{15}$-substituted or unsubstituted heteroaryl (e.g., 5 to 10 membered heteroaryl, 5 to 9 membered heteroaryl, or 5 to 6 membered heteroaryl). In embodiments, $R^{3A}$ and $R^{3B}$ substituents bonded to the same nitrogen atom are joined to form an $R^{15}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{15}$-substituted or unsubstituted heteroaryl (e.g., 5 to 10 membered heteroaryl, 5 to 9 membered heteroaryl, or 5 to 6 membered heteroaryl). In embodiments, $R^{3A}$ and $R^{3B}$ substituents bonded to the same nitrogen atom are joined to form an $R^{15}$-substituted or unsubstituted heterocycloalkyl (e.g., 3 to 8 membered heterocycloalkyl, 3 to 6 membered heterocycloalkyl. In embodiments, $R^{3A}$ and $R^{3B}$ substituents bonded to the same nitrogen atom are joined to form an $R^{15}$-substituted or unsubstituted heteroaryl (e.g., 5 to 10 membered heteroaryl, 5 to 9 membered heteroaryl, or 5 to 6 membered heteroaryl).

In embodiments, $R^{3C}$ is unsubstituted methyl. In embodiments, $R^{3C}$ is unsubstituted ethyl. In embodiments, $R^{3C}$ is unsubstituted propyl. In embodiments, $R^{3C}$ is unsubstituted butyl. In embodiments, $R^{3C}$ is unsubstituted tert-butyl. In embodiments, $R^{3C}$ is unsubstituted cyclopropyl. In embodiments, $R^{3C}$ is unsubstituted cyclobutyl. In embodiments, $R^{3C}$ is unsubstituted cyclopentyl. In embodiments, $R^{3C}$ is unsubstituted cyclohexyl.

In embodiments, $R^4$ is substituted or unsubstituted alkyl (e.g. $C_1$-$C_8$ alkyl, $C_1$-$C_6$ alkyl, or $C_1$-$C_4$ alkyl). In embodiments, $R^4$ is substituted alkyl (e.g. $C_1$-$C_8$ alkyl, $C_1$-$C_6$ alkyl, or $C_1$-$C_4$ alkyl). In embodiments, $R^4$ is an unsubstituted alkyl (e.g. $C_1$-$C_1$ alkyl, $C_1$-$C_6$ alkyl, or $C_1$-$C_4$ alkyl).

In embodiments, $R^4$ is $R^{18}$-substituted or unsubstituted alkyl (e.g. $C_1$-$C_8$ alkyl, $C_1$-$C_6$ alkyl, or $C_1$-$C_4$ alkyl). In embodiments, $R^4$ is $R^{11}$-substituted alkyl (e.g. $C_1$-$C_8$ alkyl, $C_1$-$C_6$ alkyl, or $C_1$-$C_4$ alkyl). In embodiments, $R^4$ is an unsubstituted alkyl (e.g. $C_1$-$C_8$ alkyl, $C_1$-$C_6$ alkyl, or $C_1$-$C_4$ alkyl). In embodiments, $R^4$ is hydrogen. In embodiments, $R^4$ is unsubstituted methyl. In embodiments, $R^4$ is unsubstituted ethyl. In embodiments, $R^4$ is unsubstituted propyl.

$R^{18}$ is independently halogen, —$CX^{18}_3$, —$CHX^{18}_2$, —$CH_2X^{18}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)OH$, —NHOH, —$OCX^{18}_3$, —$OCHX^{18}_3$, —$OCHX^{18}_2$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^{18}$ is —F, —Cl, —Br, or —I.

In embodiments, $R^5$ is substituted or unsubstituted alkyl (e.g. $C_1$-$C_8$ alkyl, $C_1$-$C_6$ alkyl, or $C_1$-$C_4$ alkyl). In embodiments, $R^5$ is substituted alkyl (e.g. $C_1$-$C_8$ alkyl, $C_1$-$C_6$ alkyl, or $C_1$-$C_4$ alkyl). In embodiments, $R^5$ is an unsubstituted alkyl (e.g. $C_1$-$C_8$ alkyl, $C_1$-$C_6$ alkyl, or $C_1$-$C_4$ alkyl).

In embodiments, $R^5$ is $R^{19}$-substituted or unsubstituted alkyl (e.g. $C_1$-$C_8$ alkyl, $C_1$-$C_6$ alkyl, or $C_1$-$C_4$ alkyl). In embodiments, $R^5$ is substituted alkyl (e.g. $C_1$-$C_8$ alkyl, $C_1$-$C_6$ alkyl, or $C_1$-$C_4$ alkyl). In embodiments, $R^5$ is an unsubstituted alkyl (e.g. $C_1$-$C_8$ alkyl, $C_1$-$C_6$ alkyl, or $C_1$-$C_4$ alkyl). In embodiments, $R^5$ is hydrogen. In embodiments, $R^5$ is unsubstituted methyl. In embodiments, $R^5$ is unsubstituted ethyl. In embodiments, $R^5$ is unsubstituted propyl.

$R^{19}$ is independently halogen, —$CX^{19}_3$, —$CHX^{19}_2$, —$CH_2X^{19}$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, NHC=(O)$NHNH_2$, NHC=(O)$NH_2$, —$NHSO_2H$, —NHC=(O)H, —NHC(O)OH, —NHOH, —$OCX^{19}_3$, —$OCHX^{19}_2$, —$OCH_2X^{19}$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^{19}$ is —F, —Cl, —Br, and —I.

In embodiments, $R^6$ is substituted or unsubstituted alkyl (e.g. $C_1$-$C_8$ alkyl, $C_1$-$C_6$ alkyl, or $C_1$-$C_4$ alkyl). In embodiments, $R^6$ is substituted alkyl (e.g. $C_1$-$C_8$ alkyl, $C_1$-$C_6$ alkyl, or $C_1$-$C_4$ alkyl). In embodiments, $R^6$ is an unsubstituted alkyl (e.g. $C_1$-$C_8$ alkyl, $C_1$-$C_6$ alkyl, or $C_1$-$C_4$ alkyl). In embodiments, $R^6$ is substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl). In embodiments, $R^6$ is substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl). In embodiments, $R^6$ is unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl).

In embodiments, $R^6$ is $R^{20}$-substituted or unsubstituted alkyl (e.g. $C_1$-$C_8$ alkyl, $C_1$-$C_6$ alkyl, or $C_1$-$C_4$ alkyl). In embodiments, $R^6$ is $R^{20}$-substituted alkyl (e.g. $C_1$-$C_8$ alkyl, $C_1$-$C_6$ alkyl, or $C_1$-$C_4$ alkyl). In embodiments, $R^6$ is an unsubstituted alkyl (e.g. $C_1$-$C_8$ alkyl, $C_1$-$C_6$ alkyl, or $C_1$-$C_4$ alkyl). In embodiments, $R^6$ is $R^{20}$-substituted or unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl). In embodiments, $R^6$ is $R^{20}$-substituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl). In embodiments, $R^6$ is unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl). In embodiments, $R^6$ is hydrogen. In embodiments, $R^6$ is unsubstituted methyl. In embodiments, $R^6$ is unsubstituted ethyl. In embodiments, $R^6$ is unsubstituted propyl.

In embodiments, $W^1$ and $R^6$ are joined to form a substituted or unsubstituted heterocycloalkyl, or substituted or unsubstituted heteroaryl. In embodiments, $W^1$ and $R^6$ are joined to form a substituted or unsubstituted heterocycloalkyl. In embodiments, $W^1$ and $R^6$ are joined to form a substituted heterocycloalkyl. In embodiments, $W^1$ and $R^6$ are joined to form an unsubstituted heterocycloalkyl. In embodiments, $W^1$ and $R^6$ are joined to form a substituted or unsubstituted heteroaryl. In embodiments, $W^1$ and $R^6$ are joined to form a substituted heteroaryl. In embodiments, $W^1$ and $R^6$ are joined to form an unsubstituted heteroaryl. In embodiments, $W^1$ and $R^6$ are joined to form a substituted or unsubstituted 5 to 6 membered heterocycloalkyl, or substituted or unsubstituted 5 to 6 membered heteroaryl. In embodiments, $W^1$ and $R^6$ are joined to form a substituted or unsubstituted 5 to 6 membered heterocycloalkyl. In embodiments, $W^1$ and $R^6$ are joined to form a substituted 5 to 6 membered heterocycloalkyl. In embodiments, $W^1$ and $R^6$ are joined to form an unsubstituted 5 to 6 membered heterocycloalkyl. In embodiments, $W^1$ and $R^6$ are joined to form a substituted or unsubstituted 5 to 6 membered heteroaryl. In embodiments, $W^1$ and $R^6$ are joined to form a substituted 5 to 6 membered heteroaryl. In embodiments, $W^1$ and $R^6$ are joined to form an unsubstituted 5 to 6 membered heteroaryl.

In embodiments, $W^1$ and $R^6$ are joined to form $R^{20}$-substituted or unsubstituted heterocycloalkyl (e.g. 3 to 8 membered heterocycloalkyl, 4 to 8 membered heterocycloalkyl, or 5 to 6 membered heterocycloalkyl) or V-substituted or unsubstituted heteroaryl (e.g. 5 to 10 membered heteroaryl, 5 to 9 membered heteroaryl, or 5 to 6 membered heteroaryl).

In embodiments, $W^1$ and $R^6$ are joined to form $R^{20}$-substituted heterocycloalkyl (e.g. 3 to 8 membered heterocycloalkyl, 4 to 8 membered heterocycloalkyl, or 5 to 6 membered heterocycloalkyl) or $R^{20}$-substituted heteroaryl (e.g. 5 to 10 membered heteroaryl, 5 to 9 membered heteroaryl, or 5 to 6 membered heteroaryl). In embodiments, $W^1$ and $R^6$ are joined to form an unsubstituted heterocycloalkyl (e.g. 3 to 8 membered heterocycloalkyl, 4 to 8 membered heterocycloalkyl, or 5 to 6 membered heterocycloalkyl) or unsubstituted heteroaryl (e.g. 5 to 10 membered heteroaryl, 5 to 9 membered heteroaryl, or 5 to 6 membered heteroaryl).

In embodiments, $W^1$ and $R^6$ are joined to form $R^{20}$-substituted heterocycloalkyl (e.g. 3 to 8 membered heterocycloalkyl, 4 to 8 membered heterocycloalkyl, or 5 to 6 membered heterocycloalkyl). In embodiments, $W^1$ and $R^6$ are joined to form $R^{20}$-substituted heteroaryl (e.g. 5 to 10 membered heteroaryl, 5 to 9 membered heteroaryl, or 5 to 6 membered heteroaryl). In embodiments, $W^1$ and $R^6$ are joined to form an unsubstituted heterocycloalkyl (e.g. 3 to 8 membered heterocycloalkyl, 4 to 8 membered heterocycloalkyl, or 5 to 6 membered heterocycloalkyl). In embodiments, $W^1$ and $R^6$ are joined to form an unsubstituted heteroaryl (e.g. 5 to 10 membered heteroaryl, 5 to 9 membered heteroaryl, or 5 to 6 membered heteroaryl).

$R^{20}$ is independently oxo, halogen, —$CX^{20}_3$, —$CHX^{20}_2$, —$CH_2X^{20}$, —CN, —OH, —$NH_2$, —COOH, —$CONH_2$, —$NO_2$, —SH, —$SO_3H$, —$SO_4H$, —$SO_2NH_2$, —$NHNH_2$, $ONH_2$, NHC=(O)$NHNH_2$, NHC=(O)$NH_2$, —$NHSO_2H$, —NHC=(O)H, —NHC(O)OH, —NHOH, —$OCX^{20}_3$, —$OCHX^{20}_2$, —$OCH_2X^{20}$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^{20}$ is —F, —Cl, —Br, or —I.

In embodiments, $R^7$ is independently hydrogen, oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl (e.g., $C_1$-$C_6$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^7$ is independently —F. In embodiments, $R^7$ is independently —Cl. In embodiments, $R^7$ is independently —Br. In embodiments, $R^7$ is independently —I.

In embodiments, $R^7$ is independently hydrogen, oxo, halogen, —$CF_3$, —$CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, $R^{21}$-substituted or unsubstituted alkyl (e.g., $C_1$-$C_8$ alkyl, $C_1$-$C_6$ alkyl, or $C_1$-$C_4$ alkyl), $R^{21}$-substituted or unsubstituted heteroalkyl (e.g., 2 to 8 membered heteroalkyl, 2 to 6 membered heteroalkyl, or 2 to 4 membered heteroalkyl), $R^{21}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{21}$-substituted or unsubstituted heterocycloalkyl (e.g., 3 to 8 membered heterocycloalkyl, 3 to 6 membered heterocycloalkyl, or 5 to 6 membered heterocycloalkyl), $R^{21}$-substituted or unsubstituted aryl (e.g., $C_6$-$C_{10}$ aryl, $C_{10}$ aryl, or phenyl), or $R^{21}$-substituted or unsubstituted heteroaryl (e.g., 5 to 10 membered heteroaryl, 5 to 9 membered heteroaryl, or 5 to 6 membered heteroaryl).

In embodiments, $R^7$ is independently hydrogen, oxo, halogen, —$CF_3$, $CBr_3$, —$CCl_3$, —$CI_3$, —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_6$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^7$ is $R^{21}$-substituted or unsubstituted alkyl (e.g., $C_1$-$C_8$ alkyl, $C_1$-$C_6$ alkyl, or $C_1$-$C_4$ alkyl). In embodiments, $R^7$ is $R^{21}$-substituted alkyl (e.g., $C_1$-$C_8$ alkyl, $C_1$-$C_6$ alkyl, or $C_1$-$C_4$ alkyl). In embodiments, $R^7$ is an unsubstituted alkyl (e.g., $C_1$-$C_8$ alkyl, $C_1$-$C_8$ alkyl, or $C_1$-$C_4$ alkyl). In embodiments, $R^7$ is $R^{21}$-substituted or unsubstituted heteroalkyl (e.g., 2 to 8 membered heteroalkyl, 2 to 6 membered heteroalkyl, or 2 to 4 membered heteroalkyl). In embodiments, $R^7$ is $R^{21}$-substituted heteroalkyl (e.g., 2 to 8 membered heteroalkyl, 2 to 6 membered heteroalkyl, or 2 to 4 membered heteroalkyl). In embodiments, $R^7$ is an unsubstituted heteroalkyl (e.g., 2 to 8 membered heteroalkyl, 2 to 6 membered heteroalkyl, or 2 to 4 membered heteroalkyl). In embodiments, $R^7$ is $R^{21}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^7$ is $R^{21}$-substituted cycloalkyl (e.g., $C_3$-$C_8$ cycloalkyl, $C_3$-$C_6$ cycloalkyl, or $C_5$-$C_6$ cycloalkyl). In embodiments, $R^7$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^7$ is $R^{21}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^7$ is $R^{21}$-substituted heterocycloalkyl (e.g., 3 to 8 membered heterocycloalkyl, 3 to 6 membered heterocycloalkyl, or 5 to 6 membered heterocycloalkyl). In embodiments, $R^7$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^7$ is $R^{21}$-substituted or unsubstituted aryl (e.g., $C_6$-$C_{10}$ aryl, $C_{10}$ aryl, or phenyl). In embodiments, $R^7$ is $R^{21}$-substituted aryl (e.g., $C_6$-$C_{10}$ aryl, $C_{10}$ aryl, or phenyl). In embodiments, $R^7$ is an unsubstituted aryl (e.g., $C_6$-$C_{10}$ aryl, $C_{10}$ aryl, or phenyl). In embodiments, $R^7$ is $R^{21}$-substituted or unsubstituted heteroaryl (e.g., 5 to 10 membered heteroaryl, 5 to 9 membered heteroaryl, or 5 to 6 membered heteroaryl). In embodiments, $R^7$ is $R^{21}$-substituted heteroaryl (e.g., 5 to 10 membered heteroaryl, 5 to 9 membered heteroaryl, or 5 to 6 membered heteroaryl). In embodiments, $R^7$ is an unsubstituted heteroaryl (e.g., 5 to 10 membered heteroaryl, 5 to 9 membered heteroaryl, or 5 to 6 membered heteroaryl).

In embodiments, $R^7$ is substituted or unsubstituted cyclohexyl, substituted or unsubstituted adamantyl, substituted or unsubstituted 1,2,3,4-tetrahydronaphthalenyl, 6,7,8,9-tetrahydro-5H-benzo[7]annulenyl, substituted or unsubstituted 2,3-dihydro-1H-indenyl, substituted or unsubstituted (2r, 3as,5r,6as)-octahydro-2,5-methanopentyl, substituted or unsubstituted bicyclo[3.1.1]heptanyl, substituted or unsubstituted bicyclo[2.2.2]octanyl, substituted or unsubstituted spiro[2.5]octane, substituted or unsubstituted spiro[3.3]heptanyl, substituted or unsubstituted spiro[5.5]undecanyl, substituted or unsubstituted (1r,3r,5r,7r)-spiro[adamantane-2,1'-cyclohexanyl], substituted or unsubstituted (1R,3r,8S)-tricyclo[4.3.1.13,8]undecanyl, or substituted or unsubstituted bicyclo[2.2.1]heptan-2-yl.

In embodiments, $R^7$ is $R^{11}$-substituted or unsubstituted cyclohexyl, $R^{21}$-substituted or unsubstituted adamantyl, $R^{21}$-substituted or unsubstituted 1,2,3,4-tetrahydronaphthalenyl, $R^{21}$-substituted or unsubstituted 2,3-dihydro-1H-indenyl, $R^{21}$-substituted or unsubstituted (2r,3as,5r,6as)-octahydro-2,5-methanopentyl, $R^{2"}$-substituted or unsubstituted bicyclo[3.1.1]heptanyl, $R^{21}$-substituted or unsubstituted bicyclo[2.2.2]octanyl, $R^{21}$-substituted or unsubstituted spiro[2.5]octane, $R^{2"}$-substituted or unsubstituted spiro[3.3]heptanyl, $R^{21}$-substituted or unsubstituted spiro[5.5]undecanyl, $R^{21}$-substituted or unsubstituted (1r,3r,5r,7r)-spiro[adamantane-2,1'-cyclohexanyl], $R^{21}$-substituted or unsubstituted (1R,3r,8S)-tricyclo[4.3.1.13,8]undecanyl, or R²¹-substituted or unsubstituted bicyclo[2.2.1]heptan-2-yl.

In embodiments, R⁷ is substituted cyclohexyl, substituted adamantyl, substituted 1,2,3,4-tetrahydronaphthalenyl, substituted 2,3-dihydro-1H-indenyl, substituted (2r,3as,5r,6as)-octahydro-2,5-methanopentyl, substituted bicyclo[3.1.1]heptanyl, substituted bicyclo[2.2.2]octanyl, substituted spiro[2.5]octane, substituted spiro[3.3]heptanyl, substituted spiro[5.5]undecanyl, substituted (1r,3r,5r,7r)-spiro[adamantane-2,1'-cyclohexanyl], substituted (1R,3r,8S)-tricyclo[4.3.1.13,8]undecanyl, or substituted bicyclo[2.2.1]heptan-2-yl. In embodiments, R⁷ is substituted cyclohexyl. In embodiments, R⁷ is substituted adamantly. In embodiments, R⁷ is substituted 1,2,3,4-tetrahydronaphthalenyl. In embodiments, R⁷ is substituted 2,3-dihydro-1H-indenyl, substituted (2r,3as,5r,6as)-octahydro-2,5-methanopentyl. In embodiments, R⁷ is substituted bicyclo[3.1.1]heptanyl. In embodiments, R⁷ is substituted bicyclo[2.2.2]octanyl. In embodiments, R⁷ is substituted spiro[2.5]octane. In embodiments, R⁷ is substituted spiro[3.3]heptanyl. In embodiments, R⁷ is substituted spiro[5.5]undecanyl. In embodiments, R⁷ is substituted (1r,3r,5r,7r)-spiro[adamantane-2,1'-cyclohexanyl]. In embodiments, R⁷ is substituted (1R,3r,8S)-tricyclo[4.3.1.13,8]undecanyl. In embodiments, R⁷ is substituted bicyclo[2.2.1]heptan-2-yl.

In embodiments, R⁷ is R²¹-substituted cyclohexyl, substituted adamantyl, R²¹-substituted 1,2,3,4-tetrahydronaphthalenyl, substituted 2,3-dihydro-1H-indenyl, R²¹-substituted (2r,3as,5r,6as)-octahydro-2,5-methanopentyl, R²¹-substituted bicyclo[3.1.1]heptanyl, R²¹-substituted bicyclo[2.2.2]octanyl, R²¹-substituted spiro[2.5]octane, R²¹-substituted spiro[3.3]heptanyl, R²¹-substituted spiro[5.5]undecanyl, R²¹-substituted (1r,3r,5r,7r)-spiro[adamantane-2,1'-cyclohexanyl], R²¹-substituted (1R,3r,8S)-tricyclo[4.3.1.13,8]undecanyl, or R²¹-substituted bicyclo[2.2.1]heptan-2-yl. In embodiments, R⁷ is R²¹-substituted cyclohexyl. In embodiments, R⁷ is R²¹-substituted adamantly. In embodiments, R⁷ is R²¹-substituted 1,2,3,4-tetrahydronaphthalenyl. In embodiments, R⁷ is R²¹-substituted 2,3-dihydro-1H-indenyl, R²¹-substituted (2r,3as,5r,6as)-octahydro-2,5-methanopentyl. In embodiments, R⁷ is R²¹-substituted bicyclo[3.1.1]heptanyl. In embodiments, R⁷ is R²¹-substituted bicyclo[2.2.2]octanyl. In embodiments, R⁷ is R²¹-substituted spiro[2.5]octane. In embodiments, R⁷ is R²¹-substituted spiro[3.3]heptanyl. In embodiments, R⁷ is R²¹-substituted spiro[5.5]undecanyl. In embodiments, R⁷ is R²¹-substituted (1r,3r,5r,7r)-spiro[adamantane-2,1'-cyclohexanyl]. In embodiments, R⁷ is R²¹-substituted (1R,3r,8S)-tricyclo[4.3.1.13,8]undecanyl. In embodiments, R⁷ is R²¹-substituted bicyclo[2.2.1]heptan-2-yl.

In embodiments, R⁷ is unsubstituted cyclohexyl, unsubstituted adamantyl, unsubstituted 1,2,3,4-tetrahydronaphthalenyl, unsubstituted 2,3-dihydro-1H-indenyl, unsubstituted (2r,3as,5r,6as)-octahydro-2,5-methanopentyl, unsubstituted bicyclo[3.1.1]heptanyl, unsubstituted bicyclo[2.2.2]octanyl, unsubstituted spiro[2.5]octane, unsubstituted spiro[3.3]heptanyl, unsubstituted spiro[5.5]undecanyl, unsubstituted (1r,3r,5r,7r)-spiro[adamantane-2,1'-cyclohexanyl], unsubstituted (1R,3r,8S)-tricyclo[4.3.1.13,8]undecanyl, or unsubstituted bicyclo[2.2.1]heptan-2-yl. In embodiments, R⁷ is unsubstituted cyclohexyl. In embodiments, R⁷ is unsubstituted adamantly. In embodiments, R⁷ is unsubstituted 1,2,3,4-tetrahydronaphthalenyl. In embodiments, R⁷ is unsubstituted 2,3-dihydro-1H-indenyl. In embodiments, R⁷ is unsubstituted (2r,3as,5r,6as)-octahydro-2,5-methanopentyl. In embodiments, R⁷ is unsubstituted bicyclo[3.1.1]heptanyl. In embodiments, R⁷ is unsubstituted bicyclo[2.2.2]octanyl. In embodiments, R⁷ is unsubstituted spiro[2.5]octane. In embodiments, R⁷ is unsubstituted spiro[3.3]heptanyl. In embodiments, R⁷ is unsubstituted spiro[5.5]undecanyl. In embodiments, R⁷ is unsubstituted (1r,3r,5r,7r)-spiro[adamantane-2,1'-cyclohexanyl]. In embodiments, R⁷ is unsubstituted (1R,3r,88)-tricyclo[4.3.1.13,8]undecanyl. In embodiments, R⁷ is unsubstituted bicyclo[2.2.1]heptan-2-yl.

In embodiments, R⁷ is substituted or unsubstituted phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuranyl, isobenzofuranyl, indolyl, isoindolyl, benzothiophenyl, isoquinolyl, quinoxalinyl, or quinolyl.

In embodiments, R⁷ is R²¹-substituted or unsubstituted phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuranyl, isobenzofuranyl, indolyl, isoindolyl, benzothiophenyl, isoquinolyl, quinoxalinyl, or quinolyl.

In embodiments, R⁷ is substituted or unsubstituted benzimidazolyl, indolyl, or benzofuranyl. In embodiments, R⁷ is unsubstituted benzimidazolyl. In embodiments, R⁷ is unsubstituted indolyl. In embodiments, R⁷ is unsubstituted benzofuranyl.

In embodiments, R⁷ is R²¹-substituted or unsubstituted benzimidazolyl, indolyl, or benzofuranyl. In embodiments, R⁷ is unsubstituted benzimidazolyl. In embodiments, R⁷ is unsubstituted indolyl. In embodiments, R⁷ is unsubstituted benzofuranyl.

In embodiments, R⁷ is

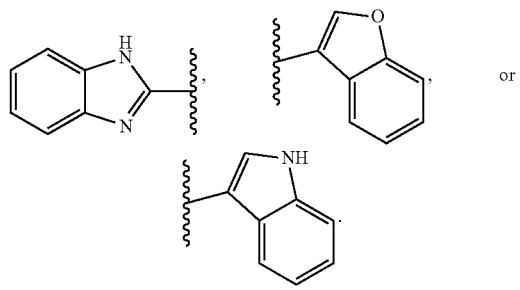

In embodiments, R⁷ is substituted or unsubstituted naphthyl. In embodiments, R⁷ is unsubstituted naphthyl.

In embodiments, R⁷ is

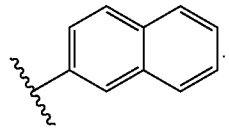 [SMILES: *c1ccc2ccccc2c1]

In embodiments, R⁷ is

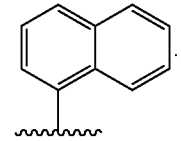 [SMILES: *c1cccc2ccccc12]

In embodiments, $R^7$ is
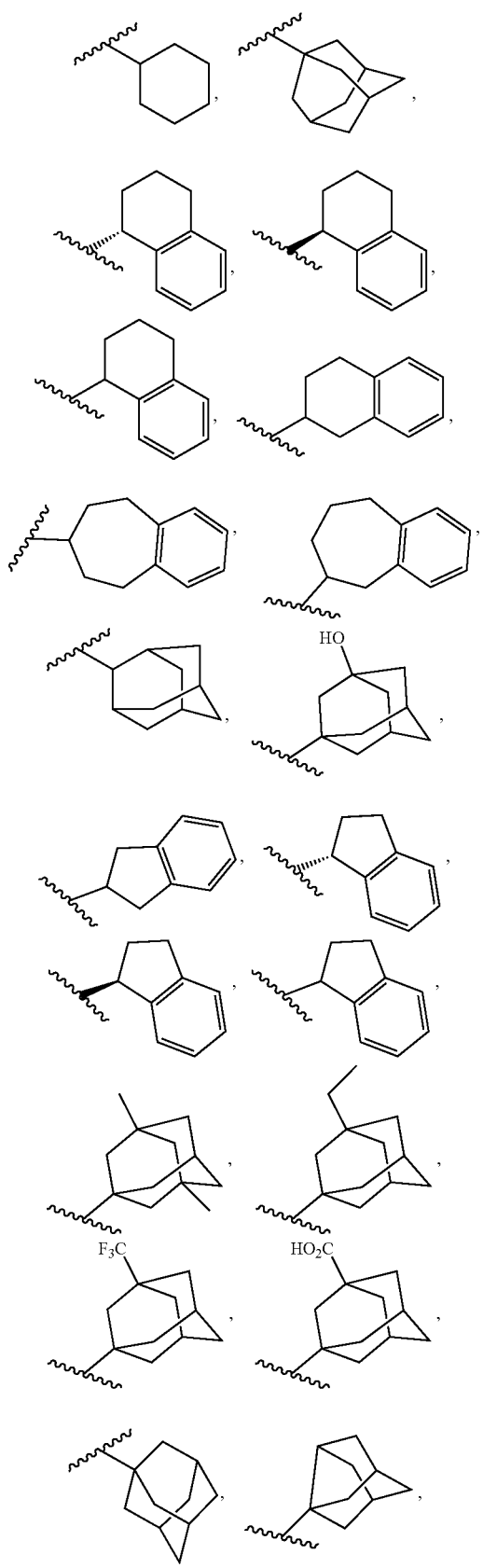
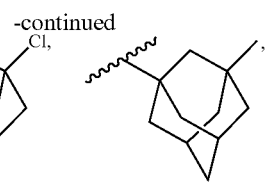
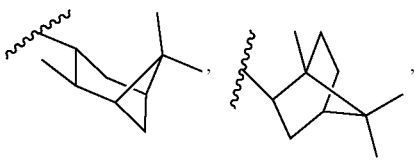
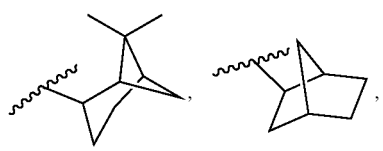
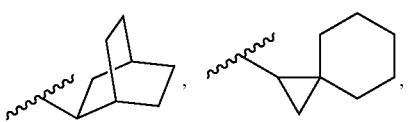
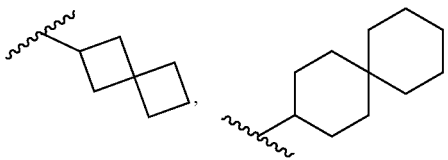
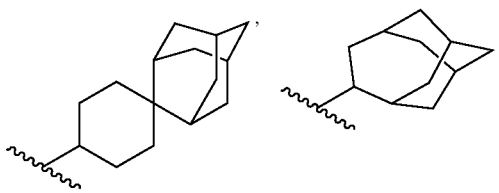
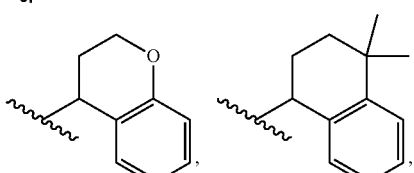
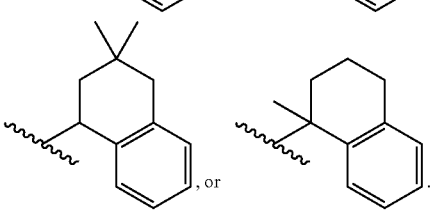
In embodiments, $R^7$ is
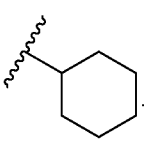 [SMILES: *C1CCCCC1]

In embodiments, R⁷ is
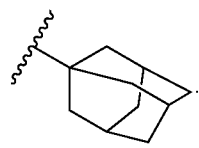 [SMILES: *C12CC3CC(CC(C3)C1)C2]
In embodiments, R⁷ is
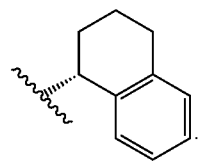 [SMILES: *[C@@H]1CCCc2ccccc21]
In embodiments, R⁷ is
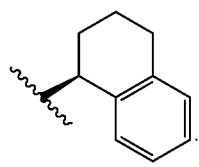 [SMILES: *[C@H]1CCCc2ccccc21]
In embodiments, R⁷ is
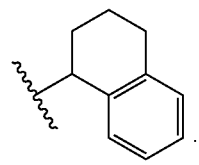 [SMILES: *C1CCCc2ccccc21]
In embodiments, R⁷ is
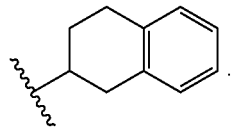 [SMILES: *C1CCc2ccccc2C1]
In embodiments, R⁷ is
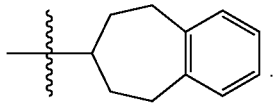 [SMILES: *C1CCc2ccccc2CC1]
In embodiments, R⁷ is
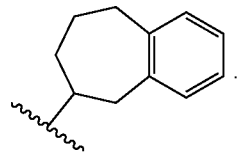 [SMILES: *C1CCCc2ccccc2C1]
In embodiments, R⁷ is
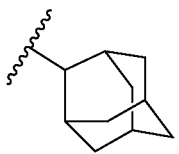
In embodiments, R⁷ is
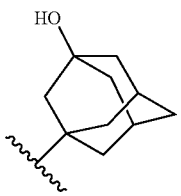
In embodiments, R⁷ is
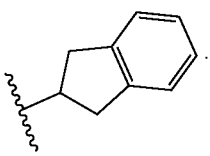 [SMILES: *C1Cc2ccccc2C1]
In embodiments, R⁷ is
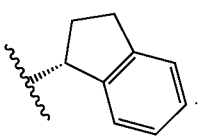 [SMILES: *[C@@H]1CCc2ccccc21]
In embodiments, R⁷ is
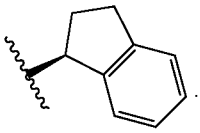 [SMILES: *[C@H]1CCc2ccccc21]
In embodiments, R⁷ is
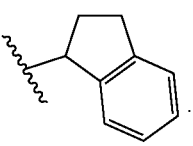 [SMILES: *C1CCc2ccccc21]
In embodiments, R⁷ is
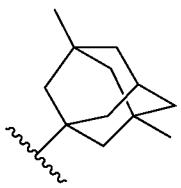

In embodiments, $R^7$ is
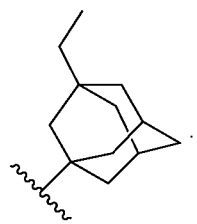 [SMILES: *C12CC3CC(C1)CC(CC)(C3)C2]
In embodiments, $R^7$ is
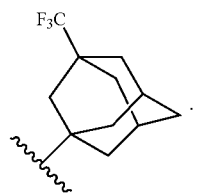 [SMILES: *C12CC3CC(C1)CC(C(F)(F)F)(C3)C2]
In embodiments, $R^7$ is
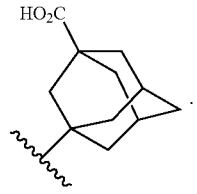 [SMILES: *C12CC3CC(C1)CC(C(=O)O)(C3)C2]
In embodiments, $R^7$ is
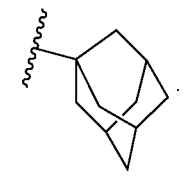 [SMILES: *C12CC3CC(CC(C3)C1)C2]
In embodiments, $R^7$ is
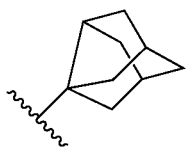
In embodiments, $R^7$ is
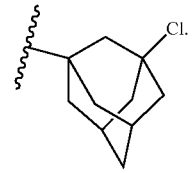 [SMILES: *C12CC3CC(C1)CC(Cl)(C3)C2]
In embodiments, $R^7$ is
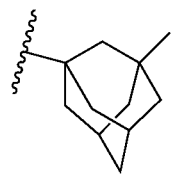
In embodiments, $R^7$ is
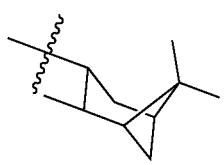
In embodiments, $R^7$ is
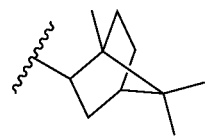
In embodiments, $R^7$ is
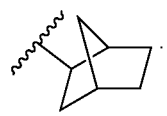
In embodiments, $R^7$ is
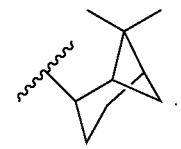 [SMILES: *C1CCC2CC1C2(C)C]
In embodiments, $R^7$ is
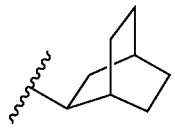
In embodiments, $R^7$ is
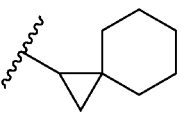

In embodiments, R⁷ is
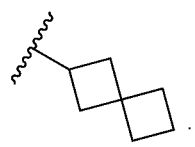 [SMILES: *C1CC2(CCC2)C1]
In embodiments, R⁷ is
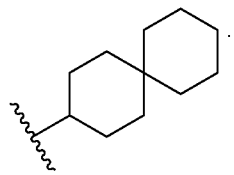 [SMILES: *C1CCC2(CCCCC2)CC1]
In embodiments, R⁷ is
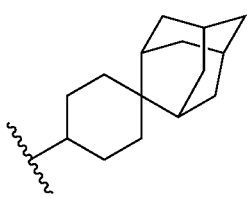
In embodiments, R⁷ is
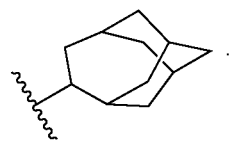 [SMILES: *C1CC2CC3CC(C2)CC1C3]
In embodiments, R⁷ is
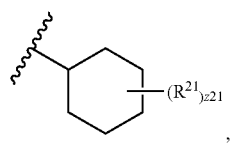
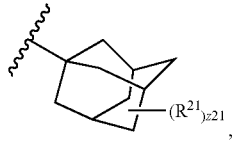
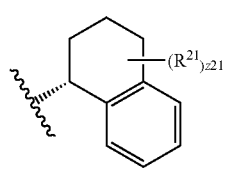
-continued
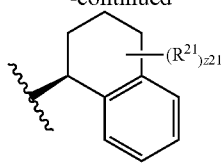
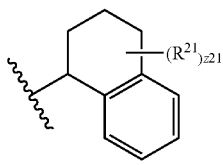
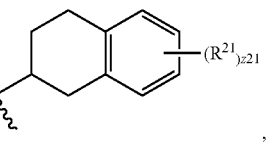
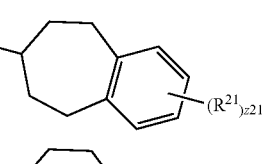
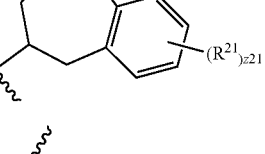
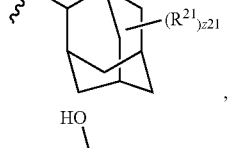
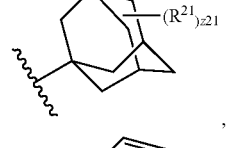
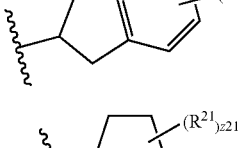
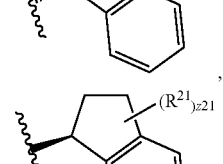
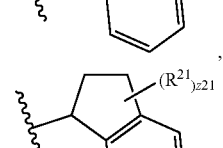
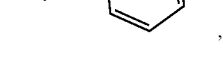

-continued
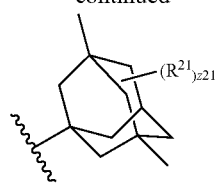,
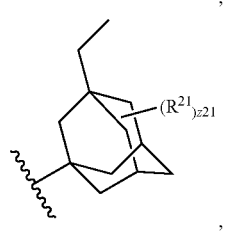,
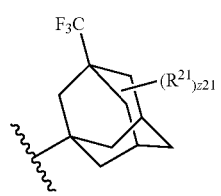,
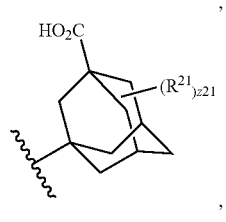,
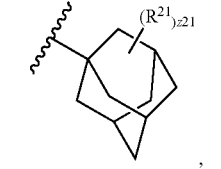,
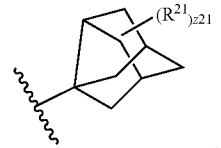,
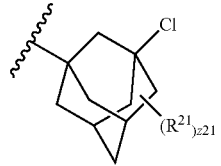,
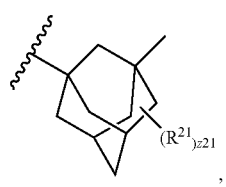,
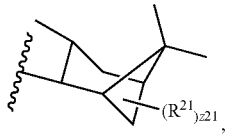,
-continued
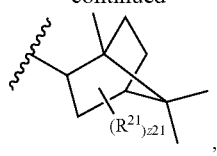,
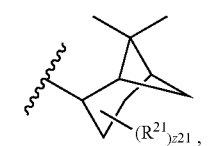,
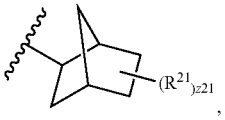,
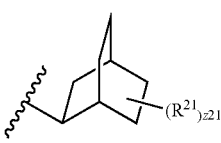,
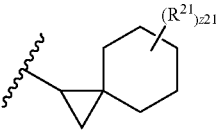,
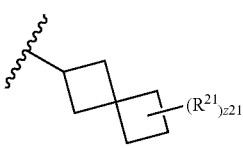,
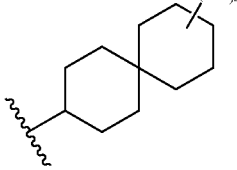,
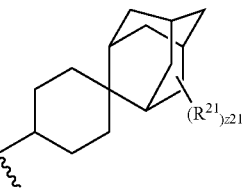,
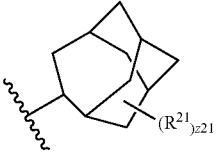,
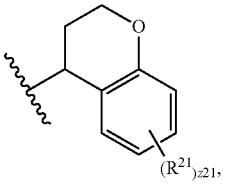, -continued
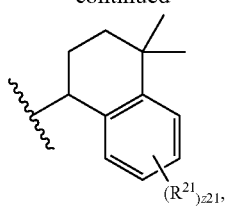
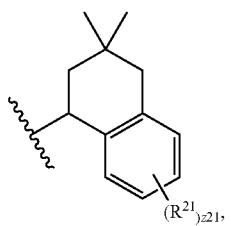
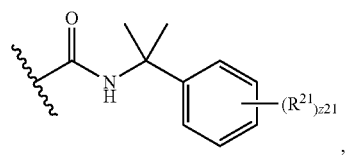
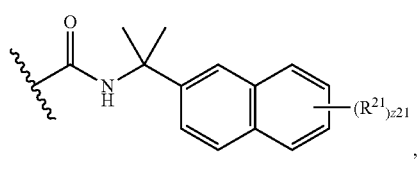
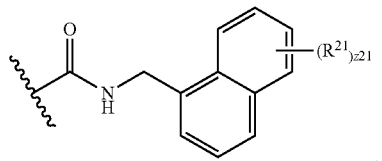
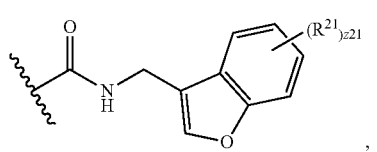
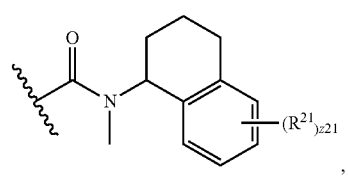
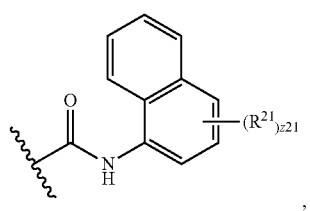
-continued
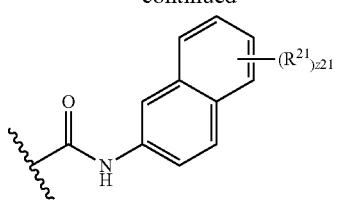
, or
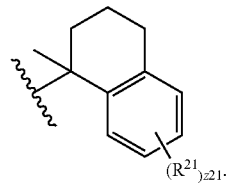
In embodiments, $R^7$ is
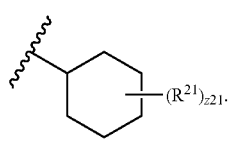
In embodiments, $R^7$ is
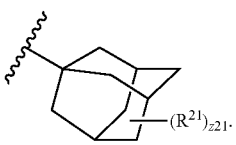
In embodiments, $R^7$ is
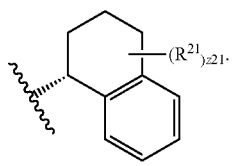
In embodiments, $R^7$ is
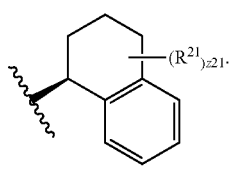
In embodiments, $R^7$ is
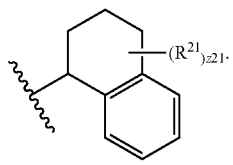

In embodiments, R⁷ is
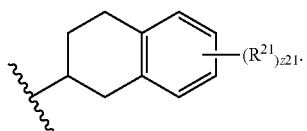
In embodiments, R⁷ is
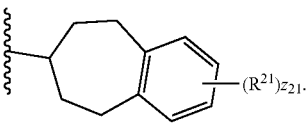
In embodiments, R⁷ is
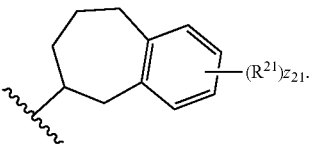
In embodiments, R⁷ is
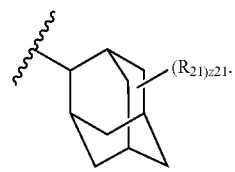
In embodiments, R⁷ is
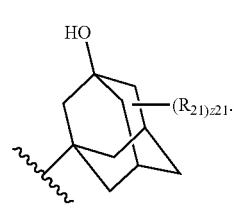
In embodiments, R⁷ is
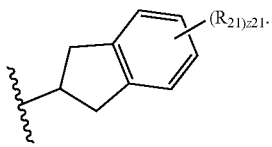
In embodiments, R⁷ is
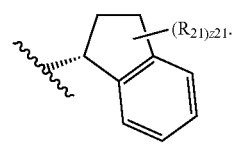
In embodiments, R⁷ is
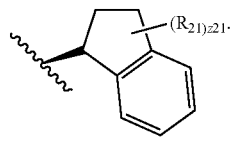
In embodiments, R⁷ is
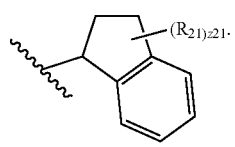
In embodiments, R⁷ is
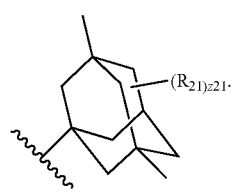
In embodiments, R⁷ is
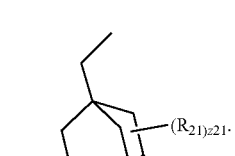
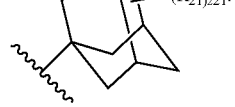
In embodiments, R⁷ is
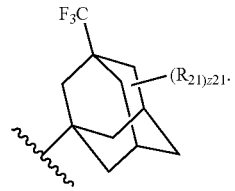
In embodiments, R⁷ is
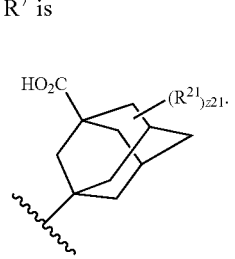

In embodiments, $R^7$ is

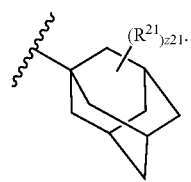

In embodiments, $R^7$ is

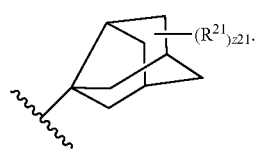

In embodiments, $R^7$ is

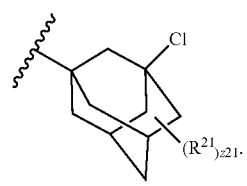

In embodiments, $R^7$ is

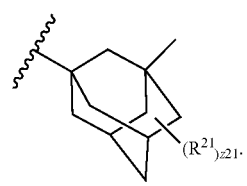

In embodiments, $R^7$ is

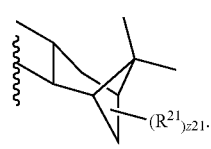

In embodiments, $R^7$ is

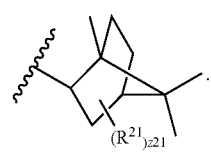

In embodiments, $R^7$ is

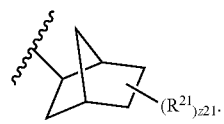

In embodiments, $R^7$ is

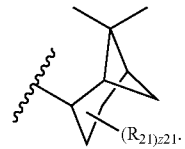

In embodiments, $R^7$ is

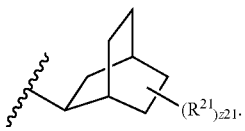

In embodiments, $R^7$ is

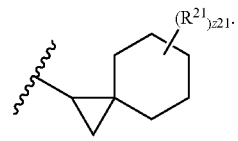

In embodiments, $R^7$ is

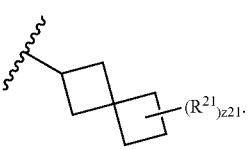

In embodiments, $R^7$ is

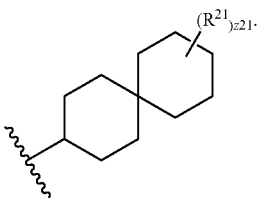

In embodiments, $R^7$ is

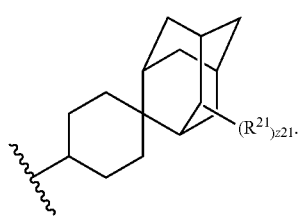

In embodiments, $R^7$ is

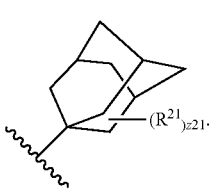

In embodiments, $R^7$ is cycloalkyl. In embodiments, $R^7$ is monocyclic cycloalkyl. In embodiments, $R^7$ is bicyclic cycloalkyl. In embodiments, $R^7$ is tricyclic cycloalkyl. In embodiments, $R^7$ is bridged monocyclic cycloalkyl. In embodiments, $R^7$ is bridged bicyclic cycloalkyl. In embodiments, $R^7$ is bridged tricyclic cycloalkyl. In embodiments, $R^7$ is fused bicyclic cycloalkyl. In embodiments, $R^7$ is fused tricyclic cycloalkyl.

In embodiments, $R^7$ is cycloalkyl (e.g., $C_5$-$C_6$ cycloalkyl). In embodiments, $R^7$ is monocyclic cycloalkyl (e.g., $C_5$-$C_6$ cycloalkyl). In embodiments, $R^7$ is bicyclic cycloalkyl (e.g., $C_9$-$C_{11}$ cycloalkyl or $C_7$-$C_{12}$ cycloalkyl). In embodiments, $R^7$ is tricyclic cycloalkyl (e.g., $C_9$-$C_{11}$ cycloalkyl or $C_7$-$C_{12}$ cycloalkyl). In embodiments, $R^7$ is bridged bicyclic cycloalkyl (e.g., $C_9$-$C_{11}$ cycloalkyl or $C_7$-$C_{12}$ cycloalkyl). In embodiments, $R^7$ is bridged tricyclic cycloalkyl (e.g., $C_9$-$C_{11}$ cycloalkyl or $C_7$-$C_{12}$ cycloalkyl). In embodiments, $R^7$ is fused bicyclic cycloalkyl (e.g., $C_9$-$C_{11}$ cycloalkyl or $C_7$-$C_{12}$ cycloalkyl). In embodiments, $R^7$ is fused tricyclic cycloalkyl (e.g., $C_9$-$C_{11}$ cycloalkyl or $C_7$-$C_{12}$ cycloalkyl).

In embodiments, $R^7$ is substituted or unsubstituted fused bicyclic cycloalkyl (e.g., $C_9$-$C_{11}$ cycloalkyl or $C_7$-$C_{12}$ cycloalkyl). In embodiments, $R^7$ is substituted or unsubstituted $C_7$-$C_{12}$ fused bicyclic cycloalkyl. In embodiments, $R^7$ is substituted or unsubstituted $C_7$-$C_{11}$ fused bicyclic cycloalkyl. In embodiments, $R^7$ is substituted or unsubstituted $C_7$-$C_{10}$ fused bicyclic cycloalkyl. In embodiments, $R^7$ is substituted or unsubstituted $C_7$-$C_9$ fused bicyclic cycloalkyl. In embodiments, $R^7$ is substituted or unsubstituted $C_7$-$C_8$ fused bicyclic cycloalkyl. In embodiments, $R^7$ is substituted or unsubstituted $C_8$-$C_{11}$ fused bicyclic cycloalkyl. In embodiments, $R^7$ is substituted or unsubstituted $C_8$-$C_{10}$ fused bicyclic cycloalkyl. In embodiments, $R^7$ is substituted or unsubstituted $C_8$-$C_9$ fused bicyclic cycloalkyl. In embodiments, $R^7$ is substituted $C_7$-$C_{12}$ fused bicyclic cycloalkyl. In embodiments, $R^7$ is substituted $C_7$-$C_{11}$ fused bicyclic cycloalkyl. In embodiments, $R^7$ is substituted $C_7$-$C_{10}$ fused bicyclic cycloalkyl. In embodiments, $R^7$ is substituted $C_7$-$C_9$ fused bicyclic cycloalkyl. In embodiments, $R^7$ is substituted $C_7$-$C_{11}$ fused bicyclic cycloalkyl. In embodiments, $R^7$ is substituted $C_8$-$C_{11}$ fused bicyclic cycloalkyl. In embodiments, $R^7$ is substituted $C_8$-$C_{10}$ fused bicyclic cycloalkyl. In embodiments, $R^7$ is substituted $C_8$-$C_9$ fused bicyclic cycloalkyl. In embodiments, $R^7$ is unsubstituted $C_7$-$C_{12}$ fused bicyclic cycloalkyl. In embodiments, $R^7$ is unsubstituted $C_7$-$C_{11}$ fused bicyclic cycloalkyl. In embodiments, $R^7$ is unsubstituted $C_7$-$C_{10}$ fused bicyclic cycloalkyl. In embodiments, $R^7$ is unsubstituted $C_7$-$C_9$ fused bicyclic cycloalkyl. In embodiments, $R^7$ is substituted or unsubstituted $C_7$-$C_8$ fused bicyclic cycloalkyl. In embodiments, $R^7$ is unsubstituted $C_8$-$C_{11}$ fused bicyclic cycloalkyl. In embodiments, $R^7$ is unsubstituted $C_8$-$C_{10}$ fused bicyclic cycloalkyl. In embodiments, $R^7$ is unsubstituted $C_8$-$C_9$ fused bicyclic cycloalkyl.

In embodiments, $R^7$ is $R^{21}$-substituted or unsubstituted fused bicyclic cycloalkyl (e.g., $C_9$-$C_{11}$ cycloalkyl or $C_7$-$C_{12}$ cycloalkyl). In embodiments, $R^7$ is $R^{21}$-substituted or unsubstituted $C_7$-$C_{12}$ fused bicyclic cycloalkyl. In embodiments, $R^7$ is $R^{21}$-substituted or unsubstituted C7-$C_{11}$ fused bicyclic cycloalkyl. In embodiments, $R^7$ is $R^{21}$-substituted or unsubstituted $C_7$-$C_{10}$ fused bicyclic cycloalkyl. In embodiments, $R^7$ is $R^{21}$-substituted or unsubstituted $C_7$-$C_9$ fused bicyclic cycloalkyl. In embodiments, $R^7$ is $R^{21}$-substituted or unsubstituted $C_7$-$C_8$ fused bicyclic cycloalkyl. In embodiments, $R^7$ is $R^{21}$-substituted or unsubstituted $C_8$-$C_{11}$ fused bicyclic cycloalkyl. In embodiments, $R^7$ is $W^1$-substituted or unsubstituted $C_8$-$C_{10}$ fused bicyclic cycloalkyl. In embodiments, $R^7$ is $R^{21}$-substituted or unsubstituted $C_8$-$C_9$ fused bicyclic cycloalkyl. In embodiments, $R^7$ is $R^{21}$-substituted $C_7$-$C_{12}$ fused bicyclic cycloalkyl. In embodiments, $R^7$ is $R^{21}$-substituted $C_7$-$C_{11}$ fused bicyclic cycloalkyl. In embodiments, $R^7$ is $R^{21}$-substituted $C_7$-$C_{10}$ fused bicyclic cycloalkyl. In embodiments, $R^7$ is $R^{21}$-substituted $C_7$-$C_9$ fused bicyclic cycloalkyl. In embodiments, $R^7$ is $R^{21}$-substituted $C_7$-$C_8$ fused bicyclic cycloalkyl. In embodiments, $R^7$ is $R^{21}$-substituted $C_8$-$C_{11}$ fused bicyclic cycloalkyl. In embodiments, $R^7$ is $R^{21}$-substituted $C_8$-$C_{10}$ fused bicyclic cycloalkyl. In embodiments, $R^7$ is $R^{21}$-substituted $C_8$-$C_9$ fused bicyclic cycloalkyl.

In embodiments, $R^7$ is substituted or unsubstituted bridged bicyclic cycloalkyl (e.g., $C_9$-$C_{11}$ cycloalkyl or $C_7$-$C_{12}$ cycloalkyl). In embodiments, $R^7$ is substituted or unsubstituted $C_7$-$C_{12}$ bridged bicyclic cycloalkyl. In embodiments, $R^7$ is substituted or unsubstituted $C_7$-$C_{11}$ bridged bicyclic cycloalkyl. In embodiments, $R^7$ is substituted or unsubstituted $C_7$-$C_{10}$ bridged bicyclic cycloalkyl. In embodiments, $R^7$ is substituted or unsubstituted $C_7$-$C_9$ bridged bicyclic cycloalkyl. In embodiments, $R^7$ is substituted or unsubstituted $C_7$-$C_{11}$ bridged bicyclic cycloalkyl. In embodiments, $R^7$ is substituted or unsubstituted $C_8$-$C_{11}$ bridged bicyclic cycloalkyl. In embodiments, $R^7$ is substituted or unsubstituted $C_8$-$C_{10}$ bridged bicyclic cycloalkyl. In embodiments, $R^7$ is substituted or unsubstituted $C_8$-$C_9$ bridged bicyclic cycloalkyl. In embodiments, $R^7$ is substituted $C_7$-$C_{12}$ bridged bicyclic cycloalkyl. In embodiments, $R^7$ is substituted $C_7$-$C_{11}$ bridged bicyclic cycloalkyl. In embodiments, $R^7$ is substituted $C_7$-$C_{10}$ bridged bicyclic cycloalkyl. In embodiments, $R^7$ is substituted $C_7$-$C_9$ bridged bicyclic cycloalkyl. In embodiments, $R^7$ is substituted $C_7$-$C_8$ bridged bicyclic cycloalkyl. In embodiments, $R^7$ is substituted C8-$C_{11}$ bridged bicyclic cycloalkyl. In embodiments, $R^7$ is substituted $C_8$-$C_{10}$ bridged bicyclic cycloalkyl. In embodiments, $R^7$ is substituted $C_8$-$C_9$ bridged bicyclic cycloalkyl. In embodiments, $R^7$ is unsubstituted $C_7$-$C_{12}$ bridged bicyclic cycloalkyl. In embodiments, $R^7$ is unsubstituted C7-$C_{11}$ bridged bicyclic cycloalkyl. In embodiments, $R^7$ is unsubstituted $C_7$-$C_{10}$ bridged bicyclic cycloalkyl. In embodiments, $R^7$ is unsubstituted $C_7$-$C_9$ bridged bicyclic cycloalkyl. In embodiments, $R^7$ is substituted or unsubstituted $C_7$-$C_8$ bridged bicyclic cycloalkyl. In embodiments, $R^7$ is unsubstituted $C_8$-$C_{11}$ bridged bicyclic cycloalkyl. In embodiments, $R^7$ is unsubstituted $C_8$-$C_{10}$ bridged bicyclic cycloalkyl. In embodiments, $R^7$ is unsubstituted $C_8$-$C_9$ bridged bicyclic cycloalkyl.

In embodiments, $R^7$ is $R^{21}$-substituted or unsubstituted bridged bicyclic cycloalkyl (e.g., $C_9$-$C_{11}$ cycloalkyl or $C_7$-$C_{12}$ cycloalkyl). In embodiments, $R^7$ is $R^{21}$-substituted or unsubstituted $C_7$-$C_{12}$ bridged bicyclic cycloalkyl. In embodiments, $R^7$ is $R^{21}$-substituted or unsubstituted $C_7$-$C_{11}$ bridged bicyclic cycloalkyl. In embodiments, $R^7$ is $R^{21}$-substituted or unsubstituted $C_7$-$C_{10}$ bridged bicyclic cycloalkyl. In embodiments, $R^7$ is $R^{21}$-substituted or unsubstituted $C_7$-$C_9$ bridged bicyclic cycloalkyl. In embodiments, $R^7$ is $R^{21}$-substituted or unsubstituted $C_7$-$C_8$ bridged bicyclic cycloalkyl. In embodiments, $R^7$ is $R^{21}$-substituted or unsubstituted $C_8$-$C_{11}$ bridged bicyclic cycloalkyl. In embodiments, $R^7$ is $R^{21}$-substituted or unsubstituted $C_8$-$C_{10}$ bridged bicyclic cycloalkyl. In embodiments, $R^7$ is $R^{21}$-substituted or unsubstituted $C_8$-$C_9$ bridged bicyclic cycloalkyl. In embodiments, $R^7$ is $R^{21}$-substituted C7-$C_{12}$ bridged bicyclic cycloalkyl. In embodiments, $R^7$ is $R^{21}$-substituted $C_7$-$C_{11}$ bridged bicyclic cycloalkyl. In embodiments, $R^7$ is $R^{21}$-substituted $C_7$-$C_{10}$ bridged bicyclic cycloalkyl. In embodiments, $R^7$ is $R^{21}$-substituted $C_7$-$C_9$ bridged bicyclic cycloalkyl. In embodiments, $R^7$ is $R^{21}$-substituted $C_7$-$C_8$ bridged bicyclic cycloalkyl. In embodiments, $R^7$ is $R^{21}$-substituted $C_8$-$C_{11}$ bridged bicyclic cycloalkyl. In embodiments, $R^7$ is $R^{21}$-substituted $C_8$-$C_{12}$ bridged bicyclic cycloalkyl. In embodiments, $R^7$ is $R^{21}$-substituted $C_8$-$C_9$ bridged bicyclic cycloalkyl.

In embodiments, $R^7$ is substituted or unsubstituted spirocyclic bicyclic cycloalkyl (e.g., $C_9$-$C_{11}$ cycloalkyl, $C_7$-$C_{12}$ cycloalkyl, or $C_7$-$C_{15}$ cycloalkyl). In embodiments, $R^7$ is substituted or unsubstituted $C_7$-$C_{15}$ spirocyclic bicyclic cycloalkyl. In embodiments, $R^7$ is substituted or unsubstituted $C_7$-$C_{12}$ spirocyclic bicyclic cycloalkyl. In embodiments, $R^7$ is substituted or unsubstituted $C_7$-$C_{11}$ spirocyclic bicyclic cycloalkyl. In embodiments, $R^7$ is substituted or unsubstituted $C_7$-$C_{10}$ spirocyclic bicyclic cycloalkyl. In embodiments, $R^7$ is substituted or unsubstituted $C_7$-$C_9$ spirocyclic bicyclic cycloalkyl. In embodiments, $R^7$ is substituted or unsubstituted $C_7$-$C_8$ spirocyclic bicyclic cycloalkyl. In embodiments, $R^7$ is substituted or unsubstituted $C_8$-$C_{11}$ spirocyclic bicyclic cycloalkyl. In embodiments, $R^7$ is substituted or unsubstituted $C_8$-$C_{10}$ spirocyclic bicyclic cycloalkyl. In embodiments, $R^7$ is substituted or unsubstituted $C_8$-$C_9$ spirocyclic bicyclic cycloalkyl. In embodiments, $R^7$ is substituted $C_7$-$C_{15}$ spirocyclic bicyclic cycloalkyl. In embodiments, $R^7$ is substituted $C_7$-$C_{12}$ spirocyclic bicyclic cycloalkyl. In embodiments, $R^7$ is substituted $C_7$-$C_{11}$ spirocyclic bicyclic cycloalkyl. In embodiments, $R^7$ is substituted $C_7$-$C_{10}$ spirocyclic bicyclic cycloalkyl. In embodiments, $R^7$ is substituted $C_7$-$C_9$ spirocyclic bicyclic cycloalkyl. In embodiments, $R^7$ is substituted $C_7$-$C_{11}$ spirocyclic bicyclic cycloalkyl. In embodiments, $R^7$ is substituted $C_8$-$C_{11}$ spirocyclic bicyclic cycloalkyl. In embodiments, $R^7$ is substituted $C_8$-$C_{10}$ spirocyclic bicyclic cycloalkyl. In embodiments, $R^7$ is substituted $C_8$-$C_9$ spirocyclic bicyclic cycloalkyl. In embodiments, $R^7$ is unsubstituted $C_7$-$C_{15}$ spirocyclic bicyclic cycloalkyl. In embodiments, $R^7$ is unsubstituted $C_7$-$C_{12}$ spirocyclic bicyclic cycloalkyl. In embodiments, $R^7$ is unsubstituted $C_7$-$C_{11}$ spirocyclic bicyclic cycloalkyl. In embodiments, $R^7$ is unsubstituted $C_7$-$C_{10}$ spirocyclic bicyclic cycloalkyl. In embodiments, $R^7$ is unsubstituted $C_7$-$C_9$ spirocyclic bicyclic cycloalkyl. In embodiments, $R^7$ is substituted or unsubstituted $C_7$-$C_8$ spirocyclic bicyclic cycloalkyl. In embodiments, $R^7$ is unsubstituted $C_8$-$C_{11}$ spirocyclic bicyclic cycloalkyl. In embodiments, $R^7$ is unsubstituted $C_8$-$C_{10}$ spirocyclic bicyclic cycloalkyl. In embodiments, $R^7$ is unsubstituted $C_8$-$C_9$ spirocyclic bicyclic cycloalkyl.

In embodiments, $R^7$ is $R^{21}$-substituted or unsubstituted spirocyclic bicyclic cycloalkyl (e.g., $C_9$-$C_{11}$ cycloalkyl, $C_7$-$C_{12}$ cycloalkyl, or $C_7$-$C_{15}$ cycloalkyl). In embodiments, $R^7$ is $R^{21}$-substituted or unsubstituted $C_7$-$C_{15}$ spirocyclic bicyclic cycloalkyl. In embodiments, $R^7$ is $R^{21}$-substituted or unsubstituted $C_7$-$C_{12}$ spirocyclic bicyclic cycloalkyl. In embodiments, $R^7$ is $R^{21}$-substituted or unsubstituted $C_7$-$C_{11}$ spirocyclic bicyclic cycloalkyl. In embodiments, $R^7$ is $R^{21}$-substituted or unsubstituted $C_7$-$C_{10}$ spirocyclic bicyclic cycloalkyl. In embodiments, $R^7$ is $R^{21}$-substituted or unsubstituted $C_7$-$C_9$ spirocyclic bicyclic cycloalkyl. In embodiments, $R^7$ is $R^{21}$-substituted or unsubstituted $C_7$-$C_8$ g spirocyclic bicyclic cycloalkyl. In embodiments, $R^7$ is $R^{21}$-substituted or unsubstituted $C_8$-$C_{11}$ spirocyclic bicyclic cycloalkyl. In embodiments, $R^7$ is $R^{21}$-substituted or unsubstituted $C_8$-$C_{10}$ spirocyclic bicyclic cycloalkyl. In embodiments, $R^7$ is $R^{21}$-substituted or unsubstituted $C_8$-$C_9$ spirocyclic bicyclic cycloalkyl. In embodiments, $R^7$ is $R^{21}$-substituted $C_7$-$C_{15}$ spirocyclic bicyclic cycloalkyl. In embodiments, $R^7$ is $R^{21}$-substituted $C_7$-$C_{12}$ spirocyclic bicyclic cycloalkyl. In embodiments, $R^7$ is $R^{21}$-substituted $C_7$-$C_{11}$ spirocyclic bicyclic cycloalkyl. In embodiments, $R^7$ is $R^{21}$-substituted $C_7$-$C_{10}$ spirocyclic bicyclic cycloalkyl. In embodiments, $R^7$ is $R^{21}$-substituted $C_7$-$C_9$ spirocyclic bicyclic cycloalkyl. In embodiments, $R^7$ is $R^{21}$-substituted $C_7$-$C_8$ spirocyclic bicyclic cycloalkyl. In embodiments, $R^7$ is $R^{21}$-substituted $C_8$-$C_{11}$ spirocyclic bicyclic cycloalkyl. In embodiments, $R^7$ is $R^{21}$-substituted $C_8$-$C_{10}$ spirocyclic bicyclic cycloalkyl. In embodiments, $R^7$ is $R^{21}$-substituted $C_8$-$C_9$ spirocyclic bicyclic cycloalkyl.

In embodiments, $R^7$ is substituted or unsubstituted fused tricyclic cycloalkyl (e.g., $C_9$-$C_{11}$ cycloalkyl, $C_7$-$C_{12}$ cycloalkyl, or $C_7$-$C_{15}$ cycloalkyl). In embodiments, $R^7$ is substituted or unsubstituted $C_7$-$C_{15}$ fused tricyclic cycloalkyl. In embodiments, $R^7$ is substituted or unsubstituted $C_7$-$C_{12}$ fused tricyclic cycloalkyl. In embodiments, $R^7$ is substituted or unsubstituted $C_7$-$C_{11}$ fused tricyclic cycloalkyl. In embodiments, $R^7$ is substituted or unsubstituted $C_7$-$C_{10}$ fused tricyclic cycloalkyl. In embodiments, $R^7$ is substituted or unsubstituted $C_7$-$C_9$ fused tricyclic cycloalkyl. In embodiments, $R^7$ is substituted or unsubstituted $C_7$-$C_{11}$ fused tricyclic cycloalkyl. In embodiments, $R^7$ is substituted or unsubstituted $C_8$-$C_{11}$ fused tricyclic cycloalkyl. In embodiments, $R^7$ is substituted or unsubstituted $C_8$-$C_{10}$ fused tricyclic cycloalkyl. In embodiments, $R^7$ is substituted or unsubstituted $C_8$-$C_9$ fused tricyclic cycloalkyl. In embodiments, $R^7$ is substituted $C_7$-$C_{15}$ fused tricyclic cycloalkyl. In embodiments, $R^7$ is substituted $C_7$-$C_{12}$ fused tricyclic cycloalkyl. In embodiments, $R^7$ is substituted $C_7$-$C_{11}$ fused tricyclic cycloalkyl. In embodiments, $R^7$ is substituted $C_7$-$C_{10}$ fused tricyclic cycloalkyl. In embodiments, $R^7$ is substituted $C_7$-$C_9$ fused tricyclic cycloalkyl. In embodiments, $R^7$ is substituted $C_7$-$C_8$ fused tricyclic cycloalkyl. In embodiments, $R^7$ is substituted $C_8$-$C_{11}$ fused tricyclic cycloalkyl. In embodiments, $R^7$ is substituted $C_8$-$C_{10}$ fused tricyclic cycloalkyl. In embodiments, $R^7$ is substituted $C_8$-$C_9$ fused tricyclic cycloalkyl. In embodiments, $R^7$ is unsubstituted $C_7$-$C_{15}$ fused tricyclic cycloalkyl. In embodiments, $R^7$ is unsubstituted $C_7$-$C_{12}$ fused tricyclic cycloalkyl. In embodiments, $R^7$ is unsubstituted $C_7$-$C_{11}$ fused tricyclic cycloalkyl. In embodiments, $R^7$ is unsubstituted $C_7$-$C_{10}$ fused tricyclic cycloalkyl. In embodiments, $R^7$ is unsubstituted $C_7$-$C_9$ fused tricyclic cycloalkyl. In embodiments, $R^7$ is substituted or unsubstituted $C_7$-$C_{11}$ fused tricyclic cycloalkyl. In embodiments, $R^7$ is unsubstituted $C_8$-$C_{11}$ fused tricyclic cycloalkyl. In embodiments, $R^7$ is unsubstituted $C_8$-$C_{10}$ fused tricyclic cycloalkyl. In embodiments, $R^7$ is unsubstituted $C_8$-$C_9$ fused tricyclic cycloalkyl.

In embodiments, $R^7$ is $R^{21}$-substituted or unsubstituted fused tricyclic cycloalkyl (e.g., $C_9$-$C_{11}$ cycloalkyl, $C_7$-$C_{12}$ cycloalkyl, or $C_7$-$C_{15}$ cycloalkyl). In embodiments, $R^7$ is $R^{21}$-substituted or unsubstituted $C_7$-$C_{15}$ fused tricyclic cycloalkyl. In embodiments, $R^7$ is $R^{21}$-substituted or unsubstituted $C_7$-$C_{12}$ fused tricyclic cycloalkyl. In embodiments, $R^7$ is $R^{21}$-substituted or unsubstituted $C_7$-$C_{11}$ fused tricyclic cycloalkyl. In embodiments, $R^7$ is $R^{21}$-substituted or unsubstituted $C_7$-$C_{10}$ fused tricyclic cycloalkyl. In embodiments, $R^7$ is $R^{21}$-substituted or unsubstituted $C_7$-$C_9$ fused tricyclic cycloalkyl. In embodiments, $R^7$ is $R^{21}$-substituted or unsubstituted $C_7$-$C_{11}$ fused tricyclic cycloalkyl. In embodiments, $R^7$ is $R^{21}$-substituted or unsubstituted $C_8$-$C_{11}$ fused tricyclic cycloalkyl. In embodiments, $R^7$ is $R^{21}$-substituted or unsubstituted $C_8$-$C_{10}$ fused tricyclic cycloalkyl. In embodiments, $R^7$ is $R^{21}$-substituted substituted or unsubstituted $C_8$-$C_9$ fused tricyclic cycloalkyl. In embodiments, $R^7$ is $R^{21}$-substituted $C_7$-$C_{15}$ fused tricyclic cycloalkyl. In embodiments, $R^7$ is $R^{21}$-substituted $C_7$-$C_{12}$ fused tricyclic cycloalkyl. In embodiments, $R^7$ is $R^{21}$-substituted $C_7$-$C_{11}$ fused tricyclic cycloalkyl. In embodiments, $R^7$ is $R^{21}$-substituted $C_7$-$C_{10}$ fused tricyclic cycloalkyl. In embodiments, $R^7$ is $R^{21}$-substituted $C_7$-$C_9$ fused tricyclic cycloalkyl. In embodiments, $R^7$ is $R^{21}$-substituted $C_7$-$C_8$ fused tricyclic cycloalkyl. In embodiments, $R^7$ is $R^{21}$-substituted $C_8$-$C_{11}$ fused tricyclic cycloalkyl. In embodiments, $R^7$ is $R^{21}$-substituted $C_8$-$C_{10}$ fused tricyclic cycloalkyl. In embodiments, $R^7$ is $R^{21}$-substituted $C_8$-$C_9$ fused tricyclic cycloalkyl.

In embodiments, $R^7$ is substituted or unsubstituted bridged tricyclic cycloalkyl (e.g., $C_9$-$C_{11}$ cycloalkyl, $C_7$-$C_{12}$ cycloalkyl, or $C_7$-$C_{15}$ cycloalkyl). In embodiments, $R^7$ is substituted or unsubstituted $C_7$-$C_{15}$ bridged tricyclic cycloalkyl. In embodiments, $R^7$ is substituted or unsubstituted $C_7$-$C_{12}$ bridged tricyclic cycloalkyl. In embodiments, $R^7$ is substituted or unsubstituted $C_7$-$C_{11}$ bridged tricyclic cycloalkyl. In embodiments, $R^7$ is substituted or unsubstituted $C_7$-$C_{10}$ bridged tricyclic cycloalkyl. In embodiments, $R^7$ is substituted or unsubstituted $C_7$-$C_9$ bridged tricyclic cycloalkyl. In embodiments, $R^7$ is substituted or unsubstituted $C_7$-$C_8$ bridged tricyclic cycloalkyl. In embodiments, $R^7$ is substituted or unsubstituted $C_8$-$C_{11}$ bridged tricyclic cycloalkyl. In embodiments, $R^7$ is substituted or unsubstituted $C_8$-$C_{10}$ bridged tricyclic cycloalkyl. In embodiments, $R^7$ is substituted or unsubstituted $C_8$-$C_9$ bridged tricyclic cycloalkyl. In embodiments, $R^7$ is substituted $C_7$-$C_{15}$ bridged tricyclic cycloalkyl. In embodiments, $R^7$ is substituted $C_7$-$C_{12}$ bridged tricyclic cycloalkyl. In embodiments, $R^7$ is substituted $C_7$-$C_{11}$ bridged tricyclic cycloalkyl. In embodiments, $R^7$ is substituted $C_7$-$C_{10}$ bridged tricyclic cycloalkyl. In embodiments, $R^7$ is substituted $C_7$-$C_9$ bridged tricyclic cycloalkyl. In embodiments, $R^7$ is substituted $C_7$-$C_8$ bridged tricyclic cycloalkyl. In embodiments, $R^7$ is substituted $C_8$-$C_{11}$ bridged tricyclic cycloalkyl. In embodiments, $R^7$ is substituted $C_8$-$C_{10}$ bridged tricyclic cycloalkyl. In embodiments, $R^7$ is substituted $C_8$-$C_9$ bridged tricyclic cycloalkyl. In embodiments, $R^7$ is unsubstituted $C_7$-$C_{15}$ bridged tricyclic cycloalkyl. In embodiments, $R^7$ is unsubstituted $C_7$-$C_{12}$ bridged tricyclic cycloalkyl. In embodiments, $R^7$ is unsubstituted $C_7$-$C_{11}$ bridged tricyclic cycloalkyl. In embodiments, $R^7$ is unsubstituted $C_7$-$C_{10}$ bridged tricyclic cycloalkyl. In embodiments, $R^7$ is unsubstituted $C_7$-$C_9$ bridged tricyclic cycloalkyl. In embodiments, $R^7$ is substituted or unsubstituted $C_7$-$C_8$ bridged tricyclic cycloalkyl. In embodiments, $R^7$ is unsubstituted $C_8$-$C_{11}$ bridged tricyclic cycloalkyl. In embodiments, $R^7$ is unsubstituted $C_8$-$C_{10}$ bridged tricyclic cycloalkyl. In embodiments, $R^7$ is unsubstituted $C_8$-$C_9$ bridged tricyclic cycloalkyl.

In embodiments, $R^7$ is $R^{21}$-substituted or unsubstituted bridged tricyclic cycloalkyl (e.g., $C_9$-$C_{11}$ cycloalkyl, $C_7$-$C_{12}$ cycloalkyl, or $C_7$-$C_{15}$ cycloalkyl). In embodiments, $R^7$ is $R^{21}$-substituted or unsubstituted $C_7$-$C_{15}$ bridged tricyclic cycloalkyl. In embodiments, $R^7$ is $R^{21}$-substituted or unsubstituted $C_7$-$C_{12}$ bridged tricyclic cycloalkyl. In embodiments, $R^7$ is $R^{21}$-substituted or unsubstituted $C_7$-$C_{11}$ bridged tricyclic cycloalkyl. In embodiments, $R^7$ is $R^{21}$-substituted or unsubstituted $C_7$-$C_{10}$ bridged tricyclic cycloalkyl. In embodiments, $R^7$ is $R^{21}$-substituted or unsubstituted $C_7$-$C_9$ bridged tricyclic cycloalkyl. In embodiments, $R^7$ is $R^{21}$-substituted or unsubstituted $C_7$-$C_8$ bridged tricyclic cycloalkyl. In embodiments, $R^7$ is $R^{21}$-substituted or unsubstituted $C_8$-$C_{11}$ bridged tricyclic cycloalkyl. In embodiments, $R^7$ is $R^{21}$-substituted or unsubstituted $C_8$-$C_{10}$ bridged tricyclic cycloalkyl. In embodiments, $R^7$ is $R^{21}$-substituted or unsubstituted $C_8$-$C_9$ bridged tricyclic cycloalkyl. In embodiments, $R^7$ is $R^{21}$-substituted $C_7$-$C_{15}$ bridged tricyclic cycloalkyl. In embodiments, $R^7$ is $R^{21}$-substituted $C_7$-$C_{12}$ bridged tricyclic cycloalkyl. In embodiments, $R^7$ is $R^{21}$-substituted $C_7$-$C_{11}$ bridged tricyclic cycloalkyl. In embodiments, $R^7$ is $R^{21}$-substituted $C_7$-$C_{10}$ bridged tricyclic cycloalkyl. In embodiments, $R^7$ is $R^{21}$-substituted $C_7$-$C_9$ bridged tricyclic cycloalkyl. In embodiments, $R^7$ is $R^{21}$-substituted $C_7$-$C_8$ bridged tricyclic cycloalkyl. In embodiments, $R^7$ is $R^{21}$-substituted $C_8$-$C_{11}$ bridged tricyclic cycloalkyl. In embodiments, $R^7$ is $R^{21}$-substituted $C_8$-$C_{10}$ bridged tricyclic cycloalkyl. In embodiments, $R^7$ is $R^{21}$-substituted $C_8$-$C_9$ bridged tricyclic cycloalkyl.

In embodiments, $R^7$ is substituted or unsubstituted spirocyclic tricyclic cycloalkyl (e.g., $C_9$-$C_{11}$ cycloalkyl, $C_9$-$C_{15}$ cycloalkyl, or $C_{12}$-$C_{18}$ cycloalkyl). In embodiments, $R^7$ is substituted or unsubstituted $C_{12}$-$C_{18}$ spirocyclic tricyclic cycloalkyl. In embodiments, $R^7$ is substituted or unsubstituted $C_9$-$C_{15}$ spirocyclic tricyclic cycloalkyl. In embodiments, $R^7$ is substituted or unsubstituted $C_9$-$C_{12}$ spirocyclic tricyclic cycloalkyl. In embodiments, $R^7$ is substituted or unsubstituted $C_9$-$C_{11}$ spirocyclic tricyclic cycloalkyl. In embodiments, $R^7$ is substituted or unsubstituted $C_{12}$-$C_{18}$ spirocyclic tricyclic cycloalkyl. In embodiments, $R^7$ is substituted $C_9$-$C_{15}$ spirocyclic tricyclic cycloalkyl. In embodiments, $R^7$ is substituted $C_9$-$C_{12}$ spirocyclic tricyclic cycloalkyl. In embodiments, $R^7$ is substituted $C_9$-$C_{11}$ spirocyclic tricyclic cycloalkyl. In embodiments, $R^7$ is substituted $C_9$-$C_{10}$ spirocyclic tricyclic cycloalkyl. In embodiments, $R^7$ is unsubstituted $C_{12}$-$C_{18}$ spirocyclic tricyclic cycloalkyl. In embodiments, $R^7$ is unsubstituted $C_9$-$C_{15}$ spirocyclic tricyclic cycloalkyl. In embodiments, $R^7$ is unsubstituted $C_9$-$C_{12}$ spirocyclic tricyclic cycloalkyl. In embodiments, $R^7$ is unsubstituted $C_9$-$C_{11}$ spirocyclic tricyclic cycloalkyl. In embodiments, $R^7$ is unsubstituted $C_9$-$C_{10}$ spirocyclic tricyclic cycloalkyl.

In embodiments, $R^7$ is $R^{21}$-substituted or unsubstituted spirocyclic tricyclic cycloalkyl (e.g., $C_9$-$C_{11}$ cycloalkyl, $C_9$-$C_{15}$ cycloalkyl, or $C_{12}$-$C_{18}$ cycloalkyl). In embodiments, $R^7$ is $R^{21}$-substituted or unsubstituted $C_{12}$-$C_{18}$ spirocyclic tricyclic cycloalkyl. In embodiments, $R^7$ is $R^{21}$-substituted or unsubstituted $C_9$-$C_{15}$ spirocyclic tricyclic cycloalkyl. In embodiments, $R^7$ is $R^{21}$-substituted or unsubstituted $C_9$-$C_{12}$ spirocyclic tricyclic cycloalkyl. In embodiments, $R^7$ is $R^{21}$-substituted or unsubstituted $C_9$-$C_{11}$ spirocyclic tricyclic cycloalkyl. In embodiments, $R^7$ is $R^{21}$-substituted or unsubstituted $C_{12}$-$C_{18}$ spirocyclic tricyclic cycloalkyl. In embodiments, $R^7$ is $R^{21}$-substituted $C_9$-$C_{15}$ spirocyclic tricyclic cycloalkyl. In embodiments, $R^7$ is $R^{21}$-substituted $C_9$-$C_{12}$ spirocyclic tricyclic cycloalkyl. In embodiments, $R^7$ is $R^{21}$-substituted $C_9$-$C_{11}$ spirocyclic tricyclic cycloalkyl. In embodiments, $R^7$ is $R^{21}$-substituted $C_9$-$C_{10}$ spirocyclic tricyclic cycloalkyl.

In embodiments, $R^7$ is a $C_9$-$C_{14}$ fused bicyclic aryl. In embodiments, $R^7$ is a $C_9$ fused bicyclic aryl. In embodiments, $R^7$ is a $C_{10}$ fused bicyclic aryl. In embodiments, $R^7$ is a $C_{11}$ fused bicyclic aryl. In embodiments, $R^7$ is a $C_{12}$ fused bicyclic aryl. In embodiments, $R^7$ is a CH fused bicyclic aryl. In embodiments, $R^7$ is a $C_{14}$ fused bicyclic aryl. In embodiments, $R^7$ is a fused bicyclic aryl wherein a cycloalkyl ring is fused to a phenyl group. In embodiments, $R^7$ is a fused bicyclic aryl wherein a cycloalkyl ring is fused to an aryl group. In embodiments, $R^7$ is an 8 to 12 membered fused bicyclic heteroaryl. In embodiments, $R^7$ is an 8 to 10 membered fused bicyclic heteroaryl. In embodiments, $R^7$ is a fused bicyclic heteroaryl wherein a cycloalkyl ring is fused to a heteroaryl group. In embodiments, $R^7$ is a fused bicyclic heteroaryl wherein a cycloalkyl ring is fused to a 6-membered heteroaryl group. In embodiments, $R^7$ is a fused bicyclic heteroaryl wherein a cycloalkyl ring is fused to a 5-membered heteroaryl group. In embodiments, $R^7$ is an 8-membered fused bicyclic heteroaryl wherein a cycloalkyl is fused to a heteroaryl ring with three heteroatoms. In embodiments, $R^7$ is a 9-membered fused bicyclic heteroaryl wherein a cycloalkyl is fused to a heteroaryl ring with two heteroatoms. In embodiments, $R^7$ is a 10-membered fused bicyclic heteroaryl wherein a cycloalkyl is fused to a heteroaryl ring with one heteroatom. In embodiments, $R^7$ is an 8-membered fused bicyclic heteroaryl wherein a cycloalkyl is fused to a heteroaryl ring with three heteroatoms. In embodiments, $R^7$ is a 9-membered fused bicyclic heteroaryl wherein a cycloalkyl is fused to a heteroaryl ring with two heteroatoms. In embodiments, $R^7$ is a 10-membered fused bicyclic heteroaryl wherein a cycloalkyl is fused to a heteroaryl ring with one heteroatom.

In embodiments, $R^7$ is heterocycloalkyl. In embodiments, $R^7$ is monocyclic heterocycloalkyl. In embodiments, $R^7$ is bicyclic heterocycloalkyl. In embodiments, $R^7$ is tricyclic heterocycloalkyl. In embodiments, $R^7$ is bridged monocyclic heterocycloalkyl. In embodiments, $R^7$ is bridged bicyclic heterocycloalkyl. In embodiments, $R^7$ is bridged tricyclic heterocycloalkyl. In embodiments, $R^7$ is fused bicyclic heterocycloalkyl. In embodiments, $R^7$ is fused tricyclic heterocycloalkyl.

In embodiments, $R^7$ is heterocycloalkyl (e.g., $C_5$-$C_6$ heterocycloalkyl). In embodiments, $R^7$ is monocyclic heterocycloalkyl (e.g., $C_5$-$C_6$ heterocycloalkyl). In embodiments, $R^7$ is bicyclic heterocycloalkyl (e.g., $C_9$-$C_{11}$ heterocycloalkyl or $C_7$-$C_{12}$ heterocycloalkyl). In embodiments, $R^7$ is tricyclic heterocycloalkyl (e.g., $C_9$-$C_{11}$ heterocycloalkyl or $C_7$-$C_{12}$ heterocycloalkyl). In embodiments, $R^7$ is bridged bicyclic heterocycloalkyl (e.g., $C_9$-$C_{11}$ heterocycloalkyl or $C_7$-$C_{12}$ heterocycloalkyl). In embodiments, $R^7$ is bridged tricyclic heterocycloalkyl (e.g., $C_9$-$C_{11}$ heterocycloalkyl or $C_7$-$C_{12}$ heterocycloalkyl). In embodiments, $R^7$ is fused bicyclic heterocycloalkyl (e.g., $C_9$-$C_{11}$ heterocycloalkyl or $C_7$-$C_{12}$ heterocycloalkyl). In embodiments, $R^7$ is fused tricyclic heterocycloalkyl (e.g., $C_9$-$C_{11}$ heterocycloalkyl or $C_7$-$C_{12}$ heterocycloalkyl).

In embodiments, $R^7$ is a $C_9$-$C_{10}$ fused bicyclic heterocycloalkyl. In embodiments, $R^7$ is a $C_9$ fused bicyclic heterocycloalkyl. In embodiments, $R^7$ is a $C_{10}$ fused bicyclic heterocycloalkyl.

In embodiments, $R^7$ is substituted or unsubstituted fused bicyclic heterocycloalkyl (e.g., $C_9$-$C_{11}$ heterocycloalkyl or $C_7$-$C_{12}$ heterocycloalkyl). In embodiments, $R^7$ is substituted or unsubstituted $C_7$-$C_{12}$ fused bicyclic heterocycloalkyl. In embodiments, $R^7$ is substituted or unsubstituted $C_7$-$C_{11}$ fused bicyclic heterocycloalkyl. In embodiments, $R^7$ is substituted or unsubstituted $C_7$-$C_{10}$ fused bicyclic heterocycloalkyl. In embodiments, $R^7$ is substituted or unsubstituted $C_7$-$C_9$ fused bicyclic heterocycloalkyl. In embodiments, $R^7$ is substituted or unsubstituted $C_7$-$C_{11}$ fused bicyclic heterocycloalkyl. In embodiments, $R^7$ is substituted or unsubstituted $C_8$-$C_{11}$ fused bicyclic heterocycloalkyl. In embodiments, $R^7$ is substituted or unsubstituted $C_8$-$C_{10}$ fused bicyclic heterocycloalkyl. In embodiments, $R^7$ is substituted or unsubstituted $C_8$-$C_9$ fused bicyclic heterocycloalkyl. In embodiments, $R^7$ is substituted $C7$-$C_{12}$ fused bicyclic heterocycloalkyl. In embodiments, $R^7$ is substituted $C_7$-$C_{11}$ fused bicyclic heterocycloalkyl. In embodiments, $R^7$ is substituted $C_7$-$C_{10}$ fused bicyclic heterocycloalkyl. In embodiments, $R^7$ is substituted $C_7$-$C_9$ fused bicyclic heterocycloalkyl. In embodiments, $R^7$ is substituted $C_7$-$C_{11}$ fused bicyclic heterocycloalkyl. In embodiments, $R^7$ is substituted $C_8$-$C_{11}$ fused bicyclic heterocycloalkyl. In embodiments, $R^7$ is substituted $C_8$-$C_{10}$ fused bicyclic heterocycloalkyl. In embodiments, $R^7$ is substituted $C_8$-$C_9$ fused bicyclic heterocycloalkyl. In embodiments, $R^7$ is unsubstituted $C_7$-$C_{12}$ fused bicyclic heterocycloalkyl. In embodiments, $R^7$ is unsubstituted $C_7$-$C_{11}$ fused bicyclic heterocycloalkyl. In embodiments, $R^7$ is unsubstituted $C_7$-$C_{10}$ fused bicyclic heterocycloalkyl. In embodiments, $R^7$ is unsubstituted $C_7$-$C_9$ fused bicyclic heterocycloalkyl. In embodiments, $R^7$ is substituted or unsubstituted $C_7$-$C_8$ fused bicyclic heterocycloalkyl. In embodiments, $R^7$ is unsubstituted $C_8$-$C_{11}$ fused bicyclic heterocycloalkyl. In embodiments, $R^7$ is unsubstituted $C_8$-$C_{10}$ fused bicyclic heterocycloalkyl. In embodiments, $R^7$ is unsubstituted $C_8$-$C_9$ fused bicyclic heterocycloalkyl.

In embodiments, $R^7$ is $R^{21}$-substituted or unsubstituted fused bicyclic heterocycloalkyl (e.g., $C_9$-$C_{11}$ heterocycloalkyl or $C_7$-$C_{12}$ heterocycloalkyl). In embodiments, $R^7$ is $R^{21}$-substituted or unsubstituted $C_7$-$C_{12}$ fused bicyclic heterocycloalkyl. In embodiments, $R^7$ is $R^{21}$-substituted or unsubstituted $C_7$-$C_{11}$ fused bicyclic heterocycloalkyl. In embodiments, $R^7$ is $R^{21}$-substituted or unsubstituted $C_7$-$C_{10}$ fused bicyclic heterocycloalkyl. In embodiments, $R^7$ is $R^{21}$-substituted or unsubstituted $C_7$-$C_9$ fused bicyclic heterocycloalkyl. In embodiments, $R^7$ is $R^{21}$-substituted or unsubstituted $C_7$-$C_{11}$ fused bicyclic heterocycloalkyl. In embodiments, $R^7$ is $R^{21}$-substituted or unsubstituted $C_8$-$C_{11}$ fused bicyclic heterocycloalkyl. In embodiments, $R^7$ is $R^{21}$-substituted or unsubstituted $C_8$-$C_{10}$ fused bicyclic heterocycloalkyl. In embodiments, $R^7$ is $R^{21}$-substituted or unsubstituted $C_8$-$C_9$ fused bicyclic heterocycloalkyl. In embodiments, $R^7$ is $R^{21}$-substituted $C_7$-$C_{12}$ fused bicyclic heterocycloalkyl. In embodiments, $R^7$ is $R^{21}$-substituted $C_7$-$C_{11}$ fused bicyclic heterocycloalkyl. In embodiments, $R^7$ is $R^{21}$-substituted $C_7$-$C_{10}$ fused bicyclic heterocycloalkyl. In embodiments, $R^7$ is $R^{21}$-substituted $C_7$-$C_9$ fused bicyclic heterocycloalkyl. In embodiments, $R^7$ is $R^{21}$-substituted $C_7$-$C_8$ fused bicyclic heterocycloalkyl. In embodiments, $R^7$ is $R^{21}$-substituted $C_8$-$C_{11}$ fused bicyclic heterocycloalkyl. In embodiments, $R^7$ is $R^{21}$-substituted $C_8$-$C_{10}$ fused bicyclic heterocycloalkyl. In embodiments, $R^7$ is $R^{21}$-substituted $C_8$-$C_9$ fused bicyclic heterocycloalkyl.

In embodiments, $R^7$ is substituted or unsubstituted bridged bicyclic heterocycloalkyl (e.g., 9 to 11 membered heterocycloalkyl or 7 to 12 membered heterocycloalkyl). In embodiments, $R^7$ is substituted or unsubstituted 7 to 12 membered bridged bicyclic heterocycloalkyl. In embodiments, $R^7$ is substituted or unsubstituted 7 to 11 membered bridged bicyclic heterocycloalkyl. In embodiments, $R^7$ is substituted or unsubstituted 7 to 10 membered bridged bicyclic heterocycloalkyl. In embodiments, $R^7$ is substituted or unsubstituted 7 to 9 membered bridged bicyclic heterocycloalkyl. In embodiments, $R^7$ is substituted or unsubstituted 7 to 8 membered bridged bicyclic heterocycloalkyl. In embodiments, $R^7$ is substituted or unsubstituted 8 to 11 membered bridged bicyclic heterocycloalkyl. In embodiments, $R^7$ is substituted or unsubstituted 8 to 10 membered bridged bicyclic heterocycloalkyl. In embodiments, $R^7$ is substituted or unsubstituted 8 to 9 membered bridged bicyclic heterocycloalkyl. In embodiments, $R^7$ is substituted 7 to 12 membered bridged bicyclic heterocycloalkyl. In embodiments, $R^7$ is substituted 7 to 11 membered bridged bicyclic heterocycloalkyl. In embodiments, $R^7$ is substituted 7 to 10 membered bridged bicyclic heterocycloalkyl. In embodiments, $R^7$ is substituted 7 to 9 membered bridged bicyclic heterocycloalkyl. In embodiments, $R^7$ is substituted 7 to 8 membered bridged bicyclic heterocycloalkyl. In embodiments, $R^7$ is substituted 8 to 11 membered bridged bicyclic heterocycloalkyl. In embodiments, $R^7$ is substituted 8 to 10 membered bridged bicyclic heterocycloalkyl. In embodiments, $R^7$ is substituted 8 to 9 membered bridged bicyclic heterocycloalkyl. In embodiments, $R^7$ is unsubstituted 7 to 12 membered bridged bicyclic heterocycloalkyl. In embodiments, $R^7$ is unsubstituted 7 to 11 membered bridged bicyclic heterocycloalkyl. In embodiments, $R^7$ is unsubstituted 7 to 10 membered bridged bicyclic heterocycloalkyl. In embodiments, $R^7$ is unsubstituted 7 to 9 membered bridged bicyclic heterocycloalkyl. In embodiments, $R^7$ is substituted or unsubstituted 7 to 8 membered bridged bicyclic heterocycloalkyl. In embodiments, $R^7$ is unsubstituted 8 to 11 membered bridged bicyclic heterocycloalkyl. In embodiments, $R^7$ is unsubstituted 8 to 10 membered bridged bicyclic heterocycloalkyl. In embodiments, $R^7$ is unsubstituted 8 to 9 membered bridged bicyclic heterocycloalkyl.

In embodiments, $R^7$ is $R^{21}$-substituted or unsubstituted bridged bicyclic heterocycloalkyl (e.g., 9 to 11 membered heterocycloalkyl or 7 to 12 membered heterocycloalkyl). In embodiments, $R^7$ is $R^{21}$-substituted or unsubstituted 7 to 12 membered bridged bicyclic heterocycloalkyl. In embodiments, $R^7$ is $R^{21}$-substituted or unsubstituted 7 to 11 membered bridged bicyclic heterocycloalkyl. In embodiments, $R^7$ is $R^{21}$-substituted or unsubstituted 7 to 10 membered bridged bicyclic heterocycloalkyl. In embodiments, $R^7$ is $R^{21}$-substituted or unsubstituted 7 to 9 membered bridged bicyclic heterocycloalkyl. In embodiments, $R^7$ is $R^{21}$-substituted or unsubstituted 7 to 8 membered bridged bicyclic heterocycloalkyl. In embodiments, $R^7$ is $R^{21}$-substituted or unsubstituted 8 to 11 membered bridged bicyclic heterocycloalkyl. In embodiments, $R^7$ is $R^{21}$-substituted or unsubstituted 8 to 10 membered bridged bicyclic heterocycloalkyl. In embodiments, $R^7$ is $R^{21}$-substituted or unsubstituted 8 to 9 membered bridged bicyclic heterocycloalkyl. In embodiments, $R^7$ is $R^{21}$-substituted 7 to 12 membered bridged bicyclic heterocycloalkyl. In embodiments, $R^7$ is $R^{21}$-substituted 7 to 11 membered bridged bicyclic heterocycloalkyl. In embodiments, $R^7$ is $R^{21}$-substituted 7 to 10 membered bridged bicyclic heterocycloalkyl. In embodiments, $R^7$ is $R^{21}$-substituted 7 to 9 membered bridged bicyclic heterocycloalkyl. In embodiments, $R^7$ is $R^{21}$-substituted 7 to 8 membered bridged bicyclic heterocycloalkyl. In embodiments, $R^7$ is $R^{21}$-substituted 8 to 11 membered bridged bicyclic heterocycloalkyl. In embodiments, $R^7$ is $R^{21}$-substituted 8 to 10 membered bridged bicyclic heterocycloalkyl. In embodiments, $R^7$ is $R^{21}$-substituted 8 to 9 membered bridged bicyclic heterocycloalkyl.

In embodiments, $R^7$ is substituted or unsubstituted spirocyclic bicyclic heterocycloalkyl (e.g., 9 to 11 membered heterocycloalkyl, 7 to 12 membered heterocycloalkyl, or 7 to 15 membered heterocycloalkyl). In embodiments, $R^7$ is substituted or unsubstituted 7 to 15 membered spirocyclic bicyclic heterocycloalkyl. In embodiments, $R^7$ is substituted or unsubstituted 7 to 12 membered spirocyclic bicyclic heterocycloalkyl. In embodiments, $R^7$ is substituted or unsubstituted 7 to 11 membered spirocyclic bicyclic heterocycloalkyl. In embodiments, $R^7$ is substituted or unsubstituted 7 to 10 membered spirocyclic bicyclic heterocycloalkyl. In embodiments, $R^7$ is substituted or unsubstituted 7 to 9 membered spirocyclic bicyclic heterocycloalkyl. In embodiments, $R^7$ is substituted or unsubstituted 7 to 8 membered spirocyclic bicyclic heterocycloalkyl. In embodiments, $R^7$ is substituted or unsubstituted 8 to 11 membered spirocyclic bicyclic heterocycloalkyl. In embodiments, $R^7$ is substituted or unsubstituted 8 to 10 membered spirocyclic bicyclic heterocycloalkyl. In embodiments, $R^7$ is substituted or unsubstituted 8 to 9 membered spirocyclic bicyclic heterocycloalkyl. In embodiments, $R^7$ is substituted 7 to 15 membered spirocyclic bicyclic heterocycloalkyl. In embodiments, $R^7$ is substituted 7 to 12 membered spirocyclic bicyclic heterocycloalkyl. In embodiments, $R^7$ is substituted 7 to 11 membered spirocyclic bicyclic heterocycloalkyl. In embodiments, $R^7$ is substituted 7 to 10 membered spirocyclic bicyclic heterocycloalkyl. In embodiments, $R^7$ is substituted 7 to 9 membered spirocyclic bicyclic heterocycloalkyl. In embodiments, $R^7$ is substituted 7 to 8 membered spirocyclic bicyclic heterocycloalkyl. In embodiments, $R^7$ is substituted 8 to 11 membered spirocyclic bicyclic heterocycloalkyl. In embodiments, $R^7$ is substituted 8 to 10 membered spirocyclic bicyclic heterocycloalkyl. In embodiments, $R^7$ is substituted 8 to 9 membered spirocyclic bicyclic heterocycloalkyl. In embodiments, $R^7$ is unsubstituted 7 to 15 membered spirocyclic bicyclic heterocycloalkyl. In embodiments, $R^7$ is unsubstituted 7 to 12 membered spirocyclic bicyclic heterocycloalkyl. In embodiments, $R^7$ is unsubstituted 7 to 11 membered spirocyclic bicyclic heterocycloalkyl. In embodiments, $R^7$ is unsubstituted 7 to 10 membered spirocyclic bicyclic heterocycloalkyl. In embodiments, $R^7$ is unsubstituted 7 to 9 membered spirocyclic bicyclic heterocycloalkyl. In embodiments, $R^7$ is substituted or unsubstituted 7 to 8 membered spirocyclic bicyclic heterocycloalkyl. In embodiments, $R^7$ is unsubstituted 8 to 11 membered spirocyclic bicyclic heterocycloalkyl. In embodiments, $R^7$ is unsubstituted 8 to 10 membered spirocyclic bicyclic heterocycloalkyl. In embodiments, $R^7$ is unsubstituted 8 to 9 membered spirocyclic bicyclic heterocycloalkyl.

In embodiments, $R^7$ is $R^{21}$-substituted or unsubstituted spirocyclic bicyclic heterocycloalkyl (e.g., 9 to 11 membered heterocycloalkyl, 7 to 12 membered heterocycloalkyl, or 7 to 15 membered heterocycloalkyl). In embodiments, $R^7$ is $R^{21}$-substituted or unsubstituted 7 to 15 membered spirocyclic bicyclic heterocycloalkyl. In embodiments, $R^7$ is $R^{21}$-substituted or unsubstituted 7 to 12 membered spirocyclic bicyclic heterocycloalkyl. In embodiments, $R^7$ is $R^{21}$-substituted or unsubstituted 7 to 11 membered spirocyclic bicyclic heterocycloalkyl. In embodiments, $R^7$ is $R^{21}$-substituted or unsubstituted 7 to 10 membered spirocyclic bicyclic heterocycloalkyl. In embodiments, $R^7$ is $R^{21}$-substituted or unsubstituted 7 to 9 membered spirocyclic bicyclic heterocycloalkyl. In embodiments, $R^7$ is $R^{21}$-substituted or unsubstituted 7 to 8 membered spirocyclic bicyclic heterocycloalkyl. In embodiments, $R^7$ is $R^{21}$-substituted or unsubstituted 8 to 11 membered spirocyclic bicyclic heterocycloalkyl. In embodiments, $R^7$ is $R^{21}$-substituted or unsubstituted 8 to 10 membered spirocyclic bicyclic heterocycloalkyl. In embodiments, $R^7$ is $R^{21}$-substituted or unsubstituted 8 to 9 membered spirocyclic bicyclic heterocycloalkyl. In embodiments, $R^7$ is $R^{21}$-substituted 7 to 15 membered spirocyclic bicyclic heterocycloalkyl. In embodiments, $R^7$ is $R^{21}$-substituted 7 to 12 membered spirocyclic bicyclic heterocycloalkyl. In embodiments, $R^7$ is 10-substituted 7 to 11 membered spirocyclic bicyclic heterocycloalkyl. In embodiments, $R^7$ is $R^{21}$-substituted 7 to 10 membered spirocyclic bicyclic heterocycloalkyl. In embodiments, $R^7$ is $R^{21}$-substituted 7 to 9 membered spirocyclic bicyclic heterocycloalkyl. In embodiments, $R^7$ is $R^{21}$-substituted 7 to 8 membered spirocyclic bicyclic heterocycloalkyl. In embodiments, $R^7$ is $R^{21}$-substituted 8 to 11 membered spirocyclic bicyclic heterocycloalkyl. In embodiments, $R^7$ is $R^{21}$-substituted 8 to 10 membered spirocyclic bicyclic heterocycloalkyl. In embodiments, $R^7$ is $R^{21}$-substituted 8 to 9 membered spirocyclic bicyclic heterocycloalkyl.

In embodiments, $R^7$ is substituted or unsubstituted fused tricyclic heterocycloalkyl (e.g., 9 to 11 membered heterocycloalkyl, 7 to 12 membered heterocycloalkyl, or 7 to 15 membered heterocycloalkyl). In embodiments, $R^7$ is substituted or unsubstituted 7 to 15 membered fused tricyclic heterocycloalkyl. In embodiments, $R^7$ is substituted or unsubstituted 7 to 12 membered fused tricyclic heterocycloalkyl. In embodiments, $R^7$ is substituted or unsubstituted 7 to 11 membered fused tricyclic heterocycloalkyl. In embodiments, $R^7$ is substituted or unsubstituted 7 to 10 membered fused tricyclic heterocycloalkyl. In embodiments, $R^7$ is substituted or unsubstituted 7 to 9 membered fused tricyclic heterocycloalkyl. In embodiments, $R^7$ is substituted or unsubstituted 7 to 8 membered fused tricyclic heterocycloalkyl. In embodiments, $R^7$ is substituted or unsubstituted 8 to 11 membered fused tricyclic heterocycloalkyl. In embodiments, $R^7$ is substituted or unsubstituted 8 to 10 membered fused tricyclic heterocycloalkyl. In embodiments, $R^7$ is substituted or unsubstituted 8 to 9 membered fused tricyclic heterocycloalkyl. In embodiments, $R^7$ is substituted 7 to 15 membered fused tricyclic heterocycloalkyl. In embodiments, $R^7$ is substituted 7 to 12 membered fused tricyclic heterocycloalkyl. In embodiments, $R^7$ is substituted 7 to 11 membered fused tricyclic heterocycloalkyl. In embodiments, $R^7$ is substituted 7 to 10 membered fused tricyclic heterocycloalkyl. In embodiments, $R^7$ is substituted 7 to 9 membered fused tricyclic heterocycloalkyl. In embodiments, $R^7$ is substituted 7 to 8 membered fused tricyclic heterocycloalkyl. In embodiments, $R^7$ is substituted 8 to 11 membered fused tricyclic heterocycloalkyl. In embodiments, $R^7$ is substituted 8 to 10 membered fused tricyclic heterocycloalkyl. In embodiments, $R^7$ is substituted 8 to 9 membered fused tricyclic heterocycloalkyl. In embodiments, $R^7$ is unsubstituted 7 to 15 membered fused tricyclic heterocycloalkyl. In embodiments, $R^7$ is unsubstituted 7 to 12 membered fused tricyclic heterocycloalkyl. In embodiments, $R^7$ is unsubstituted 7 to 11 membered fused tricyclic heterocycloalkyl. In embodiments, $R^7$ is unsubstituted 7 to 10 membered fused tricyclic heterocycloalkyl. In embodiments, $R^7$ is unsubstituted 7 to 9 membered fused tricyclic heterocycloalkyl. In embodiments, $R^7$ is substituted or unsubstituted 7 to 8 membered fused tricyclic heterocycloalkyl. In embodiments, $R^7$ is unsubstituted 8 to 11 membered fused tricyclic heterocycloalkyl. In embodiments, $R^7$ is unsubstituted 8 to 10 membered fused tricyclic heterocycloalkyl. In embodiments, $R^7$ is unsubstituted 8 to 9 membered fused tricyclic heterocycloalkyl.

In embodiments, $R^7$ is $R^{21}$-substituted or unsubstituted fused tricyclic heterocycloalkyl (e.g., 9 to 11 membered heterocycloalkyl, 7 to 12 membered heterocycloalkyl, or 7 to 15 membered heterocycloalkyl). In embodiments, $R^7$ is $R^{21}$-substituted or unsubstituted 7 to 15 membered fused tricyclic heterocycloalkyl. In embodiments, $R^7$ is $R^{21}$-substituted or unsubstituted 7 to 12 membered fused tricyclic heterocycloalkyl. In embodiments, $R^7$ is $R^{21}$-substituted or unsubstituted 7 to 11 membered fused tricyclic heterocycloalkyl. In embodiments, $R^7$ is $R^{21}$-substituted or unsubstituted 7 to 10 membered fused tricyclic heterocycloalkyl. In embodiments, $R^7$ is $R^{21}$-substituted or unsubstituted 7 to 9 membered fused tricyclic heterocycloalkyl. In embodiments, $R^7$ is $R^{21}$-substituted or unsubstituted 7 to 8 membered fused tricyclic heterocycloalkyl. In embodiments, $R^7$ is $R^{21}$-substituted or unsubstituted 8 to 11 membered fused tricyclic heterocycloalkyl. In embodiments, $R^7$ is $R^{21}$-substituted or unsubstituted 8 to 10 membered fused tricyclic heterocycloalkyl. In embodiments, $R^7$ is $R^{21}$-substituted or unsubstituted 8 to 9 membered fused tricyclic heterocycloalkyl. In embodiments, $R^7$ is $R^{21}$-substituted 7 to 15 membered fused tricyclic heterocycloalkyl. In embodiments, $R^7$ is $R^{21}$-substituted 7 to 12 membered fused tricyclic heterocycloalkyl. In embodiments, $R^7$ is $R^{21}$-substituted 7 to 11 membered fused tricyclic heterocycloalkyl. In embodiments, $R^7$ is $R^{21}$-substituted 7 to 10 membered fused tricyclic heterocycloalkyl. In embodiments, $R^7$ is $R^{21}$-substituted 7 to 9 membered fused tricyclic heterocycloalkyl. In embodiments, $R^7$ is $R^{21}$-substituted 7 to 8 membered fused tricyclic heterocycloalkyl. In embodiments, $R^7$ is $R^{21}$-substituted 8 to 11 membered fused tricyclic heterocycloalkyl. In embodiments, $R^7$ is $R^{21}$-substituted 8 to 10 membered fused tricyclic heterocycloalkyl. In embodiments, $R^7$ is $R^{21}$-substituted 8 to 9 membered fused tricyclic heterocycloalkyl.

In embodiments, $R^7$ is substituted or unsubstituted bridged tricyclic heterocycloalkyl (e.g., 9 to 11 membered heterocycloalkyl, 7 to 12 membered heterocycloalkyl, or 7 to 15 membered heterocycloalkyl). In embodiments, $R^7$ is substituted or unsubstituted 7 to 15 membered bridged tricyclic heterocycloalkyl. In embodiments, $R^7$ is substituted or unsubstituted 7 to 12 membered bridged tricyclic heterocycloalkyl. In embodiments, $R^7$ is substituted or unsubstituted 7 to 11 membered bridged tricyclic heterocycloalkyl. In embodiments, $R^7$ is substituted or unsubstituted 7 to 10 membered bridged tricyclic heterocycloalkyl. In embodiments, $R^7$ is substituted or unsubstituted 7 to 9 membered bridged tricyclic heterocycloalkyl. In embodiments, $R^7$ is substituted or unsubstituted 7 to 8 membered bridged tricyclic heterocycloalkyl. In embodiments, $R^7$ is substituted or unsubstituted 8 to 11 membered bridged tricyclic heterocycloalkyl. In embodiments, $R^7$ is substituted or unsubstituted 8 to 10 membered bridged tricyclic heterocycloalkyl. In embodiments, $R^7$ is substituted or unsubstituted 8 to 9 membered bridged tricyclic heterocycloalkyl. In embodiments, $R^7$ is substituted 7 to 15 membered bridged tricyclic heterocycloalkyl. In embodiments, $R^7$ is substituted 7 to 12 membered bridged tricyclic heterocycloalkyl. In embodiments, $R^7$ is substituted 7 to 11 membered bridged tricyclic heterocycloalkyl. In embodiments, $R^7$ is substituted 7 to 10 membered bridged tricyclic heterocycloalkyl. In embodiments, $R^7$ is substituted 7 to 9 membered f bridged used tricyclic heterocycloalkyl. In embodiments, $R^7$ is substituted 7 to 8 membered bridged tricyclic heterocycloalkyl. In embodiments, $R^7$ is substituted 8 to 11 membered bridged tricyclic heterocycloalkyl. In embodiments, $R^7$ is substituted 8 to 10 membered bridged tricyclic heterocycloalkyl. In embodiments, $R^7$ is substituted 8 to 9 membered bridged tricyclic heterocycloalkyl. In embodiments, $R^7$ is unsubstituted 7 to 15 membered bridged tricyclic heterocycloalkyl. In embodiments, $R^7$ is unsubstituted 7 to 12 membered bridged tricyclic heterocycloalkyl. In embodiments, $R^7$ is unsubstituted 7 to 11 membered bridged tricyclic heterocycloalkyl. In embodiments, $R^7$ is unsubstituted 7 to 10 membered bridged tricyclic heterocycloalkyl. In embodiments, $R^7$ is unsubstituted 7 to 9 membered bridged tricyclic heterocycloalkyl. In embodiments, $R^7$ is substituted or unsubstituted 7 to 8 membered bridged tricyclic heterocycloalkyl. In embodiments, $R^7$ is unsubstituted 8 to 11 membered bridged tricyclic heterocycloalkyl. In embodiments, $R^7$ is unsubstituted 8 to 10 membered bridged tricyclic heterocycloalkyl. In embodiments, $R^7$ is unsubstituted 8 to 9 membered bridged tricyclic heterocycloalkyl.

In embodiments, $R^7$ is $R^{21}$-substituted or unsubstituted bridged tricyclic heterocycloalkyl (e.g., 9 to 11 membered heterocycloalkyl, 7 to 12 membered heterocycloalkyl, or 7 to 15 membered heterocycloalkyl). In embodiments, $R^7$ is $R^{21}$-substituted or unsubstituted 7 to 15 membered bridged tricyclic heterocycloalkyl. In embodiments, $R^7$ is $R^{21}$-substituted or unsubstituted 7 to 12 membered bridged tricyclic heterocycloalkyl. In embodiments, $R^7$ is $R^{21}$-substituted or unsubstituted 7 to 11 membered bridged tricyclic heterocycloalkyl. In embodiments, $R^7$ is $R^{21}$-substituted or unsubstituted 7 to 10 membered bridged tricyclic heterocycloalkyl. In embodiments, $R^7$ is $R^{21}$-substituted or unsubstituted 7 to 9 membered bridged tricyclic heterocycloalkyl. In embodiments, $R^7$ is $R^{21}$-substituted or unsubstituted 7 to 8 membered bridged tricyclic heterocycloalkyl. In embodiments, $R^7$ is $R^{21}$-substituted or unsubstituted 8 to 11 membered bridged tricyclic heterocycloalkyl. In embodiments, $R^7$ is $W^1$-substituted or unsubstituted 8 to 10 membered bridged tricyclic heterocycloalkyl. In embodiments, $R^7$ is $W^1$-substituted or unsubstituted 8 to 9 membered bridged tricyclic heterocycloalkyl. In embodiments, $R^7$ is $R^{21}$-substituted 7 to 15 membered bridged tricyclic heterocycloalkyl. In embodiments, $R^7$ is $R^{21}$-substituted 7 to 12 membered bridged tricyclic heterocycloalkyl. In embodiments, $R^7$ is $R^{21}$-substituted 7 to 11 membered bridged tricyclic heterocycloalkyl. In embodiments, $R^7$ is $R^{21}$-substituted 7 to 10 membered bridged tricyclic heterocycloalkyl. In embodiments, $R^7$ is $R^{21}$-substituted 7 to 9 membered bridged tricyclic heterocycloalkyl. In embodiments, $R^7$ is $R^{21}$-substituted 7 to 8 membered bridged tricyclic heterocycloalkyl. In embodiments, $R^7$ is $R^{21}$-substituted 8 to 11 membered bridged tricyclic heterocycloalkyl. In embodiments, $R^7$ is $R^{21}$-substituted 8 to 10 membered bridged tricyclic heterocycloalkyl. In embodiments, $R^7$ is $R^{21}$-substituted 8 to 9 membered bridged tricyclic heterocycloalkyl.

In embodiments, $R^7$ is substituted or unsubstituted spirocyclic tricyclic heterocycloalkyl (e.g., 9 to 11 membered heterocycloalkyl, 9 to 15 membered heterocycloalkyl, or 12 to 18 membered heterocycloalkyl). In embodiments, $R^7$ is substituted or unsubstituted 12 to 18 membered spirocyclic tricyclic heterocycloalkyl. In embodiments, $R^7$ is substituted or unsubstituted 9 to 15 membered spirocyclic tricyclic heterocycloalkyl. In embodiments, $R^7$ is substituted or unsubstituted 9 to 12 membered spirocyclic tricyclic heterocycloalkyl. In embodiments, $R^7$ is substituted or unsubstituted 9 to 11 membered spirocyclic tricyclic heterocycloalkyl. In embodiments, $R^7$ is substituted or unsubstituted 12 to 18 membered spirocyclic tricyclic heterocycloalkyl. In embodiments, $R^7$ is substituted 9 to 15 spirocyclic tricyclic heterocycloalkyl. In embodiments, $R^7$ is substituted 9 to 12 membered spirocyclic tricyclic heterocycloalkyl. In embodiments, $R^7$ is substituted 9 to 11 membered spirocyclic tricyclic heterocycloalkyl. In embodiments, $R^7$ is substituted 9 to 10 membered spirocyclic tricyclic heterocycloalkyl. In embodiments, $R^7$ is unsubstituted 12 to 18 membered spirocyclic tricyclic heterocycloalkyl. In embodiments, $R^7$ is unsubstituted 9 to 15 membered spirocyclic tricyclic heterocycloalkyl. In embodiments, $R^7$ is unsubstituted 9 to 12 membered spirocyclic tricyclic heterocycloalkyl. In embodiments, $R^7$ is unsubstituted 9 to 11 membered spirocyclic tricyclic heterocycloalkyl. In embodiments, $R^7$ is unsubstituted 9 to 10 membered spirocyclic tricyclic heterocycloalkyl.

In embodiments, $R^7$ is $R^{21}$-substituted or unsubstituted spirocyclic tricyclic heterocycloalkyl (e.g., 9 to 11 membered heterocycloalkyl, 9 to 15 membered heterocycloalkyl, or 12 to 18 membered heterocycloalkyl). In embodiments, $R^7$ is $R^{21}$-substituted or unsubstituted 12 to 18 membered spirocyclic tricyclic heterocycloalkyl. In embodiments, $R^7$ is $R^{21}$-substituted or unsubstituted 9 to 15 membered spirocyclic tricyclic heterocycloalkyl. In embodiments, $R^7$ is $R^{21}$-substituted or unsubstituted 9 to 12 membered spirocyclic tricyclic heterocycloalkyl. In embodiments, $R^7$ is $R^{21}$-substituted or unsubstituted 9 to 11 membered spirocyclic tricyclic heterocycloalkyl. In embodiments, $R^7$ is $R^{21}$-substituted or unsubstituted 12 to 18 membered spirocyclic tricyclic heterocycloalkyl. In embodiments, $R^7$ is $R^{21}$-substituted 9 to 15 membered spirocyclic tricyclic heterocycloalkyl. In embodiments, $R^7$ is $R^{21}$-substituted 9 to 12 membered spirocyclic tricyclic heterocycloalkyl. In embodiments, $R^7$ is $R^{21}$-substituted 9 to 11 membered spirocyclic tricyclic heterocycloalkyl. In embodiments, $R^7$ is $R^{21}$-substituted 9 to 10 membered spirocyclic tricyclic heterocycloalkyl.

In embodiments, $R^7$ is a $C_9$-$C_{10}$ fused bicyclic aryl. In embodiments, $R^7$ is a $C_9$ fused bicyclic aryl. In embodiments, $R^7$ is a $C_{10}$ fused bicyclic aryl. In embodiments, $R^7$ is a fused bicyclic aryl wherein a heterocycloalkyl ring is fused to a phenyl group. In embodiments, $R^7$ is a fused bicyclic aryl wherein a heterocycloalkyl ring is fused to an aryl group. In embodiments, $R^7$ is a $C_6$-$C_8$ used bicyclic heteroaryl. In embodiments, $R^7$ is a $C_7$-$C_9$ fused bicyclic heteroaryl. In embodiments, $R^7$ is a fused bicyclic heteroaryl wherein a heterocycloalkyl ring is fused to a heteroaryl group. In embodiments, $R^7$ is a fused bicyclic heteroaryl wherein a heterocycloalkyl ring is fused to a 6-membered heteroaryl group. In embodiments, $R^7$ is a fused bicyclic heteroaryl wherein a heterocycloalkyl ring is fused to a 5-membered heteroaryl group. In embodiments, $R^7$ is a $C_6$ fused bicyclic heteroaryl wherein a heterocycloalkyl is fused to a heteroaryl ring with three heteroatoms. In embodiments, $R^7$ is a $C_7$ fused bicyclic heteroaryl wherein a heterocycloalkyl is fused to a heteroaryl ring with two heteroatoms. In embodiments, $R^7$ is a $C_8$ fused bicyclic heteroaryl wherein a heterocycloalkyl is fused to a heteroaryl ring with one heteroatom. In embodiments, $R^7$ is a $C_7$ fused bicyclic heteroaryl wherein a heterocycloalkyl is fused to a heteroaryl ring with three heteroatoms. In embodiments, $R^7$ is a $C_8$ fused bicyclic heteroaryl wherein a heterocycloalkyl is fused to a heteroaryl ring with two heteroatoms. In embodiments, $R^7$ is a $C_9$ fused bicyclic heteroaryl wherein a heterocycloalkyl is fused to a heteroaryl ring with one heteroatom.

In embodiments, $R^7$ is cycloalkyl and $L^2$ is a bond. In embodiments, $R^7$ is monocyclic cycloalkyl and $L^2$ is a bond. In embodiments, $R^7$ is bicyclic cycloalkyl and $L^2$ is a bond. In embodiments, $R^7$ is tricyclic cycloalkyl and $L^2$ is a bond. In embodiments, $R^7$ is bridged monocyclic cycloalkyl and $L^2$ is a bond. In embodiments, $R^7$ is bridged bicyclic cycloalkyl and $L^2$ is a bond. In embodiments, $R^7$ is bridged tricyclic cycloalkyl and $L^2$ is a bond. In embodiments, $R^7$ is fused bicyclic cycloalkyl and $L^2$ is a bond. In embodiments, $R^7$ is fused tricyclic cycloalkyl and $L^2$ is a bond.

In embodiments, $R^7$ is cycloalkyl and $L^2$ is $C_1$-$C_3$ alkylene. In embodiments, $R^7$ is monocyclic cycloalkyl and $L^2$ is $C_1$-$C_3$ alkylene. In embodiments, $R^7$ is bicyclic cycloalkyl and $L^2$ is $C_1$-$C_3$ alkylene. In embodiments, $R^7$ is tricyclic cycloalkyl and $L^2$ is $C_1$-$C_3$ alkylene.

In embodiments, $R^7$ is bridged monocyclic cycloalkyl and $L^2$ is C1-$C_3$ alkylene. In embodiments, $R^7$ is bridged bicyclic cycloalkyl and $L^2$ is $C_1$-$C_3$ alkylene. In embodiments, $R^7$ is bridged tricyclic cycloalkyl and $L^2$ is $C_1$-$C_3$ alkylene. In embodiments, $R^7$ is fused bicyclic cycloalkyl and $L^2$ is $C_1$-$C_3$ alkylene. In embodiments, $R^7$ is fused tricyclic cycloalkyl and $L^2$ is $C_1$-$C_3$ alkylene.

In embodiments, $R^7$ is substituted or unsubstituted adamantyl and $L^2$ is a bond. In embodiments, $R^7$ is substituted or unsubstituted adamantyl and $L^2$ is $C_1$-$C_3$ alkylene. In embodiments, $R^7$ is substituted or unsubstituted tetrahydronaphthyl and $L^2$ is a bond. In embodiments, $R^7$ is substituted or unsubstituted tetrahydronaphthyl and $L^2$ is $C_1$-$C_3$ alkylene. In embodiments, $R^7$ is substituted or unsubstituted 6,7,8,9-tetrahydro-5H-benzo[7]annulenyl, and $L^2$ is a bond. In embodiments, $R^7$ is substituted or unsubstituted 6,7,8,9-tetrahydro-5H-benzo[7]annulenyl, and $L^2$ is $C_1$-$C_3$ alkylene. In embodiments, $R^7$ is substituted or unsubstituted dihydroindenyl and $L^2$ is a bond. In embodiments, $R^7$ is substituted or unsubstituted dihydroindenyl and $L^2$ is $C_1$-$C_3$ alkylene. In embodiments, $R^7$ is substituted or unsubstituted bicyclo[3.3.1]heptanyl and $L^2$ is a bond. In embodiments, $R^7$ is substituted or unsubstituted bicyclo[3.3.1]heptanyl and $L^2$ is $C_1$-$C_3$ alkylene. In embodiments, $R^7$ is substituted or unsubstituted 2,3-dihydro-1H-indenyl and $L^2$ is a bond. In embodiments, $R^7$ is substituted or unsubstituted 2,3-dihydro-1H-indenyl and $L^2$ is $C_1$-$C_3$ alkylene.

In embodiments, $R^7$ is substituted adamantyl and $L^2$ is a bond. In embodiments, $R^7$ is substituted adamantyl and $L^2$ is $C_1$-$C_3$ alkylene. In embodiments, $R^7$ is substituted tetrahydronaphthyl and $L^2$ is a bond. In embodiments, $R^7$ is substituted tetrahydronaphthyl and $L^2$ is $C_1$-$C_3$ alkylene. In embodiments, $R^7$ is substituted 6,7,8,9-tetrahydro-5H-benzo[7]annulenyl, and $L^2$ is a bond. In embodiments, $R^7$ is substituted 6,7,8,9-tetrahydro-5H-benzo[7]annulenyl, and $L^2$ is $C_1$-$C_3$ alkylene. In embodiments, $R^7$ is substituted dihydroindenyl and $L^2$ is a bond. In embodiments, $R^7$ is substituted dihydroindenyl and $L^2$ is $C_1$-$C_3$ alkylene. In embodiments, $R^7$ is substituted bicyclo[3.3.1]heptanyl and $L^2$ is a bond. In embodiments, $R^7$ is substituted bicyclo[3.3.1]heptanyl and $L^2$ is $C_1$-$C_3$ alkylene. In embodiments, $R^7$ is substituted 2,3-dihydro-1H-indenyl and $L^2$ is a bond. In embodiments, $R^7$ is substituted 2,3-dihydro-1H-indenyl and $L^2$ is $C_1$-$C_3$ alkylene. In embodiments, $R^7$ is unsubstituted adamantyl and $L^2$ is a bond. In embodiments, $R^7$ is unsubstituted adamantyl and $L^2$ is $C_1$-$C_3$ alkylene. In embodiments, $R^7$ is unsubstituted tetrahydronaphthyl and $L^2$ is a bond. In embodiments, $R^7$ is unsubstituted tetrahydronaphthyl and $L^2$ is $C_1$-$C_3$ alkylene. In embodiments, $R^7$ is unsubstituted 6,7,8,9-tetrahydro-5H-benzo[7]annulenyl, and $L^2$ is a bond. In embodiments, $R^7$ is unsubstituted 6,7,8,9-tetrahydro-5H-benzo[7]annulenyl, and $L^2$ is $C_1$-$C_3$ alkylene. In embodiments, $R^7$ is substituted or unsubstituted dihydroindenyl and $L^2$ is a bond. In embodiments, $R^7$ is substituted or unsubstituted dihydroindenyl and $L^2$ is $C_1$-$C_3$ alkylene. In embodiments, $R^7$ is substituted or unsubstituted bicyclo[3.3.1]heptanyl and $L^2$ is a bond. In embodiments, $R^7$ is substituted or unsubstituted bicyclo[3.3.1]heptanyl and $L^2$ is $C_1$-$C_3$ alkylene. In embodiments, $R^7$ is unsubstituted 2,3-dihydro-1H-indenyl and $L^2$ is a bond. In embodiments, $R^7$ is unsubstituted 2,3-dihydro-1H-indenyl and $L^2$ is $C_1$-$C_3$ alkylene.

In embodiments, $R^7$ is $R^{21}$-substituted or unsubstituted adamantyl and $L^2$ is a bond. In embodiments, $R^7$ is $R^{21}$-substituted or unsubstituted adamantyl and $L^2$ is $C_1$-$C_3$ alkylene. In embodiments, $R^7$ is $R^{21}$-substituted or unsubstituted tetrahydronaphthyl and $L^2$ is a bond. In embodiments, $R^7$ is $R^{21}$-substituted or unsubstituted tetrahydronaphthyl and $L^2$ is $C_1$-$C_3$ alkylene. In embodiments, $R^7$ is $R^{21}$-substituted or unsubstituted 6,7,8,9-tetrahydro-5H-benzo[7]annulenyl, and $L^2$ is a bond. In embodiments, $R^7$ is $R^{21}$-substituted or unsubstituted 6,7,8,9-tetrahydro-5H-benzo[7]annulenyl, and $L^2$ is $C_1$-$C_3$ alkylene. In embodiments, $R^7$ is $R^{21}$-substituted or unsubstituted dihydroindenyl and $L^2$ is a bond. In embodiments, $R^7$ is $R^{21}$-substituted or unsubstituted dihydroindenyl and $L^2$ is $C_1$-$C_3$ alkylene. In embodiments, $R^7$ is $R^{21}$-substituted or unsubstituted bicyclo[3.3.1]heptanyl and $L^2$ is a bond. In embodiments, $R^7$ is $R^{21}$-substituted or unsubstituted bicyclo[3.3.1]heptanyl and $L^2$ is $C_1$-$C_3$ alkylene. In embodiments, $R^7$ is $R^{21}$-substituted or unsubstituted 2,3-dihydro-1H-indenyl and $L^2$ is a bond. In embodiments, $R^7$ is $R^{21}$-substituted or unsubstituted 2,3-dihydro-1H-indenyl and $L^2$ is $C_1$-$C_3$ alkylene.

In embodiments, $R^7$ is $R^{21}$-substituted adamantyl and $L^2$ is a bond. In embodiments, $R^7$ is $R^{21}$-substituted adamantyl and $L^2$ is $C_1$-$C_3$ alkylene. In embodiments, $R^7$ is $R^{21}$-substituted tetrahydronaphthyl and $L^2$ is a bond. In embodiments, $R^7$ is $R^{21}$-substituted tetrahydronaphthyl and $L^2$ is $C_1$-$C_3$ alkylene. In embodiments, $R^7$ is $R^{21}$-substituted 6,7,8,9-tetrahydro-5H-benzo[7]annulenyl, and $L^2$ is a bond. In embodiments, $R^7$ is $R^{21}$-substituted 6,7,8,9-tetrahydro-5H-benzo[7]annulenyl, and $L^2$ is $C_1$-$C_3$ alkylene. In embodiments, $R^7$ is $R^{21}$-substituted dihydroindenyl and $L^2$ is a bond. In embodiments, $R^7$ is $R^{21}$-substituted dihydroindenyl and $L^2$ is $C_1$-$C_3$ alkylene. In embodiments, $R^7$ is $R^{21}$-substituted bicyclo[3.3.1]heptanyl and $L^2$ is a bond. In embodiments, $R^7$ is $R^{21}$-substituted bicyclo[3.3.1]heptanyl and $L^2$ is $C_1$-$C_3$ alkylene. In embodiments, $R^7$ is $R^{21}$-substituted 2,3-dihydro-1H-indenyl and $L^2$ is a bond. In embodiments, $R^7$ is $R^{21}$-substituted 2,3-dihydro-1H-indenyl and $L^2$ is $C_1$-$C_3$ alkylene. In embodiments, $R^7$ is unsubstituted adamantyl and $L^2$ is a bond. In embodiments, $R^7$ is unsubstituted adamantyl and $L^2$ is $C_1$-$C_3$ alkylene. In embodiments, $R^7$ is unsubstituted tetrahydronaphthyl and $L^2$ is a bond. In embodiments, $R^7$ is unsubstituted tetrahydronaphthyl and $L^2$ is $C_1$-$C_3$ alkylene. In embodiments, $R^7$ is unsubstituted 6,7,8,9-tetrahydro-5H-benzo[7]annulenyl, and $L^2$ is a bond. In embodiments, $R^7$ is unsubstituted 6,7,8,9-tetrahydro-5H-benzo[7]annulenyl, and $L^2$ is $C_1$-$C_3$ alkylene. In embodiments, $R^7$ is $R^{21}$-substituted or unsubstituted dihydroindenyl and $L^2$ is a bond. In embodiments, $R^7$ is $R^{21}$-substituted or unsubstituted dihydroindenyl and $L^2$ is $C_1$-$C_3$ alkylene. In embodiments, $R^7$ is $R^{21}$-substituted or unsubstituted bicyclo[3.3.1]heptanyl and $L^2$ is a bond. In embodiments, $R^7$ is $R^{21}$-substituted or unsubstituted bicyclo[3.3.1]heptanyl and $L^2$ is $C_1$-$C_3$ alkylene. In embodiments, $R^7$ is unsubstituted 2,3-dihydro-1H-indenyl and $L^2$ is a bond. In embodiments, $R^7$ is unsubstituted 2,3-dihydro-1H-indenyl and $L^2$ is $C_1$-$C_3$ alkylene.

In embodiments, $R^{21}$ is independently oxo, halogen, —$CCl_3$, —$CBr_3$, —$CF_3$, —$Cl_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{22}$-substituted or unsubstituted alkyl (e.g., $C_1$-$C_8$ alkyl, $C_1$-$C_6$ alkyl, or $C_1$-$C_4$ alkyl), $R^{22}$-substituted or unsubstituted heteroalkyl (e.g., 2 to 8 membered heteroalkyl, 2 to 6 membered heteroalkyl, or 2 to 4 membered heteroalkyl), $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22}$-substituted or unsubstituted aryl (e.g., $C_6$-$C_{10}$ aryl, $C_{10}$ aryl, or phenyl), or $R^{22}$-substituted or unsubstituted heteroaryl (e.g., 5 to 10 membered heteroaryl, 5 to 9 membered heteroaryl, or 5 to 6 membered heteroaryl). In embodiments, $R^{21}$ is independently oxo, halogen, —$CF_3$, —$CBr_3$, —$CCl_3$, —$Cl_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{21}$ is independently oxo. In embodiments, $R^{21}$ is independently halogen. In embodiments, $R^{21}$ is independently —F. In embodiments, $R^{21}$ is independently —Cl. In embodiments, $R^{21}$ is independently —Br. In embodiments, $R^{21}$ is independently —I. In embodiments, $R^{21}$ is independently —CCl$_3$. In embodiments, $R^{21}$ is independently —CBr$_3$. In embodiments, $R^{21}$ is independently —CF$_3$. In embodiments, $R^{21}$ is independently —CI$_3$. In embodiments, $R^{21}$ is independently CHCl$_2$. In embodiments, $R^{21}$ is independently —CHBr$_2$. In embodiments, $R^{21}$ is independently —CHF$_2$. In embodiments, $R^{21}$ is independently —CHI$_2$. In embodiments, $R^{21}$ is independently —CH$_2$Cl. In embodiments, $R^{21}$ is independently —CH$_2$Br. In embodiments, $R^{21}$ is independently —CH$_2$F. In embodiments, $R^{21}$ is independently —CH$_2$I. In embodiments, $R^{21}$ is independently —CN. In embodiments, $R^{21}$ is independently —OH. In embodiments, $R^{21}$ is independently —NH$_2$. In embodiments, $R^{21}$ is independently —COOH. In embodiments, $R^{21}$ is independently —CONH$_2$. In embodiments, $R^{21}$ is independently —NO$_2$. In embodiments, $R^{21}$ is independently —SH. In embodiments, $R^{21}$ is independently —SO$_3$H. In embodiments, $R^{21}$ is independently —SO$_4$H. In embodiments, $R^{21}$ is independently —SO$_2$NH$_2$. In embodiments, $R^{21}$ is independently NHNH$_2$. In embodiments, $R^{21}$ is independently —ONH$_2$. In embodiments, $R^{21}$ is independently NHC(O)NHNH$_2$. In embodiments, $R^{21}$ is independently NHC(O)NH$_2$. In embodiments, $R^{21}$ is independently —NHSO$_2$H. In embodiments, $R^{21}$ is independently —NHC(O)H. In embodiments, $R^{21}$ is independently —NHC(O)OH. In embodiments, $R^{21}$ is independently —NHOH. In embodiments, $R^{21}$ is independently —OCCl$_3$. In embodiments, $R^{21}$ is independently —OCF$_3$. In embodiments, $R^{21}$ is independently —OCBr$_3$. In embodiments, $R^{21}$ is independently —OCI$_3$. In embodiments, $R^{21}$ is independently —OCHCl$_2$. In embodiments, $R^{21}$ is independently —OCHBr$_2$. In embodiments, $R^{21}$ is independently —OCHI$_2$. In embodiments, $R^{21}$ is independently —OCHF$_2$. In embodiments, $R^{21}$ is independently —OCH$_2$Cl. In embodiments, $R^{21}$ is independently —OCH$_2$Br. In embodiments, $R^{21}$ is independently —OCH$_2$I. In embodiments, $R^{21}$ is independently —OCH$_2$F. In embodiments, $R^{21}$ is independently —N$_3$.

In embodiments, $R^{21}$ is $R^{22}$-substituted or unsubstituted alkyl (e.g., $C_1$-$C_8$ alkyl, $C_1$-$C_6$ alkyl, or $C_1$-$C_4$ alkyl). In embodiments, $R^{21}$ is $R^{22}$-substituted alkyl (e.g., $C_1$-$C_8$ alkyl, $C_1$-$C_6$ alkyl, or $C_1$-$C_4$ alkyl). In embodiments, $R^{21}$ is an unsubstituted alkyl (e.g., $C_1$-$C_8$ alkyl, $C_1$-$C_6$ alkyl, or $C_1$-$C_4$ alkyl). In embodiments, $R^{21}$ is $R^{22}$-substituted methyl. In embodiments, $R^{21}$ is $R^{22}$-substituted ethyl. In embodiments, $R^{21}$ is $R^{22}$-substituted propyl. In embodiments, $R^{21}$ is $R^{22}$-substituted butyl. In embodiments, $R^{21}$ is $R^{22}$-substituted t-butyl. In embodiments, $R^{21}$ is $R^{22}$-substituted pentyl. In embodiments, $R^{21}$ is unsubstituted methyl. In embodiments, $R^{21}$ is unsubstituted ethyl. In embodiments, $R^{21}$ is unsubstituted propyl. In embodiments, $R^{21}$ is unsubstituted butyl. In embodiments, $R^{21}$ is unsubstituted t-butyl. In embodiments, $R^{21}$ is unsubstituted pentyl.

In embodiments, $R^{21}$ is $R^{22}$-substituted or unsubstituted heteroalkyl (e.g., 2 to 8 membered heteroalkyl, 2 to 6 membered heteroalkyl, or 2 to 4 membered heteroalkyl). In embodiments, $R^{21}$ is $R^{22}$-substituted heteroalkyl (e.g., 2 to 8 membered heteroalkyl, 2 to 6 membered heteroalkyl, or 2 to 4 membered heteroalkyl). In embodiments, $R^{21}$ is an unsubstituted heteroalkyl (e.g., 2 to 8 membered heteroalkyl, 2 to 6 membered heteroalkyl, or 2 to 4 membered heteroalkyl).

In embodiments, $R^{21}$ is $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{21}$ is $R^{22}$-substituted cycloalkyl (e.g., $C_3$-$C_8$ cycloalkyl, $C_3$-$C_6$ cycloalkyl, or $C_5$-$C_6$ cycloalkyl). In embodiments, $R^{21}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{21}$ is $R^{22}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{21}$ is $R^{22}$-substituted heterocycloalkyl (e.g., 3 to 8 membered heterocycloalkyl, 3 to 6 membered heterocycloalkyl, or 5 to 6 membered heterocycloalkyl). In embodiments, $R^{21}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{21}$ is $R^{22}$-substituted or unsubstituted aryl (e.g., $C_6$-$C_{10}$ aryl, $C_{10}$ aryl, or phenyl). In embodiments, $R^{21}$ is $R^{22}$-substituted aryl (e.g., $C_6$-$C_{10}$ aryl, $C_{10}$ aryl, or phenyl). In embodiments, $R^{21}$ is an unsubstituted aryl (e.g., $C_6$-$C_{10}$ aryl, $C_{10}$ aryl, or phenyl).

In embodiments, $R^{21}$ is $R^{22}$-substituted or unsubstituted heteroaryl (e.g., 5 to 10 membered heteroaryl, 5 to 9 membered heteroaryl, or 5 to 6 membered heteroaryl). In embodiments, $R^{21}$ is $R^{22}$-substituted heteroaryl (e.g., 5 to 10 membered heteroaryl, 5 to 9 membered heteroaryl, or 5 to 6 membered heteroaryl). In embodiments, $R^{21}$ is an unsubstituted heteroaryl (e.g., 5 to 10 membered heteroaryl, 5 to 9 membered heteroaryl, or 5 to 6 membered heteroaryl). In embodiments, two adjacent $R^{21}$ substituents are joined to form an $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22}$-substituted or unsubstituted aryl (e.g., $C_6$-$C_{10}$ aryl, $C_{10}$ aryl, or phenyl), or $R^{22}$-substituted or unsubstituted heteroaryl (e.g., 5 to 10 membered heteroaryl, 5 to 9 membered heteroaryl, or 5 to 6 membered heteroaryl). In embodiments, two adjacent $R^{21}$ substituents are joined to form an $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, two adjacent $R^{21}$ substituents are joined to form an $R^{22}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, two adjacent $R^{21}$ substituents are joined to form an $R^{22}$-substituted or unsubstituted aryl (e.g., $C_6$-$C_{10}$ aryl, $C_{10}$ aryl, or phenyl). In embodiments, two adjacent $R^{21}$ substituents are joined to form an $R^{22}$-substituted or unsubstituted heteroaryl (e.g., 5 to 10 membered heteroaryl, 5 to 9 membered heteroaryl, or 5 to 6 membered heteroaryl).

In embodiments, $R^{21A}$, $R^{21B}$, $R^{21C}$, and $R^{21D}$ are independently hydrogen, halogen, —CF$_3$, —CBr$_3$, —CCl$_3$, —CI$_3$ —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —S O$_2$NH$_2$, —NHNH$_2$, —ONH$_2$, —NHC(O)NHNH$_2$ $R^{22}$-substituted or unsubstituted alkyl (e.g., $C_1$-$C_8$ alkyl, $C_1$-$C_6$ alkyl, or $C_1$-$C_4$ alkyl), $R^{22}$-substituted or unsubstituted heteroalkyl (e.g., 2 to 8 membered heteroalkyl, 2 to 6 membered heteroalkyl, or 2 to 4 membered heteroalkyl), $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22}$-substituted or unsubstituted aryl (e.g., $C_6$-$C_{10}$ aryl, $C_{10}$ aryl, or phenyl), or $R^{22}$-substituted or unsubstituted heteroaryl (e.g., 5 to 10 membered heteroaryl, 5 to 9 membered heteroaryl, or 5 to 6 membered heteroaryl). In embodiments, $R^{21A}$ and $R^{21B}$ substituents bonded to the same nitrogen atom are joined to form an $R^{22}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{22}$-substituted or unsubstituted heteroaryl (e.g., 5 to 10 membered heteroaryl, 5 to 9 membered heteroaryl, or 5 to 6 membered heteroaryl). In embodiments, $R^{21A}$ and $R^{21B}$ substituents bonded to the same nitrogen atom are joined to form an $R^{22}$-substituted or unsubstituted heterocycloalkyl (e.g., 3 to 8 membered heterocycloalkyl, 3 to 6 membered heterocycloalkyl. In embodiments, $R^{21A}$ and $R^{21B}$ substituents bonded to the same nitrogen atom are joined to form an $R^{22}$-substituted or unsubstituted heteroaryl (e.g., 5 to 10 membered heteroaryl, 5 to 9 membered heteroaryl, or 5 to 6 membered heteroaryl).

$R^{22}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{23}$-substituted or unsubstituted alkyl (e.g., $C_1$-$C_8$ alkyl, $C_1$-$C_6$ alkyl, or $C_1$-$C_4$ alkyl), $R^{23}$-substituted or unsubstituted heteroalkyl (e.g., 2 to 8 membered heteroalkyl, 2 to 6 membered heteroalkyl, or 2 to 4 membered heteroalkyl), $R^{23}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{23}$-substituted or unsubstituted heterocycloalkyl (e.g., 3 to 8 membered heterocycloalkyl, 3 to 6 membered heterocycloalkyl, or 5 to 6 membered heterocycloalkyl), $R^{23}$-substituted or unsubstituted aryl (e.g., $C_6$-$C_{10}$ aryl, $C_{10}$ aryl, or phenyl), or $R^{23}$-substituted or unsubstituted heteroaryl (e.g., 5 to 10 membered heteroaryl, 5 to 9 membered heteroaryl, or 5 to 6 membered heteroaryl). In embodiments, $R^{22}$ is independently oxo, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{22}$ is independently —OH. In embodiments, $R^{22}$ is independently —$OCH_3$. In embodiments, $R^{22}$ is independently —$OCH_2CH_3$. In embodiments, $R^{22}$ is independently —F. In embodiments, $R^{22}$ is independently —NHC(O)$CH_3$. In embodiments, $R^{22}$ is independently —COOH. In embodiments, $R^{22}$ is independently —$SO_2NH_2$.

In embodiments, $R^{23}$ is independently oxo. In embodiments, $R^{23}$ is independently halogen. In embodiments, $R^{23}$ is independently —F. In embodiments, $R^{23}$ is independently —Cl. In embodiments, $R^{23}$ is independently —Br. In embodiments, $R^{23}$ is independently —I. In embodiments, $R^{23}$ is independently —$CCl_3$. In embodiments, $R^{23}$ is independently —$CBr_3$. In embodiments, $R^{23}$ is independently —$CF_3$. In embodiments, $R^{23}$ is independently —$CI_3$. In embodiments, $R^{23}$ is independently $CHCl_2$. In embodiments, $R^{23}$ is independently —$CHBr_2$. In embodiments, $R^{23}$ is independently —$CHF_2$. In embodiments, $R^{23}$ is independently —$CHI_2$. In embodiments, $R^{23}$ is independently —$CH_2Cl$. In embodiments, $R^{23}$ is independently —$CH_2Br$. In embodiments, $R^{23}$ is independently —$CH_2F$. In embodiments, $R^{23}$ is independently —$CH_2I$. In embodiments, $R^{23}$ is independently —CN. In embodiments, $R^{23}$ is independently —OH. In embodiments, $R^{23}$ is independently —$NH_2$. In embodiments, $R^{23}$ is independently —COOH. In embodiments, $R^{23}$ is independently —$CONH_2$. In embodiments, $R^{23}$ is independently —$NO_2$. In embodiments, $R^{23}$ is independently —SH. In embodiments, $R^{23}$ is independently —$SO_3H$. In embodiments, $R^{23}$ is independently —$SO_4H$. In embodiments, $R^{23}$ is independently —$SO_2NH_2$.

In embodiments, $R^{23}$ is independently $NHNH_2$. In embodiments, $R^{23}$ is independently —$ONH_2$. In embodiments, $R^{23}$ is independently —NHC(O)$NHNH_2$. In embodiments, $R^{23}$ is independently —NHC(O)$NH_2$. In embodiments, $R^{23}$ is independently —$NHSO_2H$. In embodiments, $R^{23}$ is independently —NHC(O)H. In embodiments, $R^{23}$ is independently —NHC(O)OH. In embodiments, $R^{23}$ is independently —NHOH. In embodiments, $R^{23}$ is independently —$OCCl_3$. In embodiments, $R^{23}$ is independently —$OCF_3$. In embodiments, $R^{23}$ is independently —$OCBr_3$. In embodiments, $R^{23}$ is independently —$OCI_3$. In embodiments, $R^{23}$ is independently —$OCHCl_2$. In embodiments, $R^{23}$ is independently —$OCHBr_2$. In embodiments, $R^{23}$ is independently —$OCHI_2$. In embodiments, $R^{23}$ is independently —$OCHF_2$. In embodiments, $R^{23}$ is independently —$OCH_2Cl$. In embodiments, $R^{23}$ is independently —$OCH_2Br$. In embodiments, $R^{23}$ is independently —$OCH_2I$. In embodiments, $R^{23}$ is independently —$OCH_2F$. In embodiments, $R^{23}$ is independently —$N_3$.

In embodiments, $R^{23}$ is independently halogen. In embodiments, $R^{23}$ is independently —$CX^{23}_3$. In embodiments, $R^{23}$ is independently —$CHX^{23}_2$. In embodiments, $R^{23}$ is independently —$CH_2X^{23}$. In embodiments, $R^{23}$ is independently —$OCX^{23}_3$. In embodiments, $R^{23}$ is independently —$OCH_2X^{23}$. In embodiments, $R^{23}$ is independently —$OCHX^{23}_2$. In embodiments, $R^{23}$ is independently —CN. In embodiments, $R^{23}$ is independently —$SO_{n23}H$. In embodiments, $R^{23}$ is independently —SH. In embodiments, $R^{23}$ is independently —$SO_2H$. In embodiments, $R^{23}$ is independently —$SO_{v23}NH_2$. In embodiments, $R^{23}$ is independently —$SO_2NH_2$. In embodiments, $R^{23}$ is independently —NHC(O)$NH_2$. In embodiments, $R^{23}$ is independently —$N(O)_{m23}$. In embodiments, $R^{23}$ is independently —$NH^2$. In embodiments, $R^{23}$ is independently —C(O)H. In embodiments, $R^{23}$ is independently —C(O)—OH. In embodiments, $R^{23}$ is independently —C(O)$NH_2$. In embodiments, $R^{23}$ is independently —OH.

In embodiments, $R^{23}$ is independently —$NHSO_2H$. In embodiments, $R^{23}$ is independently NHC(O)H. In embodiments, $R^{23}$ is independently —NHC(O)OH. In embodiments, $R^{23}$ is independently —NHOH. In embodiments, $R^{23}$ is independently methoxy. In embodiments, $R^{23}$ is independently ethoxy. In embodiments, $R^{23}$ is independently propoxy. In embodiments, $R^{23}$ is independently butoxy. In embodiments, $R^{23}$ is independently pentoxy. $X^{23}$ is —F, —Cl, —Br, and —I.

In embodiments, $R^{23}$ is independently oxo, halogen, —CF$_3$, —CBr$_3$, —CCl$_3$, —CI$_3$—CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{22}$ is independently oxo. In embodiments, $R^{22}$ is independently halogen. In embodiments, $R^{22}$ is independently —F. In embodiments, $R^{22}$ is independently —Cl. In embodiments, $R^{22}$ is independently —Br. In embodiments, $R^{22}$ is independently —I. In embodiments, $R^{22}$ is independently —CCl$_3$. In embodiments, $R^{22}$ is independently —CBr$_3$. In embodiments, $R^{22}$ is independently —CF$_3$. In embodiments, $R^{22}$ is independently —CI$_3$. In embodiments, $R^{22}$ is independently CHCl$_2$. In embodiments, $R^{22}$ is independently —CHBr$_2$. In embodiments, $R^{22}$ is independently —CHF$_2$. In embodiments, $R^{22}$ is independently —CHI$_2$. In embodiments, $R^{22}$ is independently —CH$_2$Cl. In embodiments, $R^{22}$ is independently —CH$_2$Br. In embodiments, $R^{22}$ is independently —CH$_2$F. In embodiments, $R^{22}$ is independently —CH$_2$I. In embodiments, $R^{22}$ is independently —CN. In embodiments, $R^{22}$ is independently —OH. In embodiments, $R^{22}$ is independently —NH$_2$. In embodiments, $R^{22}$ is independently —COOH. In embodiments, $R^{22}$ is independently —CONH$_2$. In embodiments, $R^{22}$ is independently —NO$_2$. In embodiments, $R^{22}$ is independently —SH. In embodiments, $R^{22}$ is independently —SO$_3$H. In embodiments, $R^{22}$ is independently —SO$_4$H. In embodiments, $R^{22}$ is independently —SO$_2$NH$_2$. In embodiments, $R^{22}$ is independently —NHNH$_2$. In embodiments, $R^{22}$ is independently —ONH$_2$. In embodiments, $R^{22}$ is independently —NHC(O)NHNH$_2$. In embodiments, $R^{22}$ is independently —NHC(O)NH$_2$. In embodiments, $R^{22}$ is independently —NHSO$_2$H. In embodiments, $R^{22}$ is independently —NHC(O)H. In embodiments, $R^{22}$ is independently —NHC(O)OH. In embodiments, $R^{22}$ is independently —NHOH. In embodiments, $R^{22}$ is independently —OCCl$_3$. In embodiments, $R^{22}$ is independently —OCF$_3$. In embodiments, $R^{22}$ is independently —OCBr$_3$. In embodiments, $R^{22}$ is independently —OCI$_3$. In embodiments, $R^{22}$ is independently —OCHCl$_2$. In embodiments, $R^{22}$ is independently —OCHBr$_2$. In embodiments, $R^{22}$ is independently —OCHI$_2$. In embodiments, $R^{22}$ is independently —OCHF$_2$. In embodiments, $R^{22}$ is independently —OCH$_2$Cl. In embodiments, $R^{22}$ is independently —OCH$_2$Br. In embodiments, $R^{22}$ is independently —OCH$_2$I. In embodiments, $R^{22}$ is independently —OCH$_2$F. In embodiments, $R^{22}$ is independently —N$_3$.

In embodiments, $R^{22}$ is independently halogen. In embodiments, $R^{22}$ is independently —CX$^{22}{}_3$. In embodiments, $R^{22}$ is independently —CHX$^{22}{}_2$. In embodiments, $R^{22}$ is independently —CH$_2$X$^{22}$. In embodiments, $R^{22}$ is independently —OCX$^{22}{}_3$. In embodiments, $R^{22}$ is independently —OCH$_2$X$^{22}$. In embodiments, $R^{22}$ is independently —OCHX$^{22}{}_2$. In embodiments, $R^{22}$ is independently —CN. In embodiments, $R^{22}$ is independently —SO$_2$H. In embodiments, $R^{22}$ is independently —SH. In embodiments, $R^{22}$ is independently —SO$_2$H. In embodiments, $R^{22}$ is independently —SO$_2$NH$_2$R$^{22}$. In embodiments, $R^{22}$ is independently SO$_2$NH$_2$. In embodiments, $R^{22}$ is independently —NHC(O)NH$_2$. In embodiments, $R^{22}$ is independently —N(O)$_2$. In embodiments, $R^{22}$ is independently —NH$_2$. In embodiments, $R^{22}$ is independently —C(O)R$^{22C}$. In embodiments, $R^{22}$ is independently —C(O)—OH. In embodiments, $R^{22}$ is independently —C(O)NH$_2$. In embodiments, $R^{22}$ is independently —OH. In embodiments, $R^{22}$ is independently —NHSO$_2$H. In embodiments, $R^{22}$ is independently —NHC(O) H. In embodiments, $R^{22}$ is independently —NHC(O) OH. In embodiments, $R^{22}$ is independently —NHOH. In embodiments, $R^{22}$ is independently methoxy. In embodiments, $R^{22}$ is independently ethoxy. In embodiments, $R^{22}$ is independently propoxy. In embodiments, $R^{22}$ is independently butoxy. In embodiments, $R^{22}$ is independently pentoxy. $X^{22}$ is —F, —Cl, —Br, and —I.

In embodiments, $R^7$ is $R^{21}$-substituted or unsubstituted alkyl (e.g., C$_1$-C$_8$ alkyl, C$_1$-C$_6$ alkyl, or C$_1$-C$_4$ alkyl). In embodiments, $R^7$ is $R^{21}$-substituted alkyl (e.g., C$_1$-C$_8$ alkyl, C$_1$-C$_6$ alkyl, or C$_1$-C$_4$ alkyl). In embodiments, $R^7$ is an unsubstituted alkyl (e.g., C$_1$-C$_8$ alkyl, C$_1$-C$_6$ alkyl, or C$_1$-C$_4$ alkyl). In embodiments, $R^7$ is $R^{21}$-substituted or unsubstituted heteroalkyl (e.g., 2 to 8 membered heteroalkyl, 2 to 6 membered heteroalkyl, or 2 to 4 membered heteroalkyl). In embodiments, $R^7$ is $R^{21}$-substituted heteroalkyl (e.g., 2 to 8 membered heteroalkyl, 2 to 6 membered heteroalkyl, or 2 to 4 membered heteroalkyl). In embodiments, $R^7$ is an unsubstituted heteroalkyl (e.g., 2 to 8 membered heteroalkyl, 2 to 6 membered heteroalkyl, or 2 to 4 membered heteroalkyl). In embodiments, $R^7$ is $R^{21}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, $R^7$ is $R^{21}$-substituted cycloalkyl (e.g., C$_3$-C$_8$ cycloalkyl, C$_3$-C$_6$ cycloalkyl, or C$_5$-C$_6$ cycloalkyl). In embodiments, $R^7$ is an unsubstituted cycloalkyl (e.g., C$_3$-C$_8$ cycloalkyl, C$_3$-C$_6$ cycloalkyl, or C$_5$-C$_6$ cycloalkyl). In embodiments, $R^7$ is $R^{21}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^7$ is $R^{21}$-substituted heterocycloalkyl (e.g., 3 to 8 membered heterocycloalkyl, 3 to 6 membered heterocycloalkyl, or 5 to 6 membered heterocycloalkyl). In embodiments, $R^7$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^7$ is $R^{21}$-substituted or unsubstituted aryl (e.g., C$_6$-C$_{10}$ aryl, C$_{10}$ aryl, or phenyl). In embodiments, $R^7$ is $R^{21}$-substituted aryl (e.g., C$_6$-C$_{10}$ aryl, C$_{10}$ aryl, or phenyl). In embodiments, $R^7$ is an unsubstituted aryl (e.g., C$_6$-C$_{10}$ aryl, C$_{10}$ aryl, or phenyl). In embodiments, $R^7$ is $R^{21}$-substituted or unsubstituted heteroaryl (e.g., 5 to 10 membered heteroaryl, 5 to 9 membered heteroaryl, or 5 to 6 membered heteroaryl). In embodiments, $R^7$ is $R^{21}$-substituted heteroaryl (e.g., 5 to 10 membered heteroaryl, 5 to 9 membered heteroaryl, or 5 to 6 membered heteroaryl). In embodiments, $R^7$ is an unsubstituted heteroaryl (e.g., 5 to 10 membered heteroaryl, 5 to 9 membered heteroaryl, or 5 to 6 membered heteroaryl). In embodiments, $R^7$ is hydrogen.

In embodiments, $R^{7A}$, $R^{7B}$, $R^{7C}$, and $R^{7D}$ are independently hydrogen, halogen, —CF$_3$, —CBr$_3$, —CCl$_3$, —Cl$_3$, —CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCl$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, $R^{21}$-substituted or unsubstituted alkyl (e.g., $C_1$-$C_8$ alkyl, $C_1$-$C_6$ alkyl, or $C_1$-$C_4$ alkyl), $R^{21}$-substituted or unsubstituted heteroalkyl (e.g., 2 to 8 membered heteroalkyl, 2 to 6 membered heteroalkyl, or 2 to 4 membered heteroalkyl), $R^{21}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{21}$-substituted or unsubstituted heterocycloalkyl (e.g., 3 to 8 membered heterocycloalkyl, 3 to 6 membered heterocycloalkyl, or 5 to 6 membered heterocycloalkyl), $R^{21}$-substituted or unsubstituted aryl (e.g., $C_6$-$C_{10}$ aryl, $C_{10}$ aryl, or phenyl), or $R^{21}$-substituted or unsubstituted heteroaryl (e.g., 5 to 10 membered heteroaryl, 5 to 9 membered heteroaryl, or 5 to 6 membered heteroaryl). In embodiments, $R^{7A}$ and $R^{7B}$ substituents bonded to the same nitrogen atom are joined to form an $R^{21}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{21}$-substituted or unsubstituted heteroaryl (e.g., 5 to 10 membered heteroaryl, 5 to 9 membered heteroaryl, or 5 to 6 membered heteroaryl). In embodiments, $R^{7A}$ and $R^{7B}$ substituents bonded to the same nitrogen atom are joined to form an $R^{21}$-substituted or unsubstituted heterocycloalkyl (e.g., 3 to 8 membered heterocycloalkyl, 3 to 6 membered heterocycloalkyl. In embodiments, $R^{7A}$ and $R^{7B}$ substituents bonded to the same nitrogen atom are joined to form an $R^{21}$-substituted or unsubstituted heteroaryl (e.g., 5 to 10 membered heteroaryl, 5 to 9 membered heteroaryl, or 5 to 6 membered heteroaryl).

In embodiments, $R^{21}$ is independently halogen, —CX$^{21}_3$, —CHX$^{21}_2$, —CH$_2$X$^{21}$, —OCX$^{21}_3$, —OCH$_2$X$^{21}$, —OCHX$^{21}_2$, —CN, —SO$_{n21}$R$^{21D}$, —SO$_{v21}$NR$^{21A}$R$^{21B}$, —NHC(O)NR$^{21A}$R$^{21B}$, —N(O)$_{m21}$, —NR$^{21A}$R$^{21B}$, —C(O)R$^{21C}$, —C(O)—OR$^{21C}$, —C(O)NR$^{21A}$R$^{21B}$, —OR$^{21D}$, —NR$^{21A}$SO$_2$R$^{21D}$, —NR$^{21A}$C(O)R$^{21C}$, —NR$^{21A}$C(O)OR$^{21C}$, —NR$^{21A}$OR$^{21C}$, $R^{22}$-substituted or unsubstituted alkyl (e.g., $C_1$-$C_8$ alkyl, $C_1$-$C_6$ alkyl, or $C_1$-$C_4$ alkyl), $R^{22}$-substituted or unsubstituted heteroalkyl (e.g., 2 to 8 membered heteroalkyl, 2 to 6 membered heteroalkyl, or 2 to 4 membered heteroalkyl), $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{22}$-substituted or unsubstituted heterocycloalkyl (e.g., 3 to 8 membered heterocycloalkyl, 3 to 6 membered heterocycloalkyl, or 5 to 6 membered heterocycloalkyl), $R^{22}$-substituted or unsubstituted aryl (e.g., $C_6$-$C_{10}$ aryl, $C_{10}$ aryl, or phenyl), or $R^{22}$-substituted or unsubstituted heteroaryl (e.g., 5 to 10 membered heteroaryl, 5 to 9 membered heteroaryl, or 5 to 6 membered heteroaryl). In embodiments, $R^{21}$ is halogen, —CX$^{21}_3$, —CHX$^{21}_2$, —CH$_2$X$^{21}$, —OCX$^{21}_3$, —OCH$_2$X$^{21}$, —OCHX$^{21}_2$, —CN, —SO$_{n21}$R$^{21D}$, —SO$_{v21}$NR$^{21A}$R$^{21B}$, —NHC(O)NR$^{21A}$R$^{21B}$, —N(O)$_{m21}$, —NR$^{21A}$R$_{21B}$, —C(O)R$_{21C}$, —C(O)—OR$^{21C}$, —C(O)NR$^{21A}$R$^{21B}$, —OR$^{21D}$, —NR$^{21A}$SO$_2$R$_{21D}$, —NR$^{21A}$C(O)R$^{21C}$, —NR$^{21A}$C(O)OR$^{21C}$, —NR$^{21A}$OR$^{21C}$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). $X^{21}$ is independently halogen. In embodiments, $X^{21}$ is independently —F. In embodiments, $X^{21}$ is independently —Cl. In embodiments, $X^{21}$ is independently —Br. In embodiments, $X^{21}$ is independently —I.

In embodiments, $R^{21}$ is independently halogen. In embodiments, $R^{21}$ is independently —CX$^{21}_3$. In embodiments, $R^{21}$ is independently —CHX$^{21}_2$. In embodiments, $R^{21}$ is independently —CH$_2$X$^{21}$. In embodiments, $R^{21}$ is independently —OCX$^{21}_3$. In embodiments, $R^{21}$ is independently —OCH$_2$X$^{21}$. In embodiments, $R^{21}$ is independently —OCHX$^{21}_2$. In embodiments, $R^{21}$ is independently —CN. In embodiments, $R^{21}$ is independently —SO$_{n21}$R$^{21D}$. In embodiments, $R^{21}$ is independently —SR$^{21D}$. In embodiments, $R^{21}$ is independently —SO$_2$R$^{21D}$. In embodiments, $R^{21}$ is independently —SO$_{v21}$NR$^{21A}$R$^{21B}$. In embodiments, $R^{21}$ is independently —SO$_2$NR$^{21A}$R$^{21B}$. In embodiments, $R^{21}$ is independently —NHC(O)NR$^{21A}$R$^{21B}$. In embodiments, $R^{21}$ is independently —N(O)$_{m21}$. In embodiments, $R^{21}$ is independently —NR$^{21A}$R$^{21B}$. In embodiments, $R^{21}$ is independently —C(O)R$^{21C}$. In embodiments, $R^{21}$ is independently —C(O)—OR$^{21C}$. In embodiments, $R^{21}$ is independently —C(O)NR$^{21A}$R$^{21B}$. In embodiments, $R^{21}$ is independently —OR$^{21D}$. In embodiments, $R^{21}$ is independently —NR$^{21A}$SO$_2$R$^{21C}$. In embodiments, $R^{21}$ is independently —NR$^{21A}$C(O)R$^{21C}$. In embodiments, $R^{21}$ is independently —NR$^{21A}$C(O)OR$^{21C}$. In embodiments, $R^{21}$ is independently —NR$^{21A}$SO$_2$R$^{21D}$. In embodiments, $R^{21}$ is independently methoxy. In embodiments, $R^{21}$ is independently ethoxy. In embodiments, $R^{21}$ is independently propoxy. In embodiments, $R^{21}$ is independently butoxy. In embodiments, $R^{21}$ is independently pentoxy.

In embodiments, $R^{21A}$ is independently hydrogen. In embodiments, $R^{21A}$ is independently —CF$_3$. In embodiments, $R^{21A}$ is independently —CBr$_3$. In embodiments, $R^{21A}$ is independently —CCl$_3$. In embodiments, $R^{21A}$ is independently —Cl$_3$. In embodiments, $R^{21A}$ is independently —CHF$_2$. In embodiments, $R^{21A}$ is independently —CHBr$_2$. In embodiments, $R_{21A}$ is independently —CHCl$_2$. In embodiments, $R^{21A}$ is independently —CHI$_2$. In embodiments, $R^{21A}$ is independently —CH$_2$F. In embodiments, $R^{21A}$ is independently —CH$_2$Br. In embodiments, $R^{21A}$ is independently —CH$_2$Cl. In embodiments, $R^{21A}$ is independently —CH$_2$I. In embodiments, $R^{21A}$ is independently —OH. In embodiments, $R^{21A}$ is independently —COOH. In embodiments, $R^{21A}$ is independently —CON$_2$. In embodiments, $R^{21A}$ is independently $R^{22}$-substituted or unsubstituted alkyl (e.g., $C_1$-$C_8$ alkyl, $C_1$-$C_6$ alkyl, or $C_1$-$C_4$ alkyl). In embodiments, $R^{21A}$ is independently $R^{22}$-substituted or unsubstituted heteroalkyl (e.g., 2 to 8 membered heteroalkyl, 2 to 6 membered heteroalkyl, or 2 to 4 membered heteroalkyl). In embodiments, $R^{21A}$ is independently $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{21A}$ is independently $R^{22}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{21A}$ is independently $R^{22}$-substituted or unsubstituted aryl (e.g., $C_6$-$C_{10}$ aryl, $C_{10}$ aryl, or phenyl). In embodiments, $R^{21A}$ is independently $R^{22}$-substituted or unsubstituted heteroaryl (e.g., 5 to 10 membered heteroaryl, 5 to 9 membered heteroaryl, or 5 to 6 membered heteroaryl). In embodiments, $R^{21A}$ is independently unsubstituted methyl. In embodiments, $R^{21A}$ is independently unsubstituted ethyl. In embodiments, $R^{21A}$ is independently unsubstituted propyl. In embodiments, $R^{21A}$ is independently unsubstituted butyl. In embodiments, $R^{21A}$ is independently unsubstituted pentyl. In embodiments, $R^{21A}$ is independently unsubstituted hexyl.

In embodiments, $R^{21B}$ is independently hydrogen. In embodiments, $R^{21}$ is independently —$CF_3$. In embodiments, $R^{21}$ is independently —$CBr_3$. In embodiments, $R^{21B}$ is independently —$CCl_3$. In embodiments, $R^{21B}$ is independently —$CI_3$. In embodiments, $R^{21B}$ is independently —$CHF_2$. In embodiments, $R^{21B}$ is independently —$CHBr_2$. In embodiments, $R^{21B}$ is independently —$CHCl_2$. In embodiments, $R^{21}$ is independently —$CHI_2$. In embodiments, $R^{21}$ is independently —$CH_2F$. In embodiments, $R^{21}$ is independently —$CH_2Br$. In embodiments, $R^{21B}$ is independently —$CH_2Cl$. In embodiments, $R^{21B}$ is independently —$CH_2I$. In embodiments, $R^{21}$ is independently —OH. In embodiments, $R^{21}$ is independently —COOH. In embodiments, $R^{21}$ is independently —$CONH_2$. In embodiments, $R^{21B}$ is independently $R^{22}$-substituted or unsubstituted alkyl (e.g., $C_1$-$C_8$ alkyl, $C_1$-$C_6$ alkyl, or $C_1$-$C_4$ alkyl). In embodiments, $R^{21B}$ is independently $R^{22}$-substituted or unsubstituted heteroalkyl (e.g., 2 to 8 membered heteroalkyl, 2 to 6 membered heteroalkyl, or 2 to 4 membered heteroalkyl). In embodiments, $R^{21B}$ is independently $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{21}$ is independently $R^{22}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{21B}$ is independently $R^{22}$-substituted or unsubstituted aryl (e.g., $C_6$-$C_{10}$ aryl, $C_{10}$ aryl, or phenyl). In embodiments, $R^{21}$ is independently $R^{22}$-substituted or unsubstituted heteroaryl (e.g., 5 to 10 membered heteroaryl, 5 to 9 membered heteroaryl, or 5 to 6 membered heteroaryl). In embodiments, $R^{21}$ is independently unsubstituted methyl. In embodiments, $R^{21}$ is independently unsubstituted ethyl. In embodiments, $R^{21}$ is independently unsubstituted propyl. In embodiments, $R^{21B}$ is independently unsubstituted butyl. In embodiments, $R^{21B}$ is independently unsubstituted pentyl. In embodiments, $R^{21B}$ is independently unsubstituted hexyl.

In embodiments, $R^{21C}$ is independently hydrogen. In embodiments, $R^{21C}$ is independently —$CF_3$. In embodiments, $R^{21C}$ is independently —$CBr_3$. In embodiments, $R^{21C}$ is independently —$CCl_3$. In embodiments, $R^{21C}$ is independently —$CI_3$. In embodiments, $R^{21C}$ is independently —$CHF_2$. In embodiments, $R^{21C}$ is independently —$CHBr_2$. In embodiments, $R^{21C}$ is independently —$CHCl_2$. In embodiments, $R^{21C}$ is independently —$CHI_2$. In embodiments, $R^{21C}$ is independently —$CH_2F$. In embodiments, $R^{21C}$ is independently —$CH_2Br$. In embodiments, $R^{21C}$ is independently —$CH_2Cl$. In embodiments, $R^{21C}$ is independently —$CH_2I$. In embodiments, $R^{21C}$ is independently —OH. In embodiments, $R^{21C}$ is independently —COOH. In embodiments, $R^{21C}$ is independently —$CONH_2$. In embodiments, $R^{21C}$ is independently $R^{22}$-substituted or unsubstituted alkyl (e.g., $C_1$-$C_8$ alkyl, $C_1$-$C_6$ alkyl, or $C_1$-$C_4$ alkyl). In embodiments, $R^{21C}$ is independently $R^{22}$-substituted or unsubstituted heteroalkyl (e.g., 2 to 8 membered heteroalkyl, 2 to 6 membered heteroalkyl, or 2 to 4 membered heteroalkyl). In embodiments, $R^{21C}$ is independently $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{21C}$ is independently $R^{22}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{21C}$ is independently $R^{22}$-substituted or unsubstituted aryl (e.g., $C_6$-$C_{10}$ aryl, $C_{10}$ aryl, or phenyl). In embodiments, $R^{21C}$ is independently $R^{22}$-substituted or unsubstituted heteroaryl (e.g., 5 to 10 membered heteroaryl, 5 to 9 membered heteroaryl, or 5 to 6 membered heteroaryl). In embodiments, $R^{21C}$ is independently unsubstituted methyl. In embodiments, $R^{21C}$ is independently unsubstituted ethyl. In embodiments, $R^{21C}$ is independently unsubstituted propyl. In embodiments, $R^{21C}$ is independently unsubstituted butyl. In embodiments, $R^{21C}$ is independently unsubstituted pentyl. In embodiments, $R^{21C}$ is independently unsubstituted hexyl.

In embodiments, $R^{21D}$ is independently hydrogen. In embodiments, $R^{21D}$ is independently —$CF_3$. In embodiments, $R^{21D}$ is independently —$CBr_3$. In embodiments, $R^{21D}$ is independently —$CCl_3$. In embodiments, $R^{21D}$ is independently —$CI_3$. In embodiments, $R^{21D}$ is independently —$CHF_2$. In embodiments, $R^{21D}$ is independently —$CHBr_2$. In embodiments, $R^{21}$ is independently —$CHCl_2$. In embodiments, $R^{21}$ is independently —$CHI_2$. In embodiments, $R^{21D}$ is independently —$CH_2F$. In embodiments, $R^{21D}$ is independently —$CH_2Br$. In embodiments, $R^{21D}$ is independently —$CH_2Cl$. In embodiments, $R^{21D}$ is independently —$CH_2I$. In embodiments, $R^{21}$ is independently —OH. In embodiments, $R^{21}$ is independently —COOH. In embodiments, $R^{21}$ is independently —$CONH_2$. In embodiments, $R^{21}$ is independently $R^{22}$-substituted or unsubstituted alkyl (e.g., $C_1$-$C_8$ alkyl, $C_1$-$C_6$ alkyl, or $C_1$-$C_4$ alkyl). In embodiments, $R^{21D}$ is independently $R^{22}$-substituted or unsubstituted heteroalkyl (e.g., 2 to 8 membered heteroalkyl, 2 to 6 membered heteroalkyl, or 2 to 4 membered heteroalkyl). In embodiments, $R^{21D}$ is independently $R^{22}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{21D}$ is independently $R^{22}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{21D}$ is independently $R^{22}$-substituted or unsubstituted aryl (e.g., $C_6$-$C_{10}$ aryl, $C_{10}$ aryl, or phenyl). In embodiments, $R^{21D}$ is independently $R^{22}$-substituted or unsubstituted heteroaryl (e.g., 5 to 10 membered heteroaryl, 5 to 9 membered heteroaryl, or 5 to 6 membered heteroaryl). In embodiments, $R^{21D}$ is independently unsubstituted methyl. In embodiments, $R^{21D}$ is independently unsubstituted ethyl. In embodiments, $R^{21D}$ is independently unsubstituted propyl. In embodiments, $R^{21D}$ is independently unsubstituted butyl. In embodiments, $R^{21D}$ is independently unsubstituted pentyl. In embodiments, $R^{21D}$ is independently unsubstituted hexyl.

In embodiments, $R^1$ is substituted or unsubstituted alkyl (e.g. $C_1$-$C_8$ alkyl, $C_1$-$C_6$ alkyl, or $C_1$-$C_4$ alkyl). In embodiments, $R^8$ is substituted alkyl (e.g. $C_1$-$C_8$ alkyl, $C_1$-$C_6$ alkyl, or $C_1$-$C_4$ alkyl). In embodiments, $R^8$ is an unsubstituted alkyl (e.g. $C_1$-$C_8$ alkyl, $C_1$-$C_6$ alkyl, or $C_1$-$C_4$ alkyl).

In embodiments, $R^8$ is $R^{24}$-substituted or unsubstituted alkyl (e.g. $C_1$-$C_8$ alkyl, $C_1$-$C_6$ alkyl, or $C_1$-$C_4$ alkyl). In embodiments, $R^8$ is $R^{24}$-substituted alkyl (e.g. $C_1$-$C_8$ alkyl, $C_1$-$C_6$ alkyl, or $C_1$-$C_4$ alkyl). In embodiments, $R^8$ is an unsubstituted alkyl (e.g. $C_1$-$C_8$ alkyl, $C_1$-$C_6$ alkyl, or $C_1$-$C_4$ alkyl). In embodiments, $R^8$ is hydrogen. In embodiments, $R^8$ is unsubstituted methyl. In embodiments, $R^8$ is unsubstituted ethyl. In embodiments, $R^8$ is unsubstituted propyl.

$R^{24}$ is independently halogen, —$CX^{24}_3$, —$CHX^{24}_2$, —$CH_2X^{24}$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(=O)$NHNH_2$, NHC(=O)$NH_2$, —$NHSO_2H$, —NHC(=O)H, —NHC(O)OH, —NHOH, —$OCX^{24}_3$, —$OCHX^{24}_2$, —$OCH_2X^{24}$, unsubstituted alkyl (e.g. $C_1$-$C_8$ alkyl, $C_1$-$C_6$ alkyl, or $C_1$-$C_4$ alkyl), unsubstituted heteroalkyl (e.g. 2 to 10 membered heteroalkyl, 2 to 8 membered heteroalkyl, 4 to 8 membered heteroalkyl, 2 to 6 membered heteroalkyl, or 2 to 4 membered heteroalkyl), unsubstituted cycloalkyl (e.g. $C_3$-$C_8$ cycloalkyl, $C_4$-$C_8$ cycloalkyl, or $C_5$-$C_6$ cycloalkyl), unsubstituted heterocycloalkyl (e.g. 3 to 8 membered heterocycloalkyl, 4 to 8 membered heterocycloalkyl, or 5 to 6 membered heterocycloalkyl), unsubstituted aryl (e.g. $C_6$-$C_{10}$ aryl or $C_6$ aryl), or unsubstituted heteroaryl (e.g. 5 to 10 membered heteroaryl, 5 to 9 membered heteroaryl, or 5 to 6 membered heteroaryl). $X^{24}$ is —F, —Cl, —Br, and —I.

In embodiments, $R^9$ is independently oxo, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^9$ is independently —F. In embodiments, $R^9$ is independently —Cl. In embodiments, $R^9$ is independently —Br. In embodiments, $R^9$ is independently —I.

In embodiments, $R^9$ is independently oxo, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, $R^{25}$-substituted or unsubstituted alkyl (e.g., $C_1$-$C_8$ alkyl, $C_1$-$C_6$ alkyl, or $C_1$-$C_4$ alkyl), $R^{25}$-substituted or unsubstituted heteroalkyl (e.g., 2 to 8 membered heteroalkyl, 2 to 6 membered heteroalkyl, or 2 to 4 membered heteroalkyl), $R^{25}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{25}$-substituted or unsubstituted heterocycloalkyl (e.g., 3 to 8 membered heterocycloalkyl, 3 to 6 membered heterocycloalkyl, or 5 to 6 membered heterocycloalkyl), $R^{25}$-substituted or unsubstituted aryl (e.g., $C_6$-$C_{10}$ aryl, $C_{10}$ aryl, or phenyl), or $R^{25}$-substituted or unsubstituted heteroaryl (e.g., 5 to 10 membered heteroaryl, 5 to 9 membered heteroaryl, or 5 to 6 membered heteroaryl).

In embodiments, $R^9$ is independently oxo, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^9$ is independently oxo. In embodiments, $R^9$ is independently halogen. In embodiments, $R^9$ is independently —$CCl_3$. In embodiments, $R^9$ is independently —$CBr_3$. In embodiments, $R^9$ is independently —$CF_3$. In embodiments, $R^9$ is independently —$CI_3$. In embodiments, $R^9$ is independently $CHCl_2$. In embodiments, $R^9$ is independently —$CHBr_2$. In embodiments, $R^9$ is independently —$CHF_2$. In embodiments, $R^9$ is independently —$CHI_2$. In embodiments, $R^9$ is independently —$CH_2Cl$. In embodiments, $R^9$ is independently —$CH_2Br$. In embodiments, $R^9$ is independently —$CH_2F$. In embodiments, $R^9$ is independently —$CH_2I$. In embodiments, $R^9$ is independently —CN. In embodiments, $R^9$ is independently —OH. In embodiments, $R^9$ is independently —$NH_2$. In embodiments, $R^9$ is independently —COOH. In embodiments, $R^9$ is independently —$CONH_2$. In embodiments, $R^9$ is independently —$NO_2$. In embodiments, $R^9$ is independently —SH. In embodiments, $R^9$ is independently —$SO_3H$. In embodiments, $R^9$ is independently —$SO_4H$. In embodiments, $R^9$ is independently —$SO_2NH_2$. In embodiments, $R^9$ is independently —$NHNH_2$. In embodiments, $R^9$ is independently —$ONH_2$. In embodiments, $R^9$ is independently —NHC(O)$NHNH_2$. In embodiments, $R^9$ is independently —NHC(O)$NH_2$. In embodiments, $R^9$ is independently —$NHSO_2H$. In embodiments, $R^9$ is independently —NHC(O)H. In embodiments, $R^9$ is independently —NHC(O)OH. In embodiments, $R^9$ is independently —NHOH. In embodiments, $R^9$ is independently —$OCCl_3$. In embodiments, $R^9$ is independently —$OCF_3$. In embodiments, $R^9$ is independently —$OCBr_3$. In embodiments, $R^9$ is independently —$OCI_3$. In embodiments, $R^9$ is independently —$OCHCl_2$. In embodiments, $R^9$ is independently —$OCHBr_2$. In embodiments, $R^9$ is independently —$OCHI_2$. In embodiments, $R^9$ is independently —$OCHF_2$. In embodiments, $R^9$ is independently —$OCH_2Cl$. In embodiments, $R^9$ is independently —$OCH_2Br$. In embodiments, $R^9$ is independently —$OCH_2I$. In embodiments, $R^9$ is independently —$OCH_2F$. In embodiments, $R^9$ is independently —$N_3$.

In embodiments, $R^9$ is $R^{25}$-substituted or unsubstituted alkyl (e.g., $C_1$-$C_8$ alkyl, $C_1$-$C_6$ alkyl, or $C_1$-$C_4$ alkyl). In embodiments, $R^9$ is $R^{25}$-substituted alkyl (e.g., $C_1$-$C_8$ alkyl, $C_1$-$C_6$ alkyl, or $C_1$-$C_4$ alkyl). In embodiments, $R^9$ is an unsubstituted alkyl (e.g., $C_1$-$C_8$ alkyl, $C_1$-$C_6$ alkyl, or $C_1$-$C_4$ alkyl). In embodiments, $R^9$ is $R^{25}$-substituted or unsubstituted heteroalkyl (e.g., 2 to 8 membered heteroalkyl, 2 to 6 membered heteroalkyl, or 2 to 4 membered heteroalkyl). In embodiments, $R^9$ is $R^{25}$-substituted heteroalkyl (e.g., 2 to 8 membered heteroalkyl, 2 to 6 membered heteroalkyl, or 2 to 4 membered heteroalkyl). In embodiments, $R^9$ is an unsubstituted heteroalkyl (e.g., 2 to 8 membered heteroalkyl, 2 to 6 membered heteroalkyl, or 2 to 4 membered heteroalkyl). In embodiments, $R^9$ is $R^{25}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^9$ is $R^{25}$-substituted cycloalkyl (e.g., $C_3$-$C_8$ cycloalkyl, $C_3$-$C_6$ cycloalkyl, or $C_5$-$C_6$ cycloalkyl). In embodiments, $R^9$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^9$ is $R^{25}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^9$ is $R^{25}$-substituted heterocycloalkyl (e.g., 3 to 8 membered heterocycloalkyl, 3 to 6 membered heterocycloalkyl, or 5 to 6 membered heterocycloalkyl). In embodiments, $R^9$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^9$ is $R^{25}$-substituted or unsubstituted aryl (e.g., $C_6$-$C_{10}$ aryl, $C_{10}$ aryl, or phenyl). In embodiments, $R^9$ is $R^{25}$-substituted aryl (e.g., $C_6$-$C_{10}$ aryl, $C_{10}$ aryl, or phenyl). In embodiments, $R^9$ is an unsubstituted aryl (e.g., $C_6$-$C_{10}$ aryl, $C_{10}$ aryl, or phenyl). In embodiments, $R^9$ is $R^{25}$-substituted or unsubstituted heteroaryl (e.g., 5 to 10 membered heteroaryl, 5 to 9 membered heteroaryl, or 5 to 6 membered heteroaryl). In embodiments, $R^9$ is $R^{25}$-substituted heteroaryl (e.g., 5 to 10 membered heteroaryl, 5 to 9 membered heteroaryl, or 5 to 6 membered heteroaryl). In embodiments, $R^9$ is an unsubstituted heteroaryl (e.g., 5 to 10 membered heteroaryl, 5 to 9 membered heteroaryl, or 5 to 6 membered heteroaryl). In embodiments, two adjacent $R^9$ substituents are joined to form an $R^{25}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{25}$-substituted or unsubstituted heterocycloalkyl (e.g., 3 to 8 membered heterocycloalkyl, 3 to 6 membered heterocycloalkyl, or 5 to 6 membered heterocycloalkyl), $R^{25}$-substituted or unsubstituted aryl (e.g., $C_6$-$C_{10}$ aryl, $C_{10}$ aryl, or phenyl), or $R^{25}$-substituted or unsubstituted heteroaryl (e.g., 5 to 10 membered heteroaryl, 5 to 9 membered heteroaryl, or 5 to 6 membered heteroaryl). In embodiments, two adjacent $R^9$ substituents are joined to form an $R^{25}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, two adjacent $R^9$ substituents are joined to form an $R^{25}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, two adjacent $R^9$ substituents are joined to form an $R^{25}$-substituted or unsubstituted aryl (e.g., $C_6$-$C_{10}$ aryl, $C_{10}$ aryl, or phenyl). In embodiments, two adjacent $R^9$ substituents are joined to form an $R^{25}$-substituted or unsubstituted heteroaryl (e.g., 5 to 10 membered heteroaryl, 5 to 9 membered heteroaryl, or 5 to 6 membered heteroaryl).

$R^{25}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{26}$-substituted or unsubstituted alkyl (e.g., $C_1$-$C_8$ alkyl, $C_1$-$C_6$ alkyl, or $C_1$-$C_4$ alkyl), $R^{26}$-substituted or unsubstituted heteroalkyl (e.g., 2 to 8 membered heteroalkyl, 2 to 6 membered heteroalkyl, or 2 to 4 membered heteroalkyl), $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{26}$-substituted or unsubstituted heterocycloalkyl (e.g., 3 to 8 membered heterocycloalkyl, 3 to 6 membered heterocycloalkyl, or 5 to 6 membered heterocycloalkyl), $R^{26}$-substituted or unsubstituted aryl (e.g., $C_6$-$C_{10}$ aryl, $C_{10}$ aryl, or phenyl), or $R^{26}$-substituted or unsubstituted heteroaryl (e.g., 5 to 10 membered heteroaryl, 5 to 9 membered heteroaryl, or 5 to 6 membered heteroaryl). In embodiments, $R^{25}$ is independently oxo, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH$_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{25}$ is independently oxo. In embodiments, $R^{25}$ is independently halogen. In embodiments, $R^{25}$ is independently —$CCl_3$. In embodiments, $R^{25}$ is independently —$CBr_3$. In embodiments, $R^{25}$ is independently —$CF_3$. In embodiments, $R^{25}$ is independently —$CI_3$. In embodiments, $R^{25}$ is independently $CHCl_2$. In embodiments, $R^{25}$ is independently —$CHBr_2$. In embodiments, $R^{25}$ is independently —$CHF_2$. In embodiments, $R^{25}$ is independently —$CHI_2$. In embodiments, $R^{25}$ is independently —$CH_2Cl$. In embodiments, $R^{25}$ is independently —$CH_2Br$. In embodiments, $R^{25}$ is independently —$CH_2F$. In embodiments, $R^{25}$ is independently —$CH_2I$. In embodiments, $R^{25}$ is independently —CN. In embodiments, $R^{25}$ is independently —OH. In embodiments, $R^{25}$ is independently —$NH_2$. In embodiments, $R^{25}$ is independently —COOH. In embodiments, $R^{25}$ is independently —$CONH_2$. In embodiments, $R^{25}$ is independently —$NO_2$. In embodiments, $R^{25}$ is independently —SH. In embodiments, $R^{25}$ is independently —$SO_3H$. In embodiments, $R^{25}$ is independently —$SO_4H$. In embodiments, $R^{25}$ is independently —$SO_2NH_2$. In embodiments, $R^{25}$ is independently —$NHNH_2$. In embodiments, $R^{25}$ is independently —$ONH_2$. In embodiments, $R^{25}$ is independently —NHC(O)NHNH$_2$. In embodiments, $R^{25}$ is independently —NHC(O)NH$_2$. In embodiments, $R^{25}$ is independently —HNSO$_2$H. In embodiments, $R^{25}$ is independently —NHC(O)H. In embodiments, $R^{25}$ is independently —NHC(O)OH. In embodiments, $R^{25}$ is independently —NHOH. In embodiments, $R^{25}$ is independently —OCCl$_3$. In embodiments, $R^{25}$ is independently —OCF$_3$. In embodiments, $R^{25}$ is independently —OCBr$_3$. In embodiments, $R^{25}$ is independently OCI$_3$. In embodiments, $R^{25}$ is independently —OCHCl$_2$. In embodiments, $R^{25}$ is independently —OCHBr$_2$. In embodiments, $R^{25}$ is independently —OCHI$_2$. In embodiments, $R^{25}$ is independently —OCHF$_2$. In embodiments, $R^{25}$ is independently —OCH$_2$Cl. In embodiments, $R^{25}$ is independently —OCH$_2$Br. In embodiments, $R^{25}$ is independently —OCH$_2$I. In embodiments, $R^{25}$ is independently —OCH$_2$F. In embodiments, $R^{25}$ is independently —N$_3$.

In embodiments, $R^{25}$ is $R^{26}$-substituted or unsubstituted alkyl (e.g., $C_1$-$C_8$ alkyl, $C_1$-$C_6$ alkyl, or $C_1$-$C_4$ alkyl). In embodiments, $R^{25}$ is $R^{26}$-substituted alkyl (e.g., $C_1$-$C_8$ alkyl, $C_1$-$C_6$ alkyl, or $C_1$-$C_4$ alkyl). In embodiments, $R^{25}$ is an unsubstituted alkyl (e.g., $C_1$-$C_8$ alkyl, $C_1$-$C_6$ alkyl, or $C_1$-$C_4$ alkyl)

In embodiments, $R^{25}$ is $R^{26}$-substituted or unsubstituted heteroalkyl (e.g., 2 to 8 membered heteroalkyl, 2 to 6 membered heteroalkyl, or 2 to 4 membered heteroalkyl). In embodiments, $R^{25}$ is $R^{26}$-substituted heteroalkyl (e.g., 2 to 8 membered heteroalkyl, 2 to 6 membered heteroalkyl, or 2 to 4 membered heteroalkyl). In embodiments, $R^{25}$ is an unsubstituted heteroalkyl (e.g., 2 to 8 membered heteroalkyl, 2 to 6 membered heteroalkyl, or 2 to 4 membered heteroalkyl).

In embodiments, $R^{25}$ is $R^{26}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{25}$ is $R^{26}$-substituted cycloalkyl (e.g., $C_3$-$C_8$ cycloalkyl, $C_3$-$C_6$ cycloalkyl, or $C_5$-$C_6$ cycloalkyl). In embodiments, $R^{25}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{25}$ is $R^{26}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{25}$ is $R^{26}$-substituted heterocycloalkyl (e.g., 3 to 8 membered heterocycloalkyl, 3 to 6 membered heterocycloalkyl, or 5 to 6 membered heterocycloalkyl). In embodiments, $R^{25}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{25}$ is $R^{26}$-substituted or unsubstituted aryl (e.g., $C_6$-$C_{10}$ aryl, $C_{10}$ aryl, or phenyl). In embodiments, $R^{25}$ is $R^{26}$-substituted aryl (e.g., $C_6$-$C_{10}$ aryl, $C_{10}$ aryl, or phenyl). In embodiments, $R^{25}$ is an unsubstituted aryl (e.g., $C_6$-$C_{10}$ aryl, $C_{10}$ aryl, or phenyl).

In embodiments, $R^{25}$ is $R^{26}$-substituted or unsubstituted heteroaryl (e.g., 5 to 10 membered heteroaryl, 5 to 9 membered heteroaryl, or 5 to 6 membered heteroaryl). In embodiments, $R^{25}$ is $R^{26}$-substituted heteroaryl (e.g., 5 to 10 membered heteroaryl, 5 to 9 membered heteroaryl, or 5 to 6 membered heteroaryl). In embodiments, $R^{25}$ is an unsubstituted heteroaryl (e.g., 5 to 10 membered heteroaryl, 5 to 9 membered heteroaryl, or 5 to 6 membered heteroaryl).

$R^{26}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, —NHC(O)NH_2, —NHSO_2H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^{26}$-substituted or unsubstituted alkyl (e.g., $C_1$-$C_8$ alkyl, $C_1$-$C_6$ alkyl, or $C_1$-$C_4$ alkyl), $R^{27}$-substituted or unsubstituted heteroalkyl (e.g., 2 to 8 membered heteroalkyl, 2 to 6 membered heteroalkyl, or 2 to 4 membered heteroalkyl), $R^{27}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{27}$-substituted or unsubstituted heterocycloalkyl (e.g., 3 to 8 membered heterocycloalkyl, 3 to 6 membered heterocycloalkyl, or 5 to 6 membered heterocycloalkyl), $R^{27}$-substituted or unsubstituted aryl (e.g., $C_6$-$C_{10}$ aryl, $C_{10}$ aryl, or phenyl), or $R^{27}$-substituted or unsubstituted heteroaryl (e.g., 5 to 10 membered heteroaryl, 5 to 9 membered heteroaryl, or 5 to 6 membered heteroaryl). In embodiments, $R^{26}$ is independently oxo, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{26}$ is independently —OH. In embodiments, $R^{26}$ is independently —$OCH_3$. In embodiments, $R^{26}$ is independently —$OCH_2CH_3$. In embodiments, $R^{26}$ is independently —F. In embodiments, $R^{26}$ is independently —NHC(O)CH_3. In embodiments, $R^{26}$ is independently —COOH. In embodiments, $R^{26}$ is independently —$SO_2NH_2$.

In embodiments, $R^{27}$ is independently oxo, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{9A}$, $R^{9B}$, $R^{9C}$, and $R^{9D}$ are independently hydrogen, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)NHNH_2, $R^{25}$-substituted or unsubstituted alkyl (e.g., $C_1$-$C_8$ alkyl, $C_1$-$C_6$ alkyl, or $C_1$-$C_4$ alkyl), $R^{25}$-substituted or unsubstituted heteroalkyl (e.g., 2 to 8 membered heteroalkyl, 2 to 6 membered heteroalkyl, or 2 to 4 membered heteroalkyl), $R^{25}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{25}$-substituted or unsubstituted heterocycloalkyl (e.g., 3 to 8 membered heterocycloalkyl, 3 to 6 membered heterocycloalkyl, or 5 to 6 membered heterocycloalkyl), $R^{25}$-substituted or unsubstituted aryl (e.g., $C_6$-$C_{10}$ aryl, $C_{10}$ aryl, or phenyl), or $R^{25}$-substituted or unsubstituted heteroaryl (e.g., 5 to 10 membered heteroaryl, 5 to 9 membered heteroaryl, or 5 to 6 membered heteroaryl). In embodiments, $R^{9A}$ and $R^{9B}$ substituents bonded to the same nitrogen atom are joined to form an $R^{25}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{25}$-substituted or unsubstituted heteroaryl (e.g., 5 to 10 membered heteroaryl, 5 to 9 membered heteroaryl, or 5 to 6 membered heteroaryl). In embodiments, $R^{9A}$ and $R^{9B}$ substituents bonded to the same nitrogen atom are joined to form an $R^{25}$-substituted or unsubstituted heterocycloalkyl (e.g., 3 to 8 membered heterocycloalkyl, 3 to 6 membered heterocycloalkyl. In embodiments, $R^{9A}$ and $R^{9B}$ substituents bonded to the same nitrogen atom are joined to form an $R^{25}$-substituted or unsubstituted heteroaryl (e.g., 5 to 10 membered heteroaryl, 5 to 9 membered heteroaryl, or 5 to 6 membered heteroaryl).

In embodiments, $R^{10}$ is independently oxo, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl). In embodiments, $R^{10}$ is independently —F. In embodiments, $R^{10}$ is independently —Cl. In embodiments, $R^m$ is independently —Br. In embodiments, $R^{10}$ is independently —I.

In embodiments, $R^{10}$ is independently oxo, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, $R^{28}$-substituted or unsubstituted alkyl (e.g., $C_1$-$C_8$ alkyl, $C_1$-$C_6$ alkyl, or $C_1$-$C_4$ alkyl), $R^{28}$-substituted or unsubstituted heteroalkyl (e.g., 2 to 8 membered heteroalkyl, 2 to 6 membered heteroalkyl, or 2 to 4 membered heteroalkyl), $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28}$-substituted or unsubstituted aryl (e.g., $C_6$-$C_{10}$ aryl, $C_{10}$ aryl, or phenyl), or $R^{28}$-substituted or unsubstituted heteroaryl (e.g., 5 to 10 membered heteroaryl, 5 to 9 membered heteroaryl, or 5 to 6 membered heteroaryl).

In embodiments, $R^{10}$ is independently oxo, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{10}$ s $R^{28}$-substituted or unsubstituted alkyl (e.g., $C_1$-$C_8$ alkyl, $C_1$-$C_6$ alkyl, or $C_1$-$C_4$ alkyl). In embodiments, $R^{10}$ is $R^{28}$-substituted alkyl (e.g. $C_1$-$C_8$ alkyl, $C_1$-$C_6$ alkyl, or $C_1$-$C_4$ alkyl). In embodiments, $R^{10}$ is an unsubstituted alkyl (e.g., $C_1$-$C_8$ alkyl, $C_1$-$C_6$ alkyl, or $C_1$-$C_4$ alkyl). In embodiments, $R^{10}$ is $R^{28}$-substituted or unsubstituted heteroalkyl (e.g. 2 to 8 membered heteroalkyl, 2 to 6 membered heteroalkyl, or 2 to 4 membered heteroalkyl). In embodiments, $R^{10}$ is $R^{28}$-substituted heteroalkyl (e.g., 2 to 8 membered heteroalkyl, 2 to 6 membered heteroalkyl, or 2 to 4 membered heteroalkyl). In embodiments, $R^{10}$ is an unsubstituted heteroalkyl (e.g., 2 to 8 membered heteroalkyl, 2 to 6 membered heteroalkyl, or 2 to 4 membered heteroalkyl). In embodiments, $R^{10}$ is $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{10}$ is $R^{28}$-substituted cycloalkyl (e.g., $C_3$-$C_6$ cycloalkyl, $C_3$-$C_6$ cycloalkyl, or $C_5$-$C_6$ cycloalkyl). In embodiments, $R^{10}$ is an unsubstituted cycloalkyl (e.g., $C_3$-$C_8$ cycloalkyl, $C_3$-$C_6$ cycloalkyl, or $C_5$-$C_6$ cycloalkyl). In embodiments, $R^{10}$ is $R^{28}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{10}$ is $R^{28}$-substituted heterocycloalkyl (e.g., 3 to 8 membered heterocycloalkyl, 3 to 6 membered heterocycloalkyl, or 5 to 6 membered heterocycloalkyl). In embodiments, $R^{10}$ is an unsubstituted heterocycloalkyl (e.g., 3 to 8 membered heterocycloalkyl, 3 to 6 membered heterocycloalkyl, or 5 to 6 membered heterocycloalkyl). In embodiments, $R^{10}$ is $R^{28}$-substituted or unsubstituted aryl (e.g., $C_6$-$C_{10}$ aryl, $C_{10}$ aryl, or phenyl). In embodiments, $R^{10}$ is $R^{28}$-substituted aryl (e.g., $C_6$-$C_{10}$ aryl, $C_{10}$ aryl, or phenyl). In embodiments, $R^{10}$ is an unsubstituted aryl (e.g., $C_6$-$C_{10}$ aryl, $C_{10}$ aryl, or phenyl). In embodiments, $R^{10}$ is $R^{28}$-substituted or unsubstituted heteroaryl (e.g., 5 to 10 membered heteroaryl, 5 to 9 membered heteroaryl, or 5 to 6 membered heteroaryl). In embodiments, $R^{10}$ is $R^{28}$-substituted heteroaryl (e.g., 5 to 10 membered heteroaryl, 5 to 9 membered heteroaryl, or 5 to 6 membered heteroaryl). In embodiments, $R^{10}$ is an unsubstituted heteroaryl (e.g., 5 to 10 membered heteroaryl, 5 to 9 membered heteroaryl, or 5 to 6 membered heteroaryl). In embodiments, two adjacent $R^{10}$ substituents are joined to form an $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28}$-substituted or unsubstituted aryl (e.g., $C_6$-$C_{10}$ aryl, $C_{10}$ aryl, or phenyl), or $R^{28}$-substituted or unsubstituted heteroaryl (e.g., 5 to 10 membered heteroaryl, 5 to 9 membered heteroaryl, or 5 to 6 membered heteroaryl). In embodiments, two adjacent $R^m$ substituents are joined to form an $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, two adjacent $R^m$ substituents are joined to form an $R^{28}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, two adjacent $R^{10}$ substituents are joined to form an $R^{28}$-substituted or unsubstituted aryl (e.g., $C_6$-$C_{10}$ aryl, $C_{10}$ aryl, or phenyl). In embodiments, two adjacent $R^{10}$ substituents are joined to form an $R^{28}$-substituted or unsubstituted heteroaryl (e.g., 5 to 10 membered heteroaryl, 5 to 9 membered heteroaryl, or 5 to 6 membered heteroaryl).

In embodiments, $R^{10}$ is independently oxo. In embodiments, $R^{10}$ is independently halogen. In embodiments, $R^{10}$ is independently —CCl$_3$. In embodiments, $R^1$ is independently —CBr$_3$. In embodiments, $R^{10}$ is independently —CF$_3$. In embodiments, $R^{10}$ is independently —CI$_3$. In embodiments, $R^{10}$ is independently CHCl$_2$. In embodiments, $R^{10}$ is independently —CHBr$_2$. In embodiments, $R^{10}$ is independently —CHF$_2$. In embodiments, $R^{10}$ is independently —CHI$_2$. In embodiments, $R^{10}$ is independently —CH$_2$Cl. In embodiments, $R^{10}$ is independently —CH$_2$Br. In embodiments, $R^{10}$ is independently —CH$_2$F. In embodiments, $R^{10}$ is independently —CH$_2$I. In embodiments, $R^{10}$ is independently —CN. In embodiments, $R^{10}$ is independently —OH. In embodiments, $R^{10}$ is independently —NH$_2$. In embodiments, $R^{10}$ is independently —COOH. In embodiments, $R^{10}$ is independently —CONH$_2$. In embodiments, $R^{10}$ is independently —NO$_2$. In embodiments, $R^1$ is independently —SH. In embodiments, $R^{10}$ is independently —SO$_3$H. In embodiments, $R^{10}$ is independently —SO$_4$H. In embodiments, $R^{10}$ is independently —SO$_2$NH$_2$. In embodiments, $R^{10}$ is independently —NHNH$_2$. In embodiments, $R^{10}$ is independently —ONH$_2$. In embodiments, $R^{10}$ is independently —NHC(O)NHNH$_2$. In embodiments, $R^{10}$ is independently —NHC(O)NH$_2$. In embodiments, $R^{10}$ is independently —HNSO$_2$H. In embodiments, $R^{10}$ is independently —NHC(O)H. In embodiments, $R^{10}$ is independently —NHC(O)OH. In embodiments, $R^{10}$ is independently —NHOH. In embodiments, $R^{10}$ is independently —OCCl$_3$. In embodiments, $R^{10}$ is independently —OCF$_3$. In embodiments, $R^{10}$ is independently —OCBr$_3$. In embodiments, $R^{10}$ is independently OCI$_3$. In embodiments, $R^{10}$ is independently —OCHCl$_2$. In embodiments, $R^{10}$ is independently —OCHBr$_2$. In embodiments, $R^{10}$ is independently —OCHI$_2$. In embodiments, $R^{10}$ is independently —OCHF$_2$. In embodiments, $R^{10}$ is independently —OCH$_2$Cl. In embodiments, $R^{10}$ is independently —OCH$_2$Br. In embodiments, $R^{10}$ is independently —OCH$_2$I. In embodiments, $R^{10}$ is independently —OCH$_2$F. In embodiments, $R^{10}$ is independently —N$_3$.

$R^{28}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, $R^{26}$-substituted or unsubstituted alkyl (e.g., $C_1$-$C_8$ alkyl, $C_1$-$C_6$ alkyl, or $C_1$-$C_4$ alkyl), $R^{29}$-substituted or unsubstituted heteroalkyl (e.g., 2 to 8 membered heteroalkyl, 2 to 6 membered heteroalkyl, or 2 to 4 membered heteroalkyl), $R^{29}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{29}$-substituted or unsubstituted heterocycloalkyl (e.g., 3 to 8 membered heterocycloalkyl, 3 to 6 membered heterocycloalkyl, or 5 to 6 membered heterocycloalkyl), $R^{29}$-substituted or unsubstituted aryl (e.g., $C_6$-$C_{10}$ aryl, $C_{10}$ aryl, or phenyl), or $R^{29}$-substituted or unsubstituted heteroaryl (e.g., 5 to 10 membered heteroaryl, 5 to 9 membered heteroaryl, or 5 to 6 membered heteroaryl). In embodiments, $R^{28}$ is independently oxo, halogen, —CF$_3$, —CBr$_3$, —CCl$_3$, —CI$_3$—CHF$_2$, —CHBr$_2$, —CHCl$_2$, —CHI$_2$, —CH$_2$F, —CH$_2$Br, —CH$_2$Cl, —CH$_2$I, —OCF$_3$, —OCBr$_3$, —OCCl$_3$, —OCI$_3$, —OCHF$_2$, —OCHBr$_2$, —OCHCl$_2$, —OCHI$_2$, —OCH$_2$F, —OCH$_2$Br, —OCH$_2$Cl, —OCH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, unsubstituted alkyl (e.g., C1-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{28}$ is independently oxo. In embodiments, $R^{28}$ is independently halogen. In embodiments, $R^{28}$ is independently —CCl$_3$. In embodiments, $R^{28}$ is independently —CBr$_3$. In embodiments, $R^{28}$ is independently —CF$_3$. In embodiments, $R^{28}$ is independently —CI$_3$. In embodiments, $R^{28}$ is independently CHCl$_2$. In embodiments, $R^{28}$ is independently —CHBr$_2$. In embodiments, $R^{28}$ is independently —CHF$_2$. In embodiments, $R^{28}$ is independently —CHI$_2$. In embodiments, $R^{28}$ is independently —CH$_2$Cl. In embodiments, $R^{28}$ is independently —CH$_2$Br. In embodiments, $R^{28}$ is independently —CH$_2$F. In embodiments, $R^{28}$ is independently —CH$_2$I. In embodiments, $R^{28}$ is independently —CN. In embodiments, $R^{28}$ is independently —OH. In embodiments, $R^{28}$ is independently —NH$_2$. In embodiments, $R^{28}$ is independently —COOH. In embodiments, $R^{28}$ is independently —CONH$_2$. In embodiments, $R^{28}$ is independently —NO$_2$. In embodiments, $R^{28}$ is independently —SH. In embodiments, $R^{28}$ is independently —SO$_3$H. In embodiments, $R^{28}$ is independently —SO$_4$H. In embodiments, $R^{28}$ is independently —SO$_2$NH$_2$. In embodiments, $R^{28}$ is independently —NHNH$_2$. In embodiments, $R^{28}$ is independently —ONH$_2$. In embodiments, $R^{28}$ is independently —NHC(O)NHNH$_2$. In embodiments, $R^{28}$ is independently NHC(O)NH$_2$. In embodiments, $R^{28}$ is independently —HNSO$_2$H. In embodiments, $R^{28}$ is independently —NHC(O)H. In embodiments, $R^{28}$ is independently —NHC(O)OH. In embodiments, $R^{28}$ is independently —NHOH. In embodiments, $R^{28}$ is independently —OCCl$_3$. In embodiments, $R^{28}$ is independently —OCF$_3$. In embodiments, $R^{28}$ is independently —OCBr$_3$. In embodiments, $R^{28}$ is independently OCI$_3$. In embodiments, $R^{28}$ is independently —OCHCl$_2$. In embodiments, $R^{28}$ is independently —OCHBr$_2$. In embodiments, $R^{28}$ is independently —OCHI$_2$. In embodiments, $R^{28}$ is independently —OCHF$_2$. In embodiments, $R^{28}$ is independently —OCH$_2$Cl. In embodiments, $R^{28}$ is independently —OCH$_2$Br. In embodiments, $R^{28}$ is independently —OCH$_2$I. In embodiments, $R^{28}$ is independently —OCH$_2$F. In embodiments, $R^{28}$ is independently —N$_3$.

In embodiments, $R^{28}$ is $R^{29}$-substituted or unsubstituted alkyl (e.g., $C_1$-$C_8$ alkyl, $C_1$-$C_6$ alkyl, or $C_1$-$C_4$ alkyl). In embodiments, $R^{28}$ is $R^{29}$-substituted alkyl (e.g., $C_1$-$C_8$ alkyl, $C_1$-$C_6$ alkyl, or $C_1$-$C_4$ alkyl). In embodiments, $R^{28}$ is an unsubstituted alkyl (e.g., $C_1$-$C_8$ alkyl, $C_1$-$C_6$ alkyl, or $C_1$-$C_4$ alkyl)

In embodiments, $R^{28}$ is $R^{29}$-substituted or unsubstituted heteroalkyl (e.g., 2 to 8 membered heteroalkyl, 2 to 6 membered heteroalkyl, or 2 to 4 membered heteroalkyl). In embodiments, $R^{28}$ is $R^{29}$-substituted heteroalkyl (e.g., 2 to 8 membered heteroalkyl, 2 to 6 membered heteroalkyl, or 2 to 4 membered heteroalkyl). In embodiments, $R^{28}$ is an unsubstituted heteroalkyl (e.g., 2 to 8 membered heteroalkyl, 2 to 6 membered heteroalkyl, or 2 to 4 membered heteroalkyl).

In embodiments, $R^{28}$ is $R^{29}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{28}$ is $R^{29}$-substituted cycloalkyl (e.g., $C_3$-$C_8$ cycloalkyl, $C_3$-$C_6$ cycloalkyl, or $C_5$-$C_6$ cycloalkyl). In embodiments, $R^{28}$ is an unsubstituted cycloalkyl (e.g., $C_3$-$C_8$ cycloalkyl, $C_3$-$C_6$ cycloalkyl, or $C_5$-$C_6$ cycloalkyl).

In embodiments, $R^{28}$ is $R^{29}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{28}$ is $R^{29}$-substituted heterocycloalkyl (e.g., 3 to 8 membered heterocycloalkyl, 3 to 6 membered heterocycloalkyl, or 5 to 6 membered heterocycloalkyl). In embodiments, $R^{28}$ is an unsubstituted heterocycloalkyl (e.g., 3 to 8 membered heterocycloalkyl, 3 to 6 membered heterocycloalkyl, or 5 to 6 membered heterocycloalkyl).

In embodiments, $R^{28}$ is $R^{29}$-substituted or unsubstituted aryl (e.g., $C_6$-$C_{10}$ aryl, $C_{10}$ aryl, or phenyl). In embodiments, $R^{28}$ is $R^{29}$-substituted aryl (e.g., $C_6$-$C_{10}$ aryl, $C_{10}$ aryl, or phenyl). In embodiments, $R^{28}$ is an unsubstituted aryl (e.g., $C_6$-$C_{10}$ aryl, $C_{10}$ aryl, or phenyl).

In embodiments, $R^{28}$ is $R^{29}$-substituted or unsubstituted heteroaryl (e.g., 5 to 10 membered heteroaryl, 5 to 9 membered heteroaryl, or 5 to 6 membered heteroaryl). In embodiments, $R^{28}$ is $R^{29}$-substituted heteroaryl (e.g., 5 to 10 membered heteroaryl, 5 to 9 membered heteroaryl, or 5 to 6 membered heteroaryl). In embodiments, $R^{28}$ is an unsubstituted heteroaryl (e.g., 5 to 10 membered heteroaryl, 5 to 9 membered heteroaryl, or 5 to 6 membered heteroaryl).

$R^{29}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, $R^N$-substituted or unsubstituted alkyl (e.g., $C_1$-$C_8$ alkyl, $C_1$-$C_6$ alkyl, or $C_1$-$C_4$ alkyl), $R^{30}$-substituted or unsubstituted heteroalkyl (e.g., 2 to 8 membered heteroalkyl, 2 to 6 membered heteroalkyl, or 2 to 4 membered heteroalkyl), $R^N$-substituted or unsubstituted cycloalkyl (e.g., $C_3$-$C_8$ cycloalkyl, $C_3$-$C_6$ cycloalkyl, or $C_5$-$C_6$ cycloalkyl), $R^N$-substituted or unsubstituted heterocycloalkyl (e.g., 3 to 8 membered heterocycloalkyl, 3 to 6 membered heterocycloalkyl, or 5 to 6 membered heterocycloalkyl), $R^N$-substituted or unsubstituted aryl (e.g., $C_6$-$C_{10}$ aryl, $C_{10}$ aryl, or phenyl), or $R^N$-substituted or unsubstituted heteroaryl (e.g., 5 to 10 membered heteroaryl, 5 to 9 membered heteroaryl, or 5 to 6 membered heteroaryl). In embodiments, $R^{29}$ is independently oxo, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). In embodiments, $R^{29}$ is independently —OH. In embodiments, $R^{29}$ is independently —$OCH_3$. In embodiments, $R^{29}$ is independently —$OCH_2CH_3$. In embodiments, $R^{29}$ is independently —F. In embodiments, $R^{29}$ is independently —NHC(O)$CH_3$. In embodiments, $R^{29}$ is independently —COOH. In embodiments, $R^{29}$ is independently —$SO_2NH_2$.

In embodiments, $R^{30}$ is independently oxo, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, unsubstituted alkyl (e.g., C1-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

In embodiments, $R^{10A}$, $R^{10B}$, $R^{10C}$, and $R^{10D}$ are independently hydrogen, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCl_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, $R^{28}$-substituted or unsubstituted alkyl (e.g., $C_1$-$C_8$ alkyl, $C_1$-$C_6$ alkyl, or $C_1$-$C_4$ alkyl), $R^{28}$-substituted or unsubstituted heteroalkyl (e.g., 2 to 8 membered heteroalkyl, 2 to 6 membered heteroalkyl, or 2 to 4 membered heteroalkyl), $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28}$-substituted or unsubstituted aryl (e.g., $C_6$-$C_{10}$ aryl, $C_{10}$ aryl, or phenyl), or $R^{28}$-substituted or unsubstituted heteroaryl (e.g., 5 to 10 membered heteroaryl, 5 to 9 membered heteroaryl, or 5 to 6 membered heteroaryl). In embodiments, $R^{10A}$ and $R^{10B}$ substituents bonded to the same nitrogen atom are joined to form an $R^{28}$-substituted or unsubstituted heterocycloalkyl (e.g., 3 to 8 membered heterocycloalkyl, 3 to 6 membered heterocycloalkyl, or 5 to 6 membered heterocycloalkyl) or $R^{28}$-substituted or unsubstituted heteroaryl (e.g., 5 to 10 membered heteroaryl, 5 to 9 membered heteroaryl, or 5 to 6 membered heteroaryl). In embodiments, $R^{10A}$ and $R^{10B}$ substituents bonded to the same nitrogen atom are joined to form an $R^{28}$-substituted or unsubstituted heterocycloalkyl (e.g., 3 to 8 membered heterocycloalkyl, 3 to 6 membered heterocycloalkyl. In embodiments, $R^{10A}$ and $R^{10B}$ substituents bonded to the same nitrogen atom are joined to form an $R^{28}$-substituted or unsubstituted heteroaryl (e.g., 5 to 10 membered heteroaryl, 5 to 9 membered heteroaryl, or 5 to 6 membered heteroaryl).

In embodiments, $R^{10}$ is independently halogen, —$CX^{10}_3$, —$CHX^{10}_2$, —$CH_2X^{10}$, —$OCX^{10}_3$, —$OCH_2X^{10}$, —$OCHX^{10}_2$, —CN, —$SO_{n10}R^{10D}$, —$SO_{v10}NR^{10A}R^{10B}$, —NHC(O)$NR^{10A}R^{10B}$, —N(O)$_{m10}$, —$NR^{10A}R^{10B}$, —C(O)$R^{10C}$, —C(O)—$OR^{10C}$, —C(O)$NR^{10A}R^{10B}$, —$OR^{10D}$, —NR$^{10A}$SO$_2$R$^{10D}$, —NR$^{10A}$C(O)R$^{10C}$, —NR$^{10A}$C(O)OR$^{10C}$, —NR$^{10A}$OR$^{10C}$, R$^{28}$-substituted or unsubstituted alkyl (e.g., C$_1$-C$_8$alkyl, C$_1$-C$_6$ alkyl, or C$_1$-C$_4$ alkyl), R$^{28}$-substituted or unsubstituted alkyl (e.g., 2to 8 membered heteroalkyl, 2 to 6 membered heteroalkyl, or 2 to 4 membered heteroalkyl), R$^{28}$-substituted or unsubstituted cycloalkyl (e.g., C$_3$-C$_8$ cycloalkyl, C$_3$-C$_6$ cycloalkyl, or C$_5$-C$_6$ cycloalkyl), R$^{28}$-substituted or unsubstituted heterocycloalkyl (e.g., 3 to 8 membered heterocycloalkyl, 3 to 6 membered heterocycloalkyl, or 5 to 6 membered heterocycloalkyl), R$^{28}$-substituted or unsubstituted aryl (e.g., C$_6$-C$_{10}$ aryl, C$_{10}$ aryl, or phenyl), or R$^{28}$-substituted or unsubstituted heteroaryl (e.g., 5 to 10 membered heteroaryl, 5 to 9 membered heteroaryl, or 5 to 6 membered heteroaryl). In embodiments, R$^{10}$ is halogen —CX$^{10}_3$, —CHX$^{10}_2$, —CH$_2$X$^{10}$, —OCX$^{10}_3$, —OCH$_2$X$^{10}$, —OCHX$^{10}_2$, —CN, —SO$_{n10}$R$^{10D}$, —SO$_{v10}$NR$^{10A}$R$^{10B}$, —NHC(O)NR$^{10A}$R$^{10B}$, —N(O)$_{m10}$, —NR$^{10A}$R$^{10B}$, —C(O)R$^{10C}$, —C(O)—OR$^{10C}$, —C(O)NR$^{10A}$R$^{10B}$, —OR$^{10D}$, —NR$^{10A}$SO$_2$R$^{10D}$, —NR$^{10A}$C(O)R$^{10C}$, —NR$^{10A}$C(O)OR$^{10C}$, —NR$^{10A}$OR$^{10C}$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl). X$^{10}$ is independently halogen. In embodiments, X$^{10}$ is independently —F. In embodiments, X$^{10}$ is independently —Cl. In embodiments, X$^{10}$ is independently —Br. In embodiments, X$^{10}$ is independently —I.

In embodiments, R$^{10}$ is independently halogen. In embodiments, R$^{10}$ is independently —CX$^{10}_3$. In embodiments, R$^{10}$ is independently —CHX$^{10}_2$. In embodiments, R$^{10}$ is independently —CH$_2$X$^{10}$. In embodiments, R$^1$ is independently —OCX$^{10}_3$. In embodiments, R$^{10}$ is independently —OCH$_2$X$^{10}$. In embodiments, R$^{10}$ is independently —OCHX$^{10}$ 2. In embodiments, R$^{10}$ is independently —CN. In embodiments, R$^{10}$ is independently —SO$_{n10}$R$^{10D}$. In embodiments, R$^{10}$ is independently —SR$^{10D}$. In embodiments, R$^{10}$ is independently —SO$_2$R$^{10D}$. In embodiments, R$^{10}$ is independently —SO$_{v10}$NR$^{10A}$R$^{10B}$. In embodiments, R$^{10}$ is independently —SO$_2$NR$^{10A}$R$^{10B}$. In embodiments, R$^{10}$ is independently —NHC(O)NR$^{10A}$R$^{10B}$. In embodiments, R$^{10}$ is independently —N(O)$_{m10}$. In embodiments, R$^{10}$ is independently —NR$^{10A}$R$^{10B}$. In embodiments, R$^{10}$ is independently —C(O)R$^{10C}$. In embodiments, R$^{10}$ is independently —C(O)—OR$^{10C}$. In embodiments, R$^{10}$ is independently —C(O)NR$^{10A}$R$^{10B}$. In embodiments, R$^{10}$ is independently —OR$^{10D}$. In embodiments, R$^{10}$ is independently —C(O)—OR$^{10A}$R$^{10B}$. In embodiments, R$^{10}$ is independently —NR$^{10A}$C(O)R$^{10C}$. In embodiments, R$^{10}$ is independently —NR$^{10A}$C(O)OR$^{10C}$. In embodiments, R$^{10}$ is independently —NR$^{10A}$OR$^{10C}$. In embodiments, R$^{10}$ is independently methoxy. In embodiments, R$^{10}$ is independently ethoxy. In embodiments, R$^{10}$ is independently propoxy. In embodiments, R$^{10}$ is independently butoxy. In embodiments, R$^{10}$ is independently pentoxy.

In embodiments, R$^{10A}$ is independently hydrogen. In embodiments, R$^{10A}$ is independently —CF$_3$. In embodiments, R$^{10A}$ is independently —CBr$_3$. In embodiments, R$^{10A}$ is independently —CCl$_3$. In embodiments, R$^{10A}$ is independently —CI$_3$. In embodiments, R$^{10A}$ is independently —CHF$_2$. In embodiments, R$^{10A}$ is independently —CHBr$_2$. In embodiments, R$^{10A}$ is independently —CHCl$_2$. In embodiments, R$^{10A}$ is independently —CHI$_2$. In embodiments, R$^{10A}$ is independently —CH$_2$F. In embodiments, R$^{10A}$ is independently —CH$_2$Br. In embodiments, R$^{10A}$ is independently —CH$_2$Cl. In embodiments, R$^{10A}$ is independently —CH$_2$I. In embodiments, R$^{10A}$ is independently —OH. In embodiments, R$^{10A}$ is independently —COOH. In embodiments, R$^{10A}$ is independently —CONH$_2$. In embodiments, R$^{10A}$ is independently R$^{28}$-substituted or unsubstituted alkyl (e.g., C$_1$-C$_8$ alkyl, C$_1$-C$_6$ alkyl, or C$_1$-C$_4$ alkyl). In embodiments, R$^{10A}$ is independently R$^{28}$-substituted or unsubstituted heteroalkyl (e.g., 2 to 8 membered heteroalkyl, 2 to 6 membered heteroalkyl, or 2 to 4 membered heteroalkyl). In embodiments, R$^{10A}$ is independently R$^{28}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{10A}$ is independently R$^{28}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{10A}$ is independently R$^{28}$-substituted or unsubstituted aryl (e.g., C$_6$-C$_{10}$ aryl, C$_{10}$ aryl, or phenyl). In embodiments, R$^{10A}$ is independently R$^{28}$-substituted or unsubstituted heteroaryl (e.g., 5 to 10 membered heteroaryl, 5 to 9 membered heteroaryl, or 5 to 6 membered heteroaryl). In embodiments, R$^{10A}$ is independently unsubstituted methyl. In embodiments, R$^{10A}$ is independently unsubstituted ethyl. In embodiments, R$^{10A}$ is independently unsubstituted propyl. In embodiments, R$^{10A}$ is independently unsubstituted butyl. In embodiments, R$^{10A}$ is independently unsubstituted pentyl. In embodiments, R$^{10A}$ is independently unsubstituted hexyl.

In embodiments, R$^{10B}$ is independently hydrogen. In embodiments, R$^{10B}$ is independently —CF$_3$. In embodiments, R$^{10B}$ is independently —CBr$_3$. In embodiments, R$^{10B}$ is independently —CCl$_3$. In embodiments, R$^{10B}$ is independently —CI$_3$. In embodiments, R$^{10B}$ is independently —CHF$_2$. In embodiments, R$^{10B}$ is independently —CHBr$_2$. In embodiments, R$^{10B}$ is independently —CHCl$_2$. In embodiments, R$^{10B}$ is independently —CHI$_2$. In embodiments, R$^{10B}$ is independently —CH$_2$F. In embodiments, R$^{10B}$ is independently —CH$_2$Br. In embodiments, R$^{10B}$ is independently —CH$_2$Cl. In embodiments, R$^{10B}$ is independently —CH$_2$I. In embodiments, R$^{10B}$ is independently —OH. In embodiments, R$^{10B}$ is independently —COOH. In embodiments, R$^{10B}$ is independently —CONH$_2$. In embodiments, R$^{10B}$ is independently R$^{28}$-substituted or unsubstituted alkyl (e.g., C$_1$-C$_8$ alkyl, C$_1$-C$_6$ alkyl, or C$_1$-C$_4$ alkyl). In embodiments, R$^{10B}$ is independently R$^{28}$-substituted or unsubstituted heteroalkyl (e.g., 2 to 8 membered heteroalkyl, 2 to 6 membered heteroalkyl, or 2 to 4 membered heteroalkyl). In embodiments, R$^{10B}$ is independently R$^{28}$-substituted or unsubstituted cycloalkyl (e.g., C$_3$-C$_8$ cycloalkyl, C$_3$-C$_6$ cycloalkyl, or C$_5$-C$_6$ cycloalkyl). In embodiments, R$^{10B}$ is independently R$^{28}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, R$^{10B}$ is independently R$^{28}$-substituted or unsubstituted aryl (e.g., C$_6$-C$_{10}$ aryl, C$_{10}$ aryl, or phenyl). In embodiments, R$^{10B}$ is independently 10-substituted or unsubstituted heteroaryl (e.g., 5 to 10 membered heteroaryl, 5 to 9 membered heteroaryl, or 5 to 6 membered heteroaryl). In embodiments, R$^{10B}$ is independently unsubstituted methyl. In embodiments, R$^{10B}$ is independently unsubstituted ethyl. In embodiments, R$^{10B}$ is independently unsubstituted propyl. In embodiments, R$^{10B}$ is independently unsubstituted butyl. In embodiments, R$^{10B}$ is independently unsubstituted pentyl. In embodiments, $R^{10B}$ is independently unsubstituted hexyl.

In embodiments, $R^{10C}$ is independently hydrogen. In embodiments, $R^{10C}$ is independently —$CF_3$. In embodiments, $R^{10C}$ is independently —$CBr_3$. In embodiments, $R^{10C}$ is independently —$CCl_3$. In embodiments, $R^{10C}$ is independently —$CI_3$. In embodiments, $R^{10C}$ is independently —$CHF_2$. In embodiments, $R^{10C}$ is independently —$CHBr_2$. In embodiments, $R^{10C}$ is independently —$CHCl_2$. In embodiments, $R^{10C}$ is independently —$CHI_2$. In embodiments, $R^{10C}$ is independently —$CH_2F$. In embodiments, $R^{10C}$ is independently —$CH_2Br$. In embodiments, $R^{10C}$ is independently —$CH_2Cl$. In embodiments, $R^{10C}$ is independently —$CH_2I$. In embodiments, $R^{10C}$ is independently —OH. In embodiments, $R^{10C}$ is independently —COOH. In embodiments, $R^{10C}$ is independently —$CONH_2$. In embodiments, $R^{10C}$ is independently $R^{28}$-substituted or unsubstituted alkyl (e.g., $C_1$-$C_8$ alkyl, $C_1$-$C_6$ alkyl, or $C_1$-$C_4$ alkyl). In embodiments, $R^{10C}$ is independently $R^{28}$-substituted or unsubstituted heteroalkyl (e.g., 2 to 8 membered heteroalkyl, 2 to 6 membered heteroalkyl, or 2 to 4 membered heteroalkyl). In embodiments, $R^{10C}$ is independently $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{10C}$ is independently $R^{28}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{10C}$ is independently $R^{28}$-substituted or unsubstituted aryl (e.g., $C_6$-$C_{10}$ aryl, $C_{10}$ aryl, or phenyl). In embodiments, $R^{10C}$ is independently $R^{28}$-substituted or unsubstituted heteroaryl (e.g., 5 to 10 membered heteroaryl, 5 to 9 membered heteroaryl, or 5 to 6 membered heteroaryl). In embodiments, $R^{10C}$ is independently unsubstituted methyl. In embodiments, $R^{10C}$ is independently unsubstituted ethyl. In embodiments, $R^{10C}$ is independently unsubstituted propyl. In embodiments, $R^{10C}$ is independently unsubstituted butyl. In embodiments, $R^{10C}$ is independently unsubstituted pentyl. In embodiments, $R^{10C}$ is independently unsubstituted hexyl.

In embodiments, $R^{10D}$ is independently hydrogen. In embodiments, $R^{10D}$ is independently —$CF_3$. In embodiments, $R^{10D}$ is independently —$CBr_3$. In embodiments, $R^{10D}$ is independently —$CCl_3$. In embodiments, $R^{10D}$ is independently —$CI_3$. In embodiments, $R^{10D}$ is independently —$CHF_2$. In embodiments, $R^{10D}$ is independently —$CHBr_2$. In embodiments, $R^{10D}$ is independently —$CHCl_2$. In embodiments, $R^{10D}$ is independently —$CHI_2$. In embodiments, $R^{10D}$ is independently —$CH_2F$. In embodiments, $R^{10D}$ is independently —$CH_2Br$. In embodiments, $R^{10D}$ is independently —$CH_2Cl$. In embodiments, $R^{10D}$ is independently —$CH_2I$. In embodiments, $R^{10D}$ is independently —OH. In embodiments, $R^{10D}$ is independently —COOH. In embodiments, $R^{10D}$ is independently —$CONH_2$. In embodiments, $R^{10D}$ is independently $R^{28}$-substituted or unsubstituted alkyl (e.g., $C_1$-$C_8$ alkyl, $C_1$-$C_6$ alkyl, or $C_1$-$C_4$ alkyl). In embodiments, $R^{10D}$ is independently $R^{28}$-substituted or unsubstituted heteroalkyl (e.g., 2 to 8 membered heteroalkyl, 2 to 6 membered heteroalkyl, or 2 to 4 membered heteroalkyl). In embodiments, $R^{10.1}$ is independently $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl). In embodiments, $R^{10D}$ is independently $R^{28}$-substituted or unsubstituted heterocycloalkyl (e.g., 3 to 8 membered heterocycloalkyl, 3 to 6 membered heterocycloalkyl, or 5 to 6 membered heterocycloalkyl). In embodiments, $R^{10D}$ is independently $R^{28}$-substituted or unsubstituted aryl (e.g., $C_6$-$C_{10}$ aryl, $C_{10}$ aryl, or phenyl). In embodiments, $R^{10D}$ is independently $R^{28}$-substituted or unsubstituted heteroaryl (e.g., 5 to 10 membered heteroaryl, 5 to 9 membered heteroaryl, or 5 to 6 membered heteroaryl). In embodiments, $R^{10D}$ is independently unsubstituted methyl. In embodiments, $R^{10D}$ is independently unsubstituted ethyl. In embodiments, $R^{10D}$ is independently unsubstituted propyl. In embodiments, $R^{10D}$ is independently unsubstituted butyl. In embodiments, $R^{10D}$ is independently unsubstituted pentyl. In embodiments, $R^{10D}$ is independently unsubstituted hexyl.

In embodiments, $R^{10.1}$ is independently hydrogen, oxo, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{10.1}$ is independently hydrogen, halogen, —$CX^{10.1}_3$, —$CHX^{10.1}_2$, —$CH_2X^{10.1}$, —$OCX^{10.1}_3$, —$OCH_2X^{10.1}$, —$OCHX^{10.1}_2$, —CN, —$SO_{n10}R^{10D}$, —$SO_{v10}NR^{10A}R^{10B}$, —$NHC(O)NR^{10A}R^{10B}$, —$N(O)_{m10}$, —$NR^{10A}R^{10B}$, —$C(O)R^{10C}$, —C(O)—$OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, $R^{28}$-substituted or unsubstituted alkyl (e.g., $C_1$-$C_8$alkyl, $C_1$-$C_6$ alkyl, or $C_1$-$C_4$ alkyl), $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28}$-substituted or unsubstituted aryl (e.g., $C_6$-$C_{10}$ aryl, $C_{10}$ aryl, or phenyl), or $R^{28}$-substituted or unsubstituted heteroaryl (e.g., 5 to 10 membered heteroaryl, 5 to 9 membered heteroaryl, or 5 to 6 membered heteroaryl). In embodiments, $R^{10.1}$ is halogen, —$CX^{10.1}_3$, —$CHX^{10.1}_2$, —$CH_2X^{10.1}$, —$OCX^{10.1}_3$, —$OCH_2X^{10.1}$, —$OCHX^{10.1}_2$, —CN, —$SO_{n10}R^{10D}$, —$SO_{v10}NR^{10A}R^{10B}$, —$NHC(O)NR^{10A}R^{10B}$, —$N(O)_{m10}$, —$NR^{10A}R^{10B}$, —$C(O)R^{10C}$, —C(O)—$OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, unsubstituted alkyl (e.g., $C_1$-$C_8$alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). $X^{10.1}$ is independently halogen. In embodiments, $X^{10.1}$ is independently —F. In embodiments, $X^{10.1}$ is independently —Cl. In embodiments, $X^{10.1}$ is independently —Br. In embodiments, $X^{10.1}$ is independently —I.

In embodiments, $R^{10.1}$ is independently halogen. In embodiments, $R^{10.1}$ is independently —$CX^{10.1}_3$. In embodiments, $R^{10.1}$ is independently —$CHX^{10.1}_2$. In embodiments, $R^{10.1}$ is independently —$CH_2X^{10.1}$. In embodiments, $R^{10.1}$ is independently —$OCX^{10.1}_3$. In embodiments, $R^{10.1}$ is independently —$OCH_2X^{10.1}$. In embodiments, $R^{10.1}$ is independently —$OCHX^{10.1}_2$. In embodiments, $R^{10.1}$ is independently —CN. In embodiments, $R^{10.1}$ is independently —$SO_{n10}R^{10D}$. In embodiments, $R^{10.1}$ is independently —$SR^{10D}$. In embodiments, $R^{10.1}$ is independently —$SO_2R^{10D}$. In embodiments, $R^{10.1}$ is independently —$SO_{v10}NR^{10A}R^{10B}$. In embodiments, $R^{10.1}$ is independently —$SO_2NR^{10A}R^{10B}$. In embodiments, $R^{10.1}$ is independently —$NHC(O)^{10A}R^{10B}$. In embodiments, $R^{10.1}$ is independently —$N(O)_{m10}$. In embodiments, $R^{10.1}$ is independently —$NR^{10A}R^{10B}$. In embodiments, $R^{10.1}$ is independently —$C(O)R^{10C}$. In embodiments, $R^{10.1}$ is independently —$C(O)$—$OR^{10C}$. In embodiments, $R^{10.1}$ is independently —$C(O)NR^{10A}R^{10B}$. In embodiments, $R^{10.1}$ is independently —$OR^{10D}$. In embodiments, $R^{10.1}$ is independently —$NR^{10A}SO_2R^{10D}$. In embodiments, $R^{10.1}$ is independently —$NR^{10A}C(O)R^{10B}$. In embodiments, $R^{10.1}$ is independently —$NR^{10A}C(O)OR^{10C}$. In embodiments, $R^{10.1}$ is independently —$NR^{10A}OR^{10C}$. In embodiments, $R^{10.1}$ is independently methoxy. In embodiments, $R^{10.1}$ is independently ethoxy. In embodiments, $R^{10.1}$ is independently propoxy. In embodiments, $R^{10.1}$ is independently butoxy. In embodiments, $R^{10.1}$ is independently pentoxy. In embodiments, $R^{10}$ is independently —F. In embodiments, $R^{10}$ is independently —Cl. In embodiments, $R^{10.1}$ is independently —Br. In embodiments, $R^{10.1}$ is independently —I. In embodiments, $R^{10.1}$ is independently oxo. In embodiments, $R^{10.1}$ is independently halogen. In embodiments, $R^{10.1}$ is independently —$CCl_3$. In embodiments, $R^{10.1}$ is independently —$CBr_3$. In embodiments, $R^{10.1}$ is independently —$CF_3$. In embodiments, $R^{10.1}$ is independently —$CI_3$. In embodiments, $R^{10.1}$ is independently $CHCl_2$. In embodiments, $R^{10.1}$ is independently —$CHBr_2$. In embodiments, $R^{10.1}$ is independently —$CHF_2$. In embodiments, $R^{10.1}$ is independently —$CHI_2$. In embodiments, $R^{10.1}$ is independently —$CH_2Cl$. In embodiments, $R^{10.1}$ is independently —$CH_2Br$. In embodiments, $R^{10}$ is independently —$CH_2F$. In embodiments, $R^{10.1}$ is independently —$CH_2I$. In embodiments, $R^{10}$ is independently —CN. In embodiments, $R^{10.1}$ is independently —OH. In embodiments, $R^{10.1}$ is independently —$NH_2$. In embodiments, $R^{10.1}$ is independently —COOH. In embodiments, $R^{10.1}$ is independently —$CONH_2$. In embodiments, $R^{10.1}$ is independently —$NO_2$. In embodiments, $R^{10}$ is independently —SH. In embodiments, $R^{10.1}$ is independently —$SO_3H$. In embodiments, $R^{10}$ is independently —$SO_4H$. In embodiments, $R^{10.1}$ is independently —$SO_2NH_2$. In embodiments, $R^{10.1}$ is independently —$NHNH_2$. In embodiments, $R^{10.1}$ is independently —$ONH_2$. In embodiments, $R^{10.1}$ is independently —$NHC(O)NHNH_2$. In embodiments, $R^{10.1}$ is independently —$NHC(O)NH_2$. In embodiments, $R^{10.1}$ is independently —$HNSO_2H$. In embodiments, $R^{10.1}$ is independently —$NHC(O)H$. In embodiments, $R^{10.1}$ is independently —$NHC(O)OH$. In embodiments, $R^{10.1}$ is independently —NHOH. In embodiments, $R^{10.1}$ is independently —$OCCl_3$. In embodiments, $R^{10.1}$ is independently —$OCF_3$. In embodiments, $R^{10.1}$ is independently —$OCBr_3$. In embodiments, $R^{10.1}$ is independently —$OCI_3$. In embodiments, $R_{10.1}$ independently —$OCHCl_2$. In embodiments, $R^{10.1}$ is independently —$OCHBr_2$. In embodiments, $R^{10.1}$ is independently —$OCHI_2$. In embodiments, $R^{10}$ is independently —$OCHF_2$. In embodiments, $R^{10.1}$ is independently —$OCH_2Cl$. In embodiments, $R^{10.1}$ is independently —$OCH_2Br$. In embodiments, $R^{10.1}$ is independently —$OCH_2I$. In embodiments, $R^{10.1}$ independently —$OCH_2F$. In embodiments, $R^{10.1}$ is independently —$N_3$. In embodiments, $R^{10.1}$ is independently —$CH_3$. In embodiments, $R^{10.1}$ is independently —$OCH(CH_3)_2$. In embodiments, $R^{10.1}$ is independently —$OCH_3$. In embodiments, $R^{10.1}$ is independently hydrogen. In embodiments, $R^{10.1}$ is independently unsubstituted $C_1$-$C_8$ alkoxy. In embodiments, $R^{10.1}$ is independently unsubstituted $C_1$-$C_6$ alkoxy. In embodiments, $R^{10.1}$ is independently unsubstituted $C_1$-$C_4$ alkoxy.

In embodiments, $R^{10.1}$ is independently hydrogen, oxo, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{10.2}$ is independently hydrogen, halogen, —$CX^{10.2}_3$, —$CHX^{10.2}_2$, —$CH_2X^{10.2}$, —$OCX^{10.2}_3$, —$OCH_2X^{10.2}$, —$OCHX^{10.2}_2$, —CN, —$SO_{n10}R^{10D}$, —$SO_{v10}NR^{10A}R^{10B}$, —$NHC(O)NR^{10A}R^{10B}$, —$N(O)_{m10}$, —$NR^{10A}R^{10B}$, —$C(O)R^{10C}$, —$C(O)$—$OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, $R^{28}$-substituted or unsubstituted alkyl (e.g., $C_1$-$C_8$ alkyl, $C_1$-$C_6$ alkyl, or $C_1$-$C_4$ alkyl), $R^{28}$-substituted or unsubstituted heteroalkyl (e.g., 2 to 8 membered heteroalkyl, 2 to 6 membered heteroalkyl, or 2 to 4 membered heteroalkyl), $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28}$-substituted or unsubstituted aryl (e.g., $C_6$-$C_{10}$ aryl, $C_{10}$ aryl, or phenyl), or $R^{28}$-substituted or unsubstituted heteroaryl (e.g., 5 to 10 membered heteroaryl, 5 to 9 membered heteroaryl, or 5 to 6 membered heteroaryl). In embodiments, $R^{10.2}$ is halogen, —$CX^{10.2}_3$, —$CHX^{10.2}_2$, —$CH_2X^{10.2}$, —$OCX^{10.2}_3$, —$OCH_2X^{10.2}$, —$OCHX^{10.2}_2$, —CN, —$SO_{n10}R^{10D}$, —$SO_{v10}NR^{10A}R^{10B}$, —$NHC(O)NR^{10A}R^{10B}$, —$N(O)_{m10}$, —$NR^{10A}R^{10B}$, —$C(O)R^{10C}$, —$C(O)$—$OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). $X^{10.2}$ is independently halogen. In embodiments, $X^{10.2}$ is independently —F. In embodiments, $X^{10.2}$ is independently —Cl. In embodiments, $X^{10.2}$ is independently —Br. In embodiments, $X^{10.2}$ is independently —I.

In embodiments, $R^{10.2}$ is independently halogen. In embodiments, $R^{10.1}$ is independently —$CX^{10.2}{}_3$. In embodiments, $R^{10.2}$ is independently —$CHX^{10.2}{}_2$. In embodiments, $R^{10.2}$ is independently —$CH_2X^{10.2}$. In embodiments, $R^{10.2}$ is independently —$OCX^{10.2}{}_3$. In embodiments, $R^{10.2}$ is independently —$OCH_2X^{10.2}$. In embodiments, $R^{10.1}$ is independently —$OCHX^{10.2}{}_2$. In embodiments, $R^{10.2}$ is independently —CN. In embodiments, $R^{10.2}$ is independently —$SO_{n10}R^{10D}$. In embodiments, $R^{10.2}$ is independently —$SR^{10D}$. In embodiments, $R^{10.2}$ is independently —$SO_2R^{10D}$. In embodiments, $R^{10.2}$ is independently —$SO_{v10}NR^{10A}R^{10B}$. In embodiments, $R^{10.2}$ is independently —$SO_2NR^{10A}R^{10B}$. In embodiments, $R^{10.2}$ is independently —$NHC(O)NR^{10A}R^{10B}$. In embodiments, $R^{10.2}$ is independently —$N(O)_{m10}$. In embodiments, $R^{10.2}$ is independently —$NR^{10A}R^{10B}$. In embodiments, $R^{10.2}$ is independently —$C(O)R^{10C}$. In embodiments, $R^{10.2}$ is independently —$C(O)$—$OR^{10C}$. In embodiments, $R^{10.2}$ is independently —$C(O)NR^{10A}R^{10b}$. In embodiments, $R^{10.2}$ is independently —$OR^{10D}$ In embodiments, $R^{10.2}$ is independently —$NR^{10A}SO_2R^{10D}$. In embodiments, $R^{10.2}$ is independently —$NR^{10A}C(O)R^{10C}$. In embodiments, $R^{10.2}$ is independently —$NR^{10A}C(O)OR^{10C}$. In embodiments, $R^{10.2}$ is independently —$NR^{10A}OR^{10C}$. In embodiments, $R^{10.2}$ is independently methoxy. In embodiments, $R^{10.2}$ is independently ethoxy. In embodiments, $R^{10.2}$ is independently propoxy. In embodiments, $R^{10.2}$ is independently butoxy. In embodiments, $R^{10.2}$ is independently pentoxy. In embodiments, $R^{10.2}$ is independently —F. In embodiments, $R^{10.2}$ is independently —Cl. In embodiments, 10.2 is independently —Br. In embodiments, $R^{10.2}$ is independently —I. In embodiments, $R^{10.2}$ is independently oxo. In embodiments, $R^{10.2}$ is independently halogen. In embodiments, $R^{10.2}$ is independently —$CCl_3$. In embodiments, $R^{10.2}$ is independently —$CBr_3$. In embodiments, $R^{10.2}$ is independently —$CF_3$. In embodiments, $R^{10.2}$ is independently —$CI_3$. In embodiments, $R^{10.2}$ is independently $CHCl_2$. In embodiments, $R^{10.2}$ is independently —$CHBr_2$. In embodiments, $R^{10.2}$ is independently —$CHF_2$. In embodiments, $R^{10.2}$ is independently —$CHI_2$. In embodiments, $R^{10.2}$ is independently —$CH_2Cl$. In embodiments, $R^{10.2}$ is independently —$CH_2Br$. In embodiments, $R^{10.2}$ is independently —$CH_2F$. In embodiments, $R^{10.2}$ is independently —$CH_2I$. In embodiments, $R^{10.2}$ is independently —CN. In embodiments, $R^{10.2}$ is independently —OH. In embodiments, $R^{10.2}$ is independently —$NH_2$. In embodiments, $R^{10.2}$ is independently —COOH. In embodiments, $R^{10.2}$ is independently —$CONH_2$. In embodiments, $R^{10.2}$ is independently —$NO_2$. In embodiments, $R^{10.2}$ is independently —SH. In embodiments, $R^{10.2}$ is independently —$SO_3H$. In embodiments, $R^{10.2}$ is independently —$SO_4H$. In embodiments, $R^{10.2}$ is independently —$SO_2NH_2$. In embodiments, $R^{10.2}$ is independently —$NHNH_2$. In embodiments, $R^{10.2}$ is independently —$ONH_2$. In embodiments, $R^{10.2}$ is independently —$NHC(O)NHNH_2$. In embodiments, $R^{10.2}$ is independently —$NHC(O)NH_2$. In embodiments, $R^{10.2}$ is independently —$NHSO_2H$. In embodiments, $R^{10.2}$ is independently —$NHC(O)H$. In embodiments, $R^{10.2}$ is independently —$NHC(O)OH$. In embodiments, $R^{10.2}$ is independently —NHOH. In embodiments, $R^{10.2}$ is independently —$OCCl_3$. In embodiments, $R^{10.2}$ is independently —$OCF_3$. In embodiments, $R^{10.2}$ is independently —$OCBr_3$. In embodiments, $R^{10.2}$ is independently —$OCI_3$. In embodiments, $R^{10.2}$ is independently —$OCHCl_2$. In embodiments, $R^{10.2}$ is independently —$OCHBr_2$. In embodiments, $R^{10.2}$ is independently —$OCHI_2$. In embodiments, $R^{10.2}$ is independently —$OCHF_2$. In embodiments, $R^{10.2}$ is independently —$OCH_2Cl$. In embodiments, $R^{10.2}$ is independently —$OCH_2Br$. In embodiments, $R^{10.2}$ is independently —$OCH_2I$. In embodiments, $R^{10.2}$ is independently —$OCH_2F$. In embodiments, $R^{10.2}$ is independently —$N_3$. In embodiments, $R^{10.2}$ is independently —$CH_3$. In embodiments, $R^{10.2}$ is independently —$OCH(CH_3)_2$. In embodiments, $R^{10.2}$ is independently —$OCH_3$. In embodiments, $R^{10.2}$ is independently hydrogen. In embodiments, $R^{10.2}$ is independently unsubstituted $C_1$-$C_8$ alkoxy. In embodiments, $R^{10.2}$ is independently unsubstituted $C_1$-$C_6$ alkoxy. In embodiments, $R^{10.2}$ is independently unsubstituted $C_1$-$C_4$ alkoxy.

In embodiments, $R^{10.3}$ is independently hydrogen, oxo, halogen, —$CF_3$, —$CBr_3$, —$CCl_3$, —$CI_3$ —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{10.3}$ is independently hydrogen, halogen, —$CX^{10.3}{}_3$, —$CHX^{10.3}{}_2$, —$CH_2X^{10.3}$, —$OCX^{10.3}{}_3$, —$OCH_2X^{10.3}$, —$OCHX^{10.3}{}_2$, —CN, —$SO_{n10}R^{10D}$, —$SO_{v10}NR^{10A}R^{10B}$, —$NHC(O)NR^{10A}R^{10B}$, —$N(O)_{m10}$, —$NR^{10A}R^{10B}$, —$C(O)R^{10C}$, —$C(O)$—$OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, $R^{28}$-substituted or unsubstituted alkyl (e.g., $C_1$-$C_8$ alkyl, $C_1$-$C_6$ alkyl, or $C_1$-$C_4$ alkyl), $R^{28}$-substituted or unsubstituted heteroalkyl (e.g., 2 to 8 membered heteroalkyl, 2 to 6 membered heteroalkyl, or 2 to 4 membered heteroalkyl), $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28}$-substituted or unsubstituted aryl (e.g., $C_6$-$C_{10}$ aryl, $C_{10}$ aryl, or phenyl), or $R^{28}$-substituted or unsubstituted heteroaryl (e.g., 5 to 10 membered heteroaryl, 5 to 9 membered heteroaryl, or 5 to 6 membered heteroaryl). In embodiments, $R^{10.3}$ is halogen, —$CX^{10.3}{}_3$, —$CHX^{10.3}{}_2$, —$CH_2X^{10.3}$, —$OCX^{10.3}{}_3$, —$OCH_2X^{10.3}$, —$OCHX^{10.3}{}_2$, —CN, —$SO_{n10}R^{10D}$, —$SO_{v10}NR^{10A}R^{10B}$, —$NHC(O)NR^{10A}R^{10B}$, —$N(O)_{m10}$, —$NR^{10A}R^{10B}$, —$C(O)R^{10C}$, —$C(O)$—$OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). $X^{10.3}$ is independently halogen. In embodiments, $X^{10.3}$ is independently —F. In embodiments, $X^{10.3}$ is independently —Cl. In embodiments, $X^{10.3}$ is independently —Br. In embodiments, $X^{10.3}$ is independently —I.

In embodiments, $R^{10.3}$ is independently halogen. In embodiments, $R^{10.3}$ is independently —$CX^{10.3}_3$. In embodiments, $R^{10.3}$ is independently —$CHX^{10.3}_2$. In embodiments, $R^{10.3}$ is independently —$CH_2X^{10.3}$. In embodiments, $R^{10.3}$ is independently —$OCX^{10.3}_3$. In embodiments, $R^{10.3}$ is independently —$OCH_2X^{10.3}$. In embodiments, $R^{10.3}$ is independently —$OCHX^{10.3}_2$. In embodiments, $R^{10.3}$ is independently —CN. In embodiments, $R^{10.3}$ is independently —$SO_{n10}R^{10D}$. In embodiments, $R^{10.3}$ is independently —$SR^{10D}$. In embodiments, $R^{10.3}$ is independently —$OCH_2X^{10.3}$. In embodiments, $R^{10.3}$ is independently —$SO_{v10}NR^{10A}R^{10B}$. In embodiments, $R^{10.3}$ is independently —$SO_2NR^{10A}R^{10B}$. In embodiments, $R^{10.3}$ is independently —$NHC(O)NR^{10A}R^{10B}$. In embodiments, $R^{10.3}$ is independently —$N(O)_{m10}$. In embodiments, $R^{10.3}$ is independently —$NR^{10A}R^{10B}$. In embodiments, $R^{10.3}$ is independently —$C(O)R^{10C}$. In embodiments, $R^{10.3}$ is independently —$C(O)$—$OR^{10C}$. In embodiments, $R^{10.3}$ is independently —$C(O)NR^{10A}R^{10B}$. In embodiments, $R^{10.3}$ is independently —$OR^{10D}$. In embodiments, $R^{10.3}$ is independently —$NR^{10A}SO_2R^{10D}$. In embodiments, $R^{10.3}$ is independently —$NR^{10A}C(O)R^{10C}$. In embodiments, $R^{10.3}$ is independently —$NR^{10A}C(O)OR^{10C}$. In embodiments, $R^{10.3}$ is independently —$NR^{10A}OR^{10C}$. In embodiments, $R^{10.3}$ is independently methoxy. In embodiments, $R^{10.3}$ is independently ethoxy. In embodiments, $R^{10.3}$ is independently propoxy. In embodiments, $R^{10.3}$ is independently butoxy. In embodiments, $R^{10.3}$ is independently pentoxy. In embodiments, $R^{10.3}$ is independently —F. In embodiments, $R^{10.3}$ is independently —Cl. In embodiments, $R^{10.3}$ is independently —Br. In embodiments, $R^{10.3}$ is independently —I. In embodiments, $R^{10.3}$ is independently oxo. In embodiments, $R^{10.3}$ is independently halogen. In embodiments, $R^{10.3}$ is independently —$CCl_3$. In embodiments, $R^{10.3}$ is independently —$CBr_3$. In embodiments, $R^{10.3}$ is independently —$CF_3$. In embodiments, $R^{10.3}$ is independently —$CI_3$. In embodiments, $R^{10.3}$ is independently $CHCl_2$. In embodiments, $R^{10.3}$ is independently —$CHBr_2$. In embodiments, $R^{10.3}$ is independently —$CHF_2$. In embodiments, $R^{10.3}$ is independently —$CHI_2$. In embodiments, $R^{10.3}$ is independently —$CH_2Cl$. In embodiments, $R^{10.3}$ is independently —$CH_2Br$. In embodiments, $R^{10.3}$ is independently —$CH_2F$. In embodiments, $R^{10.3}$ is independently —$CH_2I$. In embodiments, $R^{10.3}$ is independently —CN. In embodiments, $R^{10.3}$ is independently —OH. In embodiments, $R^{10.3}$ is independently —$NH_2$. In embodiments, $R^{10.3}$ is independently —COOH. In embodiments, $R^{10.3}$ is independently —$CONH_2$. In embodiments, $R^{10.3}$ is independently —$NO_2$. In embodiments, $R^{10.3}$ is independently —SH. In embodiments, $R^{10.3}$ is independently —$SO_3H$. In embodiments, $R^{10.3}$ is independently —$SO_4H$. In embodiments, $R^{10.3}$ is independently —$SO_2NH_2$. In embodiments, $R^{10.3}$ is independently —$NHNH_2$. In embodiments, $R^{10.3}$ is independently —$ONH_2$. In embodiments, $R^{10.3}$ is independently —$NHC(O)NHNH_2$. In embodiments, $R^{10.3}$ is independently —$HNSO_2H$. In embodiments, $R^{10.3}$ is independently —NHC(O)H. In embodiments, $R^{10.3}$ is independently —NHC(O)OH. In embodiments, $R^{10.3}$ is independently —NHOH. In embodiments, $R^{10.3}$ is independently —$OCCl_3$. In embodiments, $R^{10.3}$ is independently —$OCF_3$. In embodiments, $R^{10.3}$ is independently —$OCBr_3$. In embodiments, $R^{10.3}$ is independently —$OCI_3$. In embodiments, $R^{10.3}$ is independently —$OCHCl_2$. In embodiments, $R^{10.3}$ is independently —$OCHBr_2$. In embodiments, $R^{10.3}$ is independently —$OCHI_2$. In embodiments, $R^{10.3}$ is independently —$OCHF_2$. In embodiments, $R^{10.3}$ is independently —$OCH_2Cl$. In embodiments, $R^{10.3}$ is independently —$OCH_2Br$. In embodiments, $R^{10.3}$ is independently —$OCH_2I$. In embodiments, $R^{10.3}$ is independently —$OCH_2F$. In embodiments, $R^{10.3}$ is independently —$N_3$. In embodiments, $R^{10.3}$ is independently —$CH_3$. In embodiments, $R^{10.3}$ is independently $OCH(CH_3)_2$. In embodiments, $R^{10.3}$ is independently $OCH_3$. In embodiments, $R^{10.3}$ is independently hydrogen. In embodiments, $R^{10.3}$ is independently unsubstituted $C_1$-$C_8$ alkoxy. In embodiments, $R^{10.3}$ is independently unsubstituted $C_1$-$C_6$ alkoxy. In embodiments, $R^{10.3}$ is independently unsubstituted $C_1$-$C_4$ alkoxy.

In embodiments, $R^{10.4}$ is independently hydrogen, oxo, halogen, —$CF_3$, —$CBr_3$, —$CCl_3$, —$CI_3$ —$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, $NHNH_2$, $ONH_2$, $NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{10.4}$ is independently hydrogen, halogen, —$CX^{10.4}_3$, —$CHX^{10.4}_2$, —$CH_2X^{10.4}$, —$OCX^{10.4}_3$, —$OCH_2X^{10.4}$, —$OCHX^{10.4}_2$, —CN, —$SO_{n10}R^{10D}$, —$SO_{v10}NR^{10A}R^{10B}$, —$NHC(O)NR^{10A}R^{10B}$, —$N(O)_{m10}$, —$NR^{10A}R^{10B}$, —$C(O)R^{10C}$, —$C(O)$—$OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, $R^{28}$-substituted or unsubstituted alkyl (e.g., $C_1$-$C_8$ alkyl, $C_1$-$C_6$ alkyl, or $C_1$-$C_4$ alkyl), $R^{28}$-substituted or unsubstituted heteroalkyl (e.g., 2 to 8 membered heteroalkyl, 2 to 6 membered heteroalkyl, or 2 to 4 membered heteroalkyl), $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28}$-substituted or unsubstituted aryl (e.g., $C_6$-$C_{10}$ aryl, $C_{10}$ aryl, or phenyl), or $R^{28}$-substituted or unsubstituted heteroaryl (e.g., 5 to 10 membered heteroaryl, 5 to 9 membered heteroaryl, or 5 to 6 membered heteroaryl). In embodiments, $R^{10.4}$ is halogen, —$CX^{10.4}_3$, —$CHX^{10.4}_2$, —$CH_2X^{10.4}$, —$OCX^{10.4}_3$, —$OCH_2X^{10.4}$, —$OCHX^{10.4}_2$, —CN, —$SO_{n10}R^{10D}$, —$SO_{v10}NR^{10A}R^{10B}$, —$NHC(O)NR^{10A}R^{10B}$, —$N(O)_{m10}$, —$NR^{10A}R^{10B}$, —$C(O)R^{10C}$, —$C(O)$—$OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, unsubstituted alkyl (e.g., $C_1$-$C_8$ alkyl, $C_1$-$C_6$ alkyl, or $C_1$-$C_4$ alkyl) unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). $X^{10.4}$ is independently halogen. In embodiments, $X^{10.4}$ is independently —F. In embodiments, $X^{10.4}$ is independently —Cl. In embodiments, $X^{10.4}$ is independently —Br. In embodiments, $X^{10.4}$ is independently —I.

In embodiments, $R^{10.4}$ is independently halogen. In embodiments, $R^{10.4}$ is independently —$CX^{10.4}_3$. In embodiments, $R^{10.4}$ is independently —$CHX^{10.4}_2$. In embodiments, $R^{10.4}$ is independently —$CH_2X^{10.4}$. In embodiments, $R^{10.4}$ is independently —$OCX^{10.4}_3$. In embodiments, $R^{10.4}$ is independently —$OCH_2X^{10.4}$. In embodiments, $R^{10.4}$ is independently —$OCHX^{10.4}_2$. In embodiments, $R^{10.4}$ is independently —CN. In embodiments, $R^{10.4}$ is independently —$SO_{n10}R^{10D}$. In embodiments, $R^{10.4}$ is independently —$SR^{10D}$. In embodiments, $R^{10.4}$ is independently —$SO_2R^{10D}$. In embodiments, $R^{10.4}$ is independently —$SO_{v10}NR^{10.4}R^{10B}$. In embodiments, $R^{10.4}$ is independently —$SO_2NR^{10.4}R^{10B}$. In embodiments, $R^{10.4}$ is independently —$NHC(O)NR^{10.4}R^{10B}$. In embodiments, $R^{10.4}$ is independently —$N(O)_{m10}$. In embodiments, $R^{10.4}$ is independently —$NR^{10.4}R^{10B}$. In embodiments, $R^{10.4}$ is independently —$C(O)R^{10C}$. In embodiments, $R^{10.4}$ is independently —$C(O)$—$OR^{10C}$. In embodiments, $R^{10.4}$ is independently —$C(O)NR^{10.4}R^{10B}$. In embodiments, $R^{10.4}$ is independently —$OR^{10D}$. In embodiments, $R^{10.4}$ is independently —$NR^{10.4}SO_2R^{10D}$. In embodiments, $R^{10.4}$ is independently —$NR^{10.4}C(O)R^{10C}$. In embodiments, $R^{10.4}$ is independently —$NR^{10.4}C(O)OR^{10C}$. In embodiments, $R^{10.4}$ is independently —$NR^{10.4}OR^{10C}$. In embodiments, $R^{10.4}$ is independently methoxy. In embodiments, $R^{10.4}$ is independently ethoxy. In embodiments, $R^{10.4}$ is independently propoxy. In embodiments, $R^{10.4}$ is independently butoxy. In embodiments, $R^{10.4}$ is independently pentoxy. In embodiments, $R^{10.4}$ is independently —F. In embodiments, $R^{10.4}$ is independently —Cl. In embodiments, $R^{10.4}$ is independently —Br. In embodiments, $R^{10.4}$ is independently —I. In embodiments, $R^{10.4}$ is independently oxo. In embodiments, $R^{10.4}$ is independently halogen. In embodiments, $R^{10.4}$ is independently —$CCl_3$. In embodiments, $R^{10.4}$ is independently —$CBr_3$. In embodiments, $R^{10.4}$ is independently —$CF_3$. In embodiments, $R^{10.4}$ is independently —$CI_3$. In embodiments, $R^{10.4}$ is independently $CHCl_2$. In embodiments, $R^{10.4}$ is independently —$CHBr_2$. In embodiments, $R^{10.4}$ is independently —$CHF_2$. In embodiments, $R^{10.4}$ is independently —$CHI_2$. In embodiments, $R^{10.4}$ is independently —$CH_2Cl$. In embodiments, $R^{10.4}$ is independently —$CH_2Br$. In embodiments, $R^{10.4}$ is independently —$CH_2F$. In embodiments, $R^{10.4}$ is independently —$CH_2I$. In embodiments, $R^{10.4}$ is independently —CN. In embodiments, $R^{10.4}$ is independently —OH. In embodiments, $R^{10.4}$ is independently —$NH_2$. In embodiments, $R^{10.4}$ is independently —COOH. In embodiments, $R^{10.4}$ is independently —$CONH_2$. In embodiments, $R^{10.4}$ is independently —$NO_2$. In embodiments, $R^{10.4}$ is independently —SH. In embodiments, $R^{10.4}$ is independently —$SO_3H$. In embodiments, $R^{10.4}$ is independently —$SO_4H$. In embodiments, $R^{10.4}$ is independently —$SO_2NH_2$. In embodiments, $R^{10.4}$ is independently —$NHNH_2$. In embodiments, $R^{10.4}$ is independently —$ONH_2$. In embodiments, $R^{10.4}$ is independently —$NHC(O)NHNH_2$. In embodiments, $R^{10.4}$ is independently —$NHC(O)NH_2$. In embodiments, $R^{10.4}$ is independently —$HNSO_2H$. In embodiments, $R^{10.4}$ is independently —$NHC(O)H$. In embodiments, $R^{10.4}$ is independently —$NHC(O)OH$. In embodiments, $R^{10.4}$ is independently —NHOH. In embodiments, $R^{10.4}$ is independently —$OCCl_3$. In embodiments, $R^{10.4}$ is independently —$OCF_3$. In embodiments, $R^{10.4}$ is independently —$OCBr_3$. In embodiments, $R^{10.4}$ is independently —$OCI_3$. In embodiments, $R^{10.4}$ is independently —$OCHCl_2$. In embodiments, $R^{10.4}$ is independently —$OCHBr_2$. In embodiments, $R^{10.4}$ is independently —$OCHI_2$. In embodiments, $R^{10.4}$ is independently —$OCHF_2$. In embodiments, $R^{10.4}$ is independently —$OCH_2Cl$. In embodiments, $R^{10.4}$ is independently —$OCH_2Br$. In embodiments, $R^{10.4}$ is independently —$OCH_2I$. In embodiments, $R^{10.4}$ is independently —$OCH_2F$. In embodiments, $R^{10.4}$ is independently —$N_3$. In embodiments, $R^{10.4}$ is independently —$CH_3$. In embodiments, $R^{10.4}$ is independently —$OCH(CH_3)_2$. In embodiments, $R^{10.4}$ is independently —$OCH_3$. In embodiments, $R^{10.4}$ is independently hydrogen. In embodiments, $R^{10.4}$ is independently unsubstituted $C_1$-$C_8$ alkoxy. In embodiments, $R^{10.4}$ is independently unsubstituted $C_1$-$C_6$ alkoxy. In embodiments, $R^{10.4}$ is independently unsubstituted $C_1$-$C_4$ alkoxy.

In embodiments, $R^{10.5}$ is independently hydrogen, oxo, halogen, —$CF_3$, —$CBr_3$, —$CCl_3$, —$CI_3$—$CHF_2$, —$CHBr_2$, —$CHCl_2$, —$CHI_2$, —$CH_2F$, —$CH_2Br$, —$CH_2Cl$, —$CH_2I$, —$OCF_3$, —$OCBr_3$, —$OCCl_3$, —$OCI_3$, —$OCHF_2$, —$OCHBr_2$, —$OCHCl_2$, —$OCHI_2$, —$OCH_2F$, —$OCH_2Br$, —$OCH_2Cl$, —$OCH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, substituted or unsubstituted alkyl (e.g., $C_1$-$C_8$ alkyl, $C_1$-$C_6$ alkyl, or $C_1$-$C_4$ alkyl), substituted or unsubstituted heteroalkyl (e.g., 2 to 8 membered heteroalkyl, 2 to 6 membered heteroalkyl, or 2 to 4 membered heteroalkyl), substituted or unsubstituted cycloalkyl (e.g., $C_3$-$C_8$ cycloalkyl, $C_3$-$C_6$ cycloalkyl, or $C_5$-$C_6$ cycloalkyl), substituted or unsubstituted heterocycloalkyl (e.g., 3 to 8 membered heterocycloalkyl, 3 to 6 membered heterocycloalkyl, or 5 to 6 membered heterocycloalkyl), substituted or unsubstituted aryl (e.g., $C_6$-$C_{10}$ aryl, $C_{10}$ aryl, or phenyl), or substituted or unsubstituted heteroaryl (e.g., 5 to 10 membered heteroaryl, 5 to 9 membered heteroaryl, or 5 to 6 membered heteroaryl).

In embodiments, $R^{10.5}$ is independently hydrogen, halogen, —$CX^{10.5}_3$, —$CHX^{10.5}_2$, —$CH_2X^{10.5}$, —$OCX^{10.5}_3$, —$OCH_2X^{10.5}$, —$OCHX^{10.5}_2$, —CN, —$SO_{n10}R^{10D}$, —$SO_{v10}NR^{10.4}R^{10B}$, —$NHC(O)NR^{10.4}R^{10B}$, —$N(O)_{m10}$, —$NR^{10.4}R^{10B}$, —$C(O)R^{10C}$, —$C(O)$—$OR^{10C}$, —$C(O)NR^{10.4}R^{10B}$, —$OR^{10D}$, —$NR^{10.4}SO_2R^{10D}$, —$NR^{10.4}C(O)R^{10C}$, —$NR^{10.4}C(O)OR^{10C}$, —$NR^{10.4}OR^{10C}$, $R^{28}$-substituted or unsubstituted alkyl (e.g., $C_1$-$C_8$ alkyl, $C_1$-$C_6$ alkyl, or $C_1$-$C_4$ alkyl), $R^{28}$-substituted or unsubstituted heteroalkyl (e.g., 2 to 8 membered heteroalkyl, 2 to 6 membered heteroalkyl, or 2 to 4 membered heteroalkyl), $R^{28}$-substituted or unsubstituted cycloalkyl (e.g., $C_3$-$C_8$ cycloalkyl, $C_3$-$C_6$ cycloalkyl, or $C_5$-$C_6$ cycloalkyl), $R^{28}$-substituted or unsubstituted heterocycloalkyl (e.g., 3 to 8 membered heterocycloalkyl, 3 to 6 membered heterocycloalkyl, or 5 to 6 membered heterocycloalkyl), $R^{28}$-substituted or unsubstituted aryl (e.g., $C_6$-$C_{10}$ aryl, $C_{10}$ aryl, or phenyl), or $R^{28}$-substituted or unsubstituted heteroaryl (e.g., 5 to 10 membered heteroaryl, 5 to 9 membered heteroaryl, or 5 to 6 membered heteroaryl). In embodiments, $R^{10.5}$ is halogen, —$CX^{10.5}_3$, —$CHX^{10.5}_2$, —$CH_2X^{10.5}$, —$OCX^{10.5}_3$, —$OCH_2X^{10.5}$, —$OCHX^{10.5}_2$, —CN, —$SO_{n10}R^{10D}$, —$SO_{v10}NR^{10A}R^{10B}$, —$NHC(O)NR^{10A}R^{10B}$, —$N(O)_{m10}$, —$NR^{10A}R^{10B}$, —$C(O)R^{10C}$, —$C(O)$—$OR^{10C}$, —$C(O)NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl). $X^{10.5}$ is independently halogen. In embodiments, $X^{10.5}$ is independently —F. In embodiments, $X^{10.5}$ is independently —Cl. In embodiments, $X^{10.5}$ is independently —Br. In embodiments, $X^{10.5}$ is independently —I.

In embodiments, $R^{10.5}$ is independently halogen. In embodiments, $R^{10.5}$ is independently —$CX^{10.5}_3$. In embodiments, $R^{10.5}$ is independently —$CHX^{10.5}$ In embodiments, $R^{10.5}$ is independently —$CH_2X^{10.5}$. In embodiments, $R^{10.5}$ is independently —$OCX^{10.5}_3$. In embodiments, $R^{10.5}$ is independently —$OCH_2X^{10.5}$. In embodiments, $R^{10.5}$ is independently —$OCHX^{10.5}_2$. In embodiments, $R^{10.5}$ is independently —CN. In embodiments, $R^{10.5}$ is independently —$SO_{n10}R^{10D}$. In embodiments, $R^{10.5}$ is independently —$SR^{10D}$. In embodiments, $R^{10.5}$ is independently —$SO_2R^{10D}$. In embodiments, $R^{10.5}$ is independently —$SO_{v10}NR^{10A}R^{10B}$. In embodiments, $R^{10.5}$ is independently —$SO_2NR^{10A}R^{10B}$. In embodiments, $R^{10.5}$ is independently —$NHC(O)NR^{10A}R^{10B}$. In embodiments, $R^{10.5}$ is independently —$N(O)_{m10}$. In embodiments, $R^{10.5}$ is independently —$NR^{10A}R^{10B}$. In embodiments, $R^{10.5}$ is independently —$C(O)R^{10C}$. In embodiments, $R^{10.5}$ is independently —$C(O)$—$OR^{10C}$. In embodiments, $R^{10.5}$ is independently —$C(O)NR^{10A}R^{10B}$. In embodiments, $R^{10.5}$ is independently —$OR^{10D}$. In embodiments, $R^{10.5}$ is independently —$NR^{10A}SO_2R^{10D}$. In embodiments, $R^{10.5}$ is independently —$NR^{10A}C(O)R^{10C}$. In embodiments, $R^{10.5}$ is independently —$NR^{10A}C(O)R^{10C}$. In embodiments, $R^{10.5}$ is independently —$NR^{10A}OR^{10C}$. In embodiments, $R^{10.5}$ is independently methoxy. In embodiments, $R^{10.5}$ is independently ethoxy. In embodiments, $R^{10.5}$ is independently propoxy. In embodiments, $R^{10.5}$ is independently butoxy. In embodiments, $R^{10.5}$ is independently pentoxy. In embodiments, $R^{10.5}$ is independently —F. In embodiments, $R^{10.5}$ is independently —Cl. In embodiments, $R^{10.5}$ is independently —Br. In embodiments, $R^{10.5}$ is independently —I. In embodiments, $R^{10.5}$ is independently oxo. In embodiments, $R^{10.5}$ is independently halogen. In embodiments, $R^{10.5}$ is independently —$CCl_3$. In embodiments, $R^{10.5}$ is independently —$CBr_3$. In embodiments, $R^{10.5}$ is independently —$CF_3$. In embodiments, $R^{10.5}$ is independently —$CI_3$. In embodiments, $R^{10.5}$ is independently $CHCl_2$. In embodiments, $R^{10.5}$ is independently —$CHBr_2$. In embodiments, $R^{10.5}$ is independently —$CHF_2$. In embodiments, $R^{10.5}$ is independently —$CHI_2$. In embodiments, $R^{10.5}$ is independently —$CH_2Cl$. In embodiments, $R^{10.5}$ is independently —$CH_2Br$. In embodiments, $R^{10.5}$ is independently —$CH_2F$. In embodiments, $R^{10.5}$ is independently —$CH_2I$. In embodiments, $R^{10.5}$ is independently —CN. In embodiments, $R^{10.5}$ is independently —OH. In embodiments, $R^{10.5}$ is independently —$NH_2$. In embodiments, $R^{10.5}$ is independently —COOH. In embodiments, $R^{10.5}$ is independently —$CONH_2$. In embodiments, $R^{10.5}$ is independently —$NO_2$. In embodiments, $R^{10.5}$ is independently —SH. In embodiments, $R^{10.5}$ is independently —$SO_3H$. In embodiments, $R^{10.5}$ is independently —$SO_4H$. In embodiments, $R^{10.5}$ is independently —$SO_2NH_2$. In embodiments, $R^{10.5}$ is independently —$NHNH_2$. In embodiments, $R^{10.5}$ is independently —$ONH_2$. In embodiments, $R^{10.5}$ is independently —$NHC(O)NHNH_2$. In embodiments, $R^{10.5}$ is independently —$NHC(O)NH_2$. In embodiments, $R^{10.5}$ is independently —$HNSO_2H$. In embodiments, $R^{10.5}$ is independently —$NHC(O)H$. In embodiments, $R^{10.5}$ is independently —$NHC(O)OH$. In embodiments, $R^{10.5}$ is independently —NHOH. In embodiments, $R^{10.5}$ is independently —$OCCl_3$. In embodiments, $R^{10.5}$ is independently —$OCF_3$. In embodiments, $R^{10.5}$ is independently —$OCBr_3$. In embodiments, $R^{10.5}$ is independently —$OCI_3$. In embodiments, $R^{10.5}$ is independently —$OCHCl_2$. In embodiments, $R^{10.5}$ is independently —$OCHBr_2$. In embodiments, $R^{10.5}$ is independently —$OCHI_2$. In embodiments, $R^{10.5}$ is independently —$OCHF_2$. In embodiments, $R^{10.5}$ is independently —$OCH_2Cl$. In embodiments, $R^{10.5}$ is independently —$OCH_2Br$. In embodiments, $R^{10.5}$ is independently —$OCH_2I$. In embodiments, $R^{10.5}$ is independently —$OCH_2F$. In embodiments, $R^{10.5}$ is independently —$N_3$. In embodiments, $R^{10.5}$ is independently $CH_3$. In embodiments, $R^{10.5}$ is independently $OCH(CH_3)_2$. In embodiments, $R^{10.5}$ is independently $OCH_3$. In embodiments, $R^{10.5}$ is independently hydrogen. In embodiments, $R^{10.5}$ is independently unsubstituted $C_1$-$C_8$ alkoxy. In embodiments, $R^{10.5}$ is independently unsubstituted $C_1$-$C_6$ alkoxy. In embodiments, $R^{10.5}$ is independently unsubstituted $C_1$-$C_4$ alkoxy.

In embodiments, X, $X^3$, $X^7$, $X^9$, and $X^{10}$ are independently —F, —Cl, —Br, or —I. In embodiments, X is —F. In embodiments, X is —Cl. In embodiments, X is —Br. In embodiments, X is —I.

In embodiments, $X^1$ is F. In embodiments, $X^1$ is Cl. In embodiments, $X^1$ is Br. In embodiments, $X^1$ is I. In embodiments, $X^2$ is F. In embodiments, $X^2$ is Cl. In embodiments, $X^2$ is Br. In embodiments, $X^2$ is I. In embodiments, $X^3$ is F. In embodiments, $X^3$ is Cl. In embodiments, $X^3$ is Br. In embodiments, $X^3$ is I. In embodiments, $X^4$ is F. In embodiments, $X^4$ is Cl. In embodiments, $X^4$ is Br. In embodiments, $X^4$ is I. In embodiments, $X^5$ is F. In embodiments, $X^5$ is Cl. In embodiments, $X^5$ is Br. In embodiments, $X^5$ is I. In embodiments, $X^6$ is F. In embodiments, $X^6$ is Cl. In embodiments, $X^6$ is Br. In embodiments, $X^6$ is I. In embodiments, $X^7$ is F. In embodiments, $X^7$ is Cl. In embodiments, $X^7$ is Br. In embodiments, $X^7$ is I. In embodiments, $X^8$ is F. In embodiments, $X^8$ is Cl. In embodiments, $X^8$ is Br. In embodiments, $X^8$ is I. In embodiments, $X^9$ is F. In embodiments, $X^9$ is Cl. In embodiments, $X^9$ is Br. In embodiments, $X^9$ is I. In embodiments, $X^{10}$ is F. In embodiments, $X^{10}$ is Cl. In embodiments, $X^{10}$ is Br. In embodiments, $X^{10}$ is I. In embodiments, $X^{21}$ is F. In embodiments, $X^{21}$ is Cl. In embodiments, $X^{21}$ is Br. In embodiments, $X^{21}$ is I.

In embodiments, z7 is 0. In embodiments, z7 is 1. In embodiments, z7 is 2. In embodiments, z7 is 3. In embodiments, z7 is 4. In embodiments, z7 is 5. In embodiments, z9 is 0. In embodiments, z9 is 1. In embodiments, z9 is 2. In embodiments, z9 is 3. In embodiments, z9 is 4. In embodiments, z9 is 5. In embodiments, z10 is 0. In embodiments, z10 is 1. In embodiments, z10 is 2. In embodiments, z10 is 3. In embodiments, z10 is 4. In embodiments, z10 is 5. In embodiments, z21 is 0. In embodiments, z21 is 1. In embodiments, z21 is 2. In embodiments, z21 is 3. In embodiments, z21 is 4. In embodiments, z21 is 5.

In embodiments, n3 is 0. In embodiments, n3 is 1. In embodiments, n3 is 2. In embodiments, n3 is 3. In embodiments, n3 is 4. In embodiments, n7 is 0. In embodiments, n7 is 1. In embodiments, n7 is 2. In embodiments, n7 is 3. In embodiments, n7 is 4. In embodiments, n9 is 0. In embodiments, n9 is 1. In embodiments, n9 is 2. In embodiments, n9 is 3. In embodiments, n9 is 4. In embodiments, n10 is 0. In embodiments, n10 is 1. In embodiments, n10 is 2. In embodiments, n10 is 3. In embodiments, n10 is 4. In embodiments, n21 is 0. In embodiments, n21 is 1. In embodiments, n21 is 2. In embodiments, n21 is 3. In embodiments, n21 is 4.

In embodiments, m3 is 1. In embodiments, m3 is 2. In embodiments, v3 is 1. In embodiments, v3 is 2. In embodiments, m7 is 1. In embodiments, m7 is 2. In embodiments, v7 is 1. In embodiments, v7 is 2. In embodiments, m9 is 1. In embodiments, m9 is 2. In embodiments, v9 is 1. In embodiments, v9 is 2. In embodiments, m10 is 1. In embodiments, m10 is 2. In embodiments, v10 is 1. In embodiments, v10 is 2. In embodiments, m21 is 1. In embodiments, m21 is 2. In embodiments, v21 is 1. In embodiments, v21 is 2.

Ring A may be cycloalkyl. Ring A may be $C_3$-$C_8$ cycloalkyl.

Ring A may be 3 to 8 membered heterocycloalkyl. Ring A may be a 4 to 6 membered heterocycloalkyl. Ring A may be a 5 or 6 membered heterocycloalkyl. Ring A may be 5 membered heterocycloalkyl. Ring A may be 6 membered heterocycloalkyl.

In embodiments, Ring A is a $C_6$-$C_{12}$ aryl. In embodiments, Ring A is a $C_6$-$C_{10}$ aryl. In embodiments, Ring A is phenyl. In embodiments, Ring A is naphthyl. In embodiments, Ring A is biphenyl.

In embodiments, Ring A is 5 to 10 membered heteroaryl. In embodiments, Ring A is a 5 to 6 membered heteroaryl. In embodiments, Ring A is 5 membered heteroaryl. In embodiments, Ring A is 6 membered heteroaryl.

In embodiments, Ring A is pyrrolyl. In embodiments, Ring A is pyrazolyl. In embodiments, Ring A is imidazolyl. In embodiments, Ring A is thienyl. In embodiments, Ring A is thiophenyl. In embodiments, Ring A is thienyl. In embodiments, Ring A is oxazolyl. In embodiments, Ring A is isoxazolyl. In embodiments, Ring A is isothiazolyl. In embodiments, Ring A is thiazolyl. In embodiments, Ring A is oxadiazolyl. In embodiments, Ring A is pyridyl. In embodiments, Ring A is pyridazinyl. In embodiments, Ring A is pyrimidinyl. In embodiments, Ring A is pyrazinyl. In embodiments, Ring A is triazinyl. In embodiments, Ring A is indolyl. In embodiments, Ring A is benzofuranyl. In embodiments, Ring A is naphthyl. In embodiments, Ring A is tetrahydronaphthyl. In embodiments, Ring A is dihydrobenzopyranyl. In embodiments, Ring A is 2,3-dihydro-1H-indenyl.

In embodiments, the compound is

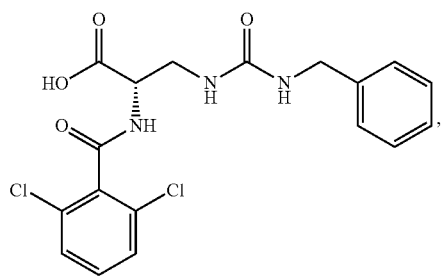

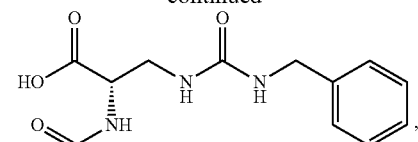

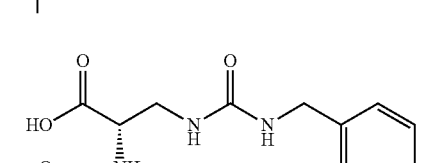

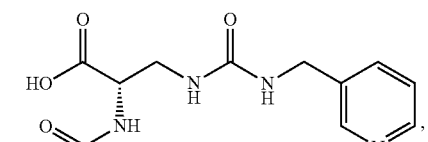

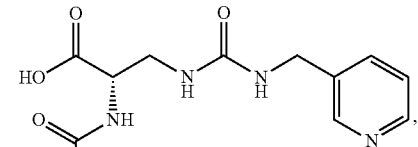

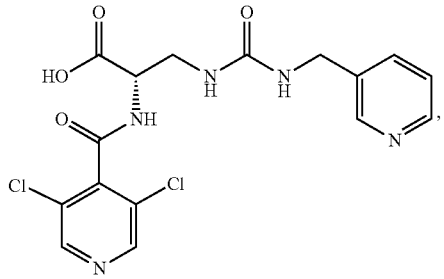

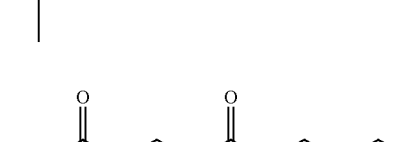

185
-continued
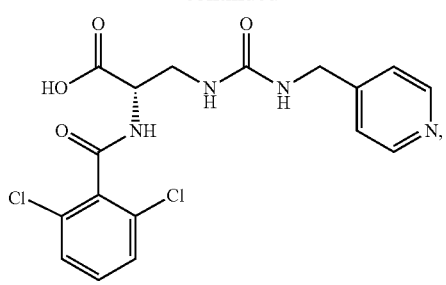
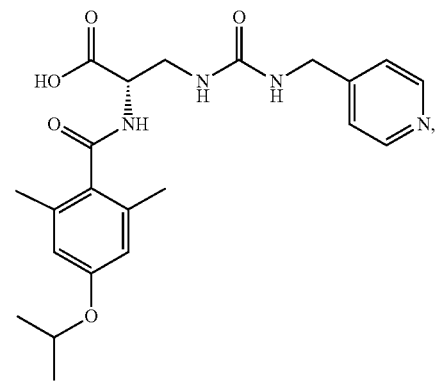
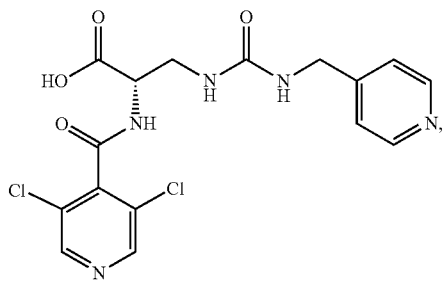
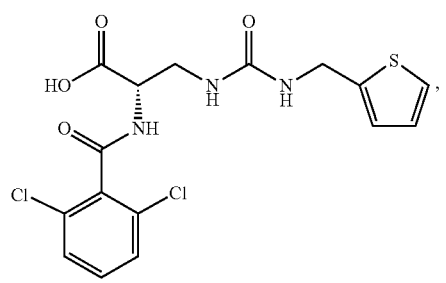
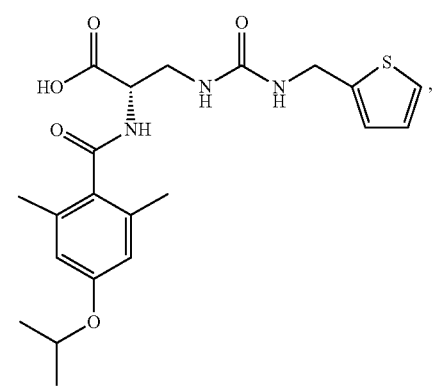
186
-continued
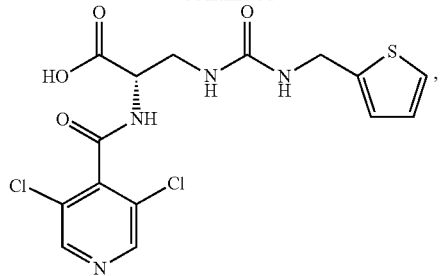
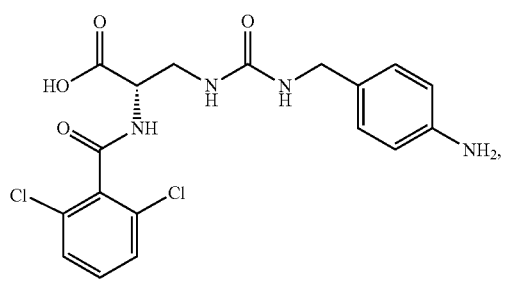
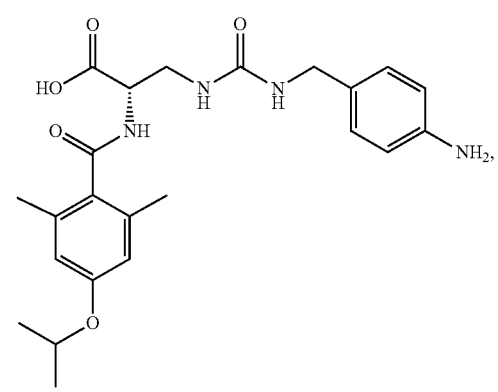
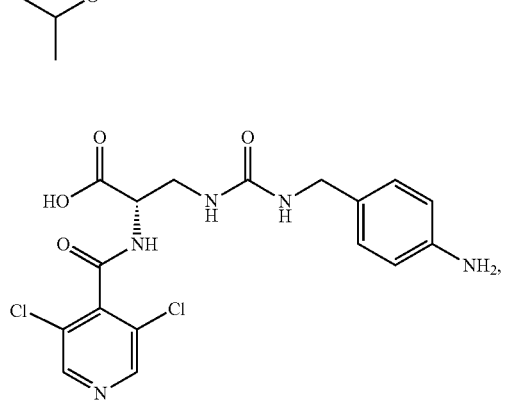
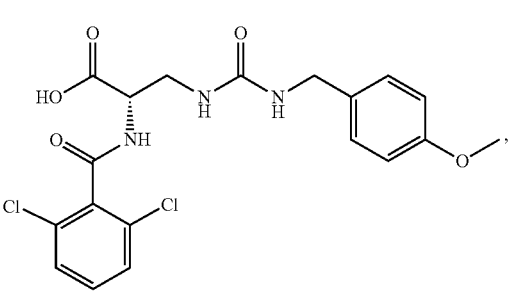

187
-continued
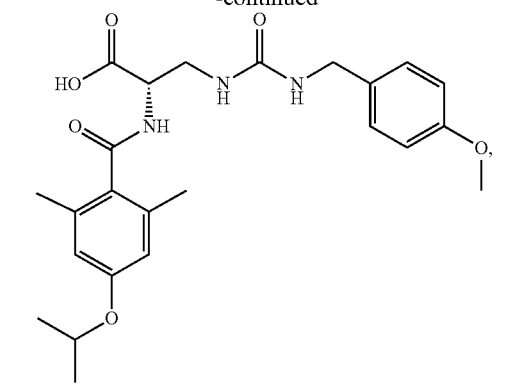
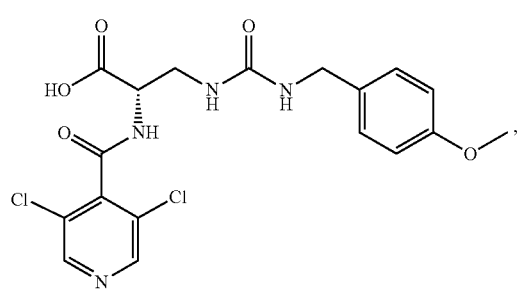
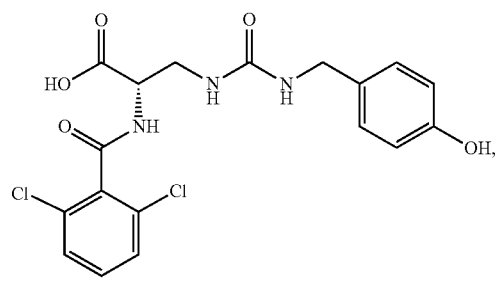
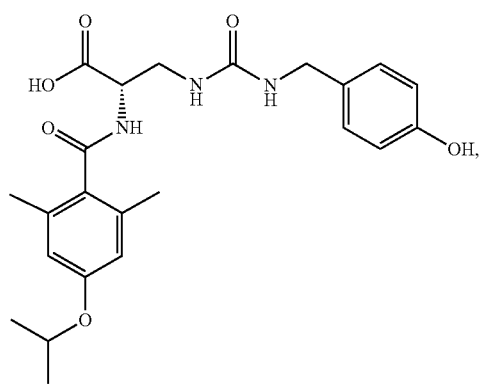
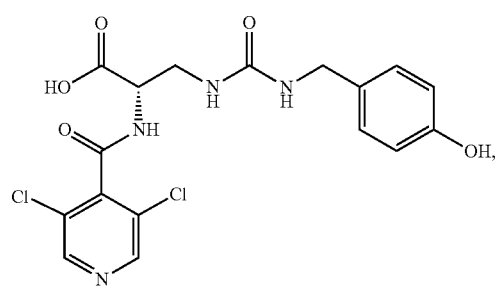
188
-continued
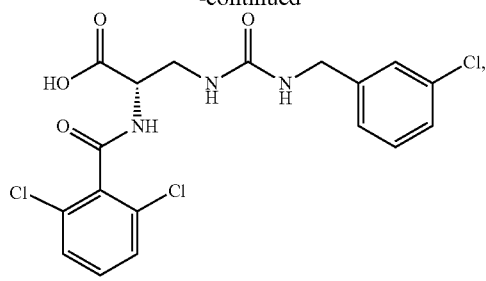
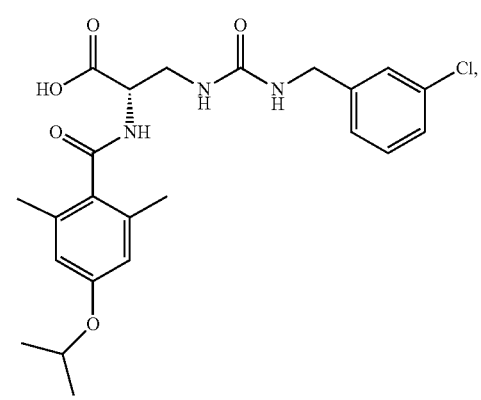
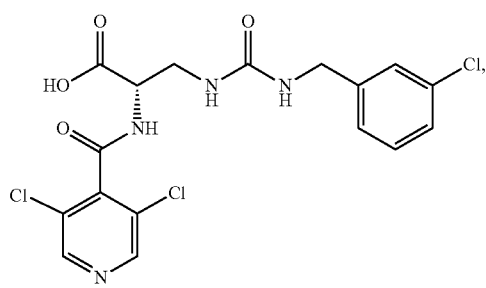
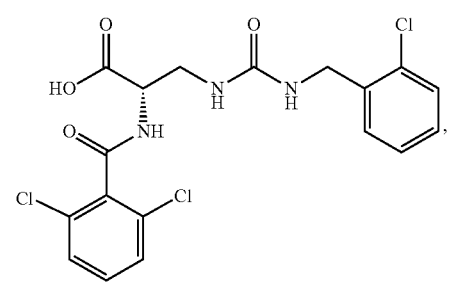
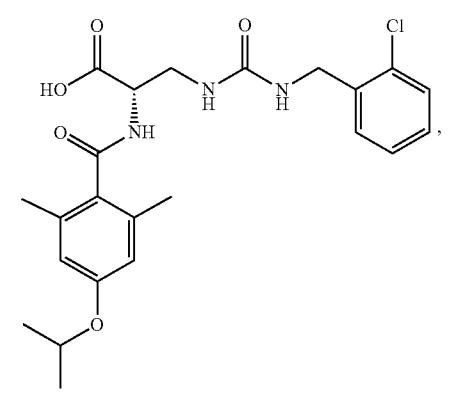

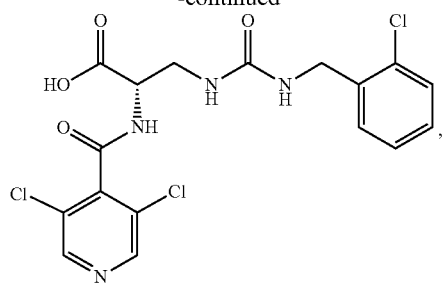
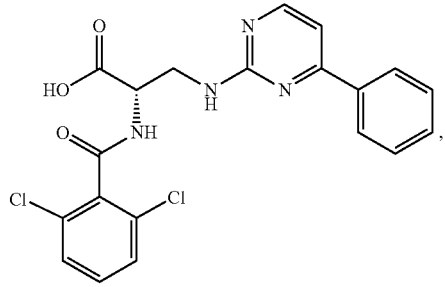
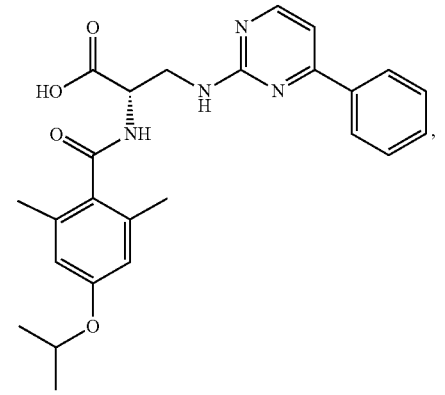
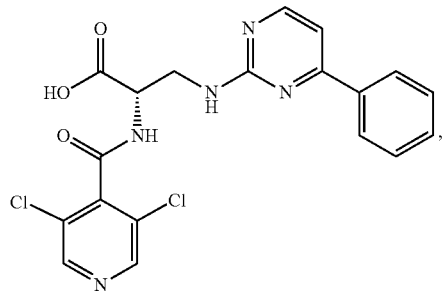
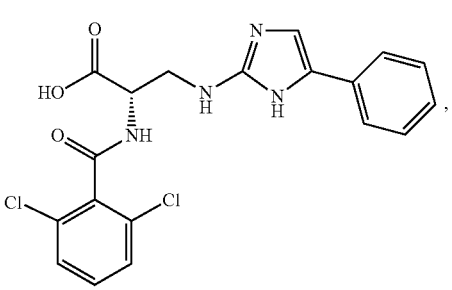
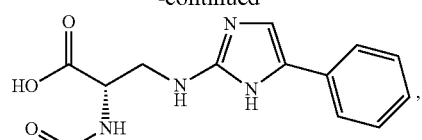
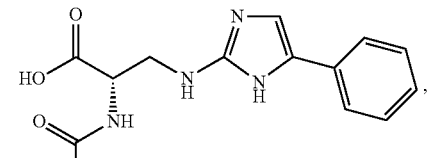
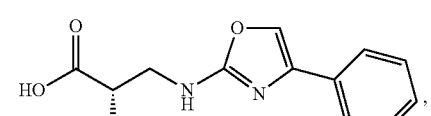
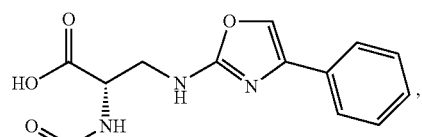
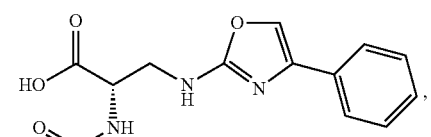

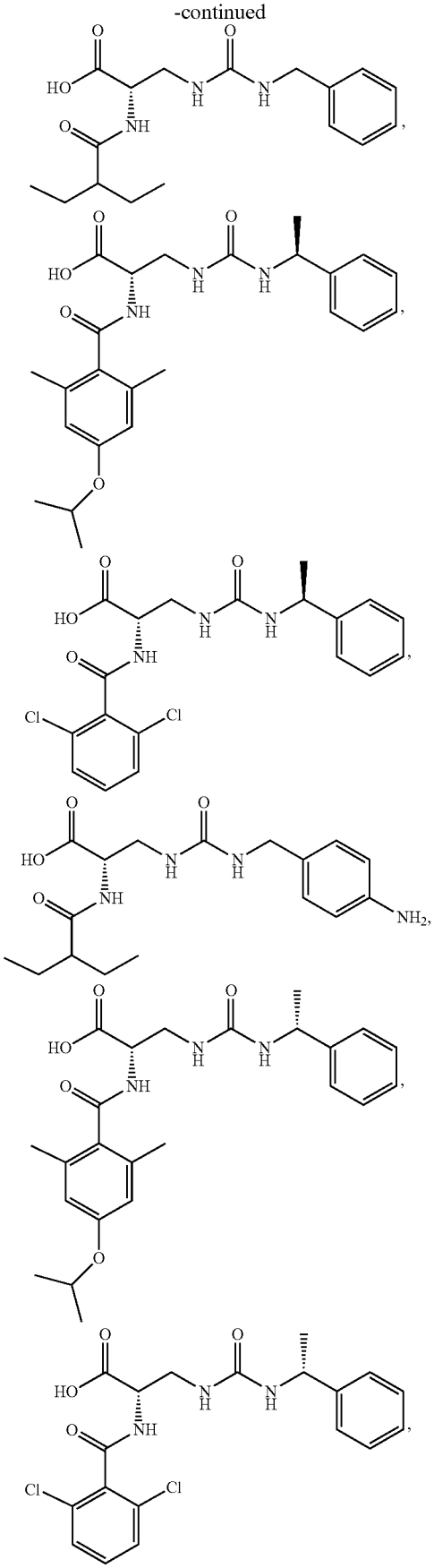
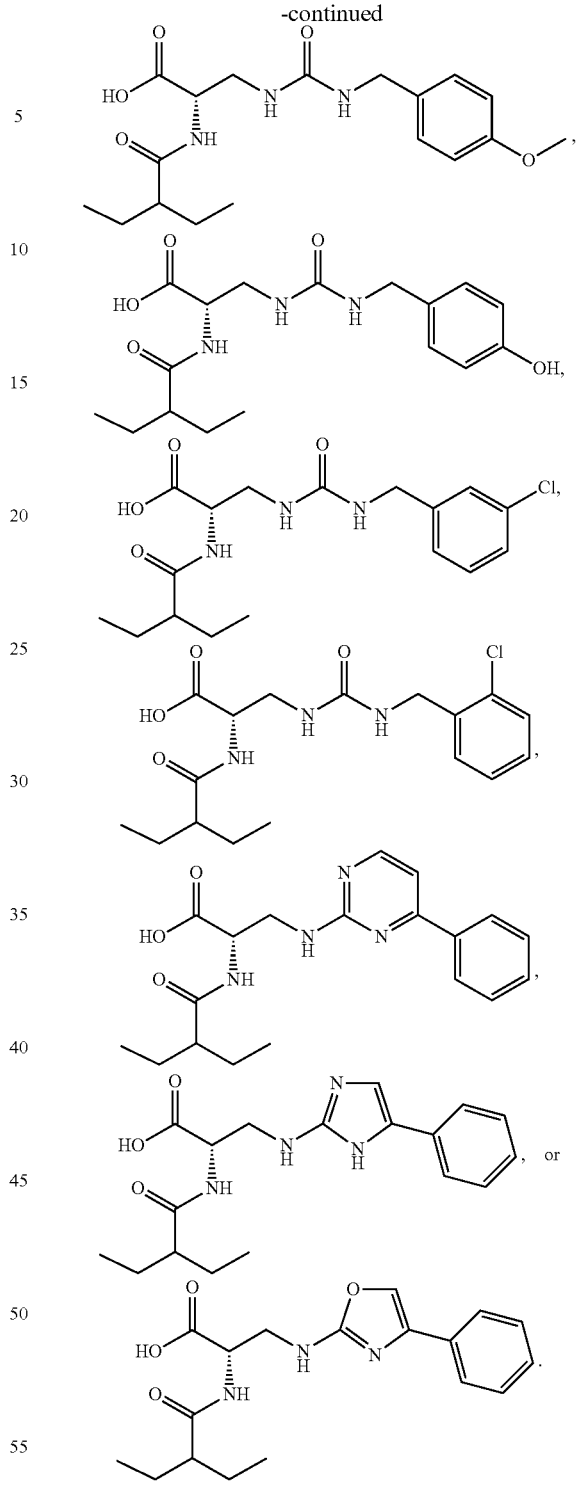
In embodiments, the compound is a compound described herein (e.g., in an aspect, embodiment, example, figures, table, or claim).
In embodiments, the compound is A2-26, A2-27, A2-28, A2-60, A2-29, A2-35, A2-36, A2-61, A2-38, A2-37, A2-63, A2-64, KZ-1-18, KZ-1-39, KZ-1-14, KZ-1-16, KZ-1-15, KZ-1-26, KZ-1-20, KZ-1-30, KZ-1-23, A2-72, A2-39, KZ-1-34, KZ-1-38, KZ-1-17, KZ-1-36, KZ-1-3, A2-123, A2-124, A2-125, A2-126, A2-127, A2-128, A2-129, A2-130, A2-131, A2-132, A2-133, A2-134, A2-143, KZ-1-9, KZ-1-

37, KZ-1-32, KZ-1-33, KZ-1-12, KZ-1-13, KZ-1-11, KZ-1-25, A2-73, KZ-1-19, KZ-1-40, A2-70, A2-71, KZ-1-27, KZ-1-22, A2-83, A2-87, A2-84, A2-85, A2-86, KZ-1-21, A2-154, A2-155, A2-156, A2-157, A2-170, A2-171, A2-172, A2-173, A2-174, A2-175, A2-176, A2-177, A2-178, A2-179, A2-180, A2-181, A2-144, A2-145, A2-152, A2-153, A2-189, A2-190, A2-191, A2-192, A2-193, A2-194, A2-202, A2-203, A2-204, A2-207, A2-208, KZ-1-80, or KZ-1-81.

In embodiments, the compound is A2-29, A2-123, A2-124, A2-125, A2-126, A2-130, A2-85, A2-171, or A2-172.

In embodiments, the compound is

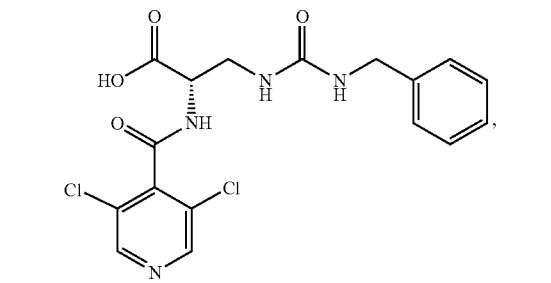 [SMILES: O=C(NCc1ccccc1)NC[C@H](NC(=O)c1c(Cl)cccc1Cl)C(=O)O ; "."]

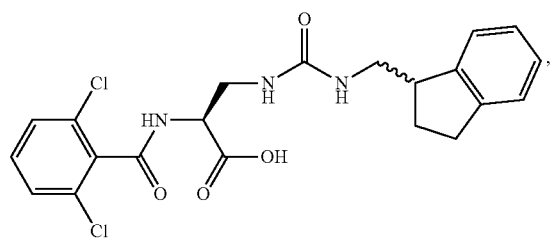

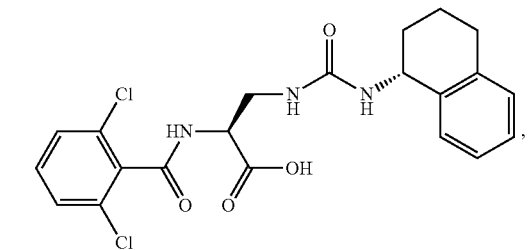

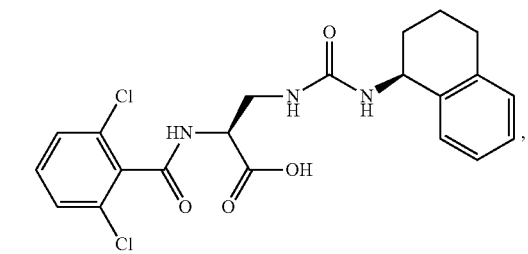

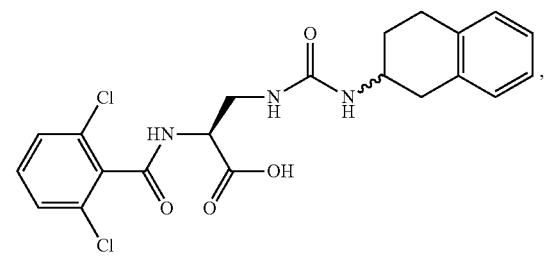

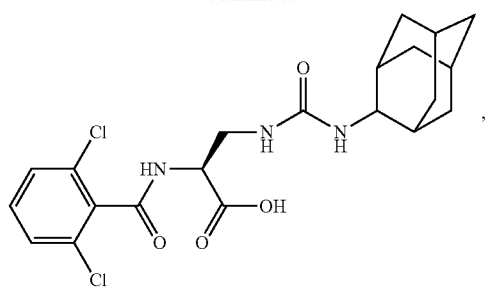

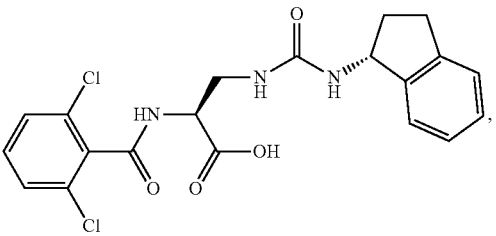

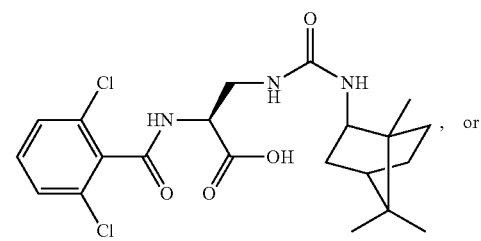

, or

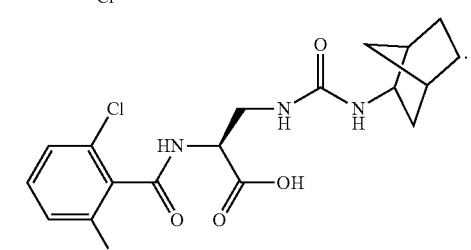

In some embodiments, a compound as described herein may include multiple instances of $R^7$, $R^{10}$, and/or other variables. In such embodiments, each variable may optional be different and be appropriately labeled to distinguish each group for greater clarity. For example, where each $R^{21}$, $R^7$, $R^9$, and/or $R^{10}$ is different, they may be referred to, for example, as $R^{21.1}$, $R^{21.2}$, $R^{21.3}$, $R^{21.4}$, $R^{21.5}$, $R^{7.1}$, $R^{7.2}$, $R^{7.3}$, $R^{7.4}$, $R^{7.5}$, $R^{9.1}$, $R^{9.2}$, $R^{9.3}$, $R^{9.4}$, $R^{9.5}$, $R^{10.1}$, $R^{10.2}$, $R^{10.3}$, $R^{10.4}$, $R^{10.5}$, $R^{10.6}$, $R^{10.7}$, $R^{10.8}$, $R^{10.9}$, respectively, wherein the definition of $R^{21}$ is assumed by $R^{21.1}$, $R^{21.2}$, $R^{21.3}$, $R^{21.4}$, $R^{21.5}$; $R^7$ is assumed by $R^{7.1}$, $R^{7.2}$, $R^{7.3}$, $R^{7.4}$, $R^{7.5}$; $R^9$ is assumed by $R^{9.1}$, $R^{9.2}$, $R^{9.3}$, $R^{9.4}$, $R^{9.5}$; $R^{10}$ is assumed by $R^{10.1}$, $R^{10.2}$, $R^{10.3}$, $R^{10.4}$, $R^{10.5}$, $R^{10.6}$, $R^{10.7}$, $R^{10.8}$, $R^{10.9}$. The variables used within a definition of $R^{21}$, $R^7$, $R^9$, $R^{10}$, and/or other variables that appear at multiple instances and are different may similarly be appropriately labeled to distinguish each group for greater clarity. In some embodiments, the compound is a compound described herein (e.g., in an aspect, embodiment, example, claim, or table).

In embodiments, the compound is not a compound described in Jpn. Kokai Tokkyo Koho (2003), JP 2003277340 A 20031002, JP 2003277340, or laid open JP application JP 2003277340, each of which is incorporated by reference it its entirety for all purposes.

III. Pharmaceutical Compositions

In an aspect is provided a pharmaceutical composition including a compound described herein, or pharmaceutically acceptable salt thereof, and a pharmaceutically acceptable excipient.

In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating asthma. In embodiments, the second agent is an anti-inflammatory agent. In embodiments, the second agent is an anti-autoimmune disease agent.

IV. Methods of Use

In an aspect is provided a method of treating asthma, the method including administering to a subject in need thereof an effective amount of an integrin α2β1 inhibitor. In embodiments, the α2β1 inhibitor is a nucleic acid (e.g., DNA, RNA, siRNA, or antisense oligonucleotide), protein (e.g., antibody or antigen-binding fragment thereof), or compound (e.g., compound described herein).

In an aspect is provided a method of treating asthma, the method including administering to a subject in need thereof an effective amount of a compound, or a pharmaceutically acceptable salt thereof, described herein.

In embodiments, the compound is

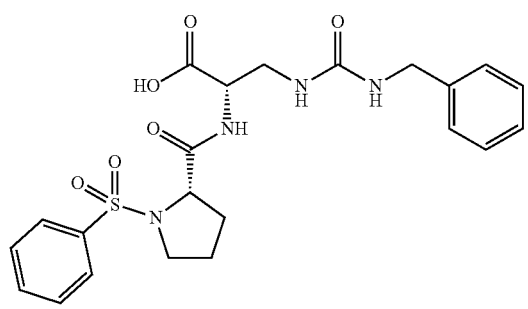

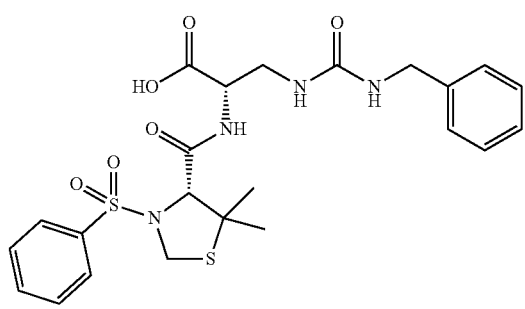

, or

-continued

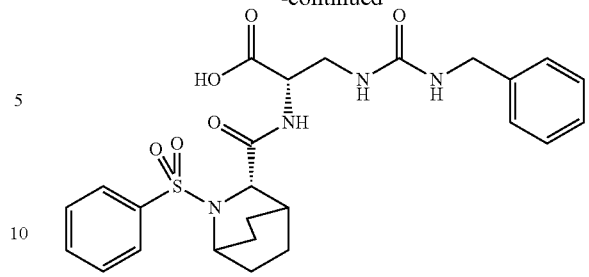

In embodiments, the compound is

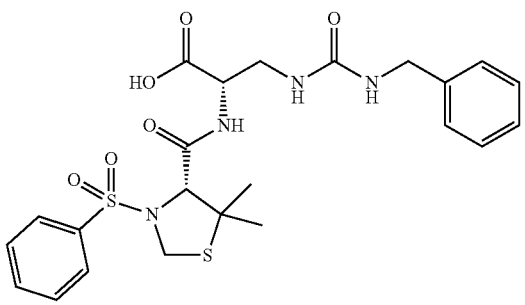

In embodiments, compound is

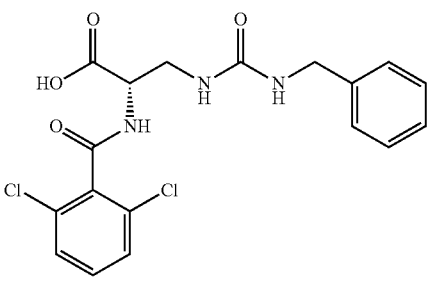

In embodiments, compound is a compound (e.g., genus of compounds or exemplified compound) described in PCT/US06/22225, which is incorporate by reference in its entirety for all purposes. In embodiments, compound is a compound (e.g., genus of compounds or exemplified compound) described in US 2009/0197861, which is incorporate by reference in its entirety for all purposes. In embodiments, compound is a compound (e.g., genus of compounds or exemplified compound) described in U.S. Pat. No. 8,258,159, which is incorporate by reference in its entirety for all purposes. In embodiments, compound is a compound (e.g., genus of compounds or exemplified compound) described in Halland, N., H. Blum, et al. (2014). "Small Macrocycles As Highly Active Integrin alpha 2 beta 1 Antagonists." Acs Medicinal Chemistry Letters 5(2): 193-198, which is incorporate by reference in its entirety for all purposes. In embodiments, compound is a compound (e.g., genus of compounds or exemplified compound) described in Miller, M. W., S. Basra, et al. (2009). "Small-molecule inhibitors of integrin alpha2beta 1 that prevent pathological thrombus formation via an allosteric mechanism." Proc Natl Acad Sci USA 106(3): 719-724., which is incorporate by reference in its entirety for all purposes. In embodiments, compound is a compound (e.g., genus of compounds or exemplified compound) described in Choi, S., G. Vilaire, et al. (2007). "Small molecule inhibitors of integrin alpha2beta1." J Med Chem 50(22): 5457-5462., which is incorporate by reference in its entirety for all purposes.

Provided herein are methods for treating asthma. In embodiments, the asthma is severe asthma. In embodiments, the asthma is acute severe asthma. In embodiments, the asthma is moderate asthma. In one aspect, is a method for treating asthma by administering to a subject in need thereof an α2β1-inhibitor (e.g., where the α2β1-inhibitor is a compound having a formulae described herein, including embodiments thereof). In an embodiment, is a method for treating asthma by administering to a subject in need thereof a therapeutically effective amount of an α2β1-inhibitor, where the α2β1-inhibitor is an α2β1-inhibitor compound having the formulae described herein, including embodiments thereof. The α2β1-inhibitor compound may be a compound having a formula described herein, including embodiments thereof. The α2β1-inhibitor compound may be a pharmaceutical composition as described herein, including embodiments thereof.

In an embodiment, is a method for treating asthma by administering to a subject in need thereof a therapeutically effective amount of an α2β1-inhibitor wherein the administering is by inhalation.

In an aspect is provided a method of treating an inflammatory disease including administering to a subject in need thereof an effective amount of a compound described herein.

In embodiments, the inflammatory disease is arthritis, rheumatoid arthritis, psoriatic arthritis, juvenild idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, or atopic dermatitis.

In an aspect is provided a method of treating an autoimmune disease including administering to a subject in need thereof an effective amount of a compound described herein.

In embodiments, the autoimmune disease is arthritis, rheumatoid arthritis, psoriatic arthritis, juvenild idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, sarcoidosis, transplant rejection, interstitial cystitis, atherosclerosis, scleroderma, or atopic dermatitis.

In embodiments, the method includes administering a second agent (e.g. therapeutic agent). In embodiments, the method includes administering a second agent (e.g. therapeutic agent) in a therapeutically effective amount. In embodiments, the second agent is an anti-inflammatory agent.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Embodiments

Embodiment P1. A compound having the formula:

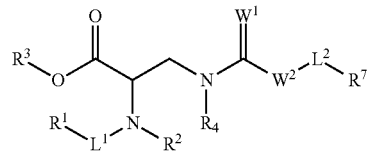

wherein, $R^1$ is substituted or unsubstituted alkyl, substituted or unsubstituted heteroalkyl, substituted or unsubstituted aryl, or substituted or unsubstituted heteroaryl;

$L^1$ is a bond or —C(O)—;

$R^2$ is hydrogen or substituted or unsubstituted alkyl;

$R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —NHC(O)$NR^{3A}R^{3B}$, —$N(O)_{m3}$, —$NR^{3A}R^{3B}$, —C(O)$R^{3C}$, —C(O)—$OR^{3C}$, —C(O) $NR^{3A}R^{3B}$, —$OR^{3D}$, —$NR^{3A}SO_2R^{3D}$, —$NR^{3A}C(O)R^{3C}$, —$NR^3C(O)OR^3$, —$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^4$ is hydrogen or substituted or unsubstituted alkyl;

$W^1$ is O, S, $NR^8$;

$W^2$ is O, S, $NR^5$;

$R^5$ is hydrogen or substituted or unsubstituted alkyl;

$L^2$ is a bond or —$CHR^6$—;

$R^6$ is hydrogen, substituted or unsubstituted alkyl, or substituted or unsubstituted heteroalkyl;

$W^1$ and $R^6$ may optionally be joined to form a substituted or unsubstituted 5 to 6 membered heterocycloalkyl, or substituted or unsubstituted 5 to 6 membered heteroaryl;

$R^7$ is hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}NR^{7A}R^{7B}$, —NHC(O)$NR^{7A}R^{7B}$, —$N(O)_{m7}$, —$NR^{7A}R^{7B}$, —C(O)$R^{7C}$, —C(O)—$OR^{7C}$, —C(O) $NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

$R^8$ is hydrogen or substituted or unsubstituted alkyl;

$R^{3A}$, $R^{3B}$, $R^{3C}$, $R^{3D}$, $R^{7A}$, $R^{7B}$, $R^7$, and $R^{7D}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl;

each X, $X^3$, and $X^7$ are independently —F, —Cl, —Br, or —I;

n3 and n7 are independently an integer from 0 to 3; and m3, m7, v3 and v7 are independently 1 or 2.

Embodiment P2. The compound of embodiment P1 having the formula:

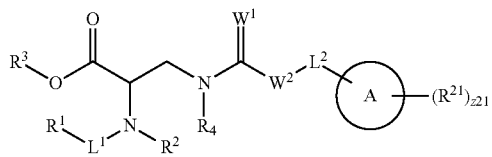

wherein,

Ring A is cycloalkyl, heterocycloalkyl, aryl, or heteroaryl;

$R^{21}$ is independently halogen, —$CX^{21}_3$, —$CHX^{21}_2$, —$CH_2X^{21}$, —$OCX^{21}_3$, —$OCH_2X^{21}$, —$OCHX^{21}_2$, —CN, —$SO_{n21}R^{21D}$, —$SO_{v21}NR^{21A}R^{21B}$, —NHC(O)$NR^{21A}R^{3B}$, —$N(O)_{m21}$, —$NR^{21A}R^{21B}$, —C(O)$R^{21C}$, —C(O)—$OR^{21C}$, —C(O)$NR^{21A}R^{21B}$, —$OR^{21D}$, —$NR^{21A}SO_2R^{21D}$, —$NR^{21A}C(O)R^{21C}$, —$NR^{21}C(O)OR^{21C}$, —$NR^{21A}OR^{21C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

z21 is an integer from 0 to 5;

$R_{21A}$, $R^{21B}$, $R^{21C}$, and $R^{21D}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{21A}$ and $R^{21B}$ substituents bonded to the same nitrogen atom may optionally be joined to form a substituted or unsubstituted heterocycloalkyl or substituted or unsubstituted heteroaryl;

each X and $X^{21}$ are independently —F, —Cl, —Br, or —I;

n21 is an integer from 0 to 3; and m21 and v21 are independently 1 or 2.

Embodiment P3. The compound of one of embodiments P1 to P2 wherein $R^1$ is unsubstituted $C_1$-$C_6$ alkyl.

Embodiment P4. The compound of one of embodiments P1 to P2 wherein $R^1$ is

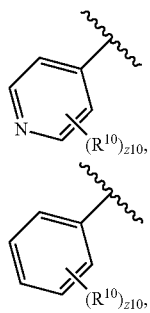

or substituted or unsubstituted $C_4$-$C_8$ alkyl;

wherein, $R^{10}$ is independently halogen, —$CX^{10}_3$, —$CHX^{10}_2$, —$CH_2X^{10}$, —$OCX^{10}_3$, —$OCH_2X^{10}$, —$OCHX^{10}_2$, —CN, —$SO_{n10}R^{10D}$, —$SO_{v10}NR^{10A}R^{10B}$, —NHC(O)$NR^{10A}R^{10B}$, —$N(O)_{m10}$, —$NR^{10A}R^{10B}$, —C(O)$R^{10C}$, —C(O)—$OR^{10C}$, —C(O)$NR^{10A}R^{10B}$, —$OR^{10D}$, —$NR^{10A}SO_2R^{10D}$, —$NR^{10A}C(O)R^{10C}$, —$NR^{10A}C(O)OR^{10C}$, —$NR^{10A}OR^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^{10}$ substituents may optionally be joined to form a substituted or unsubstituted cycloalkyl, substituted or unsubstituted heterocycloalkyl, substituted or unsubstituted aryl, or substituted or unsubstituted heteroaryl;

$R^{10A}$, $R^{10B}$, $R^{10C}$, and $R^{10D}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10A}$ and $R^{10B}$ substituents bonded to the same nitrogen atom may optionally be joined to form a substituted or unsubstituted heterocycloalkyl or substituted or unsubstituted heteroaryl;

X and $X^{10}$ are independently —F, —Cl, —Br, or —I;

n10 is independently an integer from 0 to 4;

m10 and v10 are independently 1 or 2; and z10 is an integer from 0 to 5.

Embodiment P5. The compound of one of embodiments P1 to P4 wherein $L^2$ is —$CHR^6$—;

Embodiment P6. The compound of one of embodiments P1 to P4 wherein $L^2$ is a bond.

Embodiment P7. The compound of one of embodiments P1 to P5 wherein $R^6$ is unsubstituted alkyl.

Embodiment P8. The compound of one of embodiments P1 to P5 wherein $R^6$ is hydrogen.

Embodiment P9. The compound of one of embodiments P1 to P8 wherein $W^1$ is NH.

Embodiment P10. The compound of one of embodiments P1 to P8 wherein $W^1$ is S.

Embodiment P11. The compound of one of embodiments P1 to P8 wherein $W^1$ is O.

Embodiment P12. The compound of one of embodiments P1 to P11 wherein $W^2$ is NH.

Embodiment P13. The compound of one of embodiments P1 to P11 wherein $W^2$ is S.

Embodiment P14. The compound of one of embodiments P1 to P11 wherein $W^2$ is O.

Embodiment P15. The compound of one of embodiments P1 to P14 wherein $W^1$ and $R^6$ are joined to form a substituted or unsubstituted 5 to 6 membered heterocycloalkyl or substituted or unsubstituted 5 to 6 membered heteroaryl.

Embodiment P16. The compound of one of embodiments P1 to P14 wherein $W^1$ and $R^6$ are joined to form a substituted or unsubstituted 5 to 6 membered heteroaryl.

Embodiment P17. The compound of one of embodiments P1 to P14 wherein $W^1$ and $R^6$ are joined to form

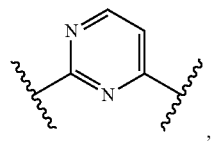

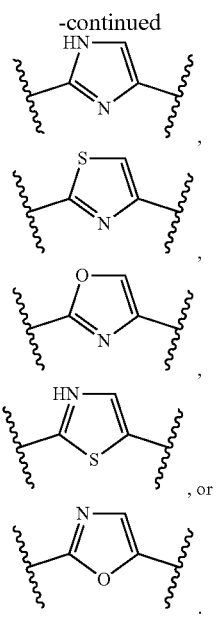

Embodiment P18. The compound of one of embodiments P1 to P17 wherein $R^2$, $R^4$, $R^5$, and $R^8$ are hydrogen.

Embodiment P19. The compound of one of embodiments P1 to P18 wherein $R^3$ is substituted or unsubstituted $C_1$-$C_6$ alkyl.

Embodiment P20. The compound of one of embodiments P1 to P18 wherein $R^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl Embodiment P21. The compound of one of embodiments P1 to P18 wherein $R^3$ is hydrogen.

Embodiment P22. The compound of one of embodiments P1 to P21, wherein $L^1$ is a bond.

Embodiment P23. The compound of one of embodiments P1 to P21, wherein $L^1$ is —C(O)—.

Embodiment P24. The compound of one of embodiments P1 and P3 to P23, wherein $R^7$ is unsubstituted $C_1$-$C_6$ alkyl.

Embodiment P25. The compound of one of embodiments P1 and P3 to P23, wherein $R^7$ is unsubstituted alkyl, substituted or unsubstituted cycloalkyl, substituted or unsubstituted heterocycloalkyl, substituted or unsubstituted aryl, or substituted or unsubstituted heteroaryl.

Embodiment P26. The compound of one of embodiments P2 to P23, wherein Ring A is 5 to 6 membered heteroaryl.

Embodiment P27. The compound of one of embodiments P2 to P23, wherein Ring A is phenyl.

Embodiment P28. The compound of one of embodiments P2 to P27, wherein z21 is an integer from 1 to 5.

Embodiment P29. The compound of one of embodiments P2 to P27, wherein z21 is 0.

Embodiment P30. The compound of one of embodiments P1 to P29, having the formula:

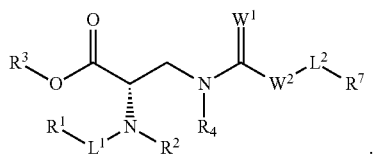

Embodiment P31. The compound of one of embodiments P1 to P29, having the formula:

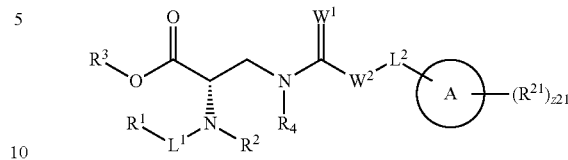

Embodiment P32. The compound of one of embodiments P1 to P29, having the formula:

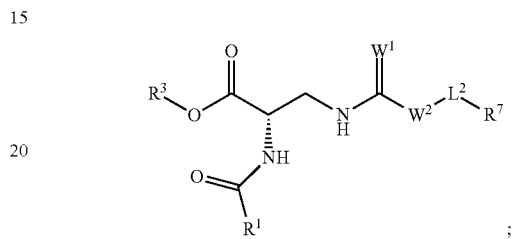

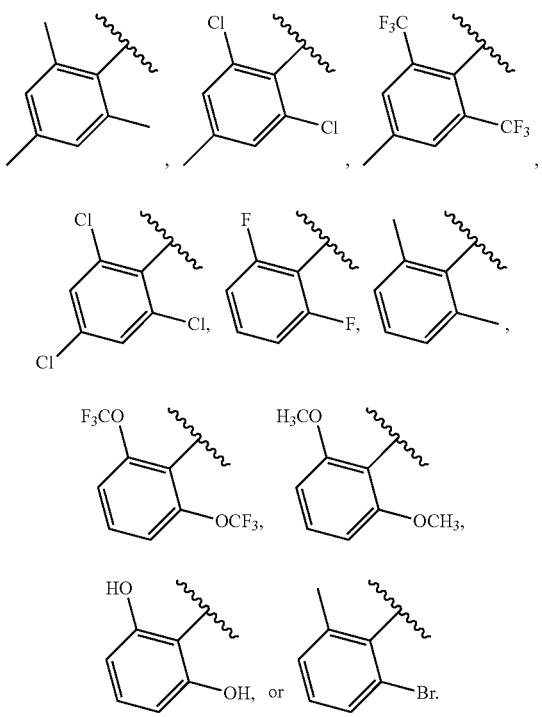

wherein $R^1$ is

Embodiment P33. The compound of embodiment P32, wherein

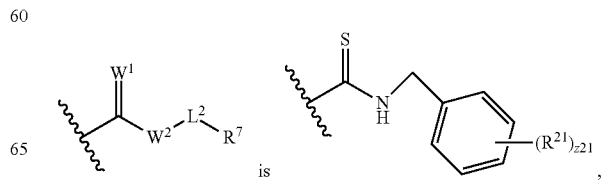

is

203
-continued
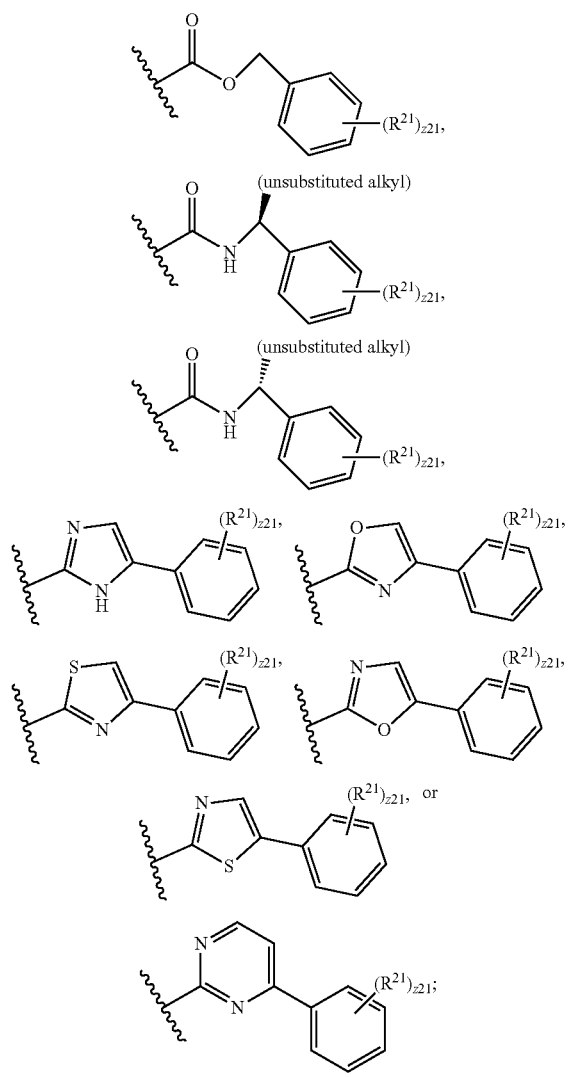
wherein z21 is an integer from 0 to 5;
an integer from 0 to 4;
204
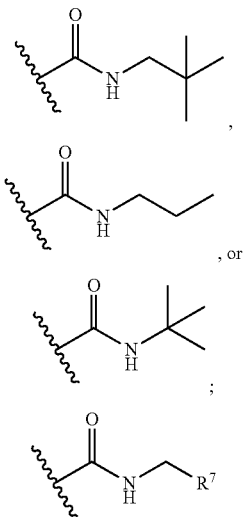
wherein R[7] is substituted or unsubstituted cycloalkyl;
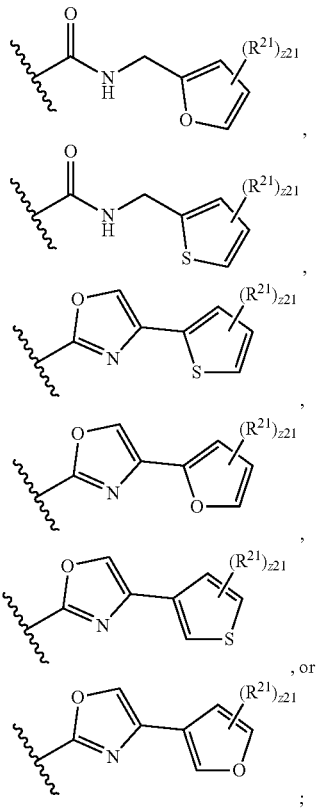
wherein z21 is an integer from 0 to 3;
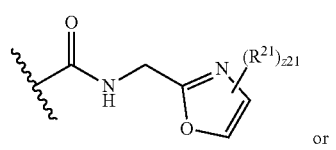
or -continued
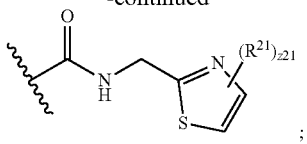
wherein z21 is an integer from 0 to 2; or
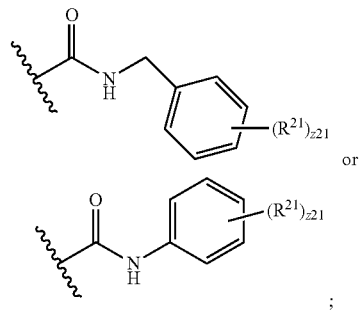
wherein z21 is an integer from 1 to 5.
Embodiment P34. The compound of one of embodiments P1 to P29, having the formula:
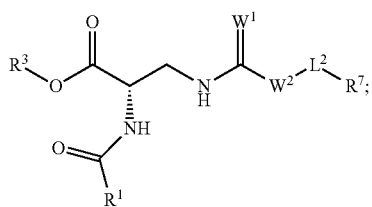
wherein R¹ is
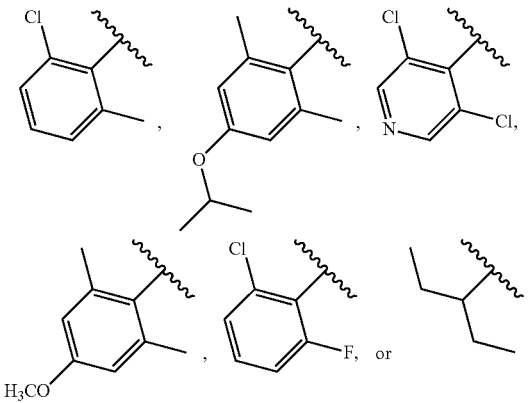
Embodiment P35. The compound of embodiment P34, wherein
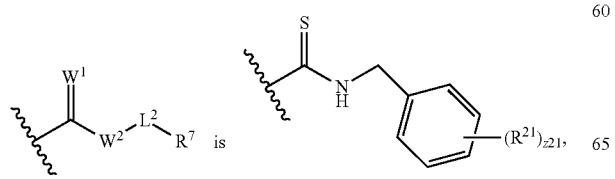 is
-continued
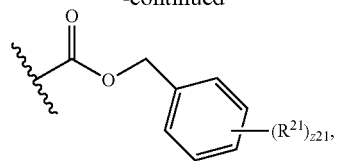
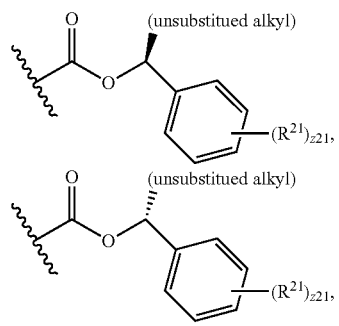
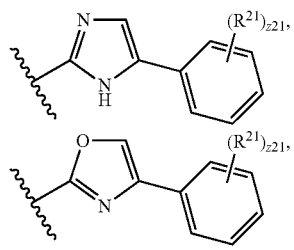
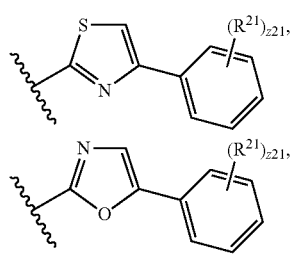
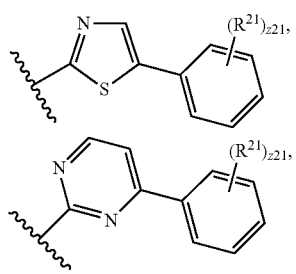
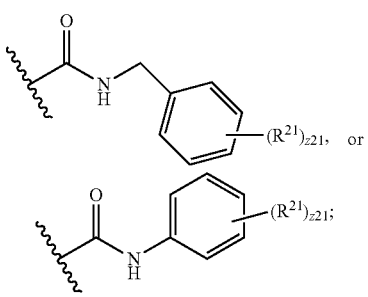
wherein z21 is an integer from 0 to 5;

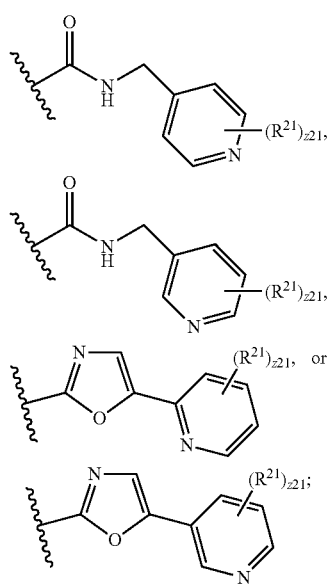

wherein z21 is an integer from 0 to 4;

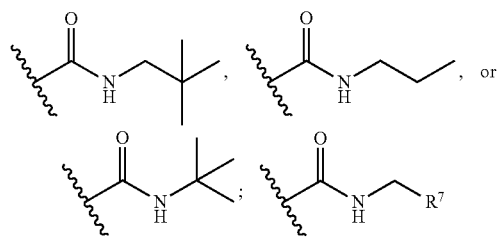

wherein R[7] is substituted or unsubstituted cycloalkyl;

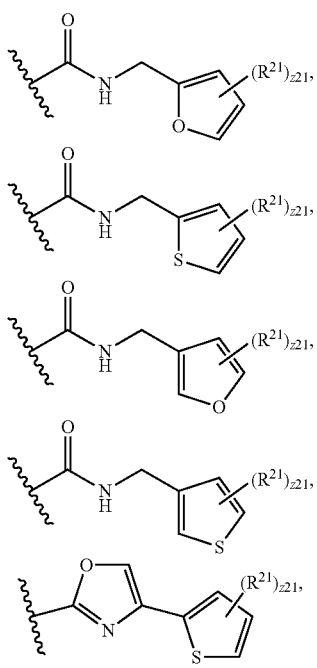

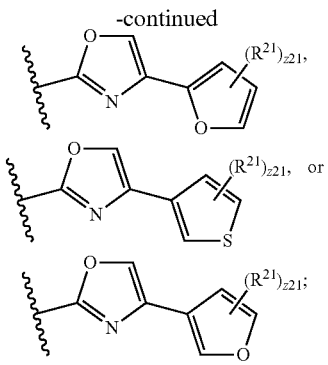

wherein z21 is an integer from 0 to 3; or

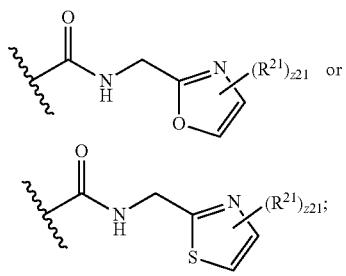

wherein z21 is an integer from 0 to 2.

Embodiment P36. The compound of embodiment P1, having the formula:

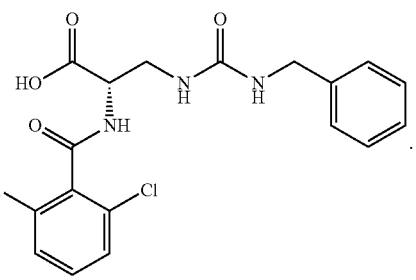

Embodiment P37. A pharmaceutical composition comprising a pharmaceutically acceptable excipient and a compound of one of embodiments P1 to P36.

Embodiment P38. A method of treating asthma, the method comprising administering to a subject in need thereof an effective amount of an integrin α2β1 inhibitor.

Embodiment P39. The method of embodiment P38, wherein the α2β1 inhibitor is a nucleic acid, protein, or compound.

Embodiment P40. The method of embodiment P38, wherein the α2β1 inhibitor is compound of one of embodiments P1 to P36.

Embodiment P41. A method of treating asthma, the method comprising administering to a subject in need thereof an effective amount of a compound of one of embodiments P1 to P36.

Embodiment P42. A method of treating asthma, the method comprising administering to a subject in need thereof an effective amount of a compound, or a pharmaceutically, having the formula:

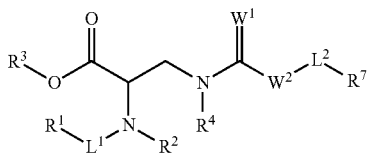

wherein,

R¹ substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

L¹ is a bond or —C(O)—;

R² is hydrogen or substituted or unsubstituted alkyl;

R³ is hydrogen, halogen, —CX³$_3$, —CHX³$_2$, —CH$_2$X³, —OCX³$_3$, —OCH$_2$X³, —OCHX³$_2$, —CN, —SO$_{n3}$R³$^D$, —SO$_{v3}$NR³$^A$R³$^B$, —NHC(O)NR³$^A$R³$^B$, —N(O)$_{m3}$, —NR³$^A$R³$^B$, —C(O)R³$^C$, —C(O)—OR³$^C$, —C(O)NR³$^A$R³$^B$, —OR³$^D$, —NR³$^A$SO$_2$R³$^D$, —NR³$^A$C(O)R³$^C$, —NR³$^A$C(O)OR³$^C$—NR³$^A$OR³$^C$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R⁴ is hydrogen or substituted or unsubstituted alkyl;

W¹ is O, S, NR⁸;

W² is O, S, NR⁵;

R⁵ is hydrogen or substituted or unsubstituted alkyl;

L² is a bond or —CHR⁶—;

R⁶ is hydrogen, substituted or unsubstituted alkyl, or substituted or unsubstituted heteroalkyl;

W¹ and R⁶ may optionally be joined to form a substituted or unsubstituted 5 to 6 membered heterocycloalkyl, or substituted or unsubstituted 5 to 6 membered heteroaryl;

R⁷ is hydrogen, halogen, —CX⁷$_3$, —CHX⁷$_2$, —CH$_2$X⁷, —OCX⁷$_3$, —OCH$_2$X⁷, —OCHX⁷$_2$, —CN, —SO$_{v7}$R⁷$^D$, —SO$_{v7}$NR⁷$^A$R⁷$^B$, —NHC(O)NR⁷$^A$R⁷$^B$, —N(O)$_{m7}$, —NR⁷$^A$R⁷$^B$, —C(O)R⁷$^C$, —C(O)—OR⁷$^C$, —C(O)NR⁷$^A$R⁷$^B$, —OR⁷$^D$, —NR⁷$^A$SO$_2$R⁷$^D$, —NR⁷$^A$C(O)R⁷$^C$, —NR⁷$^A$C(O)OR⁷$^C$, —NR⁷$^A$OR⁷$^C$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

R⁸ is hydrogen or substituted or unsubstituted alkyl;

R³$^A$, R³$^B$, R³$^C$, R³$^D$, R⁷$^A$, R⁷$^B$, R⁷$^C$, and R⁷$^D$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R³$^A$ and R³$^B$ substituents bonded to the same nitrogen atom may optionally be joined to form a substituted or unsubstituted heterocycloalkyl or substituted or unsubstituted heteroaryl; R$_{7A}$ and R⁷$^B$ substituents bonded to the same nitrogen atom may optionally be joined to form a substituted or unsubstituted heterocycloalkyl or substituted or unsubstituted heteroaryl;

each X, X³, and X⁷ are independently —F, —Cl, —Br, or —I; n3 and n7 are independently an integer from 0 to 3; and m3, m7, v3 and v7 are independently 1 or 2.

Embodiment P43. The method of embodiment P42, wherein R¹ is

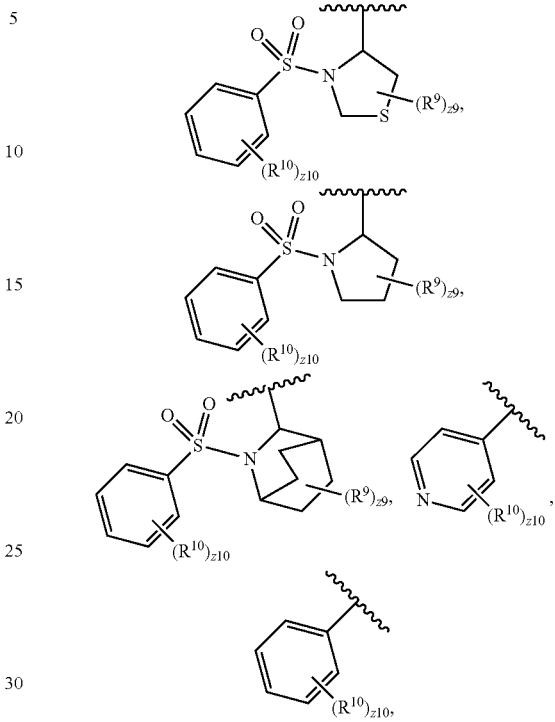

or substituted or unsubstituted C$_4$-C$_8$ alkyl;

wherein,

R⁹ is independently halogen, —CX⁹$_3$, —CHX⁹$_2$, —CH$_2$X⁹, —OCX⁹$_3$, —OCH$_2$X⁹, —OCHX⁹$_2$, —CN, —SO$_{n9}$R⁹$^D$, —SO$_{v9}$NR⁹$^A$R⁹$^B$, —NHC(O)NR⁹$^A$R⁹$^B$, —N(O)$_{m9}$, —NR⁹$^A$R⁹$^B$, —C(O)R⁹$^C$, —C(O)—OR⁹$^C$, —C(O)NR⁹$^A$R⁹$^B$, —OR⁹$^D$, —NR⁹$^A$SO$_2$R⁹$^D$, —NR⁹$^A$C(O)R⁹$^C$, —NR⁹$^A$C(O)O R⁹$^C$, —NR⁹$^A$OR⁹$^C$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R⁹ substituents may optionally be joined to form a substituted or unsubstituted cycloalkyl, substituted or unsubstituted heterocycloalkyl, substituted or unsubstituted aryl, or substituted or unsubstituted heteroaryl;

R¹⁰ is independently halogen, —CX¹⁰$_3$, —CHX¹⁰$_2$, —CH$_2$X¹⁰, —OCX¹⁰$_3$, —OCH$_2$X¹⁰, —OCHX¹⁰$_2$, —CN, —SO$_{n10}$R¹⁰$^D$, —SO$_{v10}$NR¹⁰$^A$R¹⁰$^B$, —NHC(O)NR¹⁰$^A$R¹⁰$^B$, —N(O)$_{m10}$, —NR¹⁰$^A$R¹⁰$^B$, C(O)R¹⁰$^C$, —C(O)—OR¹⁰$^C$, —C(O)NR¹⁰$^A$R¹⁰$^B$, —OR¹⁰$^D$, —NR¹⁰$^A$SO$_2$R¹⁰$^D$, —NR¹⁰$^A$C(O)R¹⁰$^C$, —NR¹⁰$^A$ C(O)OR¹⁰$^C$, —NR¹⁰$^A$OR¹⁰$^C$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^m$ substituents may optionally be joined to form a substituted or unsubstituted cycloalkyl, substituted or unsubstituted heterocycloalkyl, substituted or unsubstituted aryl, or substituted or unsubstituted heteroaryl;

R⁹$^A$, R⁹$^B$, R⁹$^C$, R⁹$^D$, R¹⁰$^A$, R¹⁰$^B$, R¹⁰$^C$, and R¹⁰$^D$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R⁹$^A$ and R⁹$^B$ substituents bonded to the same nitrogen atom may optionally be joined to form a substituted or unsubstituted heterocycloalkyl or substituted or unsubstituted heteroaryl; $R^{10A}$ and $R^{10B}$ substituents bonded to the same nitrogen atom may optionally be joined to form a substituted or unsubstituted heterocycloalkyl or substituted or unsubstituted heteroaryl;

X, $X^9$, and $X^{10}$ are independently —F, —Cl, —Br, or —I;
n9 and n10 are independently an integer from 0 to 4;
m9, m10, v9 and v10 are independently 1 or 2;
z9 is an integer from 0 to 5; and
z10 is an integer from 0 to 5.

Embodiment P44. The method of one of embodiments P42 to P43, wherein $R^1$ is

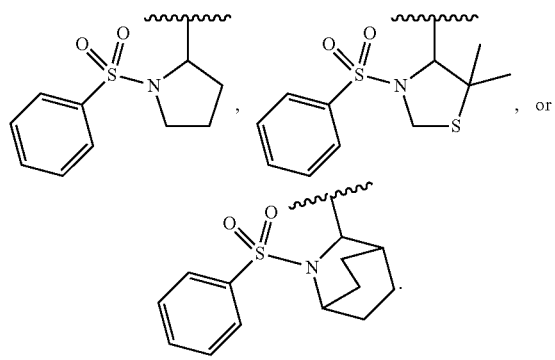

Embodiment P45. The method of embodiment P42, wherein the compound is

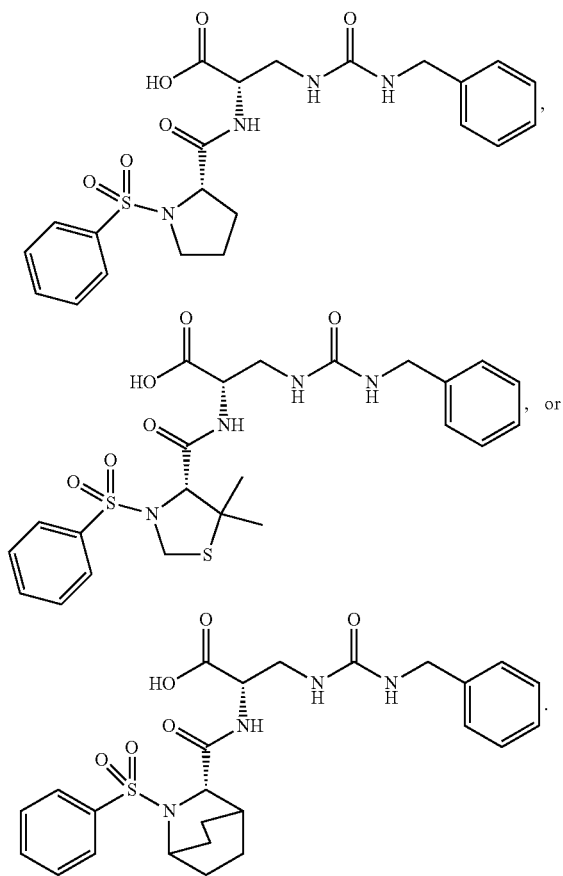

Embodiment P46. The method of embodiment P42, wherein the compound is

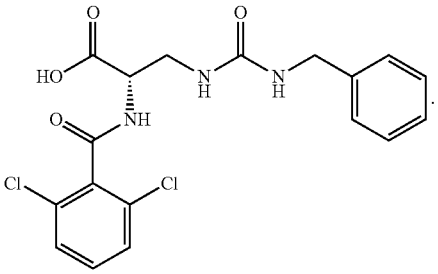 [SMILES: O=C(NCc1ccccc1)NC[C@H](NC(=O)c1c(Cl)cccc1Cl)C(=O)O]

VI. Additional Embodiments

Embodiment 1. A compound having the formula:

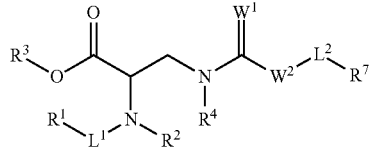

wherein,
$R^1$ is substituted or unsubstituted alkyl, substituted or unsubstituted heteroalkyl, substituted or unsubstituted aryl, or substituted or unsubstituted heteroaryl;
$L^1$ is a bond or —C(O)—;
$R^2$ is hydrogen or substituted or unsubstituted alkyl;
$R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —$NHC(O)NR^{3A}R^{3B}$, —$N(O)_{m3}$, —$NR^{3A}R^{3B}$, —$C(O)R^{3C}$, —$C(O)$—$OR^{3C}$, —$C(O)NR^{3A}R^{3B}$, —$OR^{3D}$, —$NR^{3A}SO_2R^{3D}$, —$NR^{3A}C(O)R^{3C}$, —$NR^{3A}C(O)OR^{3C}$, —$NR^4OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl; or —$OR^3$ is a prodrug moiety;
$R^4$ is hydrogen or substituted or unsubstituted alkyl;
$W^1$ is O, S, NW;
$W^2$ is O, S, $NR^5$;
$R^5$ is hydrogen or substituted or unsubstituted alkyl;
$L^2$ is a bond or —$C(R^6)_2$—;
$R^6$ is hydrogen, =NH, substituted or unsubstituted alkyl, or substituted or unsubstituted heteroalkyl;
$W^1$ and $R^6$ may optionally be joined to form a substituted or unsubstituted 5 to 6 membered heterocycloalkyl, or substituted or unsubstituted 5 to 6 membered heteroaryl;
$R^7$ is hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}NR^{7A}R^{7B}$, —$NHC(O)NR^{7A}R^{7B}$, —$N(O)_{m7}$, —$NR^{7A}R^{7B}$, —$C(O)R^{7C}$, —$C(O)$—$OR^{7C}$, —$C(O)NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}OR^{7C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
$R^8$ is hydrogen or substituted or unsubstituted alkyl;

$R^{3A}$, $R_{3B}$, $R^{3C}$, $R^{3D}$, $R^{7A}$, $R^{7B}$, $R^{7C}$, and $R^{7D}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $W^A$ and $R^{7B}$ substituents bonded to the same nitrogen atom may optionally be joined to form a substituted or unsubstituted heterocycloalkyl or substituted or unsubstituted heteroaryl;

each X, $X^3$, and $X^7$ are independently —F, —Cl, —Br, or —I;

n3 and n7 are independently an integer from 0 to 3; and m3, m7, v3 and v7 are independently 1 or 2.

Embodiment 2. The compound of embodiment 1 having the formula:

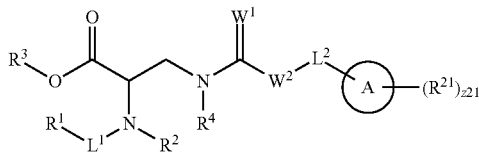

wherein,

Ring A is cycloalkyl, heterocycloalkyl, aryl, or heteroaryl;

$R^{21}$ is independently halogen, —CX$^{21}_3$, —CHX$^{21}_2$, —CH$_2$X$^{21}$, —OCX$^{21}_3$, —OCH$_2$X$^{21}$, —OCHX$^{21}_2$, —CN, —SO$_{n21}$R$^{21D}$, —SO$_{v21}$NR$^{21A}$R$^{21B}$, —N(O)$_{m21}$, —NR$^{21A}$R$^{21B}$, —C(O)R$^{21C}$, —C(O)—OR$^{21C}$, —C(O)NR$^{21A}$R$^{21B}$, —OR$^{21D}$, —NR$^{21A}$SO$_2$R$^{21D}$, —NR$^{21A}$C(O)R$^{21C}$, —NR$^{21A}$C(O)OR$^{21C}$, —NR$^{21A}$OR$^{21C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;

z21 is an integer from 0 to 5;

$R^{21A}$, $R^{21B}$, $R^{21C}$, and $R^{21D}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{21A}$ and $R^{21B}$ substituents bonded to the same nitrogen atom may optionally be joined to form a substituted or unsubstituted heterocycloalkyl or substituted or unsubstituted heteroaryl;

each X and $X^{21}$ are independently —F, —Cl, —Br, or —I;

n21 is independently an integer from 0 to 3; and m21 and v21 are independently 1 or 2.

Embodiment 3. The compound of one of embodiments 1 to 2 wherein $R^1$ is unsubstituted $C_1$-$C_6$ alkyl.

Embodiment 4. The compound of one of embodiments 1 to 2 wherein $R^1$ is

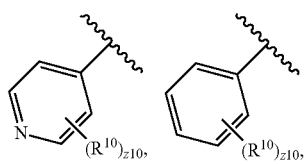

or substituted or unsubstituted $C_4$-$C_8$ alkyl;

wherein, $R^{10}$ is independently halogen, —CX$^{10}_3$, —CHX$^{10}_2$, —CH$_2$X$^{10}$, —OCX$^{10}_3$, —OCH$_2$X$^{10}$, —OCHX$^{10}_2$, —CN, —SO$_{n10}$R$^{10D}$, —SO$_{v10}$NR$^{10A}$R$^{10B}$, —NHC(O)NR$^{10A}$R$^{10B}$, —N(O)$_{m10}$, —NR$^{10A}$R$^{10B}$, C(O)R$^{10C}$, —C(O)—OR$^{10C}$, —C(O)NR$^{10A}$R$^{10B}$, —OR$^{10D}$, —NR$^{10A}$SO$_2$R$^{10D}$, —NR$^{10A}$C(O)R$^{10C}$, —NR$^{10A}$ C(O)OR$^{10C}$, —NR$^{10A}$OR$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^{10}$ substituents may optionally be joined to form a substituted or unsubstituted cycloalkyl, substituted or unsubstituted heterocycloalkyl, substituted or unsubstituted aryl, or substituted or unsubstituted heteroaryl;

$R^{10A}$, $R^{10B}$, $R^{10C}$, and $R^{10D}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{10A}$ and $R^{10B}$ substituents bonded to the same nitrogen atom may optionally be joined to form a substituted or unsubstituted heterocycloalkyl or substituted or unsubstituted heteroaryl;

X and $X^{10}$ are independently —F, —Cl, —Br, or —I;

n10 is independently an integer from 0 to 4;

m10 and v10 are independently 1 or 2; and z10 is an integer from 0 to 5.

Embodiment 5. The compound of one of embodiments 1 to 4 wherein $L^2$ is —C(R$^6$)$_2$—.

Embodiment 6. The compound of one of embodiments 1 to 4 wherein $L^2$ is —CHR$^6$—.

Embodiment 7. The compound of one of embodiments 1 to 4 wherein $L^2$ is a bond.

Embodiment 8. The compound of one of embodiments 1 to 6 wherein $R^6$ is unsubstituted alkyl.

Embodiment 9. The compound of one of embodiments 1 to 6 wherein $R^6$ is hydrogen.

Embodiment 10. The compound of one of embodiments 1 to 9 wherein $W^1$ is NH.

Embodiment 11. The compound of one of embodiments 1 to 9 wherein $W^1$ is S.

Embodiment 12. The compound of one of embodiments 1 to 9 wherein $W^1$ is O.

Embodiment 13. The compound of one of embodiments 1 to 12 wherein $W^2$ is NH.

Embodiment 14. The compound of one of embodiments 1 to 12 wherein $W^2$ is S.

Embodiment 15. The compound of one of embodiments 1 to 12 wherein $W^2$ is O.

Embodiment 16. The compound of one of embodiments 1 to 15 wherein $W^1$ and $R^6$ are joined to form a substituted or unsubstituted 5 to 6 membered heterocycloalkyl or substituted or unsubstituted 5 to 6 membered heteroaryl.

Embodiment 17. The compound of one of embodiments 1 to 15 wherein $W^1$ and $R^6$ are joined to form a substituted or unsubstituted 5 to 6 membered heteroaryl.

Embodiment 18. The compound of one of embodiments 1 to 15 wherein $W^1$ and $R^6$ are joined to form

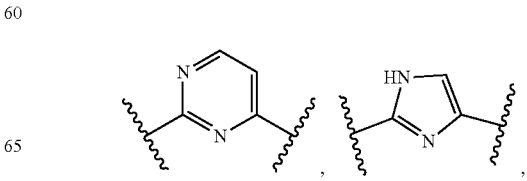

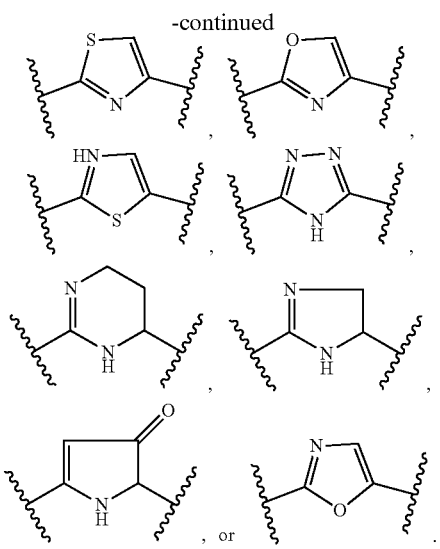
, or

Embodiment 19. The compound of one of embodiments 1 to 18 wherein $R^2$, $R^4$, $R^5$, and $R^8$ are hydrogen.

Embodiment 20. The compound of one of embodiments 1 to 19 wherein $R^3$ is substituted or unsubstituted $C_1$-$C_6$ alkyl.

Embodiment 21. The compound of one of embodiments 1 to 19 wherein $R^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl.

Embodiment 22. The compound of one of embodiments 1 to 19 wherein —$OR^3$ is a prodrug moiety.

Embodiment 23. The compound of one of embodiments 1 to 19 wherein —$OR^3$ is a prodrug moiety capable of being cleaved from the remainder of the compound by an esterase or amidase.

Embodiment 24. The compound of one of embodiments, 1 to 19 wherein $R^3$ is substituted or unsubstituted $C_1$-$C_8$ alkyl,

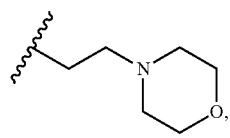

substituted or unsubstituted aryl, (acyloxy)alkyl, [(alkoxycarbonyl)oxy]methyl, or (oxodioxolyl)methyl.

Embodiment 25. The compound of one of embodiments 1 to 19 wherein $R^3$ is hydrogen.

Embodiment 26. The compound of one of embodiments 1 to 25, wherein $L^1$ is a bond.

Embodiment 27. The compound of one of embodiments 1 to 25, wherein $L^1$ is —C(O)—.

Embodiment 28. The compound of one of embodiments 1 and 3 to 27, wherein $R^7$ is unsubstituted $C_1$-$C_6$ alkyl.

Embodiment 29. The compound of one of embodiments 1 and 3 to 27, wherein $R^7$ is unsubstituted alkyl, substituted or unsubstituted cycloalkyl, substituted or unsubstituted heterocycloalkyl, substituted or unsubstituted aryl, or substituted or unsubstituted heteroaryl.

Embodiment 30. The compound of one of embodiments 1 and 3 to 27, wherein $R^7$ is substituted or unsubstituted cyclohexyl.

Embodiment 31. The compound of one of embodiments 1 and 3 to 27, wherein $R^7$ is substituted or unsubstituted cyclohexyl, adamantyl, tetrahydronaphthyl, dihydroindenyl, or bicyclo[3.3.1]heptanyl, 2,3-dihydro-1H-indenyl.

Embodiment 32. The compound of one of embodiments 1 and 3 to 27, wherein $R^7$ is substituted or unsubstituted $C_7$-$C_{12}$ fused cycloalkyl.

Embodiment 33. The compound of one of embodiments 1 and 3 to 27, wherein $R^7$ is substituted or unsubstituted $C_7$-$C_{12}$ bridged cycloalkyl.

Embodiment 34. The compound of one of embodiments 1 and 3 to 27, wherein $R^7$ is substituted or unsubstituted $C_7$-$C_{15}$ spirocyclic cycloalkyl.

Embodiment 35. The compound of one of embodiments 1 and 3 to 27, wherein wherein

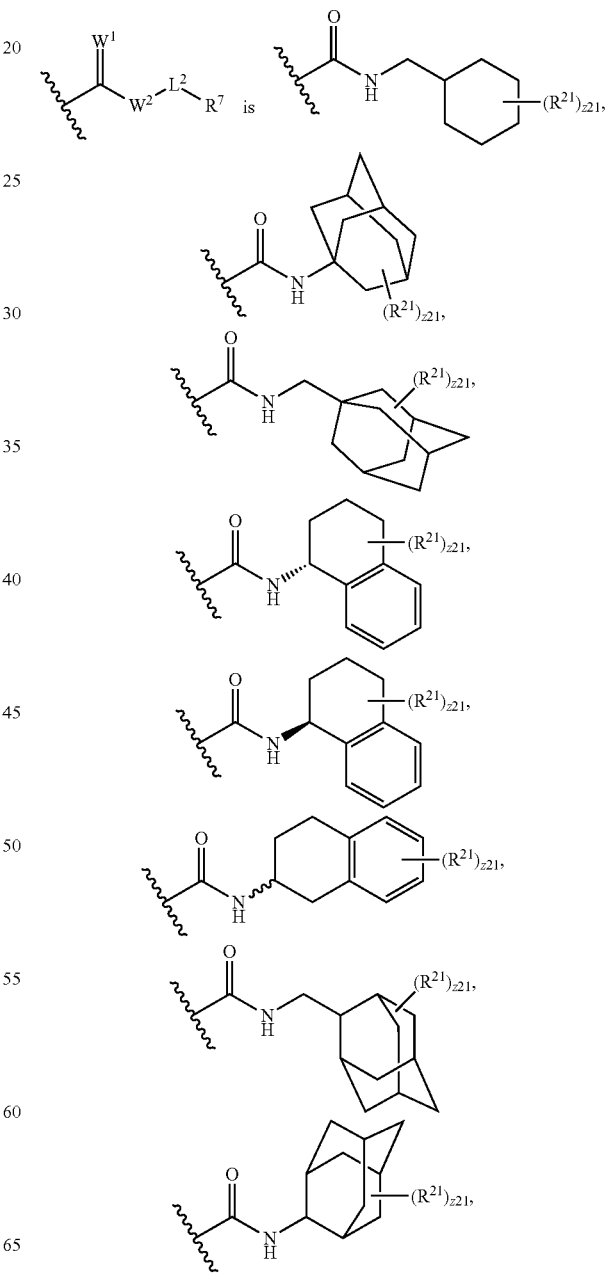

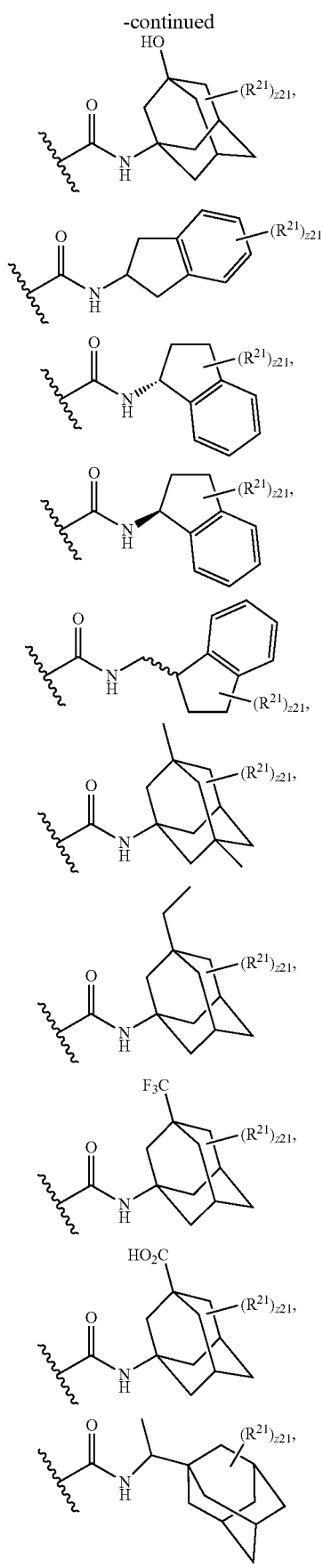
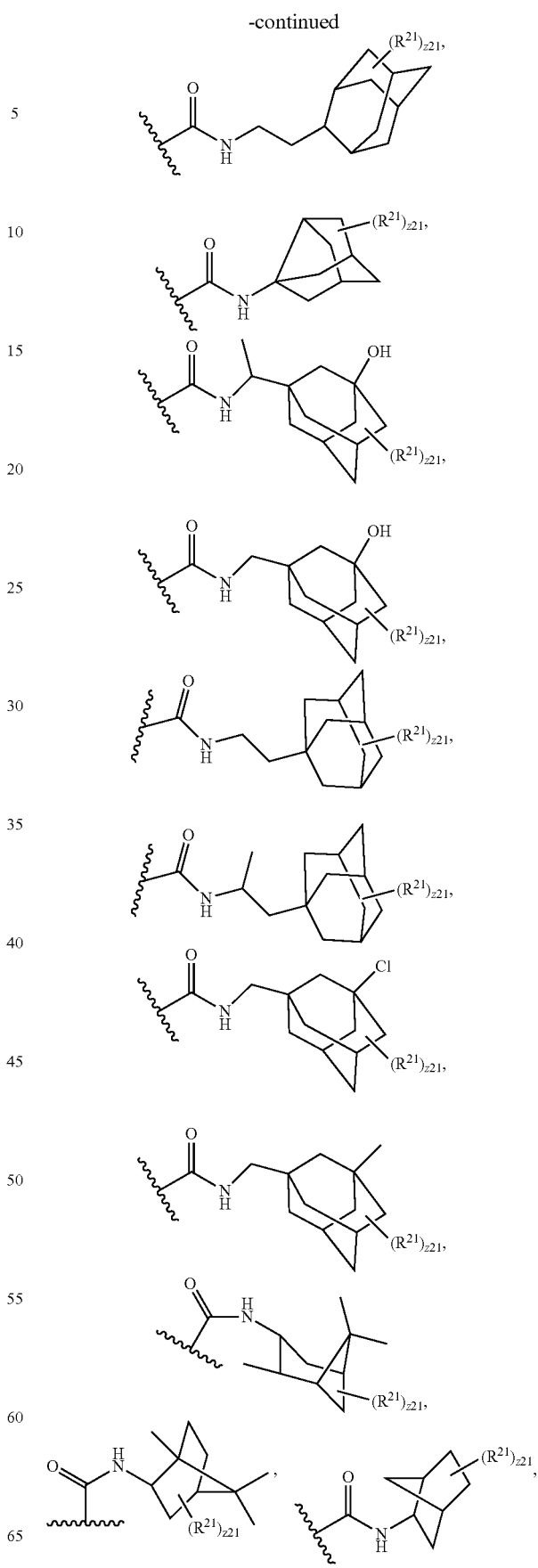

-continued
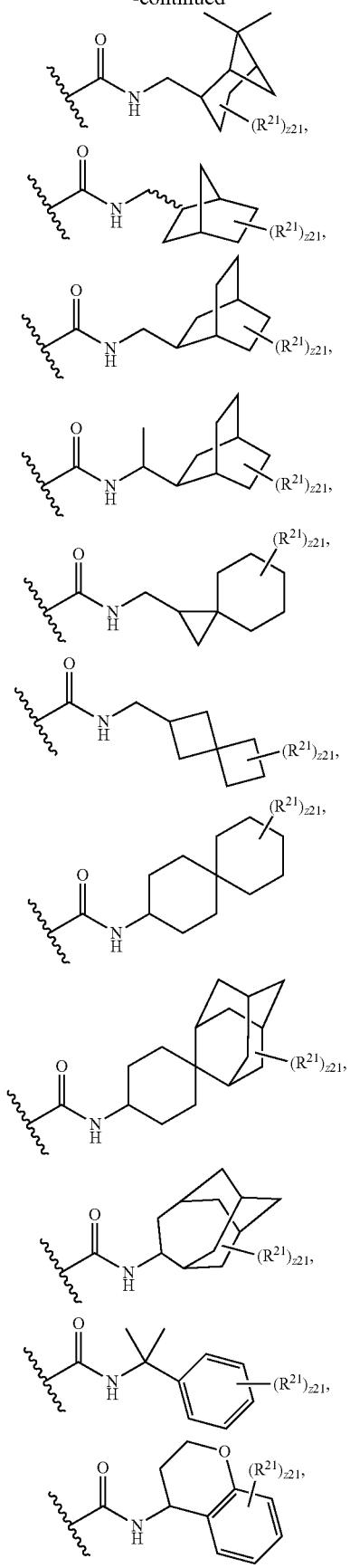
-continued
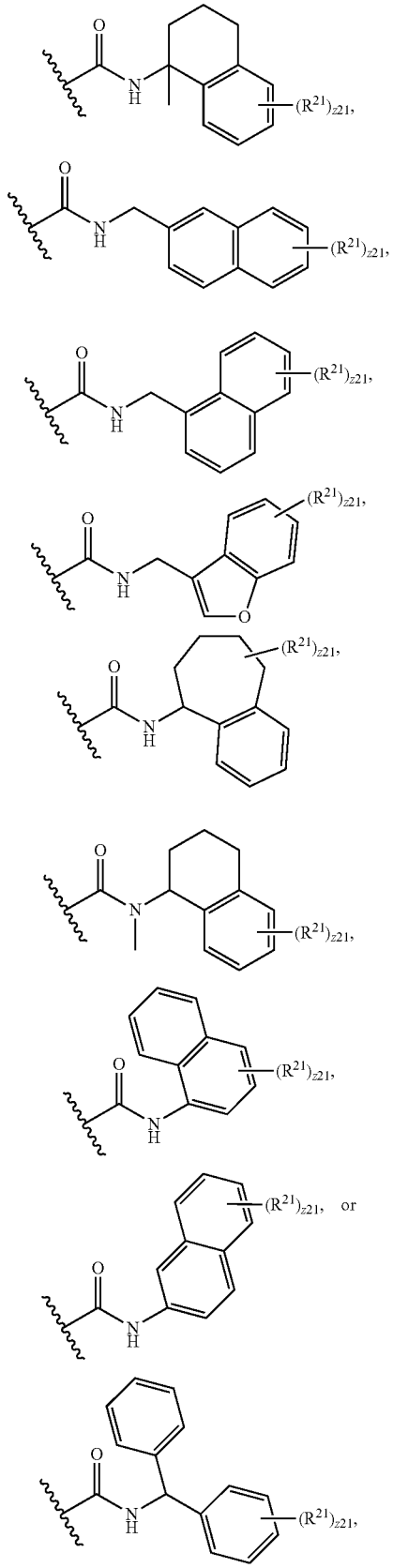
wherein z21 is an integer from 0 to 5.

Embodiment 36. The compound of one of embodiments 1 and 3 to 27, wherein wherein
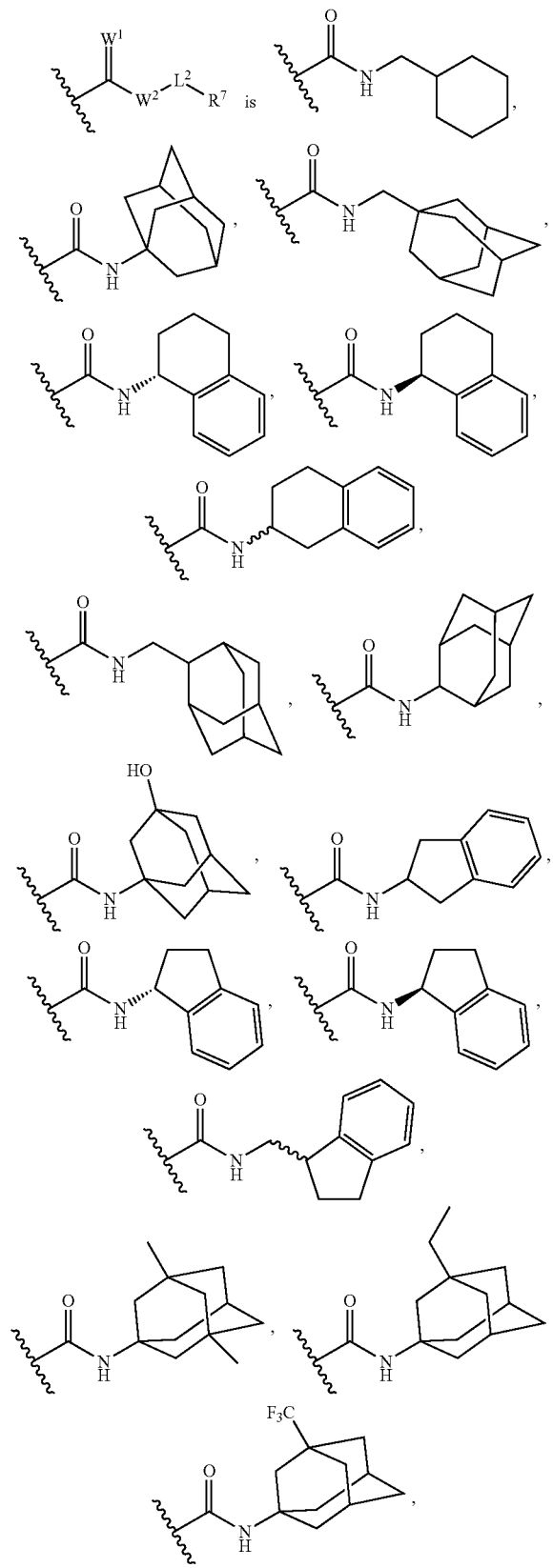
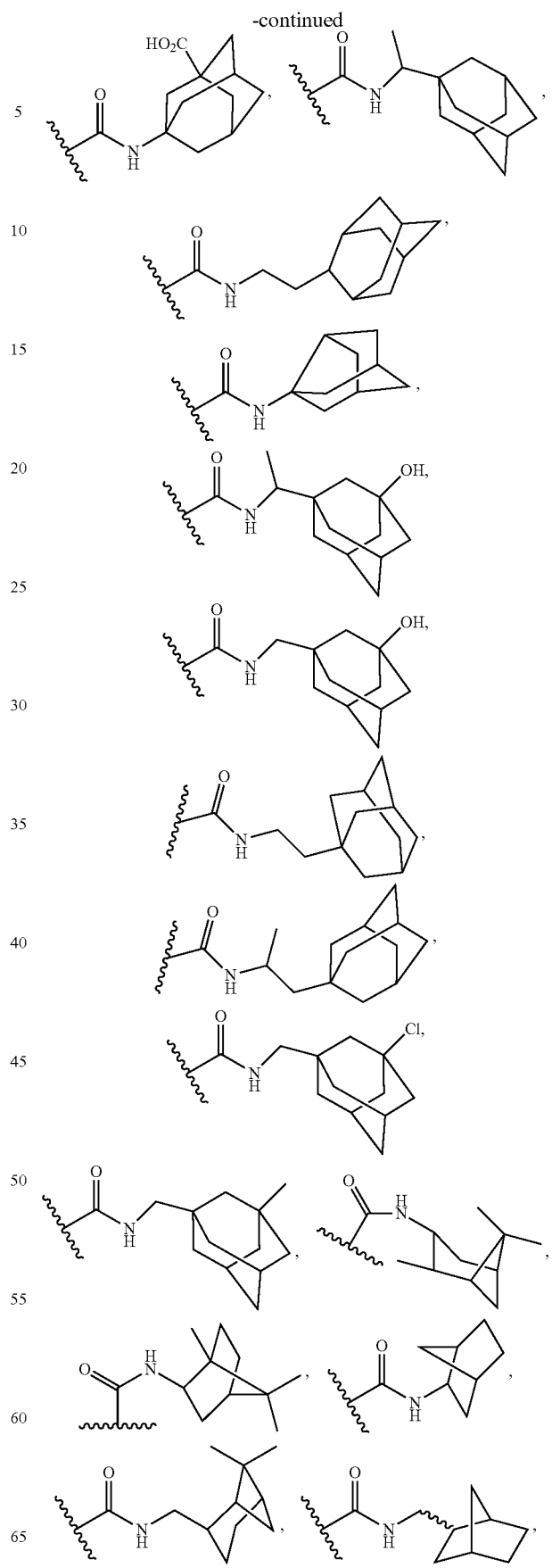

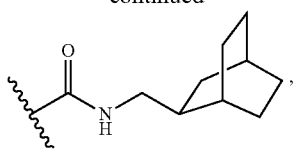
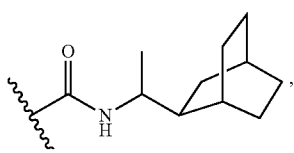
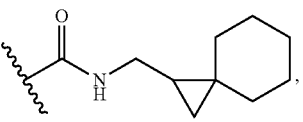
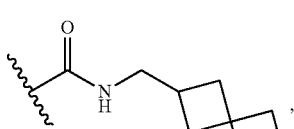
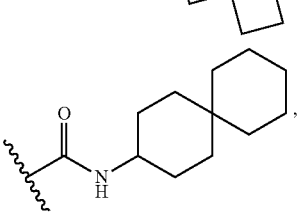
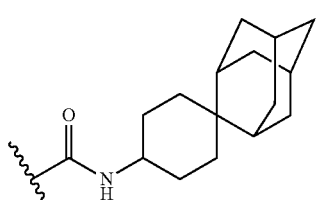
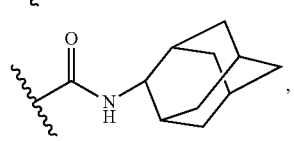
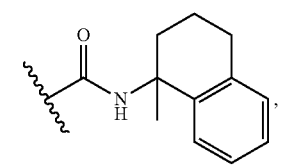
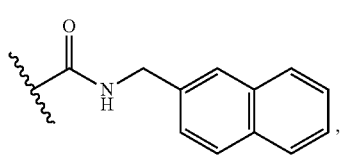

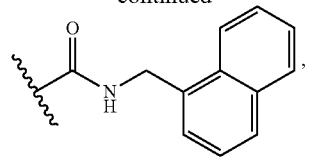
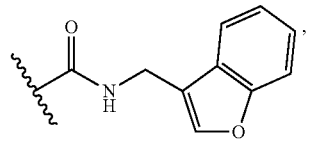
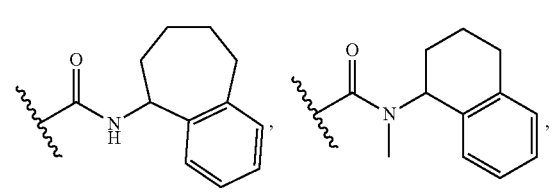
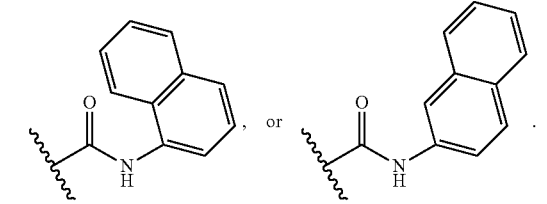

Embodiment 37. The compound of one of embodiments 2 to 27, wherein Ring A is 5 to 6 membered heteroaryl.

Embodiment 38. The compound of one of embodiments 2 to 27, wherein Ring A is phenyl.

Embodiment 39. The compound of one of embodiments 2 to 27, wherein Ring A is a bicyclic $C_9$-$C_{10}$ aryl or bicyclic 8 to 10 membered heteroaryl.

Embodiment 40. The compound of one of embodiments 2 to 39, wherein z21 is an integer from 1 to 5.

Embodiment 41. The compound of one of embodiments 2 to 39, wherein z21 is 0.

Embodiment 42. The compound of one of embodiments 1 to 39, having the formula:

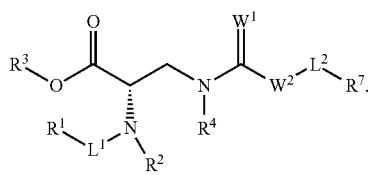

Embodiment 43. The compound of one of embodiments 1 to 39, having the formula:

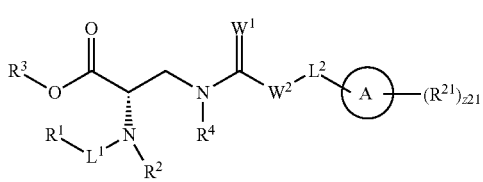

Embodiment 44. The compound of one of embodiments 1 to 39, having the formula:
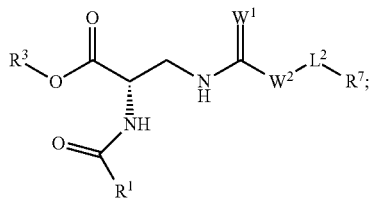
wherein R[1] is
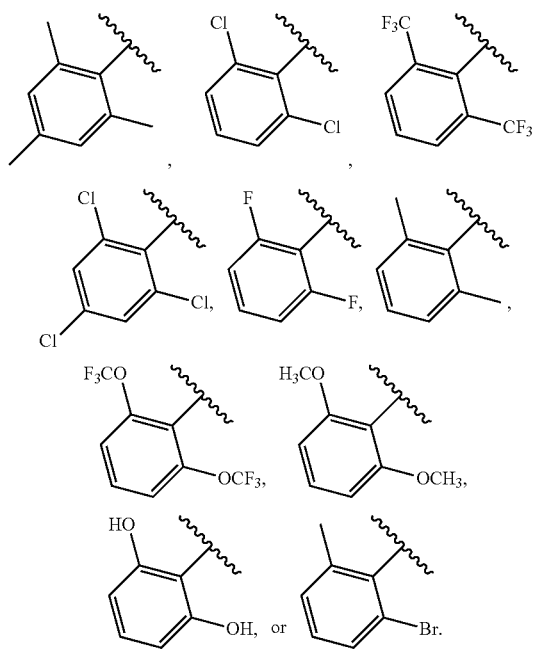
Embodiment 45. The compound of embodiment 44, wherein
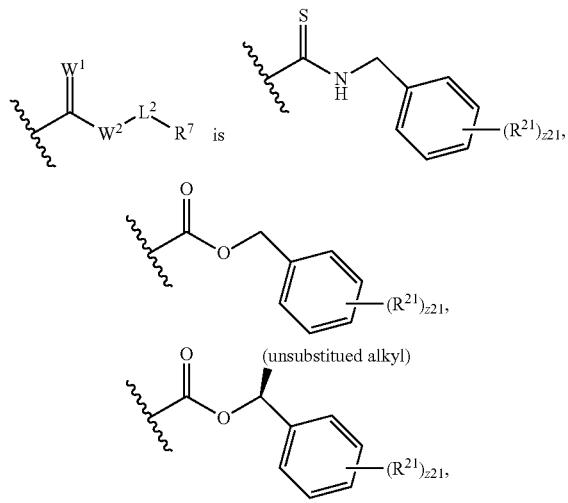
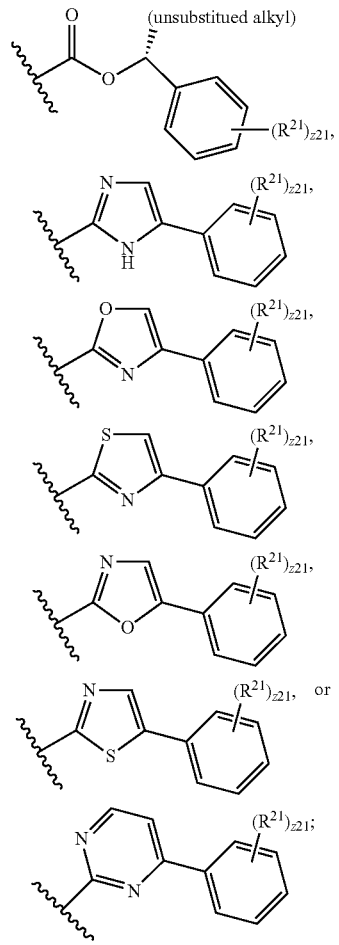
wherein z21 is an integer from 0 to 5;
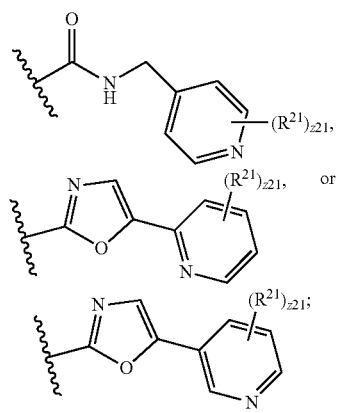
wherein z21 is an integer from 0 to 4;
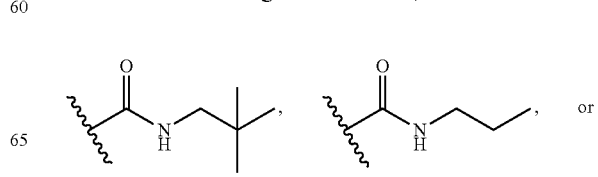

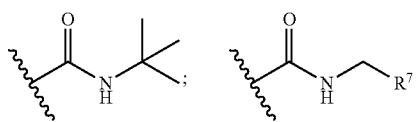
wherein R⁷ is substituted or unsubstituted cycloalkyl;
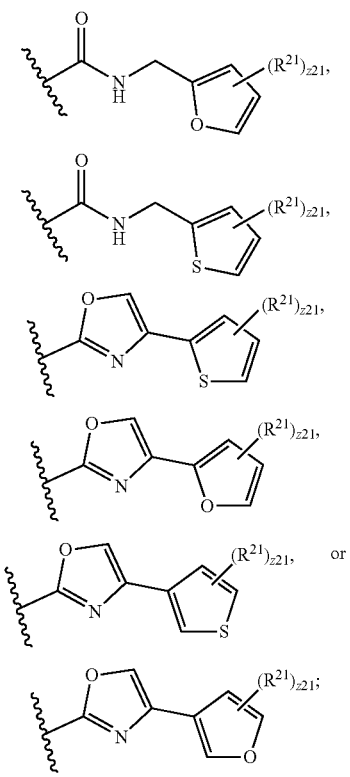
wherein z21 is an integer from 0 to 3;
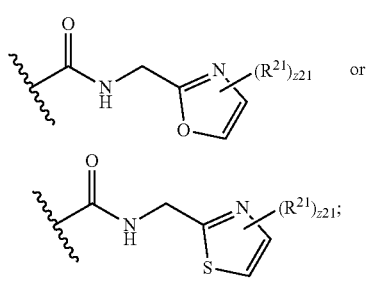
wherein z21 is an integer from 0 to 2; or
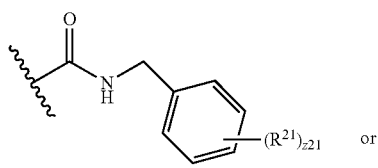
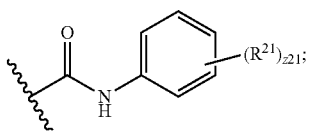
wherein z21 is an integer from 1 to 5.
Embodiment 46. The compound of one of embodiments 1 to 39, having the formula:
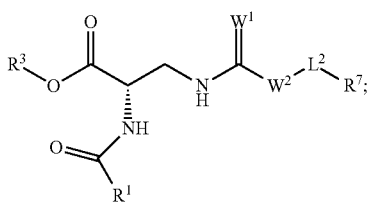
wherein R¹ is
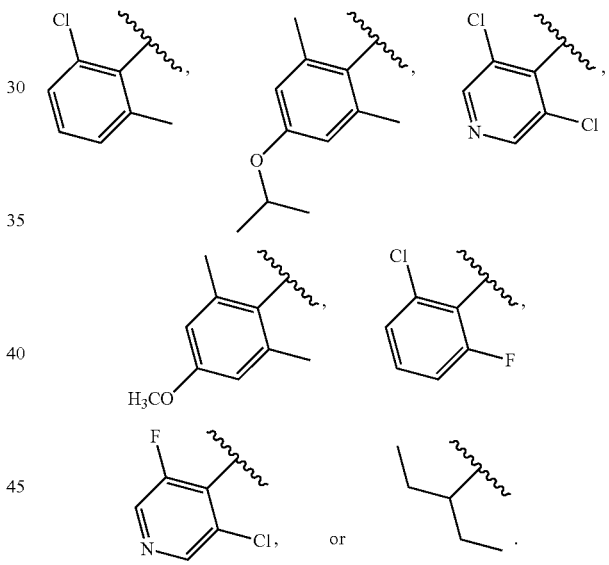
Embodiment 47. The compound of embodiment 46, wherein
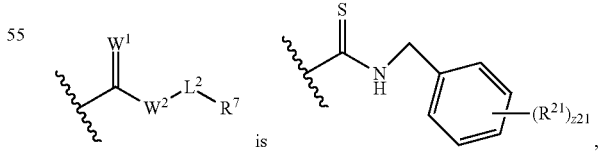
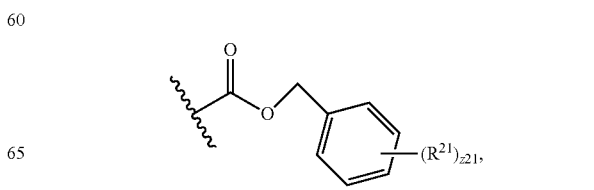

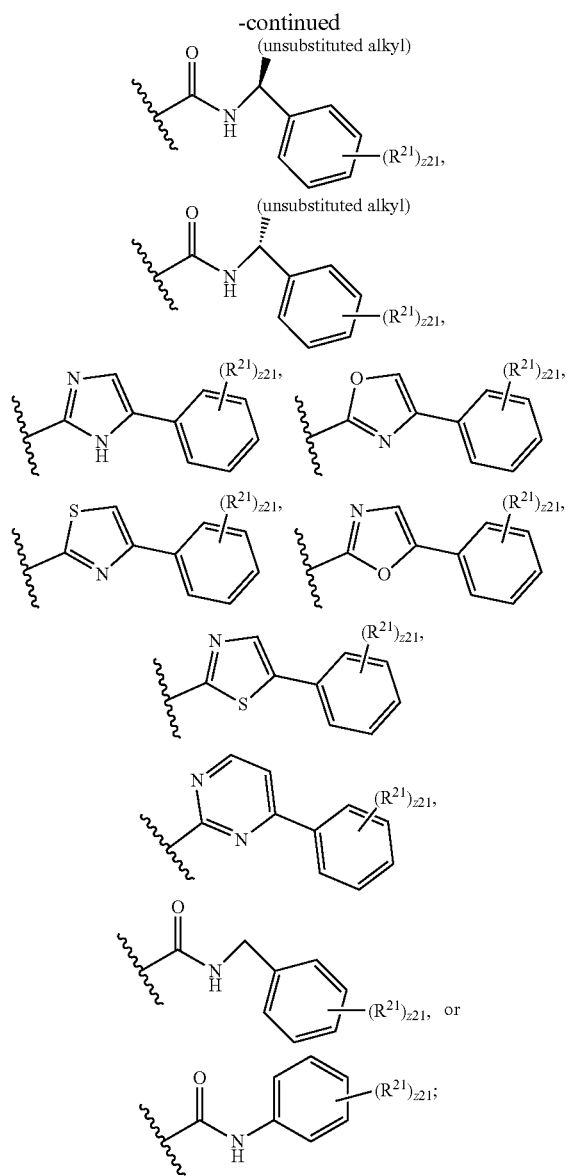
wherein z21 is an integer from 0 to 5;
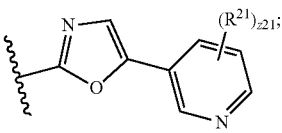
wherein z21 is an integer from 0 to 4;
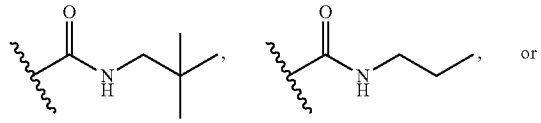
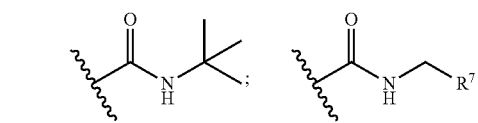
wherein $R^7$ is substituted or unsubstituted cycloalkyl;
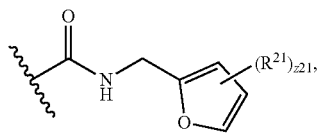
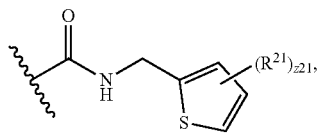
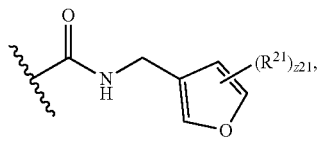
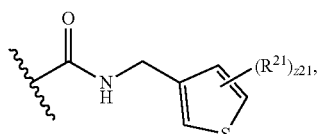
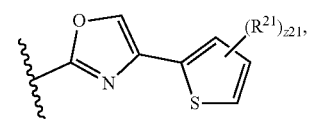
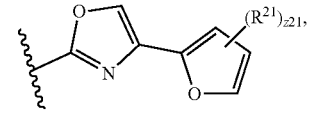
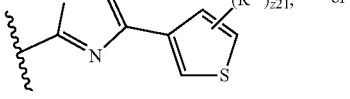

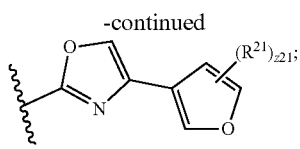

wherein z21 is an integer from 0 to 3; or

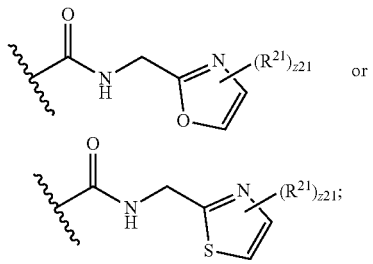

wherein z21 is an integer from 0 to 2.

Embodiment 48. The compound of embodiment 1, having the formula:

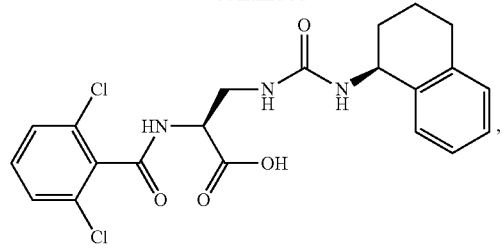

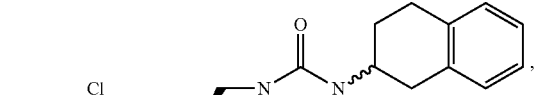

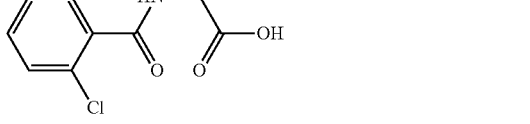

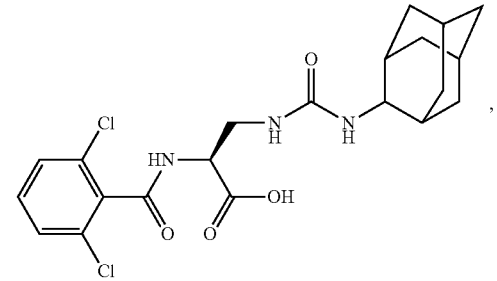

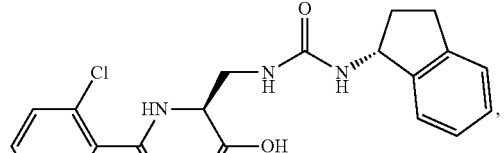

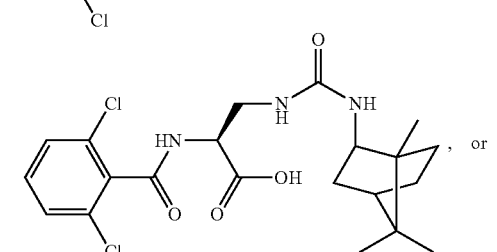

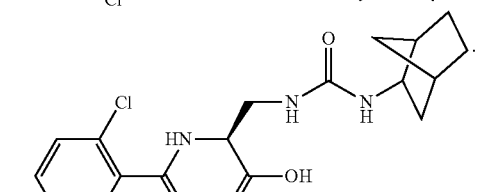

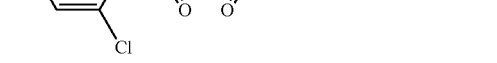

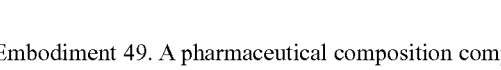

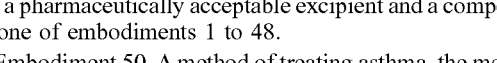

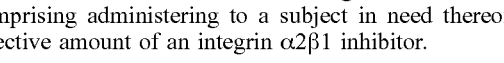

Embodiment 49. A pharmaceutical composition comprising a pharmaceutically acceptable excipient and a compound of one of embodiments 1 to 48.

Embodiment 50. A method of treating asthma, the method comprising administering to a subject in need thereof an effective amount of an integrin α2β1 inhibitor.

Embodiment 51. The method of embodiment 50, wherein the α2β1 inhibitor is a nucleic acid, protein, or compound.

Embodiment 52. The method of embodiment 50, wherein the α2β1 inhibitor is compound of one of embodiments 1 to 48.

Embodiment 53. A method of treating asthma, the method comprising administering to a subject in need thereof an effective amount of a compound of one of embodiments 1 to 48.

Embodiment 54. A method of treating asthma, the method comprising administering to a subject in need thereof an effective amount of a compound, or a pharmaceutically, having the formula:

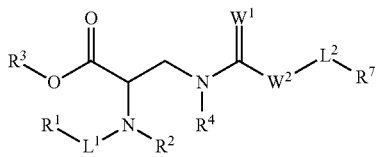

wherein,
$R^1$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$L^1$ is a bond or —C(O)—;
$R^2$ is hydrogen or substituted or unsubstituted alkyl;
$R^3$ is hydrogen, halogen, —$CX^3_3$, —$CHX^3_2$, —$CH_2X^3$, —$OCX^3_3$, —$OCH_2X^3$, —$OCHX^3_2$, —CN, —$SO_{n3}R^{3D}$, —$SO_{v3}NR^{3A}R^{3B}$, —$NHC(O)NR^{3A}R^{3B}$, —$N(O)_{m3}$, —$NR^{3A}R^{3B}$, —$C(O)R^{3C}$, —C(O)—$OR^{3C}$, —C(O)$NR^{3A}R^{3B}$, —$OR^{3D}$, —$NR^{3A}SO_2R^{3D}$, —$NR^{3A}C(O)R^{3C}$, —$NR^{3A}C(O)OR^{3C}$—$NR^{3A}OR^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
$R^4$ is hydrogen or substituted or unsubstituted alkyl;
$W^1$ is O, S, $NR^8$;
$W^2$ is O, S, $NR^5$;
$R^5$ is hydrogen or substituted or unsubstituted alkyl;
$L^2$ is a bond or —$CHR^6$—;
$R^6$ is hydrogen, =NH, substituted or unsubstituted alkyl, or substituted or unsubstituted heteroalkyl;
$W^1$ and $R^6$ may optionally be joined to form a substituted or unsubstituted 5 to 6 membered heterocycloalkyl, or substituted or unsubstituted 5 to 6 membered heteroaryl;
$R^7$ is hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7D}$, —$SO_{v7}NR^{7A}R^{7B}$, —$NHC(O)NR^{7A}R^{7B}$, —$N(O)_{m7}$, —$NR^{7A}R^{7B}$, —$C(O)R^{7C}$, —C(O)—$OR^{7C}$, —C(O)$NR^{7A}R^{7B}$, —$OR^{7D}$, —$NR^{7A}SO_2R^{7D}$, —$NR^{7A}C(O)R^{7C}$, —$NR^{7A}C(O)OR^{7C}$, —$NR^{7A}OR^7$, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl;
$R^8$ is hydrogen or substituted or unsubstituted alkyl;
$R^{3A}$, $R^{3B}$, $R^{3C}$, $R^{3D}$, $R^{7A}$, $R^{7B}$, $R^{7C}$, and $R^{7D}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl;
each X, $X^3$, and $X^7$ are independently —F, —Cl, —Br, or —I;
n3 and n7 are independently an integer from 0 to 3; and
m3, m7, v3 and v7 are independently 1 or 2.

Embodiment 55. The method of embodiment 54, wherein $R^1$ is

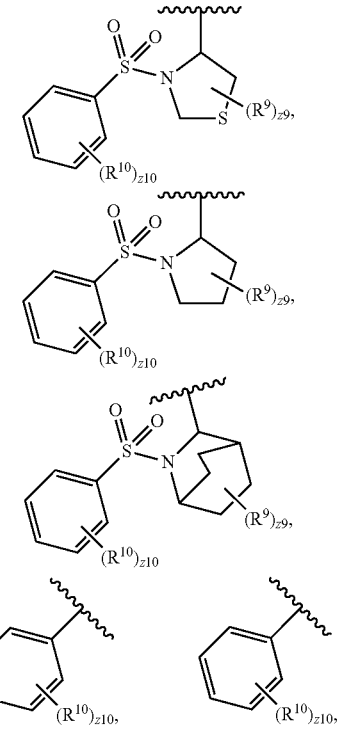

or substituted or unsubstituted $C_4$-$C_8$ alkyl;
wherein,
$R^9$ is independently halogen, —$CX^9_3$, —$CHX^9_2$, —$CH_2X^9$, —$OCX^9_3$, —$OCH_2X^9$, —$OCHX^9_2$, —CN, —$SO_{n9}R^{9D}$, —$SO_{v9}NR^{9A}R^{9B}$, —$NHC(O)NR^{9A}R^{9B}$, —$N(O)_{m9}$, —$NR^{9A}R^{9B}$, —$C(O)R^{9C}$, —C(O)—$OR^{9C}$, —C(O)$NR^{9A}R^{9B}$, —$OR^{9D}$, —$NR^{9A}SO_2R^{9D}$, —$NR^{9A}C(O)R^{9C}$—$NR^{9A}C(O)O R^{9C}$, —$NR^{9A}OR^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^9$ substituents may optionally be joined to form a substituted or unsubstituted cycloalkyl, substituted or unsubstituted heterocycloalkyl, substituted or unsubstituted aryl, or substituted or unsubstituted heteroaryl;
$R^{10}$ is independently halogen, —$CX^{10}_3$, —$CHX^{10}_2$, —$CH_2X^{10}$, —$OCX^{10}_3$, —$OCH_2X^{10}$, —$OCHX^{10}_2$, —CN, —$SO_{n10}R^{10D}$, —$SO_{v10}NR^{10A}R^{10B}$, —$NHC(O)NR^{10A}R^{10B}$, —$N(O)_{m10}$, —$NR^{10A}R^{10B}$, —$C(O)R^{10C}$, —C(O)—$OR^{10C}$, —C(O)$NR^{10A}R^{10B}$, —$OR^{10D}$, 13 $NR^{10A}SO_2R^{10D}$, —$NR^{10A}C(O)R^{10C}$, —$NR^{10A}C(O)OR^{10C}$, —$NR^{10A}OR^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^{10}$ substituents may optionally be joined to form a substituted or unsubstituted cycloalkyl, substituted or unsubstituted heterocycloalkyl, substituted or unsubstituted aryl, or substituted or unsubstituted heteroaryl;

$R^{9A}$, $R^{9B}$, $R^{9C}$, $R^{9D}$, $R^{10A}$, $R^{10B}$, $R^{10C}$, and $R^{10D}$ are independently hydrogen, —$CX_3$, —CN, —COOH, —$CONH_2$, —$CHX_2$, —$CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{9A}$ and $R^{9B}$ substituents bonded to the same nitrogen atom may optionally be joined to form a substituted or unsubstituted heterocycloalkyl or substituted or unsubstituted heteroaryl; $R^{10A}$ and $R^{10B}$ substituents bonded to the same nitrogen atom may optionally be joined to form a substituted or unsubstituted heterocycloalkyl or substituted or unsubstituted heteroaryl;

X, $X^9$, and $X^{10}$ are independently —F, —Cl, —Br, or —I;

n9 and n10 are independently an integer from 0 to 4;

m9, m10, v9 and v10 are independently 1 or 2;

z9 is an integer from 0 to 5; and z10 is an integer from 0 to 5.

Embodiment 56. The method of one of embodiments 54 to 55, wherein $R^1$ is

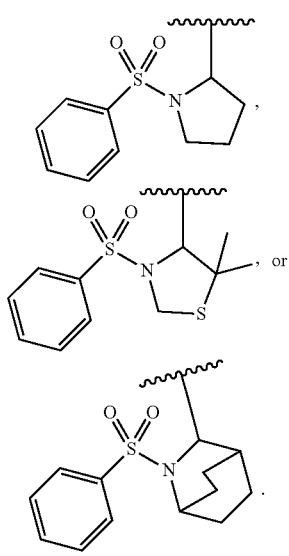

Embodiment 57. The method of one of embodiments 54 to 56, wherein the compound is

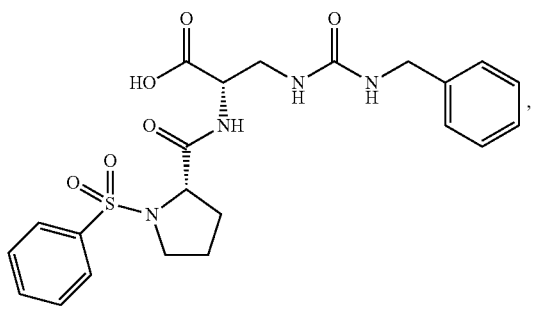

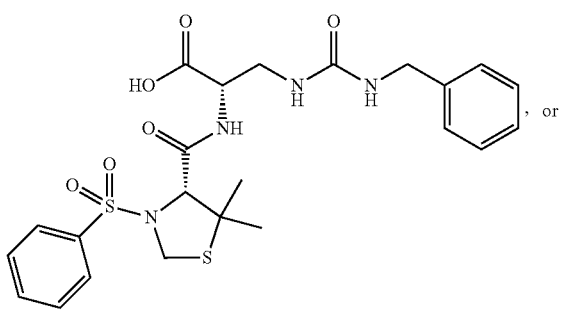

, or

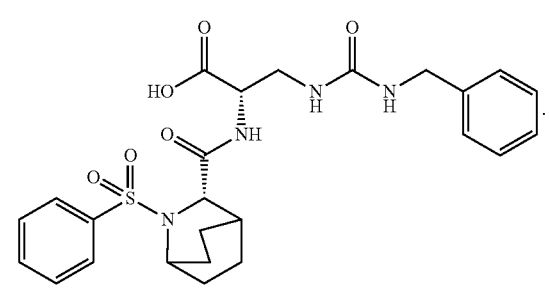

.

Embodiment 58. The method of embodiment 54, wherein the compound is

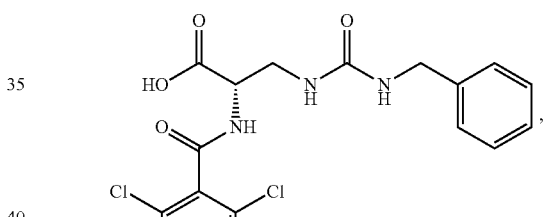

,

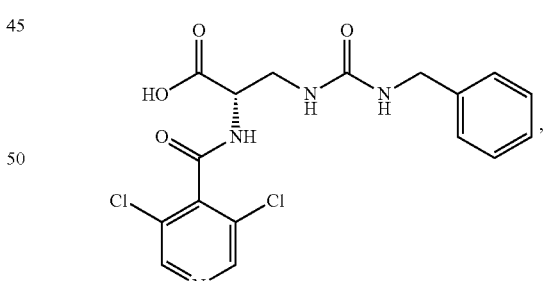

,

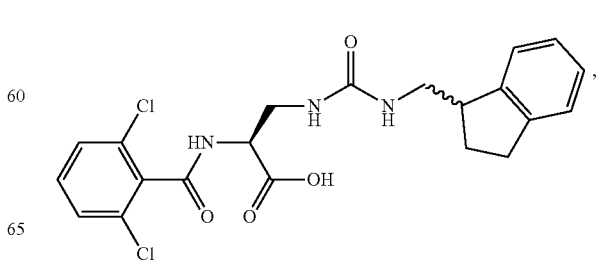

,

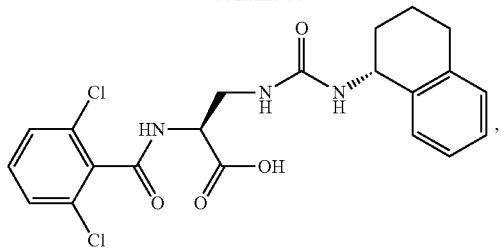,

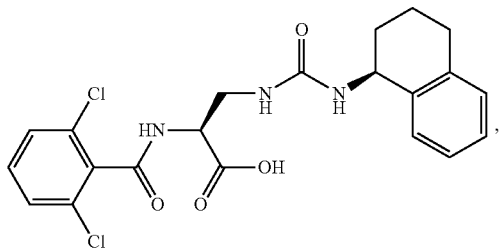,

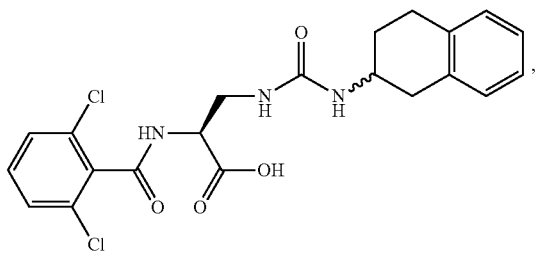,

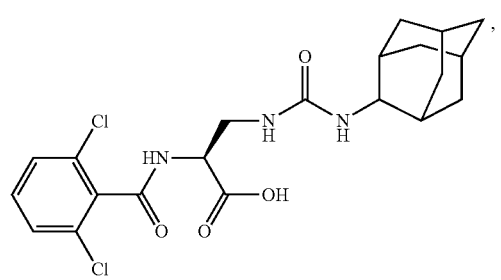,

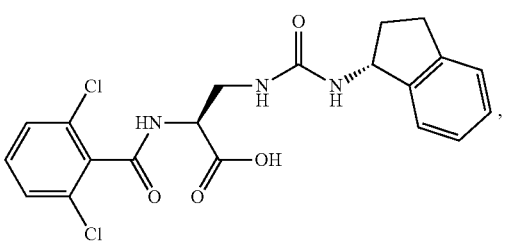,

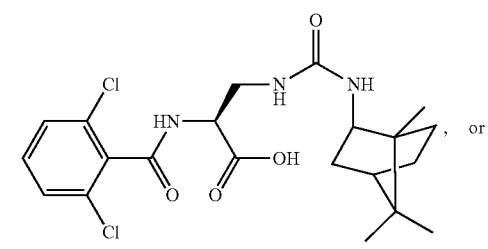, or

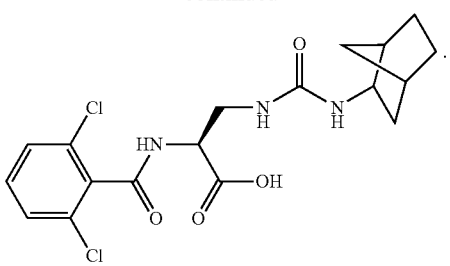.

Embodiment 59. The method of one of embodiments 54 to 56, wherein $R^7$ is substituted or unsubstituted cycloalkyl.

Embodiment 60. The method of one of embodiments 54 to 56, wherein $R^7$ is substituted or unsubstituted cyclohexyl, adamantly, tetrahydronaphthyl, dihydroindenyl, or bicyclo[3.3.1]heptanyl, 2,3-dihydro-1H-indenyl.

Embodiment 61. The method of one of embodiments 54 and 56, wherein

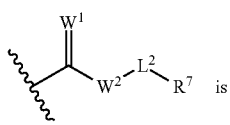 is

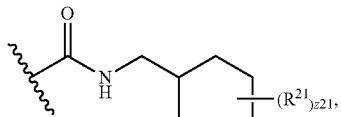,

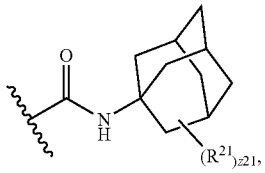,

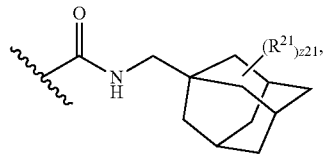,

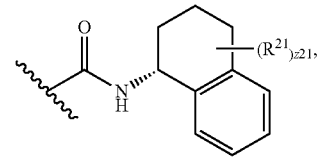,

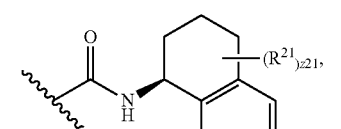,

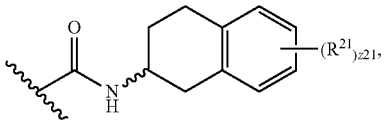,

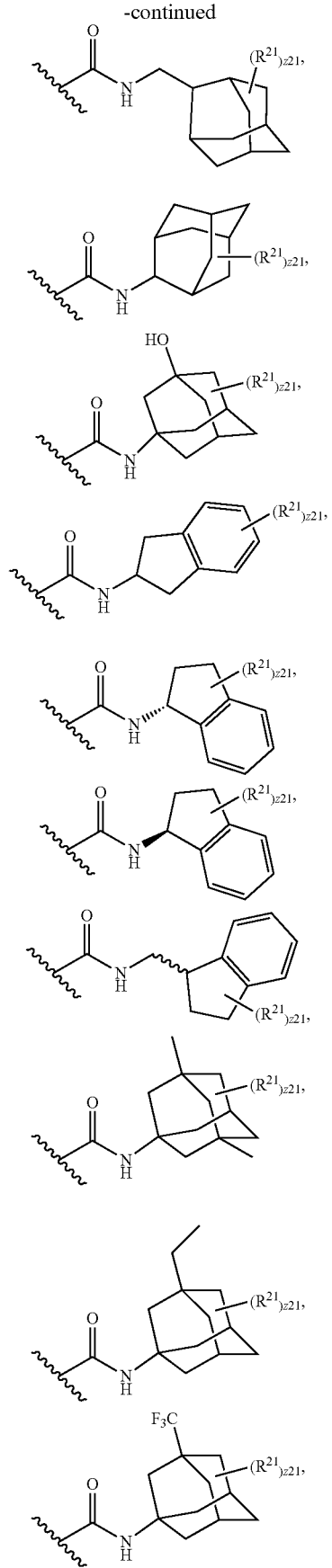
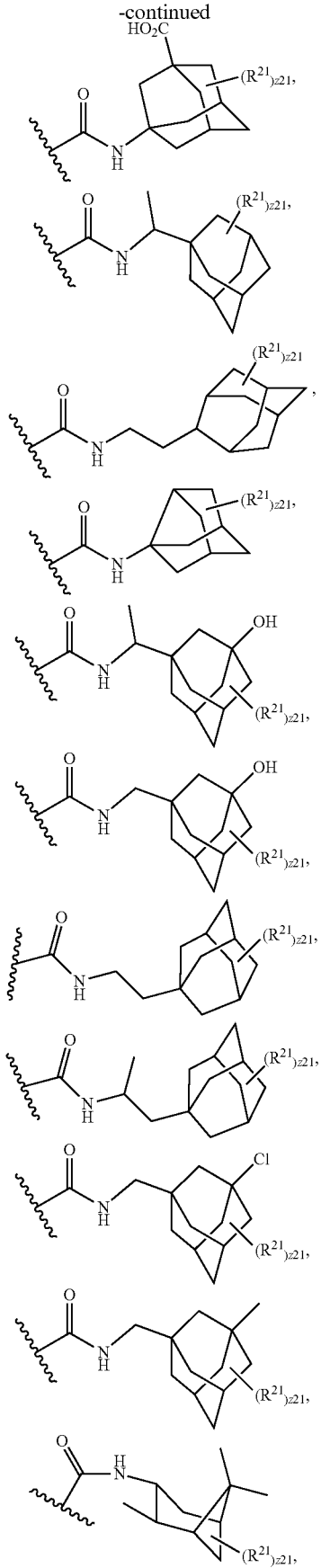

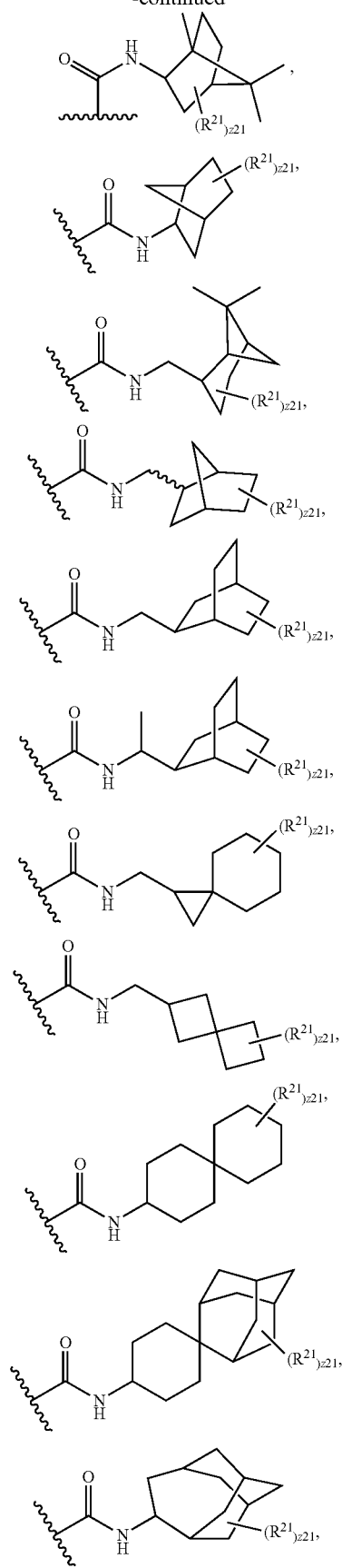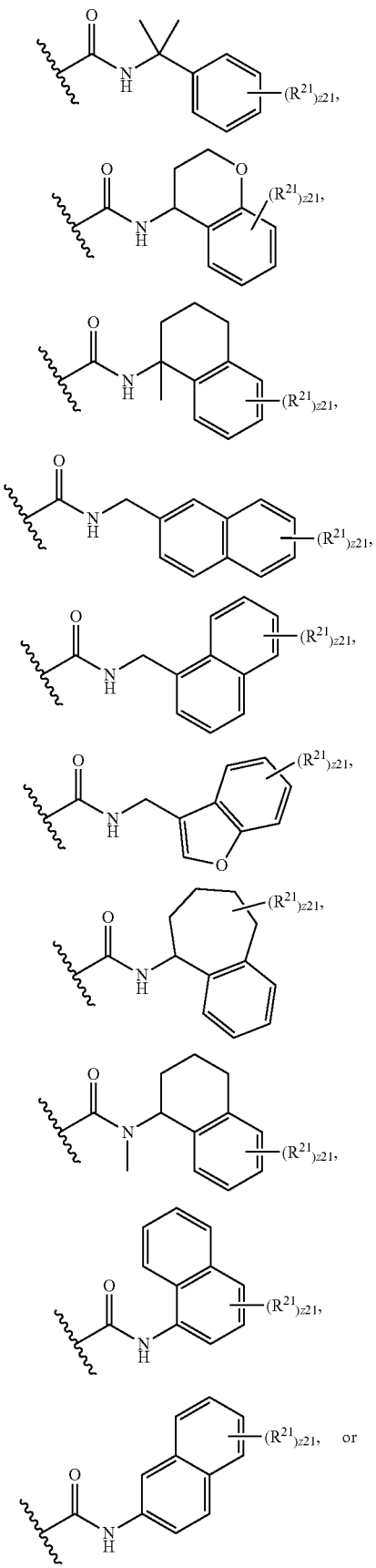

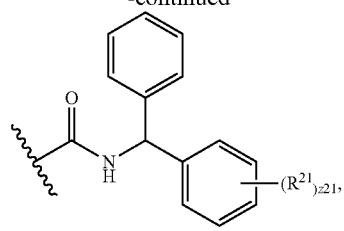
wherein z21 is an integer from 0 to 5.
Embodiment 62. The method of one of embodiments 54 and 56, wherein
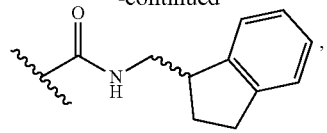 is
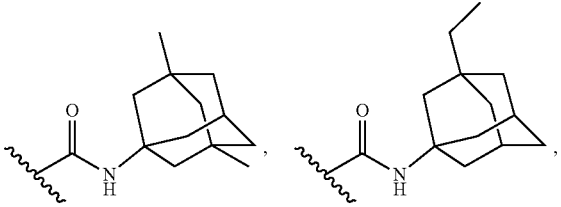
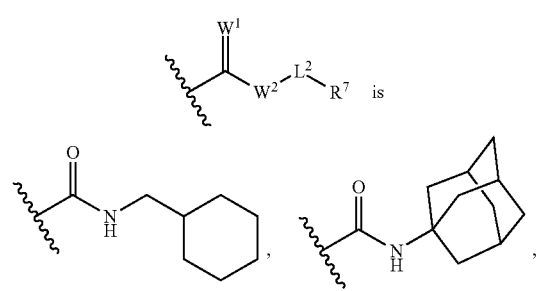
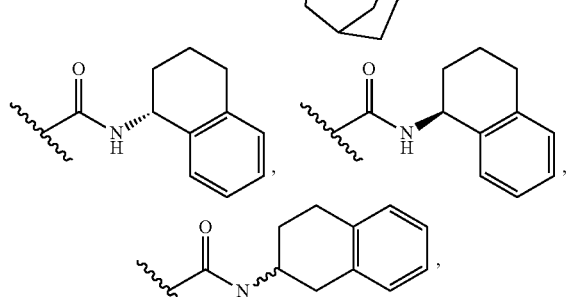
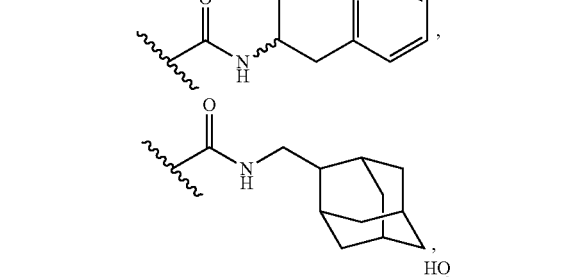
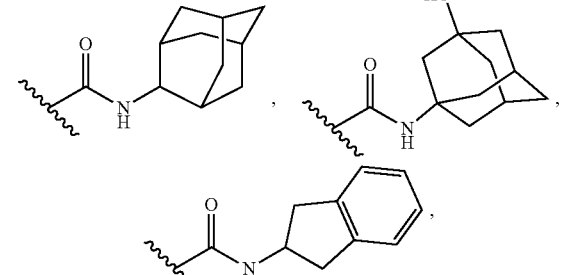
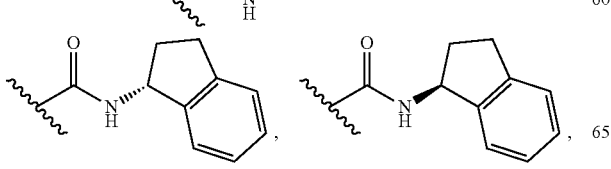
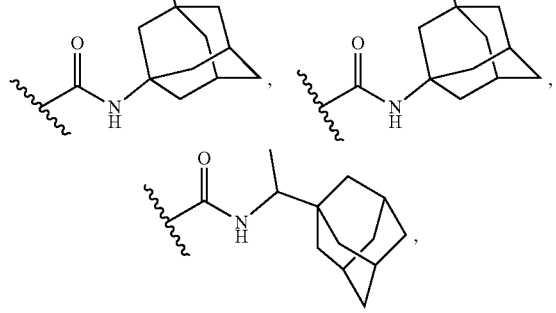
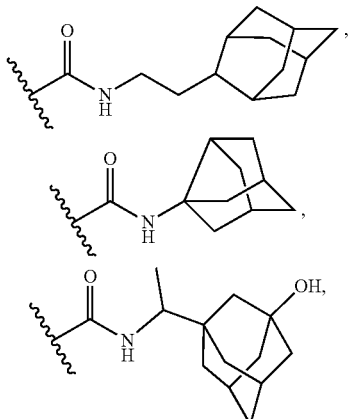
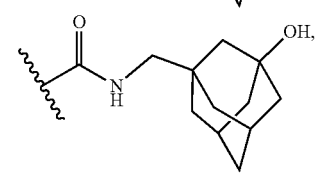
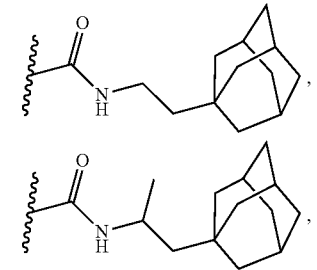
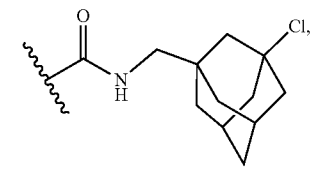

-continued

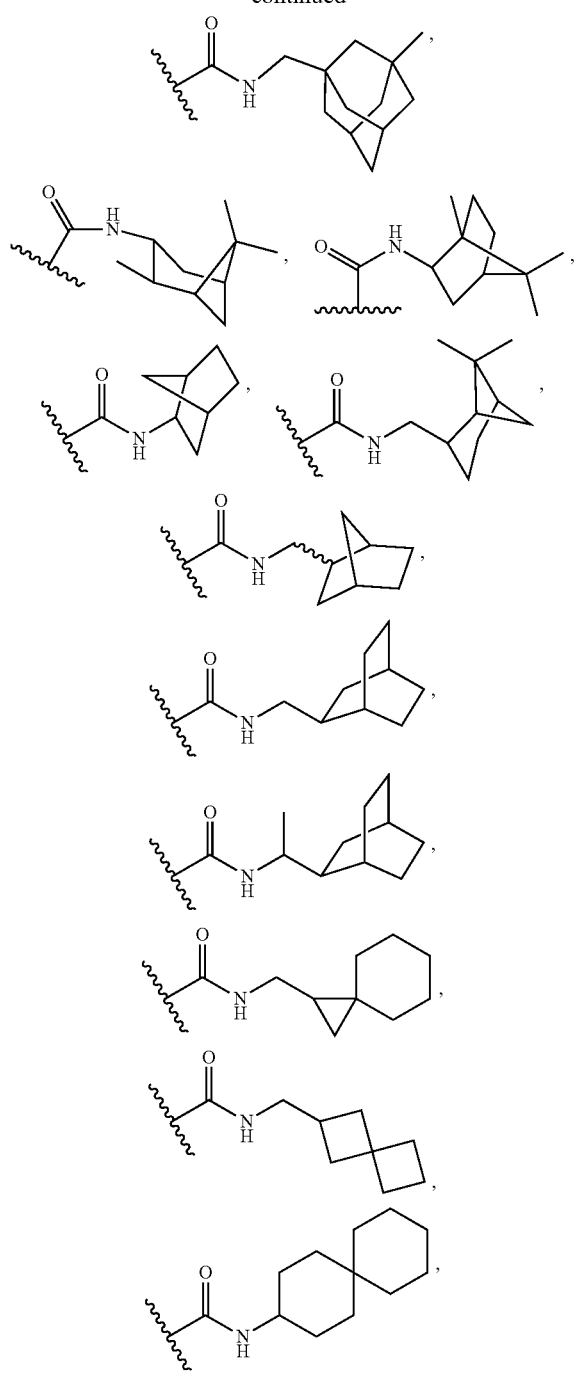

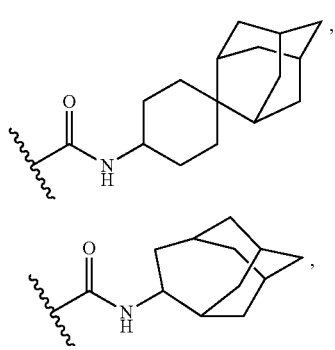

-continued

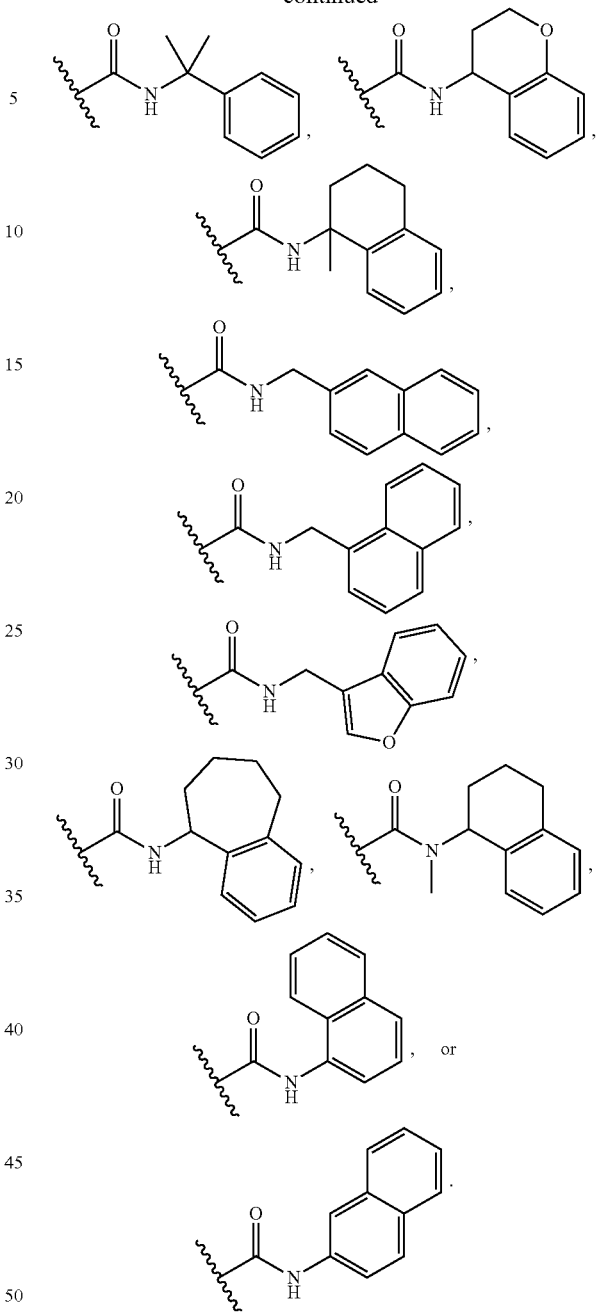

Embodiment 63. The method of one of embodiments 54 to 56, wherein Ring A is a bicyclic $C_9$-$C_{10}$ aryl or bicyclic 8 to 10 membered heteroaryl.

EXAMPLES

Inhibitors of Integrin $\alpha_2\beta_1$ to Mitigate Smooth Muscle Contraction in Asthma. Integrin $\alpha_2\beta_1$ plays an important role in mediating adhesion of airway smooth muscle cells to collagen, which is increased in the airway wall of patients with asthma. We also found that blockade of this integrin inhibits cytokine-enhanced force generation in mouse tracheal rings. Currently available inhibitors of integrin $\alpha_2\beta_1$ are limited by poor cell permeability and short in vivo half-life. Described herein is the development of $\alpha_2\beta_1$ inhibitors. Efforts will also focus on inhibitors optimized for oral or aerosol delivery. Such a drug could be used either alone or in conjunction with other currently available therapies to enhance smooth muscle relaxation in patients suffering from severe persistent asthma. Such an approach has the potential to benefit the more than four million patients with severe asthma and persistent symptoms despite maximal medical therapy and would be an important addition to the otherwise limited options for smooth-muscle targeted therapy in acute exacerbations of asthma.

Described herein is research focused on therapeutically leveraging an independently regulated alternate pathway used by smooth muscle cells to transmit the tension generated by an individual cell to the surrounding tissue via transmembrane integrins (10), which are bound intracellularly to focal adhesion complexes and extracellularly to matrix proteins (11, 12). Previous work from our laboratory has shown that mice lacking the $\alpha_v\beta_6$ integrin are protected from airway hyperreactivity, and that this effect is mediated in part by the effect of TGF-$\beta$ on the suppression of mouse mast cell protease-4 (mMCP-4) (13). Human mast cell chymase is the closest orthologue of mMCP-4, and has been suggested to be protective against asthma severity in humans (14). Our lab has shown that chymase protects against IL-13 enhanced contraction, and does so without modulating the classical actin-myosin contractile apparatus. Rather, chymase cleaves the extracellular matrix protein fibronectin to impair tension transmission. Integrin $\alpha_5\beta_1$ is the primary contributor to fibronectin-mediated adhesion, and blockade of $\alpha_5\beta_1$ not only recapitulates the protective effects of chymase, but acts synergistically with existing bronchodilators to enhance relaxation of pre-contracted airways (15).

In addition to fibronectin, collagen is a well-established extracellular matrix protein that is upregulated in the asthmatic airway. Of the canonical collagen binding integrins ($\alpha_1\beta_1$, $\alpha_2\beta_1$, $\alpha_{10}\beta_1$, and $\alpha_{11}\beta_1$), we found that $\alpha_2\beta_1$ is highly expressed by human airway smooth muscle cells. In preliminary studies that form the basis for this proposal, we have found that blockade of integrin $\alpha_2\beta_1$ inhibits adhesion to collagen, and is protective against the development of airway hyperresponsiveness ex vivo and in vivo. Additionally, it enhances isoproterenol-induced relaxation, establishing its efficacy as an important adjunctive agent to aid in smooth muscle relaxation. Of note, integrin $\alpha_2\beta_1$ deficient mice have no hemostatic defects, and human deficiencies of integrin $\alpha_2\beta_1$ result in only a mild bleeding diathesis. In vitro, inhibition of $\alpha_2\beta_1$ has also been described to result in decreased thrombus formation only on type I collagen, suggesting that this integrin is only a secondary mediator of microvascular thrombosis. We anticipate that blockade of this integrin will not result in significant vascular side effects. Targeting cell-matrix interactions via blockade of integrin $\alpha_2\beta_1$ to impair tension transmission is a novel therapeutic strategy for bronchoconstriction. Currently available inhibitors of integrin $\alpha_2\beta_1$ are limited by poor cell permeability and short in vivo half-life, and there is room for development of novel inhibitors that could be used for oral or inhaled therapy, either alone or as an adjunctive agent, with the goal of reducing the need for other asthmatic medications that carry more significant side effects (e.g. corticosteroids).

The contribution of integrin-mediated matrix associations to smooth muscle force generation in asthma is a novel idea. This therapeutic strategy was validated with blockade of integrin $\alpha_5\beta_1$ association with fibronectin, with measurable decreases in airway contraction in both ex vivo and in vivo models of disease. Based on the preliminary data that blockade of integrin $\alpha_2\beta_1$ protects against airway contraction in both in vivo and ex vivo models of disease, and the pharmacologic limitations of currently available inhibitors, described herein are efforts to design and synthesize novel small molecule inhibitors of integrin $\alpha_2\beta_1$ with improved pharmacokinetic and pharmacodynamics properties and validate their therapeutic efficacy in a mouse model of asthma.

Described herein is the synthesis of candidate compounds, followed by a combination of cell-based screening, ex vivo contraction assays, PK assessments, and in vivo responses to allergen sensitization and challenge to identify a lead compound that is a potent and specific inhibitor of integrin $\alpha_2\beta_1$. This compound will be designed with the goal of being used via oral or inhalational routes, either alone or in combination with other currently available bronchodilator therapy, to reduce force transmission by airway smooth muscle to relieve pathologic airway narrowing.

Disruption of cell tethering to the matrix via selective integrin blockade has functional consequences on force generation in smooth muscle. We showed that inhibition of integrin $\alpha 5\beta 1$, the major fibronectin receptor on airway smooth muscle, not only inhibits IL-13-mediated enhanced force generation by mouse tracheal and human bronchial rings, but also inhibits airway hyperresponsiveness in a mouse model of asthma (FIG. 1A). Furthermore, targeting integrin-mediated cell tethering (and consequently force transmission) results in additive relaxation responses to currently available bronchodilator therapy (FIG. 1B) (15).

Figure 2:
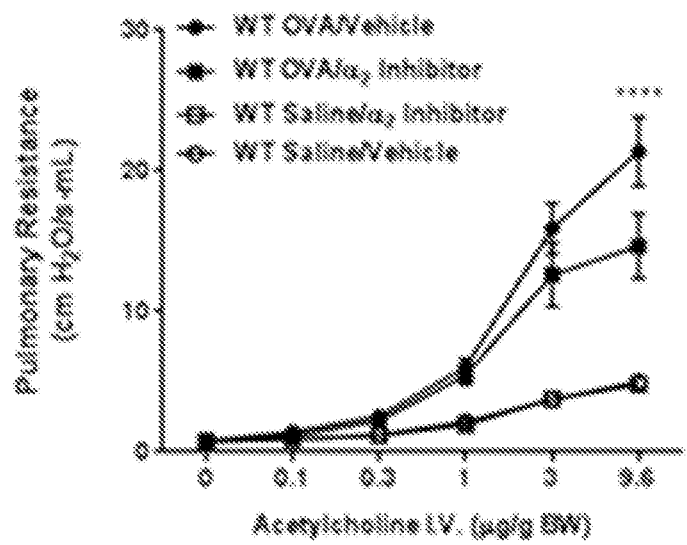
FIG. 2: Intraperitoneal delivery of an inhibitor of integrin α2β1 (C15) to ovalbumin sensitized and challenged mice protects against airway hyperresponsiveness in vivo (A, upper). Cell adhesion assay of integrin α2β1 (C15) inhibitor. (B, lower).
Figure 2:
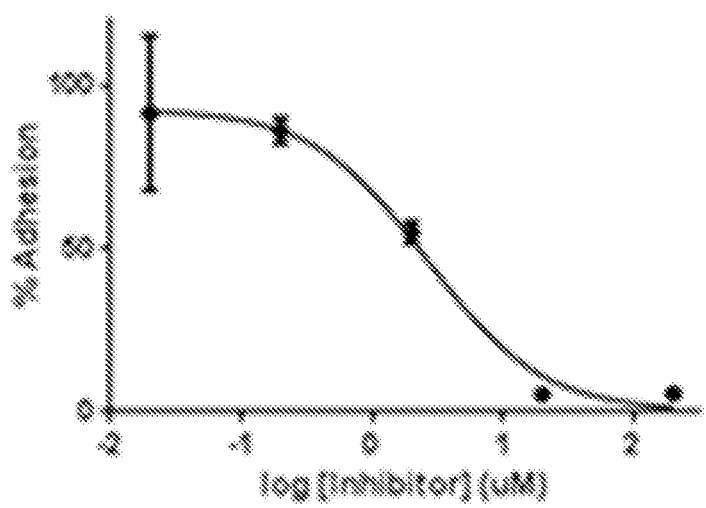
Figure 3:
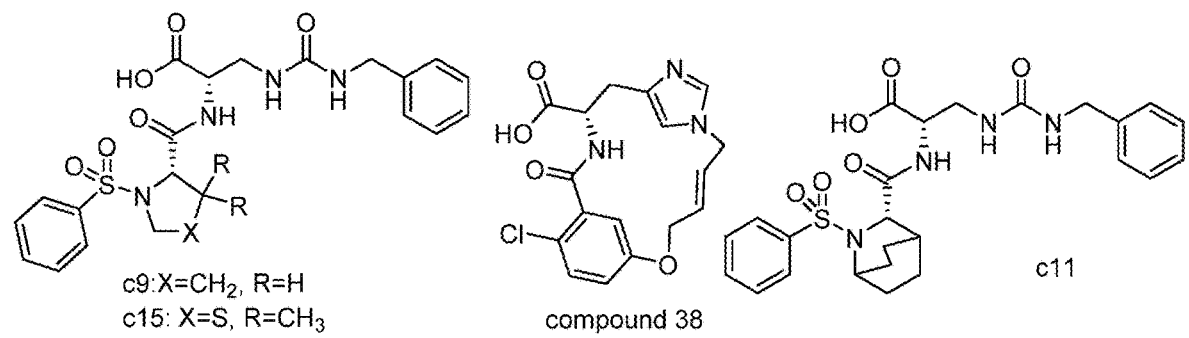
FIG. 3. (top) Structures of known integrin inhibitors. The common amidocarboxylic acid is shown. (bottom) Ligand interaction diagram of C15 with the modelled integrin α2β1. Key interactions include metal-carboxylate interaction between magnesium and the compound and backbone hydrogen bonding between Leu225 and the compound.
Figure 3:
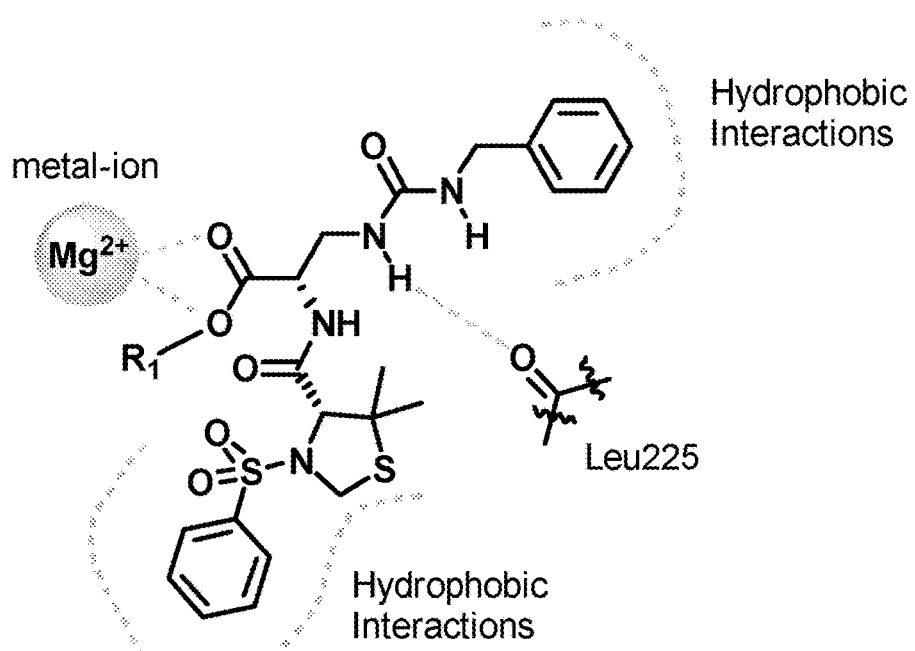
Figure 4:
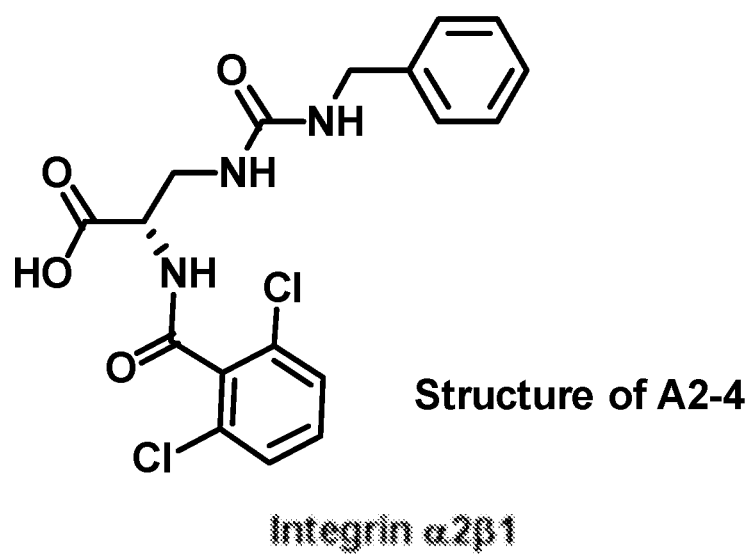
FIG. 4. Structure of A2-4 (novel compound) and cell adhesion assay data.
Figure 4:
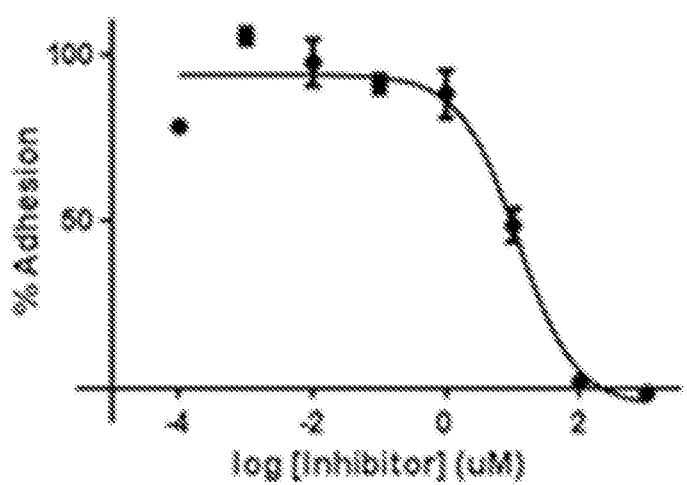

Collagen is a matrix protein that is upregulated in the asthmatic airway, so we reasoned that integrins participating in collagen-mediated adhesion may also play a role in tension transmission. We performed a qRT-PCR screen to identify integrins present in human airway smooth muscle. Of the canonical collagen binding integrins ($\alpha_1\beta_1$, $\alpha_2\beta_1$, $\alpha_{10}\beta_1$, and $\alpha_{11}\beta_1$), integrin $\alpha_2\beta_1$ is highly expressed in airway smooth muscle. Blockade of integrin $\alpha_2\alpha_1$ inhibits adhesion to collagen in vitro (FIG. 2A) and also protects against IL-13 enhanced contraction ex vivo (FIG. 2B). We therefore investigated the effect of inhibition of integrin $\alpha_2\beta_1$ in vivo and found that mice were protected from the development of airway hyperresponsiveness in a mouse model of asthma (FIG. 3A), using our inhibitor, C15, which has an in vitro IC50 of ~2 $\mu$M (FIG. 3B). Currently available inhibitors of integrin $\alpha_2\beta_1$ are limited by poor cell permeability, only modest potency, and short half-life, thus laying the groundwork for the experiments that follow.

The first small molecule inhibitors of integrin $\alpha_2\beta_1$, including compound 9 (C9) (16) (FIG. 3) C9 showed a nanomolar potency (IC$_{50}$=15 nM) in platelet adhesion assays and good selectivity over integrins $\alpha_4\beta_1$ and $\alpha_5\beta_1$. Subsequently, others reported the cyclic peptide compound 38 (17) as another integrin $\alpha_2\beta_1$ inhibitor, which also contains the aminocarboxylic acid with C9. Unfortunately, compound 38 suffered from low cellular permeability. We also discovered that modification of the N-benzenesulfonyl thiazolidine moiety in C$_9$ and C15 (18) greatly improved in vivo efficacy in a mouse model of renal fibrosis (19). However, C15 was administered by intraperitoneal (IP) injection.

Figure 5:
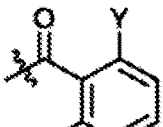
FIG. 5. Select Compounds.
Figure 6:
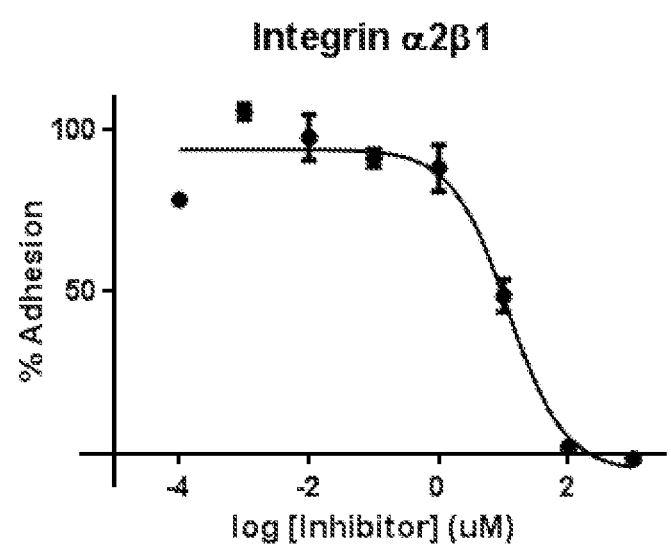
FIG. 6. Cell adhesion assay data using airway smooth muscle cells on collagen with compound shown.
Figure 6:
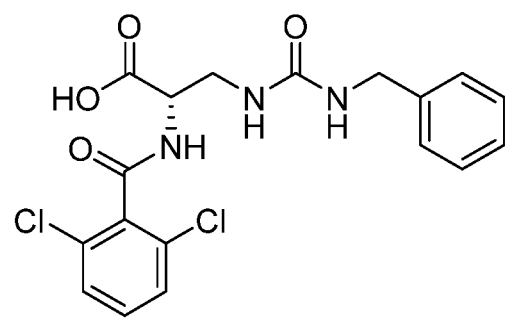

We are developing a second generation of integrin $\alpha_2\beta_1$ inhibitors with improved drug-like properties. We are modifying C15 to increase oral availability at multiple sites (FIG. 5). The phenylsulfonyl-thiazolidine derivative adds both peptidic character and increases both the polarity and the MW (the heavy atom count of this moiety is 19 in c15) of the inhibitor. Through extensive SARs of other integrin $\beta_1$ inhibitors (20, 21, 22) we found that this group can be substituted by 2,6-disubstituted phenylamide, certain alkyl amides or substituted pyrimidines. Indeed, we recently synthesized an analogue A2-4 with a much smaller $R_1$ group (half the heavy atom count of $R_1$ in c15) which was only 2-fold less potent in a cell adhesion assay.

Thus, a focused effort at optimizing the $R_1$ substituent will be successful. These moieties could be easily installed on the common intermediate to facilitate compound synthesis. Improved potency and lipophilicity will be also pursued by replacing the urea ($R_2$) with diverse heterocycles, and adding substituents to the terminal aryl ring. Virtual docking will be used to interpret SAR and to prioritize molecules for synthesis and prodrugs of the acid are being explored.

i. Synthesis and Characterization Data of the Compounds

LC-MS condition A: AB Sciex 3200 LC/MS/MS with Shimadzu HPLC System, Column: ACEUltraCore 2.5 SuperC18 (2.1×50 mm) buffer A: 0.1% TFA in $H_2O$, buffer B: 0.1% TFA in acetonitrile-$H_2O$ (99:1). Flow rate: 0.4 mL/min, gradient 5 to 100% B over 3 min.

LC-MS condition B: AB Sciex 3200 LC/MS/MS with Shimadzu HPLC System, Column: ACEUltraCore 2.5 SuperC18 (2.1×50 mm) buffer A: 0.1% TFA in $H_2O$, buffer B: 0.1% TFA in 2-propanol-acetonitrile-$H_2O$ (60:30:10). Flow rate: 0.6 mL/min, gradient 5 to 100% B over 2 min LC-MS condition C: AB Sciex 3200 LC/MS/MS with Shimadzu HPLC System, Column: Agilent poroshell 120, EC-$C_8$ (2.1×50 mm) buffer A: 0.1% TFA in $H_2O$, buffer B: 0.1% TFA in acetonitrile. Flow rate: 0.4 mL/min, gradient 0 to 100% B over 3 min.

LC-MS condition D: AB Sciex 3200 LC/MS/MS with Shimadzu HPLC System, Column: ACEUltraCore 2.5 SuperC18 (2.1×50 mm) buffer A: 0.1% TFA in $H_2O$, buffer B: 0.1% TFA in 2-propanol-acetonitrile-$H_2O$ (60:30:10). Flow rate: 0.4 mL/min, gradient 5 to 100% B over 2 min Analytical HPLC condition A: Column Jupiter, 5 μm, C4, 300 Å, 4.6 mm i.d.×250 mm, buffer A: 0.1% TFA in $H_2O$, buffer B: 0.1% TFA in acetonitrile-$H_2O$ (99:1). Flow rate: 1 mL/min, a gradient of 5-100% B over 40 min

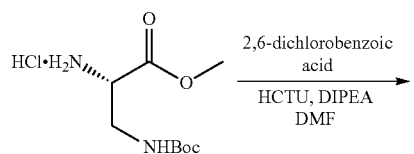

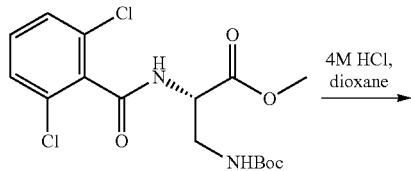

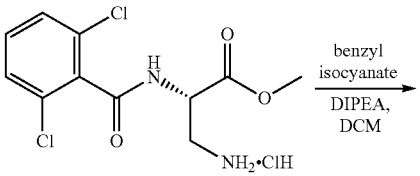

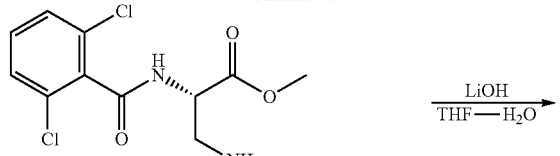

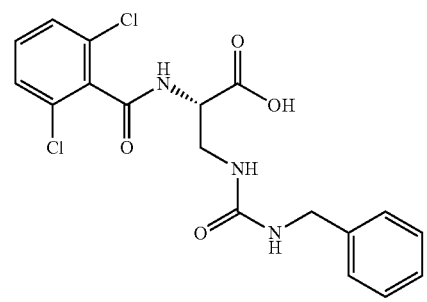

To a solution of Boc-DAP-OMe (1 mmol) in DMF (3 mL) was added DIPEA (4 eq.) followed by 2,6-dichlorobenzoic acid (1.3 eq.) and HCTU (0.95 eq). at rt. The mixture was stirred for 2 h and diluted with ethyl acetate. The organic layer was washed with 1M hydrochloric acid, Sat. NaHCO3, and brine successively and concentrated under vacuo. The crude residue was purified by flash column chromatography (DCM:MeOH=100:0 to 95:5) to yield the product (240 mg). MS (ESI, positive)=413.4 (MNa$^+$). The product was treated with 4M HCl in dioxane (3 mL) for 2 h at rt and concentrated. The crude residue was triturated with diethyl ether to yield the amine (130 mg). The amine (0.2 mmol) was dissolved inn DCM (3 mL) and DIPEA (5 eq.) was added at rt. To the mixture was added benzyl isocyanate (5 eq.). The mixture was stirred overnight and concentrated. The crude mixture was purified by flash column chromatography (DCM:MeOH=100:0 to 90:10). The ester was dissolved in THF:$H_2O$ (4:1, 5 mL) and treated with 1M LiOH (0.5 mL) for 2 h. The mixture was acidified to pH=2 and concentrated and purified RP-HPLC. MS (ESI, positive)=410.5 (MH$^+$).

(S)-3-(3-benzylureido)-2-(2,6-dichlorobenzamido)propanoic acid (A2-4): $^1$H NMR (300 MHz, CDCl$_3$+CD$_3$OD) δ ppm 7.36-7.27 (m, 8H), 4.7 (br s, 1H), 4.32-4.3 (m, 2H), 3.7 (br s, 2H). LC-MS (condition A) m/z=410.5 (MEI$^+$), Retention time=4.93 min.

A2-189

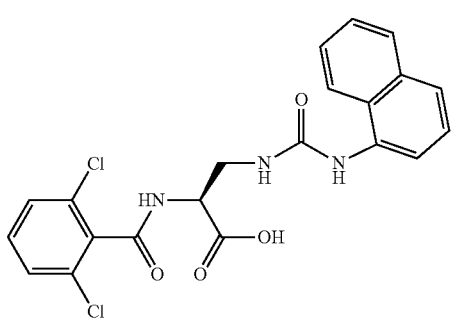

(S)-2-(2,6-dichlorobenzamido)-3-(3-(naphthalen-1-yl) ureido)propanoic acid (A2-189) Prepared from 1-naphthylisocyanate according to the procedure for A2-4. $^1$H NMR (300 MHz, CDCl$_3$+CD$_3$OD) δ ppm 7.99 (d, J=7.5 Hz, 1H), 7.84 (d, J=7.8 Hz, 1H), 7.72-7.63 (m, 2H), 7.54-7.25 (m, 6H), 4.74 (br s, 1H), 3.90-3.70 (m, 2H). LC-MS (condition B) m/z=446.4 (MH$^+$), Retention time=2.00 min.

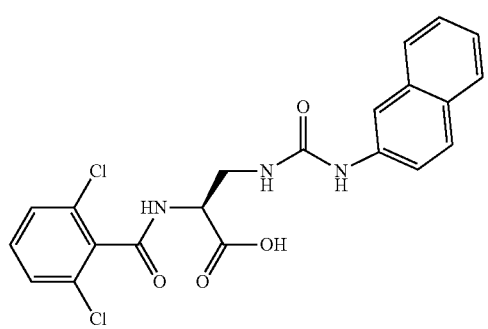

A2-190

(S)-2-(2,6-dichlorobenzamido)-3-(3-(naphthalen-2-yl) ureido)propanoic acid (A2-190) Prepared from 2-naphthylisocyanate according to the procedure for A2-4. $^1$H NMR (300 MHz, CDCl$_3$+CD$_3$OD) δ ppm 7.90 (br s, 1H), 7.75-7.68 (m, 3H), 7.44-7.20 (m, 6H), 4.81-4.77 (m, 1H), 3.89-3.71 (m, 2H). LC-MS (condition B) m/z=446.4 (MH$^+$), Retention time=2.00 min.

Synthesis of A2-26

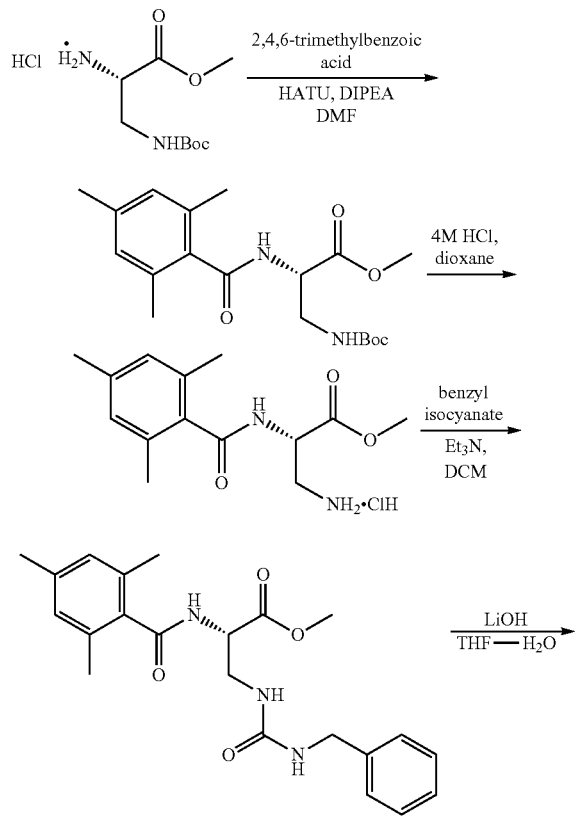

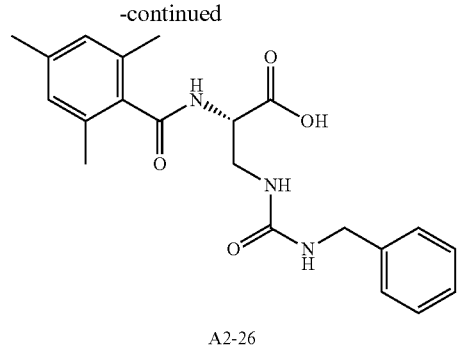

A2-26

To a solution of Boc-DAP-OMe (2 mmol) in DMF (8 mL) was added DIPEA (2.3 eq.) followed by 2,6-dichlorobenzoic acid (1 eq) and HATU (0.95 eq). at rt. The mixture was stirred for 2 h and diluted with ethyl acetate. The organic layer was washed with 1M hydrochloric acid, Sat. NaHCO$_3$, and brine successively and concentrated under vacuo. The crude product was treated with 4M HCl in dioxane (8 mL) for 3 h at rt and concentrated. The crude residue was triturated with diethyl ether and the solid was isolated and dried in vacuo. To the crude amine HCl salt (100 mg, 0.3 mmol) was dissolved in DCM (3 mL) and Et$_3$N (5 eq) was added at rt. To the mixture was added benzyl isocyanate (2 eq). The mixture was stirred overnight and the organic layer was washed with 0.5 M HCl followed by sat. NaHCO$_3$ solution. The mixture was dried over Na$_2$SO$_4$ and concentrated in vacuo. The crude mixture was dissolved in THF: H$_2$O (4:1, 5 mL) and treated with 1M LiOH (0.3 mL) for 2 h. The mixture was acidified to pH=2 and purified by RP-HPLC to provide A2-26.

(S)-3-(3-benzylureido)-2-(2,4,6-trimethylbenzamido)propanoic acid (A2-26): $^1$H NMR (300 MHz, CDCl$_3$+CD$_3$OD) δ ppm 7.28-7.18 (m, 5H), 6.78 (s, 2H), 4.63-4.59 (m, 1H), 4.24 (s, 2H), 3.64-3.6 (m, 2H). LC-MS (condition A) m/z=384.7 (MW), Retention time=5.27 min

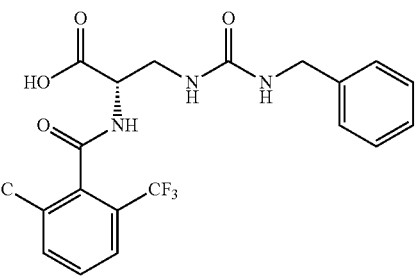

A2-27

(S)-3-(3-benzylureido)-2-(2,6-bis(trifluoromethyl)benzamido)propanoic acid (A2-27): Prepared from 2,6-ditrfluoromethylbenzoic acid according to the procedure for A2-26. $^1$H NMR (300 MHz, CDCl$_3$+CD$_3$OD) δ ppm 7.94-7.91 (d, J=8.1 Hz, 2H), 7.69 (t, J=8.4 Hz, 1H), 7.33-7.26 (m, 5H), 4.59 (t, J=4.2 Hz, 1H), 4.24 (s, 2H), 3.76-3.55 (m, 2H). LC-MS (condition A) m/z=478.5 (MH$^+$), Retention time=5.25 min

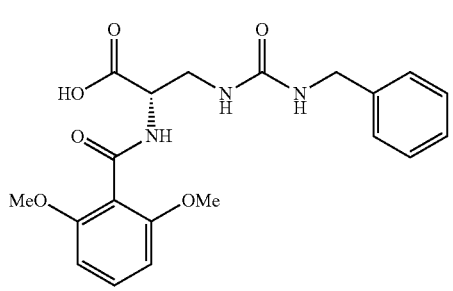

A2-28

(S)-3-(3-benzylureido)-2-(2,6-dimethoxybenzamido)propanoic acid (A2-28): Prepared from 2,6-dimethoxybenzoic acid according to the procedure for A2-26. $^1$H NMR (300 MHz, CDCl$_3$+CD$_3$OD) δ ppm 7.32-7.22 (m, 6H), 6.56 (d, J=8.4 Hz, 2H), 4.67 (t, J=4.5 Hz, 1H), 4.32 (s, 2H), 3.77 (s, 6H), 3.76-3.6 (m, 1H), 3.58-3.52 (m, 1H). LC-MS (condition A) m/z=402.5 (MH$^+$), Retention time=4.69 min

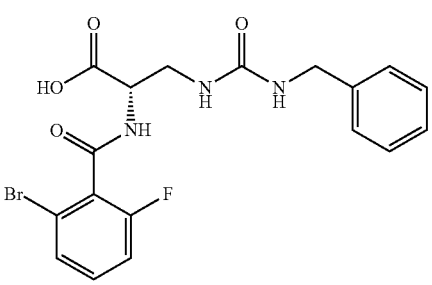

A2-36

(S)-3-(3-benzylureido)-2-(2-bromo-6-fluorobenzamido)propanoic acid (A2-36): Prepared from 2-bromo-6-fluorobenzoic acid according to the procedure for A2-26. $^1$H NMR (300 MHz, CDCl$_3$+CD$_3$OD) δ ppm 7.37 (d, J=8.1 Hz, 1H), 7.30-7.18 (m, 6H), 7.07 (t, J=8.4 Hz, 1H), 4.66 (t, J=5.1 Hz, 1H), 4.30 (s, 2H), 3.72-3.6 (m, 2H). LC-MS (condition A) m/z=438.4 (MH$^+$), Retention time=4.92 min

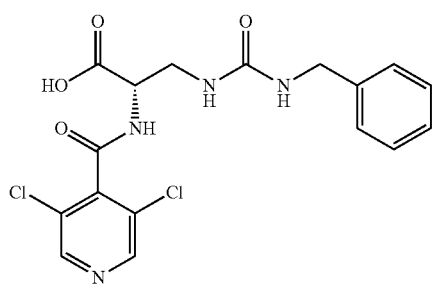

A2-29

(S)-3-(3-benzylureido)-2-(3,5-dichloroisonicotinamido)propanoic acid (A2-29) Prepared from 3,5-dichloropyridine-4-carboxylic acid according to the procedure for A2-26. $^1$H NMR (300 MHz, CDCl$_3$+CD$_3$OD) δ ppm 8.52 (s, 2H), 7.30-7.22 (m, 5H), 4.71 (t, J=6 Hz, 1H), 4.36-4.22 (m, 2H), 3.72-3.66 (m, 2H). LC-MS (condition A) m/z=411.6 (MH$^+$), Retention time=4.60 min

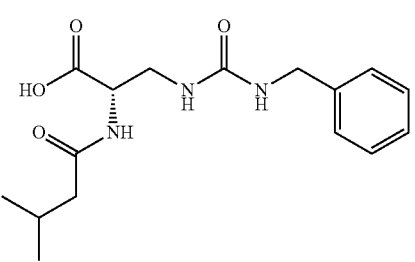

A2-37

(S)-3-(3-benzylureido)-2-(3-methylbutanamido)propanoic acid (A2-37): Prepared from 3-methylbutanoic acid according to the procedure for A2-26. $^1$H NMR (300 MHz, CDCl$_3$+CD$_3$OD) δ ppm 7.33-7.2 (m, 5H), 4.46-4.43 (m, 1H), 4.32 (s, 2H), 3.57 (d, J=5.7 Hz, 2H), 2.11-2.07 (m, 3H), 0.94-0.92 (s, 6H). LC-MS (condition A) m/z=322.7 (MH$^+$), Retention time=4.65 min

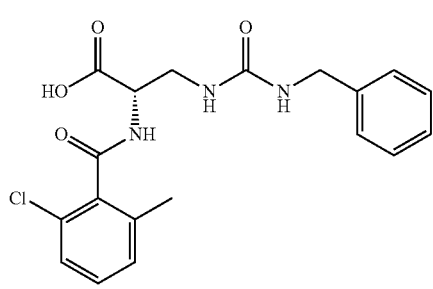

A2-35

(S)-3-(3-benzylureido)-2-(2-chloro-6-methylbenzamido)propanoic acid (A2-35) Prepared from 2-chloro-6-methylbenzoic acid according to the procedure for A2-26. $^1$H NMR (300 MHz, CDCl$_3$+CD$_3$OD) δ ppm 7.32-7.15 (m, 7H), 7.09-7.06 (m, 1H), 4.64 (m, 1H), 4.27 (s, 2H), 3.74-3.58 (m, 2H), 2.31 (s, 3H). LC-MS (condition A) m/z=390.5 (MH$^+$), Retention time=5.00 min

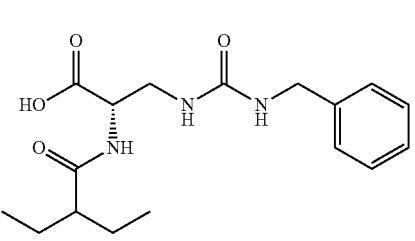

A2-38

(S)-3-(3-benzylureido)-2-(2-ethylbutanamido)propanoic acid (A2-38): Prepared from 2-ethylbutanoic acid according to the procedure for A2-26. $^1$H NMR (300 MHz, CDCl$_3$+CD$_3$OD) δ ppm 7.3-7.18 (m, 5H), 4.45-4.40 (m, 1H), 4.38-4.25 (m, 2H), 3.57-3.52 (m, 2H), 2.00-1.98 (m, 1H), 1.60-1.43 (m, 4H), 11-2.07 (m, 3H), 0.91-0.80 (m, 6H). LC-MS (condition A) m/z=336.5 (MH$^+$), Retention time=4.87 min

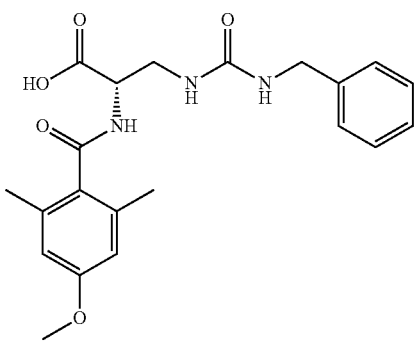

(S)-3-(3-benzylureido)-2-(4-methoxy-2,6-dimethylbenzamido)propanoic acid (A2-60): Prepared from 4-methoxy-2,4-dimethylbenzoic acid according to the procedure for A2-26. $^1$H NMR (300 MHz, CDCl$_3$+CD$_3$OD) δ ppm 7.30-7.18 (m, 5H), 6.51 (s, 2H), 4.62-4.59 (m, 1H), 4.25 (s, 2H), 3.76 (s, 3H), 3.64-3.61 (m, 2H), 2.25 (s, 6H). LC-MS (condition A) m/z=400.6 (MH$^+$), Retention time=5.00 min

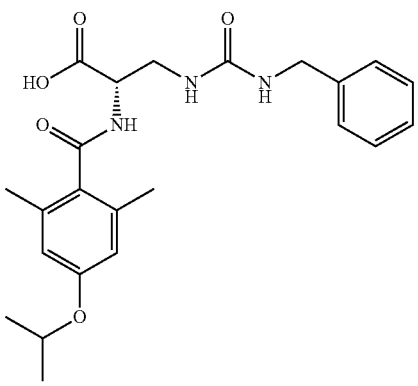

(S)-3-(3-benzylureido)-2-(4-isopropoxy-2,6-dimethylbenzamido)propanoic acid (A2-61): Prepared from 4-isopropoxy-2,4-dimethylbenzoic acid according to the procedure for A2-26. $^1$H NMR (300 MHz, CDCl$_3$+CD$_3$OD) δ ppm 7.30-7.18 (m, 5H), 6.52 (s, 2H), 4.64-4.59 (m, 1H), 4.5-4.45 (m, 1H), 4.27 (s, 2H), 3.64-3.62 (m, 2H), 2.25 (s, 6H), 1.30 (d, J=5.7 Hz, 6H). LC-MS (condition A) m/z=428.6 (MH$^{30}$), Retention time=5.53 min.

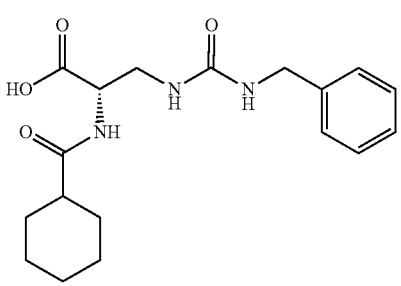

(S)-3-(3-benzylureido)-2-(cyclohexanecarboxamido)propanoic acid (A2-63): Prepared from cyclohexane carboxylic acid according to the procedure for A2-26. $^1$H NMR (300 MHz, CDCl$_3$+CD$_3$OD) δ ppm 7.33-7.22 (m, 5H), 4.38-4.37 (m, 1H), 4.32 (s, 2H), 3.63-3.47 (m, 2H), 2.14 (m, 1H), 1.4-1.2 (m, 5H). LC-MS (condition A) m/z=348.5 (MH$^+$), Retention time=4.97 min.

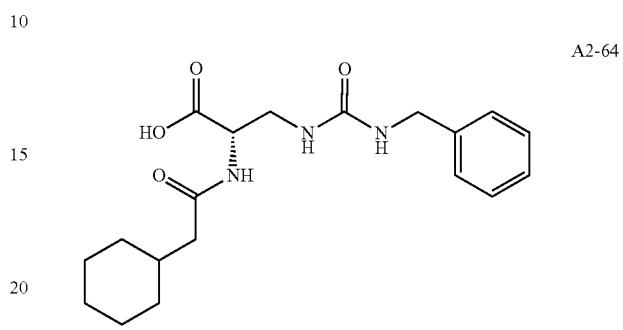

(S)-3-(3-benzylureido)-2-(2-cyclohexylacetamido)propanoic acid (A2-64): Prepared from cyclohexyl acetic acid according to the procedure for A2-26. $^1$H NMR (300 MHz, CDCl$_3$+CD$_3$OD) δ ppm 7.33-7.22 (m, 5H), 4.5-4.37 (m, 3H), 3.62-3.49 (m, 2H), 2.12-2.08 (m, 2H),1.72-1.65 (m, 6H), 1.3-0.8 (m, 5H). LC-MS (condition A) m/z=379.6 (MH$^+$), Retention time=5.62 min.

Synthesis of A2-39

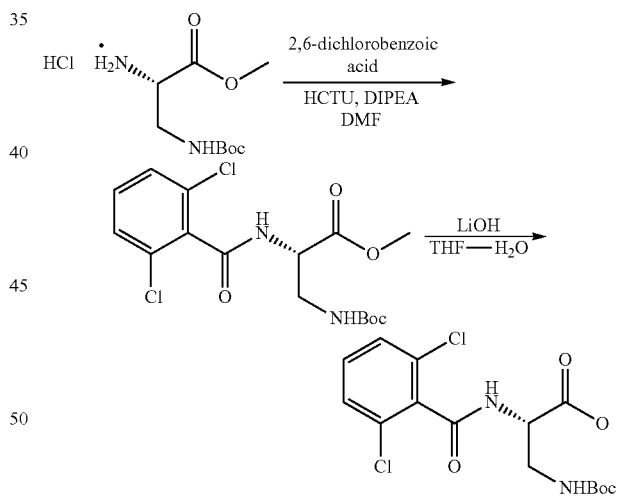

To a solution of Boc-DAP-OMe (0.39 mmol) in DMF (2 mL) was added a solution of DIPEA (4 eq.), 2,6-dichlorobenzoic acid (1.0 eq.) and HCTU (0.95 eq). at rt. The mixture was stirred for 2 h and diluted with ethyl acetate. The organic layer was washed with water and brine successively and dried over Na2SO4. The mixture was concentrated under vacuo and was dissolved in THF-H$_2$O (3:1, 4 mL). LiOH solution (1M, 900 uL) was added and stirred for 2 h. The solution was neutralized by HCl solution to pH=7 and lyophilized. Final product was purified by RP-HPLC to yield the product.

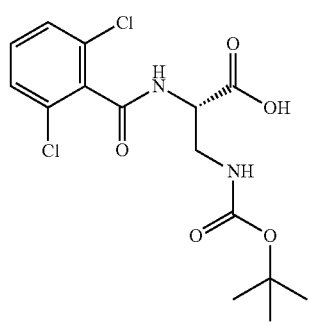

A2-39

(S)-3-((tert-butoxycarbonyl)amino)-2-(2,6-dichlorobenzamido)propanoic acid (A2-39): $^1$H NMR (300 MHz, CDCl$_3$+CD$_3$OD) δ ppm 7.36-7.25 (m, 5H), 4.76 (br s, 1H), 3.72-3.60 (m, 2H), 1.42 (s, 9H). LC-MS (condition A) m/z=377.4 (MH$^+$), Retention time=5.19 min.

Synthesis of A2-70

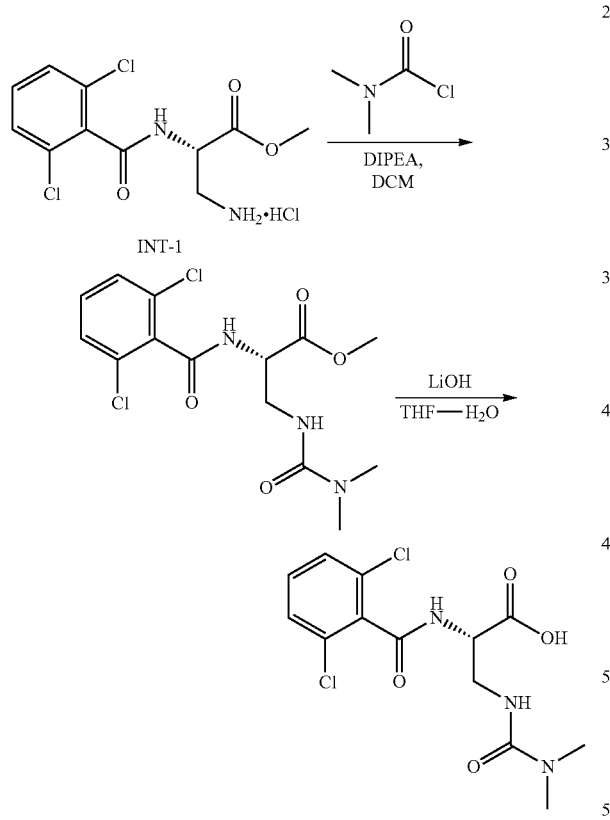

To a solution of INT-1 (0.34 mmol) and DIPEA (3 eq) in DCM (4 mL) was added dimethylcarbamoyl chloride (1.5 eq) at rt and stirred for 2 h. Then additional DIPEA (200 uL) and dimethylcarbamoyl chloride (1.5 eq) was added and stirred overnight. The solution was washed with 1M HCl solution and Sat. NaHCO$_3$ solution successively and concentrated under reduced pressure. The crude mixture was dissolved in THF:H$_2$O (4:1, 5 mL) and treated with 1M LiOH (0.6 mL) for 2 h. The mixture was acidified to pH=2 and purified by RP-HPLC to provide A2-70.

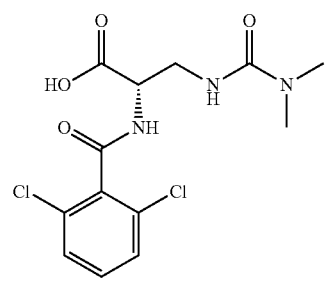

A2-70

(S)-2-(2,6-dichlorobenzamido)-3-(3,3-dimethylureido) propanoic acid (A2-70): $^1$H NMR (300 MHz, CDCl$_3$+CD$_3$OD) δ ppm 7.36-7.25 (m, 3H), 4.73-4.69 (m, 1H), 3.81-3.61 (m, 2H), 2.89 (s, 6H). LC-MS (condition A) m/z=348.3 (MH$^+$), Retention time=4.15 min (S)-2-(2,6-dichlorobenzamido)-3-(3,3-diethylureido)propanoic acid (A2-71): Prepared from diethylcarbamoyl chloride according to the procedure for A2-70. $^1$H NMR (300 MHz, CDCl$_3$+CD$_3$OD) δ ppm 7.36-7.25 (m, 3H), 4.68-4.64 (m, 1H), 3.84-3.61 (m, 2H), 3.29-3.22 (m, 4H), 1.14 (t, J=6.9 Hz, 6H) LC-MS (condition A) m/z=376.3 (MH$^+$), Retention time=4.69 min.

Synthesis of A2-72

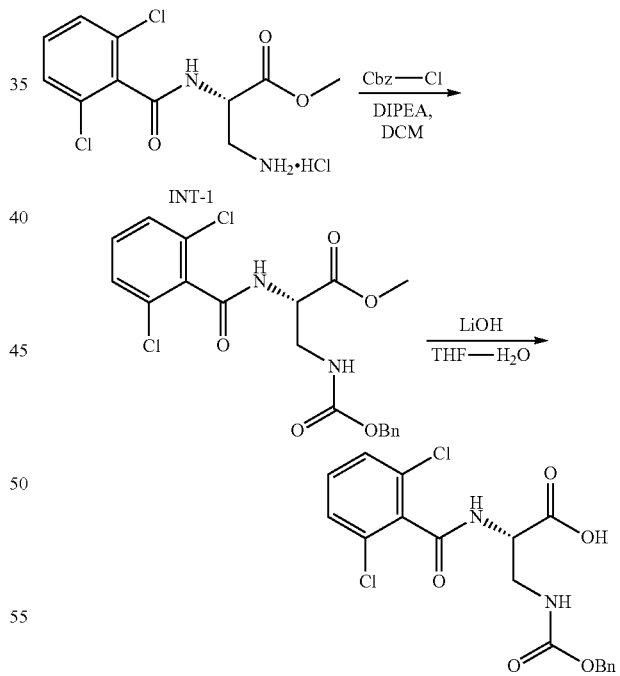

To a solution of INT-1 (0.34 mmol) and DIPEA (3 eq) in DCM (4 mL) was added dimethylcarbamoyl chloride (1.5 eq) at rt and stirred for 2 h. The solution was washed with 1M HCl solution and Sat. NaHCO$_3$ solution successively and concentrated under reduced pressure. The crude mixture was dissolved in THF:H$_2$O (4:1, 5 mL) and treated with 1M LiOH (0.6 mL) for 2 h. The mixture was acidified to pH=2 and purified by RP-HPLC to provide A2-72.

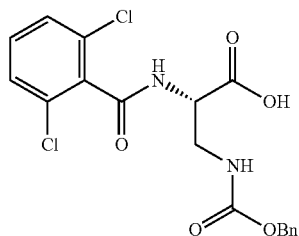

A2-72

(S)-3-(((benzyloxy)carbonyl)amino)-2-(2,6-dichlorobenzamido)propanoic acid (A2-72): $^1$H NMR (300 MHz, CDCl$_3$+CD$_3$OD) δ ppm 7.36-7.25 (m, 8H), 5.12-5.02 (m, 2H), 4.83-4.81 (m, 1H), 3.75-3.73 (m, 2H), 3.29-3.22 (m, 4H), 1.14 (t, J=6.9 Hz, 6H). LC-MS (condition A) m/z=411.4 (MH$^+$), Retention time=5.37 min.

Synthesis of A2-73

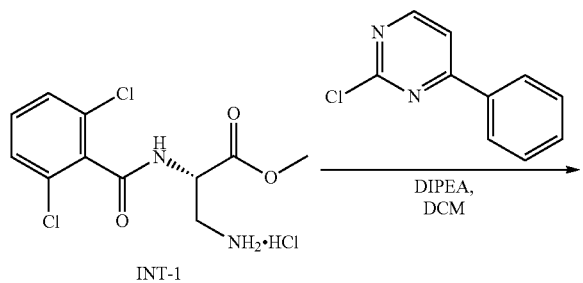

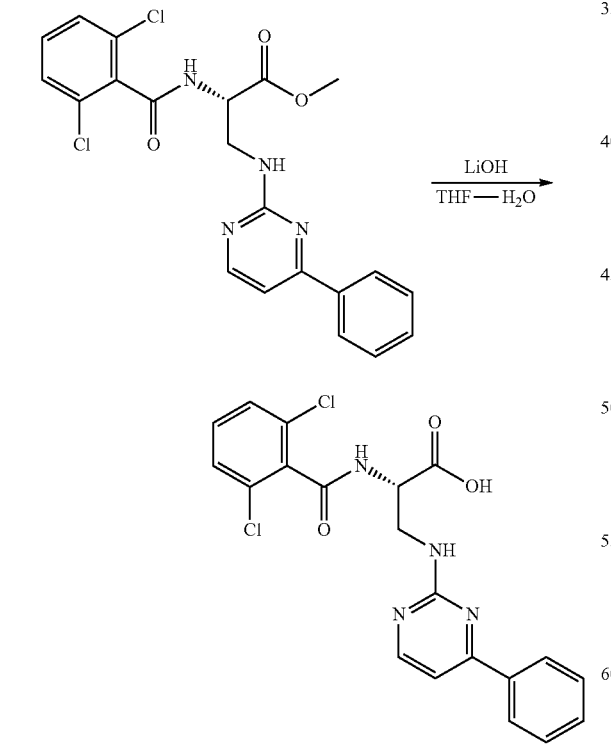

To a solution of INT-1 (0.34 mmol) and DIPEA (3 eq) in DMF (4 mL) was added 2-chloro-4-phenylpyrimidine (1.5 eq) at rt and stirred for 2 h at 85° C. After cool to rt, another portion of DIPEA (3 eq) and 2-chloro-4-phenylpyrimidine (1.5 eq) were added and stirred for 3 h at 85° C. After cooling to rt, the reaction mixture was diluted with ethyl acetate and washed with 1M HCl solution and Sat. NaHCO3 solution successively and concentrated under reduced pressure. The crude mixture was dissolved in THF:H$_2$O (4:1, 5 mL) and treated with 1M LiOH (0.6 mL) for 2 h. The mixture was acidified to pH=2 and purified by RP-HPLC to provide A2-73.

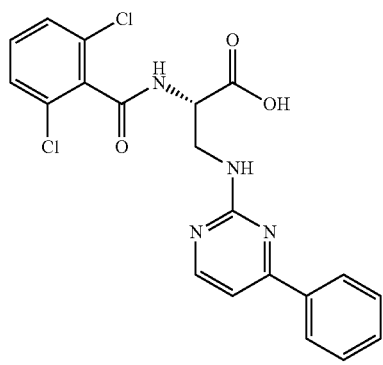 [SMILES: O=C(N[C@@H](CNc1nccc(-c2ccccc2)n1)C(=O)O)c1c(Cl)cccc1Cl]

(S)-2-(2,6-dichlorobenzamido)-3-((4-phenylpyrimidin-2-yl)amino)propanoic acid (A2-73): $^1$H NMR (300 MHz, CDCl$_3$+CD$_3$OD) δ ppm 8.22-8.15 (m, 3H), 7.64-7.52 (m, 3H), 7.3-7.2 (m, 4H), 5.2-5.1 (m, 1H), 4.4-4.3 (m, 1H), 4.1-4.05 (m, 1H). LC-MS (condition A) m/z=431.3 (MH$^+$), Retention time=5.28 min.

Synthesis A2-87

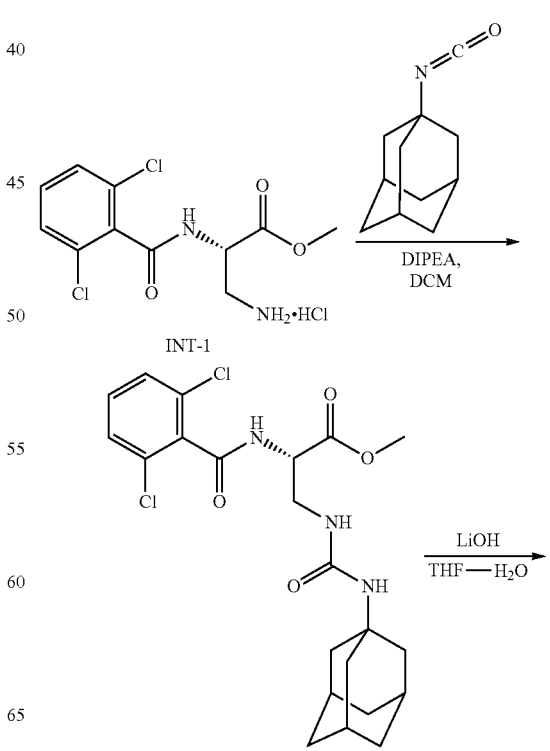

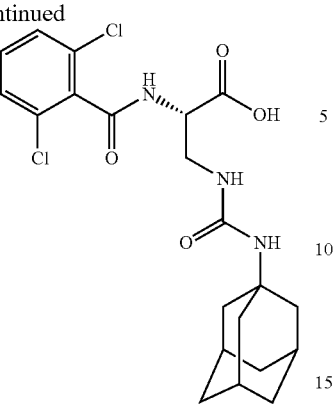

To a solution of INT-1 (0.34 mmol) and DIPEA (3 eq) in DMF (3 mL) was added amantadine isocyante (1 eq) and stirred overnight at rt. The reaction mixture was diluted with ethyl acetate and washed with 0.5 M HCl solution and Sat. NaHCO₃ solution successively and concentrated under reduced pressure. The crude mixture was purified by column chromatography (0% to 10% MeOH in DCM)(ESI-MS: 468.6 (MH+)). The ester was dissolved in THF:H₂O (4:1, 4 mL) and treated with 1M LiOH (0.5 mL) for 2 h. The mixture was acidified to pH=2 and purified by RP-HPLC to provide A2-87.

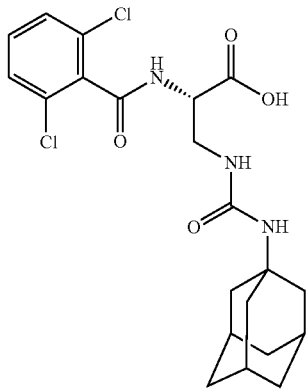

A2-87

(S)-3-(((3R,5R,7R)-adamantan-1-yl)amino)-2-(2,6-dichlorobenzamido)propanoic acid (A2-87): ¹H NMR (300 MHz, CDCl₃+CD₃OD) δ 8.22-8.15 (m, 3H), 7.64-7.52 (m, 3H), 7.3-7.2 (m, 4H), 5.2-5.1 (m, 1H), 4.4-4.3 (m, 1H), 4.1-4.05 (m, 1H). LC-MS (condition A) m/z=431.3 (MH⁺), Retention time=5.28 min.

Synthesis of A2-83

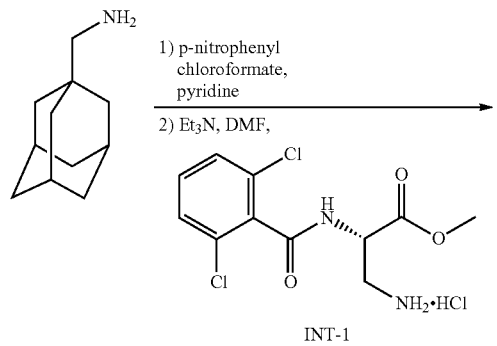

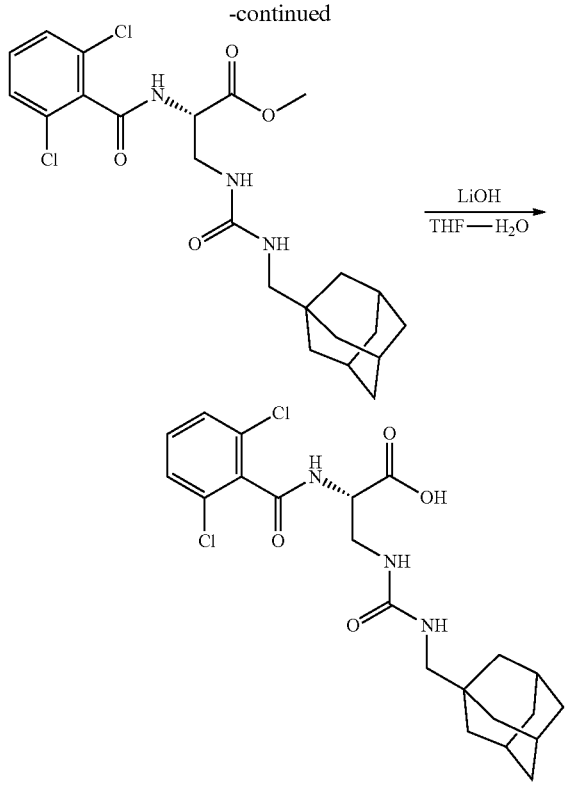

To a stirred solution of aminomethyladamantane (1 mmol) and pyridine (1.5 eq) in anhydrous DCM (4 mL) was added p-nitrophenylchloroformate (1 eq) at 0° C. The mixture was warmed to rt and stirred for 4 h. The mixture was concentrated under reduced pressure and filtered through a short pad of silica (washed with 0 to 100% ethyl acetate in hexanes) to separate the p-nitrophenylcarbamate product which was dissolved in anhydrous DMF (3 mL). To this mixture was added a solution of INT-1 (0.3 mmol) and Et₃N (1 mmol) in DMT (1 mL) at rt. The mixture was stirred overnight and diluted with ethyl acetate. The organic layer was washed with 0.5 M HCl solution (5 mL), sat. NaHCO₃ (6 mL) and brine, successively. After concentration under reduced pressure, the crude ester was purified by silica gel column chromatography (Eluant: 0 to 15% MeOH in DCM). (ESI-MS: 482.5 (MH⁺). The ester was dissolved in THF: H₂O (4:1, 3 mL) and treated with 1M LiOH (0.22 mL) for 2 h. The mixture was acidified to pH=2 and purified by RP-HPLC to provide A2-83.

A2-83

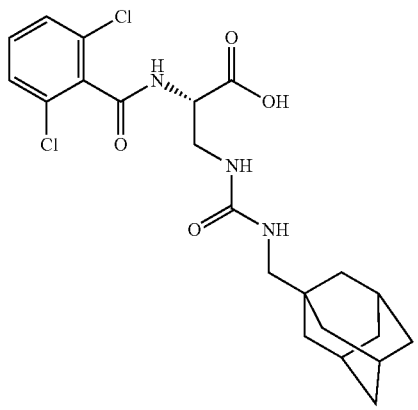

(2S)-3-(3-(((1s,3R)-adamantan-1-yl)methylureido)-2-(2,6-dichlorobenzamido)propanoic acid (A2-83): ¹H NMR (300 MHz, CDCl₃+CD₃OD) δ 7.34-7.26 (m, 3H), 4.62-4.59 (m, 1H), 3.67-3.51 (m, 2H), 2.04 (s, 3H), 1.90 (s, 6H), 1.64 (s, 6H). LC-MS (condition B) m/z=454.4 (MH⁺), Retention time=2.59 min.

pared from (S)-1,2,3,4-tetrahydronaphthalen-1-amine according to the procedure for A2-83. ¹H NMR (300 MHz, CDCl₃+CD₃OD) δ 7.35-7.25 (m, 4H), 7.16-7.2 (m, 2H), 4.68-4.65 (m, 1H), 4.00-3.97 (m, 1H), 3.68 (br s, 2H), 3.1-3.0 (m, 1H), 2.66-2.58 (m, 1H), 2.05-1.95 (m, 1H), 1.74-1.71 (m, 1H). LC-MS (condition B) m/z=450.3 (MH⁺), Retention time=2.45 min.

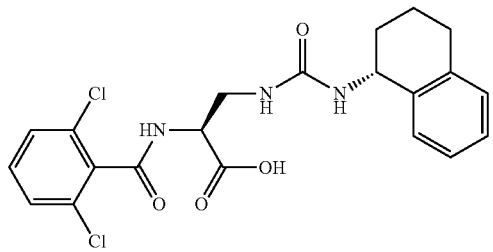

A2-124

(2S)-2-(2,6-dichlorobenzamido)-3-(3-(1,2,3,4-tetrahydronaphthalen-1-yl)ureido)propanoic acid (A2-124): Prepared from 1,2,3,4-tetrahydronaphthalen-1-amine according to the procedure for A2-83. ¹H NMR (300 MHz, CDCl₃+CD₃OD) δ ppm 7.35-7.26 (m, 4H), 7.16-7.02 (m, 2H), 4.87 (s, 1H), 4.65 (s, 1H), 3.80-3.60 (m, 2H), 2.69 (m, 2H), 2.00-1.95 (m, 1H), 1.79 (m, 3H). LC-MS (condition B) m/z=450.3 (MH⁺), Retention time=2.43 min.

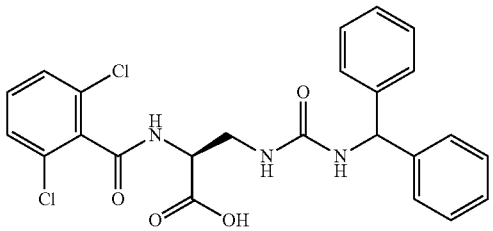

A2-127

(S)-3-(3-benzhydrylureido)-2-(2,6-dichlorobenzamido)propanoic acid (A2-127): Prepared from diphenylmethanimine according to the procedure for A2-83. ¹H NMR (300 MHz, CDCl₃+CD₃OD) δ ppm 7.61-7.35 (m, 13H), 5.94 (br s, 1H), 4.66-4.63 (m, 1H), 3.69-3.68 (m, 2H), 3.1-3.0 (m, 1H), 2.66-2.58 (m, 1H), 2.05-1.95 (m, 1H), 1.74-1.71 (m, 1H). LC-MS (condition B) m/z=486.1 (MH⁺), Retention time=2.50 min.

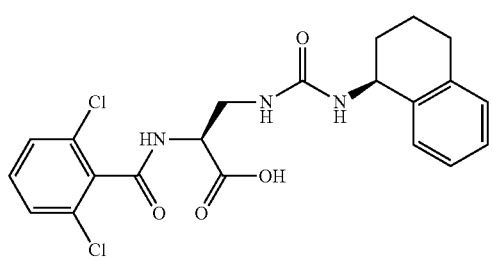

A2-125

(S)-2-(2,6-dichlorobenzamido)-3-(3-((S)-1,2,3,4-tetrahydronaphthalen-1-yl)ureido)propanoic acid (A2-125): Prepared from (S)-1,2,3,4-tetrahydronaphthalen-1-amine according to the procedure for A2-83. ¹H NMR (300 MHz, CDCl₃+CD₃OD) δ 7.35-7.26 (m, 4H), 7.16-7.02 (m, 2H), 4.87 (s, 1H), 4.69-4.66 (m, 1H), 3.80-3.60 (m, 2H), 2.8-2.62 (m, 2H), 2.00-1.96 (m, 1H), 1.79 (m, 3H). LC-MS (condition B) m/z=450.4 (MH⁺), Retention time=2.44 min A2-126 was similarly prepared using 1,2,3,4-tetrahydronaphthalen-1-amine instead of aminomethyladamantane.

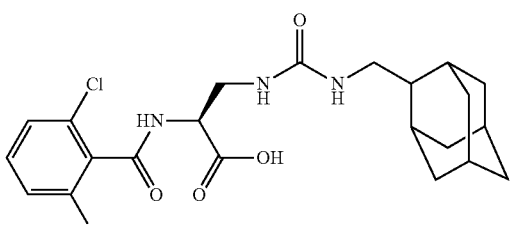

A2-133

(S)-3-(3-((adamantan-1-yl)methyl)ureido)-2-(2,6-dichlorobenzamido)propanoic acid (A2-133): Prepared from (adamantan-1-yl)methanamine according to the procedure for A2-83. ¹H NMR (300 MHz, CDCl₃+CD₃OD) δ ppm 7.35-7.27 (m, 3H), 4.66-4.63 (m, 1H), 3.70-3.64 (m, 2H), 3.26-3.22 (m, 2H), 1.89-1.70 (m, 13H), 1.53-1.49 (m, 2H). LC-MS (condition B) m/z=468.4 (MH⁺), Retention time=2.67 min.

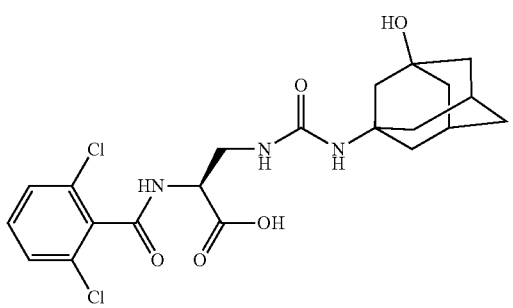

A2-144

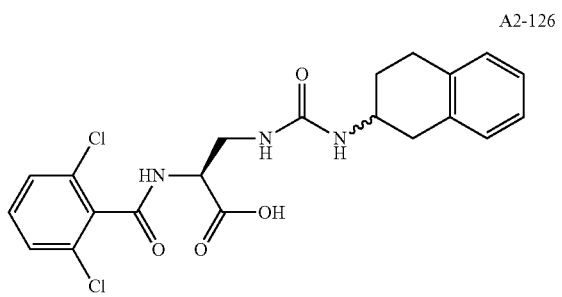 [SMILES: O=C(NC[C@H](NC(=O)c1c(Cl)cccc1Cl)C(=O)O)NC1CCc2ccccc2C1]

A2-126

(2S)-2-(2,6-dichlorobenzamido)-3-(3-(1,2,3,4-tetrahydronaphthalen-2-yl)ureido)propanoic acid (A2-126): Pre- (S)-2-(2,6-dichlorobenzamido)-3-(3-(3-hydroxyadamantan-1-yl)ureido)propanoic acid (A2-144): Prepared from 3-aminoadamantan-1-ol according to the procedure for A2-83. ¹H NMR (300 MHz, CDCl₃+CD₃OD) δ ppm 7.33-7.25 (m, 3H), 4.65-4.60 (m, 1H), 3.65-3.55 (m, 2H), 2.23 (br s, 2H), 1.88-1.75 (m, 4H), 1.65 (br s, 3H), 1.52 (br s, 2H), 1.25-1.18 (m, 3H). LC-MS (condition B) m/z=470.2 (MH⁺), Retention time=1.94 min.

Synthesis of A2-84

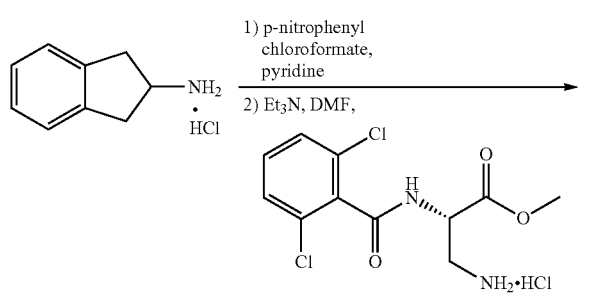

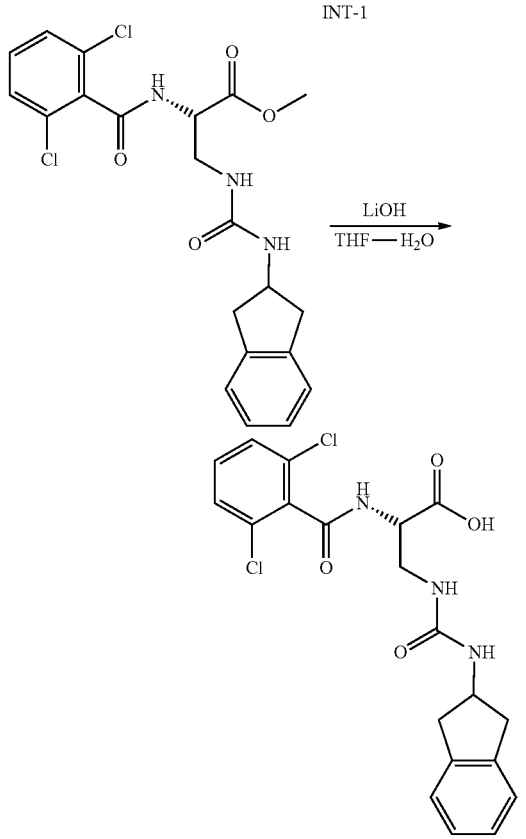

To a stirred solution of 2,3-dihydro-1H-inden-2-amine HCl salt (1 mmol) and Et₃N (1 eq) and pyridine (1.5 eq) in anhydrous DCM (4 mL) was added p-nitrophenylchloroformate (1 eq) at 0° C. The mixture was warmed to rt and stirred for 4 h. The mixture was concentrated under reduced pressure and filtered through a short pad of silica (washed with 0 to 100% ethyl acetate in hexanes) to separate the p-nitrophenylcarbamate product which was dissolved in anhydrous DMF (3 mL). To this mixture was added a solution of INT-1 (0.25 mmol) and Et₃N (0.75 mmol) in DMF (1 mL) at rt. The mixture was stirred overnight and diluted with ethyl acetate. The organic layer was washed with 0.5 M HCl solution (5 mL), sat. NaHCO₃ (6 mL) and brine, successively. After concentration under reduced pressure, the crude ester was purified by silica gel column chromatography (Eluant: 0 to 15% MeOH in DCM). (ESI-MS: 450.4 (MH⁺). The ester was dissolved in THF:H₂O (4:1, 3 mL) and treated with 1M LiOH (0.22 mL) for 2 h. The mixture was acidified to pH=2 and purified by RP-HPLC to provide A2-84.

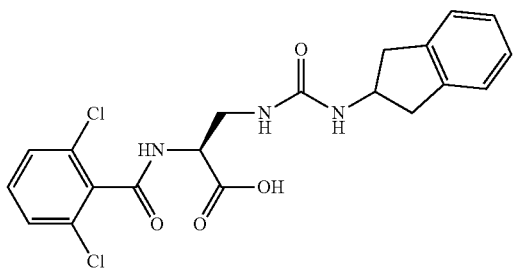

(S)-2-(2,6-dichlorobenzamido)-3-(3-(2,3-dihydro-1H-inden-2-yl)ureido)propanoic acid (A2-84): ¹H NMR (300 MHz, CDCl₃+CD₃OD) δ ppm 7.35-7.26 (m, 3H), 7.22-7.13 (m, 4H), 4.67-4.64 (m, 1H), 4.47-4.43 (m, 1H), 3.67-3.65 (m, 2H), 3.33-3.18 (m, 2H), 2.79-2.72 (m, 2H). LC-MS (condition B) m/z=436.4 (MH⁺), Retention time=2.38 min.

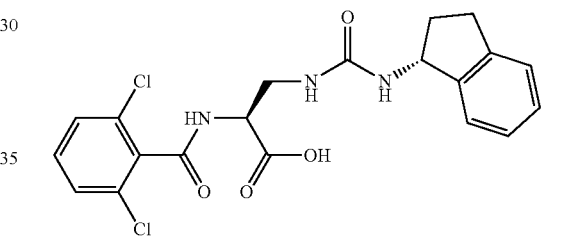

(S)-2-(2,6-dichlorobenzamido)-3-(3-((R)-2,3-dihydro-1H-inden-1-yl)ureido)propanoic acid (A2-85): Prepared from (R)-2,3-dihydro-1H-inden-1-amine HCl salt according to the procedure for A2-84. ¹H NMR (300 MHz, CDCl₃+CD₃OD) δ ppm 7.35-7.15 (m, 7H), 5.21-5.16 (m, 1H), 4.72-4.68 (m, 1H), 3.72 (d, J=5.2 Hz, 2H), 2.97-2.75 (m, 2H), 67-4.64 (m, 1H), 4.47-4.43 (m, 1H), 3.67-3.65 (m, 2H), 3.33-3.18 (m, 2H), 2.79-2.72 (m, 2H), 2.54-2.48 (m, 1H), 1.8-1.7 (m, 1H). LC-MS (condition B) m/z=436.4 (MH⁺), Retention time=2.00 min.

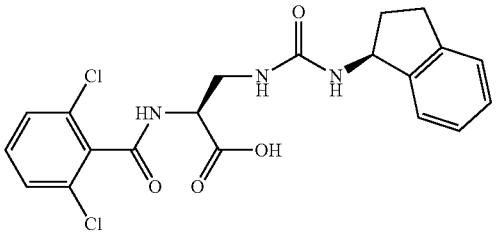

(S)-2-(2,6-dichlorobenzamido)-3-(3-((S)-2,3-dihydro-1H-inden-1-yl)ureido)propanoic acid (A2-86): Prepared from (S)-2,3-dihydro-1H-inden-1-amine HCl salt according to the procedure for A2-84. ¹H NMR (300 MHz, CDCl₃+

CD$_3$OD) δ ppm 7.35-7.15 (m, 7H), 5.17 (t, J=7.35, 1H), 4.70-4.67 (m, 1H), 3.71 (d, J=5.2 Hz, 2H), 2.96-2.74 (m, 2H), 2.53-2.48 (m, 1H), 1.78-1.74 (m, 1H). LC-MS (condition B) m/z=436.4 (MH$^+$), Retention time=2.26 min.

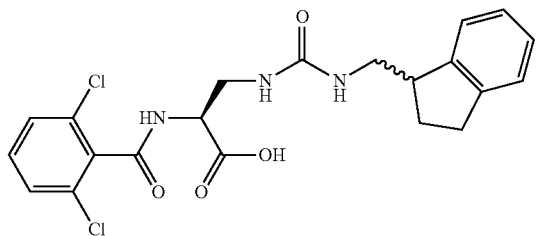

A2-123

(2S)-2-(2,6-dichlorobenzamido)-3-(3-((2,3-dihydro-1H-inden-1-yl)methyl)ureido)propanoic acid) (A2-123): Prepared from (2,3-dihydro-1H-inden-1-yl)methanamine yl)methanamine HCl salt according to the procedure for A2-84. $^1$H NMR (300 MHz, CDCl$_3$+CD$_3$OD) δ ppm 7.3-7.15 (m, 7H), 4.65-4.64 (m, 1H), 3.78-3.6 (m, 2H), 3.59-3.17 (m, 3H), 2.94-2.74 (m, 1H), 2.26-2.20 (m, 1H), 1.83-1.77 (m, 1H). LC-MS (condition B) m/z=450.4 (MH$^+$), Retention time=2.45 min.

A2-128

(S)-2-(2,6-dichlorobenzamido)-3-(3-(3,5-dimethyladamantan-1-yl)ureido)propanoic acid (A2-128): Prepared from 3,5-dimethyladamantan-1-amine HCl salt according to the procedure for A2-84. $^1$H NMR (300 MHz, CDCl$_3$+CD$_3$OD) δ ppm 7.35-7.26 (m, 3H), 4.61-4.57 (m, 1H), 3.61-3.58 (m, 2H), 2.14-2.05 (m, 1H), 1.73 (br s, 1H), 1.58-1.54 (m, 4H), 1.36-1.24 (m, 4H), 1.12 (br s, 2H), 0.82 (s, 6H). LC-MS (condition B) m/z=482.4 (MH$^+$), Retention time=2.75 min.

A2-129

(S)-2-(2,6-dichlorobenzamido)-3-(3-(3-ethyladamantan-1-yl)ureido)propanoic acid (A2-129): Prepared from 3-eth-yladamantan-1-amine HCl salt according to the procedure for A2-84. $^1$H NMR (300 MHz, CDCl$_3$+CD$_3$OD) δ ppm 7.35-7.26 (m, 3H), 4.61-4.57 (m, 1H), 3.69-3.50 (m, 2H), 2.09 (br s, 2H), 1.83 (br s, 4H), 1.60-1.50 (m, 4H), 1.37 (br s, 4H), 1.17-1.12 (m, 2H), 0.80-0.75 (t, J=7.3 Hz, 3H). LC-MS (condition B) m/z=482.3 (MH$^+$), Retention time=2.75 min.

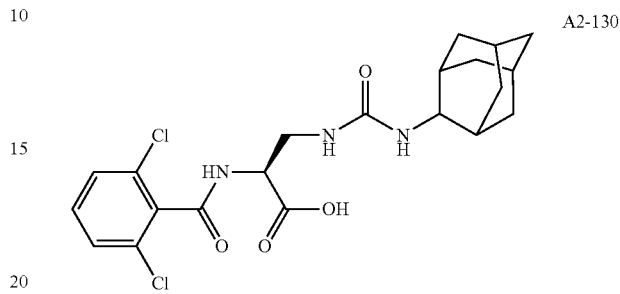

A2-130

(S)-3-(3-(adamantan-2-yl)ureido)-2-(2,6-dichlorobenzamido)propanoic acid (A2-130): Prepared from adamantan-2-amine HCl salt according to the procedure for A2-84. $^1$H NMR (300 MHz, CDCl$_3$+CD$_3$OD) δ ppm 7.35-7.26 (m, 3H), 4.69-4.65 (m, 1H), 3.73-3.66 (m, 3H), 1.81-1.55 (m, 14H). LC-MS (condition B) m/z=454.3 (MH$^+$), Retention time=2.59 min.

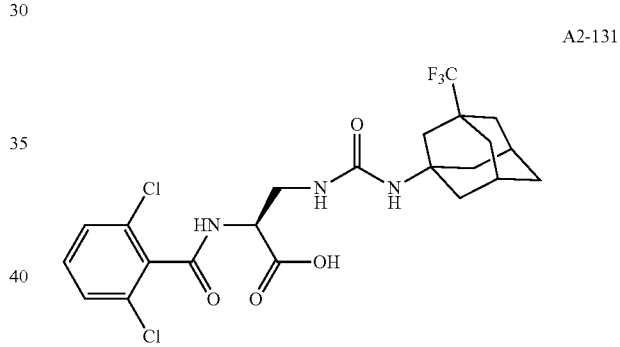

A2-131

(S)-2-(2,6-dichlorobenzamido)-3-(3-(3-(trifluoromethyl)adamantan-1-yl)ureido)propanoic acid (A2-131): Prepared from 3-(trifluoromethyl)adamantan-1-amine HCl salt according to the procedure for A2-84. $^1$H NMR (300 MHz, CDCl$_3$+CD$_3$OD) δ 7.35-7.26 (m, 3H), 4.61-4.57 (m, 1H), 3.67-3.52 (m, 2H), 1.98-1.85 (m, 4H), 1.81-1.56 (m, 8H). LC-MS (condition B) m/z=522.3 (MH$^+$), Retention time=2.65 min.

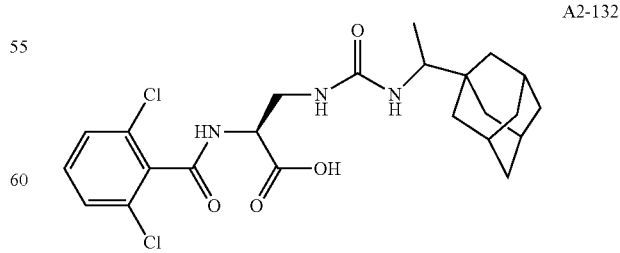

A2-132

(2S)-3-(3-(1-(adamantan-1-yl)ethyl)ureido)-2-(2,6-dichlorobenzamido)propanoic acid (A2-132): Prepared from 1-(adamantan-1-yl)ethan-1-amine HCl salt according to the procedure for A2-84. $^1$H NMR (300 MHz, CDCl$_3$+CD$_3$OD)

δ ppm 7.36-7.26 (m, 3H), 4.63-4.60 (m, 1H), 3.78-3.52 (m, 2H), 3.41-3.35 (m, 1H), 1.97 (br s, 3H), 1.72-1.4 (m, 12H), 1.01-0.98 (m, 3H). LC-MS (condition B) m/z=482.4 (MH+), Retention time=2.70 min.

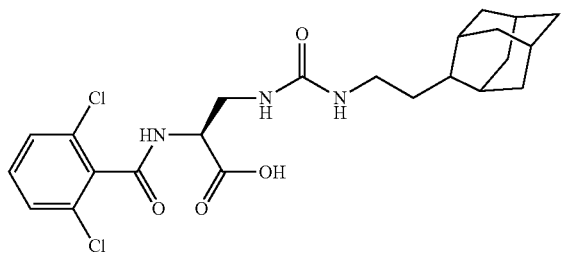

A2-134

(S)-3-(3-(2-((adamantan-1-yl)ethyl)ureido)-2-(2,6-dichlorobenzamido)propanoic acid (A2-134): Prepared from 2-((adamantan-1-yl) ethan-1-amine HCl salt according to the procedure for A2-84. ¹H NMR (300 MHz, CDCl₃+CD₃OD) δ ppm 7.36-7.26 (m, 3H), 4.67-4.63 (m, 1H), 3.67-3.66 (m, 2H), 3.12-3.08 (m, 2H), 1.90-1.48 (m, 17H). LC-MS (condition B) m/z=482.4 (MH+), Retention time=2.73 min.

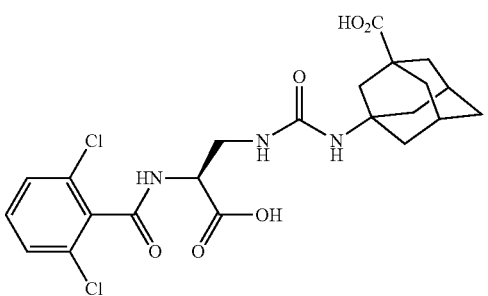

A2-143

3-(3-((S)-2-carboxy-2-(2,6-dichlorobenzamido)ethyl)ureido)adamantane-1-carboxylic acid (A2-143): Prepared from methyl 3-aminoadamantane-1-carboxylate HCl salt according to the procedure for A2-84. ¹H NMR (300 MHz, CDCl₃+CD₃OD) δ ppm 7.34-7.25 (m, 3H), 4.61-4.59 (m, 1H), 3.65-3.53 (m, 2H), 2.16 (br s, 2H), 2.03 (br s, 2H), 1.89 (br s, 4H), 1.8 (br s, 4H), 1.62 (br s, 2H). LC-MS (condition B) m/z=498.5 (MH+), Retention time=1.87 min.

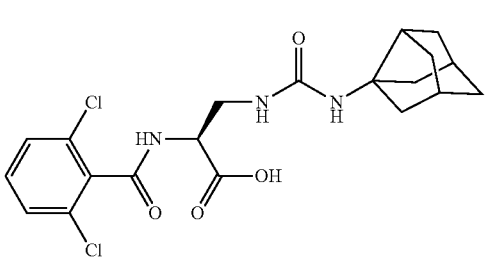

A2-145

(2S)-2-(2,6-dichlorobenzamido)-3-(3-(hexahydro-2,5-methanopentalen-3a(1H)-yl)ureido)propanoic acid (A2-145): Prepared from hexahydro-2,5-methanopentalen-3a (1H)-amine HCl salt according to the procedure for A2-84. ¹H NMR (300 MHz, CDCl₃+CD₃OD) δ ppm 7.33-7.24 (m, 3H), 4.65-4.63 (m, 1H), 3.65-3.53 (m, 2H), 2.31-2.18 (m, 3H), 1.94 (br s, 4H), 1.84-1.81 (m, 2H), 1.61-1.45 (m, 4H). LC-MS (condition B) m/z=440.4 (MH+), Retention time=2.52 min.

Synthesis of A2-152

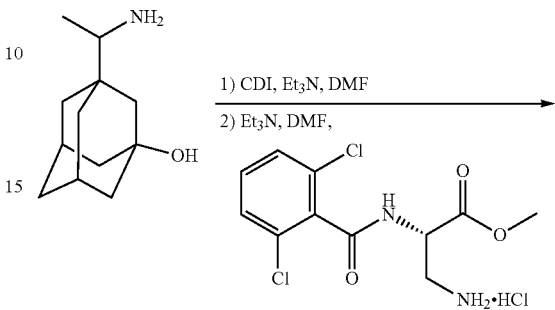

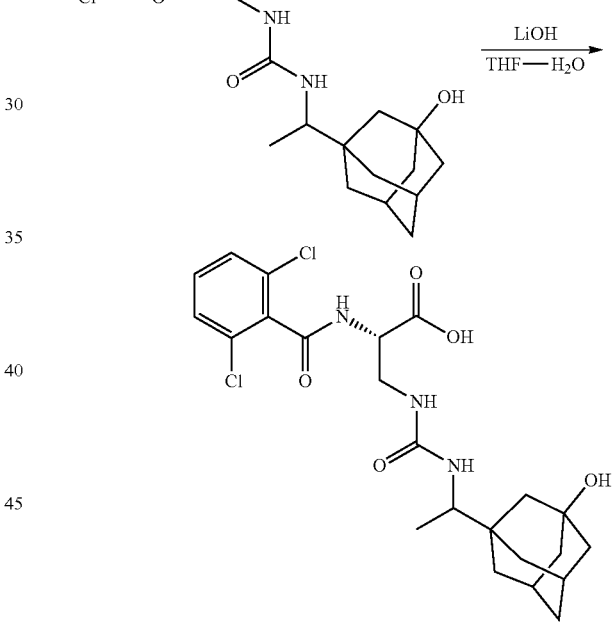

To a solution of 3-(1-aminoethyl)adamantan-1-ol (0.25 mmol) in anhydrous DMF (2 mL) was added anhydrous Et₃N (5 eq) and stirred for 10 min. Then 1,1-carbonyldiimidazole was added to the mixture and stirred for 1 h at rt. INT-1 was added to the mixture and stirred overnight at rt. The mixture was diluted with ethyl acetate and the organic layer was washed with 0.5 M HCl solution and sat. NaHCO₃ successively. After concentration under reduced pressure, the crude ester was purified by silica gel column chromatography (Eluant: 0 to 15% MeOH in DCM). (ESI-MS: 512.4 (MH+). The ester was dissolved in THF:H₂O (4:1, 4 mL) and treated with 1M LiOH (0.20 mL) for 2 h. The mixture was acidified to pH=2 and purified by RP-HPLC to provide A2-152.

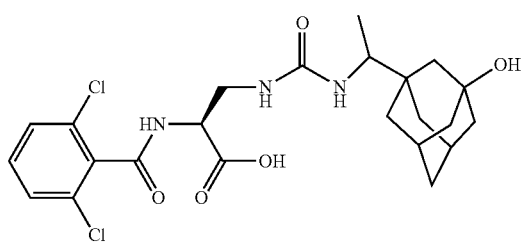

A2-152

(2S)-2-(2,6-dichlorobenzamido)-3-(3-(1-(3-hydroxyadamantan-1-yl)ethyl)ureido)propanoic acid (A2-152): $^1$H NMR (300 MHz, CDCl$_3$+CD$_3$OD) δ 7.35-7.24 (m, 3H), 4.72-4.65 (m, 1H), 3.74-3.4 (m, 3H), 2.20 (br s, 2H) 1.68-1.20 (m, 12H), 1.01 (d, J=6.7 Hz, 3H). LC-MS (condition B) m/z=498.5 (MH$^+$), Retention time=2.15 min.

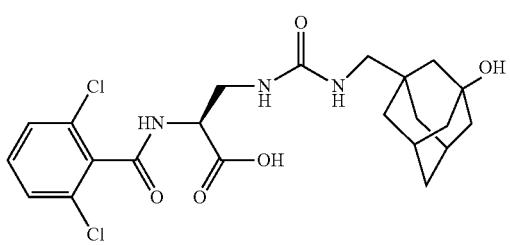

A2-153

(S)-2-(2,6-dichlorobenzamido)-3-(34(3-hydroxyadamantan-1-yl)methyl)ureido)propanoic acid (A2-153): Prepared from 3-(aminomethypadamantan-1-ol HCl salt according to the procedure for A2-152. $^1$H NMR (300 MHz, CDCl$_3$+CD$_3$OD) δ ppm 7.33-7.24 (m, 3H), 4.70-4.64 (m, 1H), 3.66 (d, J=4.8 Hz, 2H), 2.95-2.79 (m, 4H), 2.16 (br s, 2H), 1.67-1.45 (m, 6H), 1.40-1.25 (m, 6H). LC-MS (condition B) m/z=484.4 (MH$^+$), Retention time=2.04 min.

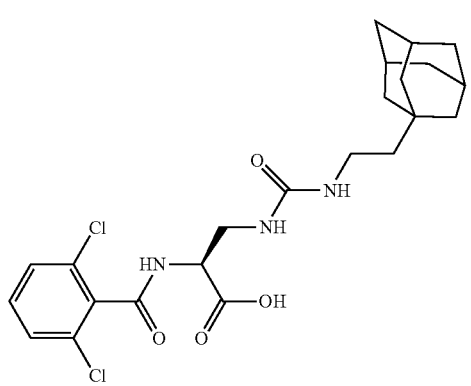

A2-154

(S)-3-(3-(2-(adamantan-1-yl)ethyl)ureido)-2-(2,6-dichlorobenzamido)propanoic acid (A2-154): Prepared from 2-(adamantan-1-yl)ethan-1-amine HCl salt according to the procedure for A2-152. $^1$H NMR (300 MHz, CDCl$_3$+CD$_3$OD) δ ppm 7.35-7.24 (m, 3H), 4.71-4.61 (m, 1H), 3.67 (br s, 2H), 3.12 (br s, 2H), 1.94 (br s, 3H), 1.74-1.42 (m, 12H), 1.24 (br s, 2H). LC-MS (condition B) m/z=482.5 (MH$^+$), Retention time=2.72 min.

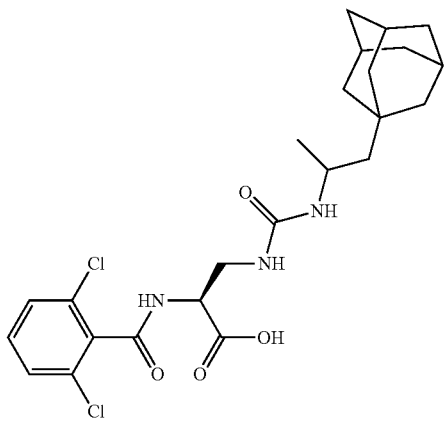

A2-155

(2S)-3-(3-(1-(adamantan-1-yl)propan-2-yl)ureido)-2-(2,6-dichlorobenzamido)propanoic acid (A2-155): Prepared from 1-(adamantan-1-yl)propan-2-amine according to the procedure for A2-152. $^1$H NMR (300 MHz, CDCl$_3$+CD$_3$OD) δ ppm 7.35-7.25 (m, 3H), 4.63-4.58 (m, 1H), 3.85-3.5 (m, 3H), 1.91 (br s, 3H), 1.75-1.40 (m, 12H), 1.2-1.06 (m, 5H). LC-MS (condition B) m/z=496.6 (MH$^+$), Retention time=2.76 min.

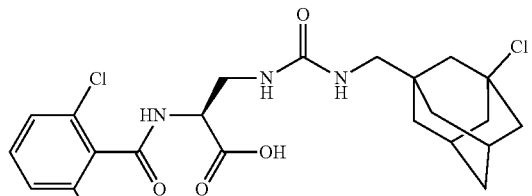

A2-156

(S)-3-(3-((3-chloroadamantan-1-yl)methyl)ureido)-2-(2,6-dichlorobenzamido)propanoic acid (A2-156): Prepared from (3-chloroadamantan-1-yl)methanamine HCl salt according to the procedure for A2-152. $^1$H NMR (300 MHz, CDCl$_3$+CD$_3$OD) δ ppm 7.35-7.25 (m, 3H), 4.66 (br s, 1H), 3.66 (d, J=4.05 Hz, 2H), 2.93-2.81 (m, 2H), 2.16-1.9 (m, 6. LC-MS (condition B) m/z=502.4 (MH$^+$), Retention time=2.58 min.

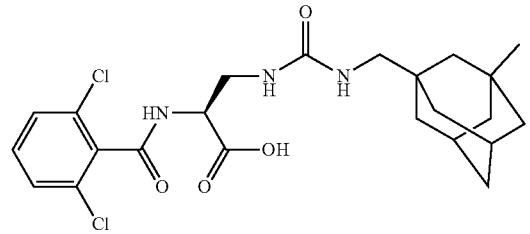

A2-157

(S)-2-(2,6-dichlorobenzamido)-3-(3-(3-methyladamantan-1-yl)ureido)propanoic acid (A2-157): Prepared from 3-methyladamantan-1-amine HCl salt according to the procedure for A2-152. $^1$H NMR (300 MHz, CDCl$_3$+CD$_3$OD) δ ppm 7.33-7.24 (m, 3H), 4.59 (br s, 1H), 3.62-3.51 (m, 2H), 2.07 (br s, 2. LC-MS (condition B) m/z=468.4 (MH⁺), Retention time=2.67 min.

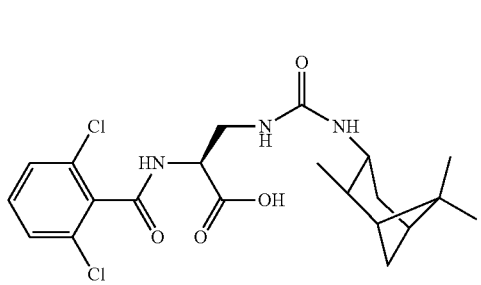

A2-170

(S)-2-(2,6-dichlorobenzamido)-3-(3-((1R,2R,3R,5S)-2,6,6-trimethylbicyclo[3.1.1]heptan-3-yl)ureido)propanoic acid (A2-170) Prepared from (1R,2R,3R,5 S)-2,6,6-trimethylbicyclo[3.1.1]heptan-3-amine (also known as (−)-Isopinocampheylamine) according to the procedure for A2-152. ¹H NMR (300 MHz, CDCl₃+CD₃OD) δ ppm 7.33-7.24 (m, 3H), 4.66 (br s, 1H), 3.7-3.65 (m, 3H), 2.53-2.45 (m, 1H), 2.39-2.23 (m, 1H), 1.89 (br s, 1H), 1.75-1.65 (m, 2H), 1.54-1.45 (m, 1H), 1.19 (s, 3H), 1.05 (d, J=7.05 Hz, 3H), 0.99 (s, 3H), 0.80 (d, J=9.7 Hz, 1H). LC-MS (condition B) m/z=456.4 (MH⁺), Retention time=2.62 min.

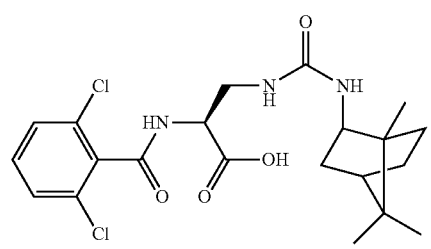

A2-171

(2S)-2-(2,6-dichlorobenzamido)-3-(3-(1,7,7-trimethylbicyclo[2.2.1]heptan-2-yl)ureido)propanoic acid (A2-171): Prepared from endo-(1R)-1,7,7-Trimethylbicyclo[2.2.1]heptan-2-amine (also known as R-(+)-Bornylamine) according to the procedure for A2-152. ¹H NMR (300 MHz, CDCl₃+CD₃OD) δ ppm 7.34-7.24 (m, 3H), 4.65 (br s, 1H), 3.67-3.60 (m, 2H), 2.31-2.23 (m, 1H), 1.68-1.45 (m, 3H), 1.4-1.05 (m, 3H), 0.90 (s, 3H), 0.84 (s, 3H), 0.83-0.80 (m, 1H), 0.77 (s, 3H). LC-MS (condition B) m/z=456.4 (MH⁺), Retention time=2.61 min.

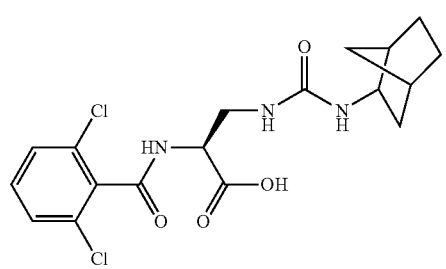

A2-172

(2S)-3-(3-(bicyclo[2.2.1]heptan-2-yl)ureido)-2-(2,6-dichlorobenzamido)propanoic acid (A2-172): Prepared from bicyclo[2.2.1]heptan-2-amine (also known as exo-2-aminonorbornane) according to the procedure for A2-152. ¹H NMR (300 MHz, CDCl₃+CD₃OD) δ ppm 7.34-7.24 (m, 3H), 4.66 (br s, 1H), 3.66-3.65 (m, 2H), 3.39 (br s, 1H), 2.21-2.1 (m, 2H), 1.73-1.66 (m, 1H), 1.5-1.0 (m, 7H). LC-MS (condition B) m/z=414.5 (MH⁺), Retention time=2.30 min.

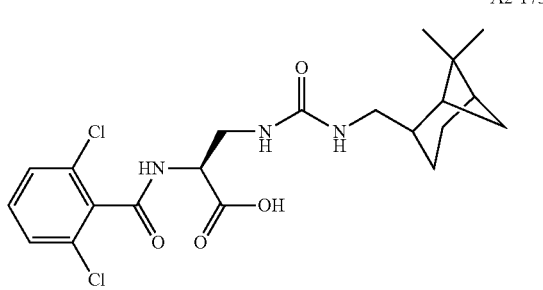

A2-173

(S)-2-(2,6-dichlorobenzamido)-3-(3-0(1R,2S,5R)-6,6-dimethylbicyclo[3.1.1]heptan-2-yl)methyl)ureido)propanoic acid (A2-173): Prepared from ((1R,2S,5R)-6,6-dimethylbicyclo[3.1.1]heptan-2-yl)methanamine (also known as (−)-cis-Myrtanylamine) according to the procedure for A2-152. ¹H NMR (300 MHz, CDCl₃+CD₃OD) δ ppm 7.33-7.24 (m, 3H), 4.65 (br s, 1H), 3.66-3.65 (m, 2H), 3.15-3.01 (m, 2H), 2.31 (br s, 1H), 2.12-2.07 (m, 1H), 1.9-1.7 (m, 5H), 1.42-1.37 (m, 1H), 1.15 (s, 3H), 0.97 (s, 3H), 0.85 (d, J=9.4 Hz, 1H). LC-MS (condition B) m/z=456.4 (MH⁺), Retention time=2.64 min.

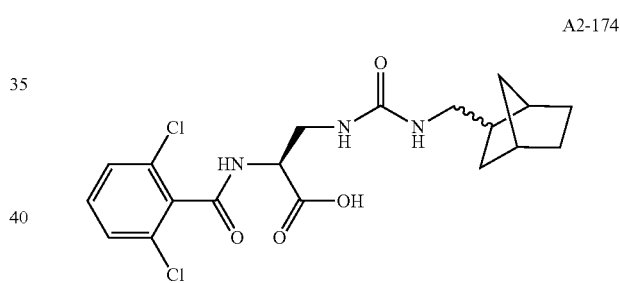

A2-174

(2S)-3-(3-(bicyclo[2.2.1]heptan-2-ylmethyl)ureido)-2-(2,6-dichlorobenzamido)propanoic acid (A2-174): Prepared from bicyclo[2.2.1]heptan-2-ylmethanamine HCl salt according to the procedure for A2-152. ¹H NMR (300 MHz, CDCl₃+CD₃OD) δ ppm 7.33-7.24 (m, 3H), 4.65 (br s, 1H), 3.66-3.65 (m, 2H), 3.11-2.95 (m, 2H), 1.8-1.2 (m, 10H), 0.98-0.92 (m, 1H). LC-MS (condition B) m/z=442.4 (MW), Retention time=2.55 min.

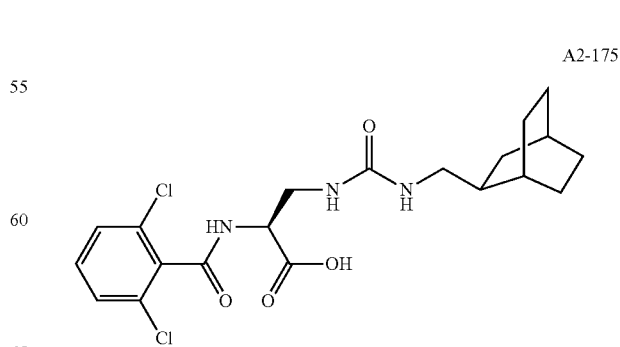

A2-175

(2S)-3-(3-((bicyclo[2.2.2]octan-2-yl)methylureido)-2-(2,6-dichlorobenzamido)propanoic acid (A2-175): Prepared from bicyclo[2.2.2]octan-2-yl)methanamine HCl salt according to the procedure for A2-152. ¹H NMR (300 MHz, CDCl₃+CD₃OD) δ ppm 7.33-7.24 (m, 3H), 4.67 (br s, 1H), 3.68-3.65 (m, 2H), 3.19-3.12 (m, 1H), 3.1-2.85 (m, 1H), 2.14 (br s, 2H), 2.00-1.85 (m, 1H), 1.73-1.64 (m, 1H), 1.6-0.9 (m, 8H), 0.6-0.57 (m, 1H). LC-MS (condition B) m/z=428.5 (MH⁺), Retention time=2.48 min.

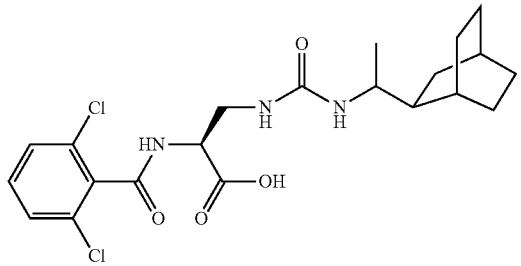

A2-176

(2S)-3-(3-(1-((1S,4R)-bicyclo[2.2.1] heptan-2-yl)ethyl)ureido)-2-(2,6-dichlorobenzamido)propanoic acid (A2-176): Prepared from 1-bicyclo[2.2.1]hept-2-ylethyl)amine according to the procedure for A2-152. ¹H NMR (300 MHz, CDCl₃+CD₃OD) δ ppm 7.33-7.24 (m, 3H), 4.63 (br s, 1H), 3.66-3.57 (m, 2H), 3.38-3.2 (m, 1H), 2.18-2.06 (m, 2H), 1.5-0.9 (m, 12H). LC-MS (condition B) m/z=442.6 (MH⁺), Retention time=2.58 min.

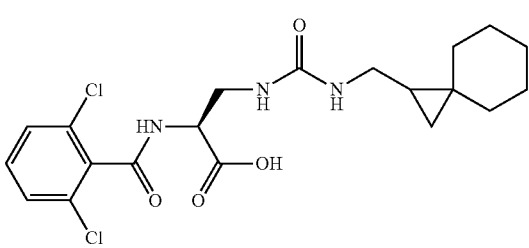

A2-177

(2S)-2-(2,6-dichlorobenzamido)-3-(3-(spiro[2.5]octan-1-ylmethyl)ureido)propanoic acid (A2-177): Prepared from spiro[2.5]octan-1-ylmethanamine HCl salt according to the procedure for A2-152. ¹H NMR (300 MHz, CDCl₃+CD₃OD) δ ppm 7.3-7.18 (m, 3H), 4.64 (br s, 1H), 3.66-3.58 (m, 2H), 3.08-2.98 (m, 2H), 1.5-1.2 (m, 10H), 1.1-1.0 (m, 1H), 0.7-0.55 (m, 1H), 0.47-0.3 (m, 1H). LC-MS (condition B) m/z=442.4 (MH⁺), Retention time=2.57 min

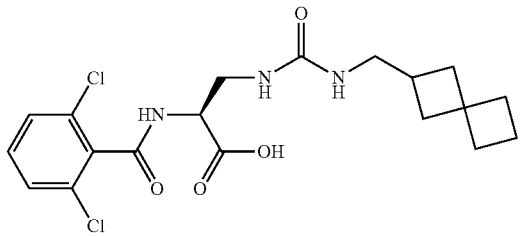

A2-178

(S)-2-(2,6-dichlorobenzamido)-3-(3-(spiro[3.3]heptan-2-ylmethyl)ureido)propanoic acid (A2-178): Prepared from spiro[3.3]heptan-2-ylmethanamine HCl salt according to the procedure for A2-152. ¹H NMR (300 MHz, CDCl₃+CD₃OD) δ ppm 7.35-7.2 (m, 3H), 4.65 (br s, 1H), 3.66-3.62 (m, 2H), 3.06-3.04 (m, 2H), 2.25-2.15 (m, 1H), 2.1-1.9 (m, 4H), 1.9-1.7 (m, 4H), 1.63-1.5 (m, 2H). LC-MS (condition B) m/z=428.4 (MH⁺), Retention time=2.53 min.

A2-179

(S)-2-(2,6-dichlorobenzamido)-3-(3-(spiro[5.5]undecan-3-yl)ureido)propanoic acid (A2-179): Prepared from spiro[5.5]undecan-3-amine HCl salt according to the procedure for A2-152. ¹H NMR (300 MHz, CDCl₃+CD₃OD) δ ppm 7.32-7.25 (m, 3H), 4.63 (br s, 1H), 3.65-3.55 (m, 2H), 3.38 (br s, 1H), 1.7-1.5 (m, 4H), 1.5-1.05 (m, 16H). LC-MS (condition B) m/z=470.5 (MH⁺), Retention time=2.69 min

A2-180

(S)-2-(2,6-dichlorobenzamido)-3-(3-(spiro[adamantane-2,1'-cyclohexan]-4'-yl)ureido)propanoic acid (A2-180): Prepared from spiro[adamantane-2,1'-cyclohexan]-4'-amine HCl salt according to the procedure for A2-152. ¹H NMR (300 MHz, CDCl₃+CD₃OD) δ ppm 7.33-7.25 (m, 3H), 4.66 (br s, 1H), 3.67-3.63 (m, 2H), 3.47-3.33 (br s, 1H), 2.17-1.9 (m, 5H), 1.81 (br s, 3H), 1.66 (br s, 4H), 1.58-1.43 (m, 4H), 1.3-1.0 (m, 6H). LC-MS (condition B) m/z=522.4 (MH⁺), Retention time=2.80 min.

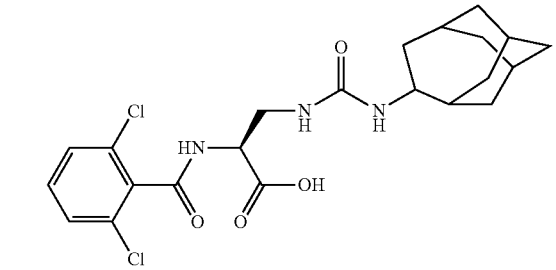

A2-181

(2S)-2-(2,6-dichlorobenzamido)-3-(3-(tricyclo[4.3.1.1³,⁸] undecan-3-yl)ureido)propanoic acid (A2-181): Prepared from tricyclo[4.3.1.1³,⁸]undecan-3-amine according to the procedure for A2-152. ¹H NMR (300 MHz, CDCl₃+CD₃OD) δ ppm 7.33-7.25 (m, 3H), 4.60 (br s, 1H), 3.62-3.54 (m, 2H), 2.1-1.6 (m, 13H), 1.6-1.4 (m, 4H). LC-MS (condition B) m/z=468.4 (MH⁺), Retention time=2.66 min.

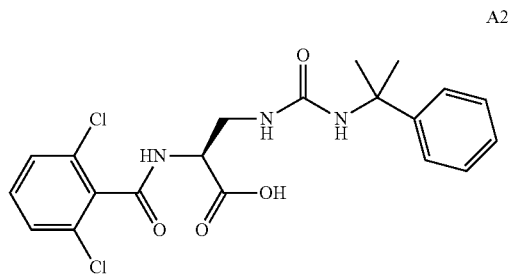

A2-191

(S)-2-(2,6-dichlorobenzamido)-3-(3-(2-phenylpropan-2-yl)ureido)propanoic acid (A2-191) Prepared from 2-phenylpropan-2-amine according to the procedure for A2-152. ¹H NMR (300 MHz, CDCl₃+CD₃OD) δ ppm 7.4-7.1 (m, 8H), 4.6-4.55 (m, 1H), 3.60-3.57 (m, 1H), 1.62 (s, 3H), 1.59 (s, 3H). LC-MS (condition B) m/z=438.4 (MH⁺), Retention time=2.09 min

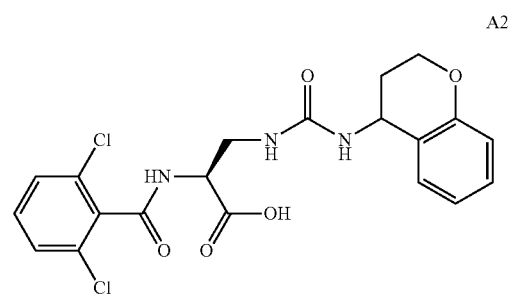

A2-192

(2S)-3-(3-(chroman-4-yl)ureido)-2-(2,6-dichlorobenzamido)propanoic acid (A2-192) Prepared from chroman-4-amine according to the procedure for A2-152. ¹H NMR (300 MHz, CDCl₃+CD₃OD) δ ppm 7.35-7.1 (m, 5H), 6.88 (t, J=7.2 Hz, 1H), 6.79 (d, J=8.2 Hz, 1H), 4.89-4.85 (m, 1H), 4.70 (t, J=5.8 Hz, 1H), 4.25-4.11 (m, 2H), 3.73-3.6 (m, 2H), 2.2-1.9 (m, 2H). LC-MS (condition B) m/z=452.3 (MH⁺), Retention time=2.09 min.

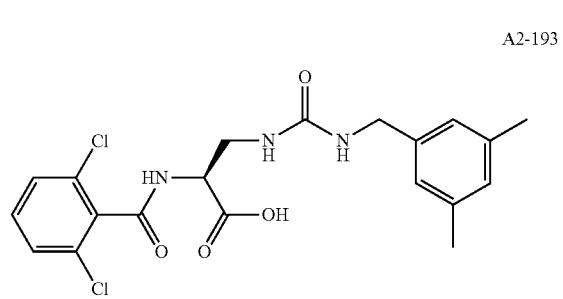 [SMILES: Cc1cc(C)cc(CNC(=O)NC[C@H](NC(=O)c2c(Cl)cccc2Cl)C(=O)O)c1]

A2-193

(S)-2-(2,6-dichlorobenzamido)-3-(3-(3,5-dimethylbenzyl)ureido)propanoic acid (A2-193) Prepared from (3,5-dimethylphenyl)methanamine according to the procedure for A2-152. ¹H NMR (300 MHz, CDCl₃+CD₃OD) δ ppm 7.35-7.2 (m, 3H), 6.87 (s, 3H), 4.69 (t, J=5.2 Hz, 1H), 4.29-4.17 (m, 2H), 3.69 (d, J=4.9 Hz, 1H), 2.27 (s, 6H). LC-MS (condition D) m/z=438.5 (MH⁺), Retention time=2.96 min.

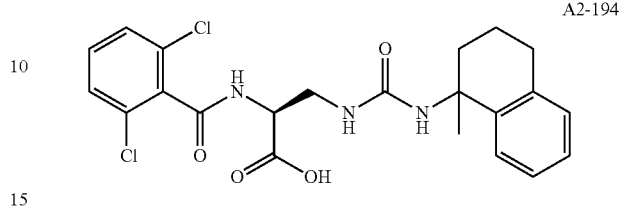

A2-194

(2S)-2-(2,6-dichlorobenzamido)-3-(3-(4,4-dimethyl-1,2,3,4-tetrahydronaphthalen-1-yl)ureido)propanoic acid (A2-194) Prepared from 4,4-dimethyl-1,2,3,4-tetrahydronaphthalen-1-amine according to the procedure for A2-152. ¹H NMR (300 MHz, CDCl₃+CD₃OD) δ ppm 7.35-7.2 (m, 3H),7.2-6.97 (m, 4H, 4.57 (br s, 1H), 3.7-3.4 (m, 2H), 2.9-2.7 (m, 2H), 2.48-2.46 (m, 1H), 1.83-1.76 (m, 3H), 1.56 (d, J=4.5 Hz, 3H). LC-MS (condition D) m/z=438.5 (MH⁺), Retention time=2.96 min.

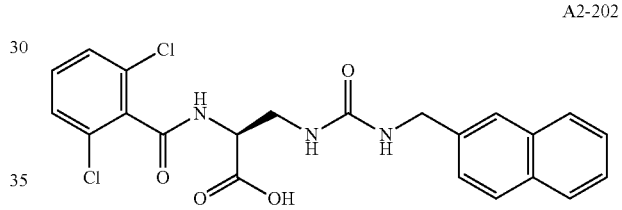

A2-202

(S)-2-(2,6-dichlorobenzamido)-3-(3-(naphthalen-2-ylmethyl)ureido)propanoic acid (A2-202) Prepared from naphthalen-2-ylmethanamine according to the procedure for A2-152. ¹H NMR (300 MHz, CDCl₃+CD₃OD) δ ppm 7.82-7.77 (m, 3H), 7.71 (br s, 1H), 7.47-7.27 (m, 6H), 4.71 (t, J=5.6 Hz, 1H), 4.52-4.4 (m, 2H), 3.74-3.71 (m, 2H). LC-MS (condition D) m/z=460.3 (MH⁺), Retention time=2.90 min.

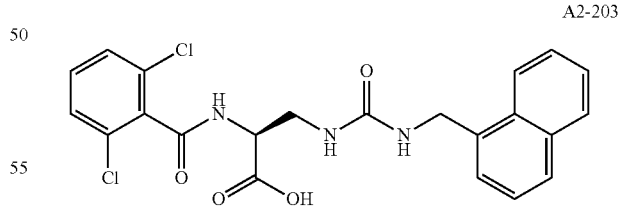

A2-203

(S)-2-(2,6-dichlorobenzamido)-3-(3-(naphthalen-1-ylmethyl)ureido)propanoic acid (A2-203) Prepared from naphthalen-1-ylmethanamine according to the procedure for A2-152. ¹H NMR (300 MHz, CDCl₃+CD₃OD) δ ppm 8.01 (d, 7.7 Hz, 1H), 7.85 (d, J=7.9 Hz, 1H), 7.77 (d, J=7.5 Hz, 1H), 7.56-7.2 (m, 7H), 4.84-4.68 (m, 3H), 3.73-3.71 (m, 2H). LC-MS (condition D) m/z=460.5 (MH⁺), Retention time=2.89 min.

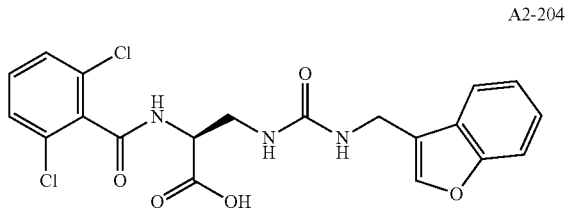 [SMILES: O=C(NCc1coc2ccccc12)NC[C@H](NC(=O)c1c(Cl)cccc1Cl)C(=O)O]

A2-204

(S)-3-(3-(benzofuran-3-ylmethyl)ureido)-2-(2,6-dichlorobenzamido)propanoic acid (A2-204) Prepared from benzofuran-3-ylmethanamine according to the procedure for A2-152. $^1$H NMR (300 MHz, CDCl$_3$+CD$_3$OD) δ ppm 7.62-7.55 (m, 2H), 7.45 (d, J=7.9 Hz, 1H), 7.32-7.2 (m, 4H), 4.70 (t, J=5.2 Hz, 1H), 4.5-4.3 (m, 2H), 3.72-3.68 (m, 2H)hZ4-4.68 (m, 3H), 3.73-3.71 (m, 2H). LC-MS (condition D) m/z=450.3 (MH$^+$), Retention time=2.80 min.

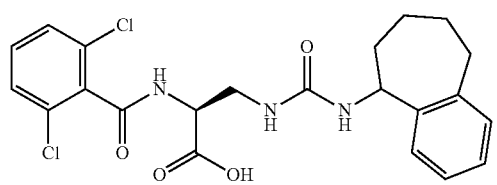

A2-207

(2S)-2-(2,6-dichlorobenzamido)-3-(3-(6,7,8,9-tetrahydro-5H-benzo[7]annulen-5-yl)ureido)propanoic acid (A2-207) Prepared from 6,7,8,9-tetrahydro-5H-benzo[7]annulen-5-amine according to the procedure for A2-152. $^1$H NMR (300 MHz, CDCl$_3$+CD$_3$OD) δ ppm 7.3-7.05 (m, 7H), 4.88 (br s, 1H), 4.7-4.65 (m, 1H), 3.69-3.67 (m, 2H), 2.85-2.83 (m, 2H), 2.0-1.5 (m, 6H). LC-MS (condition D) m/z=464.3 (MH$^+$), Retention time=2.97 min.

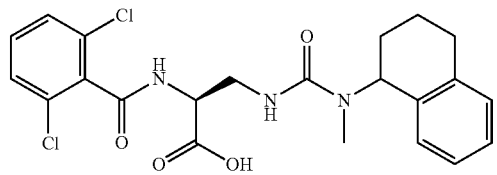

A2-208

(2S)-2-(2,6-dichlorobenzamido)-3-(3-methyl-3-(1,2,3,4-tetrahydronaphthalen-1-yl)ureido)propanoic acid (A2-208) Prepared from N-methyl-1,2,3,4-tetrahydronaphthalen-1-amine according to the procedure for A2-152. $^1$H NMR (300 MHz, CDCl$_3$+CD$_3$OD) δ ppm 7.35-7.2 (m, 3H),7.15-7.0 (m, 4H), 5.48 (br s, 1H),4.79-4.76 (m, 1H), 3.89-3.69 (m, 2H), 2.8-2.6 (m, 2H), 2.59 (d, J=3 Hz, 3H), 2.1-19.5 (m, 2H), 1.8-1.65 (m, 2H). LC-MS (condition D) m/z=464.5 (MH$^+$), Retention time=2.96 min.

Synthesis of INT-2 (on the polymer support)

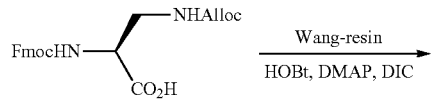

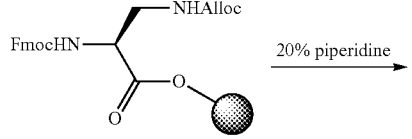

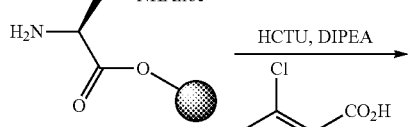

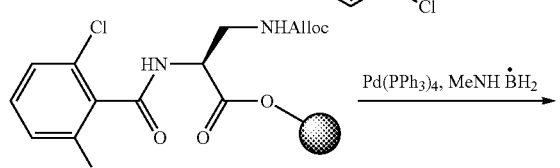

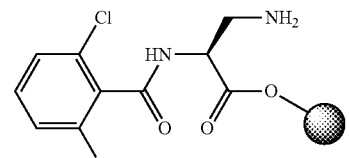

INT-2 a. Fmoc-Dap(Alloc) on Wang-ChemMatrix® resin: In a round bottom flask suspend the resin in 9:1 (VN DCM/DMF) (15 mL/g of resin). In a separate flask dissolve 2 equivalent of the carboxylic acid in a minimum amount of DMF, which was added the same equivalent of HOBt and stir the mixture until HOBt dissolves. Then add the solution to the resin. In another separate flask dissolve 0.1 equivalent of DMAP in a minimum amount of DMF. Add 1.0 equivalent of DIC to the resin mixture and then add the DMAP solution. Agitate the mixture with a mechanical shaker for 2-3 h at room temperature. Add 2 equivalent of acetic anhydride and pyridine to the reaction flask and mix an additional 30 min at room temperature to consume the unreacted hydroxyl group on the resin. Filter the resin, wash it with DCM (×3) and dried under vacuum.

b. Removal of Fmoc group: The Fmoc amino resin (3.83 mmol/g assumed) was treated with 20% 4-methylpiperidine in DMF (200 mL) for 5 min and repeated once. The resin was washed with DMF (×3), DCM (×3), and MeOH(×3) and dried under vacuum.

c. Synthesis of amide: To a DCM swollen amino resin (3.83 mmol/g assumed) was added 2,6-dichloro benzoic acid (3.64 g, 19.15 mmol, 5 equiv), DIPEA (6.7 mL, 38.3 mmol, 10 equiv), and HATU (7.2 g, 18.96 mmol, 4.95 equiv) in DCM and shaken overnight. The resin was filtered and washed with DCM and DMF successively to give the resin.

d. Removal of Alloc group: To a DCM swollen amino resin (3.83 mmol/g assumed) was added Pd(PPh$_3$)$_4$ (89 mg, 0.077 mmol, 0.02 equiv) and Me$_2$NH.BH$_3$ (2.26 g, 38.3 mmol, 10 equiv) in DCM and shaken 15 min. The resin was filtered and washed with DCM, repeated two times more and dried it in vacuo.

Synthesis of KZ-1-3

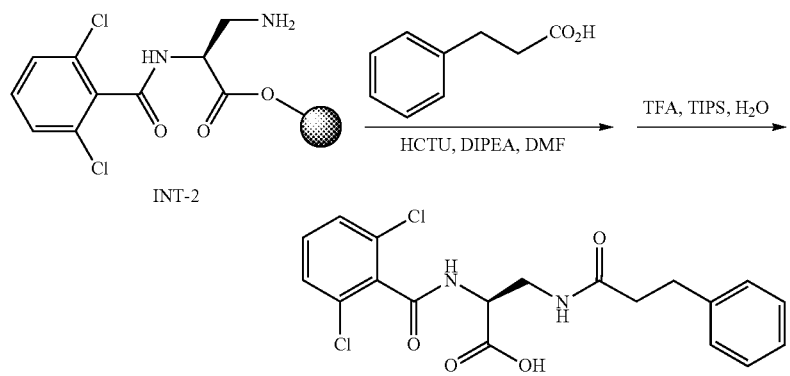

a. Syntheses of analogs: To a DMF swollen INT-2 on resin (0.5 g, 3.83 mmol/g assumed) was added 3-phenylpropanoic acid (225 mg, 1.5 mmol, 5 equiv), HCTU (638 mg, 4.95 equiv), and DIPEA (0.52 mL, 10 equiv) in DMF and shaken overnight. The resin was filtered and washed with DMF, DCM, and dried it in vacuo.

b. Cleavage: The resin was treated with a mixture of TFA:TIPS:$H_2O$ (95:2.5:2.5) (10 mL) for 3 h and filtered. The filtrate was concentrated under a stream of $N_2$. The crude product was purified by RP-HPLC and the purity was confirmed by LC-MS.

(S)-2-(2,6-dichlorobenzamido)-3-(3-phenethylureido) propanoic acid (KZ-1-3):. $^1$H NMR (300 MHz, $CDCl_3$+$CD_3OD$, δ) 7.36-7.33 (m, 3H), 7.26-7.23 (m, 2H), 7.19-7.16 (m, 3H), 4.74 (t, J=5.7 Hz, 1H), 3.72 (d, J=5.7 Hz, 2H), 2.92 (t, J=7.5 Hz, 2H), 2.49 (t, J=7.5 Hz, 2H). LC-MS (condition A) m/z=409.5 (MH$^+$), Retention time=5.18 min Synthesis of KZ-1-9

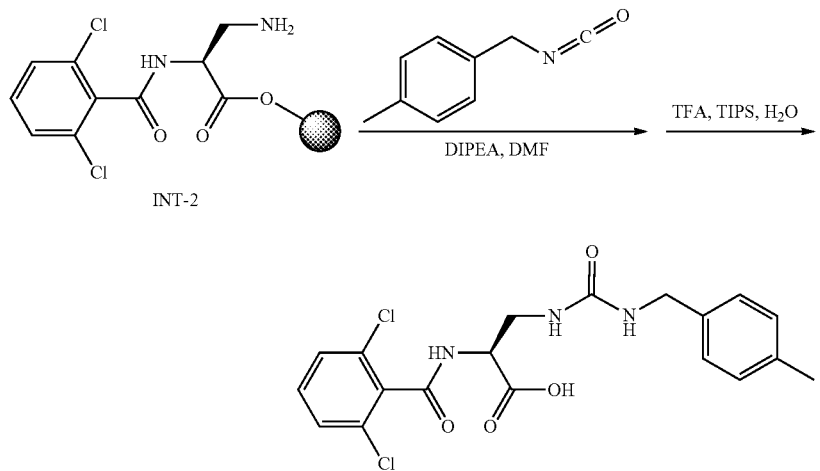

a. Syntheses of analogs: To a DMF swollen INT-2 on resin (0.5 g, 3.83 mmol/g assumed) was added 1-(isocyanatomethyl)-4-methylbenzene (10 equiv) and DIPEA (6 equiv) in DMF and shaken overnight. The resin was filtered and washed with DMF, DCM, and dried it in vacuo.

b. Cleavage: The resin was treated with a mixture of TFA:TIPS:$H_2O$ (95:2.5:2.5) (10 mL) for 3 h and filtered. The filtrate was concentrated under a stream of $N_2$. The crude product was purified by RP-HPLC and the purity was confirmed by LC-MS.

(S)-2-(2,6-dichlorobenzamido)-3-(3-(4-methylbenzyl) ureido)propanoic acid (KZ-1-9): $^1$H NMR (300 MHz, $CDCl_3$+$CD_3OD$, δ) 7.33-7.29 (m, 3H), 7.13-7.11 (m, 4H), 4.65-4.63 (m, 1H), 4.29 (s, 2H), 3.71-3.70 (m, 2H), 2.32 (s, 3H). LC-MS (condition A) m/z=424.7 (MH$^+$), Retention time=5.22 min.

KZ-1-11

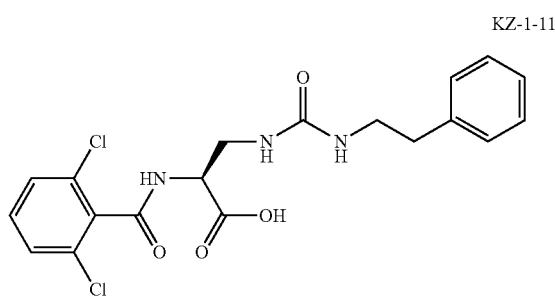 [SMILES: O=C(NCCc1ccccc1)NC[C@H](NC(=O)c1c(Cl)cccc1Cl)C(=O)O]

(S)-2-(2,6-dichlorobenzamido)-3-(3-phenethylureido)propanoic acid (KZ-1-11). Prepared from (2-isocyanatoethyl)benzene according to the procedure for KZ-1-9. $^1$H NMR (300 MHz, CDCl$_3$+CD$_3$OD, δ) 7.34-7.25 (m, 5H), 7.21-7.15 (m, 3H), 4.58-4.56 (m, 1H), 3.73-3.56 (m, 2H), 3.49-3.38 (m, 2H), 2.80-2.75 (m, 2H). LC-MS (condition A) m/z=424.4 (MH$^+$), Retention time=5.15 min.

KZ-1-12

(S)-2-(2,6-dichlorobenzamido)-3-(3-((R)-1-phenylethyl)ureido)propanoic acid (KZ-1-12). Prepared from (R)-(1-isocyanatoethyl)benzene according to the procedure for KZ-1-9. $^1$H NMR (300 MHz, CDCl$_3$+CD$_3$OD, δ) 7.31-7.29 (m, 4H), 7.27-7.23 (m, 4H), 4.71 (s, 1H), 4.60-4.56 (m, 1H), 3.73-3.62 (m, 2H), 1.40 (d, J=9.0 Hz, 3H). LC-MS (condition A) m/z=424.6 (MH$^+$), Retention time=5.15 min.

KZ-1-13

(S)-2-(2,6-dichlorobenzamido)-3-(3-((S)-1-phenylethyl)ureido)propanoic acid (KZ-1-13). Prepared from (S)-(1-isocyanatoethyl)benzene according to the procedure for KZ-1-9. $^1$H NMR (300 MHz, CDCl$_3$+CD$_3$OD, δ) 7.28-7.26 (m, 8H), 4.76 (s, 1H), 4.62-4.56 (m, 1H), 3.55-3.39 (m, 2H), 1.39 (d, J=6.0 Hz, 3H). LC-MS (condition A) m/z=424.5 (MH$^+$), Retention time=5.14 min.

KZ-1-14

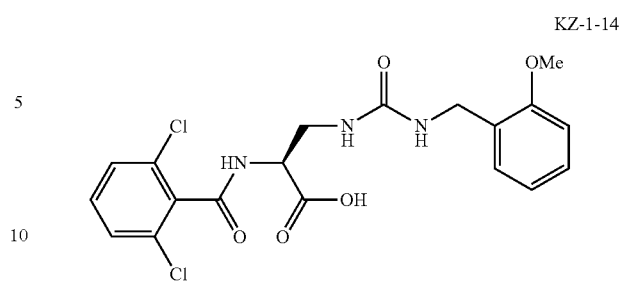

(S)-2-(2,6-dichlorobenzamido)-3-(3-(2-methoxybenzyl)ureido)propanoic acid (KZ-1-14). Prepared from 1-(isocyanatomethyl)-2-methoxybenzene according to the procedure for KZ-1-9. $^1$H NMR (300 MHz, CDCl$_3$+CD$_3$OD, δ) 7.32-7.20 (m, 5H), 6.91-6.83 (m, 2H), 4.63-4.61 (m, 1H), 4.32 (s, 2H), 3.83 (s, 3H), 3.64-3.61 (m, 2H). LC-MS (condition A) m/z=440.5 (MH$^+$), Retention time=5.06 min.

KZ-1-15

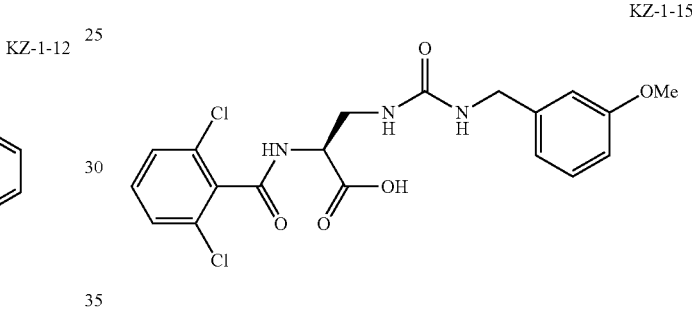

(S)-2-(2,6-dichlorobenzamido)-3-(3-(3-methoxybenzyl)ureido)propanoic acid (KZ-1-15). Prepared from 1-(isocyanatomethyl)-3-methoxybenzene according to the procedure for KZ-1-9. $^1$H NMR (300 MHz, CDCl$_3$+CD$_3$OD, δ) 7.29-7.23 (m, 3H), 7.19-7.14 (m, 1H), 6.80-6.72 (m, 3H), 4.64-4.62 (m, 1H), 4.25 (s, 2H), 3.75 (s, 3H), 3.64-3.61 (m, 2H). LC-MS (condition A) m/z=440.5 (MH$^+$), Retention time=4.98 min.

KZ-1-16

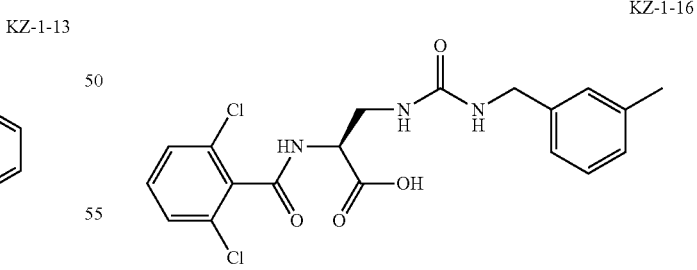

(S)-2-(2,6-dichlorobenzamido)-3-(3-(3-methylbenzyl)ureido)propanoic acid (KZ-1-16). Prepared from 1-(isocyanatomethyl)-3-methylbenzene according to the procedure for KZ-1-9. $^1$H NMR (300 MHz, CDCl$_3$+CD$_3$OD, δ) 7.33-7.28 (m, 3H), 7.20-7.15 (m, 1H), 7.05-7.03 (m, 3H), 4.68-4.66 (m, 1H), 4.29 (s, 2H), 3.81-3.69 (m, 2H), 2.31 (s, 3H). LC-MS (condition A) m/z=424.4 (MH$^+$), Retention time=5.22 min.

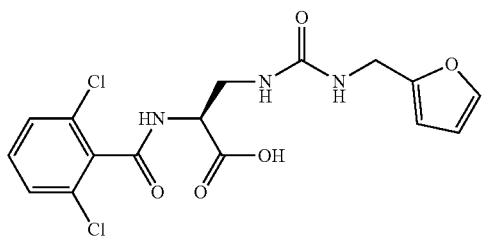

KZ-1-17

(S)-2-(2,6-dichlorobenzamido)-3-(3-(furan-2-ylmethyl) ureido)propanoic acid (KZ-1-17). Prepared from 2-(isocyanatomethyl)furan according to the procedure for KZ-1-9. $^1$H NMR (300 MHz, CDCl$_3$+CD$_3$OD, δ) 7.38-7.31 (m, 4H), 6.31 (s, 1H), 6.22 (s, 1H), 4.64-4.55 (m, 1H), 4.35 (s, 2H), 3.92-3.76 (m, 2H). LC-MS (condition A) m/z=400.5 (MH$^+$), Retention time=4.65 min.

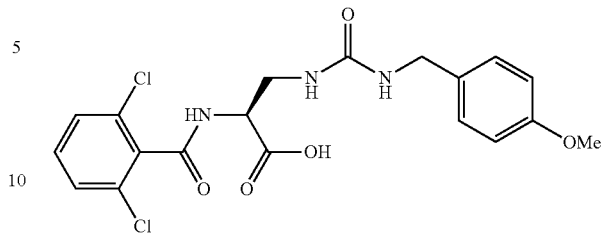

KZ-1-20

(S)-2-(2,6-dichlorobenzamido)-3-(3-(4-methoxybenzyl) ureido)propanoic acid (KZ-1-20). Prepared from 1-(isocyanatomethyl)-4-methoxybenzene according to the procedure for KZ-1-9. $^1$H NMR (300 MHz, CDCl$_3$+CD$_3$OD, δ) 7.34-7.30 (m, 2H), 7.29-7.27 (m, 1H), 7.19-7.16 (m, 2H), 6.85-6.81 (m, 2H), 4.62-4.56 (m, 1H), 4.27 (s, 2H), 3.79 (s, 3H), 3.63-3.61 (m, 2H). LC-MS (condition A) m/z=440.4 (MH$^+$), Retention time=4.94 min.

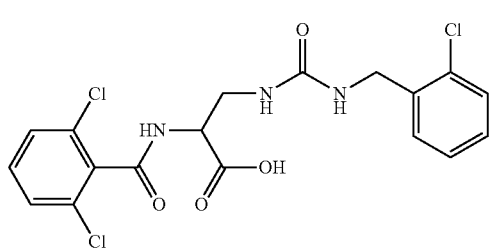

KZ-1-18

(S)-3-(3-(2-chlorobenzyl)ureido)-2-(2,6-dichlorobenzamido)propanoic acid (KZ-1-18). Prepared from 1-chloro-2-(isocyanatomethyl)benzene according to the procedure for KZ-1-9. $^1$H NMR (300 MHz, CDCl$_3$+CD$_3$OD, δ) 7.29-7.21 (m, 5H), 7.15-7.12 (m, 2H), 4.67-4.65 (m, 1H), 4.31 (s, 2H), 3.78-3.67 (m, 2H). LC-MS (condition A) m/z=444.4 (MH$^+$), Retention time=5.29 min.

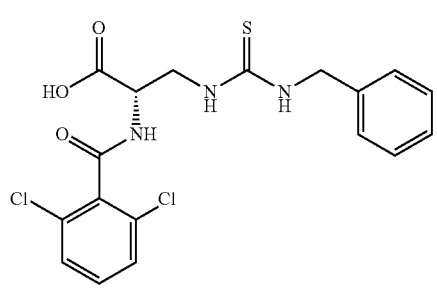

KZ-1-21

(S)-3-(3-benzylthioureido)-2-(2,6-dichlorobenzamido) propanoic acid (KZ-1-21). Prepared from (isothiocyanatomethyl)benzene according to the procedure for KZ-1-9. $^1$H NMR (300 MHz, CDCl$_3$+CD$_3$OD, δ) 7.29-7.28 (m, 5H), 7.20-7.17 (m, 3H), 4.78-4.76 (m, 1H), 4.62 (s, 2H), 3.64-3.44 (m, 2H). LC-MS (condition A) m/z=426.1 (MH$^+$), Retention time=5.43 min.

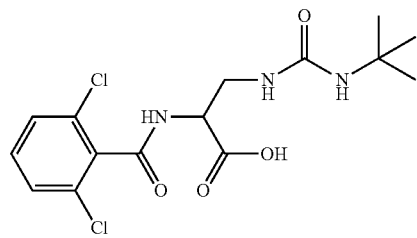

KZ-1-19

(S)-2-(2,6-dichlorobenzamido)-3-(3-(4-methylbenzyl) ureido)propanoic acid (KZ-1-19). Prepared from 2-isocyanato-2-methylpropane according to the procedure for KZ-1-9. $^1$H NMR (300 MHz, CDCl$_3$+CD$_3$OD, δ) 7.36-7.33 (m, 1H), 7.32-7.28 (m, 2H), 4.58-4.57 (m, 1H), 3.78-3.71 (m, 2H), 1.31 (s, 9H). LC-MS (condition A) m/z=376.5 (MH$^+$), Retention time=4.87 min.

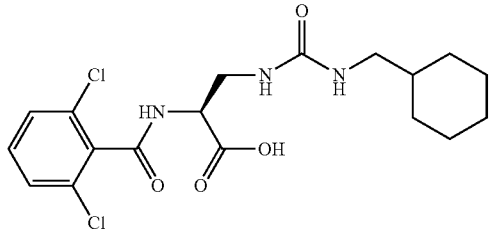

KZ-1-22

(S)-3-(3-(cyclohexylmethyl)ureido)-2-(2,6-dichlorobenzamido)propanoic acid (KZ-1-22). Prepared from (isocyanatomethyl)cyclohexane according to the procedure for KZ-1-9. $^1$H NMR (300 MHz, CDCl$_3$+CD$_3$OD, δ) 7.33-7.28 (m, 3H), 4.65-4.64 (m, 1H), 3.83-3.68 (m, 2H), 2.97-2.95 (m, 2H), 1.68-1.66 (m, 5H), 1.44-1.35 (m, 1H), 1.21-1.09 (m, 3H), 0.91-0.83 (m, 2H). LC-MS (condition A) m/z=416.2 (MH$^+$), Retention time=5.46 min.

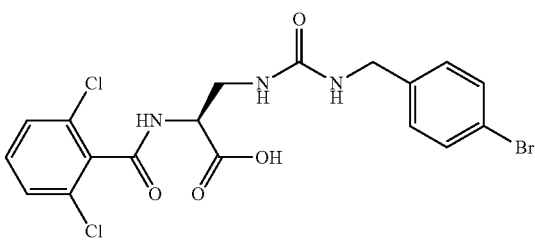

KZ-1-23

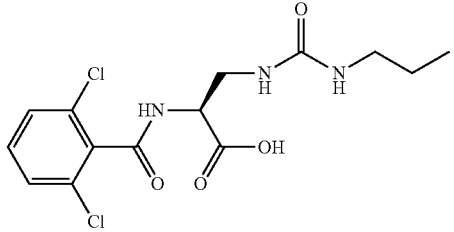

KZ-1-27

(S)-3-(3-(4-bromobenzyl)ureido)-2-(2,6-dichlorobenzamido)propanoic acid (KZ-1-23). Prepared from 1-bromo-4-(isocyanatomethyl)benzene according to the procedure for KZ-1-9. $^1$H NMR (300 MHz, CDCl$_3$+CD$_3$OD, δ) 7.44-7.42 (m, 2H), 7.36-7.30 (m, 3H), 7.17-7.14 (m, 2H), 4.73-4.69 (m, 1H), 4.27-4.25 (m, 2H), 3.72-3.66 (m, 2H). LC-MS (condition A) m/z=488.0 (MH$^+$), Retention time=5.42 min.

(S)-2-(2,6-dichlorobenzamido)-3-(3-propylureido)propanoic acid (KZ-1-27). Prepared from 1-isocyanatopropane according to the procedure for KZ-1-9. $^1$H NMR (300 MHz, CDCl$_3$+CD$_3$OD, δ) 7.37-7.29 (m, 3H), 4.64-4.62 (m, 1H), 4.27 (s, 2H), 3.80-3.76 (m, 2H), 3.14-3.10 (m, 2H), 1.55-1.46 (m, 3H), 0.91 (t, J=7.3 Hz, 3H). LC-MS (condition A) m/z=362.0 (MH$^+$), Retention time=4.46 min.

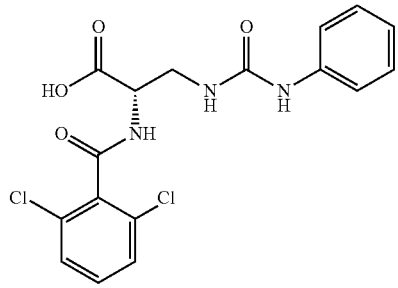

KZ-1-25

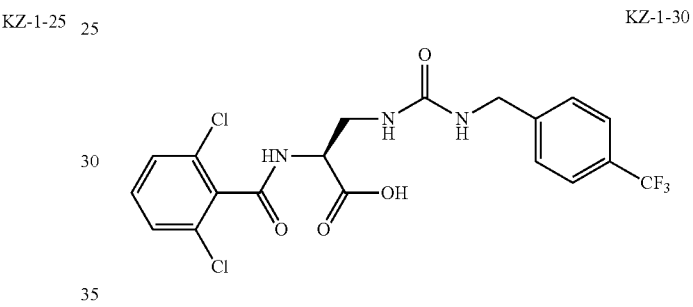

KZ-1-30

(S)-2-(2,6-dichlorobenzamido)-3-(3-phenylureido)propanoic acid (KZ-1-25). Prepared from isocyanatobenzene according to the procedure for KZ-1-9. $^1$H NMR (300 MHz, CDCl$_3$+CD$_3$OD, δ) 7.35-7.23 (m, 7H), 7.02-6.98 (m, 1H), 4.80-4.76 (m, 1H), 3.80-3.72 (m, 2H). LC-MS (condition A) m/z=396.2 (MH$^+$), Retention time=4.97 min.

(S)-2-(2,6-dichlorobenzamido)-3-(3-(4-(trifluoromethyl)benzyl)ureido)propanoic acid (KZ-1-30). Prepared from 1-(isocyanatomethyl)-4-(trifluoromethyl)benzene according to the procedure for KZ-1-9. $^1$H NMR (300 MHz, CDCl$_3$+CD$_3$OD, δ) 7.63-7.54 (m, 2H), 7.42-7.33 (m, 5H), 4.69-4.64 (m, 1H), 4.37 (s, 2H), 3.44-3.35 (m, 2H). LC-MS (condition A) m/z=477.9 (MH$^+$), Retention time=5.52 min.

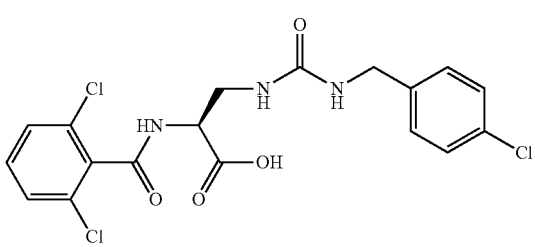

KZ-1-26

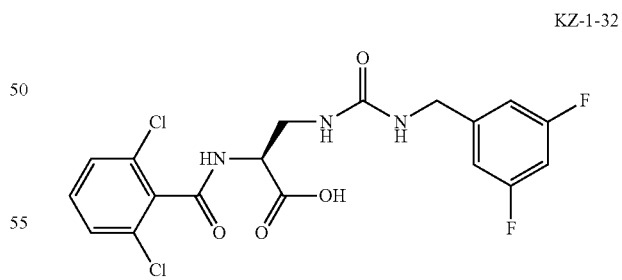

KZ-1-32

(S)-3-(3-(4-chlorobenzyl)ureido)-2-(2,6-dichlorobenzamido)propanoic acid (KZ-1-26). Prepared from 1-chloro-4-(isocyanatomethyl)benzene according to the procedure for KZ-1-9. $^1$H NMR (300 MHz, CDCl$_3$+CD$_3$OD, δ) 7.29-7.28 (m, 4H), 7.25-7.13 (m, 3H), 4.62-4.59 (m, 1H), 4.27 (s, 2H), 3.80-3.76 (m, 2H). LC-MS (condition A) m/z=444.1 (MH$^+$), Retention time=5.33 min.

(S)-2-(2,6-dichlorobenzamido)-3-(3-(3,5-difluorobenzyl)ureido)propanoic acid (KZ-1-32). Prepared from 1,3-difluoro-5-isocyanatobenzene according to the procedure for KZ-1-9. $^1$H NMR (300 MHz, CDCl$_3$+CD$_3$OD, δ) 7.30-7.21 (m, 3H), 6.77-6.75 (m, 2H), 6.66-6.60 (m, 1H), 4.68-4.64 (m, 1H), 4.26-4.25 (m, 2H), 3.67-3.65 (m, 2H). LC-MS (condition A) m/z=446.1 (MH$^+$), Retention time=5.17 min.

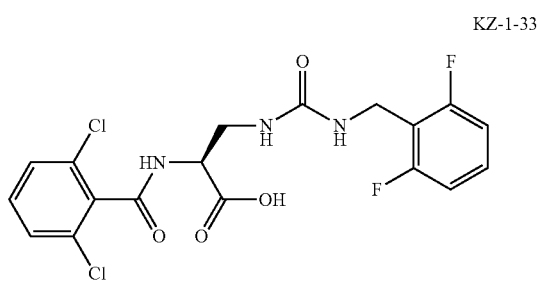 [SMILES: O=C(NCc1c(F)cccc1F)NC[C@H](NC(=O)c1c(Cl)cccc1Cl)C(=O)O]

KZ-1-33

(S)-2-(2,6-dichlorobenzamido)-3-(3-(2,6-difluorobenzyl) ureido)propanoic acid (KZ-1-33). Prepared from 1,3-difluoro-2-(isocyanatomethyl)benzene according to the procedure for KZ-1-9. $^1$H NMR (300 MHz, CDCl$_3$+CD$_3$OD, δ) 7.29-7.18 (m, 4H), 6.87-6.82 (m, 2H), 4.64-4.55 (m, 1H), 4.39 (s, 2H), 3.64-3.62 (m, 2H). LC-MS (condition A) m/z=446.1 (MH$^+$), Retention time=5.00 min.

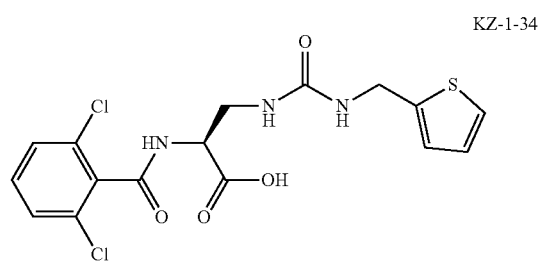 [SMILES: O=C(NCc1cccs1)NC[C@H](NC(=O)c1c(Cl)cccc1Cl)C(=O)O]

KZ-1-34

(S)-2-(2,6-dichlorobenzamido)-3-(3-(thiophen-2-ylmethyl)ureido)propanoic acid (KZ-1-34). Prepared from 2-(isocyanatomethyl)thiophene according to the procedure for KZ-1-9. $^1$H NMR (300 MHz, CDCl$_3$+CD$_3$OD, δ) 7.30-7.16 (m, 4H), 6.91 (s, 2H), 4.65-4.55 (m, 1H), 4.47 (s, 2H), 3.45-3.41 (m, 2H). LC-MS (condition A) m/z=416.6 (MH$^+$), Retention time=4.84 min.

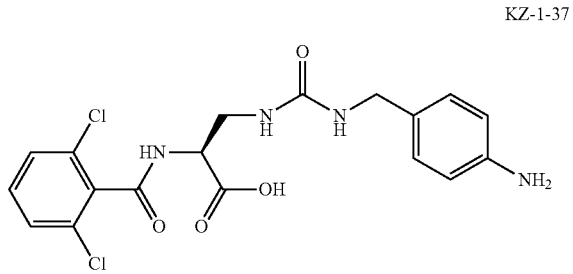 [SMILES: Nc1ccc(CNC(=O)NC[C@H](NC(=O)c2c(Cl)cccc2Cl)C(=O)O)cc1]

KZ-1-37

(S)-3-(3-(4-aminobenzyl)ureido)-2-(2,6-dichlorobenzamido)propanoic acid (KZ-1-37). Prepared from tert-butyl (4-(isocyanatomethyl)phenyl)carbamate according to the procedure for KZ-1-9. $^1$H NMR (300 MHz, CDCl$_3$+CD$_3$OD, δ) 7.28-7.07 (m, 7H), 4.71-4.53 (m, 1H), 4.23 (s, 2H), 3.55-3.46 (m, 2H). LC-MS (condition A) m/z=425.6 (MH$^+$), Retention time=3.41 min.

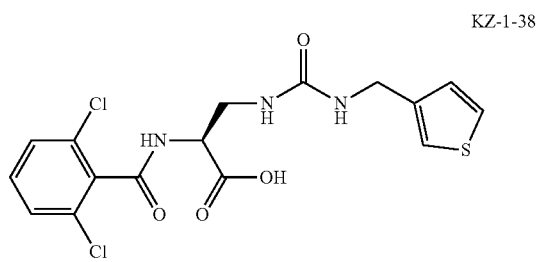 [SMILES: O=C(NCc1ccsc1)NC[C@H](NC(=O)c1c(Cl)cccc1Cl)C(=O)O]

KZ-1-38

(S)-2-(2,6-dichlorobenzamido)-3-(3-(thiophen-3-ylmethyl)ureido)propanoic acid (KZ-1-38). Prepared from 3-(isocyanatomethyl)thiophene according to the procedure for KZ-1-9. $^1$H NMR (300 MHz, CDCl$_3$+CD$_3$OD, δ) 7.33-7.25 (m, 4H), 7.11 (s, 1H), 7.00-6.98 (m, 1H), 4.61-4.60 (m, 1H), 4.33 (s, 2H), 3.82-3.77 (m, 2H). LC-MS (condition A) m/z=416.5 (MH$^+$), Retention time=4.84 min.

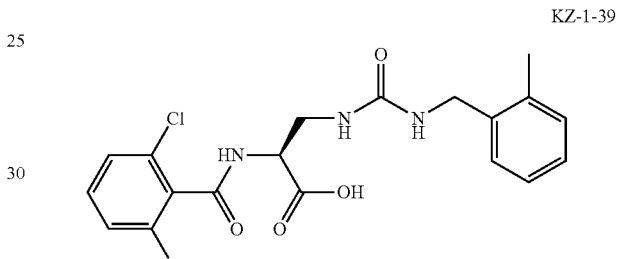

KZ-1-39

(S)-2-(2,6-dichlorobenzamido)-3-(3-(2-methylbenzyl) ureido)propanoic acid (KZ-1-39). Prepared from 1-(isocyanatomethyl)-2-methylbenzene according to the procedure for KZ-1-9. $^1$H NMR (300 MHz, CDCl$_3$+CD$_3$OD, δ) 7.29-7.23 (m, 3H), 7.21-7.10 (m, 4H), 4.62-4.60 (m, 1H), 4.25 (s, 2H), 3.75-3.624 (m, 2H), 2.24 (s, 3H). LC-MS (condition A) m/z=424.5 (MH$^+$), Retention time=5.18 min.

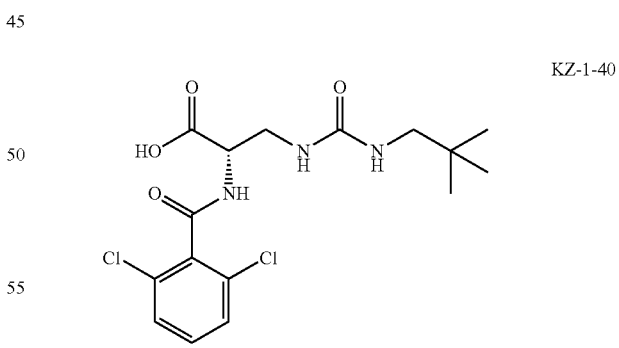

KZ-1-40

(S)-2-(2,6-dichlorobenzamido)-3-(3-neopentylureido) propanoic acid (KZ-1-40). Prepared from 1-isocyanato-2,2-dimethylpropane according to the procedure for KZ-1-9. $^1$H NMR (300 MHz, CDCl$_3$+CD$_3$OD, δ) 7.34-7.24 (m, 3H), 4.64-4.58 (m, 1H), 3.79-3.75 (m, 2H), 2.98-2.88 (m, 2H), 0.86 (s, 9H). LC-MS (condition A) m/z=390.5 (MH$^+$), Retention time=5.02 min.

Syntheses of KZ-1-80

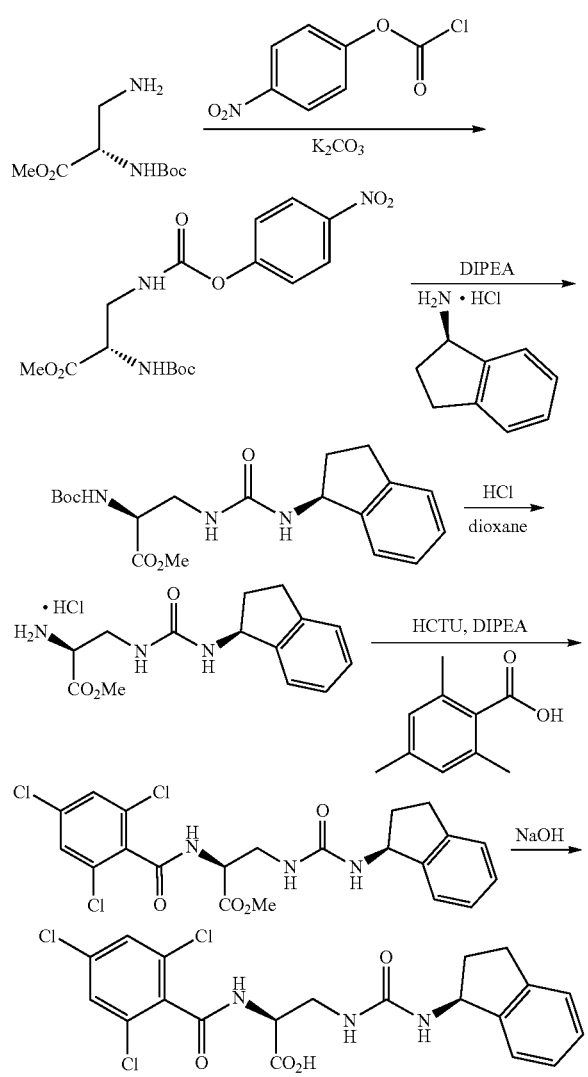

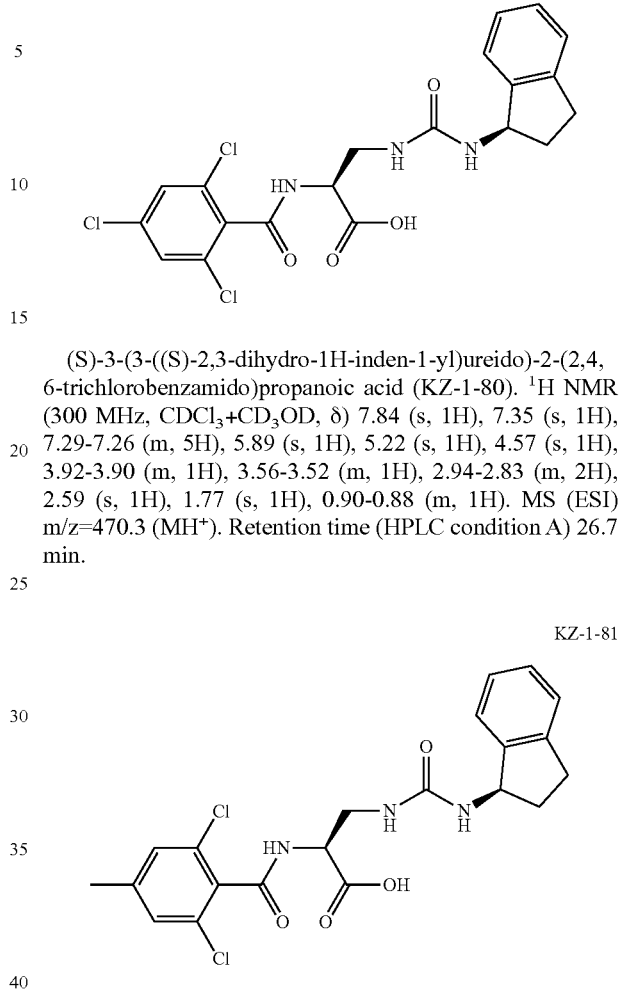

(S)-3-(3-((S)-2,3-dihydro-1H-inden-1-yl)ureido)-2-(2,4,6-trichlorobenzamido)propanoic acid (KZ-1-80). $^1$H NMR (300 MHz, $CDCl_3+CD_3OD$, δ) 7.84 (s, 1H), 7.35 (s, 1H), 7.29-7.26 (m, 5H), 5.89 (s, 1H), 5.22 (s, 1H), 4.57 (s, 1H), 3.92-3.90 (m, 1H), 3.56-3.52 (m, 1H), 2.94-2.83 (m, 2H), 2.59 (s, 1H), 1.77 (s, 1H), 0.90-0.88 (m, 1H). MS (ESI) m/z=470.3 ($MH^+$). Retention time (HPLC condition A) 26.7 min.

Boc-Dap-OMe (2 g, 9.1 mmol) was treated with 4-Nitrophenyl chloroformate (1.5 equiv) and $K_2CO_3$ (2 equiv) in DCM at room temperature. The reaction mixture was stirred over 2 hours, dried in vacuo and purified by Flash Column Chromatography (30% Ethyl acetate in hexanes). To the nitrophenylcarbamate was added (R)-1-amino indane hydrochloride (1.1 equiv) and DIPEA (2 equiv) in DMF and reacted until the starting material was consumed (monitored by TLC). The volatiles were removed in vacuo and the residue was purified by Flash Column Chromatography (50% Ethyl acetate in hexanes). To this amine (250 mg) was added 4M HCl in dioxane and stirred for 30 min. The volatiles were removed in vacuo and and the residue was dissolved in DMF. To the mixture were added 2,4,6-trichlorobenzoic acid (1.1 equiv), HCTU (1.1 equiv), and DIPEA (5 equiv) in DMF at room temperature and stirred overnight. The reaction mixture was dried in vacuo and the crude product was dissolved in THF (3 mL) and 1M NaOH (2 mL) was added at room temperature ad stirred for 3 h and then neutralized by 1M HCl. The crude product was purified by RP-HPLC (S)-2-(2,6-dichloro-4-methylbenzamido)-3-(3-((S)-2,3-dihydro-1H-inden-1-yl)ureido)propanoic acid (KZ-1-81).

Prepared from 4-methyl-2,6-dichlorobenzoic acid according to the procedure for KZ-1-80.

$^1$H NMR (300 MHz, $CDCl_3+CD_3OD$, δ) 7.62 (s, 1H), 7.29-7.10 (m, 6H), 6.31 (s, 1H), 5.61 (s, 1H), 5.20 (s, 1H), 4.59-4.58 (m, 1H), 3.91-3.86 (m, 1H), 3.61-3.57 (m, 1H), 2.93-2.80 (m, 2H), 2.58-2.52 (m, 1H), 2.34 (s, 3H), 1.80-1.68 (m, 1H). MS (ESI) m/z=450.5 ($MH^+$).

Retention time (HPLC condition A) 26 min.

ii. Biological Data

Cell adhesion Assay: Ninety-six-well flat-bottomed tissue culture plates were coated with rat tail collagen I for 1 hour at 37° C. After incubation, wells were blocked with 1% BSA at 37° C. for 1 hour. Control wells were filled with 1% BSA. HT1080 (human fibrosarcoma) cells (or human airway smooth muscle cells) were detached and resuspended in serum-free DMEM. Cells were incubated with anti-integrin alpha2 antibody control or 10-fold dilutions of each compound with a starting concentration of 10 uM for 15 minutes at 4° C. before plating. The plates were centrifuged at 10 g for 5 minutes before incubation for 1 hour at 37° C. in humidified 5% $CO_2$. Nonadherent cells were removed by centrifugation (top side down) at 10 g for 5 minutes. Attached cells were stained with 0.5% crystal violet, and the wells were washed with PBS. The relative number of cells in each well was evaluated after solubilization in 40 μl of 2% Triton X-100 by measuring absorbance at 595 nm in a microplate reader. All determinations were carried out in triplicate.

TABLE 1

IC$_{50}$s from HT 1080 Cell adhesion assay data: A: Below 10 μM, B: 10 μM-100 μM, C: >100 μM.

| Compound name | IC$_{50s}$ | Compound name | IC$_{50s}$ |
|---|---|---|---|
| A2-26 | B | KZ-1-9 | C |
| A2-27 | B | KZ-1-37 | C |
| A2-28 | C | KZ-1-32 | C |
| A2-60 | B | KZ-1-33 | C |
| A2-29 | A | KZ-1-12 | B |
| A2-35 | B | KZ-1-13 | C |
| A2-36 | B | KZ-1-11 | C |
| A2-61 | B | KZ-1-25 | C |
| A2-38 | C | A2-73 | C |
| A2-37 | C | KZ-1-19 | C |
| A2-63 | C | KZ-1-40 | C |
| A2-64 | C | A2-70 | C |
| KZ-1-18 | B | A2-71 | C |
| KZ-1-39 | B | KZ-1-27 | C |
| KZ-1-14 | B | KZ-1-22 | C |
| KZ-1-16 | B | A2-83 | B |
| KZ-1-15 | B | A2-87 | B |
| KZ-1-26 | C | A2-84 | B |
| KZ-1-20 | C | A2-85 | A |
| KZ-1-30 | C | A2-86 | B |
| KZ-1-23 | B | KZ-1-21 | B |
| A2-72 | C | A2-154 | B |
| A2-39 | B | A2-155 | B |
| KZ-1-34 | B | A2-156 | B |
| KZ-1-38 | B | A2-157 | B |
| KZ-1-17 | C | A2-170 | B |
| KZ-1-36 | C | A2-171 | A |
| KZ-1-3 | C | A2-172 | A |
| A2-123 | A | A2-173 | B |
| A2-124 | A | A2-174 | B |
| A2-125 | A | A2-175 | B |
| A2-126 | A | A2-176 | B |
| A2-127 | B | A2-177 | B |
| A2-128 | B | A2-178 | B |
| A2-129 | B | A2-179 | B |
| A2-130 | A | A2-180 | B |
| A2-131 | B | A2-181 | B |
| A2-132 | B | A2-144 | B |
| A2-133 | B | A2-145 | B |
| A2-134 | B | A2-152 | B |
| A2-143 | B | A2-153 | B |

REFERENCES

1. World Health Organization. Global surveillance, prevention and control of chronic respiratory diseases: a comprehensive approach. 2007.
2. Wenzel S E. Asthma: defining of the persistent adult phenotypes. Lancet 2006. 368(804-813)
3. Busse W W, Lemanske R F Jr. Asthma. N Engl J Med 2001. 344(350-362).
4. Holgate ST. Pathophysiology of asthma: what has our current understanding taught us about new therapeutic approaches? J Allergy Clin Immunol 2011. 128(495-505).
5. Brightling C E, Gupta S, Gonem S, Siddiqui S. Lung damage and airway remodeling in severe asthma. Clin Exp Allergy 2012. 42(638-649).
6. Benayoun L, DruilheA, Dombret M C, Aubier M, Pretolani M. Airway structural alterations selectively associated with severe asthma. Am J Respir Crit Care Med 2003. 167(1360-1368).
7. Chiba Y, Nakazawa S, Todoroki M, Shinozaki K, Sakai H, Misawa M. Interukin-13 augments bronchial smooth muscle contractility with an up-regulation of RhoA protein. Am J Respir Cell Mol Biol 2009. 40(159-167).
8. Berger P, Girodet P O, Begueret H, et al. Tryptase-stimulated human airway smooth muscle cells induce cytokine synthesis and mast cell chemotaxis. FASEB J 2003. 17(2139-2141).
9. Kudo M, Melton A, Chen C, Engler M, Huang K, Rin X, Wang Y, Bernstein X, Li J, Atabai K, Huang X, Sheppard D. IL-17A producted by αβ T cells drives airway hyper-responsiveness in mice and enhances mouse and human airway smooth muscle contraction. Nat. Med 2012. 18(547-554).
10. Zaidel-Bar R, Itzkovitz S, Ma'ayan A, Iyengar R, Geiger B. Functional atlas of the integrin adhesome. Nat Cell Biol 2007. 9(858-867).
11. Mehta D, Gunst S J. Actin polymerization stimulated by contractile activation regulates force development in canine tracheal smooth muscle. J Physiol 1999. 519(829-840).
12. Tang D, Mehta D, Gunst S J. Mechanosensitive tyrosine phosphorylation of paxillin and focal adhesion kinase in tracheal smooth muscle. Am J Physiol 1999. 276(C250-C258).
13. Sugimoto K, Kudo M, Sundaram A, Ren X, Huang K, Bernstein X, Wang Y, Raymond W, Erle D, Abrink M, Caughey G, Huang X, Sheppard D. The α$_v$β$_6$ integrin modulates airway hyperresponsiveness in mice by regulating intraepithelial mast cells. J Clin Invest 2012. February 122(2):748-758. PMC3266785.
14. Balzar S, Chu H, Strand M, Wenzel S. Relationship of Small Airway Chymase-Positive Mast Cells and Lung Function in Severe Asthma. AJRCCM 2005. 171(5):431-439.
15. Sundaram A, Chen C, Khalifeh-Soltani A, Atakilit A, Ren X, Qiu W, Jo H, DeGrado W, Huang X, Sheppard D. Targeting integrin α5β1 Ameliorates Severe Airway Hyperresponsiveness in Experimental Asthma. J Clin Invest 2017. January 127(1):365-374.
16. Choi, S., G. Vilaire, et al. (2007). "Small molecule inhibitors of integrin alpha2beta1." *J Med Chem* 50(22): 5457-5462.
17. Halland, N., H. Blum, et al. (2014). "Small Macrocycles As Highly Active Integrin alpha 2 beta 1 Antagonists." Acs Medicinal Chemistry Letters 5(2): 193-198.
18. Miller, M. W., S. Basra, et al. (2009). "Small-molecule inhibitors of integrin alpha2beta 1 that prevent pathological thrombus formation via an allosteric mechanism." *Proc Natl Acad Sci USA* 106(3): 719-724.
19. Borza, C. M., Y. Su, et al. (2012). "Inhibition of integrin alpha2beta1 ameliorates glomerular injury." *J Am Soc Nephrol* 23(6): 1027-1038.
20. Doherty, G. A., T. Kamenecka, et al. (2002). "N-aryl 2,6-dimethoxybiphenylalanine analogues as VLA-4 antagonists." *Bioorganic & Medicinal Chemistry Letters* 12(5): 729-731.
21. Porter, J. R., S. C. Archibald, et al. (2002). "N-(pyrimidin-4-yl) and N-(pyridin-2-yl) phenylalanine derivatives as VLA-4 integrin antagonists." *Bioorganic& Medicinal Chemistry Letters* 12(12): 1595-1598.
22. Tilley, J. W. (2002). "VLA-4 antagonists." *Expert Opinion on Therapeutic Patents* 12(7): 991-1008.
23. Miller, M. W., S. Basra, et al. (2009). "Small-molecule inhibitors of integrin alpha2beta 1 that prevent pathological thrombus formation via an allosteric mechanism." *Proc Natl Acad Sci USA* 106(3): 719-724.

What is claimed is:

1. A compound having the formula:

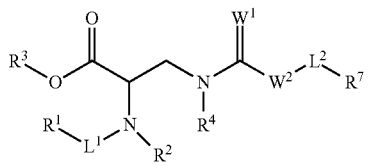

wherein, $R^1$ is substituted or unsubstituted alkyl, unsubstituted heteroalkyl, substituted or unsubstituted heterocycloalkyl, substituted or unsubstituted aryl, or substituted or unsubstituted heteroaryl;

$L^1$ is a bond or —C(O)—;

$R^2$ is hydrogen or substituted or unsubstituted alkyl;

$R^3$ is hydrogen, halogen, —CX$^3{}_3$, —CHX$^3{}_2$, —CH$_2$X$^3$, —OCX$^3{}_3$, —OCH$_2$X$^3$, —OCHX$^3{}_2$, —CN, —SO$_{n3}$R$^{3D}$, —SO$_{v3}$NR$^{3A}$R$^{3B}$, —NHC(O)NR$^{3A}$R$^{3B}$, —N(O)$_{m3}$, —NR$^{3A}$R$^{3B}$, —C(O)R$^{3C}$, —C(O)—OR$^{3C}$, —C(O)NR$^{3A}$R$^{3B}$, —OR$^{3D}$, —NR$^{3A}$SO$_2$R$^{3D}$, —NR$^{3A}$C(O)R$^{3C}$, —NR$^{3A}$C(O)OR$^{3C}$, —NR$^{3A}$OR$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; or —OR$^3$ is a prodrug moiety;

$R^4$ is hydrogen or substituted or unsubstituted alkyl;

$W^1$ is O, S, NR$^8$;

$W^2$ is O, S, NR$^5$;

$R^5$ is hydrogen;

$L^2$ is a bond or —C(R$^6$)$_2$—;

$R^6$ is independently hydrogen, =NH, substituted or unsubstituted alkyl, or substituted or unsubstituted heteroalkyl;

$W^1$ and $R^6$ may optionally be joined to form a substituted or unsubstituted 5 to 6 membered heterocycloalkyl, or substituted or unsubstituted 5 to 6 membered heteroaryl;

$R^7$ is hydrogen, halogen, —CX$^7{}_3$, —CHX$^7{}_2$, —CH$_2$X$^7$, —OCX$^7{}_3$, —OCH$_2$X$^7$, —OCHX$^7{}_2$, —CN, —SO$_{n7}$R$^{7D}$, —SO$_{v7}$NR$^{7A}$R$^{7B}$, —NHC(O)NR$^{7A}$R$^{7B}$, —N(O)$_{m7}$, —NR$^{7A}$R$^{7B}$, —C(O)R$^{7C}$, —C(O)—OR$^{7C}$, —C(O)NR$^{7A}$R$^{7B}$, —OR$^{7D}$, NR$^{7A}$C(O)OR$^{7C}$, —NR$^{7A}$OR$^{7C}$, substituted or unsubstituted 2,3-dihydro-1H-indenyl, substituted or unsubstituted bridged monocyclic cycloalkyl, substituted or unsubstituted bridged bicyclic cycloalkyl, substituted or unsubstituted spirocyclic bicyclic cycloalkyl, or substituted or unsubstituted heteroaryl;

$R^8$ is hydrogen or substituted or unsubstituted alkyl;

$R^{3A}$, $R^{3B}$, $R^{3C}$, $R^{3D}$, $R^{7A}$, $R^{7B}$, $R^{7C}$, and $R^{7D}$ are independently hydrogen, —CX$_3$, —CN, —COOH, —CONH$_2$, —CHX$_2$, —CH$_2$X, substituted or unsubstituted alkyl, substituted or unsubstituted heteroalkyl, or unsubstituted cycloalkyl, substituted or unsubstituted heterocycloalkyl, substituted or unsubstituted aryl, or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl;

each X, X$^3$, and X$^7$ are independently —F, —Cl, —Br, or —I;

n3 and n7 are independently an integer from 0 to 3; and m3, m7, v3 and v7 are independently 1 or 2.

2. The compound of claim 1 having the formula:

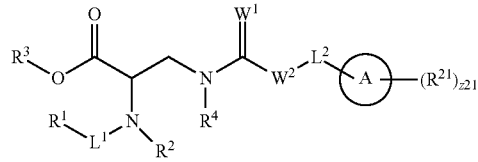

wherein,

Ring A is 2,3-dihydro-1H-indenyl, bridged monocyclic cycloalkyl, bridged bicyclic cycloalkyl, spirocyclic bicyclic cycloalkyl, or heteroaryl;

$R^{21}$ is independently halogen, —CX$^{21}{}_3$, —CHX$^{21}{}_2$, —CH$_2$X$^{21}$, —OCX$^{21}{}_3$, —OCH$_2$X$^{21}$, —OCHX$^{21}{}_2$, —CN, —SO$_{n21}$R$^{21D}$, —SO$_{v21}$NR$^{21A}$R$^{21B}$, —NHC(O)NR$^{21A}$R$^{21B}$, —N(O)$_{m21}$, —NR$^{21A}$R$^{21B}$, —C(O)R$^{21C}$, —C(O)—OR$^{21C}$, —C(O)NR$^{21A}$R$^{21B}$, —OR$^{21D}$, —OR$^{21A}$SO$_2$R$^{21D}$, —NR$^{21A}$C(O)R$^{21c}$, —NR$^{21A}$C(O)OR$^{21C}$, —NR$^{21A}$OR$^{21C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

z21 is an integer from 0 to 5;

$R^{21A}$, $R^{21B}$, $R^{21C}$, and $R^{21D}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{21A}$ and $R^{21B}$ substituents bonded to the same nitrogen atom may optionally be joined to form a substituted or unsubstituted heterocycloalkyl or substituted or unsubstituted heteroaryl;

each X and X$^{21}$ are independently —F, —Cl, —Br, or —I;

n21 is independently an integer from 0 to 3; and m21 and v21 are independently 1 or 2.

3. The compound of claim 1, wherein $R^1$ is unsubstituted $C_1$-$C_6$ alkyl; or $R^1$ is

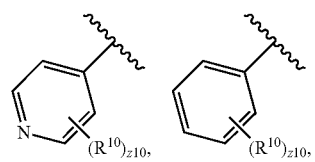

or substituted or unsubstituted $C_4$-$C_8$ alkyl;

wherein, $R^{10}$ is independently halogen, —CX$^{10}{}_3$, —CHX$^{10}{}_2$, —CH$_2$X$^{10}$, —OCX$^{10}{}_3$, —OCH$_2$X$^{10}$, —OCHX$^{10}{}_2$, —CN, —SO$_{n10}$R$^{10D}$, —SO$_{v10}$NR$^{10A}$R$^{10B}$, —NHC(O)NR$^{10A}$R$^{10B}$, —N(O)$_{m10}$, —NR$^{10A}$R$^{10B}$, —C(O)R$^{10C}$, —C(O)—OR$^{10C}$, —C(O)NR$^{10A}$R$^{10B}$, —OR$^{10D}$, —NR$^{10A}$SO$_2$R$^{10D}$, —NR$^{10A}$C(O)R$^{10C}$, —NR$^{10A}$C(O)

OR$^{10C}$, —NR$^{10A}$OR$^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^{10}$ substituents may optionally be joined to form a substituted or unsubstituted cycloalkyl, substituted or unsubstituted heterocycloalkyl, substituted or unsubstituted aryl, or substituted or unsubstituted heteroaryl;

R$^{10A}$, R$^{10B}$, R$^{10C}$, and R$^{10D}$ are independently hydrogen, —CX$_3$, —CN, —COOH, —CONH$_2$, —CHX$_2$, —CH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{10A}$ and R$^{10B}$ substituents bonded to the same nitrogen atom may optionally be joined to form a substituted or unsubstituted heterocycloalkyl or substituted or unsubstituted heteroaryl;

X and X$^{10}$ are independently —F, —Cl, —Br, or —I;

n10 is independently an integer from 0 to 4;

m10 and v10 are independently 1 or 2; and z10 is an integer from 0 to 5.

4. The compound of claim 1, wherein L$^2$ is a bond, —CHR$^6$, or —C(R$^6$)$_2$—.

5. The compound of claim 1, wherein R$^6$ is independently hydrogen or unsubstituted alkyl.

6. The compound of claim 1, wherein W$^1$ is NH, S, or O.

7. The compound of claim 1, wherein W$^2$ is NH, S, or O.

8. The compound of claim 1, wherein W$^1$ and R$^6$ are joined to form a substituted or unsubstituted 5 to 6 membered heterocycloalkyl or substituted or unsubstituted 5 to 6 membered heteroaryl.

9. The compound of claim 1, wherein W$^1$ and R$^6$ are joined to form

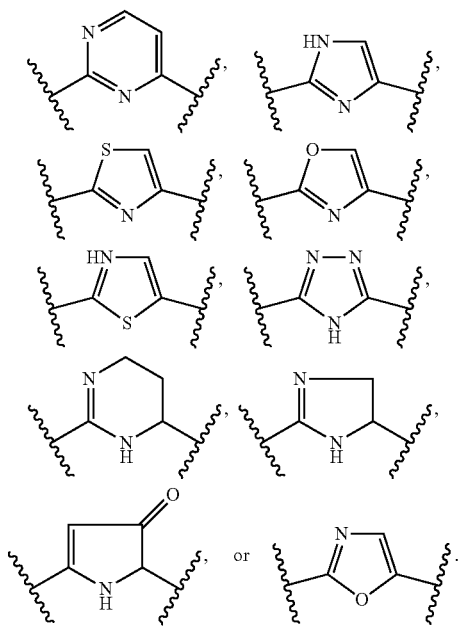

10. The compound of claim 1, wherein R$^2$, R$^4$, R$^5$, and R$^8$ are hydrogen.

11. The compound of claim 1, wherein R$^3$ is hydrogen, substituted or unsubstituted alkyl, substituted or unsubstituted heteroalkyl, substituted or unsubstituted cycloalkyl, substituted or unsubstituted heterocycloalkyl, substituted or unsubstituted heteroaryl, or R$^3$ is substituted or unsubstituted C$_1$-C$_8$ alkyl,

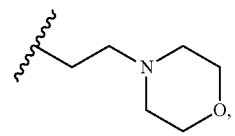 [SMILES: *CCN1CCOCC1]

substituted or unsubstituted aryl, (acyloxy)alkyl, [(alkoxycarbonyl)oxy]methyl, or (oxodioxolyl)methyl.

12. The compound of claim 1, wherein —OR$^3$ is a prodrug moiety or moiety capable of being cleaved from the remainder of the compound by an esterase or amidase.

13. The compound of claim 1, wherein R$^7$ is substituted or unsubstituted 2,3-dihydro-1H-indenyl, substituted or unsubstituted bridged monocyclic cycloalkyl, substituted or unsubstituted bridged bicyclic cycloalkyl, substituted or unsubstituted spirocyclic bicyclic cycloalkyl, or substituted or unsubstituted heteroaryl.

14. The compound of claim 1, wherein

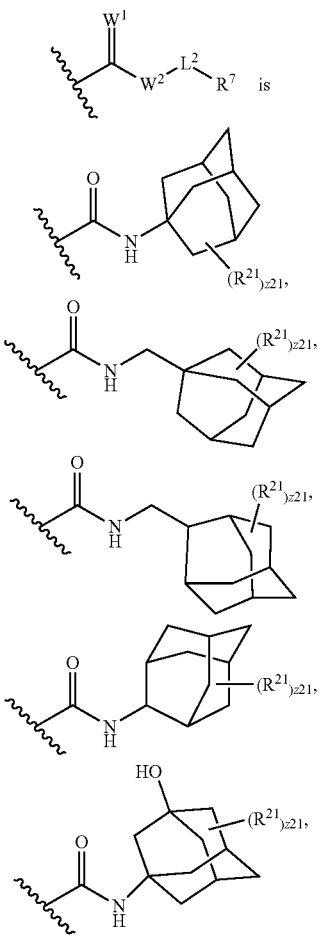

299
-continued
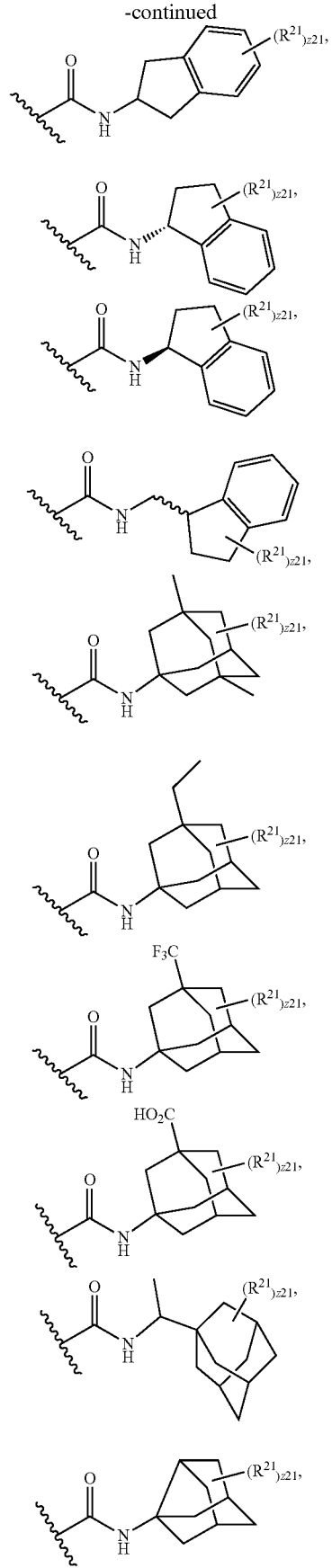
300
-continued
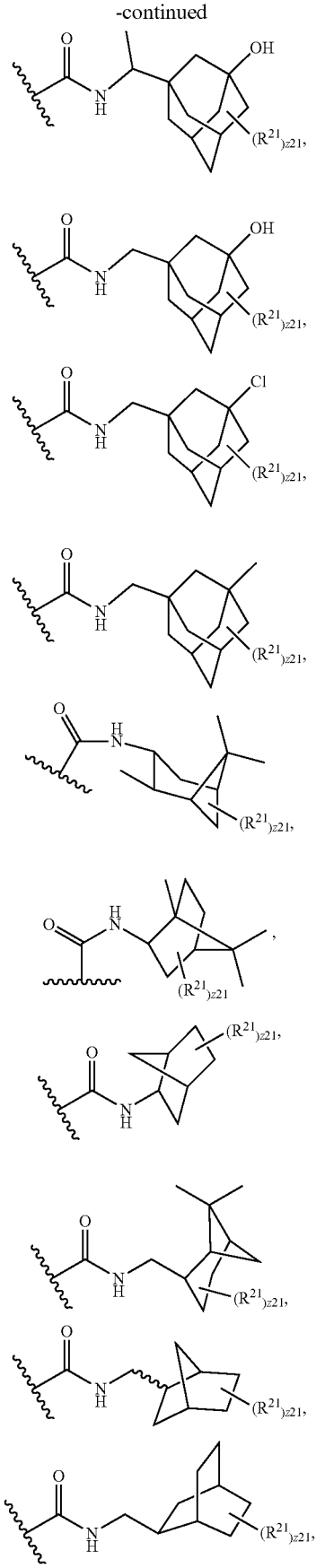

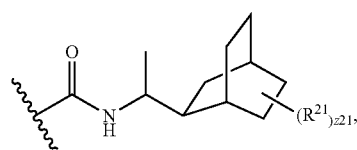
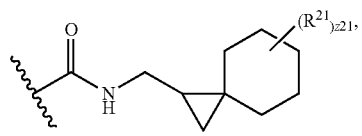
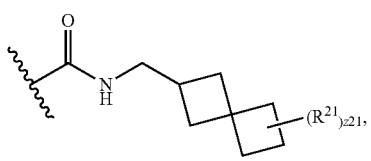
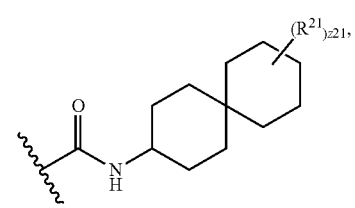
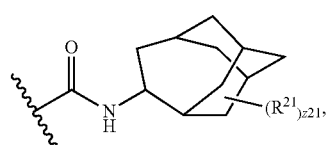
or
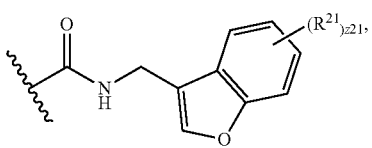
wherein z21 is an integer from 0 to 5.
15. The compound of claim 2, wherein Ring A is 5 to 6 membered heteroaryl, or bicyclic 8 to 10 membered heteroaryl.
16. The compound of claim 1, wherein
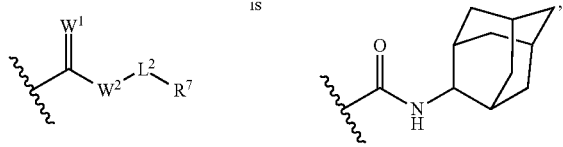
is
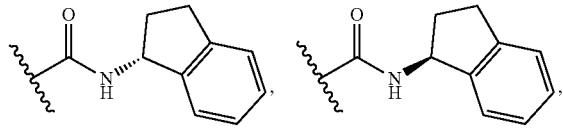
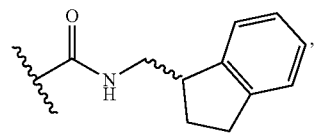
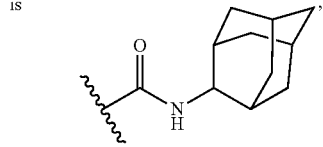
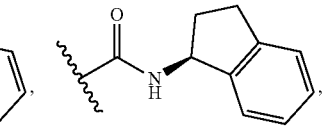
17. The compound of claim 1, having the formula:
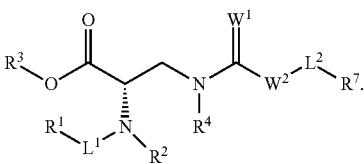
18. The compound of claim 1, having the formula:
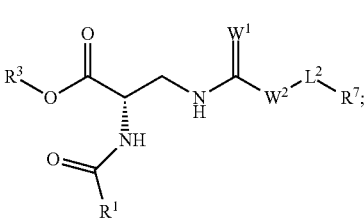
wherein $R^1$ is
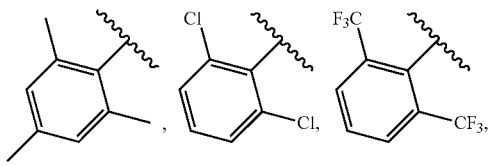
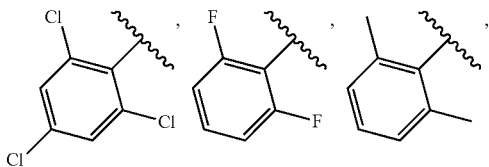
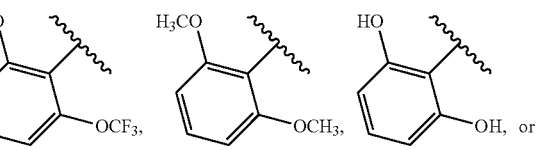

-continued

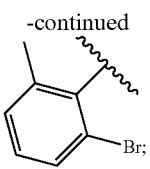

and

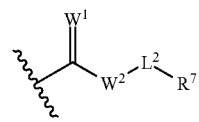

is

A)

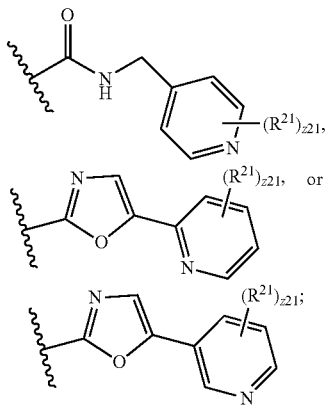

wherein z21 is an integer from 0 to 4;

B)

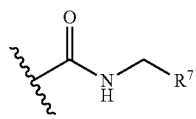

wherein $R^7$ is substituted or unsubstituted 2,3-dihydro-1H-indenyl, substituted or unsubstituted bridged monocyclic cycloalkyl, substituted or unsubstituted bridged bicyclic cycloalkyl, substituted or unsubstituted spirocyclic bicyclic cycloalkyl;

C)

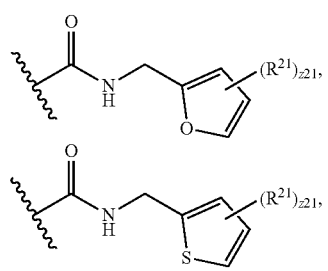

-continued

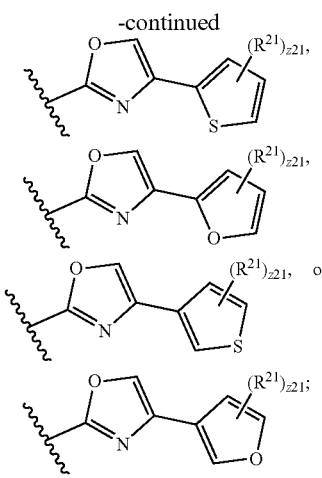

wherein z21 is an integer from 0 to 3; or

D)

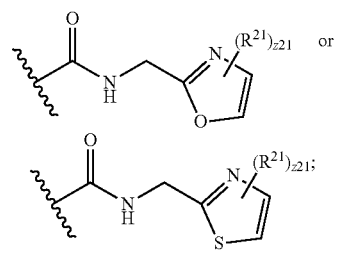

wherein z21 is an integer from 0 to 2.

19. The compound of claim 1, having the formula:

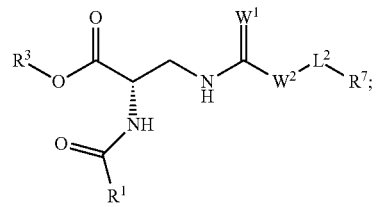

wherein $R^1$ is

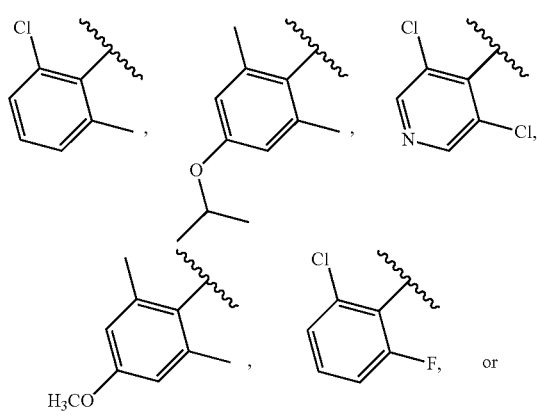

-continued

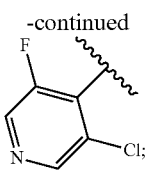

wherein

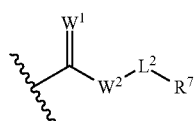

is

A)

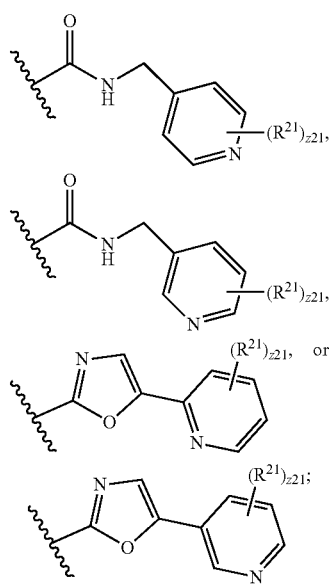

wherein z21 is an integer from 0 to 4;

B)

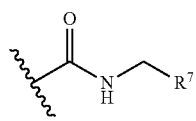

wherein $R^7$ is substituted or unsubstituted 2,3-dihydro-1H-indenyl, substituted or unsubstituted bridged monocyclic cycloalkyl, substituted or unsubstituted bridged bicyclic cycloalkyl, substituted or unsubstituted spirocyclic bicyclic cycloalkyl;

C)

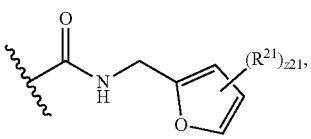

-continued

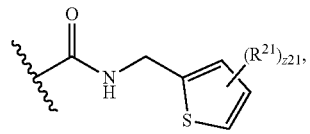

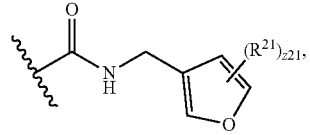

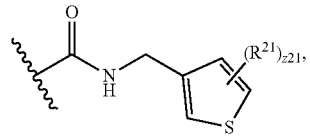

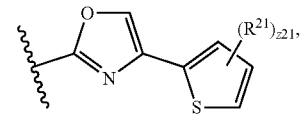

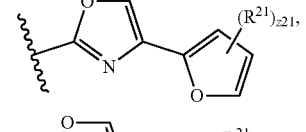

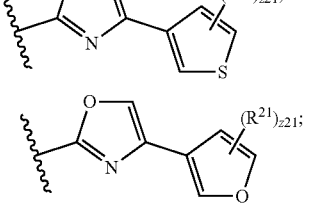

wherein z21 is an integer from 0 to 3; or

D)

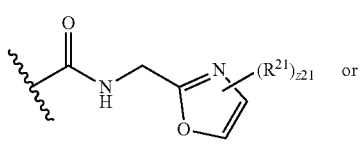

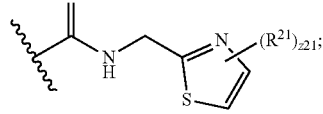

wherein z21 is an integer from 0 to 2.

20. The compound of claim 1, having the formula:

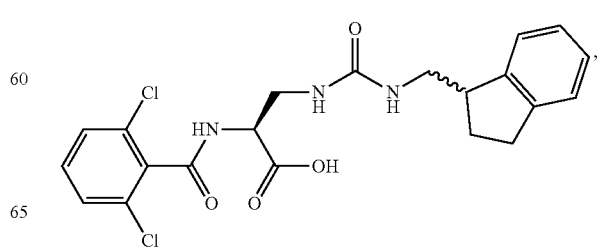

307
-continued

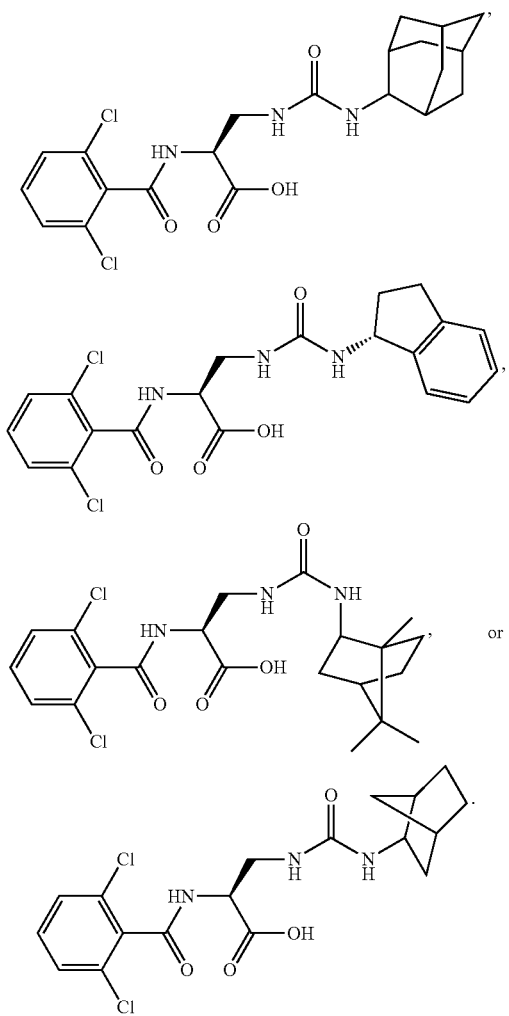

21. A pharmaceutical composition comprising a pharmaceutically acceptable excipient and a compound of claim 1, or a pharmaceutically acceptable salt thereof.

22. A method of treating asthma, the method comprising administering to a subject in need thereof an effective amount of a compound of claim 1, or a pharmaceutically acceptable salt thereof.

23. The method of claim 22, wherein $R^1$ is

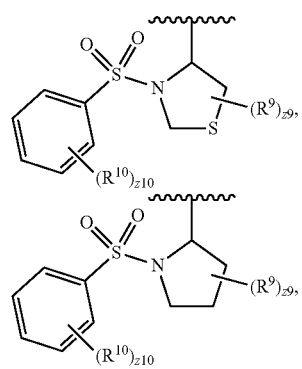

308
-continued

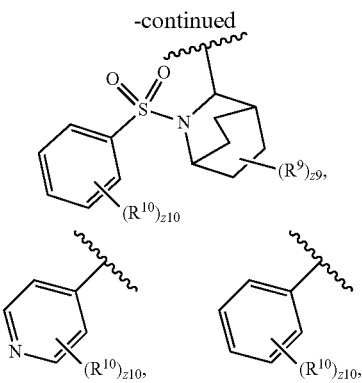

or substituted or unsubstituted $C_4$-$C_8$ alkyl;
wherein,
$R^9$ is independently halogen, $-CX^9{}_3$, $-CHX^9{}_2$, $-CH_2X^9$, $-OCX^9{}_3$, $-OCH_2X^9$, $-OCHX^9{}_2$, $-CN$, $-SO_{n9}R^{9D}$, $SO_{v9}NR^{9A}R^{9B}$, $-NHC(O)NR^{9A}R^{9B}$, $-N(O)_{m9}$, $-NR^{9A}R^{9B}$, $-C(O)R^{9C}$, $-C(O)-OR^{9C}$, $-C(O)NR^{9A}R^{9B}$, $-OR^{9D}$, $-NR^{9A}SO_2R^{9D}$, $-NR^{9A}C(O)R^{9C}$, $-NR^{9A}C(O)OR^{9C}$, $-NR^{9A}OR^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^9$ substituents may optionally be joined to form a substituted or unsubstituted cycloalkyl, substituted or unsubstituted heterocycloalkyl, substituted or unsubstituted aryl, or substituted or unsubstituted heteroaryl;

$R^{10}$ is independently halogen, $-CX^{10}{}_3$, $-CHX^{10}{}_2$, $-CH_2X^{10}$, $-OCX^{10}{}_3$, $-OCH_2X^{10}$, $-OCHX^{10}{}_2$, $-CN$, $-SO_{n10}R^{10D}$, $-SO_{v10}NR^{10A}R^{10B}$, $-NHC(O)NR^{10A}R^{10B}$, $-N(O)_{m10}$, $-NR^{10A}R^{10B}$, $-C(O)R^{10C}$, $-C(O)-OR^{10C}$, $-C(O)NR^{10A}R^{10B}$, $-OR^{10D}$, $-NR^{10A}SO_2R^{10D}$, $-NR^{10A}C(O)R^{10C}$, $-NR^{10A}C(O)OR^{10C}$, $-NR^{10A}OR^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^{10}$ substituents may optionally be joined to form a substituted or unsubstituted cycloalkyl, substituted or unsubstituted heterocycloalkyl, substituted or unsubstituted aryl, or substituted or unsubstituted heteroaryl;

$R^{9A}$, $R^{9B}$, $R^{9C}$, $R^{9D}$, $R^{10A}$, $R^{10B}$, $R^{10C}$, and $R^{10D}$ are independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{9A}$ and $R^{9B}$ substituents bonded to the same nitrogen atom may optionally be joined to form a substituted or unsubstituted heterocycloalkyl or substituted or unsubstituted heteroaryl; $R^{10A}$ and $R^{10B}$ substituents bonded to the same nitrogen atom may optionally be joined to form a substituted or unsubstituted heterocycloalkyl or substituted or unsubstituted heteroaryl;

X, $X^9$, and $X^{10}$ are independently —F, —Cl, —Br, or —I;
n9 and n10 are independently an integer from 0 to 4;
m9, m10, v9 and v10 are independently 1 or 2;
z9 is an integer from 0 to 5; and
z10 is an integer from 0 to 5.

24. The method of claim 22, wherein the compound is
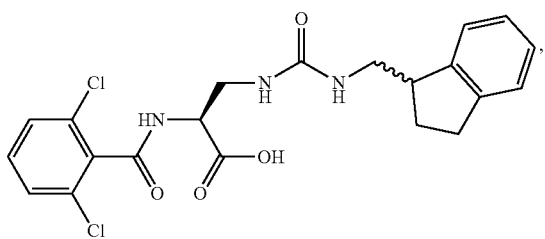 [SMILES: O=C(NCC1CCc2ccccc21)NC[C@H](NC(=O)c1c(Cl)cccc1Cl)C(=O)O]
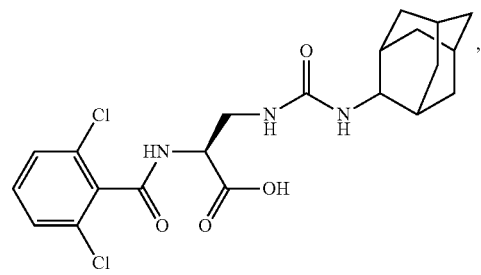
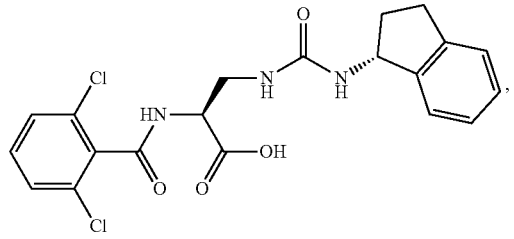
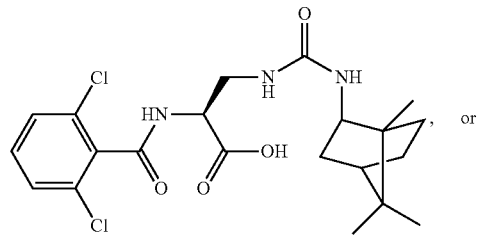, or
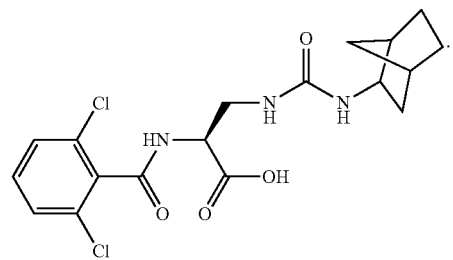
25. The method of claim 22, wherein
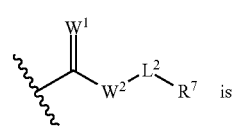 is
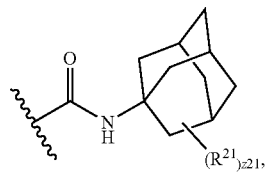
-continued
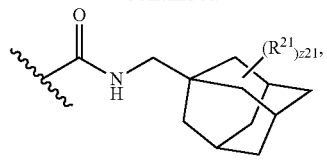
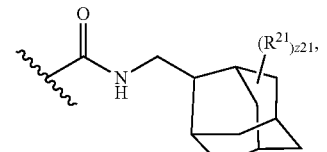
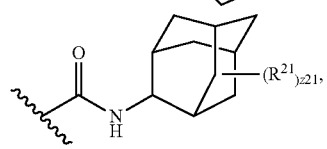
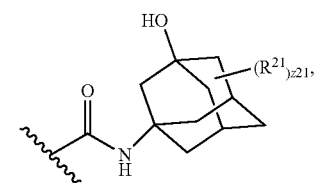
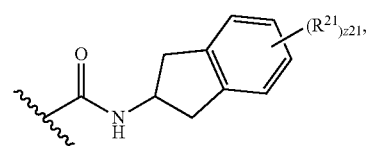
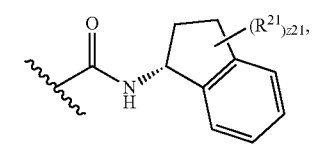
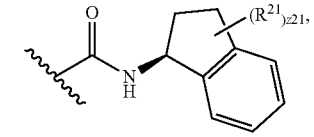
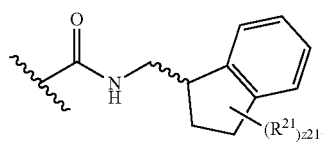
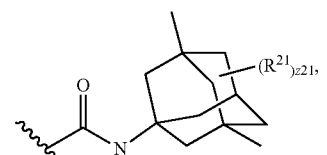
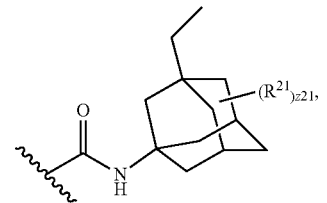

311
-continued
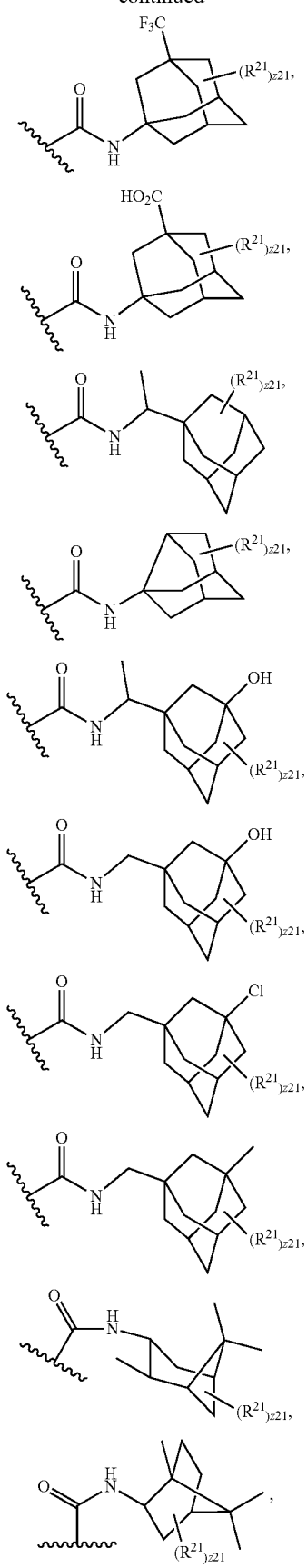
312
-continued
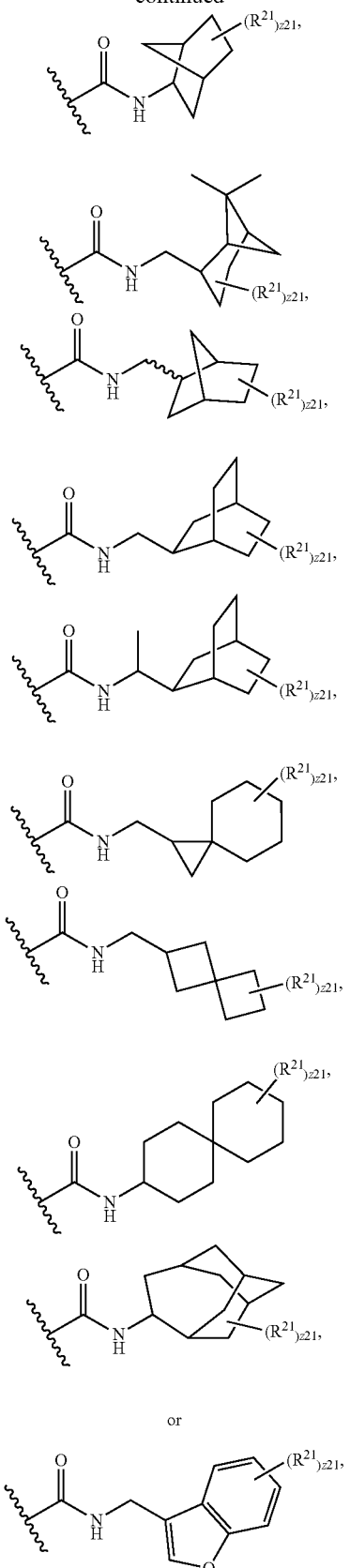
or
wherein z21 is an integer from 0 to 5.

26. The compound of claim 2, having the formula:

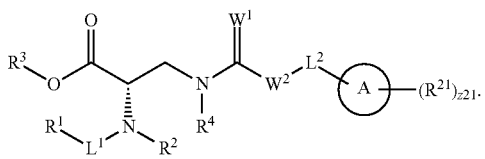

27. The compound of claim 1, wherein $R^1$ is

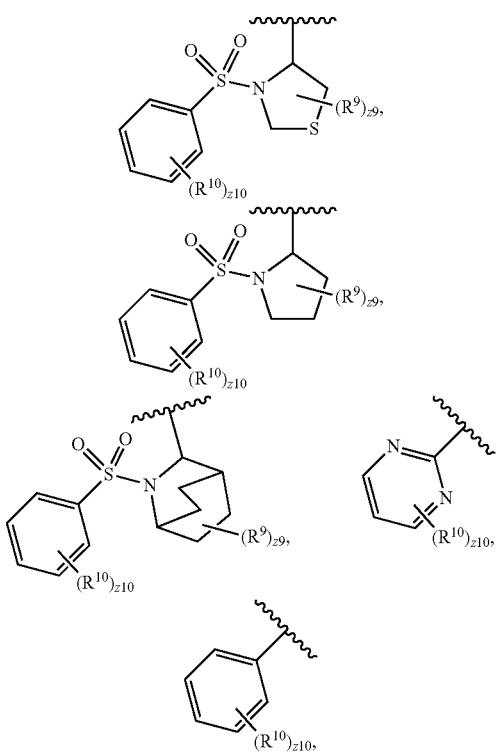

or substituted or unsubstituted $C_4$-$C_8$ alkyl;
wherein,
$R^9$ is independently halogen, $-CX^9_3$, $-CHX^9_2$, $-CH_2X^9$, $-OCX^9_3$, $-OCH_2X^9$, $-OCHX^9_2$, $-CN$, $-SO_{n9}R^{9D}$, $-SO_{v9}NR^{9A}R^{9B}$, $-NHC(O)NR^{9A}R^{9B}$, $-N(O)_{m9}$, $-NR^{9A}R^{9B}$, $-C(O)R^{9C}$, $-C(O)-OR^{9C}$, $-C(O)NR^{9A}R^{9B}$, $-OR^{9D}$, $-NR^{9A}SO_2R^{9D}$, $-NR^{9A}C(O)R^{9C}$, $-NR^{9A}C(O)OR^{9C}$, $-NR^{9A}OR^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^9$ substituents may optionally be joined to form a substituted or unsubstituted cycloalkyl, substituted or unsubstituted heterocycloalkyl, substituted or unsubstituted aryl, or substituted or unsubstituted heteroaryl;

$R^{10}$ is independently halogen, $-CX^{10}_3$, $-CHX^{10}_2$, $-CH_2X^{10}$, $-OCX^{10}_3$, $-OCH_2X^{10}$, $-OCHX^{10}_2$, $-CN$, $-SO_{n10}R^{10D}$, $-SO_{v10}NR^{10A}R^{10B}$, $-NHC(O)NR^{10A}R^{10B}$, $-N(O)_{m10}$, $-NR^{10A}R^{10B}$, $-C(O)R^{10C}$, $-C(O)-OR^{10C}$, $-C(O)NR^{10A}R^{10B}$, $-OR^{10D}$, $-NR^{10A}SO_2R^{10D}$, $-NR^{10A}C(O)R^{10C}$, $-NR^{10A}C(O)OR^{10C}$, $-NR^{10A}OR^{10C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteraryl; two adjacent $R^{10}$ substituents may optionally be joined to form a substituted or unsubstituted cycloalkyl, substituted or unsubstituted heterocycloalkyl, substituted or unsubstituted aryl, or substituted or unsubstituted heteroaryl;

$R^{9A}$, $R^{9B}$, $R^{9C}$, $R^{9D}$, $R^{10A}$, $R^{10B}$, $R^{10C}$, and $R^{10D}$ are independently hydrogen, $-CX_3$, $-CN$, $-COOH$, $-CONH_2$, $-CHX_2$, $-CH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{9A}$ and $R^{9B}$ substituents bonded to the same nirogen atom may optionally be joined to form a substituted or unsubstituted heterocycloalkyl or substituted or unsubstituted heteroaryl; $R^{10A}$ and $R^{10B}$ substituents bonded to the same nitrogen atom may optionally be joined to form a substituted or unsubstituted heterocycloalkyl or substituted or unsubstituted heteroaryl;

X, $X^9$, and $X^{10}$ are independently $-F$, $-Cl$, $-Br$, or $-I$;
n9 and n10 are independently an integer from 0 to 4;
m9, m10, v9 and v10 are independently 1 or 2;
z9 is an integer from 0 to 5; and
z10 is an integer from 0 to 5.

* * * * *